US011116827B2

(12) United States Patent
Jones et al.

(10) Patent No.: US 11,116,827 B2
(45) Date of Patent: Sep. 14, 2021

(54) COMPOSITIONS AND METHODS FOR TUMOR VACCINATION AND IMMUNOTHERAPY INVOLVING HER ANTIGENS

(71) Applicant: ETUBICS CORPORATION, Seattle, WA (US)

(72) Inventors: Frank R. Jones, Seattle, WA (US); Joseph Balint, Seattle, WA (US); Elizabeth Gabitzsch, Seattle, WA (US)

(73) Assignee: Etubics Corporation, Seattle, WA (US)

( * ) Notice: Subject to any disclaimer, the term of this patent is extended or adjusted under 35 U.S.C. 154(b) by 0 days.

(21) Appl. No.: 16/615,925

(22) PCT Filed: Jun. 2, 2018

(86) PCT No.: PCT/US2018/035759
§ 371 (c)(1),
(2) Date: Nov. 22, 2019

(87) PCT Pub. No.: WO2018/223103
PCT Pub. Date: Dec. 6, 2018

(65) Prior Publication Data
US 2020/0147193 A1    May 14, 2020

Related U.S. Application Data

(60) Provisional application No. 62/514,666, filed on Jun. 2, 2017.

(51) Int. Cl.
*C12N 15/86* (2006.01)
*A61K 39/00* (2006.01)
*C07K 16/28* (2006.01)

(52) U.S. Cl.
CPC ......... *A61K 39/001106* (2018.08); *A61K 39/00117* (2018.08); *A61K 39/001152* (2018.08); *C07K 16/2827* (2013.01); *C12N 15/86* (2013.01); *A61K 2039/523* (2013.01); *C12N 2710/10343* (2013.01)

(58) Field of Classification Search
CPC ......... C12N 15/861; C12N 15/86; C12N 2710/10343; A61K 39/001106; A61K 39/001152; A61K 39/00117; A61K 2039/523; C07K 16/2827
See application file for complete search history.

(56) References Cited

U.S. PATENT DOCUMENTS

| | | | |
|---|---|---|---|
| 2003/0053995 A1 | 3/2003 | Hung et al. | |
| 2004/0063140 A1 | 4/2004 | Kraus et al. | |
| 2007/0249043 A1 | 10/2007 | Mayall | |
| 2009/0105139 A1* | 4/2009 | Kole | C07K 14/71 514/1.1 |
| 2013/0251703 A1* | 9/2013 | Elis | A61K 39/39558 424/133.1 |
| 2014/0017259 A1* | 1/2014 | Aurisicchio | A61K 39/0011 424/172.1 |
| 2018/0282736 A1* | 10/2018 | Lyerly | A61K 45/06 |

FOREIGN PATENT DOCUMENTS

| | | | | |
|---|---|---|---|---|
| WO | WO 2016/172249 | | 10/2016 | |
| WO | WO-2016172249 A1 * | | 10/2016 | A61K 31/519 |
| WO | WO 2017/205810 | | 11/2017 | |
| WO | WO 2017/210562 | | 12/2017 | |

OTHER PUBLICATIONS

GeneCard synonym lists for HER4 downloaded Aug. 8, 2020 (Year: 2020).*
Gabitzsch et al (Oncotarget vol. 6, No. 31, published Sep. 7, 2015; IDS reference). (Year: 2015).*
GeneCard synonym lists for HER1, downloaded Aug. 8, 2020 (Year: 2020).*
GeneCard synonym lists for HER2, downloaded Aug. 8, 2020 (Year: 2020).*
GeneCard synonym lists for HER3, downloaded Aug. 8, 2020 (Year: 2020).*
GeneCard synonym lists for Brachyury, downloaded Aug. 8, 2020 (Year: 2020).*
GeneCard synonym lists for MUC1, downloaded Aug. 8, 2020 (Year: 2020).*
Gabitzsch et al., "An Ad5[E1−, E2b−]-HER2/neu vector induces immune responses and inhibits HER2/neu expressing tumor progression in Ad5 immune mice", Cancer Gene Therapy, 2011, vol. 18, Iss. 5, p. 326-335.
Extended European Search Report for European Patent Application No. 18810733.8 dated May 7, 2020, 8 pages.
Gabitzsch et al., "The Generation and Analyses of a Novel Combination of Recombinant Adenovirus Vaccines Targeting Three Tumor Antigens as an Immunotherapeutic," Oncotarget, 2015, vol. 6, No. 31, pp. 31344-31359.

(Continued)

*Primary Examiner* — Catherine S Hibbert
(74) *Attorney, Agent, or Firm* — Sheridan Ross P.C.

(57) ABSTRACT

In certain embodiments, methods and compositions are provided for generating immune responses against tumor antigens such as antigens or epitopes of HER1, HER2/neu, HER3, HER4, or any combination thereof. In particular embodiments, there may be provided methods for constructing and producing recombinant adenovirus-based vector vaccines containing nucleic acid sequences encoding tumor antigens such as antigens or epitopes of HER1, HER2/neu, HER3, HER4, or any combination thereof, that allow for vaccinations in individuals with preexisting immunity to adenovirus.

14 Claims, 19 Drawing Sheets

Specification includes a Sequence Listing.

(56) References Cited

OTHER PUBLICATIONS

Hamilton et al., "Development of Cancer Vaccines Targeting Brachyury, a Transcription Factor Associated with Tumor Epithelial-Mesenchymal Transition," Cells Tissues Organs, 2017, vol. 203, No. 2, pp. 128-138.
International Search Report and Written Opinion for International (PCT) Patent Application No. PCT/US2018/35759 dated Sep. 24, 2018, 10 pages.
International Preliminary Report on Patentability for International (PCT) Patent Application No. PCT/US2018/35759 dated Dec. 12, 2019, 8 pages.
Official Action for Australian Patent Application No. 2018275147, dated Oct. 1, 2020, 5 pages.
Official Action for Australian Patent Application No. 2018275147, dated Dec. 10, 2020, 4 pages.
Official Action for Canadian Patent Application No. 3063747, dated Nov. 17, 2020, 5 pages.
Notice of Acceptance for Australian Patent Application No. 2018275147, dated Jan. 13, 2021, 3 pages.

\* cited by examiner

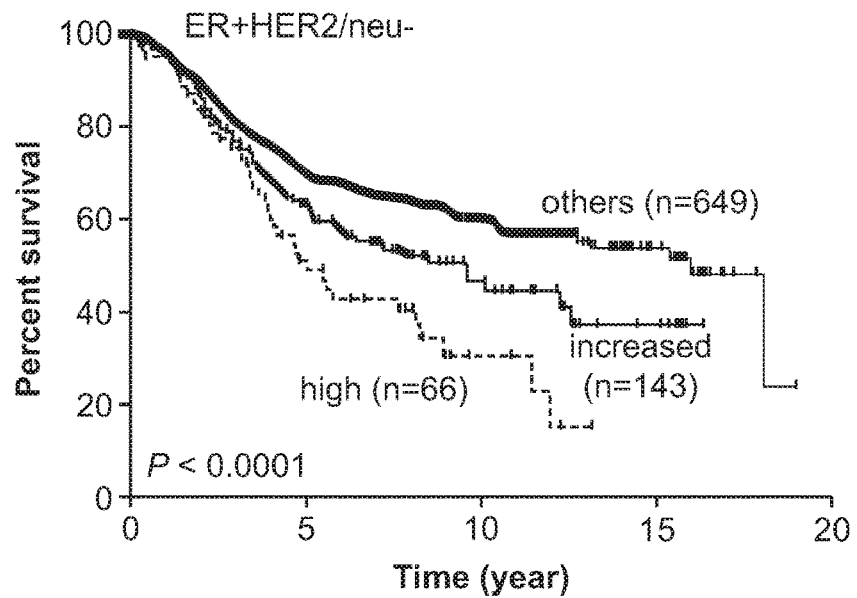
FIG. 1A
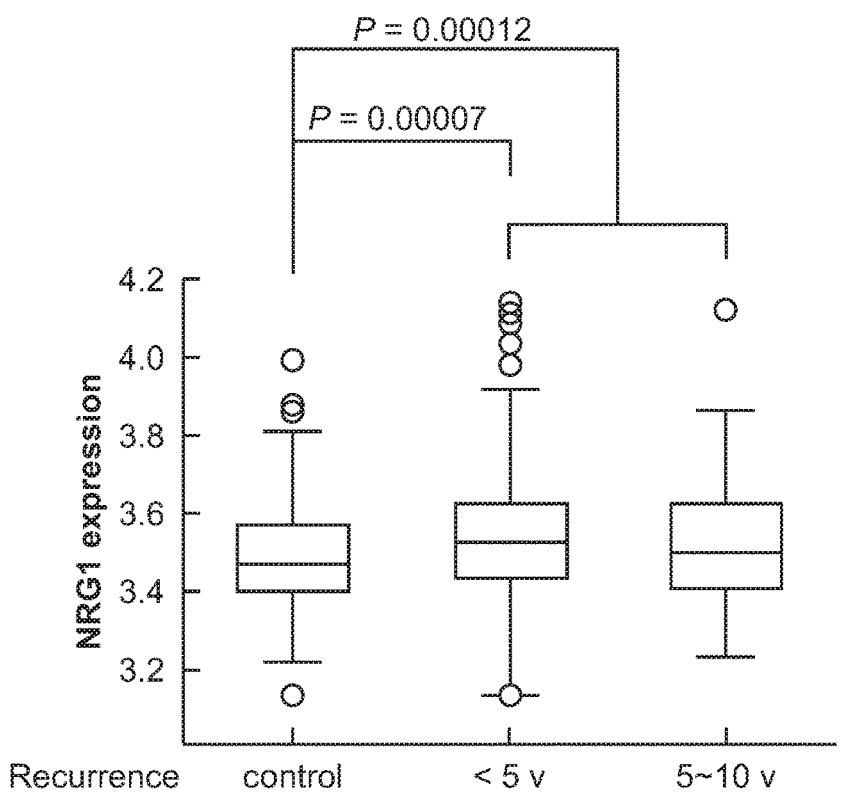
FIG. 1B
FIG. 1

SEQUENCE LISTING

<160> NUMBER OF SEQ ID NOS: 111

<210> SEQ ID NO 1
<211> LENGTH: 2075
<212> TYPE: DNA
<213> ORGANISM: Homo sapiens

<400> SEQUENCE: 1

```
ctagaatgga gctggcggcc ttgtgccgct gggggctcct cctcgccctc ttgccccccg     60
gagccgcgag cacccaagtg tgcaccggca cagacatgaa gctgcggctc cctgccagtc    120
ccgagaccca cctggacatg ctccgccacc tctaccaggg ctgccaggtg gtgcagggaa    180
acctggaact cacctacctg cccaccaatg ccagcctgtc cttcctgcag gatatccagg    240
aggtgcaggg ctacgtgctc atcgctcaca ccaagtgag gcaggtccca ctgcagaggc    300
tgcggattgt gcgaggcacc cagctctttg aggacaacta tgccctggcc gtgctagaca    360
atggagaccc gctgaacaat accaccccctg tcacaggggc ctccccagga ggcctgcggg    420
agctgcagct tcgaagcctc acagagatct tgaaaggagg ggtcttgatc cagcggaacc    480
cccagctctg ctaccaggac acgatttttgt ggaaggacat cttccacaag aacaaccagc    540
tggctctcac actgatagac accaaccgct ctcgggcctg ccaccctgt tctccgatgt    600
gtaagggctc ccgctgctgg ggagagagtt ctgaggattg tcagagcctg acgcgcactg    660
tctgtgccgg tggctgtgcc cgctgcaagg ggccactgcc cactgactgc tgccatgagc    720
agtgtgctgc cggctgcacg ggccccaagc actctgactg cctggcctgc ctccacttca    780
accacagtgg catctgtgag ctgcactgcc cagccctggt cacctacaac acagacacgt    840
ttgagtccat gcccaatccc gagggccggt atacattcgg cgccagctgt gtgactgcct    900
gtccctacaa ctaccttttct acggacgtgg atcctgcac cctcgtctgc ccctgcaca    960
accaagaggt gacagcagag gatggaacac agcggtgtga aagtgcagc aagccctgtg   1020
cccgagtgtg ctatggtctg ggcatggagc acttgcgaga ggtgagggca gttaccagtg   1080
ccaatatcca ggagtttgct ggctgcaaga gatctttgg gagcctggca tttctgccgg   1140
agagctttga tgggacccca gcctccaaca ctgccccgct ccagccagag cagctccaag   1200
tgtttgagac tctggaagag atcacaggtt acctatacat ctcagcatgg ccggacagcc   1260
tgcctgacct cagcgtcttc cagaacctgc aagtaatccg gggacgaatt ctgcacaatg   1320
gcgcctactc gctgaccctg caagggctgg gcatcagctg gctggggctg cgctcactga   1380
gggaactggg cagtggactg gccctcatcc accataacac ccacctctgc ttcgtgcaca   1440
cggtgccctg ggaccagctc tttcggaacc cgcaccaagc tctgctccac actgccaacc   1500
ggccagagga cgagtgtgtg ggcgagggcc tggcctgcca ccagctgtgc gcccgagggc   1560
actgctgggg tccagggccc acccagtgtg tcaactgcag ccagttcctt cggggccagg   1620
```

```
agtgcgtgga ggaatgccga gtactgcagg ggctccccag ggagtatgtg aatgccaggc    1680
actgtttgcc gtgccaccct gagtgtcagc cccagaatgg ctcagtgacc tgttttggac    1740
cggaggctga ccagtgtgtg gcctgtgccc actataagga ccctcccttc tgcgtggccc    1800
gctgccccag cggtgtgaaa cctgacctct cctacatgcc catctggaag tttccagatg    1860
aggagggcgc atgccagcct tgccccatca actgcaccca ctcctgtgtg gacctggatg    1920 acaaggctg ccccgccgag cagagagcca gccctctgac gtccatcgtc tctgcggtgg     1980
ttggcattct gctggtcgtg gtcttggggg tggtctttgg gatcctcatc aagcgacggc    2040
agcagaagat ccggaagtac acgtaatcta gataa                               2075
```

<210> SEQ ID NO 2
<211> LENGTH: 690
<212> TYPE: PRT
<213> ORGANISM: Homo sapiens

<400> SEQUENCE: 2

```
Met Arg Met Glu Leu Ala Ala Leu Cys Arg Trp Gly Leu Leu Leu Ala
1               5                   10                  15

Leu Leu Pro Pro Gly Ala Ala Ser Thr Gln Val Cys Thr Gly Thr Asp
            20                  25                  30

Met Lys Leu Arg Leu Pro Ala Ser Pro Glu Thr His Leu Asp Met Leu
        35                  40                  45

Arg His Leu Tyr Gln Gly Cys Gln Val Val Gln Gly Asn Leu Glu Leu
    50                  55                  60

Thr Tyr Leu Pro Thr Asn Ala Ser Leu Ser Phe Leu Gln Asp Ile Gln
65                  70                  75                  80

Glu Val Gln Gly Tyr Val Leu Ile Ala His Asn Gln Val Arg Gln Val
                85                  90                  95

Pro Leu Gln Arg Leu Arg Ile Val Arg Gly Thr Gln Leu Phe Glu Asp
            100                 105                 110

Asn Tyr Ala Leu Ala Val Leu Asp Asn Gly Asp Pro Leu Asn Asn Thr
        115                 120                 125

Thr Pro Val Thr Gly Ala Ser Pro Gly Gly Leu Arg Glu Leu Gln Leu
    130                 135                 140

Arg Ser Leu Thr Glu Ile Leu Lys Gly Gly Val Leu Ile Gln Arg Asn
145                 150                 155                 160

Pro Gln Leu Cys Tyr Gln Asp Thr Ile Leu Trp Lys Asp Ile Phe His
                165                 170                 175

Lys Asn Asn Gln Leu Ala Leu Thr Leu Ile Asp Thr Asn Arg Ser Arg
            180                 185                 190

Ala Cys His Pro Cys Ser Pro Met Cys Lys Gly Ser Arg Cys Trp Gly
        195                 200                 205

Glu Ser Ser Glu Asp Cys Gln Ser Leu Thr Arg Thr Val Cys Ala Gly
    210                 215                 220

Gly Cys Ala Arg Cys Lys Gly Pro Leu Pro Thr Asp Cys Cys His Glu
225                 230                 235                 240

Gln Cys Ala Ala Gly Cys Thr Gly Pro Lys His Ser Asp Cys Leu Ala
                245                 250                 255

Cys Leu His Phe Asn His Ser Gly Ile Cys Glu Leu His Cys Pro Ala
            260                 265                 270

Leu Val Thr Tyr Asn Thr Asp Thr Phe Glu Ser Met Pro Asn Pro Glu
        275                 280                 285
```

```
Gly Arg Tyr Thr Phe Gly Ala Ser Cys Val Thr Ala Cys Pro Tyr Asn
    290                 295                 300
Tyr Leu Ser Thr Asp Val Gly Ser Cys Thr Leu Val Cys Pro Leu His
305                 310                 315                 320
Asn Gln Glu Val Thr Ala Glu Asp Gly Thr Gln Arg Cys Glu Lys Cys
                325                 330                 335
Ser Lys Pro Cys Ala Arg Val Cys Tyr Gly Leu Gly Met Glu His Leu
            340                 345                 350
Arg Glu Val Arg Ala Val Thr Ser Ala Asn Ile Gln Glu Phe Ala Gly
        355                 360                 365
Cys Lys Lys Ile Phe Gly Ser Leu Ala Phe Leu Pro Glu Ser Phe Asp
370                 375                 380
Gly Asp Pro Ala Ser Asn Thr Ala Pro Leu Gln Pro Glu Gln Leu Gln
385                 390                 395                 400
Val Phe Glu Thr Leu Glu Glu Ile Thr Gly Tyr Leu Tyr Ile Ser Ala
                405                 410                 415
Trp Pro Asp Ser Leu Pro Asp Leu Ser Val Phe Gln Asn Leu Gln Val
            420                 425                 430
Ile Arg Gly Arg Ile Leu His Asn Gly Ala Tyr Ser Leu Thr Leu Gln
        435                 440                 445
Gly Leu Gly Ile Ser Trp Leu Gly Leu Arg Ser Leu Arg Glu Leu Gly
    450                 455                 460
Ser Gly Leu Ala Leu Ile His His Asn Thr His Leu Cys Phe Val His
465                 470                 475                 480
Thr Val Pro Trp Asp Gln Leu Phe Arg Asn Pro His Gln Ala Leu Leu
                485                 490                 495
His Thr Ala Asn Arg Pro Glu Asp Glu Cys Val Gly Glu Gly Leu Ala
            500                 505                 510
Cys His Gln Leu Cys Ala Arg Gly His Cys Trp Gly Pro Gly Pro Thr
        515                 520                 525
Gln Cys Val Asn Cys Ser Gln Phe Leu Arg Gly Gln Glu Cys Val Glu
    530                 535                 540
Glu Cys Arg Val Leu Gln Gly Leu Pro Arg Glu Tyr Val Asn Ala Arg
545                 550                 555                 560
His Cys Leu Pro Cys His Pro Glu Cys Gln Pro Gln Asn Gly Ser Val
                565                 570                 575
Thr Cys Phe Gly Pro Glu Ala Asp Gln Cys Val Ala Cys Ala His Tyr
            580                 585                 590
Lys Asp Pro Pro Phe Cys Val Ala Arg Cys Pro Ser Gly Val Lys Pro
        595                 600                 605
Asp Leu Ser Tyr Met Pro Ile Trp Lys Phe Pro Asp Glu Glu Gly Ala
    610                 615                 620
Cys Gln Pro Cys Pro Ile Asn Cys Thr His Ser Cys Val Asp Leu Asp
625                 630                 635                 640
Asp Lys Gly Cys Pro Ala Glu Gln Arg Ala Ser Pro Leu Thr Ser Ile
                645                 650                 655
Val Ser Ala Val Val Gly Ile Leu Leu Val Val Val Leu Gly Val Val
            660                 665                 670
Phe Gly Ile Leu Ile Lys Arg Arg Gln Gln Lys Ile Arg Lys Tyr Thr
        675                 680                 685
Ser Arg
    690
```

```
<210> SEQ ID NO 3
<211> LENGTH: 32295
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180 gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactgtaata gtaatcaatt     360
acggggtcat tagttcatag cccatatatg gagttccgcg ttacataact tacggtaaat     420
ggcccgcctg gctgaccgcc caacgacccc cgcccattga cgtcaataat gacgtatgtt     480
cccatagtaa cgccaatagg gactttccat tgacgtcaat gggtggagta tttacggtaa     540
actgcccact tggcagtaca tcaagtgtat catatgccaa gtacgccccc tattgacgtc     600
aatgacggta atggcccgc ctggcattat gcccagtaca tgaccttatg gactttcct      660 acttggcagt acatctacgt attagtcatc gctattacca tggtgatgcg gttttggcag     720
tacatcaatg ggcgtggata gcggtttgac tcacggggat ttccaagtct ccaccccatt     780
gacgtcaatg ggagtttgtt ttggcaccaa aatcaacggg actttccaaa atgtcgtaac     840
aactccgccc cattgacgca aatgggcggt aggcgtgtac ggtgggaggt ctatataagc     900
agagctggtt tagtgaaccg tcagatccgc tagagatctg gtaccgtcga cgcggccgct     960
cgagcctaag cttctagatg catgctcgag cggccgccag tgtgatggat atctgcagaa    1020
ttcgcccttg ctctagaatg gagctggcgg ccttgtgccg ctgggggctc ctcctcgccc    1080
tcttgccccc cggagccgcg agcacccaag tgtgcaccgg cacagacatg aagctgcggc    1140
tccctgccag tccgagacc cacctggaca tgctccgcca cctctaccag ggctgccagg    1200
tggtgcaggg aaacctggaa ctcacctacc tgcccaccaa tgccagcctg tccttcctgc    1260
aggatatcca ggaggtgcag ggctacgtgc tcatcgctca caaccaagtg aggcaggtcc    1320
cactgcagag gctgcggatt gtgcgaggca cccagctctt tgaggacaac tatgccctgg    1380
ccgtgctaga caatggagac ccgctgaaca taccacccc tgtcacaggg gcctccccag    1440
gaggcctgcg ggagctgcag cttcgaagcc tcacagagat cttgaaagga ggggtcttga    1500
tccagcggaa ccccccagctc tgctaccagg acacgatttt gtggaaggac atcttccaca    1560
agaacaacca gctggctctc acactgatag acaccaaccg ctctcgggcc tgccaccct    1620 gttctccgat gtgtaagggc tcccgctgct ggggagagag ttctgaggat tgtcagagcc    1680
tgacgcgcac tgtctgtgcc ggtggctgtg cccgctgcaa ggggccactg cccactgact    1740
gctgccatga gcagtgtgct gccggctgca cgggccccaa gcactctgac tgcctggcct    1800
gcctccactt caaccacagt ggcatctgtg agctgcactg cccagccctg gtcacctaca    1860
acacagacac gtttgagtcc atgcccaatc ccgagggccg gtatacattc ggcgccagct    1920
gtgtgactgc ctgtccctac aactaccttt ctacggacgt gggatcctgc acctcgtct    1980 gcccctgca caaccaagag gtgacagcag aggatgaac acagcggtgt gagaagtgca    2040
gcaagccctg tgcccgagtg tgctatggtc tgggcatgga gcacttgcga gaggtgaggg    2100
```

```
cagttaccag tgccaatatc caggagtttg ctggctgcaa gaagatcttt gggagcctgg    2160
catttctgcc ggagagcttt gatggggacc cagcctccaa cactgccccg ctccagccag    2220
agcagctcca agtgtttgag actctggaag agatcacagg ttacctatac atctcagcat    2280
ggccggacag cctgcctgac ctcagcgtct tccagaacct gcaagtaatc cggggacgaa    2340
ttctgcacaa tggcgcctac tcgctgaccc tgcaagggct gggcatcagc tggctggggc    2400
tgcgctcact gagggaactg ggcagtggac tggccctcat ccaccataac acccacctct    2460
gcttcgtgca cacggtgccc tgggaccagc tctttcggaa cccgcaccaa gctctgctcc    2520
acactgccaa ccgccagag gacgagtgtg tgggcgaggg cctggcctgc caccagctgt    2580
gcgcccgagg gcactgctgg ggtccagggc ccacccagtg tgtcaactgc agccagttcc    2640
ttcggggcca ggagtgcgtg gaggaatgcc gagtactgca ggggctcccc agggagtatg    2700
tgaatgccag gcactgtttg ccgtgccacc ctgagtgtca gccccagaat ggctcagtga    2760
cctgttttgg accggaggct gaccagtgtg tggcctgtgc ccactataag gaccctccct    2820
tctgcgtggc ccgctgcccc agcggtgtga aacctgacct ctcctacatg cccatctgga    2880
agtttccaga tgaggagggc gcatgccagc cttgccccat caactgcacc cactcctgtg    2940
tggacctgga tgacaagggc tgccccgccg agcagagagc cagccctctg acgtccatcg    3000
tctctgcggt ggttggcatt ctgctggtcg tggtcttggg ggtggtcttt gggatcctca    3060
tcaagcgacg gcagcagaag atccggaagt acacgtaatc tagataagat atccgatcca    3120
ccggatctag ataactgatc ataatcagcc ataccacatt tgtagaggtt ttacttgctt    3180
taaaaaacct cccacacctc cccctgaacc tgaaacataa aatgaatgca attgttgttg    3240
ttaacttgtt tattgcagct tataatggtt acaaataaag caatagcatc acaaatttca    3300
caaataaagc atttttttca ctgcattcta gttgtggttt gtccaaactc atcaatgtat    3360
cttaacgcgg atctgaagg tgctgaggta cgatgagacc cgcaccaggt gcagaccctg    3420
cgagtgtggc ggtaaacata ttaggaacca gcctgtgatg ctggatgtga ccgaggagct    3480
gaggcccgat cacttggtgc tggcctgcac ccgcgctgag tttggctcta gcgatgaaga    3540
tacagattga ggtactgaaa tgtgtgggcg tggcttaagg gtgggaaaga atatataagg    3600 tggggtctt atgtagtttt gtatctgttt tgcagcagcc gccgccgcca tgagcaccaa    3660
ctcgtttgat ggaagcattg tgagctcata tttgacaacg cgcatgcccc catgggccgg    3720
ggtgcgtcag aatgtgatgg gctccagcat tgatggtcgc cccgtcctgc ccgcaaactc    3780
tactaccttg acctacgaga ccgtgtctgg aacgccgttg gagactgcag cctccgccgc    3840
cgcttcagcc gctgcagcca ccgccgcgg gattgtgact gactttgctt tcctgagccc    3900
gcttgcaagc agtgcagctt cccgttcatc cgcccgcgat gacaagttga cggctctttt    3960
ggcacaattg gattctttga cccgggaact taatgtcgtt tctcagcagc tgttggatct    4020
gcgccagcag gttctgcccc tgaaggcttc ctcccctccc aatgcggttt aaaacataaa    4080
taaaaaacca gactctgttt ggatttggat caagcaagtg tcttgctgtc tttatttagg    4140
ggttttgcgc gcgcggtagg cccgggacca gcggtctcgg tcgttgaggg tcctgtgtat    4200
tttttccagg acgtggtaaa ggtgactctg gatgttcaga tacatgggca taagcccgtc    4260
tctggggtgg aggtagcacc actgcagagc ttcatgctgc ggggtggtgt tgtagatgat    4320
ccagtcgtag caggagcgct gggcgtggtg cctaaaaatg tctttcagta gcaagctgat    4380 tgccagggc aggcccttgg tgtaagtgtt tacaaagcgg ttaagctggg atgggtgcat    4440
```

-continued

| | | | | | |
|---|---|---|---|---|---|
| acgtggggat | atgagatgca | tcttggactg | tattttagg | ttggctatgt | tcccagccat | 4500 |
| atccctccgg | ggattcatgt | tgtgcagaac | caccagcaca | gtgtatccgg | tgcacttggg | 4560 |
| aaatttgtca | tgtagcttag | aaggaaatgc | gtggaagaac | ttggagacgc | ccttgtgacc | 4620 |
| tccaagattt | tccatgcatt | cgtccataat | gatggcaatg | ggcccacggg | cggcggcctg | 4680 |
| ggcgaagata | tttctgggat | cactaacgtc | atagttgtgt | tccaggatga | gatcgtcata | 4740 |
| ggccattttt | acaaagcgcg | ggcggagggt | gccagactgc | ggtataatgg | ttccatccgg | 4800 |
| cccaggggcg | tagttaccct | cacagatttg | catttcccac | gctttgagtt | cagatggggg | 4860 |
| gatcatgtct | acctgcgggg | cgatgaagaa | aacggtttcc | ggggtagggg | agatcagctg | 4920 |
| ggaagaaagc | aggttcctga | gcagctgcga | cttaccgcag | ccggtgggcc | cgtaaatcac | 4980 |
| acctattacc | ggctgcaact | ggtagttaag | agagctgcag | ctgccgtcat | ccctgagcag | 5040 |
| gggggccact | tcgttaagca | tgtccctgac | tcgcatgttt | tccctgacca | aatccgccag | 5100 |
| aaggcgctcg | ccgcccagcg | atagcagttc | ttgcaaggaa | gcaaagtttt | tcaacggttt | 5160 |
| gagaccgtcc | gccgtaggca | tgcttttgag | cgtttgacca | agcagttcca | ggcggtccca | 5220 |
| cagctcggtc | acctgctcta | cggcatctcg | atccagcata | tctcctcgtt | tcgcggggttg | 5280 |
| gggcggcttt | cgctgtacgg | cagtagtcgg | tgctcgtcca | gacgggccag | ggtcatgtct | 5340 |
| ttccacgggc | gcagggtcct | cgtcagcgta | gtctgggtca | cggtgaaggg | gtgcgctccg | 5400 |
| ggctgcgcgc | tggccagggt | gcgcttgagg | ctggtcctgc | tggtgctgaa | gcgctgccgg | 5460 |
| tcttcgccct | gcgcgtcggc | caggtagcat | ttgaccatgg | tgtcatagtc | cagcccctcc | 5520 |
| gcggcgtggc | ccttggcgcg | cagcttgccc | ttggaggagg | cgccgcacga | ggggcagtgc | 5580 |
| agacttttga | gggcgtagag | cttgggcgcg | agaaataccg | attccgggga | gtaggcatcc | 5640 |
| gcgccgcagg | ccccgcagac | ggtctcgcat | tccacgagcc | aggtgagctc | tggccgttcg | 5700 |
| gggtcaaaaa | ccaggtttcc | cccatgcttt | ttgatgcgtt | tcttacctct | ggtttccatg | 5760 |
| agccggtgtc | cacgctcggt | gacgaaaagg | ctgtccgtgt | ccccgtatac | agacttgaga | 5820 |
| ggcctgtcct | cgagcggtgt | tccgcggtcc | tcctcgtata | gaaactcgga | ccactctgag | 5880 |
| acaaaggctc | gcgtccaggc | cagcacgaag | gaggctaagt | gggagggta | gcggtcgttg | 5940 |
| tccactaggg | ggtccactcg | ctccagggtg | tgaagacaca | tgtcgccctc | ttcggcatca | 6000 |
| aggaaggtga | ttggtttgta | ggtgtaggcc | acgtgaccgg | gtgttcctga | agggggggcta | 6060 |
| taaaaggggg | tgggggcgcg | ttcgtcctca | ctctcttccg | catcgctgtc | tgcgagggcc | 6120 |
| agctgttggg | gtgagtactc | cctctgaaaa | gcgggcatga | cttctgcgct | aagattgtca | 6180 |
| gtttccaaaa | acgaggagga | tttgatattc | acctggcccg | cggtgatgcc | tttgagggtg | 6240 |
| gccgcatcca | tctggtcaga | aaagacaatc | tttttgttgt | caagcttggt | ggcaaacgac | 6300 |
| ccgtagaggg | cgttggacag | caacttggcg | atggagcgca | gggtttggtt | tttgtcgcga | 6360 |
| tcggcgcgct | ccttggccgc | gatgtttagc | tgcacgtatt | cgcgcgcaac | gcaccgccat | 6420 |
| tcgggaaaga | cggtggtgcg | ctcgtcgggc | accaggtgca | cgcgccaacc | gcggttgtgc | 6480 |
| agggtgacaa | ggtcaacgct | ggtggctacc | tctccgcgta | ggcgctcgtt | ggtccagcag | 6540 |
| aggcggccgc | ccttgcgcga | gcagaatggc | ggtaggggt | ctagctgcgt | ctcgtccggg | 6600 |
| gggtctgcgt | ccacggtaaa | gaccccgggc | agcaggcgcg | cgtcgaagta | gtctatcttg | 6660 |
| catccttgca | agtctagcgc | ctgctgccat | gcgcgggcgg | caagcgcgcg | ctcgtatggg | 6720 |
| ttgagtgggg | gaccccatgg | catggggtgg | gtgagcgcgg | aggcgtacat | gccgcaaatg | 6780 |
| tcgtaaacgt | agaggggctc | tctgagtatt | ccaagatatg | tagggtagca | tcttccaccg | 6840 |

```
cggatgctgg cgcgcacgta atcgtatagt tcgtgcgagg gagcgaggag gtcgggaccg    6900
aggttgctac gggcgggctg ctctgctcgg aagactatct gcctgaagat ggcatgtgag    6960
ttggatgata tggttggacg ctggaagacg ttgaagctgg cgtctgtgag acctaccgcg    7020
tcacgcacga aggaggcgta ggagtcgcgc agcttgttga ccagctcggc ggtgacctgc    7080
acgtctaggg cgcagtagtc cagggttttcc ttgatgatgt catacttatc ctgtcccttt    7140
tttttccaca gctcgcggtt gaggacaaac tcttcgcggt cttttccagta ctcttggatc    7200 ggaaacccgt cggcctccga acggtaagag cctagcatgt agaactggtt gacggcctgg    7260
taggcgcagc atcccttttc tacgggtagc gcgtatgcct gcgcggcctt ccggcatgac    7320
cagcatgaag ggcacgagct gcttcccaaa ggcccccatc caagtatagg tctctacatc    7380
gtaggtgaca aagagacgct cggtgcgagg atgcgagccg atcgggaaga actggatctc    7440
ccgccaccaa ttggaggagt ggctattgat gtggtgaaag tagaagtccc tgcgacgggc    7500
cgaacactcg tgctggcttt tgtaaaaacg tgcgcagtac tggcagcggt gcacgggctg    7560
tacatcctgc acgaggttga cctgacgacc gcgcacaagg aagcagagtg ggaatttgag    7620
cccctcgcct ggcgggtttg gctggtggtc ttctacttcg gctgcttgtc cttgaccgtc    7680
tggctgctcg aggggagtta cggtggatcg gaccaccacg ccgcgcgagc ccaaagtcca    7740
gatgtccgcg cgcggcggtc ggagcttgat gacaacatcg cgcagatggg agctgtccat    7800
ggtctggagc tcccgcggcg tcaggtcagg cgggagctcc tgcaggttta cctcgcatag    7860
acgggtcagg gcgcgggcta gatccaggtg atacctaatt tccaggggct ggttggtggc    7920
ggcgtcgatg gcttgcaaga ggccgcatcc ccgcggcgcg actacggtac cgcgcggcgg    7980
gcggtgggcc gcggggtgt ccttggatga tgcatctaaa agcggtgacg cgggcgagcc    8040
cccggaggta gggggggctc cggacccgcc gggagagggg gcaggggcac gtcggcgccg    8100
cgcgcgggca ggagctggtg ctgcgcgcgt aggttgctgg cgaacgcgac gacgcggcgg    8160
ttgatctcct gaatctggcg cctctgcgtg aagacgacgg gcccggtgag cttgaacctg    8220
aaagagagtt cgacagaatc aatttcggtg tcgttgacgg cggcctggcg caaaatctcc    8280
tgcacgtctc ctgagttgtc ttgataggcg atctcggcca tgaactgctc gatctcttcc    8340
tcctggagat ctccgcgtcc ggctcgctcc acggtggcgg cgaggtcgtt ggaaatgcgg    8400
gccatgagct gcgagaaggc gttgaggcct ccctcgttcc agacgcggct gtagaccacg    8460
cccccttcgg catcgcgggc gcgcatgacc acctgcgcga gattgagctc cacgtgccgg    8520
gcgaagacgc cgtagtttcg caggcgctga aagaggtagt tgagggtggt ggcggtgtgt    8580
tctgccacga agaagtacat aacccagcgt cgcaacgtgg attcgttgat aattgttgtg    8640
taggtactcc gccgccgagg gacctgagcg agtccgcatc gaccggatcg gaaaacctct    8700
cgagaaaggc gtctaaccag tcacagtcgc aaggtaggct gagcaccgtg gcgggcggca    8760
gcgggcggcg gtcgggggttg tttctggcgg aggtgctgct gatgatgtaa ttaaagtagg    8820
cggtcttgag acggcggatg gtcgacagaa gcaccatgtc cttgggtccg gcctgctgaa    8880
tgcgcaggcg gtcggccatg ccccaggctt cgttttgaca tcggcgcagg tctttgtagt    8940
agtcttgcat gagcctttct accggcactt cttcttctcc ttcctcttgt cctgcatctc    9000
ttgcatctat cgctgcggcg gcggcggagt ttggccgtag gtggcgccct cttcctccca    9060
tgcgtgtgac cccgaagccc ctcatcggct gaagcagggc taggtcggcg acaacgcgct    9120
cggctaatat ggcctgctgc acctgcgtga gggtagactg gaagtcatcc atgtccacaa    9180
```

```
agcggtggta tgcgcccgtg ttgatggtgt aagtgcagtt ggccataacg gaccagttaa    9240
cggtctggtg acccggctgc gagagctcgg tgtacctgag acgcgagtaa gccctcgagt    9300
caaatacgta gtcgttgcaa gtccgcacca ggtactggta tcccaccaaa aagtgcggcg    9360
gcggctggcg gtagaggggc cagcgtaggg tggccggggc tccgggggcg agatcttcca    9420
acataaggcg atgatatccg tagatgtacc tggacatcca ggtgatgccg gcggcggtgg    9480
tggaggcgcg cggaaagtcg cggacgcggt tccagatgtt gcgcagcggc aaaaagtgct    9540
ccatggtcgg gacgctctgg ccggtcaggc gcgcgcaatc gttgacgctc tagcgtgcaa    9600
aaggagagcc tgtaagcggg cactcttccg tggtctggtg gataaattcg caagggtatc    9660
atggcggacg accggggttc gagccccgta tccggccgtc cgccgtgatc catgcggtta    9720
ccgcccgcgt gtcgaaccca ggtgtgcgac gtcagacaac gggggagtgc tccttttggc    9780
ttccttccag gcgcggcggc tgctgcgcta gcttttttgg ccactggccg cgcgcagcgt    9840
aagcggttag gctggaaagc gaaagcatta agtggctcgc tccctgtagc cggagggtta    9900
ttttccaagg gttgagtcgc gggacccccg gttcgagtct cggaccggcc ggactgcggc    9960
gaacgggggt ttgcctcccc gtcatgcaag accccgcttg caaattcctc cggaaacagg   10020
gacgagcccc ttttttgctt ttcccagatg catccggtgc tgcggcagat cgcccccct   10080
cctcagcagc ggcaagagca agagcagcgg cagacatgca gggcaccctc ccctcctcct   10140
accgcgtcag gaggggcgac atccgcggtt gacgcggcag cagatggtga ttacgaaccc   10200
ccgcggcgcc gggcccggca ctacctggac ttggaggagg gcgagggcct ggcgcggcta   10260
ggagcgccct ctcctgagcg gcacccaagg gtgcagctga agcgtgatac gcgtgaggcg   10320
tacgtgccgc ggcagaacct gtttcgcgac cgcgagggag aggagcccga ggagatgcgg   10380
gatcgaaagt tccacgcagg gcgcgagctg cggcatggcc tgaatcgcga gcggttgctg   10440
cgcgaggagg actttgagcc cgacgcgcga accgggatta gtcccgcgcg cgcacacgtg   10500
gcggccgccg acctggtaac cgcatacgag cagacggtga accaggagat taactttcaa   10560
aaaagcttta caaccacgt gcgtacgctt gtggcgcgcg aggaggtggc tataggactg   10620
atgcatctgt gggactttgt aagcgcgctg gagcaaaacc caaatagcaa gccgctcatg   10680
gcgcagctgt tccttatagt gcagcacagc agggacaacg aggcattcag ggatgcgctg   10740
ctaaacatag tagagcccga gggcgctgg ctgctcgatt tgataaacat cctgcagagc   10800
atagtggtgc aggagcgcag cttgagcctg gctgacaagg tggccgccat caactattcc   10860
atgcttagcc tgggcaagtt ttacgcccgc aagatatacc ataccccctta cgttcccata   10920
gacaaggagg taaagatcga ggggttctac atgcgcatgg cgctgaaggt gcttaccttg   10980
agcgacgacc tgggcgttta tcgcaacgag cgcatccaca aggccgtgag cgtgagccgg   11040
cggcgcgagc tcagcgaccg cgagctgatg cacagcctgc aaagggccct ggctggcacg   11100
ggcagcggcg atagagaggc cgagtcctac tttgacgcgg gcgctgacct cgctggggcc   11160
ccaagccgac gcgccctgga ggcagctggg gccggacctg gctggcggt ggcacccgcg   11220
cgcgctggca acgtcggcgg cgtggaggaa tatgacgagg acgatgagta cgagccagag   11280
gacgcgagt actaagcggt gatgtttctg atcagatgat gcaagacgca acggacccgg   11340
cggtgcgggc ggcgctgcag agccagccgt ccggccttaa ctccacggac gactggcgcc   11400
aggtcatgga ccgcatcatg tcgctgactg cgcgcaatcc tgacgcgttc cggcagcagc   11460
cgcaggccaa ccgctctcc gcaattctgg aagcggtggt cccggcgcgc gcaaaccca   11520
cgcacgagaa ggtgctggcg atcgtaaacg cgctggccga aaacagggcc atccggcccg   11580
```

```
acgaggccgg cctggtctac gacgcgctgc ttcagcgcgt ggctcgttac aacagcggca   11640
acgtgcagac caacctggac cggctggtgg gggatgtgcg cgaggccgtg gcgcagcgtg   11700
agcgcgcgca gcagcagggc aacctgggct ccatggttgc actaaacgcc ttcctgagta   11760
cacagcccgc aacgtgccg cggggacagg aggactacac caactttgtg agcgcactgc   11820
ggctaatggt gactgagaca ccgcaaagtg aggtgtacca gtctgggcca gactattttt   11880
tccagaccag tagacaaggc ctgcagaccg taaacctgag ccaggctttc aaaaacttgc   11940
aggggctgtg gggggtgcgg gctcccacag gcgaccgcgc gaccgtgtct agcttgctga   12000
cgcccaactc gcgcctgttg ctgctgctaa tagcgcccct cacggacagt ggcagcgtgt   12060
cccgggacac atacctaggt cacttgctga cactgtaccg cgaggccata ggtcaggcgc   12120
atgtggacga gcatactttc caggagatta caagtgtcag ccgcgcgctg ggcaggagg   12180
acacgggcag cctggaggca accctaaact acctgctgac caaccggcgg cagaagatcc   12240
cctcgttgca cagtttaaac agcgaggagg agcgcatttt gcgctacgtg cagcagagcg   12300
tgagccttaa cctgatgcgc gacggggtaa cgcccagcgt ggcgctggac atgaccgcgc   12360
gcaacatgga accgggcatg tatgcctcaa accggccgtt tatcaaccgc ctaatggact   12420
acttgcatcg cgcggccgcc gtgaacccgc agtatttcac caatgccatc ttgaacccgc   12480
actggctacc gccccctggt ttctacaccg gggattcga ggtgcccgag ggtaacgatg   12540
gattcctctg ggacgacata gacgacagcg tgttttcccc gcaaccgcag accctgctag   12600
agttgcaaca gcgcgagcag gcagaggcgg cgctgcgaaa ggaaagcttc gcaggccaa   12660
gcagcttgtc cgatctaggc gctgcggccc cgcggtcaga tgctagtagc ccatttccaa   12720
gcttgatagg gtctcttacc agcactcgca ccacccgccc gcgcctgctg ggcgaggagg   12780
agtacctaaa caactcgctg ctgcagccgc agcgcgaaaa aaacctgcct ccggcatttc   12840
ccaacaacgg gatagagagc ctagtggaca agatgagtag atggaagacg tacgcgcagg   12900
agcacaggga cgtgccaggc ccgcgcccgc ccacccgtcg tcaaaggcac gaccgtcagc   12960
ggggtctggt gtgggaggac gatgactcgg cagacgacag cagcgtcctg gatttgggag   13020
ggagtggcaa cccgtttgcg caccttcgcc ccaggctggg gagaatgttt taaaaaaaaa   13080
aaagcatgat gcaaaataaa aaactcacca aggccatggc accgagcgtt ggttttcttg   13140
tattcccctt agtatgcggc gcgcggcgat gtatgaggaa ggtcctcctc cctcctacga   13200
gagtgtggtg agcgcggcgc cagtggcggc ggcgctgggt tctcccttcg atgctcccct   13260
ggacccgccg tttgtgcctc gcgcggtacct gcggcctacc gggggagaa acagcatccg   13320
ttactctgag ttggcacccc tattcgacac cacccgtgtg tacctggtgg acaacaagtc   13380
aacgatgtg gcatccctga actaccagaa cgaccacagc aacttctga ccacggtcat   13440
tcaaaacaat gactacagcc cgggggaggc aagcacacag accatcaatc ttgacgaccg   13500
gtcgcactgg ggcggcgacc tgaaaaccat cctgcatacc aacatgccaa atgtgaacga   13560
gttcatgttt accaataagt ttaaggcgcg ggtgatggtg tcgcgcttgc ctactaagga   13620
caatcaggtg gagctgaaat acgagtgggt ggagttcacg ctgcccgagg caactactc   13680
cgagaccatg accatagacc ttatgaacaa cgcgatcgtg gagcactact tgaaagtggg   13740
cagacagaac ggggtctgg aaagcgacat cggggtaaag tttgacaccc gcaacttcag   13800
actgggtttt gaccccgtca ctggtcttgt catgcctggg gtatatacaa acgaagcctt   13860
ccatccagac atcattttgc tgccaggatg cggggtggac ttcacccaca gccgcctgag   13920
```

```
caacttgttg ggcatccgca agcggcaacc cttccaggag ggctttagga tcacctacga   13980
tgatctggag ggtggtaaca ttcccgcact gttggatgtg gacgcctacc aggcgagctt   14040
gaaagatgac accgaacagg gcggggtgg cgcaggcggc agcaacagca gtggcagcgg    14100
cgcggaagag aactccaacg cggcagccgc ggcaatgcag ccggtggagg acatgaacga   14160
tcatgccatt cgcggcgaca cctttgccac acgggctgag gagaagcgcg ctgaggccga   14220
agcagcggcc gaagctgccg cccccgctgc gcaacccgag gtcgagaagc ctcagaagaa   14280
accggtgatc aaaccctga cagaggacag caagaaacgc agttacaacc taataagcaa    14340
tgacagcacc ttcacccagt accgcagctg gtaccttgca tacaactacg gcgaccctca   14400
gaccggaatc cgctcatgga ccctgctttg cactcctgac gtaacctgcg gctcggagca   14460
ggtctactgg tcgttgccag acatgatgca agacccgtg accttccgct ccacgcgcca    14520
gatcagcaac tttccggtgg tgggcgccga gctgttgccc gtgcactcca agagcttcta   14580
caacgaccag gccgtctact cccaactcat ccgccagttt acctctctga cccacgtgtt   14640
caatcgcttt cccgagaacc agattttggc gcgcccgcca gcccccacca tcaccaccgt   14700
cagtgaaaac gttcctgctc tcacagatca cgggacgcta ccgctgcgca acagcatcgg   14760
aggagtccag cgagtgacca ttactgacgc cagacgccgc acctgcccct acgtttacaa   14820
ggccctgggc atagtctcgc cgcgcgtcct atcgagccgc acttttgag caagcatgtc    14880
catccttata tcgcccagca ataacacagg ctggggcctg cgcttcccaa gcaagatgtt   14940
tggcggggcc aagaagcgct ccgaccaaca cccagtgcgc gtgcgcgggc actaccgcgc   15000
gccctggggc gcgcacaaac gcggccgcac tgggcgcacc accgtcgatg acgccatcga   15060
cgcggtggtg gaggaggcgc gcaactacac gcccacgccg ccaccagtgt ccacagtgga   15120
cgcggccatt cagaccgtgg tgcgcggagc ccggcgctat gctaaaatga agagacggcg   15180
gaggcgcgta gcacgtcgcc accgccgccg accggcact gccgcccaac gcgcggcggc    15240
ggccctgctt aaccgcgcac gtcgcaccgg ccgacgggcg gccatgcggg ccgctcgaag   15300
gctggccgcg ggtattgtca ctgtgccccc caggtccagg cgacgagcgg ccgccgcagc   15360
agccgcggcc attagtgcta tgactcaggg tcgcaggggc aacgtgtatt gggtgcgcga   15420
ctcggttagc ggcctgcgcg tgccgtgcg caccgccc ccgcgcaact agattgcaag      15480
aaaaaactac ttagactcgt actgttgtat gtatccagcg gcggcggcgc gcaacgaagc   15540
tatgtccaag cgcaaaatca agaagagat gctccaggtc atcgcgccgg agatctatgg    15600
ccccccgaag aaggaagagc aggattacaa gccccgaaag ctaaagcggg tcaaaaagaa   15660
aaagaaagat gatgatgatg aacttgacga cgaggtggaa ctgctgcacg ctaccgcgcc   15720
caggcgacgg gtacagtgga aaggtcgacg cgtaaaacgt gttttgcgac ccggcaccac   15780
cgtagtcttt acgcccggtg agcgctccac ccgcacctac aagcgcgtgt atgatgaggt   15840
gtacggcgac gaggacctgc ttgagcaggc caacgagcgc ctcggggagt ttgcctacgg   15900
aaagcggcat aaggacatgc tggcgttgcc gctggacagg ggcaacccaa cacctagcct   15960
aaagcccgta acactgcagc aggtgctgcc cgcgcttgca ccgtccgaag aaaagcgcgg   16020
cctaaagcgc gagtctggtg acttggcacc caccgtgcag ctgatggtac ccaagcgcca   16080
gcgactggaa gatgtcttgg aaaaaatgac cgtggaacct gggctggagc cgaggtccg    16140
cgtgcggcca atcaagcagg tggcgccggg actgggcgtg cagaccgtgg acgttcagat   16200
acccactacc agtagcacca gtattgccac cgccacagag ggcatggaga cacaaacgtc   16260
cccggttgcc tcagcggtgg cggatgccgc ggtgcaggcg gtcgctgcgg ccgcgtccaa   16320
```

```
gacctctacg gaggtgcaaa cggacccgtg gatgtttcgc gtttcagccc cccggcgccc   16380
gcgccgttcg aggaagtacg gcgccgccag cgcgctactg cccgaatatg ccctacatcc   16440
ttccattgcg cctaccccg  gctatcgtgg ctacacctac cgcccagaa  gacgagcaac   16500 tacccgacgc cgaaccacca ctggaacccg ccgccgccgt cgccgtcgcc agcccgtgct   16560
ggccccgatt tccgtgcgca gggtggctcg cgaaggaggc aggaccctgg tgctgccaac   16620
agcgcgctac caccccagca tcgtttaaaa gccggtcttt gtggttcttg cagatatggc   16680
cctcacctgc cgcctccgtt tcccggtgcc gggattccga ggaagaatgc accgtaggag   16740
gggcatggcc ggccacggcc tgacgggcgg catgcgtcgt gcgcaccacc ggcggcggcg   16800
cgcgtcgcac cgtcgcatgc gcggcggtat cctgcccctc cttattccac tgatcgccgc   16860
ggcgattggc gccgtgcccg gaattgcatc cgtggccttg caggcgcaga gacactgatt   16920
aaaaacaagt tgcatgtgga aaaatcaaaa taaaaagtct ggactctcac gctcgcttgg   16980
tcctgtaact attttgtaga atggaagaca tcaactttgc gtctctggcc ccgcgacacg   17040
gctcgcgccc gttcatggga aactggcaag atatcggcac cagcaatatg agcggtggcg   17100
ccttcagctg gggctcgctg tggagcggca ttaaaaattt cggttccacc gttaagaact   17160
atggcagcaa ggcctggaac agcagcacag gccagatgct gagggataag ttgaaagagc   17220
aaaatttcca acaaaaggtg gtagatggcc tggcctctgg cattagcggg gtggtggacc   17280
tggccaacca ggcagtgcaa aataagatta acagtaagct tgatccccgc cctcccgtag   17340
aggagcctcc accggccgtg gagacagtgt ctccagaggg gcgtggcgaa aagcgtccgc   17400
gccccgacag ggaagaaact ctggtgacgc aaatagacga gcctccctcg tacgaggagg   17460
cactaaagca aggcctgccc accacccgtc ccatcgcgcc catggctacc ggagtgctgg   17520
gccagcacac accgtaacg  ctggacctgc ctcccccgc  cgacacccag cagaaacctg   17580
tgctgccagg cccgaccgcc gttgttgtaa cccgtcctag ccgcgcgtcc ctgcgccgcg   17640
ccgccagcgg tccgcgatcg ttgcggcccg tagccagtgg caactggcaa agcacactga   17700
acagcatcgt gggtctgggg gtgcaatccc tgaagcgccg acgatgcttc tgatagctaa   17760
cgtgtcgtat gtgtgtcatg tatgcgtcca tgtcgccgcc agaggagctg ctgagccgcc   17820
gcgcgcccgc tttccaagat ggctacccct tcgatgatgc cgcagtggtc ttacatgcac   17880
atctcgggcc aggacgcctc ggagtacctg agccccgggc tggtgcagtt tgcccgcgcc   17940
accgagacgt acttcagcct gaataacaag tttagaaacc ccacggtggc gcctacgcac   18000
gacgtgacca cagaccggtc ccagcgtttg acgctgcggt tcatccctgt ggaccgtgag   18060
gatactgcgt actcgtacaa ggcgcggttc accctagctg tgggtgataa ccgtgtgctg   18120
gacatggctt ccacgtactt tgacatccgc ggcgtgctgg acaggggccc tactttaag   18180 ccctactctg gcactgccta caacgccctg gctcccaagg gtgccccaaa tccttgcgaa   18240
tgggatgaag ctgctactgc tcttgaaata aacctagaag aagaggacga tgacaacgaa   18300
gacgaagtag acgagcaagc tgagcagcaa aaaactcacg tatttgggca ggcgccttat   18360
tctggtataa atattacaaa ggagggtatt caaataggtg tcgaaggtca aacacctaaa   18420
tatgccgata aaacatttca acctgaacct caaataggaa atctcagtg  gtacgaaaca   18480 gaaattaatc atgcagctgg gagagtccta aaaagactta ccccaatgaa accatgttac   18540
ggttcatatg caaacccac  aaatgaaaat ggagggcaag gcattcttgt aaagcaacaa   18600
aatgaaaagc tagaaagtca agtggaaatg caattttctt caactactga ggcagccgca   18660
```

```
ggcaatggtg ataacttgac tcctaaagtg gtattgtaca gtgaagatgt agatatagaa   18720
accccagaca ctcatatttc ttacatgccc actattaagg aaggtaactc acgagaacta   18780
atgggccaac aatctatgcc caacaggcct aattacattg cttttaggga caattttatt   18840
ggtctaatgt attacaacag cacgggtaat atgggtgttc tggcgggcca agcatcgcag   18900
ttgaatgctg ttgtagattt gcaagacaga aacacagagc tttcatacca gcttttgctt   18960
gattccattg gtgatagaac caggtacttt tctatgtgga atcaggctgt tgacagctat   19020
gatccagatg ttagaattat tgaaaatcat ggaactgaag atgaacttcc aaattactgc   19080
tttccactgg gaggtgtgat taatacagag actcttacca aggtaaaacc taaaacaggt   19140
caggaaaatg gatgggaaaa agatgctaca gaattttcag ataaaaatga aataagagtt   19200
ggaaataatt ttgccatgga aatcaatcta aatgccaacc tgtggagaaa tttcctgtac   19260
tccaacatag cgctgtattt gcccgacaag ctaaagtaca gtccttccaa cgtaaaaatt   19320
tctgataacc caaacaccta cgactacatg aacaagcgag tggtggctcc cgggctagtg   19380
gactgctaca ttaaccttgg agcacgctgg tcccttgact atatggacaa cgtcaaccca   19440
tttaaccacc accgcaatgc tggcctgcgc taccgctcaa tgttgctggg caatggtcgc   19500
tatgtgccct tccacatcca ggtgcctcag aagttctttg ccattaaaaa cctccttctc   19560
ctgccgggct catacaccta cgagtggaac ttcaggaagg atgttaacat ggttctgcag   19620
agctccctag gaaatgacct aagggttgac ggagccagca ttaagtttga tagcatttgc   19680
ctttacgcca ccttcttccc catggcccac aacaccgcct ccacgcttga ggccatgctt   19740
agaaacgaca ccaacgacca gtcctttaac gactatctct ccgccgccaa catgctctac   19800
cctatacccg ccaacgctac caacgtgccc atatccatcc cctcccgcaa ctgggcggct   19860
ttccgcggct gggccttcac gcgccttaag actaaggaaa ccccatcact gggctcgggc   19920
tacgacccct attacaccta ctctggctct atacccaccc tagatggaac cttttacctc   19980
aaccacacct ttaagaaggt ggccattacc tttgactctt ctgtcagctg gcctggcaat   20040
gaccgcctgc ttaccccaa cgagtttgaa attaagcgct cagttgacgg ggagggttac   20100
aacgttgccc agtgtaacat gaccaaagac tggttcctgg tacaaatgct agctaactat   20160
aacattggct accagggctt ctatatccca gagagctaca aggaccgcat gtactccttc   20220
tttagaaact tccagcccat gagccgtcag gtggtggatg atactaaata caaggactac   20280
caacaggtgg gcatcctaca ccaacacaac aactctggat tgttggcta ccttgccccc   20340
accatgcgcg aaggacaggc ctaccctgct aacttcccct atccgcttat aggcaagacc   20400
gcagttgaca gcattaccca gaaaaagttt ctttgcgatc gcacccttg gcgcatccca   20460
ttctccagta actttatgtc catgggcgca ctcacagacc tgggccaaaa ccttctctac   20520
gccaactccg cccacgcgct agacatgact tttgaggtgg atcccatgga cgagcccacc   20580
cttctttatg ttttgtttga agtctttgac gtggtccgtg tgcaccagcc gcaccgcggc   20640
gtcatcgaaa ccgtgtacct gcgcacgccc ttctcggccg gcaacgccac aacataaaga   20700
agcaagcaac atcaacaaca gctgccgcca tgggctccag tgagcaggaa ctgaaagcca   20760
ttgtcaaaga tcttggttgt gggccatatt ttttgggcac ctatgacaag cgcttttccag   20820
gctttgtttc tccacacaag ctcgcctgcg ccatagtcaa tacggccggt cgcgagactg   20880
ggggcgtaca ctggatggcc tttgcctgga acccgcactc aaaaacatgc tacctctttg   20940
agcccttggc cttttctgac cagcgactca agcaggttta ccagtttgag tacgagtcac   21000
tcctgcgccg tagcgccatt gcttcttccc ccgaccgctg tataacgctg gaaaagtcca   21060
```

```
cccaaagcgt acaggggccc aactcggccg cctgtggact attctgctgc atgtttctcc   21120
acgcctttgc caactggccc caaactccca tggatcacaa ccccaccatg aaccttatta   21180
ccggggtacc caactccatg ctcaacagtc cccaggtaca gcccaccctg cgtcgcaacc   21240
aggaacagct ctacagcttc ctggagcgcc actcgcccta cttccgcagc acagtgcgc   21300
agattaggag cgccacttct ttttgtcact tgaaaaacat gtaaaaataa tgtactagag   21360
acactttcaa taaaggcaaa tgcttttatt tgtacactct cgggtgatta tttaccccca   21420
cccttgccgt ctgcgccgtt taaaaatcaa aggggttctg ccgcgcatcg ctatgcgcca   21480
ctggcaggga cacgttgcga tactggtgtt tagtgctcca cttaaactca ggcacaacca   21540
tccgcggcag ctcggtgaag ttttcactcc acaggctgcg caccatcacc aacgcgttta   21600
gcaggtcggg cgccgatatc ttgaagtcgc agttggggcc tccgccctgc gcgcgcgagt   21660
tgcgatacac agggttgcag cactggaaca ctatcagcgc cgggtggtgc acgctggcca   21720
gcacgctctt gtcggagatc agatccgcgt ccaggtcctc cgcgttgctc agggcgaacg   21780
gagtcaactt tggtagctgc cttcccaaaa agggcgcgtg cccaggcttt gagttgcact   21840
cgcaccgtag tggcatcaaa aggtgaccgt gcccggtctg ggcgttagga tacagcgcct   21900
gcataaaagc cttgatctgc ttaaaagcca cctgagcctt tgcgccttca gagaagaaca   21960
tgccgcaaga cttgccggaa aactgattgg ccggacaggc cgcgtcgtgc acgcagcacc   22020
ttgcgtcggt gttggagatc tgcaccacat ttcggcccca ccggttcttc acgatcttgg   22080
ccttgctaga ctgctccttc agcgcgcgct gcccgttttc gctcgtcaca tccatttcaa   22140
tcacgtgctc cttatttatc ataatgcttc cgtgtagaca cttaagctcg ccttcgatct   22200
cagcgcagcg gtgcagccac aacgcgcagc ccgtgggctc gtgatgcttg taggtcacct   22260
ctgcaaacga ctgcaggtac gcctgcagga atcgccccat catcgtcaca aaggtcttgt   22320
tgctggtgaa ggtcagctgc aacccgcggt gctcctcgtt cagccaggtc ttgcatacgg   22380
ccgccagagc ttccacttgg tcaggcagta gtttgaagtt cgcctttaga tcgttatcca   22440
cgtggtactt gtccatcagc gcgcgcgcag cctccatgcc cttctcccac gcagacacga   22500
tcggcacact cagcgggttc atcaccgtaa tttcactttc cgcttcgctg ggctcttcct   22560
cttcctcttg cgtccgcata ccacgcgcca ctgggtcgtc ttcattcagc cgccgcactg   22620
tgcgcttacc tcctttgcca tgcttgatta gcaccggtgg gttgctgaaa cccaccattt   22680
gtagcgccac atcttctctt tcttcctcgc tgtccacgat tacctctggt gatggcgggc   22740
gctcgggctt gggagaaggg cgcttctttt tcttcttggg cgcaatggcc aaatccgccg   22800
ccgaggtcga tggccgcggg ctgggtgtgc gcggcaccag cgcgtcttgt gatgagtctt   22860
cctcgtcctc ggactcgata cgccgcctca tccgcttttt tggggcgcc cggggaggcg   22920
gcggcgacgg ggacggggac gacacgtcct ccatggttgg gggacgtcgc gccgcaccgc   22980
gtccgcgctc gggggtggtt tcgcgctgct cctcttcccg actggccatt ccttctcct   23040
ataggcagaa aaagatcatg gagtcagtcg agaagaagga cagcctaacc gccccctctg   23100
agttcgccac caccgcctcc accgatgccg ccaacgcgcc taccaccttc cccgtcgagg   23160
cacccccgct tgaggaggag gaagtgatta tcgagcagga cccaggtttt gtaagcgaag   23220
acgacgagga ccgctcagta ccaacagagg ataaaaagca agaccaggac aacgcagagg   23280
caaacgagga acaagtcggg cggggggacg aaaggcatgg cgactaccta gatgtgggag   23340
acgacgtgct gttgaagcat ctgcagcgcc agtgcgccat tatctgcgac gcgttgcaag   23400
```

```
agcgcagcga tgtgcccctc gccatagcgg atgtcagcct tgcctacgaa cgccacctat   23460
tctcaccgcg cgtaccccc  aaacgccaag aaaacggcac atgcgagccc aacccgcgcc   23520
tcaacttcta ccccgtattt gccgtgccag aggtgcttgc cacctatcac atcttttttcc  23580 aaaactgcaa gataccccta tcctgccgtg ccaaccgcag ccgagcggac aagcagctgg   23640
ccttgcggca gggcgctgtc atacctgata tcgcctcgct caacgaagtg ccaaaaatct   23700
ttgagggtct tggacgcgac gagaagcgcg cggcaaacgc tctgcaacag gaaacagcg   23760 aaaatgaaag tcactctgga gtgttggtgg aactcgaggg tgacaacgcg cgcctagccg   23820
tactaaaacg cagcatcgag gtcacccact ttgcctaccc ggcacttaac ctaccccccca  23880 aggtcatgag cacagtcatg agtgagctga tcgtgcgccg tgcgcagccc ctggagaggg   23940
atgcaaattt gcaagaacaa acagaggagg cctacccgc agttggcgac gagcagctag    24000
cgcgctggct tcaaacgcgc gagcctgccg acttggagga gcgacgcaaa ctaatgatgg   24060
ccgcagtgct cgttaccgtg gagcttgagt gcatgcagcg gttctttgct gacccggaga   24120
tgcagcgcaa gctagaggaa acattgcact acaccttccg acagggctac gtacgccagg   24180
cctgcaagat ctccaacgtg gagctctgca acctggtctc ctaccttgga attttgcacg   24240
aaaaccgcct tgggcaaaac gtgcttcatt ccacgctcaa gggcgaggcg cgccgcgact   24300
acgtccgcga ctgcgtttac ttatttctat gctacacctg gcagacggcc atgggcgttt   24360
ggcagcagtg cttggaggag tgcaacctca aggagctgca gaaactgcta aagcaaaact   24420
tgaaggacct atggacggcc ttcaacgagc gctccgtggc cgcgcacctg gcggacatca   24480
ttttccccga acgcctgctt aaaacccctgc aacagggtct gccagacttc accagtcaaa   24540
gcatgttgca gaactttagg aactttatcc tagagcgctc aggaatcttg cccgccacct   24600
gctgtgcact tcctagcgac tttgtgccca ttaagtaccg cgaatgccct ccgccgcttt   24660
ggggccactg ctaccttctg cagctagcca actaccttgc ctaccactct gacataatgg   24720
aagacgtgag cggtgacggt ctactggagt gtcactgtcg ctgcaaccta tgcaccccgc   24780
accgctccct ggtttgcaat tcgcagctgc ttaacgaaag tcaaattatc ggtacctttg   24840
agctgcaggt tccctcgcct gacgaaaagt ccgcggctcc gggggttgaaa ctcactccgg   24900 ggctgtggac gtcggcttac cttcgcaaat ttgtacctga ggactaccac gcccacgaga   24960
ttaggttcta cgaagaccaa tcccgcccgc ctaatgcgga gcttaccgcc tgcgtcatta   25020
cccagggcca cattcttggc caattgcaag ccatcaacaa agcccgccaa gagtttctgc   25080
tacgaaaggg acgggggtt tacttggacc cccagtccgg cgaggagctc aacccaatcc    25140
ccccgccgcc gcagccctat cagcagcagc cgcgggccct tgcttcccag gatggcaccc   25200 aaaagaagc tgcagctgcc gccgccaccc acggacgagg aggaatactg ggacagtcag    25260
gcagaggagg ttttggacga ggaggaggag gacatgatgg aagactggga gagcctagac   25320
gaggaagctt ccgaggtcga gaggtgtca gacgaaacac cgtcaccctc ggtcgcattc     25380
ccctcgccgg cgcccagaa atcggcaacc ggttccagca tggctacaac ctccgctcct    25440
caggcgccgc cggcactgcc cgttcgccga cccaaccgta gatgggacac cactggaacc   25500
agggccggta agtccaagca gccgccgccg ttagcccaag agcaacaaca gcgcaaggc    25560 taccgctcat ggcgcgggca caagaacgcc atagttgctt gcttgcaaga ctgtgggggc   25620
aacatctcct tcgcccgccg ctttcttctc taccatcacg gcgtggcctt ccccgtaac    25680 atcctgcatt actaccgtca tctctacagc ccatactgca ccggcggcag cggcagcaac   25740
agcagcggcc acacagaagc aaaggcgacc ggatagcaag actctgacaa agcccaagaa   25800
```

```
atccacagcg gcggcagcag caggaggagg agcgctgcgt ctggcgccca acgaacccgt   25860
atcgacccgc gagcttagaa acaggatttt tcccactctg tatgctatat ttcaacagag   25920
caggggccaa gaacaagagc tgaaaataaa aaacaggtct ctgcgatccc tcacccgcag   25980
ctgcctgtat cacaaaagcg aagatcagct tcggcgcacg ctggaagacg cggaggctct   26040
cttcagtaaa tactgcgcgc tgactcttaa ggactagttt cgcgcccttt ctcaaattta   26100
agcgcgaaaa ctacgtcatc tccagcggcc acacccggcg ccagcacctg ttgtcagcgc   26160
cattatgagc aaggaaattc ccacgcccta catgtggagt taccagccac aaatgggact   26220
tgcggctgga gctgcccaag actactcaac ccgaataaac tacatgagcg cgggacccca   26280
catgatatcc cgggtcaacg gaatacgcgc ccaccgaaac cgaattctcc tggaacaggc   26340
ggctattacc accacacctc gtaataacct taatccccgt agttggcccg ctgcctggt   26400 gtaccaggaa agtcccgctc ccaccactgt ggtacttccc agagacgccc aggccgaagt   26460
tcagatgact aactcagggg cgcagcttgc gggcggcttt cgtcacaggg tgcggtcgcc   26520
cgggcagggt ataactcacc tgacaatcag agggcgaggt attcagctca acgacgagtc   26580
ggtgagctcc tcgcttggtc tccgtccgga cgggacattt cagatcggcg cgcgcggccg   26640
ctcttcattc acgcctcgtc aggcaatcct aactctgcag acctcgtcct ctgagccgcg   26700
ctctggaggc attggaactc tgcaatttat tgaggagttt gtgccatcgg tctactttaa   26760 cccccttctcg ggacctcccg gccactatcc ggatcaattt attcctaact ttgacgcggt   26820
aaaggactcg gcggacggct acgactgaat gttaagtgga gaggcagagc aactgcgcct   26880
gaaacacctg gtccactgtc gccgccacaa gtgctttgcc cgcgactccg gtgagttttg   26940
ctactttgaa ttgcccgagg atcatatcga gggcccggcg cacggcgtcc ggcttaccgc   27000
ccagggagag cttgcccgta gcctgattcg ggagtttacc cagcgccccc tgctagttga   27060
gcgggacagg ggaccctgtg ttctcactgt gatttgcaac tgtcctaacc ctggattaca   27120
tcaagatcct ctagttaatg tcaggtcgcc taagtcgatt aactagagta cccggggatc   27180
ttattccctt taactaataa aaaaaaataa taaagcatca cttacttaaa atcagttagc   27240
aaatttctgt ccagtttatt cagcagcacc tccttgccct cctcccagct ctggtattgc   27300
agcttcctcc tggctgcaaa ctttctccac aatctaaatg gaatgtcagt ttcctcctgt   27360
tcctgtccat ccgcacccac tatcttcatg ttgttgcaga tgaagcgcgc aagaccgtct   27420
gaagatacct tcaaccccgt gtatccatat gacacggaaa ccggtcctcc aactgtgcct   27480
tttcttactc ctcccttgt atcccccaat gggtttcaag agagtccccc tggggtactc   27540
tctttgcgcc tatccgaacc tctagttacc tccaatggca tgcttgcgct caaaatgggc   27600 aacgcctct ctctggacga ggccggcaac cttacctccc aaaatgtaac cactgtgagc   27660
ccacctctca aaaaaaccaa gtcaaacata aacctggaaa tatctgcacc cctcacagtt   27720
acctcagaag ccctaactgt ggctgccgcc gcacctctaa tggtcgcggg caacacactc   27780
accatgcaat cacaggcccc gctaaccgtg cacgactcca aacttagcat tgccacccaa   27840 ggaccctca cagtgtcaga aggaaagcta gccctgcaaa catcaggccc cctcaccacc   27900
accgatagca gtacccttac tatcactgcc tcaccccctc taactactgc cactggtagc   27960
ttgggcattg acttgaaaga gcccatttat acacaaaatg gaaaactagg actaaagtac   28020
ggggctcctt tgcatgtaac agacgaccta aacactttga ccgtagcaac tggtccaggt   28080
gtgactatta ataatacttc cttgcaaact aaagttactg gagccttggg ttttgattca   28140
```

```
caaggcaata tgcaacttaa tgtagcagga ggactaagga ttgattctca aaacagacgc   28200
cttatacttg atgttagtta tccgtttgat gctcaaaacc aactaaatct aagactagga   28260
cagggccctc tttttataaa ctcagcccac aacttggata ttaactacaa caaaggcctt   28320
tacttgttta cagcttcaaa caattccaaa aagcttgagg ttaacctaag cactgccaag   28380
gggttgatgt ttgacgctac agccatagcc attaatgcag gagatgggct tgaatttggt   28440
tcacctaatg caccaaacac aaatcccctc aaaacaaaaa ttggccatgg cctagaattt   28500
gattcaaaca aggctatggt tcctaaacta ggaactggcc ttagttttga cagcacaggt   28560
gccattacag taggaaacaa aaataatgat aagctaactt tgtggaccac accagctcca   28620
tctcctaact gtagactaaa tgcagagaaa gatgctaaac tcactttggt cttaacaaaa   28680
tgtggcagtc aaatacttgc tacagtttca gttttggctg ttaaaggcag tttggctcca   28740
atatctggaa cagttcaaag tgctcatctt attataagat ttgacgaaaa tggagtgcta   28800
ctaaacaatt ccttcctgga cccagaatat tggaacttta gaaatggaga tcttactgaa   28860
ggcacagcct atacaaacgc tgttggattt atgcctaacc tatcagctta tccaaaatct   28920
cacggtaaaa ctgccaaaag taacattgtc agtcaagttt acttaaacgg agacaaaact   28980
aaacctgtaa cactaaccat tacactaaac ggtacacagg aaacaggaga cacaactcca   29040
agtgcatact ctatgtcatt ttcatgggac tggtctggcc acaactacat taatgaaata   29100
tttgccacat cctcttacac ttttttcatac attgcccaag aataaagaat cgtttgtgtt   29160
atgtttcaac gtgtttattt ttcaattgca gaaaatttca agtcattttt cattcagtag   29220
tatagcccca ccaccacata gcttatacag atcaccgtac cttaatcaaa ctcacagaac   29280
cctagtattc aacctgccac ctccctccca acacacagag tacacagtcc tttctccccg   29340
gctggcctta aaaagcatca tatcatgggt aacagacata ttcttaggtg ttatattcca   29400
cacggtttcc tgtcgagcca aacgctcatc agtgatatta ataaactccc cgggcagctc   29460
acttaagttc atgtcgctgt ccagctgctg agccacaggc tgctgtccaa cttgcggttg   29520
cttaacgggc ggcgaaggag aagtccacgc ctacatgggg gtagagtcat aatcgtgcat   29580
caggataggg cggtggtgct gcagcagcgc gcgaataaac tgctgccgcc gccgctccgt   29640
cctgcaggaa tacaacatgg cagtggtctc ctcagcgatg attcgcaccg cccgcagcat   29700
aaggcgccct tgtcctccgg gcacagcagcg caccctgatc tcacttaaat cagcacagta   29760
actgcagcac agcaccacaa tattgttcaa aatcccacag tgcaaggcgc tgtatccaaa   29820
gctcatggcg gggaccacag aacccacgtg gccatcatac cacaagcgca ggtagattaa   29880
gtggcgaccc ctcataaaca cgctggacat aaacattacc tcttttggca tgttgtaatt   29940
caccacctcc cggtaccata taaacctctg attaaacatg gcgccatcca ccaccatcct   30000
aaaccagctg gccaaaacct gcccgccggc tatacactgc agggaaccgg gactggaaca   30060
atgacagtgg agagcccagg actcgtaacc atggatcatc atgctcgtca tgatatcaat   30120
gttggcacaa cacaggcaca cgtgcataca cttcctcagg attacaagct cctccgcgcgt   30180 tagaaccata tcccagggaa caacccattc ctgaatcagc gtaaatccca cactgcaggg   30240
aagacctcgc acgtaactca cgttgtgcat tgtcaaagtg ttacattcgg gcagcagcgg   30300
atgatcctcc agtatggtag cgcgggtttc tgtctcaaaa ggaggtagac gatccctact   30360
gtacggagtg cgccgagaca accgagatcg tgttggtcgt agtgtcatgc caaatggaac   30420
gccggacgta gtcatatttc ctgaagcaaa accaggtgcg ggcgtgacaa acagatctgc   30480
gtctccggtc tcgccgctta gatcgctctg tgtagtagtt gtagtatatc cactctctca   30540
```

```
aagcatccag gcgcccectg gcttcgggtt ctatgtaaac tccttcatgc gccgctgccc    30600
tgataacatc caccaccgca gaataagcca cacccagcca acctacacat tcgttctgcg    30660
agtcacacac gggaggagcg ggaagagctg gaagaaccat gttttttttt ttattccaaa    30720
agattatcca aaacctcaaa atgaagatct attaagtgaa cgcgctcccc tccggtggcg    30780
tggtcaaact ctacagccaa agaacagata atggcatttg taagatgttg cacaatggct    30840
tccaaaaggc aaacgccct cacgtccaag tggacgtaaa ggctaaaccc ttcagggtga    30900
atctcctcta taaacattcc agcaccttca accatgccca ataattctc atctcgccac     30960 cttctcaata tatctctaag caaatcccga atattaagtc cggccattgt aaaaatctgc    31020
tccagagcgc cctccacctt cagcctcaag cagcgaatca tgattgcaaa aattcaggtt    31080
cctcacagac ctgtataaga ttcaaaagcg aacattaac aaaaataccg cgatcccgta     31140
ggtcccttcg cagggccagc tgaacataat cgtgcaggtc tgcacggacc agcgcggcca    31200 cttcccegcc aggaaccatg acaaaagaac ccacactgat tatgacacgc atactcggag    31260
ctatgctaac cagcgtagcc ccgatgtaag cttgttgcat gggcggcgat ataaaatgca    31320
aggtgctgct caaaaaatca ggcaaagcct cgcgcaaaaa agaaagcaca tcgtagtcat    31380
gctcatgcag ataaaggcag gtaagctccg gaaccaccac agaaaaagac accattttc    31440 tctcaaacat gtctgcgggt ttctgcataa acacaaaata aaataacaaa aaacattta     31500 aacattagaa gcctgtctta caacaggaaa acaacccctt ataagcataa gacggactac    31560
ggccatgccg gcgtgaccgt aaaaaaactg gtcaccgtga ttaaaaagca ccaccgacag    31620
ctcctcggtc atgtccggag tcataatgta agactcggta aacacatcag gttgattcac    31680
atcggtcagt gctaaaaagc gaccgaaata gcccggggga atacataccc gcaggcgtag    31740
agacaacatt acagccccca taggaggtat aacaaaatta ataggagaga aaaacacata    31800
aacacctgaa aaaccctcct gcctaggcaa aatagcaccc tcccgctcca gaacaacata    31860
cagcgcttcc acagcggcag ccataacagt cagccttacc agtaaaaaag aaaacctatt    31920
aaaaaaacac cactcgacac ggcaccagct caatcagtca cagtgtaaaa aagggccaag    31980
tgcagagcga gtatatatag gactaaaaaa tgacgtaacg gttaaagtcc acaaaaaaca    32040
cccagaaaac cgcacgcgaa cctacgccca gaaacgaaag ccaaaaaacc cacaacttcc    32100
tcaaatcgtc acttccgttt tcccacgtta cgtcacttcc cattttaaga aaactacaat    32160
tcccaacaca tacaagttac tccgccctaa aacctacgtc acccgccccg ttcccacgcc    32220
ccgcgccacg tcacaaactc cacccctca ttatcatatt ggcttcaatc caaataagg     32280 tatattattg atgat                                                   32295
```

<210> SEQ ID NO 4
<211> LENGTH: 576
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
tagtaatcaa ttacgggtc attagttcat agcccatata tggagttccg cgttacataa      60
cttacggtaa atggcccgcc tggctgaccg cccaacgacc cccgcccatt gacgtcaata     120
atgacgtatg ttcccatagt aacgccaata gggactttcc attgacgtca atgggtggag    180
tatttacggt aaactgccca cttggcagta catcaagtgt atcatatgcc aagtacgccc    240
```

```
cctattgacg tcaatgacgg taaatggccc gcctggcatt atgcccagta catgacctta    300
tgggactttc ctacttggca gtacatctac gtattagtca tcgctattac catggtgatg    360
cggttttggc agtacatcaa tgggcgtgga tagcggtttg actcacgggg atttccaagt    420
ctccacccca ttgacgtcaa tgggagtttg ttttggcacc aaaatcaacg ggactttcca    480
aaatgtcgta acaactccgc cccattgacg caaatgggcg gtaggcgtgt acggtgggag    540
gtctatataa gcagagctgg tttagtgaac cgtcag                              576
```

```
<210> SEQ ID NO 5
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

```
atctagataa ctgatcataa tcagccatac cacatttgta gaggttttac ttgctttaaa     60
aaacctccca cacctccccc tgaacctgaa acataaaatg aatgcaattg ttgttgttaa    120
cttgtttatt gcagcttata atggttacaa ataaagcaat agcatcacaa atttcacaaa    180
taaagcattt ttttcactgc attctagttg tggtttgtcc aaactcatca atgtatctta    240
```

```
<210> SEQ ID NO 6
<211> LENGTH: 1992
<212> TYPE: DNA
<213> ORGANISM: Homo sapiens

<400> SEQUENCE: 6
```

```
atgagggcga acgacgctct gcaggtgctg ggcttgcttt tcagcctggc ccggggctcc     60
gaggtgggca actctcaggc agtgtgtcct gggactctga atggcctgag tgtgaccggc    120
gatgctgaga accaatacca gacactgtac aagctctacg agaggtgtga ggtggtgatg    180
gggaaccttg agattgtgct cacgggacac aatgccgacc tctccttcct gcagtggatt    240
cgagaagtga caggctatgt cctcgtggcc atgaatgaat tctctactct accattgccc    300
aacctccgcg tggtgcgagg gacccaggtc tacgatggga agtttgccat cttcgtcatg    360
ttgaactata acaccaactc cagccacgct ctgcgccagc tccgcttgac tcagctcacc    420
gagattctgt caggggtgt ttatattgag aagaacgata agctttgtca catggacaca    480
attgactggg ggacatcgt gagggaccga gatgctgaga tagtggtgaa ggacaatggc    540
agaagctgtc cccctgtca tgaggtttgc aaggggcgat gctggggtcc tggatcagaa    600
gactgccaga cattgaccaa gaccatctgt gctcctcagt gtaatggtca ctgctttggg    660
cccaacccca ccagtgctg ccatgatgag tgtgccgggg gctgctcagg ccctcaggac    720
acagactgct ttgcctgccg gcacttcaat gacagtggag cctgtgtacc tcgctgtcca    780
cagcctcttg tctacaacaa gctaactttc cagctggaac ccaatcccca caccaagtat    840
cagtatggag gagtttgtgt agccagctgt cccccataact tgtggtgga tcaaacatcc    900 tgtgtcaggg cctgtcctcc tgacaagatg gaagtagata aaaatgggct caagatgtgt    960
gagccttgtg ggggactatg tcccaaagcc tgtgagggaa caggctctgg gagccgcttc   1020
cagactgtgg actcgagcaa cattgatgga tttgtgaact gcaccaagat cctgggcaac   1080
ctggactttc tgatcaccgg cctcaatgga gaccctgc acaagatccc tgccctggac   1140
ccagagaagc tcaatgtctt ccggacagta cgggagatca caggttacct gaacatccag   1200
```

-continued

| | |
|---|---|
| tcctggccgc cccacatgca caacttcagt gttttttcca atttgacaac cattggaggc | 1260 |
| agaagcctct acaaccgggg cttctcattg ttgatcatga agaacttgaa tgtcacatct | 1320 |
| ctgggcttcc gatccctgaa ggaaattagt gctgggcgta tctatataag tgccaatagg | 1380 |
| cagtctgct accaccactc tttgaactgg accaaggtgc ttcggggggcc tacggaagag | 1440 |
| cgactagaca tcaagcataa tcggccgcgc agagactgcg tggcagaggg caaagtgtgt | 1500 |
| gacccactgt gctcctctgg gggatgctgg ggcccaggcc ctggtcagtg cttgtcctgt | 1560 |
| cgaaattata gccgaggagg tgtctgtgtg acccactgca actttctgaa tggggagcct | 1620 |
| cgagaatttg cccatgaggc cgaatgcttc tcctgccacc cggaatgcca acccatggag | 1680 |
| ggcactgcca catgcaatgg ctcgggctct gatacttgtg ctcaatgtgc ccattttcga | 1740 |
| gatgggcccc actgtgtgag cagctgcccc catggagtcc taggtgccaa gggcccaatc | 1800 |
| tacaagtacc cagatgttca gaatgaatgt cggccctgcc atgagaactg cacccagggg | 1860 |
| tgtaaaggac cagagcttca agactgttta ggacaaacac tggtgctgat cggcaaaacc | 1920 |
| catctgacaa tggctttgac agtgatagca ggattggtag tgattttcat gatgctgggc | 1980 |
| ggcactttt aa | 1992 |

<210> SEQ ID NO 7
<211> LENGTH: 2109
<212> TYPE: DNA
<213> ORGANISM: Homo sapiens

<400> SEQUENCE: 7

| | |
|---|---|
| atggagtctc cctcggcccc tccccacaga tggtgcatcc cctggcagag gctcctgctc | 60 |
| acagcctcac ttctaacctt ctggaacccg cccaccactg ccaagctcac tattgaatcc | 120 |
| acgccgttca atgtcgcaga ggggaaggag gtgcttctac ttgtccacaa tctgccccag | 180 |
| catcttttg gctacagctg gtacaaaggt gaaagagtgg atggcaaccg tcaaattata | 240 |
| ggatatgtaa taggaactca acaagctacc ccagggcccg catacagtgg tcgagagata | 300 |
| atataccca atgcatccct gctgatccag aacatcatcc agaatgacac aggattctac | 360 |
| accctacacg tcataaagtc agatcttgtg aatgaagaag caactggcca gttccgggta | 420 |
| tacccggagc tgcccaagcc ctccatctcc agcaacaact ccaaacccgt ggaggacaag | 480 |
| gatgctgtgg ccttcacctg tgaacctgag actcaggacg caacctacct gtggtgggta | 540 |
| aacaatcaga gcctcccggt cagtcccagg ctgcagctgt ccaatggcaa caggaccctc | 600 |
| actctattca atgtcacaag aaatgacaca gcaagctaca atgtgaaaac ccagaaccca | 660 |
| gtgagtgcca ggcgcagtga ttcagtcatc ctgaatgtcc tctatggccc ggatgccccc | 720 |
| accattccc ctctaaacac atcttacaga tcagggaaa atctgaacct ctcctgccac | 780 |
| gcagcctcta acccacctgc acagtactct tggtttgtca atgggacttt ccagcaatcc | 840 |
| acccaagagc tctttatccc caacatcact gtgaataata gtggatccta tacgtgccaa | 900 |
| gcccataact cagacactgg cctcaatagg accacagtca cgacgatcac agtctatgca | 960 |
| gagccaccca aaccttcat caccagcaac aactccaacc ccgtggagga tgaggatgct | 1020 |
| gtagccttaa cctgtgaacc tgagattcag aacacaacct acctgtggtg ggtaaataat | 1080 |
| cagagcctcc cggtcagtcc caggctgcag ctgtccaatg acaacaggac cctcactcta | 1140 |
| ctcagtgtca aaggaatga tgtaggaccc tatgagtgtg gaatccagaa cgaattaagt | 1200 |
| gttgaccaca gcgacccagt catcctgaat gtcctctatg gcccagacga ccccaccatt | 1260 |

```
tcccctcat acacctatta ccgtccaggg gtgaacctca gcctctcctg ccatgcagcc    1320
tctaacccac ctgcacagta ttcttggctg attgatggga acatccagca acacacacaa    1380
gagctcttta tctccaacat cactgagaag aacagcggac tctatacctg ccaggccaat    1440
aactcagcca gtggccacag caggactaca gtcaagacaa tcacagtctc tgcggagctg    1500
cccaagccct ccatctccag caacaactcc aaaccgtgg aggacaagga tgctgtggcc    1560
ttcacctgtg aacctgaggc tcagaacaca acctacctgt ggtgggtaaa tggtcagagc    1620
ctcccagtca gtcccaggct gcagctgtcc aatggcaaca ggaccctcac tctattcaat    1680
gtcacaagaa atgacgcaag agcctatgta tgtggaatcc agaactcagt gagtgcaaac    1740
cgcagtgacc cagtcaccct ggatgtcctc tatgggccgg acaccccat catttccccc    1800 ccagactcgt cttacctttc gggagcggac ctcaacctct cctgccactc ggcctctaac    1860
ccatccccgc agtattcttg gcgtatcaat gggataccgc agcaacacac acaagttctc    1920
tttatcgcca aaatcacgcc aataataac gggacctatg cctgttttgt ctctaacttg    1980
gctactggcc gcaataattc catagtcaag agcatcacac tctctgcatc tggaacttct    2040
cctggtctct cagctggggc cactgtcggc atcatgattg gagtgctggt tggggttgct    2100
ctgatatag                                                            2109
```

<210> SEQ ID NO 8
<211> LENGTH: 9
<212> TYPE: PRT
<213> ORGANISM: Homo sapiens

<400> SEQUENCE: 8

Tyr Leu Ser Gly Ala Asn Leu Asn Leu
1               5

<210> SEQ ID NO 9
<211> LENGTH: 9
<212> TYPE: PRT
<213> ORGANISM: Homo sapiens

<400> SEQUENCE: 9

Tyr Leu Ser Gly Ala Asp Leu Asn Leu
1               5

<210> SEQ ID NO 10
<211> LENGTH: 32315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg     180 gtgtgcgccg gtgtacacag gaagtgacaa ttttcgcgcg gttttaggcg gatgttgtag     240
taaatttggg cgtaaccgag taagatttgg ccattttcgc gggaaaactg aataaggaga     300
agtgaaatct gaataatttt gtgttactca tagcgcgtaa tactgtaata gtaatcaatt     360
acggggtcat tagttcatag cccatatatg gagttccgcg ttacataact tacgtaaat     420 ggcccgcctg gctgaccgcc caacgacccc cgcccattga cgtcaataat gacgtatgtt     480
```

```
cccatagtaa cgccaatagg gactttccat tgacgtcaat gggtggagta tttacggtaa    540
actgcccact tggcagtaca tcaagtgtat catatgccaa gtacgccccc tattgacgtc    600
aatgacggta aatggcccgc ctggcattat gcccagtaca tgaccttatg ggactttcct    660
acttggcagt acatctacgt attagtcatc gctattacca tggtgatgcg gttttggcag    720
tacatcaatg ggcgtggata gcggtttgac tcacggggat ttccaagtct ccaccccatt    780
gacgtcaatg ggagtttgtt ttggcaccaa aatcaacggg actttccaaa atgtcgtaac    840
aactccgccc cattgacgca aatgggcggt aggcgtgtac ggtgggaggt ctatataagc    900
agagctggtt tagtgaaccg tcagatccgc tagagatctg gtaccgtcga cgcggccgct    960
cgagcctaag cttggtaccg agctcggatc cactagtaac ggccgccagt gtgctggaat   1020
tcggcttaaa ggtacccaga gcagacagcc gccaccatgg agtctccctc ggcccctccc   1080
cacagatggt gcatcccctg gcagaggctc ctgctcacag cctcacttct aaccttctgg   1140
aacccgccca ccactgccaa gctcactatt gaatccacgc cgttcaatgt cgcagagggg   1200
aaggaggtgc ttctacttgt ccacaatctg ccccagcatc tttttggcta cagctggtac   1260
aaaggtgaaa gagtggatgg caaccgtcaa attataggat atgtaatagg aactcaacaa   1320
gctaccccag ggcccgcata cagtggtcga gagataatat accccaatgc atccctgctg   1380
atccagaaca tcatccagaa tgacacagga ttctacaccc tacacgtcat aaagtcagat   1440
cttgtgaatg aagaagcaac tggccagttc cgggtatacc cggagctgcc caagccctcc   1500
atctccagca caactccaa acccgtggag acaaggatg ctgtggcctt cacctgtgaa    1560
cctgagactc aggacgcaac ctacctgtgg tgggtaaaca atcagagcct cccggtcagt   1620
cccaggctgc agctgtccaa tggcaacagg accctcactc tattcaatgt cacaagaaat   1680
gacacagcaa gctacaaatg tgaaacccag aacccagtga gtgccaggcg cagtgattca   1740
gtcatcctga atgtcctcta tggcccggat gcccccacca tttcccctct aaacacatct   1800
tacagatcag gggaaaatct gaacctctcc tgccacgcag cctctaaccc acctgcacag   1860
tactcttggt ttgtcaatgg gactttccag caatccaccc aagagctctt tatccccaac   1920
atcactgtga ataatagtgg atcctatacg tgccaagccc ataactcaga cactggcctc   1980
aataggacca cagtcacgac gatcacagtc tatgcagagc cacccaaacc cttcatcacc   2040
agcaacaact ccaaccccgt ggaggatgag gatgctgtag ccttaacctg tgaacctgag   2100
attcagaaca caacctacct gtggtgggta aataatcaga gcctcccggt cagtcccagg   2160
ctgcagctgt ccaatgacaa caggaccctc actctactca gtgtcacaag gaatgatgta   2220
ggaccctatg agtgtggaat ccagaacgaa ttaagtgttg accacagcga cccagtcatc   2280
ctgaatgtcc tctatggccc agacgacccc accatttccc cctcatacac ctattaccgt   2340
ccaggggtga acctcagcct ctcctgccat gcagcctcta cccacctgc acagtattct   2400
tggctgattg atgggaacat ccagcaacac acacaagagc tctttatctc caacatcact   2460
gagaagaaca gcggactcta cctgccagg gccaataact cagccagtgg ccacagcagg   2520
actacagtca agacaatcac agtctctgcg gagctgccca gccctccat ctccagcaac    2580
aactccaaac ccgtgaggga caaggatgct gtggccttca cctgtgaacc tgaggctcag   2640
aacacaacct acctgtggtg ggtaaatggt cagagcctcc cagtcagtcc caggctgcag   2700
ctgtccaatg gcaacaggac cctcactcta ttcaatgtca caagaaatga cgcaagagcc   2760
tatgtatgtg gaatccagaa ctcagtgagt gcaaaccgca gtgacccagt cacccctgga   2820
gtcctctatg ggccggacac ccccatcatt tccccccag actcgtctta cctttcggga   2880
```

```
gcggacctca acctctcctg ccactcggcc tctaacccat ccccgcagta ttcttggcgt    2940
atcaatggga taccgcagca acacacacaa gttctctttta tcgccaaaat cacgccaaat    3000
aataacggga cctatgcctg ttttgtctct aacttggcta ctggccgcaa taattccata    3060
gtcaagagca tcacagtctc tgcatctgga acttctcctg gtctctcagc tggggccact    3120
gtcggcatca tgattggagt gctggttggg gttgctctga tatagcagcc ctggtgtagt    3180
ttcttcattt caggaagact gacagttgtt ttgcttcttc cttaaagcat ttgcaacagc    3240
tacagtctaa aattgcttct ttaccaagga tatttacaga aaagactctg accagagatc    3300
gagaccatcc tctagataag atatccgatc caccggatct agataactga tcataatcag    3360
ccataccaca tttgtagagg ttttacttgc tttaaaaaac ctcccacacc tcccctgaa     3420 cctgaaacat aaaatgaatg caattgttgt tgttaacttg tttattgcag cttataatgg    3480
ttacaaataa agcaatagca tcacaaattt cacaaataaa gcatttttt cactgcattc     3540 tagttgtggt ttgtccaaac tcatcaatgt atcttaacgc ggatctgggc gtggttaagg    3600
gtgggaaaga atatataagg tgggggtctt atgtagtttt gtatctgttt tgcagcagcc    3660
gccgccgcca tgagcaccaa ctcgtttgat ggaagcattg tgagctcata tttgacaacg    3720
cgcatgcccc catgggccgg ggtgcgtcag aatgtgatgg gctccagcat tgatggtcgc    3780
cccgtcctgc ccgcaaactc tactaccttg acctacgaga ccgtgtctgg aacgccgttg    3840
gagactgcag cctccgccgc cgcttcagcc gctgcagcca ccgcccgcgg gattgtgact    3900
gactttgctt tcctgagccc gcttgcaagc agtgcagctt cccgttcatc cgcccgcgat    3960
gacaagttga cggctctttt ggcacaattg gattctttga cccgggaact taatgtcgtt    4020
tctcagcagc tgttggatct cgccagcag gtttctgccc tgaaggcttc ctccctccc     4080 aatgcggttt aaaacataaa taaaaaacca gactctgttt ggatttggat caagcaagtg    4140
tcttgctgtc tttatttagg ggttttgcgc gcgcggtagg cccgggacca gcggtctcgg    4200
tcgttgaggg tcctgtgtat ttttttccagg acgtggtaaa ggtgactctg gatgttcaga    4260
tacatgggca taagcccgtc tctggggtgg aggtagcacc actgcagagc ttcatgctgc    4320
ggggtggtgt tgtagatgat ccagtcgtag caggagcgct gggcgtggtg cctaaaaatg    4380
tctttcagta gcaagctgat tgccaggggc aggcccttgg tgtaagtgtt tacaaagcgg    4440
ttaagctggg atgggtgcat acgtggggat atgagatgca tcttggactg tattttttagg    4500 ttggctatgt tcccagccat atccctccgg ggattcatgt tgtgcagaac caccagcaca    4560
gtgtatccgg tgcacttggg aaatttgtca tgtagcttag aaggaaatgc gtggaagaac    4620
ttggagacgc ccttgtgacc tccaagattt ccatgcatt cgtccataat gatggcaatg     4680
ggcccacggg cggcggcctg ggcgaagata tttctgggat cactaacgtc atagttgtgt    4740
tccaggatga gatcgtcata ggccattttt acaaagcgcg ggcggagggt gccagactgc    4800
ggtataatgg ttccatccgg cccaggggcg tagttaccct cacagatttg catttcccac    4860
gctttgagtt cagatggggg gatcatgtct acctgcgggg cgatgaagaa aacggtttcc    4920
ggggtagggg agatcagctg gaagaaaagc aggttcctga gcagctgcga cttaccgcag    4980
ccggtgggcc cgtaaatcac acctattacc ggctgcaact ggtagttaag agagctgcag    5040
ctgccgtcat ccctgagcag gggggccact tcgttaagca tgtccctgac tcgcatgttt    5100
tccctgacca aatccgccag aaggcgctcg ccgcccagcg atagcagttc ttgcaaggaa    5160
gcaaagtttt tcaacggttt gagaccgtcc gccgtaggca tgcttttgag cgtttgacca    5220
```

```
agcagttcca ggcggtccca cagctcggtc acctgctcta cggcatctcg atccagcata    5280
tctcctcgtt tcgcgggttg gggcggcttt cgctgtacgg cagtagtcgg tgctcgtcca    5340
gacgggccag ggtcatgtct ttccacgggc gcagggtcct cgtcagcgta gtctgggtca    5400
cggtgaaggg gtgcgctccg ggctgcgcgc tggccagggt gcgcttgagg ctggtcctgc    5460
tggtgctgaa gcgctgccgg tcttcgccct gcgcgtcggc caggtagcat ttgaccatgg    5520
tgtcatagtc cagcccctcc gcggcgtggc ccttggcgcg cagcttgccc ttggaggagg    5580
cgccgcacga ggggcagtgc agactttga  gggcgtagag cttgggcgcg agaaataccg    5640
attccgggga gtaggcatcc gcgccgcagg ccccgcagac ggtctcgcat tccacgagcc    5700
aggtgagctc tggccgttcg gggtcaaaaa ccaggtttcc cccatgcttt ttgatgcgtt    5760
tcttacctct ggtttccatg agccggtgtc cacgctcggt gacgaaaagg ctgtccgtgt    5820
ccccgtatac agacttgaga ggcctgtcct cgagcggtgt tccgcggtcc tcctcgtata    5880
gaaactcgga ccactctgag acaaaggctc gcgtccaggc cagcacgaag gaggctaagt    5940
gggaggggta gcggtcgttg tccactaggg ggtccactcg ctccagggtg tgaagacaca    6000
tgtcgccctc ttcggcatca aggaaggtga ttggtttgta ggtgtaggcc acgtgaccgg    6060
gtgttcctga aggggggcta taaaggggg  tgggggcgcg ttcgtcctca ctctcttccg    6120
catcgctgtc tgcgagggcc agctgttggg gtgagtactc cctctgaaaa gcgggcatga    6180
cttctgcgct aagattgtca gtttccaaaa acgaggagga tttgatattc acctggcccg    6240
cggtgatgcc tttgagggtg gccgcatcca tctggtcaga aaagacaatc ttttgttgt     6300 caagcttggt ggcaaacgac ccgtagaggg cgttggacag caacttggcg atggagcgca    6360
gggtttggtt tttgtcgcga tcggcgcgct ccttggccgc gatgtttagc tgcacgtatt    6420
cgcgcgcaac gcaccgccat tcgggaaaga cggtggtgcg ctcgtcgggc accaggtgca    6480
cgcgccaacc gcggttgtgc agggtgacaa ggtcaacgct ggtggctacc tctccgcgta    6540
ggcgctcgtt ggtccagcag aggcggccgc ccttgcgcga gcagaatggc ggtaggggt     6600 ctagctgcgt ctcgtccggg gggtctgcgt ccacggtaaa gaccccgggc agcaggcgcg    6660
cgtcgaagta gtctatcttg catccttgca agtctagcgc ctgctgccat gcgcgggcgg    6720
caagcgcgcg ctcgtatggg ttgagtgggg gaccccatgg catgggtgg  gtgagcgcgg    6780 aggcgtacat gccgcaaatg tcgtaaacgt agagggctc  tctgagtatt ccaagatatg    6840
tagggtagca tcttccaccg cggatgctgg cgcgcacgta atcgtatagt tcgtgcgagg    6900
gagcgaggag gtcgggaccg aggttgctac gggcgggctg ctctgctcgg aagactatct    6960
gcctgaagat ggcatgtgag ttggatgata tggttggacg ctggaagacg ttgaagctgg    7020
cgtctgtgag acctaccgcg tcacgcacga aggaggcgta ggagtcgcgc agcttgttga    7080
ccagctcggc ggtgacctgc acgtctaggg cgcagtagtc cagggtttcc ttgatgatgt    7140
catacttatc ctgtcccttt ttttttccaca gctcgcggtt gaggacaaac tcttcgcggt    7200
ctttccagta ctcttggatc ggaaacccgt cggcctccga acggtaagag cctagcatgt    7260
agaactggtt gacggcctgg taggcgcagc atccttttc  tacgggtagc gcgtatgcct    7320
gcgcggcctt ccggcatgac cagcatgaag ggcacgagct gcttcccaaa ggcccccatc    7380
caagtatagg tctctacatc gtaggtgaca aagagacgct cggtgcgagg atgcgagccg    7440
atcgggaaga actggatctc ccgccaccaa ttggaggagt ggctattgat gtggtgaaag    7500
tagaagtccc tgcgacgggc cgaacactcg tgctggcttt tgtaaaaacg tgcgcagtac    7560
tggcagcggt gcacgggctg tacatcctgc acgaggttga cctgacgacc gcgcacaagg    7620
```

```
aagcagagtg ggaatttgag cccctcgcct ggcgggtttg gctggtggtc ttctacttcg   7680
gctgcttgtc cttgaccgtc tggctgctcg aggggagtta cggtggatcg gaccaccacg   7740
ccgcgcgagc ccaaagtcca gatgtccgcg cgcggcggtc ggagcttgat gacaacatcg   7800
cgcagatggg agctgtccat ggtctggagc tcccgcggcg tcaggtcagg cgggagctcc   7860
tgcaggttta cctcgcatag acgggtcagg gcgcgggcta gatccaggtg atacctaatt   7920
tccaggggct ggttggtggc ggcgtcgatg gcttgcaaga ggccgcatcc ccgcggcgcg   7980
actacggtac cgcgcggcgg gcggtgggcc gcggggtgt ccttggatga tgcatctaaa   8040
agcggtgacg cgggcgagcc cccggaggta gggggggctc cggacccgcc gggagagggg   8100
gcaggggcac gtcggcgccg cgcgcgggca ggagctggtg ctgcgcgcgt aggttgctgg   8160
cgaacgcgac gacgcggcgg ttgatctcct gaatctggcg cctctgcgtg aagacgacgg   8220
gcccggtgag cttgaacctg aaagagagtt cgacagaatc aatttcggtg tcgttgacgg   8280
cggcctggcg caaaatctcc tgcacgtctc ctgagttgtc ttgataggcg atctcggcca   8340
tgaactgctc gatctcttcc tcctggagat ctccgcgtcc ggctcgctcc acggtggcgg   8400
cgaggtcgtt ggaaatgcgg gccatgagct gcgagaaggc gttgaggcct ccctcgttcc   8460
agacgcggct gtagaccacg ccccttcgg catcgcgggc gcgcatgacc acctgcgcga   8520
gattgagctc cacgtgccgg gcgaagacgg cgtagtttcg caggcgctga agaggtagt   8580 tgagggtggt ggcggtgtgt tctgccacga agaagtacat aacccagcgt cgcaacgtgg   8640
attcgttgat aattgttgtg taggtactcc gccgccgagg gacctgagcg agtccgcatc   8700
gaccggatcg gaaaacctct cgagaaaggc gtctaaccag tcacagtcgc aaggtaggct   8760
gagcaccgtg gcgggcggca gcgggcgcg gtcgggtttg tttctggcgg aggtgctgct   8820
gatgatgtaa ttaaagtagg cggtcttgag acggcggatg gtcgacagaa gcaccatgtc   8880
cttgggtccg gcctgctgaa tgcgcaggcg gtcggccatg ccccaggctt cgttttgaca   8940
tcggcgcagg tctttgtagt agtcttgcat gagccttct accggcactt cttcttctcc   9000
ttcctcttgt cctgcatctc ttgcatctat cgctgcggcg gcggcggagt ttggccgtag   9060
gtggcgccct cttcctccca tgcgtgtgac cccgaagccc ctcatcggct gaagcagggc   9120
taggtcggcg acaacgcgct cggctaatat ggcctgctgc acctgcgtga gggtagactg   9180
gaagtcatcc atgtccacaa agcggtggta tgcgcccgtg ttgatggtgt aagtgcagtt   9240
ggccataacg gaccagttaa cggtctggtg acccggctgc gagagctcgg tgtacctgag   9300
acgcgagtaa gccctcgagt caaatacgta gtcgttgcaa gtccgcacca ggtactggta   9360
tcccaccaaa aagtgcggcg gcggctggcg gtagaggggc cagcgtaggg tggccggggc   9420
tccgggggcg agatcttcca acataaggcg atgatatccg tagatgtacc tggacatcca   9480
ggtgatgccg gcggcggtgg tggaggcgcg cggaaagtcg cggacgcggt tccagatgtt   9540
gcgcagcggc aaaaagtgct ccatggtcgg gacgctctgg ccgtcaggc gcgcaatc   9600 gttgacgctc tagcgtgcaa aaggagagcc tgtaagcggg cactcttccg tggtctggtg   9660
gataaattcg caagggtatc atggcggacg accggggttc gagcccgta tccgccgtc   9720 cgccgtgatc catgcggtta ccgccgcgt gtcgaaccca ggtgtgcgac gtcagacaac   9780 ggggggagtgc tccttttggc ttccttccag gcgcggcggc tgctgcgcta gcttttttgg   9840 ccactgccg cgcgcagcgt aagcggttag gctggaaagc gaaagcatta agtgctcgc   9900 tccctgtagc cggagggtta ttttccaagg gttgagtcgc gggaccccg gttcgagtct   9960
```

```
cggaccggcc ggactgcggc gaacgggggt ttgcctcccc gtcatgcaag accccgcttg   10020
caaattcctc cggaaacagg gacgagcccc tttttgctt tcccagatg catccggtgc   10080 tgcggcagat gcgccccct cctcagcagc ggcaagagca agagcagcgg cagacatgca   10140
gggcaccctc ccctcctcct accgcgtcag gaggggcgac atccgcggtt gacgcggcag   10200
cagatggtga ttacgaaccc ccgcggcgcc gggcccggca ctacctggac ttggaggagg   10260
gcgagggcct ggcgcggcta ggagcgccct ctcctgagcg gcacccaagg gtgcagctga   10320
agcgtgatac gcgtgaggcg tacgtgccgc ggcagaacct gtttcgcgac cgcgagggag   10380
aggagcccga ggagatgcgg gatcgaaagt tccacgcagg gcgcgagctg cggcatggcc   10440
tgaatcgcga gcggttgctg cgcgaggagg actttgagcc cgacgcgcga accgggatta   10500
gtcccgcgcg cgcacacgtg gcggccgccg acctggtaac cgcatacgag cagacggtga   10560
accaggagat taactttcaa aaaagcttta caaccacgt gcgtacgctt gtggcgcgcg   10620
aggaggtggc tataggactg atgcatctgt gggactttgt aagcgcgctg gagcaaaacc   10680
caaatagcaa gccgctcatg gcgcagctgt tccttatagt gcagcacagc agggacaacg   10740
aggcattcag ggatgcgctg ctaaacatag tagagcccga gggccgctgg ctgctcgatt   10800
tgataaacat cctgcagagc atagtggtgc aggagcgcag cttgagcctg gctgacaagg   10860
tggccgccat caactattcc atgcttagcc tgggcaagtt ttacgcccgc aagatatacc   10920 ataccccctta cgttcccata gacaaggagg taaagatcga ggggttctac atgcgcatgg   10980
cgctgaaggt gcttaccttg agcgacgacc tgggcgttta tcgcaacgag cgcatccaca   11040
aggccgtgag cgtgagccgg cggcgcgagc tcagcgaccg cgagctgatg cacagcctgc   11100
aaagggccct ggctggcacg ggcagcggcg atagagaggc cgagtcctac tttgacgcgg   11160
gcgctgacct gcgctgggcc ccaagccgac gcgccctgga ggcagctggg gccggacctg   11220
ggctggcggt ggcacccgcg cgcgctggca acgtcggcgg cgtggaggaa tatgacgagg   11280
acgatgagta cgagccagag gacggcgagt actaagcggt gatgtttctg atcagatgat   11340
gcaagacgca acggacccgg cggtgcgggc ggcgctgcag agccagccgt ccggccttaa   11400
ctccacggac gactggcgcc aggtcatgga ccgcatcatg tcgctgactg cgcgcaatcc   11460
tgacgcgttc cggcagcagc cgcaggccaa ccggctctcc gcaattctgg aagcggtggt   11520
cccggcgcgc gcaaaccccca cgcacgagaa ggtgctggcg atcgtaaacg cgctggccga   11580
aaacagggcc atccggcccg acgaggccgg cctggtctac gacgcgctgc ttcagcgcgt   11640
ggctcgttac aacagcggca acgtgcagac caacctggac cggctggtgg gggatgtgcg   11700
cgaggccgtg gcgcagcgtg agcgcgcgca gcagcagggc aacctgggct ccatggttgc   11760
actaaacgcc ttcctgagta cacagcccgc caacgtgccg cggggacagg aggactacac   11820
caactttgtg agcgcactgc ggctaatggt gactgagaca ccgcaaagtg aggtgtacca   11880
gtctgggcca gactattttt tccagaccag tagacaaggc ctgcagaccg taaacctgag   11940
ccaggctttc aaaaacttgc aggggctgtg ggggtgcgg gctcccacag gcgaccgcgc   12000
gaccgtgtct agcttgctga cgcccaactc gcgcctgttg ctgctgctaa tagcgcccttt   12060 cacgacagt ggcagcgtgt cccgggacac atacctaggt cacttgctga cactgtaccg   12120
cgaggccata ggtcaggcgc atgtggacga gcatactttc caggagatta caagtgtcag   12180
ccgcgcgctg gggcaggagg acacgggcag cctggaggca accctaaact acctgctgac   12240 caaccggcg cagaagatcc cctcgttgca cagtttaaac agcgaggagg agcgcatttt   12300
gcgctacgtg cagcagagcg tgagccttaa cctgatgcgc gacggggtaa cgcccagcgt   12360
```

```
ggcgctggac atgaccgcgc gcaacatgga accgggcatg tatgcctcaa accggccgtt    12420
tatcaaccgc ctaatggact acttgcatcg cgcggccgcc gtgaacccg  agtatttcac    12480 caatgccatc ttgaacccgc actggctacc gcccctggt  ttctacaccg ggggattcga    12540
ggtgcccgag ggtaacgatg gattcctctg gacgacata  gacgacagcg tgttttcccc    12600
gcaaccgcag accctgctag agttgcaaca gcgcgagcag gcagaggcgg cgctgcgaaa    12660
ggaaagcttc cgcaggccaa gcagcttgtc cgatctaggc gctgcggccc gcggtcaga    12720 tgctagtagc ccatttccaa gcttgatagg gtctcttacc agcactcgca ccacccgccc    12780
gcgcctgctg ggcgaggagg agtacctaaa caactcgctg ctgcagccgc agcgcgaaaa    12840
aaacctgcct ccggcatttc ccaacaacgg gatagagagc ctagtggaca agatgagtag    12900
atggaagacg tacgcgcagg agcacaggga cgtgccaggc ccgcgcccgc ccacccgtcg    12960
tcaaaggcac gaccgtcagc ggggtctggt gtgggaggac gatgactcgg cagacgacag    13020
cagcgtcctg gatttgggag ggagtggcaa cccgtttgcg caccttcgcc ccaggctggg    13080
gagaatgttt taaaaaaaaa aaagcatgat gcaaaataaa aaactcacca aggccatggc    13140
accgagcgtt ggttttcttg tattcccctt agtatgcggc gcgcggcgat gtatgaggaa    13200
ggtcctcctc cctcctacga gagtgtggtg agcgcggcgc cagtggcggc ggcgctgggt    13260
tctcccttcg atgctcccct ggacccgccg tttgtgcctc cgcggtacct gcggcctacc    13320 gggggggagaa acagcatccg ttactctgag ttggcacccc tattcgacac cacccgtgtg    13380
tacctggtgg acaacaagtc aacggatgtg gcatccctga actaccagaa cgaccacagc    13440
aactttctga ccacggtcat tcaaaacaat gactacagcc cggggaggc  aagcacacag    13500 accatcaatc ttgacgaccg gtcgcactgg ggcggcgacc tgaaaaccat cctgcatacc    13560
aacatgccaa atgtgaacga gttcatgttt accaataagt ttaaggcgcg ggtgatggtg    13620
tcgcgcttgc ctactaagga caatcaggtg gagctgaaat acgagtgggt ggagttcacg    13680
ctgcccgagg gcaactactc cgagaccatg accatagacc ttatgaacaa cgcgatcgtg    13740
gagcactact tgaaagtggg cagacagaac ggggttctgg aaagcgacat cggggtaaag    13800
tttgacaccc gcaacttcag actggggttt gaccccgtca ctggtcttgt catgcctggg    13860
gtatatacaa acgaagcctt ccatccagac atcattttgc tgccaggatg cggggtggac    13920
ttcacccaca gccgcctgag caacttgttg ggcatccgca agcggcaacc cttccaggag    13980
ggctttagga tcacctacga tgatctggag ggtggtaaca ttcccgcact gttggatgtg    14040
gacgcctacc aggcgagctt gaaagatgac accgaacagg gcggggtgg  cgcaggcggc    14100 agcaacagca gtggcagcgg cgcggaagag aactccaacg cggcagccgc ggcaatgcag    14160
ccggtggagg acatgaacga tcatgccatt cgcggcgaca cctttgccac acgggctgag    14220
gagaagcgcg ctgaggccga agcagcggcc gaagctgccg cccccgctgc gcaacccgag    14280
gtcgagaagc ctcagaagaa accggtgatc aaacccctga cagaggacag caagaaacgc    14340
agttacaacc taataagcaa tgacagcacc ttcacccagt accgcagctg gtaccttgca    14400
tacaactacg cgcaccctca gaccggaatc cgctcatgga cccctgcttt  cactcctgac    14460
gtaacctgcg gctcggagca ggtctactgg tcgttgccag acatgatgca agaccccgtg    14520
accttccgct ccacgcgcca gatcagcaac tttccggtgg tgggcgccga gctgttgccc    14580
gtgcactcca agagcttcta caacgaccag gccgtctact cccaactcat ccgccagttt    14640
acctctctga cccacgtgtt caatcgcttt cccgagaacc agatttttgg cgcgcccgcca    14700
```

```
gcccccacca tcaccaccgt cagtgaaaac gttcctgctc tcacagatca cgggacgcta   14760
ccgctgcgca acagcatcgg aggagtccag cgagtgacca ttactgacgc cagacgccgc   14820
acctgcccct acgtttacaa ggccctgggc atagtctcgc cgcgcgtcct atcgagccgc   14880 acttttgag caagcatgtc catccttata tcgcccagca ataacacagg ctggggcctg    14940
cgcttcccaa gcaagatgtt tggcggggcc aagaagcgct ccgaccaaca cccagtgcgc   15000
gtgcgcgggc actaccgcgc gccctggggc gcgcacaaac gcggccgcac tgggcgcacc   15060
accgtcgatg acgccatcga cgcggtggtg gaggaggcgc gcaactacac gcccacgccg   15120
ccaccagtgt ccacagtgga cgcggccatt cagaccgtgg tgcgcggagc ccggcgctat   15180
gctaaaatga agagacggcg gaggcgcgta gcacgtcgcc accgccgccg acccggcact   15240
gccgcccaac gcgcggcggc ggccctgctt aaccgcgcac gtcgcaccgg ccgacgggcg   15300
gccatgcggg ccgctcgaag gctggccgcg ggtattgtca ctgtgccccc caggtccagg   15360
cgacgagcgg ccgccgcagc agccgcggcc attagtgcta tgactcaggg tcgcaggggc   15420
aacgtgtatt gggtgcgcga ctcggttagc ggcctgcgcg tgcccgtgcg cacccgcccc   15480
ccgcgcaact agattgcaag aaaaaactac ttagactcgt actgttgtat gtatccagcg   15540
gcggcggcgc gcaacgaagc tatgtccaag cgcaaaatca agaagagat gctccaggtc    15600 atcgcgccgg agatctatgg ccccccgaag aaggaagagc aggattacaa gccccgaaag   15660
ctaaagcggg tcaaaagaa aaagaaagat gatgatgatg aacttgacga cgaggtggaa     15720
ctgctgcacg ctaccgcgcc caggcgacgg gtacagtgga aaggtcgacg cgtaaaacgt   15780
gttttgcgac ccggcaccac cgtagtcttt acgcccggtg agcgctccac ccgcacctac   15840
aagcgcgtgt atgatgaggt gtacggcgac gaggacctgc ttgagcaggc caacgagcgc   15900
ctcggggagt ttgcctacgg aaagcggcat aaggacatgc tggcgttgcc gctggacgag   15960
ggcaacccaa cacctagcct aaagcccgta acactgcagc aggtgctgcc cgcgcttgca   16020
ccgtccgaag aaaagcgcgg cctaaagcgc gagtctggtg acttggcacc caccgtgcag   16080
ctgatggtac ccaagcgcca cgactggaa gatgtcttgg aaaaaatgac cgtggaacct    16140
gggctggagc ccgaggtccg cgtgcggcca atcaagcagg tggcgccggg actgggcgtg   16200
cagaccgtgg acgttcagat acccactacc agtagcacca gtattgccac cgccacagag   16260
ggcatggaga cacaaacgtc cccggttgcc tcagcggtgg cggatgccgc ggtgcaggcg   16320
gtcgctgcgg ccgcgtccaa gacctctacg gaggtgcaaa cggaccccgtg atgtttcgc   16380 gtttcagccc ccggcgcccc gcgccgttcg aggaagtacg cgcgccgcag cgcgctactg   16440
cccgaatatg ccctacatcc ttccattgcg cctaccccg gctatcgtgg ctacacctac     16500
cgccccagaa gacgagcaac tacccgacgc cgaaccacca ctggaacccg ccgccgccgt   16560
cgccgtcgcc agcccgtgct ggccccgatt tccgtgcgca gggtggctcg cgaaggaggc   16620
aggaccctgg tgctgccaac agcgcgctac caccccagca tcgtttaaaa gccggtctttt  16680 gtggttcttg cagatatggc cctcacctgc cgcctccgtt tcccggtgcc gggattccga   16740
ggaagaatgc accgtaggag gggcatggcc ggccacggcc tgacgggcgg catgcgtcgt   16800
gcgcaccacc ggcggcggcg cgcgtcgcac cgtcgcatgc gcggcggtat cctgcccctc   16860
cttattccac tgatcgccgc ggcgattggc gccgtgcccg gaattgcatc cgtggccttg   16920
caggcgcaga gacactgatt aaaaacaagt tgcatgtgga aaaatcaaaa taaaagtct    16980 ggactctcac gctcgcttgg tcctgtaact attttgtaga atggaagaca tcaactttgc   17040
gtctctggcc ccgcgacacg gctcgcgccc gttcatggga aactggcaag atatcggcac   17100
```

```
cagcaatatg agcggtggcg ccttcagctg gggctcgctg tggagcggca ttaaaaattt    17160
cggttccacc gttaagaact atggcagcaa ggcctggaac agcagcacag gccagatgct    17220
gagggataag ttgaaagagc aaaatttcca acaaaaggtg gtagatggcc tggcctctgg    17280
cattagcggg gtggtggacc tggccaacca ggcagtgcaa aataagatta acagtaagct    17340
tgatccccgc cctcccgtag aggagcctcc accggccgtg gagacagtgt ctccagaggg    17400
gcgtggcgaa aagcgtccgc gccccgacag ggaagaaact ctggtgacgc aaatagacga    17460
gcctccctcg tacgaggagg cactaaagca aggcctgccc accacccgtc ccatcgcgcc    17520
catggctacc ggagtgctgg gccagcacac acccgtaacg ctggacctgc ctcccccgc    17580 cgacacccag cagaaacctg tgctgccagg cccgaccgcc gttgttgtaa cccgtcctag    17640
ccgcgcgtcc ctgcgccgcg ccgccagcgg tccgcgatcg ttgcggcccg tagccagtgg    17700
caactggcaa agcacactga acagcatcgt gggtctgggg gtgcaatccc tgaagcgccg    17760
acgatgcttc tgatagctaa cgtgtcgtat gtgtgtcatg tatgcgtcca tgtcgccgcc    17820
agaggagctg ctgagccgcc gcgcgcccgc tttccaagat ggctacccct tcgatgatgc    17880
cgcagtggtc ttacatgcac atctcgggcc aggacgcctc ggagtacctg agccccgggc    17940
tggtgcagtt tgcccgcgcc accgagacgt acttcagcct gaataacaag tttagaaacc    18000
ccacggtggc gcctacgcac gacgtgacca cagaccggtc ccagcgtttg acgctgcggt    18060
tcatccctgt ggaccgtgag gatactgcgt actcgtacaa ggcgcggttc accctagctg    18120
tgggtgataa ccgtgtgctg gacatggctt ccacgtactt tgacatccgc ggcgtgctgg    18180
acaggggccc tacttttaag ccctactctg gcactgccta caacgccctg gctcccaagg    18240 gtgcccaaa tccttgcgaa tgggatgaag ctgctactgc tcttgaaata aacctagaag    18300
aagaggacga tgacaacgaa gacgaagtag acgagcaagc tgacagcaa aaaactcacg    18360 tatttgggca ggcgccttat tctggtataa atattacaaa ggagggtatt caaataggtg    18420
tcgaaggtca aacacctaaa tatgccgata aaacatttca acctgaacct caaataggag    18480
aatctcagtg gtacgaaaca gaaattaatc atgcagctgg gagagtccta aaaaagacta    18540
ccccaatgaa accatgttac ggttcatatg caaaacccac aaatgaaaat ggagggcaag    18600
gcattcttgt aaagcaacaa aatggaaagc tagaaagtca agtggaaatg caatttttct    18660
caactactga ggcagccgca ggcaatggtg taacttgac tcctaaagtg gtattgtaca    18720
gtgaagatgt agatatagaa accccagaca ctcatatttc ttacatgccc actattaagg    18780 aagtaactc acgagaacta atgggccaac aatctatgcc caacaggcct aattacattg    18840
cttttaggga caattttatt ggtctaatgt attacaacag cacgggtaat atgggtgttc    18900
tggcgggcca agcatcgcag ttgaatgctg ttgtagattt gcaagacaga aacacagagc    18960
tttcatacca gcttttgctt gattccattg gtgatagaac caggtacttt tctatgtgga    19020
atcaggctgt tgacagctat gatccagatg ttagaattat tgaaaatcat ggaactgaag    19080
atgaacttcc aaattactgc tttccactgg gaggtgtgat taatacagag actcttacca    19140
aggtaaaacc taaacaggt caggaaaatg gatgggaaa agatgctaca gaattttcag    19200
ataaaaatga aataagagtt ggaaataatt ttgccatgga aatcaatcta aatgccaacc    19260
tgtggagaaa tttcctgtac tccaacatag cgctgtattt gcccgacaag ctaaagtaca    19320
gtccttccaa cgtaaaaatt tctgataacc caaacaccta cgactacatg aacaagcgag    19380
tggtggctcc cgggctagtg gactgctaca ttaaccttgg agcacgctgg tcccttgact    19440
```

```
atatggacaa cgtcaaccca tttaaccacc accgcaatgc tggcctgcgc taccgctcaa   19500
tgttgctggg caatggtcgc tatgtgccct tccacatcca ggtgcctcag aagttctttg   19560
ccattaaaaa cctccttctc ctgccgggct catacaccta cgagtggaac ttcaggaagg   19620
atgttaacat ggttctgcag agctccctag gaaatgacct aagggttgac ggagccagca   19680
ttaagtttga tagcatttgc ctttacgcca ccttcttccc catggcccac aacaccgcct   19740
ccacgcttga ggccatgctt agaaacgaca ccaacgacca gtcctttaac gactatctct   19800
ccgccgccaa catgctctac cctatacccg ccaacgctac caacgtgccc atatccatcc   19860
cctcccgcaa ctgggcggct ttccgcggct gggccttcac gcgccttaag actaaggaaa   19920
ccccatcact gggctcgggc tacgacccct attacaccta ctctggctct ataccctacc   19980
tagatggaac cttttacctc aaccacacct ttaagaaggt ggccattacc tttgactctt   20040
ctgtcagctg gcctggcaat gaccgcctgc ttaccccccaa cgagtttgaa attaagcgct   20100
cagttgacgg ggagggttac aacgttgccc agtgtaacat gaccaaagac tggttcctgg   20160
tacaaatgct agctaactat aacattggct accagggctt ctatatccca gagagctaca   20220
aggaccgcat gtactccttc tttagaaact tccagcccat gagccgtcag gtggtggatg   20280
atactaaata caaggactac caacaggtgg gcatcctaca ccaacacaac aactctggat   20340
ttgttggcta ccttgccccc accatgcgcg aaggacaggc ctaccctgct aacttcccct   20400
atccgcttat aggcaagacc gcagttgaca gcattaccca gaaaaagttt ctttgcgatc   20460
gcaccctttg gcgcatccca ttctccagta actttatgtc catgggcgca ctcacagacc   20520
tgggccaaaa ccttctctac gccaactccg cccacgcgct agacatgact tttgaggtgg   20580
atcccatgga cgagcccacc cttctttatg ttttgtttga agtctttgac gtggtccgtg   20640
tgcaccagcc gcaccgcggc gtcatcgaaa ccgtgtacct gcgcacgccc ttctcggccg   20700
gcaacgccac aacataaaga agcaagcaac atcaacaaca gctgccgcca tgggctccag   20760
tgagcaggaa ctgaaagcca ttgtcaaaga tcttggttgt gggccatatt ttttgggcac   20820
ctatgacaag cgctttccag gctttgtttc tccacacaag ctcgcctgcg ccatagtcaa   20880
tacgccggt cgcgagactg ggggcgtaca ctggatggcc tttgcctgga acccgcactc   20940
aaaaacatgc tacctctttg agccctttgg cttttctgac cagcgactca agcaggttta   21000
ccagtttgag tacgagtcac tcctgcgccg tagcgccatt gcttcttccc ccgaccgctg   21060
tataacgctg gaaaagtcca cccaaagcgt acaggggccc aactcggccg cctgtggact   21120
attctgctgc atgtttctcc acgcctttgc caactggccc caaactccca tggatcacaa   21180
ccccaccatg aaccttatta ccggggtacc caactccatg ctcaacagtc cccaggtaca   21240
gcccaccctg cgtcgcaacc aggaacagct ctacagcttc ctggagcgcc actcgcccta   21300
cttccgcagc cacagtgcgc agattaggag cgccacttct ttttgtcact tgaaaaacat   21360
gtaaaaataa tgtactagag acactttcaa taaaggcaaa tgctttatt tgtacactct   21420
cgggtgatta tttaccccca cccttgccgt ctgcgccgtt taaaaatcaa aggggttctg   21480
ccgcgcatcg ctatgcgcca ctggcaggga cacgttgcga tactggtgtt tagtgctcca   21540
cttaaactca ggcacaacca tccgcggcag ctcggtgaag ttttcactcc acaggctgcg   21600
caccatcacc aacgcgttta gcaggtcggg cgccgatatc ttgaagtcgc agttggggcc   21660
tccgccctgc gcgcgcgagt tgcgatacac agggttgcag cactggaaca ctatcagcgc   21720
cgggtggtgc acgctggcca gcacgctctt gtcggagatc agatccgcgt ccaggtcctc   21780
cgcgttgctc agggcgaacg gagtcaactt tggtagctgc cttcccaaaa agggcgcgtg   21840
```

```
cccaggctttt gagttgcact cgcaccgtag tggcatcaaa aggtgaccgt gcccggtctg    21900
ggcgttagga tacagcgcct gcataaaagc cttgatctgc ttaaaagcca cctgagcctt    21960
tgcgccttca gagaagaaca tgccgcaaga cttgccggaa aactgattgg ccggacaggc    22020
cgcgtcgtgc acgcagcacc ttgcgtcggt gttggagatc tgcaccacat ttcggcccca    22080
ccggttcttc acgatcttgg ccttgctaga ctgctccttc agcgcgcgct gcccgttttc    22140
gctcgtcaca tccatttcaa tcacgtgctc cttatttatc ataatgcttc cgtgtagaca    22200
cttaagctcg ccttcgatct cagcgcagcg gtgcagccac aacgcgcagc ccgtgggctc    22260
gtgatgcttg taggtcacct ctgcaaacga ctgcaggtac gcctgcagga atcgccccat    22320
catcgtcaca aaggtcttgt tgctggtgaa ggtcagctgc aacccgcggt gctcctcgtt    22380
cagccaggtc ttgcatacgg ccgccagagc ttccacttgg tcaggcagta gtttgaagtt    22440
cgcctttaga tcgttatcca cgtggtactt gtccatcagc gcgcgcgcag cctccatgcc    22500
cttctcccac gcagacacga tcggcacact cagcgggttc atcaccgtaa tttcactttc    22560
cgcttcgctg ggctcttcct cttcctcttg cgtccgcata ccacgcgcca ctgggtcgtc    22620
ttcattcagc cgccgcactg tgcgcttacc tcctttgcca tgcttgatta gcaccggtgg    22680
gttgctgaaa cccaccattt gtagcgccac atcttctctt tcttcctcgc tgtccacgat    22740
tacctctggt gatggcgggc gctcgggctt gggagaaggg cgcttctttt tcttcttggg    22800
cgcaatggcc aaatccgccg ccgaggtcga tggccgcggg ctgggtgtgc gcggcaccag    22860
cgcgtcttgt gatgagtctt cctcgtcctc ggactcgata cgccgcctca tccgcttttt    22920
tgggggcgcc cggggaggcg gcggcgacgg ggacgggac gacacgtcct ccatggttgg    22980
gggacgtcgc gccgcaccgc gtccgcgctc ggggtggtt tcgcgctgct cctcttcccg    23040
actggccatt tccttctcct ataggcagaa aaagatcatg gagtcagtcg agaagaagga    23100
cagcctaacc gccccctctg agttcgccac caccgcctcc accgatgccg ccaacgcgcc    23160
taccaccttc cccgtcgagg caccccgct tgaggaggag gaagtgatta tcgagcagga    23220
cccaggtttt gtaagcgaag acgacgagga ccgctcagta ccaacagagg ataaaaagca    23280
agaccaggac aacgcagagg caaacgagga acaagtcggg cgggggacg aaaggcatgg    23340 cgactaccta gatgtgggag acgacgtgct gttgaagcat ctgcagcgcc agtgcgccat    23400
tatctgcgac gcgttgcaag agcgcagcga tgtgcccctc gccatagcgg atgtcagcct    23460
tgcctacgaa cgccacctat tctcaccgcg cgtaccccc aaacgccaag aaaacggcac    23520
atgcgagccc aacccgcgcc tcaacttcta ccccgtattt gccgtgccag aggtgcttgc    23580
cacctatcac atcttttttcc aaaactgcaa gataccccta tcctgccgtg ccaaccgcag    23640
ccgagcggac aagcagctgg ccttgcggca gggcgctgtc atacctgata tcgcctcgct    23700
caacgaagtg ccaaaaatct ttgagggtct tggacgcgac gagaagcgcg cggcaaacgc    23760
tctgcaacag gaaaacagcg aaaatgaaag tcactctgga gtgttggtgg aactcgaggg    23820
tgacaacgcg cgcctagccg tactaaaacg cagcatcgag gtcacccact ttgcctaccc    23880
ggcacttaac ctaccccca aggtcatgag cacagtcatg agtgagctga tcgtgcgccg    23940
tgcgcagccc ctggagaggg atgcaaattt gcaagaacaa acagaggagg cctaccgcg    24000 agttggcgac gagcagctag cgcgctggct tcaaacgcgc gagcctgccg acttggagga    24060
gcgacgcaaa ctaatgatgg ccgcagtgct cgttaccgtg gagcttgagt gcatgcagcg    24120
gttctttgct gacccggaga tgcagcgcaa gctagaggaa acattgcact acaccctttcg    24180
```

```
acagggctac gtacgccagg cctgcaagat ctccaacgtg gagctctgca acctggtctc   24240
ctaccttgga attttgcacg aaaaccgcct tgggcaaaac gtgcttcatt ccacgctcaa   24300
gggcgaggcg cgccgcgact acgtccgcga ctgcgtttac ttatttctat gctacacctg   24360
gcagacggcc atgggcgttt ggcagcagtg cttggaggag tgcaacctca aggagctgca   24420
gaaactgcta aagcaaaact tgaaggacct atggacggcc ttcaacgagc gctccgtggc   24480
cgcgcacctg gcggacatca ttttccccga acgcctgctt aaaaccctgc aacagggtct   24540
gccagacttc accagtcaaa gcatgttgca gaactttagg aactttatcc tagagcgctc   24600
aggaatcttg cccgccacct gctgtgcact tcctagcgac tttgtgccca ttaagtaccg   24660
cgaatgccct ccgccgcttt ggggccactg ctaccttctg cagctagcca actaccttgc   24720
ctaccactct gacataatgg aagacgtgag cggtgacggt ctactggagt gtcactgtcg   24780
ctgcaaccta tgcaccccgc accgctccct ggtttgcaat tcgcagctgc ttaacgaaag   24840
tcaaattatc ggtacctttg agctgcaggg tccctcgcct gacgaaaagt ccgcggctcc   24900
ggggttgaaa ctcactccgg ggctgtggac gtcggcttac cttcgcaaat ttgtacctga   24960
ggactaccac gcccacgaga ttaggttcta cgaagaccaa tcccgcccgc ctaatgcgga   25020
gcttaccgcc tgcgtcatta cccagggcca cattcttggc caattgcaag ccatcaacaa   25080
agcccgccaa gagtttctgc tacgaaaggg acgggggtt tacttggacc cccagtccgg   25140
cgaggagctc aacccaatcc ccccgccgcc gcagccctat cagcagcagc gcgggccct   25200
tgcttcccag gatggcaccc aaaaagaagc tgcagctgcc gccgccaccc acggacgagg   25260
aggaatactg ggacagtcag gcagaggagg ttttggacga ggaggaggag acatgatgg   25320
aagactggga gagcctagac gaggaagctt ccgaggtcga agaggtgtca gacgaaacac   25380
cgtcaccctc ggtcgcattc ccctcgccgg cgccccagaa atcggcaacc ggttccagca   25440
tggctacaac ctccgctcct caggcgccgc cggcactgcc cgttcgccga cccaaccgta   25500
gatgggacac cactggaacc agggccggta agtccaagca gccgccgccg ttagcccaag   25560
agcaacaaca gcgccaaggc taccgctcat ggcgcgggca caagaacgcc atagttgctt   25620
gcttgcaaga ctgtgggggc aacatctcct tcgcccgccg ctttcttctc taccatcacg   25680
gcgtggcctt cccccgtaac atcctgcatt actaccgtca tctctacagc ccatactgca   25740
ccggcggcag cggcagcaac agcagcggcc acacagaagc aaaggcgacc ggatagcaag   25800
actctgacaa agcccaagaa atccacagcg gcggcagcag caggaggagg agcgctgcgt   25860
ctggcgccca acgaacccgt atcgaccgc gagcttagaa acaggatttt tcccactctg   25920
tatgctatat ttcaacagag caggggccaa gaacaagagc tgaaaataaa aaacaggtct   25980
ctgcgatccc tcacccgcag ctgcctgtat cacaaaagcg aagatcagct tcggcgcacg   26040
ctggaagacg cggaggctct cttcagtaaa tactgcgcgc tgactcttaa ggactagttt   26100
cgcgcccttt ctcaaattta agcgcgaaaa ctacgtcatc tccagcggcc acacccggcg   26160
ccagcacctg ttgtcagcgc cattatgagc aaggaaattc ccacgcccta catgtggagt   26220
taccagccac aaatgggact tgcggctgga gctgcccaag actactcaac ccgaataaac   26280
tacatgagcg cggacccca catgatatcc cgggtcaacg gaatacgcgc ccaccgaaac   26340
cgaattctcc tggaacaggc ggctattacc accacacctc gtaataacct taatccccgt   26400
agttggcccg ctgccctggt gtaccaggaa agtcccgctc ccaccactgt ggtacttccc   26460
agagacgccc aggccgaagt tcagatgact aactcagggg cgcagcttgc gggcggcttt   26520
cgtcacaggg tgcggtcgcc cgggcagggt ataactcacc tgacaatcag agggcgaggt   26580
```

```
attcagctca acgacgagtc ggtgagctcc tcgcttggtc tccgtccgga cgggacattt    26640
cagatcggcg gcgccggccg ctcttcattc acgcctcgtc aggcaatcct aactctgcag    26700
acctcgtcct ctgagccgcg ctctggaggc attggaactc tgcaatttat tgaggagttt    26760
gtgccatcgg tctactttaa ccccttctcg ggacctcccg gccactatcc ggatcaattt    26820
attcctaact ttgacgcggt aaaggactcg gcggacggct acgactgaat gttaagtgga    26880
gaggcagagc aactgcgcct gaaacacctg gtccactgtc gccgccacaa gtgctttgcc    26940
cgcgactccg gtgagttttg ctactttgaa ttgcccgagg atcatatcga gggcccggcg    27000 cacgcgtcc ggcttaccgc ccagggagag cttgcccgta gcctgattcg ggagtttacc    27060
cagcgccccc tgctagttga gcgggacagg ggaccctgtg ttctcactgt gatttgcaac    27120
tgtcctaacc ctggattaca tcaagatcct ctagttaatg tcaggtcgcc taagtcgatt    27180
aactagagta cccggggatc ttattccctt taactaataa aaaaaaataa taaagcatca    27240
cttacttaaa atcagttagc aaatttctgt ccagtttatt cagcagcacc tccttgccct    27300
cctcccagct ctggtattgc agcttcctcc tggctgcaaa ctttctccac aatctaaatg    27360
gaatgtcagt ttcctcctgt tcctgtccat ccgcacccac tatcttcatg ttgttgcaga    27420
tgaagcgcgc aagaccgtct gaagatacct tcaacccgt gtatccatat gacacggaaa    27480
ccggtcctcc aactgtgcct tttcttactc ctccctttgt atcccccaat gggtttcaag    27540
agagtccccc tggggtactc tctttgcgcc tatccgaacc tctagttacc tccaatggca    27600
tgcttgcgct caaaatgggc aacggcctct ctctggacga ggccggcaac cttacctccc    27660
aaaatgtaac cactgtgagc ccacctctca aaaaaaccaa gtcaaacata aacctggaaa    27720
tatctgcacc cctcacagtt acctcagaag ccctaactgt ggctgccgcc gcacctctaa    27780
tggtcgcggg caacacactc accatgcaat cacaggcccc gctaaccgtg cacgactcca    27840
aacttagcat tgccacccaa ggaccccctca cagtgtcaga aggaaagcta gccctgcaaa    27900
catcaggccc cctcaccacc accgatagca gtacccttac tatcactgcc tcaccccctc    27960
taactactgc cactggtagc ttgggcattg acttgaaaga gcccatttat acacaaaatg    28020
gaaaactagg actaaagtac ggggctcctt tgcatgtaac agacgaccta aacactttga    28080
ccgtagcaac tggtccaggt gtgactatta ataatacttc cttgcaaact aaagttactg    28140
gagccttggg ttttgattca caaggcaata tgcaacttaa tgtagcagga ggactaagga    28200
ttgattctca aaacagacgc cttatacttg atgttagtta ccgtttgat gctcaaaacc    28260 aactaaatct aagactagga cagggccctc tttttataaa ctcagcccac aacttggata    28320
ttaactacaa caaaggcctt tacttgttta cagcttcaaa caattccaaa agcttgagg    28380 ttaacctaag cactgccaag gggttgatgt ttgacgctac agccatagcc attaatgcag    28440
gagatgggct tgaatttggt tcacctaatg caccaaacac aaatcccctc aaaacaaaaa    28500
ttggccatgg cctagaattt gattcaaaca aggctatggt tcctaaacta ggaactggcc    28560
ttagttttga cagcacaggt gccattacag taggaaacaa aaataatgat aagctaactt    28620
tgtggaccac accagctcca tctcctaact gtagactaaa tgcagagaaa gatgctaaac    28680
tcactttggt cttaacaaaa tgtggcagtc aaatacttgc tacagtttca gttttggctg    28740
ttaaaggcag tttggctcca atatctggaa cagttcaaag tgctcatctt attataagat    28800
ttgacgaaaa tggagtgcta ctaaacaatt ccttcctgga cccagaatat tggaacttta    28860
gaaatggaga tcttactgaa ggcacagcct atacaaacgc tgttggattt atgcctaacc    28920
```

```
tatcagctta tccaaaatct cacggtaaaa ctgccaaaag taacattgtc agtcaagttt    28980
acttaaacgg agacaaaact aaacctgtaa cactaaccat tacactaaac ggtacacagg    29040
aaacaggaga cacaactcca agtgcatact ctatgtcatt ttcatgggac tggtctggcc    29100
acaactacat taatgaaata tttgccacat cctcttacac tttttcatac attgcccaag    29160
aataaagaat cgtttgtgtt atgtttcaac gtgtttattt ttcaattgca gaaaatttca    29220
agtcattttt cattcagtag tatagcccca ccaccacata gcttatacag atcaccgtac    29280
cttaatcaaa ctcacagaac cctagtattc aacctgccac ctccctccca acacacagag    29340
tacacagtcc tttctccccg gctggcctta aaaagcatca tatcatgggt aacagacata    29400
ttcttaggtg ttatattcca cacggtttcc tgtcgagcca aacgctcatc agtgatatta    29460
ataaactccc cgggcagctc acttaagttc atgtcgctgt ccagctgctg agccacaggc    29520
tgctgtccaa cttgcggttg cttaacgggc ggcgaaggag aagtccacgc ctacatgggg    29580
gtagagtcat aatcgtgcat caggataggg cggtggtgct gcagcagcgc gcgaataaac    29640
tgctgccgcc gccgctccgt cctgcaggaa tacaacatgg cagtggtctc ctcagcgatg    29700
attcgcaccg cccgcagcat aaggcgcctt gtcctccggg cacagcagcg caccctgatc    29760
tcacttaaat cagcacagta actgcagcac agcaccacaa tattgttcaa aatcccacag    29820
tgcaaggcgc tgtatccaaa gctcatggcg gggaccacag aacccacgtg gccatcatac    29880
cacaagcgca ggtagattaa gtggcgaccc ctcataaaca cgctggacat aaacattacc    29940
tcttttggca tgttgtaatt caccacctcc cggtaccata taaacctctg attaaacatg    30000
gcgccatcca ccaccatcct aaaccagctg gccaaaacct gcccgccggc tatacactgc    30060
agggaaccgg gactggaaca atgacagtgg agagcccagg actcgtaacc atggatcatc    30120
atgctcgtca tgatatcaat gttggcacaa cacaggcaca cgtgcataca cttcctcagg    30180
attacaagct cctcccgcgt tagaaccata tcccagggaa caacccattc ctgaatcagc    30240
gtaaatccca cactgcaggg aagacctcgc acgtaactca cgttgtgcat tgtcaaagtg    30300
ttacattcgg gcagcagcgg atgatcctcc agtatggtag cgcgggtttc tgtctcaaaa    30360
ggaggtagac gatccctact gtacggagtg cgccgagaca accgagatcg tgttggtcgt    30420
agtgtcatgc caaatggaac gccggacgta gtcatatttc ctgaagcaaa accaggtgcg    30480
ggcgtgacaa acagatctgc gtctccggtc tcgccgctta gatcgctctg tgtagtagtt    30540
gtagtatatc cactctctca aagcatccag gcgcccctg gcttcgggtt ctatgtaaac     30600
tccttcatgc gccgctgccc tgataacatc caccaccgca gaataagcca cacccagcca    30660
acctacacat tcgttctgcg agtcacacac gggaggagcg ggaagagctg gaagaaccat    30720
gtttttttt ttattccaaa agattatcca aaacctcaaa atgaagatct attaagtgaa     30780
cgcgctcccc tccggtggcg tggtcaaact ctacagccaa agaacagata atggcatttg    30840
taagatgttg cacaatggct tccaaaaggc aaacggccct cacgtccaag tggacgtaaa    30900
ggctaaaccc ttcagggtga atctcctcta taaacattcc agcaccttca accatgccca    30960
aataattctc atctcgccac cttctcaata tatctctaag caaatcccga atattaagtc    31020
cggccattgt aaaaatctgc tccagagcgc cctccacctt cagcctcaag cagcgaatca    31080
tgattgcaaa aattcaggtt cctcacagac ctgtataaga ttcaaaagcg gaacattaac    31140
aaaaatacc g cgatcccgta ggtcccttcg cagggccagc tgaacataat cgtgcaggtc    31200
tgcacggacc agcgcggcca cttccccgcc aggaaccatg acaaaagaac ccacactgat    31260
tatgacacgc atactcggag ctatgctaac cagcgtagcc ccgatgtaag cttgttgcat    31320
```

```
gggcggcgat ataaaatgca aggtgctgct caaaaaatca ggcaaagcct cgcgcaaaaa    31380
agaaagcaca tcgtagtcat gctcatgcag ataaaggcag gtaagctccg gaaccaccac    31440
agaaaaagac accatttttc tctcaaacat gtctgcgggt ttctgcataa acacaaaata    31500
aaataacaaa aaaacattta aacattagaa gcctgtctta caacaggaaa acaacccctt    31560
ataagcataa gacggactac ggccatgccg gcgtgaccgt aaaaaaactg gtcaccgtga    31620
ttaaaaagca ccaccgacag ctcctcggtc atgtccggag tcataatgta agactcggta    31680
aacacatcag gttgattcac atcggtcagt gctaaaaagc gaccgaaata gcccggggga    31740
atacataccc gcaggcgtag agacaacatt acagccccca taggaggtat aacaaaatta    31800
ataggagaga aaacacata aacacctgaa aaaccctcct gcctaggcaa aatagcaccc    31860
tcccgctcca gaacaacata cagcgcttcc acagcggcag ccataacagt cagccttacc    31920
agtaaaaaag aaaacctatt aaaaaaacac cactcgacac ggcaccagct caatcagtca    31980
cagtgtaaaa aagggccaag tgcagagcga gtatatatag gactaaaaaa tgacgtaacg    32040
gttaaagtcc acaaaaaaca cccagaaaac cgcacgcgaa cctacgccca gaaacgaaag    32100
ccaaaaaacc cacaacttcc tcaaatcgtc acttccgttt tcccacgtta cgtcacttcc    32160
cattttaaga aaactacaat tcccaacaca tacaagttac tccgccctaa aacctacgtc    32220
acccgccccg ttcccacgcc ccgcgccacg tcacaaactc cacccctca ttatcatatt    32280 ggcttcaatc caaaataagg tatattattg atgat                              32315

<210> SEQ ID NO 11
<211> LENGTH: 1428
<212> TYPE: DNA
<213> ORGANISM: Homo sapiens

<400> SEQUENCE: 11
atgacaccgg gcacccagtc tcctttcttc ctgctgctgc tcctcacagt gcttacagtt     60
gttacgggtt ctggtcatgc aagctctacc ccaggtggag aaaaggagac ttcggctacc    120
cagagaagtt cagtgcccag ctctactgag aagaatgctg tgagtatgac cagcagcgta    180
ctctccagcc acagccccgg ttcaggctcc tccaccactc agggacagga tgtcactctg    240 gcccccggcca cggaaccagc ttcaggttca gctgcccttt ggggacagga tgtcacctcg    300
gtcccagtca ccaggccagc cctgggctcc accaccccgc cagcccacga tgtcacctca    360
gccccggaca caagccagc cccgggctcc accgccccc cagcccacgg tgtcacctcg    420
tatcttgaca ccaggccggc cccggtttat cttgcccccc cagcccatgg tgtcacctcg    480
gccccggaca caggcccgc cttgggctcc accgcccctc cagtccacaa tgtcacctcg    540
gcctcaggct ctgcatcagg ctcagcttct actctggtgc acaacggcac ctctgccagg    600
gctaccacaa ccccagccag caagagcact ccattctcaa ttcccagcca ccactctgat    660
actcctacca cccttgccag ccatagcacc aagactgatg ccagtagcac tcaccatagc    720
acggtaccct ctctcaccct ctccaatcac agcacttctc cccagttgtc tactggggtc    780
tctttctttt tcctgtcttt tcacatttca aacctccagt ttaattcctc tctggaagat    840
cccagcaccg actactacca agagctgcag agagacattt ctgaaatgtt tttgcagatt    900
tataaacaag ggggttttct gggcctctcc aatattaagt tcaggccagg atctgtggtg    960
gtacaattga ctctggcctt ccgagaaggt accatcaatg tccacgacgt ggagacacag   1020
ttcaatcagt ataaaacgga agcagcctct cgatataacc tgacgatctc agacgtcagc   1080
```

```
gtgagtgatg tgccatttcc tttctctgcc cagtctgggg ctggggtgcc aggctggggc    1140
atcgcgctgc tggtgctggt ctgtgttctg gtttatctgg ccattgtcta tctcattgcc    1200
ttggctgtcg ctcaggttcg ccgaaagaac tacgggcagc tggacatctt ccagcccgg    1260 gataaatacc atcctatgag cgagtacgct ctttaccaca cccatgggcg ctatgtgccc    1320
cctagcagtc ttttccgtag cccctatgag aaggtttctg caggtaatgg tggcagctat    1380
ctctcttaca caaacccagc agtggcagcc gcttctgcca acttgtag                 1428
```

<210> SEQ ID NO 12
<211> LENGTH: 475
<212> TYPE: PRT
<213> ORGANISM: Homo sapiens

<400> SEQUENCE: 12

| | | | | | | | | | | | | | | |
|---|---|---|---|---|---|---|---|---|---|---|---|---|---|---|
| Met | Thr | Pro | Gly | Thr | Gln | Ser | Pro | Phe | Phe | Leu | Leu | Leu | Leu | Thr |
| 1 | | | | 5 | | | | | 10 | | | | | 15 |
| Val | Leu | Thr | Val | Val | Thr | Gly | Ser | Gly | His | Ala | Ser | Ser | Thr | Pro | Gly |
| | | | 20 | | | | | 25 | | | | | 30 | | |
| Gly | Glu | Lys | Glu | Thr | Ser | Ala | Thr | Gln | Arg | Ser | Ser | Val | Pro | Ser | Ser |
| | | | 35 | | | | | 40 | | | | | 45 | | |
| Thr | Glu | Lys | Asn | Ala | Val | Ser | Met | Thr | Ser | Ser | Val | Leu | Ser | Ser | His |
| | 50 | | | | | 55 | | | | | 60 | | | | |
| Ser | Pro | Gly | Ser | Gly | Ser | Ser | Thr | Thr | Gln | Gly | Gln | Asp | Val | Thr | Leu |
| 65 | | | | | 70 | | | | | 75 | | | | | 80 |
| Ala | Pro | Ala | Thr | Glu | Pro | Ala | Ser | Gly | Ser | Ala | Ala | Leu | Trp | Gly | Gln |
| | | | | 85 | | | | | 90 | | | | | 95 | |
| Asp | Val | Thr | Ser | Val | Pro | Val | Thr | Arg | Pro | Ala | Leu | Gly | Ser | Thr | Thr |
| | | | | 100 | | | | | 105 | | | | | 110 | |
| Pro | Pro | Ala | His | Asp | Val | Thr | Ser | Ala | Pro | Asp | Asn | Lys | Pro | Ala | Pro |
| | | | 115 | | | | | 120 | | | | | 125 | | |
| Gly | Ser | Thr | Ala | Pro | Pro | Ala | His | Gly | Val | Thr | Ser | Tyr | Leu | Asp | Thr |
| | | | 130 | | | | | 135 | | | | | 140 | | |
| Arg | Pro | Ala | Pro | Val | Tyr | Leu | Ala | Pro | Pro | Ala | His | Gly | Val | Thr | Ser |
| 145 | | | | | 150 | | | | | 155 | | | | | 160 |
| Ala | Pro | Asp | Asn | Arg | Pro | Ala | Leu | Gly | Ser | Thr | Ala | Pro | Pro | Val | His |
| | | | | 165 | | | | | 170 | | | | | 175 | |
| Asn | Val | Thr | Ser | Ala | Ser | Gly | Ser | Ala | Ser | Gly | Ser | Ala | Ser | Thr | Leu |
| | | | | 180 | | | | | 185 | | | | | 190 | |
| Val | His | Asn | Gly | Thr | Ser | Ala | Arg | Ala | Thr | Thr | Thr | Pro | Ala | Ser | Lys |
| | | | 195 | | | | | 200 | | | | | 205 | | |
| Ser | Thr | Pro | Phe | Ser | Ile | Pro | Ser | His | His | Ser | Asp | Thr | Pro | Thr | Thr |
| | 210 | | | | | 215 | | | | | 220 | | | | |
| Leu | Ala | Ser | His | Ser | Thr | Lys | Thr | Asp | Ala | Ser | Ser | Thr | His | His | Ser |
| 225 | | | | | 230 | | | | | 235 | | | | | 240 |
| Thr | Val | Pro | Pro | Leu | Thr | Ser | Ser | Asn | His | Ser | Thr | Ser | Pro | Gln | Leu |
| | | | | 245 | | | | | 250 | | | | | 255 | |
| Ser | Thr | Gly | Val | Ser | Phe | Phe | Phe | Leu | Ser | Phe | His | Ile | Ser | Asn | Leu |
| | | | 260 | | | | | 265 | | | | | 270 | | |
| Gln | Phe | Asn | Ser | Ser | Leu | Glu | Asp | Pro | Ser | Thr | Asp | Tyr | Tyr | Gln | Glu |
| | | | 275 | | | | | 280 | | | | | 285 | | |
| Leu | Gln | Arg | Asp | Ile | Ser | Glu | Met | Phe | Leu | Gln | Ile | Tyr | Lys | Gln | Gly |
| | | | 290 | | | | | 295 | | | | | 300 | | |
| Gly | Phe | Leu | Gly | Leu | Ser | Asn | Ile | Lys | Phe | Arg | Pro | Gly | Ser | Val | Val |
| 305 | | | | | 310 | | | | | 315 | | | | | 320 |

```
Val Gln Leu Thr Leu Ala Phe Arg Glu Gly Thr Ile Asn Val His Asp
            325                 330                 335

Val Glu Thr Gln Phe Asn Gln Tyr Lys Thr Glu Ala Ala Ser Arg Tyr
        340                 345                 350

Asn Leu Thr Ile Ser Asp Val Ser Val Ser Asp Val Pro Phe Pro Phe
        355                 360                 365

Ser Ala Gln Ser Gly Ala Gly Val Pro Gly Trp Gly Ile Ala Leu Leu
        370                 375                 380

Val Leu Val Cys Val Leu Val Tyr Leu Ala Ile Val Tyr Leu Ile Ala
385                 390                 395                 400

Leu Ala Val Ala Gln Val Arg Arg Lys Asn Tyr Gly Gln Leu Asp Ile
                405                 410                 415

Phe Pro Ala Arg Asp Lys Tyr His Pro Met Ser Glu Tyr Ala Leu Tyr
            420                 425                 430

His Thr His Gly Arg Tyr Val Pro Pro Ser Ser Leu Phe Arg Ser Pro
        435                 440                 445

Tyr Glu Lys Val Ser Ala Gly Asn Gly Gly Ser Tyr Leu Ser Tyr Thr
    450                 455                 460

Asn Pro Ala Val Ala Ala Ser Ala Asn Leu
465                 470                 475

<210> SEQ ID NO 13
<211> LENGTH: 1233
<212> TYPE: DNA
<213> ORGANISM: Homo sapiens

<400> SEQUENCE: 13
atgagctccc ctggcaccga gagcgcggga aagagcctgc agtaccgagt ggaccacctg      60
ctgagcgccg tggagaatga gctgcaggcg ggcagcgaga agggcgaccc cacagagcgc     120
gaactgcgcg tgggcctgga ggagagcgag ctgtggctgc gcttcaagga gctcaccaat     180
gagatgatcg tgaccaagaa cggcaggagg atgtttccgg tgctgaaggt gaacgtgtct     240
ggcctggacc ccaacgccat gtactccttc ctgctggact cgtggcggc ggacaaccac      300 cgctggaagt acgtgaacgg ggaatggtg ccggggggca agccgagcc gcaggcgccc       360 agctgcgtct acatccaccc cgactcgccc aacttcgggg cccactggat gaaggctccc     420
gtctccttca gcaaagtcaa gctcaccaac aagctcaacg agggggcca gatcatgctg     480 aactccttgc ataagtatga gcctcgaatc cacatagtga gagttggggg tccacagcgc     540
atgatcacca gccactgctt ccctgagacc cagttcatag cggtgactgc tagaagtgat    600
cacaaagaga tgatggagga acccggagac agccagcaac tgggtactcc caatggggg     660 tggcttcttc ctggaaccag caccgtgtgt ccacctgcaa atcctcatcc tcagtttgga    720
ggtgccctct ccctcccctc cacgcacagc tgtgacaggt acccaaccct gaggagccac    780
cggtcctcac cctaccccag cccctatgct catcggaaca attctccaac ctattctgac    840
aactcacctg catgtttatc catgctgcaa tcccatgaca attggtccag ccttggaatg    900
cctgcccatc ccagcatgct ccccgtgagc acaatgcca gcccacctac cagctccagt     960
cagtacccca gctgtggtc tgtgagcaac ggcgccgtca cccgggctc ccaggcagca     1020 gccgtgtcca acgggctggg ggccagttc ttccggggct ccccgcgca ctacacaccc    1080 ctcacccatc cggtctcggc gccctcttcc tcgggatccc cactgtacga aggggcggcc   1140
gcggccacag acatcgtgga cagccagtac gacgccgcag cccaaggccg cctcatagcc   1200
```
tcatggacac ctgtgtcgcc accttccatg tga 1233

<210> SEQ ID NO 14
<211> LENGTH: 132
<212> TYPE: PRT
<213> ORGANISM: Mycobacterium tuberculosis

<400> SEQUENCE: 14

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Arg Ser
            20                  25                  30

Gly Gly Gly Ser Pro Thr Val His Ile Gly Pro Thr Ala Phe Leu Gly
        35                  40                  45

Leu Gly Val Val Asp Asn Asn Gly Asn Gly Ala Arg Val Gln Arg Val
50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Thr Trp
            100                 105                 110

Gln Thr Lys Ser Gly Gly Thr Arg Thr Gly Asn Val Thr Leu Ala Glu
        115                 120                 125

Gly Pro Pro Ala
    130

<210> SEQ ID NO 15
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met His His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Gly Ser Pro Thr Val His Ile
        35                  40                  45

Gly Pro Thr Ala Phe Leu Gly Leu Gly Val Val Asp Asn Asn Gly Asn
50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Asp Asp Asp
    130                 135                 140

Asp Lys Asp Pro Pro Asp Pro His Gln Pro Asp Met Thr Lys Gly Tyr
145                 150                 155                 160

Cys Pro Gly Gly Arg Trp Gly Phe Gly Asp Leu Ala Val Cys Asp Gly

-continued

```
                165                 170                 175
Glu Lys Tyr Pro Asp Gly Ser Phe Trp His Gln Trp Met Gln Thr Trp
            180                 185                 190

Phe Thr Gly Pro Gln Phe Tyr Phe Asp Cys Val Ser Gly Gly Glu Pro
            195                 200                 205

Leu Pro Gly Pro Pro Pro Gly Gly Cys Gly Gly Ala Ile Pro Ser
        210                 215                 220

Glu Gln Pro Asn Ala Pro
225                 230

<210> SEQ ID NO 16
<211> LENGTH: 578
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Ser Pro Thr Val His Ile
        35                  40                  45

Gly Pro Thr Ala Phe Leu Gly Leu Gly Val Val Asp Asn Asn Gly Asn
    50                  55                  60

Gly Ala Arg Val Gln Arg Val Val Gly Ser Ala Pro Ala Ser Leu
65                  70                  75                  80

Gly Ile Ser Thr Gly Asp Val Ile Thr Ala Val Asp Gly Ala Pro Ile
            85                  90                  95

Asn Ser Ala Thr Ala Met Ala Asp Ala Leu Asn Gly His His Pro Gly
        100                 105                 110

Asp Val Ile Ser Val Thr Trp Gln Thr Lys Ser Gly Gly Thr Arg Thr
    115                 120                 125

Gly Asn Val Thr Leu Ala Glu Gly Pro Pro Ala Glu Phe Pro Leu Val
    130                 135                 140

Pro Arg Gly Ser Pro Met Gly Ser Asp Val Arg Asp Leu Asn Ala Leu
145                 150                 155                 160

Leu Pro Ala Val Pro Ser Leu Gly Gly Gly Gly Cys Ala Leu Pro
            165                 170                 175

Val Ser Gly Ala Ala Gln Trp Ala Pro Val Leu Asp Phe Ala Pro Pro
            180                 185                 190

Gly Ala Ser Ala Tyr Gly Ser Leu Gly Gly Pro Ala Pro Pro Ala
        195                 200                 205

Pro Pro Pro Pro Pro Pro Pro Pro His Ser Phe Ile Lys Gln Glu
    210                 215                 220

Pro Ser Trp Gly Gly Ala Glu Pro His Glu Glu Gln Cys Leu Ser Ala
225                 230                 235                 240

Phe Thr Val His Phe Ser Gly Gln Phe Thr Gly Thr Ala Gly Ala Cys
            245                 250                 255

Arg Tyr Gly Pro Phe Gly Pro Pro Pro Ser Gln Ala Ser Ser Gly
        260                 265                 270

Gln Ala Arg Met Phe Pro Asn Ala Pro Tyr Leu Pro Ser Cys Leu Glu
    275                 280                 285
```

```
Ser Gln Pro Ala Ile Arg Asn Gln Gly Tyr Ser Thr Val Thr Phe Asp
    290                 295                 300

Gly Thr Pro Ser Tyr Gly His Thr Pro Ser His His Ala Ala Gln Phe
305                 310                 315                 320

Pro Asn His Ser Phe Lys His Glu Asp Pro Met Gly Gln Gln Gly Ser
                325                 330                 335

Leu Gly Glu Gln Gln Tyr Ser Val Pro Pro Val Tyr Gly Cys His
            340                 345                 350

Thr Pro Thr Asp Ser Cys Thr Gly Ser Gln Ala Leu Leu Leu Arg Thr
                355                 360                 365

Pro Tyr Ser Ser Asp Asn Leu Tyr Gln Met Thr Ser Gln Leu Glu Cys
    370                 375                 380

Met Thr Trp Asn Gln Met Asn Leu Gly Ala Thr Leu Lys Gly His Ser
385                 390                 395                 400

Thr Gly Tyr Glu Ser Asp Asn His Thr Thr Pro Ile Leu Cys Gly Ala
                405                 410                 415

Gln Tyr Arg Ile His Thr His Gly Val Phe Arg Gly Ile Gln Asp Val
            420                 425                 430

Arg Arg Val Pro Gly Val Ala Pro Thr Leu Val Arg Ser Ala Ser Glu
    435                 440                 445

Thr Ser Glu Lys Arg Pro Phe Met Cys Ala Tyr Ser Gly Cys Asn Lys
450                 455                 460

Arg Tyr Phe Lys Leu Ser His Leu Gln Met His Ser Arg Lys His Thr
465                 470                 475                 480

Gly Glu Lys Pro Tyr Gln Cys Asp Phe Lys Asp Cys Glu Arg Arg Phe
                485                 490                 495

Phe Arg Ser Asp Gln Leu Lys Arg His Gln Arg Arg His Thr Gly Val
            500                 505                 510

Lys Pro Phe Gln Cys Lys Thr Cys Gln Arg Lys Phe Ser Arg Ser Asp
    515                 520                 525

His Leu Lys Thr His Thr Arg Thr His Thr Gly Glu Lys Pro Phe Ser
    530                 535                 540

Cys Arg Trp Pro Ser Cys Gln Lys Lys Phe Ala Arg Ser Asp Glu Leu
545                 550                 555                 560

Val Arg His His Asn Met His Gln Arg Asn Met Thr Lys Leu Gln Leu
                565                 570                 575

Ala Leu

<210> SEQ ID NO 17
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Ser Pro Thr Val His Ile
        35                  40                  45

Gly Pro Thr Ala Phe Leu Gly Leu Gly Val Val Asp Asn Asn Gly Asn
    50                  55                  60
```

```
Gly Ala Arg Val Gln Arg Val Val Gly Ser Ala Pro Ala Ala Ser Leu
 65                  70                  75                  80

Gly Ile Ser Thr Gly Asp Val Ile Thr Ala Val Asp Gly Ala Pro Ile
                 85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Ile Glu Gly
    130                 135                 140

Arg Gly Ser Gly Cys Pro Leu Leu Glu Asn Val Ile Ser Lys Thr Ile
145                 150                 155                 160

Asn Pro Gln Val Ser Lys Thr Glu Tyr Lys Glu Leu Leu Gln Glu Phe
                165                 170                 175

Ile Asp Asp Asn Ala Thr Thr Asn Ala Ile Asp Glu Leu Lys Glu Cys
            180                 185                 190

Phe Leu Asn Gln Thr Asp Glu Thr Leu Ser Asn Val Glu Val Phe Met
        195                 200                 205

Gln Leu Ile Tyr Asp Ser Ser Leu Cys Asp Leu Phe
    210                 215                 220

<210> SEQ ID NO 18
<211> LENGTH: 729
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met His His His His His Thr Ala Ala Ser Asp Asn Phe Gln Leu
  1               5                  10                  15

Ser Gln Gly Gly Gln Gly Phe Ala Ile Pro Ile Gly Gln Ala Met Ala
                 20                  25                  30

Ile Ala Gly Gln Ile Arg Ser Gly Gly Gly Ser Pro Thr Val His Ile
             35                  40                  45

Gly Pro Thr Ala Phe Leu Gly Leu Gly Val Val Asp Asn Asn Gly Asn
     50                  55                  60

Gly Ala Arg Val Gln Arg Val Val Gly Ser Ala Pro Ala Ala Ser Leu
 65                  70                  75                  80

Gly Ile Ser Thr Gly Asp Val Ile Thr Ala Val Asp Gly Ala Pro Ile
                 85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205
```

-continued

```
Ala Ala Ala Ser Pro Tyr Val Ala Trp Met Ser Val Thr Ala Gly Gln
    210                 215                 220
Ala Glu Leu Thr Ala Ala Gln Val Arg Val Ala Ala Ala Tyr Glu
225                 230                 235                 240
Thr Ala Tyr Gly Leu Thr Val Pro Pro Val Ile Ala Glu Asn Arg
                245                 250                 255
Ala Glu Leu Met Ile Leu Ile Ala Thr Asn Leu Leu Gly Gln Asn Thr
                260                 265                 270
Pro Ala Ile Ala Val Asn Glu Ala Glu Tyr Gly Glu Met Trp Ala Gln
            275                 280                 285
Asp Ala Ala Met Phe Gly Tyr Ala Ala Ala Thr Ala Thr Ala Thr
290                 295                 300
Ala Thr Leu Leu Pro Phe Glu Glu Ala Pro Glu Met Thr Ser Ala Gly
305                 310                 315                 320
Gly Leu Leu Glu Gln Ala Ala Ala Val Glu Glu Ala Ser Asp Thr Ala
                325                 330                 335
Ala Ala Asn Gln Leu Met Asn Asn Val Pro Gln Ala Leu Gln Gln Leu
            340                 345                 350
Ala Gln Pro Thr Gln Gly Thr Thr Pro Ser Ser Lys Leu Gly Gly Leu
            355                 360                 365
Trp Lys Thr Val Ser Pro His Arg Ser Pro Ile Ser Asn Met Val Ser
370                 375                 380
Met Ala Asn Asn His Met Ser Met Thr Asn Ser Gly Val Ser Met Thr
385                 390                 395                 400
Asn Thr Leu Ser Ser Met Leu Lys Gly Phe Ala Pro Ala Ala Ala
                405                 410                 415
Gln Ala Val Gln Thr Ala Ala Gln Asn Gly Val Arg Ala Met Ser Ser
            420                 425                 430
Leu Gly Ser Ser Leu Gly Ser Ser Gly Leu Gly Gly Val Ala Ala
                435                 440                 445
Asn Leu Gly Arg Ala Ala Ser Val Gly Ser Leu Ser Val Pro Gln Ala
    450                 455                 460
Trp Ala Ala Asn Gln Ala Val Thr Pro Ala Ala Arg Ala Leu Pro
465                 470                 475                 480
Leu Thr Ser Leu Thr Ser Ala Ala Glu Arg Gly Pro Gly Gln Met Leu
                485                 490                 495
Gly Gly Leu Pro Val Gly Gln Met Gly Ala Arg Ala Gly Gly Gly Leu
            500                 505                 510
Ser Gly Val Leu Arg Val Pro Pro Arg Pro Tyr Val Met Pro His Ser
        515                 520                 525
Pro Ala Ala Gly Asp Ile Ala Pro Pro Ala Leu Ser Gln Asp Arg Phe
530                 535                 540
Ala Asp Phe Pro Ala Leu Pro Leu Asp Pro Ser Ala Met Val Ala Gln
545                 550                 555                 560
Val Gly Pro Gln Val Val Asn Ile Asn Thr Lys Leu Gly Tyr Asn Asn
                565                 570                 575
Ala Val Gly Ala Gly Thr Gly Ile Val Ile Asp Pro Asn Gly Val Val
            580                 585                 590
Leu Thr Asn Asn His Val Ile Ala Gly Ala Thr Asp Ile Asn Ala Phe
        595                 600                 605
Ser Val Gly Ser Gly Gln Thr Tyr Gly Val Asp Val Val Gly Tyr Asp
    610                 615                 620
```

Arg Thr Gln Asp Val Ala Val Leu Gln Leu Arg Gly Ala Gly Gly Leu
625                 630                 635                 640

Pro Ser Ala Ala Ile Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser
                725

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile
            20                  25                  30

<210> SEQ ID NO 20
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Lys Leu
            20                  25                  30

Pro Thr Val His Ile Gly Pro Thr Ala Phe Leu Gly Leu Gly Val Val
        35                  40                  45

Asp Asn Asn Gly Asn Gly Ala Arg Val Gln Arg Val Val Gly Ser Ala
    50                  55                  60

Pro Ala Ala Ser Leu Gly Ile Ser Thr Gly Asp Val Ile Thr Ala Val
65                  70                  75                  80

Asp Gly Ala Pro Ile Asn Ser Ala Thr Ala Met Ala Asp Ala Leu Asn
                85                  90                  95

Gly His His Pro Gly Asp Val Ile Ser Val Thr Trp Gln Thr Lys Ser
            100                 105                 110

Gly Gly Thr Arg Thr Gly Asn Val Thr Leu Ala Glu Gly Pro Pro Ala
        115                 120                 125

<210> SEQ ID NO 21
<211> LENGTH: 128
<212> TYPE: PRT
<213> ORGANISM: Mycobacterium tuberculosis

<400> SEQUENCE: 21

Thr Ala Ala Ser Asp Asn Phe Gln Leu Ser Gln Gly Gln Gly Phe
1               5                   10                  15

Ala Ile Pro Ile Gly Gln Ala Met Ala Ile Ala Gly Gln Ile Arg Ser
                20                  25                  30

Gly Gly Gly Ser Pro Thr Val His Ile Gly Pro Thr Ala Phe Leu Gly
            35                  40                  45

Leu Gly Val Val Asp Asn Asn Gly Asn Gly Ala Arg Val Gln Arg Val
        50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Thr Trp
                100                 105                 110

Gln Thr Lys Ser Gly Gly Thr Arg Thr Gly Asn Val Thr Leu Ala Glu
            115                 120                 125

<210> SEQ ID NO 22
<211> LENGTH: 355
<212> TYPE: PRT
<213> ORGANISM: Mycobacterium tuberculosis

<400> SEQUENCE: 22

Met Ser Asn Ser Arg Arg Arg Ser Leu Arg Trp Ser Trp Leu Leu Ser
1               5                   10                  15

Val Leu Ala Ala Val Gly Leu Gly Leu Ala Thr Ala Pro Ala Gln Ala
                20                  25                  30

Ala Pro Pro Ala Leu Ser Gln Asp Arg Phe Ala Asp Phe Pro Ala Leu
            35                  40                  45

Pro Leu Asp Pro Ser Ala Met Val Ala Gln Val Gly Pro Gln Val Val
        50                  55                  60

Asn Ile Asn Thr Lys Leu Gly Tyr Asn Asn Ala Val Gly Ala Gly Thr
65                  70                  75                  80

Gly Ile Val Ile Asp Pro Asn Gly Val Val Leu Thr Asn Asn His Val
                85                  90                  95

Ile Ala Gly Ala Thr Asp Ile Asn Ala Phe Ser Val Gly Ser Gly Gln
                100                 105                 110

Thr Tyr Gly Val Asp Val Val Gly Tyr Asp Arg Thr Gln Asp Val Ala
            115                 120                 125

Val Leu Gln Leu Arg Gly Ala Gly Gly Leu Pro Ser Ala Ala Ile Gly
        130                 135                 140

Gly Gly Val Ala Val Gly Glu Pro Val Val Ala Met Gly Asn Ser Gly
145                 150                 155                 160

Gly Gln Gly Gly Thr Pro Arg Ala Val Pro Gly Arg Val Val Ala Leu
                165                 170                 175

Gly Gln Thr Val Gln Ala Ser Asp Ser Leu Thr Gly Ala Glu Glu Thr
            180                 185                 190

Leu Asn Gly Leu Ile Gln Phe Asp Ala Ala Ile Gln Pro Gly Asp Ser
        195                 200                 205

Gly Gly Pro Val Val Asn Gly Leu Gly Gln Val Val Gly Met Asn Thr
    210                 215                 220

Ala Ala Ser Asp Asn Phe Gln Leu Ser Gln Gly Gly Gln Gly Phe Ala
225                 230                 235                 240

Ile Pro Ile Gly Gln Ala Met Ala Ile Ala Gly Gln Ile Arg Ser Gly
                245                 250                 255

Gly Gly Ser Pro Thr Val His Ile Gly Pro Thr Ala Phe Leu Gly Leu
            260                 265                 270

Gly Val Val Asp Asn Asn Gly Asn Gly Ala Arg Val Gln Arg Val Val
        275                 280                 285

Gly Ser Ala Pro Ala Ala Ser Leu Gly Ile Ser Thr Gly Asp Val Ile
    290                 295                 300

Thr Ala Val Asp Gly Ala Pro Ile Asn Ser Ala Thr Met Ala Asp
305                 310                 315                 320

Ala Leu Asn Gly His His Pro Gly Asp Val Ile Ser Val Thr Trp Gln
                325                 330                 335

Thr Lys Ser Gly Gly Thr Arg Thr Gly Asn Val Thr Leu Ala Glu Gly
            340                 345                 350

Pro Pro Ala
        355

<210> SEQ ID NO 23
<211> LENGTH: 364
<212> TYPE: PRT
<213> ORGANISM: Haemophilus influenzae

<400> SEQUENCE: 23

Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
                20                  25                  30

Ser Asp Lys Ile Ile Ile Ala His Arg Gly Ala Ser Gly Tyr Leu Pro
            35                  40                  45

Glu His Thr Leu Glu Ser Lys Ala Leu Ala Phe Ala Gln Gln Ala Asp
        50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Lys
        115                 120                 125

Asp Gly Lys Gln Ala Gln Val Tyr Pro Asn Arg Phe Pro Leu Trp Lys
    130                 135                 140

Ser His Phe Arg Ile His Thr Phe Glu Asp Glu Ile Glu Phe Ile Gln
145                 150                 155                 160

Gly Leu Glu Lys Ser Thr Gly Lys Lys Val Gly Ile Tyr Pro Glu Ile
                165                 170                 175

Lys Ala Pro Trp Phe His His Gln Asn Gly Lys Asp Ile Ala Ala Glu
            180                 185                 190

Thr Leu Lys Val Leu Lys Lys Tyr Gly Tyr Asp Lys Lys Thr Asp Met
        195                 200                 205

Val Tyr Leu Gln Thr Phe Asp Phe Asn Glu Leu Lys Arg Ile Lys Thr
    210                 215                 220

Glu Leu Leu Pro Gln Met Gly Met Asp Leu Lys Leu Val Gln Leu Ile
225                 230                 235                 240

Ala Tyr Thr Asp Trp Lys Glu Thr Gln Glu Lys Asp Pro Lys Gly Tyr
                245                 250                 255

```
Trp Val Asn Tyr Asn Tyr Asp Trp Met Phe Lys Pro Gly Ala Met Ala
            260                 265                 270

Glu Val Val Lys Tyr Ala Asp Gly Val Gly Pro Gly Trp Tyr Met Leu
            275                 280                 285

Val Asn Lys Glu Glu Ser Lys Pro Asp Asn Ile Val Tyr Thr Pro Leu
            290                 295                 300

Val Lys Glu Leu Ala Gln Tyr Asn Val Glu Val His Pro Tyr Thr Val
305                 310                 315                 320

Arg Lys Asp Ala Leu Pro Ala Phe Phe Thr Asp Val Asn Gln Met Tyr
                325                 330                 335

Asp Val Leu Leu Asn Lys Ser Gly Ala Thr Gly Val Phe Thr Asp Phe
                340                 345                 350

Pro Asp Thr Gly Val Glu Phe Leu Lys Gly Ile Lys
            355                 360

<210> SEQ ID NO 24
<211> LENGTH: 313
<212> TYPE: PRT
<213> ORGANISM: Streptococcus pneumoniae

<400> SEQUENCE: 24

Met Glu Ile Asn Val Ser Lys Leu Arg Thr Asp Leu Pro Gln Val Gly
1               5                   10                  15

Val Gln Pro Tyr Arg Gln Val His Ala His Ser Thr Gly Asn Pro His
            20                  25                  30

Ser Thr Val Gln Asn Glu Ala Asp Tyr His Trp Arg Lys Asp Pro Glu
            35                  40                  45

Leu Gly Phe Phe Ser His Ile Val Gly Asn Gly Cys Ile Met Gln Val
            50                  55                  60

Gly Pro Val Asp Asn Gly Ala Trp Asp Val Gly Gly Trp Asn Ala
65                  70                  75                  80

Glu Thr Tyr Ala Ala Val Glu Leu Ile Glu Ser His Ser Thr Lys Glu
                85                  90                  95

Glu Phe Met Thr Asp Tyr Arg Leu Tyr Ile Glu Leu Leu Arg Asn Leu
            100                 105                 110

Ala Asp Glu Ala Gly Leu Pro Lys Thr Leu Asp Thr Gly Ser Leu Ala
            115                 120                 125

Gly Ile Lys Thr His Glu Tyr Cys Thr Asn Asn Gln Pro Asn Asn His
            130                 135                 140

Ser Asp His Val Asp Pro Tyr Pro Tyr Leu Ala Lys Trp Gly Ile Ser
145                 150                 155                 160

Arg Glu Gln Phe Lys His Asp Ile Glu Asn Gly Leu Thr Ile Glu Thr
                165                 170                 175

Gly Trp Gln Lys Asn Asp Thr Gly Tyr Trp Tyr Val His Ser Asp Gly
            180                 185                 190

Ser Tyr Pro Lys Asp Lys Phe Lys Ile Asn Gly Trp Tyr Tyr
            195                 200                 205

Phe Asp Ser Ser Gly Tyr Met Leu Ala Asp Arg Trp Arg Lys His Thr
210                 215                 220

Asp Gly Asn Trp Tyr Trp Phe Asp Asn Ser Gly Glu Met Ala Thr Gly
225                 230                 235                 240

Trp Lys Lys Ile Ala Asp Lys Trp Tyr Tyr Phe Asn Glu Glu Gly Ala
                245                 250                 255

Met Lys Thr Gly Trp Val Lys Tyr Lys Asp Thr Trp Tyr Tyr Leu Asp
```

```
                     260                 265                 270
Ala Lys Glu Gly Ala Met Val Ser Asn Ala Phe Ile Gln Ser Ala Asp
                275                 280                 285

Gly Thr Gly Trp Tyr Tyr Leu Lys Pro Asp Gly Thr Leu Ala Asp Arg
            290                 295                 300

Pro Glu Phe Arg Met Ser Gln Met Ala
305                 310

<210> SEQ ID NO 25
<211> LENGTH: 166
<212> TYPE: PRT
<213> ORGANISM: Homo sapiens

<400> SEQUENCE: 25

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 26
<211> LENGTH: 233
<212> TYPE: PRT
<213> ORGANISM: Homo sapiens

<400> SEQUENCE: 26

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
```

```
                    100                 105                 110
Leu Ala Asn Gly Val Glu Leu Arg Asp Asn Gln Leu Val Pro Ser
            115                 120                 125

Glu Gly Leu Tyr Leu Ile Tyr Ser Gln Val Leu Phe Lys Gly Gln Gly
            130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
            210                 215                 220

Gln Val Tyr Phe Gly Ile Ile Ala Leu
225                 230

<210> SEQ ID NO 27
<211> LENGTH: 153
<212> TYPE: PRT
<213> ORGANISM: Homo sapiens

<400> SEQUENCE: 27

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 28
<211> LENGTH: 99
<212> TYPE: PRT
<213> ORGANISM: Homo sapiens

<400> SEQUENCE: 28

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
```

```
            35                  40                  45
Ile Lys Glu Leu Arg Val Ile Glu Ser Gly Pro His Cys Ala Asn Thr
 50                  55                  60

Glu Ile Ile Val Lys Leu Ser Asp Gly Arg Glu Leu Cys Leu Asp Pro
 65                  70                  75                  80

Lys Glu Asn Trp Val Gln Arg Val Val Glu Lys Phe Leu Lys Arg Ala
                 85                  90                  95

Glu Asn Ser

<210> SEQ ID NO 29
<211> LENGTH: 662
<212> TYPE: PRT
<213> ORGANISM: Homo sapiens

<400> SEQUENCE: 29

Met Glu Pro Leu Val Thr Trp Val Pro Leu Leu Phe Leu Phe Leu
 1               5                  10                  15

Leu Ser Arg Gln Gly Ala Ala Cys Arg Thr Ser Glu Cys Cys Phe Gln
                 20                  25                  30

Asp Pro Pro Tyr Pro Asp Ala Asp Ser Gly Ser Ala Ser Gly Pro Arg
             35                  40                  45

Asp Leu Arg Cys Tyr Arg Ile Ser Ser Asp Arg Tyr Glu Cys Ser Trp
 50                  55                  60

Gln Tyr Glu Gly Pro Thr Ala Gly Val Ser His Phe Leu Arg Cys Cys
 65                  70                  75                  80

Leu Ser Ser Gly Arg Cys Cys Tyr Phe Ala Ala Gly Ser Ala Thr Arg
                 85                  90                  95

Leu Gln Phe Ser Asp Gln Ala Gly Val Ser Val Leu Tyr Thr Val Thr
            100                 105                 110

Leu Trp Val Glu Ser Trp Ala Arg Asn Gln Thr Glu Lys Ser Pro Glu
        115                 120                 125

Val Thr Leu Gln Leu Tyr Asn Ser Val Lys Tyr Glu Pro Pro Leu Gly
    130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
            180                 185                 190

Thr Glu Ser Cys Leu Cys Pro Leu Glu Met Asn Val Ala Gln Glu Phe
        195                 200                 205

Gln Leu Arg Arg Arg Gln Leu Gly Ser Gln Gly Ser Ser Trp Ser Lys
    210                 215                 220

Trp Ser Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Arg Leu
                245                 250                 255

Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
        275                 280                 285

Leu Ser Cys Pro Cys Lys Ala Lys Ala Thr Arg Thr Leu His Leu Gly
    290                 295                 300

Lys Met Pro Tyr Leu Ser Gly Ala Ala Tyr Asn Val Ala Val Ile Ser
```

```
            305                 310                 315                 320
        Ser Asn Gln Phe Gly Pro Gly Leu Asn Gln Thr Trp His Ile Pro Ala
                        325                 330                 335

Asp Thr His Thr Glu Pro Val Ala Leu Asn Ile Ser Val Gly Thr Asn
                        340                 345                 350

Gly Thr Thr Met Tyr Trp Pro Ala Arg Ala Gln Ser Met Thr Tyr Cys
                        355                 360                 365

Ile Glu Trp Gln Pro Val Gly Gln Asp Gly Leu Ala Thr Cys Ser
            370                 375                 380

Leu Thr Ala Pro Gln Asp Pro Asp Pro Ala Gly Met Ala Thr Tyr Ser
        385                 390                 395                 400

Trp Ser Arg Glu Ser Gly Ala Met Gly Gln Glu Lys Cys Tyr Tyr Ile
                        405                 410                 415

Thr Ile Phe Ala Ser Ala His Pro Glu Lys Leu Thr Leu Trp Ser Thr
                        420                 425                 430

Val Leu Ser Thr Tyr His Phe Gly Gly Asn Ala Ser Ala Ala Gly Thr
                        435                 440                 445

Pro His His Val Ser Val Lys Asn His Ser Leu Asp Ser Val Ser Val
                        450                 455                 460

Asp Trp Ala Pro Ser Leu Leu Ser Thr Cys Pro Gly Val Leu Lys Glu
        465                 470                 475                 480

Tyr Val Val Arg Cys Arg Asp Glu Asp Ser Lys Gln Val Ser Glu His
                        485                 490                 495

Pro Val Gln Pro Thr Glu Thr Gln Val Thr Leu Ser Gly Leu Arg Ala
                        500                 505                 510

Gly Val Ala Tyr Thr Val Gln Val Arg Ala Asp Thr Ala Trp Leu Arg
                        515                 520                 525

Gly Val Trp Ser Gln Pro Gln Arg Phe Ser Ile Glu Val Gln Val Ser
                        530                 535                 540

Asp Trp Leu Ile Phe Phe Ala Ser Leu Gly Ser Phe Leu Ser Ile Leu
        545                 550                 555                 560

Leu Val Gly Val Leu Gly Tyr Leu Gly Leu Asn Arg Ala Ala Arg His
                        565                 570                 575

Leu Cys Pro Pro Leu Pro Thr Pro Cys Ala Ser Ser Ala Ile Glu Phe
                        580                 585                 590

Pro Gly Gly Lys Glu Thr Trp Gln Trp Ile Asn Pro Val Asp Phe Gln
                        595                 600                 605

Glu Glu Ala Ser Leu Gln Glu Ala Leu Val Val Glu Met Ser Trp Asp
                        610                 615                 620

Lys Gly Glu Arg Thr Glu Pro Leu Glu Lys Thr Glu Leu Pro Glu Gly
        625                 630                 635                 640

Ala Pro Glu Leu Ala Leu Asp Thr Glu Leu Ser Leu Glu Asp Gly Asp
                        645                 650                 655

Arg Cys Lys Ala Lys Met
                        660

<210> SEQ ID NO 30
<211> LENGTH: 193
<212> TYPE: PRT
<213> ORGANISM: Homo sapiens

<400> SEQUENCE: 30

Met Ala Ala Glu Pro Val Glu Asp Asn Cys Ile Asn Phe Val Ala Met
1               5                   10                  15
```

```
Lys Phe Ile Asp Asn Thr Leu Tyr Phe Ile Ala Glu Asp Glu Asn
             20                  25                  30

Leu Glu Ser Asp Tyr Phe Gly Lys Leu Glu Ser Lys Leu Ser Val Ile
         35                  40                  45

Arg Asn Leu Asn Asp Gln Val Leu Phe Ile Asp Gln Gly Asn Arg Pro
     50                  55                  60

Leu Phe Glu Asp Met Thr Asp Ser Asp Cys Arg Asp Asn Ala Pro Arg
 65                  70                  75                  80

Thr Ile Phe Ile Ile Ser Met Tyr Lys Asp Ser Gln Pro Arg Gly Met
                 85                  90                  95

Ala Val Thr Ile Ser Val Lys Cys Glu Lys Ile Ser Thr Leu Ser Cys
                100                 105                 110

Glu Asn Lys Ile Ile Ser Phe Lys Glu Met Asn Pro Pro Asp Asn Ile
             115                 120                 125

Lys Asp Thr Lys Ser Asp Ile Ile Phe Phe Gln Arg Ser Val Pro Gly
         130                 135                 140

His Asp Asn Lys Met Gln Phe Glu Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 31
<211> LENGTH: 177
<212> TYPE: PRT
<213> ORGANISM: Homo sapiens

<400> SEQUENCE: 31

Met Phe His Val Ser Phe Arg Tyr Ile Phe Gly Leu Pro Pro Leu Ile
 1               5                  10                  15

Leu Val Leu Leu Pro Val Ala Ser Ser Asp Cys Asp Ile Glu Gly Lys
             20                  25                  30

Asp Gly Lys Gln Tyr Glu Ser Val Leu Met Val Ser Ile Asp Gln Leu
         35                  40                  45

Leu Asp Ser Met Lys Glu Ile Gly Ser Asn Cys Leu Asn Asn Glu Phe
     50                  55                  60

Asn Phe Phe Lys Arg His Ile Cys Asp Ala Asn Lys Glu Gly Met Phe
 65                  70                  75                  80

Leu Phe Arg Ala Ala Arg Lys Leu Arg Gln Phe Leu Lys Met Asn Ser
                 85                  90                  95

Thr Gly Asp Phe Asp Leu His Leu Leu Lys Val Ser Glu Gly Thr Thr
                100                 105                 110

Ile Leu Leu Asn Cys Thr Gly Gln Val Lys Gly Arg Lys Pro Ala Ala
             115                 120                 125

Leu Gly Glu Ala Gln Pro Thr Lys Ser Leu Glu Glu Asn Lys Ser Leu
         130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

<210> SEQ ID NO 32
<211> LENGTH: 152
<212> TYPE: PRT
<213> ORGANISM: Homo sapiens

<400> SEQUENCE: 32

Met Ser Arg Leu Pro Val Leu Leu Leu Gln Leu Leu Val Arg Pro
1               5                   10                  15

Gly Leu Gln Ala Pro Met Thr Gln Thr Thr Ser Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 33
<211> LENGTH: 153
<212> TYPE: PRT
<213> ORGANISM: Homo sapiens

<400> SEQUENCE: 33

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 34
<211> LENGTH: 134
<212> TYPE: PRT

<213> ORGANISM: Homo sapiens

<400> SEQUENCE: 34

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser
    130

<210> SEQ ID NO 35
<211> LENGTH: 212
<212> TYPE: PRT
<213> ORGANISM: Homo sapiens

<400> SEQUENCE: 35

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met

<210> SEQ ID NO 36
<211> LENGTH: 140
<212> TYPE: PRT
<213> ORGANISM: Homo sapiens

<400> SEQUENCE: 36

```
Met Val Leu Thr Ser Ala Leu Leu Cys Ser Val Ala Gly Gln Gly
1               5                   10                  15

Cys Pro Thr Leu Ala Gly Ile Leu Asp Ile Asn Phe Leu Ile Asn Lys
            20                  25                  30

Met Gln Glu Asp Pro Ala Ser Lys Cys His Cys Ser Ala Asn Val Thr
        35                  40                  45

Ser Cys Leu Cys Leu Gly Ile Pro Ser Asp Asn Cys Thr Arg Pro Cys
    50                  55                  60

Phe Ser Glu Arg Leu Ser Gln Met Thr Asn Thr Thr Met Gln Thr Arg
65                  70                  75                  80

Tyr Pro Leu Ile Phe Ser Arg Val Lys Lys Ser Val Glu Val Leu Lys
                85                  90                  95

Asn Asn Lys Cys Pro Tyr Phe Ser Cys Glu Gln Pro Cys Asn Gln Thr
            100                 105                 110

Thr Ala Gly Asn Ala Leu Thr Phe Leu Lys Ser Leu Leu Glu Ile Phe
        115                 120                 125

Gln Lys Glu Lys Met Arg Gly Met Arg Gly Lys Ile
    130                 135                 140
```

<210> SEQ ID NO 37
<211> LENGTH: 178
<212> TYPE: PRT
<213> ORGANISM: Homo sapiens

<400> SEQUENCE: 37

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 38
<211> LENGTH: 145
<212> TYPE: PRT
<213> ORGANISM: Homo sapiens

<400> SEQUENCE: 38

Met Ala Leu Leu Leu Thr Thr Val Ile Ala Leu Thr Cys Leu Gly Gly
1               5                   10                  15

Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Gln Phe Asn Arg Asn Phe Glu Ser Ile Ile Cys Arg Asp Arg
    130                 135                 140

Thr
145

<210> SEQ ID NO 39
<211> LENGTH: 136
<212> TYPE: PRT
<213> ORGANISM: Homo sapiens

<400> SEQUENCE: 39

Met Asp Phe Gln Val Gln Ile Phe Ser Phe Leu Leu Ile Ser Ala Ser
1               5                   10                  15

Val Ile Met Ser Arg Ala Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser
    130                 135

<210> SEQ ID NO 40
<211> LENGTH: 656
<212> TYPE: PRT
<213> ORGANISM: Homo sapiens

<400> SEQUENCE: 40

```
Met Glu Gly Asp Gly Ser Asp Pro Glu Pro Pro Asp Ala Gly Glu Asp
1               5                   10                  15

Ser Lys Ser Glu Asn Gly Glu Asn Ala Pro Ile Tyr Cys Ile Cys Arg
            20                  25                  30

Lys Pro Asp Ile Asn Cys Phe Met Ile Gly Cys Asp Asn Cys Asn Glu
        35                  40                  45

Trp Phe His Gly Asp Cys Ile Arg Ile Thr Glu Lys Met Ala Lys Ala
    50                  55                  60

Ile Arg Glu Trp Tyr Cys Arg Glu Cys Arg Glu Lys Asp Pro Lys Leu
65              70                  75                  80

Glu Ile Arg Tyr Arg His Lys Lys Ser Arg Glu Arg Asp Gly Asn Glu
            85                  90                  95

Arg Asp Ser Ser Glu Pro Arg Asp Glu Gly Gly Arg Lys Arg Pro
            100                 105                 110

Val Pro Asp Pro Asn Leu Gln Arg Arg Ala Gly Ser Gly Thr Gly Val
            115                 120                 125

Gly Ala Met Leu Ala Arg Gly Ser Ala Ser Pro His Lys Ser Ser Pro
            130                 135                 140

Gln Pro Leu Val Ala Thr Pro Ser Gln His His Gln Gln Gln Gln Gln
145                 150                 155                 160

Gln Ile Lys Arg Ser Ala Arg Met Cys Gly Glu Cys Glu Ala Cys Arg
                165                 170                 175

Arg Thr Glu Asp Cys Gly His Cys Asp Phe Cys Arg Asp Met Lys Lys
            180                 185                 190

Phe Gly Gly Pro Asn Lys Ile Arg Gln Lys Cys Arg Leu Arg Gln Cys
            195                 200                 205

Gln Leu Arg Ala Arg Glu Ser Tyr Lys Tyr Phe Pro Ser Ser Leu Ser
210                 215                 220

Pro Val Thr Pro Ser Glu Ser Leu Pro Arg Pro Arg Arg Pro Leu Pro
225                 230                 235                 240

Thr Gln Gln Gln Pro Gln Pro Ser Gln Lys Leu Gly Arg Ile Arg Glu
                245                 250                 255

Asp Glu Gly Ala Val Ala Ser Ser Thr Val Lys Glu Pro Pro Glu Ala
            260                 265                 270

Thr Ala Thr Pro Glu Pro Leu Ser Asp Glu Asp Leu Pro Leu Asp Pro
            275                 280                 285

Asp Leu Tyr Gln Asp Phe Cys Ala Gly Ala Phe Asp Asp Asn Gly Leu
            290                 295                 300

Pro Trp Met Ser Asp Thr Glu Glu Ser Pro Phe Leu Asp Pro Ala Leu
305                 310                 315                 320

Arg Lys Arg Ala Val Lys Val Lys His Val Lys Arg Arg Glu Lys Lys
                325                 330                 335

Ser Glu Lys Lys Lys Glu Glu Arg Tyr Lys Arg His Arg Gln Lys Gln
            340                 345                 350

Lys His Lys Asp Lys Trp Lys His Pro Glu Arg Ala Asp Ala Lys Asp
            355                 360                 365

Pro Ala Ser Leu Pro Gln Cys Leu Gly Pro Gly Cys Val Arg Pro Ala
            370                 375                 380

Gln Pro Ser Ser Lys Tyr Cys Ser Asp Asp Cys Gly Met Lys Leu Ala
385                 390                 395                 400

Ala Asn Arg Ile Tyr Glu Ile Leu Pro Gln Arg Ile Gln Gln Trp Gln
```

```
            405                 410                 415
Gln Ser Pro Cys Ile Ala Glu Glu His Gly Lys Lys Leu Leu Glu Arg
        420                 425                 430

Ile Arg Arg Glu Gln Gln Ser Ala Arg Thr Arg Leu Gln Glu Met Glu
            435                 440                 445

Arg Arg Phe His Glu Leu Glu Ala Ile Ile Leu Arg Ala Lys Gln Gln
        450                 455                 460

Ala Val Arg Glu Asp Glu Ser Asn Glu Gly Asp Ser Asp Asp Thr
465                 470                 475                 480

Asp Leu Gln Ile Phe Cys Val Ser Cys Gly His Pro Ile Asn Pro Arg
                485                 490                 495

Val Ala Leu Arg His Met Glu Arg Cys Tyr Ala Lys Tyr Glu Ser Gln
            500                 505                 510

Thr Ser Phe Gly Ser Met Tyr Pro Thr Arg Ile Glu Gly Ala Thr Arg
        515                 520                 525

Leu Phe Cys Asp Val Tyr Asn Pro Gln Ser Lys Thr Tyr Cys Lys Arg
    530                 535                 540

Leu Gln Val Leu Cys Pro Glu His Ser Arg Asp Pro Lys Val Pro Ala
545                 550                 555                 560

Asp Glu Val Cys Gly Cys Pro Leu Val Arg Asp Val Phe Glu Leu Thr
                565                 570                 575

Gly Asp Phe Cys Arg Leu Pro Lys Arg Gln Cys Asn Arg His Tyr Cys
            580                 585                 590

Trp Glu Lys Leu Arg Arg Ala Glu Val Asp Leu Glu Arg Val Arg Val
        595                 600                 605

Trp Tyr Lys Leu Asp Glu Leu Phe Glu Gln Glu Arg Asn Val Arg Thr
    610                 615                 620

Ala Met Thr Asn Arg Ala Gly Leu Leu Ala Leu Met Leu His Gln Thr
625                 630                 635                 640

Ile Gln His Asp Pro Leu Thr Thr Asp Leu Arg Ser Ser Ala Asp Arg
                645                 650                 655

<210> SEQ ID NO 41
<211> LENGTH: 124
<212> TYPE: PRT
<213> ORGANISM: Vibrio cholerae

<400> SEQUENCE: 41

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile Tyr Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Ile Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120
```

```
<210> SEQ ID NO 42
<211> LENGTH: 258
<212> TYPE: PRT
<213> ORGANISM: Vibrio cholerae

<400> SEQUENCE: 42

Met Val Lys Ile Ile Phe Val Phe Phe Ile Phe Leu Ser Ser Phe Ser
1               5                   10                  15

Tyr Ala Asn Asp Asp Lys Leu Tyr Arg Ala Asp Ser Arg Pro Pro Asp
            20                  25                  30

Glu Ile Lys Gln Ser Gly Gly Leu Met Pro Arg Gly Gln Asn Glu Tyr
        35                  40                  45

Phe Asp Arg Gly Thr Gln Met Asn Ile Asn Leu Tyr Asp His Ala Arg
    50                  55                  60

Gly Thr Gln Thr Gly Phe Val Arg His Asp Asp Gly Tyr Val Ser Thr
65                  70                  75                  80

Ser Ile Ser Leu Arg Ser Ala His Leu Val Gly Gln Thr Ile Leu Ser
                85                  90                  95

Gly His Ser Thr Tyr Tyr Ile Tyr Val Ile Ala Thr Ala Pro Asn Met
            100                 105                 110

Phe Asn Val Asn Asp Val Leu Gly Ala Tyr Ser Pro His Pro Asp Glu
        115                 120                 125

Gln Glu Val Ser Ala Leu Gly Gly Ile Pro Tyr Ser Gln Ile Tyr Gly
    130                 135                 140

Trp Tyr Arg Val His Phe Gly Val Leu Asp Glu Gln Leu His Arg Asn
145                 150                 155                 160

Arg Gly Tyr Arg Asp Arg Tyr Tyr Ser Asn Leu Asp Ile Ala Pro Ala
                165                 170                 175

Ala Asp Gly Tyr Gly Leu Ala Gly Phe Pro Pro Glu His Arg Ala Trp
            180                 185                 190

Arg Glu Glu Pro Trp Ile His His Ala Pro Pro Gly Cys Gly Asn Ala
        195                 200                 205

Pro Arg Ser Ser Met Ser Asn Thr Cys Asp Glu Lys Thr Gln Ser Leu
    210                 215                 220

Gly Val Lys Phe Leu Asp Glu Tyr Gln Ser Lys Val Lys Arg Gln Ile
225                 230                 235                 240

Phe Ser Gly Tyr Gln Ser Asp Ile Asp Thr His Asn Arg Ile Lys Asp
                245                 250                 255

Glu Leu

<210> SEQ ID NO 43
<211> LENGTH: 124
<212> TYPE: PRT
<213> ORGANISM: Vibrio cholerae

<400> SEQUENCE: 43

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile His Thr Leu Asn Asp Lys Ile Leu Ser Tyr
        35                  40                  45

Thr Glu Ser Leu Ala Gly Asn Arg Glu Met Ala Ile Ile Thr Phe Lys
    50                  55                  60

Asn Gly Ala Thr Phe Gln Val Glu Val Pro Gly Ser Gln His Ile Asp
```

-continued

```
                65                  70                  75                  80
Ser Gln Lys Lys Ala Ile Glu Arg Met Lys Asp Thr Leu Arg Ile Ala
                    85                  90                  95

Tyr Leu Thr Glu Ala Lys Val Glu Lys Leu Cys Val Trp Asn Asn Lys
                100                 105                 110

Thr Pro His Ala Ile Ala Ala Ile Ser Met Ala Asn
                115                 120

<210> SEQ ID NO 44
<211> LENGTH: 18
<212> TYPE: PRT
<213> ORGANISM: Homo sapiens

<400> SEQUENCE: 44

Asp Pro Asn Ala Pro Lys Arg Pro Pro Ser Ala Phe Phe Leu Phe Cys
1               5                   10                  15

Ser Glu

<210> SEQ ID NO 45
<211> LENGTH: 96
<212> TYPE: PRT
<213> ORGANISM: Homo sapiens

<400> SEQUENCE: 45

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
                20                  25                  30

Cys Leu Gly Tyr Thr Asp Arg Ile Leu His Pro Lys Phe Ile Val Gly
                35                  40                  45

Phe Thr Arg Gln Leu Ala Asn Glu Gly Cys Asp Ile Asn Ala Ile Ile
            50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

<210> SEQ ID NO 46
<211> LENGTH: 92
<212> TYPE: PRT
<213> ORGANISM: Homo sapiens

<400> SEQUENCE: 46

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
                20                  25                  30

Cys Cys Phe Ser Tyr Thr Ser Arg Gln Ile Pro Gln Asn Phe Ile Ala
                35                  40                  45

Asp Tyr Phe Glu Thr Ser Ser Gln Cys Ser Lys Pro Gly Val Ile Phe
            50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90

<210> SEQ ID NO 47
<211> LENGTH: 144
```

```
<212> TYPE: PRT
<213> ORGANISM: Homo sapiens

<400> SEQUENCE: 47

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
130                 135                 140

<210> SEQ ID NO 48
<211> LENGTH: 204
<212> TYPE: PRT
<213> ORGANISM: Homo sapiens

<400> SEQUENCE: 48

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
                20                  25                  30

Leu Gly Pro Ala Ser Ser Leu Pro Gln Ser Phe Leu Leu Lys Cys Leu
            35                  40                  45

Glu Gln Val Arg Lys Ile Gln Gly Asp Gly Ala Ala Leu Gln Glu Lys
        50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200
```

```
<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Glu Ile Asn Ser Ser Tyr
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser His Pro Arg Leu Ser Ala
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Met Pro Asn Pro Met Val
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Leu Gln Gln Val Leu Leu
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

His Glu Leu Ser Val Leu Leu
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 54

Tyr Ala Pro Gln Arg Leu Pro
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Pro Arg Thr Leu Pro Thr
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Pro Val His Ser Ser Ile
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Pro Pro His Ala Leu Ser
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Phe Ser Asn Arg Phe Ile
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Val Val Pro Thr Pro Pro Tyr
1               5

<210> SEQ ID NO 60
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 60

Glu Leu Ala Pro Asp Ser Pro
1               5

<210> SEQ ID NO 61
<211> LENGTH: 69
<212> TYPE: PRT
<213> ORGANISM: Shigella dysenteriae 1

<400> SEQUENCE: 61

Thr Pro Asp Cys Val Thr Gly Lys Val Glu Tyr Thr Lys Tyr Asn Asp
1               5                   10                  15

Asp Asp Thr Phe Thr Val Lys Val Gly Asp Lys Glu Leu Phe Thr Asn
                20                  25                  30

Arg Trp Asn Leu Gln Ser Leu Leu Ser Ala Gln Ile Thr Gly Met
            35                  40                  45

Thr Val Thr Ile Lys Gln Asn Ala Cys His Asn Gly Gly Phe Ser
    50                  55                  60

Glu Val Ile Phe Arg
65

<210> SEQ ID NO 62
<211> LENGTH: 560
<212> TYPE: PRT
<213> ORGANISM: Corynephage omega

<400> SEQUENCE: 62

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
                20                  25                  30

Ser Ser Lys Ser Phe Val Met Glu Asn Phe Ser Ser Tyr His Gly Thr
            35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
                100                 105                 110

Leu Thr Lys Val Leu Ala Leu Lys Val Asp Asn Ala Glu Thr Ile Lys
            115                 120                 125

Lys Glu Leu Gly Leu Ser Leu Thr Glu Pro Leu Met Glu Gln Val Gly
        130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205
```

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
        355                 360                 365

Ile Pro Leu Val Gly Glu Leu Val Asp Ile Gly Phe Ala Ala Tyr Asn
370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
            420                 425                 430

Thr Gly Phe Gln Gly Glu Ser Gly His Asp Ile Lys Ile Thr Ala Glu
        435                 440                 445

Asn Thr Pro Leu Pro Ile Ala Gly Val Leu Leu Pro Thr Ile Pro Gly
450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
            500                 505                 510

His Val Ala Phe His Arg Ser Ser Glu Lys Ile His Ser Asn Glu
        515                 520                 525

Ile Ser Ser Asp Ser Ile Gly Val Leu Gly Tyr Gln Lys Thr Val Asp
530                 535                 540

His Thr Lys Val Asn Ser Lys Leu Ser Leu Phe Phe Glu Ile Lys Ser
545                 550                 555                 560

<210> SEQ ID NO 63
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asn Trp Val Asn Val Ile Ser Asp Leu Lys Lys Ile Glu Asp Leu Ile

```
1               5                   10                  15
Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
            50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 64
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
                35                  40                  45

Lys Ala Thr Asn Val Ala His Trp Thr Thr Pro Ser Leu Lys Cys Ile
            50                  55                  60

Arg Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
                100                 105                 110

Val Val Asp Val Ser His Glu Asp Pro Glu Val Lys Phe Asn Trp Tyr
            115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
                180                 185                 190

Pro Arg Glu Pro Gln Val Tyr Thr Leu Pro Pro Ser Arg Asp Glu Leu
            195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
```

```
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 65
<211> LENGTH: 535
<212> TYPE: PRT
<213> ORGANISM: Corynebacterium diphtheriae

<400> SEQUENCE: 65

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320
```

```
Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 66
<211> LENGTH: 1331
<212> TYPE: PRT
<213> ORGANISM: Homo Sapiens

<400> SEQUENCE: 66

Met Glu Ser His Ser Arg Ala Gly Lys Ser Arg Lys Ser Ala Lys Phe
1               5                   10                  15

Arg Ser Ile Ser Arg Ser Leu Met Leu Cys Asn Ala Lys Thr Ser Asp
            20                  25                  30

Asp Gly Ser Ser Pro Asp Glu Lys Tyr Pro Asp Pro Phe Glu Ile Ser
        35                  40                  45

Leu Ala Gln Gly Lys Glu Gly Ile Phe His Ser Ser Val Gln Leu Ala
    50                  55                  60

Asp Thr Ser Glu Ala Gly Pro Ser Ser Val Pro Asp Leu Ala Leu Ala
65                  70                  75                  80

Ser Glu Ala Ala Gln Leu Gln Ala Ala Gly Asn Asp Arg Gly Lys Thr
                85                  90                  95

Cys Arg Arg Ile Phe Phe Met Lys Glu Ser Ser Thr Ala Ser Ser Arg
            100                 105                 110

Glu Lys Pro Gly Lys Leu Glu Ala Gln Ser Ser Asn Phe Leu Phe Pro
        115                 120                 125

Lys Ala Cys His Gln Arg Ala Arg Ser Asn Ser Thr Ser Val Asn Pro
    130                 135                 140

Tyr Cys Thr Arg Glu Ile Asp Phe Pro Met Thr Lys Lys Ser Ala Ala
145                 150                 155                 160
```

```
Pro Thr Asp Arg Gln Pro Tyr Ser Leu Cys Ser Asn Arg Lys Ser Leu
                165                 170                 175

Ser Gln Gln Leu Asp Cys Pro Ala Gly Lys Ala Ala Gly Thr Ser Arg
            180                 185                 190

Pro Thr Arg Ser Leu Ser Thr Ala Gln Leu Val Gln Pro Ser Gly Gly
        195                 200                 205

Leu Gln Ala Ser Val Ile Ser Asn Ile Val Leu Met Lys Gly Gln Ala
    210                 215                 220

Lys Gly Leu Gly Phe Ser Ile Val Gly Gly Lys Asp Ser Ile Tyr Gly
225                 230                 235                 240

Pro Ile Gly Ile Tyr Val Lys Thr Ile Phe Ala Gly Gly Ala Ala Ala
                245                 250                 255

Ala Asp Gly Arg Leu Gln Glu Gly Asp Glu Ile Leu Glu Leu Asn Gly
            260                 265                 270

Glu Ser Met Ala Gly Leu Thr His Gln Asp Ala Leu Gln Lys Phe Lys
        275                 280                 285

Gln Ala Lys Lys Gly Leu Leu Thr Leu Thr Val Arg Thr Arg Leu Thr
    290                 295                 300

Ala Pro Pro Ser Leu Cys Ser His Leu Ser Pro Pro Leu Cys Arg Ser
305                 310                 315                 320

Leu Ser Ser Ser Thr Cys Ile Thr Lys Asp Ser Ser Ser Phe Ala Leu
                325                 330                 335

Glu Ser Pro Ser Ala Pro Ile Ser Thr Ala Lys Pro Asn Tyr Arg Ile
            340                 345                 350

Met Val Glu Val Ser Leu Gln Lys Glu Ala Gly Val Gly Leu Gly Ile
        355                 360                 365

Gly Leu Cys Ser Val Pro Tyr Phe Gln Cys Ile Ser Gly Ile Phe Val
    370                 375                 380

His Thr Leu Ser Pro Gly Ser Val Ala His Leu Asp Gly Arg Leu Arg
385                 390                 395                 400

Cys Gly Asp Glu Ile Val Glu Ile Ser Asp Ser Pro Val His Cys Leu
                405                 410                 415

Thr Leu Asn Glu Val Tyr Thr Ile Leu Ser Arg Cys Asp Pro Gly Pro
            420                 425                 430

Val Pro Ile Ile Val Ser Arg His Pro Asp Pro Gln Val Ser Glu Gln
        435                 440                 445

Gln Leu Lys Glu Ala Val Ala Gln Ala Val Glu Asn Thr Lys Phe Gly
    450                 455                 460

Lys Glu Arg His Gln Trp Ser Leu Glu Gly Val Lys Arg Leu Glu Ser
465                 470                 475                 480

Ser Trp His Gly Arg Pro Thr Leu Glu Lys Glu Arg Glu Lys Asn Ser
                485                 490                 495

Ala Pro Pro His Arg Ala Gln Lys Val Met Ile Arg Ser Ser Ser
            500                 505                 510

Asp Ser Ser Tyr Met Ser Gly Ser Pro Gly Gly Ser Pro Gly Ser Gly
        515                 520                 525

Ser Ala Glu Lys Pro Ser Ser Asp Val Asp Ile Ser Thr His Ser Pro
    530                 535                 540

Ser Leu Pro Leu Ala Arg Glu Pro Val Val Leu Ser Ile Ala Ser Ser
545                 550                 555                 560

Arg Leu Pro Gln Glu Ser Pro Pro Leu Pro Glu Ser Arg Asp Ser His
                565                 570                 575
```

```
Pro Pro Leu Arg Leu Lys Lys Ser Phe Glu Ile Leu Val Arg Lys Pro
            580                 585                 590

Met Ser Ser Lys Pro Lys Pro Pro Arg Lys Tyr Phe Lys Ser Asp
        595                 600                 605

Ser Asp Pro Gln Lys Ser Leu Glu Glu Arg Glu Asn Ser Ser Cys Ser
        610                 615                 620

Ser Gly His Thr Pro Thr Cys Gly Gln Glu Ala Arg Glu Leu Leu
625                 630                 635                 640

Pro Leu Leu Leu Pro Gln Glu Asp Thr Ala Gly Arg Ser Pro Ser Ala
                645                 650                 655

Ser Ala Gly Cys Pro Gly Pro Ile Gly Pro Gln Thr Lys Ser Ser
        660                 665                 670

Thr Glu Gly Glu Pro Gly Trp Arg Arg Ala Ser Pro Val Thr Gln Thr
        675                 680                 685

Ser Pro Ile Lys His Pro Leu Leu Lys Arg Gln Ala Arg Met Asp Tyr
        690                 695                 700

Ser Phe Asp Thr Thr Ala Glu Asp Pro Trp Val Arg Ile Ser Asp Cys
705                 710                 715                 720

Ile Lys Asn Leu Phe Ser Pro Ile Met Ser Glu Asn His Gly His Met
                725                 730                 735

Pro Leu Gln Pro Asn Ala Ser Leu Asn Glu Glu Glu Gly Thr Gln Gly
                740                 745                 750

His Pro Asp Gly Thr Pro Pro Lys Leu Asp Thr Ala Asn Gly Thr Pro
        755                 760                 765

Lys Val Tyr Lys Ser Ala Asp Ser Ser Thr Val Lys Lys Gly Pro Pro
770                 775                 780

Val Ala Pro Lys Pro Ala Trp Phe Arg Gln Ser Leu Lys Gly Leu Arg
785                 790                 795                 800

Asn Arg Ala Ser Asp Pro Arg Gly Leu Pro Asp Pro Ala Leu Ser Thr
                805                 810                 815

Gln Pro Ala Pro Ala Ser Arg Glu His Leu Gly Ser His Ile Arg Ala
        820                 825                 830

Ser Ser Ser Ser Ser Ser Ile Arg Gln Arg Ile Ser Ser Phe Glu Thr
835                 840                 845

Phe Gly Ser Ser Gln Leu Pro Asp Lys Gly Ala Gln Arg Leu Ser Leu
850                 855                 860

Gln Pro Ser Ser Gly Glu Ala Ala Lys Pro Leu Gly Lys His Glu Glu
865                 870                 875                 880

Gly Arg Phe Ser Gly Leu Leu Gly Arg Gly Ala Ala Pro Thr Leu Val
                885                 890                 895

Pro Gln Gln Pro Glu Gln Val Leu Ser Ser Gly Ser Pro Ala Ala Ser
        900                 905                 910

Glu Ala Arg Asp Pro Gly Val Ser Glu Ser Pro Pro Gly Arg Gln
        915                 920                 925

Pro Asn Gln Lys Thr Leu Pro Pro Gly Pro Asp Pro Leu Leu Arg Leu
        930                 935                 940

Leu Ser Thr Gln Ala Glu Glu Ser Gln Gly Pro Val Leu Lys Met Pro
945                 950                 955                 960

Ser Gln Arg Ala Arg Ser Phe Pro Leu Thr Arg Ser Gln Ser Cys Glu
                965                 970                 975

Thr Lys Leu Leu Asp Glu Lys Thr Ser Lys Leu Tyr Ser Ile Ser Ser
                980                 985                 990

Gln Val Ser Ser Ala Val Met Lys  Ser Leu Leu Cys Leu  Pro Ser Ser
```

```
                 995                1000               1005

Ile Ser Cys Ala Gln Thr Pro Cys Ile Pro Lys Glu Gly Ala Ser
         1010                1015               1020

Pro Thr Ser Ser Ser Asn Glu Asp Ser Ala Ala Asn Gly Ser Ala
         1025                1030               1035

Glu Thr Ser Ala Leu Asp Thr Gly Phe Ser Leu Asn Leu Ser Glu
         1040                1045               1050

Leu Arg Glu Tyr Thr Glu Gly Leu Thr Glu Ala Lys Glu Asp Asp
         1055                1060               1065

Asp Gly Asp His Ser Ser Leu Gln Ser Gly Gln Ser Val Ile Ser
         1070                1075               1080

Leu Leu Ser Ser Glu Glu Leu Lys Lys Leu Ile Glu Glu Val Lys
         1085                1090               1095

Val Leu Asp Glu Ala Thr Leu Lys Gln Leu Asp Gly Ile His Val
         1100                1105               1110

Thr Ile Leu His Lys Glu Glu Gly Ala Gly Leu Gly Phe Ser Leu
         1115                1120               1125

Ala Gly Gly Ala Asp Leu Glu Asn Lys Val Ile Thr Val His Arg
         1130                1135               1140

Val Phe Pro Asn Gly Leu Ala Ser Gln Glu Gly Thr Ile Gln Lys
         1145                1150               1155

Gly Asn Glu Val Leu Ser Ile Asn Gly Lys Ser Leu Lys Gly Thr
         1160                1165               1170

Thr His His Asp Ala Leu Ala Ile Leu Arg Gln Ala Arg Glu Pro
         1175                1180               1185

Arg Gln Ala Val Ile Val Thr Arg Lys Leu Thr Pro Glu Ala Met
         1190                1195               1200

Pro Asp Leu Asn Ser Ser Thr Asp Ser Ala Ala Ser Ala Ser Ala
         1205                1210               1215

Ala Ser Asp Val Ser Val Glu Ser Thr Glu Ala Thr Val Cys Thr
         1220                1225               1230

Val Thr Leu Glu Lys Met Ser Ala Gly Leu Gly Phe Ser Leu Glu
         1235                1240               1245

Gly Gly Lys Gly Ser Leu His Gly Asp Lys Pro Leu Thr Ile Asn
         1250                1255               1260

Arg Ile Phe Lys Gly Ala Ala Ser Glu Gln Ser Glu Thr Val Gln
         1265                1270               1275

Pro Gly Asp Glu Ile Leu Gln Leu Gly Gly Thr Ala Met Gln Gly
         1280                1285               1290

Leu Thr Arg Phe Glu Ala Trp Asn Ile Ile Lys Ala Leu Pro Asp
         1295                1300               1305

Gly Pro Val Thr Ile Val Ile Arg Arg Lys Ser Leu Gln Ser Lys
         1310                1315               1320

Glu Thr Thr Ala Ala Gly Asp Ser
         1325                1330

<210> SEQ ID NO 67
<211> LENGTH: 155
<212> TYPE: PRT
<213> ORGANISM: Homo Sapiens

<400> SEQUENCE: 67

Met Thr Pro Gly Lys Thr Ser Leu Val Ser Leu Leu Leu Leu Ser
1               5                   10                  15
```

```
Leu Glu Ala Ile Val Lys Ala Gly Ile Thr Ile Pro Arg Asn Pro Gly
             20                  25                  30

Cys Pro Asn Ser Glu Asp Lys Asn Phe Pro Arg Thr Val Met Val Asn
         35                  40                  45

Leu Asn Ile His Asn Arg Asn Thr Asn Thr Asn Pro Lys Arg Ser Ser
     50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                 85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 68
<211> LENGTH: 476
<212> TYPE: PRT
<213> ORGANISM: Homo Sapiens

<400> SEQUENCE: 68

Arg Ala Val Pro Gly Gly Ser Ser Pro Ala Trp Thr Gln Cys Gln Gln
 1               5                  10                  15

Leu Ser Gln Lys Leu Cys Thr Leu Ala Trp Ser Ala His Pro Leu Val
             20                  25                  30

Gly His Met Asp Leu Arg Glu Glu Gly Asp Glu Thr Thr Asn Asp
         35                  40                  45

Val Pro His Ile Gln Cys Gly Asp Gly Cys Asp Pro Gln Gly Leu Arg
     50                  55                  60

Asp Asn Ser Gln Phe Cys Leu Gln Arg Ile His Gln Gly Leu Ile Phe
 65                  70                  75                  80

Tyr Glu Lys Leu Leu Gly Ser Asp Ile Phe Thr Gly Glu Pro Ser Leu
                 85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro Ile Trp Glu Leu Lys Lys
                165                 170                 175

Asp Val Tyr Val Val Glu Leu Asp Trp Tyr Pro Asp Ala Pro Gly Glu
            180                 185                 190

Met Val Val Leu Thr Cys Asp Thr Pro Glu Glu Asp Gly Ile Thr Trp
        195                 200                 205

Thr Leu Asp Gln Ser Ser Glu Val Leu Gly Ser Gly Lys Thr Leu Thr
    210                 215                 220

Ile Gln Val Lys Glu Phe Gly Asp Ala Gly Gln Tyr Thr Cys His Lys
225                 230                 235                 240
```

```
Gly Gly Glu Val Leu Ser His Ser Leu Leu Leu His Lys Lys Glu
            245                 250                 255

Asp Gly Ile Trp Ser Thr Asp Ile Leu Lys Asp Gln Lys Glu Pro Lys
            260                 265                 270

Asn Lys Thr Phe Leu Arg Cys Glu Ala Lys Asn Tyr Ser Gly Arg Phe
            275                 280                 285

Thr Cys Trp Trp Leu Thr Thr Ile Ser Thr Asp Leu Thr Phe Ser Val
            290                 295                 300

Lys Ser Ser Arg Gly Ser Ser Asp Pro Gln Gly Val Thr Cys Gly Ala
305                 310                 315                 320

Ala Thr Leu Ser Ala Glu Arg Val Arg Gly Asp Asn Lys Glu Tyr Glu
                325                 330                 335

Tyr Ser Val Glu Cys Gln Glu Asp Ser Ala Cys Pro Ala Ala Glu Glu
            340                 345                 350

Ser Leu Pro Ile Glu Val Met Val Asp Ala Val His Lys Leu Lys Tyr
            355                 360                 365

Glu Asn Tyr Thr Ser Ser Phe Phe Ile Arg Asp Ile Ile Lys Pro Asp
            370                 375                 380

Pro Pro Lys Asn Leu Gln Leu Lys Pro Leu Lys Asn Ser Arg Gln Val
385                 390                 395                 400

Glu Val Ser Trp Glu Tyr Pro Asp Thr Trp Ser Thr Pro His Ser Tyr
                405                 410                 415

Phe Ser Leu Thr Phe Cys Val Gln Val Gln Gly Lys Ser Lys Arg Glu
            420                 425                 430

Lys Lys Asp Arg Val Phe Thr Asp Lys Thr Ser Ala Thr Val Ile Cys
            435                 440                 445

Arg Lys Asn Ala Ser Ile Ser Val Arg Ala Gln Asp Arg Tyr Tyr Ser
450                 455                 460

Ser Ser Trp Ser Glu Trp Ala Ser Val Pro Cys Ser
465                 470                 475

<210> SEQ ID NO 69
<211> LENGTH: 234
<212> TYPE: PRT
<213> ORGANISM: Homo Sapiens

<400> SEQUENCE: 69

Met Cys Phe Pro Lys Val Leu Ser Asp Asp Met Lys Lys Leu Lys Ala
1               5                   10                  15

Arg Met Val Met Leu Leu Pro Thr Ser Ala Gln Gly Leu Gly Ala Trp
            20                  25                  30

Val Ser Ala Cys Asp Thr Glu Asp Thr Val Gly His Leu Gly Pro Trp
        35                  40                  45

Arg Asp Lys Asp Pro Ala Leu Trp Cys Gln Leu Cys Leu Ser Ser Gln
    50                  55                  60

His Gln Ala Ile Glu Arg Phe Tyr Asp Lys Met Gln Asn Ala Glu Ser
65                  70                  75                  80

Gly Arg Gly Gln Val Met Ser Ser Leu Ala Glu Leu Glu Asp Asp Phe
                85                  90                  95

Lys Glu Gly Tyr Leu Glu Thr Val Ala Ala Tyr Tyr Glu Glu Gln His
            100                 105                 110

Pro Glu Leu Thr Pro Leu Leu Glu Lys Glu Arg Asp Gly Leu Arg Cys
            115                 120                 125

Arg Gly Asn Arg Ser Pro Val Pro Asp Val Glu Asp Pro Ala Thr Glu
```

```
                130                 135                 140
Glu Pro Gly Glu Ser Phe Cys Asp Lys Val Met Arg Trp Phe Gln Ala
145                 150                 155                 160

Met Leu Gln Arg Leu Gln Thr Trp Trp His Gly Val Leu Ala Trp Val
                165                 170                 175

Lys Glu Lys Val Val Ala Leu Val His Ala Val Gln Ala Leu Trp Lys
                180                 185                 190

Gln Phe Gln Ser Phe Cys Cys Ser Leu Ser Glu Leu Phe Met Ser Ser
            195                 200                 205

Phe Gln Ser Tyr Gly Ala Pro Arg Gly Asp Lys Glu Glu Leu Thr Pro
            210                 215                 220

Gln Lys Cys Ser Glu Pro Gln Ser Ser Lys
225                 230

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Met Ala Val Pro Met Gln Leu Ser Cys Ser Arg
1               5                   10

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Ser Thr Gly
1

<210> SEQ ID NO 72
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Arg
1

<210> SEQ ID NO 73
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ser Gln
1

<210> SEQ ID NO 74
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ser Ala Gly Glu
1               5

<210> SEQ ID NO 75
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Ser
1

<210> SEQ ID NO 76
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly
1

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Ser Gly Gly Ser Gly Gly Ser Gly
1               5

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Gly Ser Gly Gly Ser Gly Gly Ser Gly Gly
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Gly Ser Gly Gly Ser Gly Gly Ser Gly Gly Ser Gly Gly
```

```
1               5                   10
```

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Gly Gly Ser Gly Gly Ser Gly Gly Ser Gly Gly Ser Gly Gly Ser Gly
1               5                   10                  15

Gly
```

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Gly Gly Ser Gly Gly Ser Gly Gly Ser Gly Gly Ser Gly Gly Ser Gly
1               5                   10                  15

Gly Ser Gly Gly
            20
```

<210> SEQ ID NO 82
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

```
Gly Gly Ser Gly Gly Ser Gly Gly Ser Gly Gly Ser Gly Gly Ser Gly
1               5                   10                  15

Gly Ser Gly Gly Ser Gly Gly
            20
```

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

```
Gly Gly Ser Gly Gly Ser Gly Gly Ser Gly Gly Ser Gly Gly Ser Gly
1               5                   10                  15
```

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Gly Ser Gly Gly Ser Gly Gly Ser Gly Gly Ser Gly Gly Ser Gly Gly
1               5                   10                  15
```

-continued

```
<210> SEQ ID NO 85
<211> LENGTH: 410
<212> TYPE: PRT
<213> ORGANISM: Homo sapiens

<400> SEQUENCE: 85

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
                20                  25                  30

Glu Lys Gly Asp Pro Thr Glu Arg Glu Leu Arg Val Gly Leu Glu Glu
            35                  40                  45

Ser Glu Leu Trp Leu Arg Phe Lys Glu Leu Thr Asn Glu Met Ile Val
        50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Arg Ser Asp His Lys Glu Met Met Glu Glu Pro
        195                 200                 205

Gly Asp Ser Gln Gln Pro Gly Tyr Ser Gln Trp Gly Trp Leu Leu Pro
    210                 215                 220

Gly Thr Ser Thr Val Cys Pro Pro Ala Asn Pro His Pro Gln Phe Gly
225                 230                 235                 240

Gly Ala Leu Ser Leu Pro Ser Thr His Ser Cys Asp Arg Tyr Pro Thr
                245                 250                 255

Leu Arg Ser His Arg Ser Ser Pro Tyr Pro Ser Pro Tyr Ala His Arg
            260                 265                 270

Asn Asn Ser Pro Thr Tyr Ser Asp Asn Ser Pro Ala Cys Leu Ser Met
        275                 280                 285

Leu Gln Ser His Asp Asn Trp Ser Ser Leu Gly Met Pro Ala His Pro
    290                 295                 300

Ser Met Leu Pro Val Ser His Asn Ala Ser Pro Pro Thr Ser Ser Ser
305                 310                 315                 320

Gln Tyr Pro Ser Leu Trp Ser Val Ser Asn Gly Ala Val Thr Pro Gly
                325                 330                 335

Ser Gln Ala Ala Ala Val Ser Asn Gly Leu Gly Ala Gln Phe Phe Arg
            340                 345                 350

Gly Ser Pro Ala His Tyr Thr Pro Leu Thr His Pro Val Ser Ala Pro
        355                 360                 365

Ser Ser Ser Gly Ser Pro Leu Tyr Glu Gly Ala Ala Ala Ala Thr Asp
```

```
            370                 375                  380
Ile Val Asp Ser Gln Tyr Asp Ala Ala Gln Gly Arg Leu Ile Ala
385                      390                  395                 400

Ser Trp Thr Pro Val Ser Pro Pro Ser Met
                    405                 410

<210> SEQ ID NO 86
<211> LENGTH: 1342
<212> TYPE: PRT
<213> ORGANISM: Homo sapiens

<400> SEQUENCE: 86

Met Arg Ala Asn Asp Ala Leu Gln Val Leu Gly Leu Leu Phe Ser Leu
1                   5                   10                  15

Ala Arg Gly Ser Glu Val Gly Asn Ser Gln Ala Val Cys Pro Gly Thr
                20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335
```

```
Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
            610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
            690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
```

-continued

```
            755                 760                 765
Ala His Ile Val Arg Leu Leu Gly Leu Cys Pro Gly Ser Ser Leu Gln
            770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Asn Trp Gly Val
                    805                 810                 815

Gln Ile Ala Lys Gly Met Tyr Tyr Leu Glu Glu His Gly Met Val His
                    820                 825                 830

Arg Asn Leu Ala Ala Arg Asn Val Leu Leu Lys Ser Pro Ser Gln Val
                    835                 840                 845

Gln Val Ala Asp Phe Gly Val Ala Asp Leu Leu Pro Pro Asp Asp Lys
850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                    885                 890                 895

Tyr Gly Val Thr Val Trp Glu Leu Met Thr Phe Gly Ala Glu Pro Tyr
                    900                 905                 910

Ala Gly Leu Arg Leu Ala Glu Val Pro Asp Leu Leu Glu Lys Gly Glu
                    915                 920                 925

Arg Leu Ala Gln Pro Gln Ile Cys Thr Ile Asp Val Tyr Met Val Met
930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                    965                 970                 975

Val Ile Lys Arg Glu Ser Gly Pro Gly Ile Ala Pro Gly Pro Glu Pro
                    980                 985                 990

His Gly Leu Thr Asn Lys Lys Leu Glu Glu Val Glu Leu Glu Pro Glu
                    995                 1000                1005

Leu Asp Leu Asp Leu Asp Leu Glu Ala Glu Glu Asp Asn Leu Ala
     1010                1015                1020

Thr Thr Thr Leu Gly Ser Ala Leu Ser Leu Pro Val Gly Thr Leu
     1025                1030                1035

Asn Arg Pro Arg Gly Ser Gln Ser Leu Leu Ser Pro Ser Ser Gly
     1040                1045                1050

Tyr Met Pro Met Asn Gln Gly Asn Leu Gly Glu Ser Cys Gln Glu
     1055                1060                1065

Ser Ala Val Ser Gly Ser Ser Glu Arg Cys Pro Arg Pro Val Ser
     1070                1075                1080

Leu His Pro Met Pro Arg Gly Cys Leu Ala Ser Glu Ser Ser Glu
     1085                1090                1095

Gly His Val Thr Gly Ser Glu Ala Glu Leu Gln Glu Lys Val Ser
     1100                1105                1110

Met Cys Arg Ser Arg Ser Arg Ser Arg Ser Pro Arg Pro Arg Gly
     1115                1120                1125

Asp Ser Ala Tyr His Ser Gln Arg His Ser Leu Leu Thr Pro Val
     1130                1135                1140

Thr Pro Leu Ser Pro Pro Gly Leu Glu Glu Glu Asp Val Asn Gly
     1145                1150                1155

Tyr Val Met Pro Asp Thr His Leu Lys Gly Thr Pro Ser Ser Arg
     1160                1165                1170
```

Glu Gly Thr Leu Ser Ser Val Gly Leu Ser Ser Val Leu Gly Thr
    1175                1180                1185

Glu Glu Glu Asp Glu Asp Glu Glu Tyr Glu Tyr Met Asn Arg Arg
    1190                1195                1200

Arg Arg His Ser Pro Pro His Pro Pro Arg Pro Ser Ser Leu Glu
    1205                1210                1215

Glu Leu Gly Tyr Glu Tyr Met Asp Val Gly Ser Asp Leu Ser Ala
    1220                1225                1230

Ser Leu Gly Ser Thr Gln Ser Cys Pro Leu His Pro Val Pro Ile
    1235                1240                1245

Met Pro Thr Ala Gly Thr Thr Pro Asp Glu Asp Tyr Glu Tyr Met
    1250                1255                1260

Asn Arg Gln Arg Asp Gly Gly Gly Pro Gly Gly Asp Tyr Ala Ala
    1265                1270                1275

Met Gly Ala Cys Pro Ala Ser Glu Gln Gly Tyr Glu Glu Met Arg
    1280                1285                1290

Ala Phe Gln Gly Pro Gly His Gln Ala Pro His Val His Tyr Ala
    1295                1300                1305

Arg Leu Lys Thr Leu Arg Ser Leu Glu Ala Thr Asp Ser Ala Phe
    1310                1315                1320

Asp Asn Pro Asp Tyr Trp His Ser Arg Leu Phe Pro Lys Ala Asn
    1325                1330                1335

Ala Gln Arg Thr
    1340

<210> SEQ ID NO 87
<211> LENGTH: 663
<212> TYPE: PRT
<213> ORGANISM: Homo sapiens

<400> SEQUENCE: 87

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly

-continued

```
                180                 185                 190
Arg Cys Trp Gly Pro Gly Ser Glu Asp Cys Gln Thr Leu Thr Lys Thr
            195                 200                 205
Ile Cys Ala Pro Gln Cys Asn Gly His Cys Phe Gly Pro Asn Pro Asn
        210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
        275                 280                 285
Ser Cys Pro His Asn Phe Val Val Asp Gln Thr Ser Cys Val Arg Ala
        290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                325                 330                 335
Gly Ser Arg Phe Gln Thr Val Asp Ser Ser Asn Ile Asp Gly Phe Val
            340                 345                 350
Asn Cys Thr Lys Ile Leu Gly Asn Leu Asp Phe Leu Ile Thr Gly Leu
        355                 360                 365
Asn Gly Asp Pro Trp His Lys Ile Pro Ala Leu Asp Pro Glu Lys Leu
    370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
            420                 425                 430
Met Lys Asn Leu Asn Val Thr Ser Leu Gly Phe Arg Ser Leu Lys Glu
        435                 440                 445
Ile Ser Ala Gly Arg Ile Tyr Ile Ser Ala Asn Arg Gln Leu Cys Tyr
        450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                485                 490                 495
Gly Lys Val Cys Asp Pro Leu Cys Ser Ser Gly Gly Cys Trp Gly Pro
            500                 505                 510
Gly Pro Gly Gln Cys Leu Ser Cys Arg Asn Tyr Ser Arg Gly Gly Val
        515                 520                 525
Cys Val Thr His Cys Asn Phe Leu Asn Gly Glu Pro Arg Glu Phe Ala
        530                 535                 540
His Glu Ala Glu Cys Phe Ser Cys His Pro Glu Cys Gln Pro Met Glu
545                 550                 555                 560
Gly Thr Ala Thr Cys Asn Gly Ser Gly Ser Asp Thr Cys Ala Gln Cys
                565                 570                 575
Ala His Phe Arg Asp Gly Pro His Cys Val Ser Ser Cys Pro His Gly
            580                 585                 590
Val Leu Gly Ala Lys Gly Pro Ile Tyr Lys Tyr Pro Asp Val Gln Asn
        595                 600                 605
```

```
Glu Cys Arg Pro Cys His Glu Asn Cys Thr Gln Gly Cys Lys Gly Pro
    610                 615                 620
Glu Leu Gln Asp Cys Leu Gly Gln Thr Leu Val Leu Ile Gly Lys Thr
625                 630                 635                 640
His Leu Thr Met Ala Leu Thr Val Ile Ala Gly Leu Val Val Ile Phe
                645                 650                 655
Met Met Leu Gly Gly Thr Phe
            660

<210> SEQ ID NO 88
<211> LENGTH: 9
<212> TYPE: DNA
<213> ORGANISM: Gallus gallus
<220> FEATURE:
<221> NAME/KEY: modified_base
<222> LOCATION: (8)..(8)
<223> OTHER INFORMATION: a, c, t, g, unknown or other

<400> SEQUENCE: 88 tctctccna                                                                 9

<210> SEQ ID NO 89
<211> LENGTH: 32040
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
```

| | | | | |
|---|---|---|---|---|
| catcatcaat | aatatacctt | attttggatt | gaagccaata | tgataatgag ggggtggagt | 60 |
| ttgtgacgtg | gcgcggggcg | tgggaacggg | gcgggtgacg | tagtagtgtg gcggaagtgt | 120 |
| gatgttgcaa | gtgtggcgga | acacatgtaa | gcgacggatg | tggcaaaagt gacgtttttg | 180 |
| gtgtgcgccg | gtgtacacag | gaagtgacaa | ttttcgcgcg | gttttaggcg gatgttgtag | 240 |
| taaatttggg | cgtaaccgag | taagatttgg | ccattttcgc | gggaaaactg aataagagga | 300 |
| agtgaaatct | gaataatttt | gtgttactca | tagcgcgtaa | tactgtaata gtaatcaatt | 360 |
| acggggtcat | tagttcatag | cccatatatg | gagttccgcg | ttacataact tacggtaaat | 420 |
| ggcccgcctg | gctgaccgcc | caacgacccc | gcccattga | cgtcaataat gacgtatgtt | 480 |
| cccatagtaa | cgccaatagg | gactttccat | tgacgtcaat | gggtggagta tttacggtaa | 540 |
| actgcccact | tggcagtaca | tcaagtgtat | catatgccaa | gtacgccccc tattgacgtc | 600 |
| aatgacggta | aatggcccgc | ctggcattat | gcccagtaca | tgaccttatg ggactttcct | 660 |
| acttggcagt | acatctacgt | attagtcatc | gctattacca | tggtgatgcg gttttggcag | 720 |
| tacatcaatg | ggcgtggata | gcggtttgac | tcacggggat | ttccaagtct ccaccccatt | 780 |
| gacgtcaatg | ggagtttgtt | ttggcaccaa | aatcaacggg | actttccaaa atgtcgtaac | 840 |
| aactccgccc | cattgacgca | aatgggcggt | aggcgtgtac | ggtgggaggt ctatataagc | 900 |
| agagctggtt | tagtgaaccg | tcagatccgc | tagagatctg | gtaccgtcga cgcggccgct | 960 |
| cgagcctaag | cttctagatg | catgctcgag | cggccgccag | tgtgatggat atctgcagaa | 1020 |
| ttcgcccttg | ctcgctccac | ctctcaagca | gccagcgcct | gcctgaatct gttctgcccc | 1080 |
| ctcccccaccc | atttcaccac | caccatgaca | ccgggcaccc | agtctccttt cttcctgctg | 1140 |
| ctgctcctca | cagtgcttac | agttgttacg | ggttctggtc | atgcaagctc taccccaggt | 1200 |
| ggagaaaagg | agacttcggc | tacccagaga | agttcagtgc | ccagctctac tgagaagaat | 1260 |

```
gctgtgagta tgaccagcag cgtactctcc agccacagcc ccggttcagg ctcctccacc   1320
actcagggac aggatgtcac tctggccccg gccacggaac cagcttcagg ttcagctgcc   1380
ctttggggac aggatgtcac ctcggtccca gtcaccaggc cagccctggg ctccaccacc   1440
ccgccagccc acgatgtcac ctcagcccg gacaacaagc cagccccggg ctccaccgcc    1500
cccccagccc acggtgtcac ctcgtatctt gacaccaggc cggccccggt ttatcttgcc   1560
cccccagccc atggtgtcac ctcggccccg gacaacaggc cgccttggg ctccaccgcc    1620 cctccagtcc acaatgtcac ctcggcctca ggctctgcat caggctcagc ttctactctg   1680
gtgcacaacg gcacctctgc cagggctacc acaaccccag ccagcaagag cactccattc   1740
tcaattccca gccaccactc tgatactcct accaccctg ccagccatag caccaagact    1800
gatgccagta gcactcacca tagcacggta cctcctctca cctcctccaa tcacagcact   1860
tctccccagt tgtctactgg ggtctctttc ttttttcctgt cttttcacat ttcaaacctc   1920
cagtttaatt cctctctgga agatcccagc accgactact accaagagct gcagagagac   1980
atttctgaaa tgttttgca gatttataaa caagggggtt ttctgggcct ctccaatatt    2040
aagttcaggc caggatctgt ggtggtacaa ttgactctgg ccttccgaga aggtaccatc    2100
aatgtccacg acgtggagac acagttcaat cagtataaaa cggaagcagc ctctcgatat   2160
aacctgacga tctcagacgt cagcgtgagt gatgtgccat ttccttctc tgcccagtct    2220 ggggctgggg tgccaggctg gggcatcgcg ctgctggtgc tggtctgtgt tctggtttat   2280
ctggccattg tctatctcat tgccttggct gtcgctcagg ttcgccgaaa gaactacggg   2340
cagctggaca tctttccagc ccgggataaa taccatccta tgagcgagta cgctctttac   2400
cacacccatg gcgctatgt gccccctagc agtcttttcc gtagccccta tgagaaggtt    2460
tctgcaggta atggtggcag ctatctctct tacacaaacc cagcagtggc agccgcttct   2520
gccaacttgt aggggcacgt cgcccgctga gctgagtggc cagccagtgc cattccactc   2580
cactcaggtt cttcagggcc agagccctg caccctgttt gggctggtga ctgggagtt     2640 caggtgggct gctcacagcc tccttcagag gccccaccaa tttctcggac acttctcagt   2700
gtgtggaagc tcatgtgggc ccctgagggc tcatgcctgg gaagtgttgt ggtggggct    2760 cccaggagga ctggcccaga gagccctgag atagcgggga tcctgaactg gactgaataa   2820
aacgtggtct cccactgcgc caaaaaaaaa aaaaaaacg atccaccgga tctagataac    2880
tgatcataat cagccatacc acatttgtag aggttttact tgctttaaaa aacctcccac   2940
acctccccct gaacctgaaa cataaaatga atgcaattgt tgttgttaac ttgtttattg    3000
cagcttataa tggttacaaa taaagcaata gcatcacaaa tttcacaaat aaagcatttt   3060
tttcactgca ttctagttgt ggtttgtcca aactcatcaa tgtatcttaa cgcggatctg   3120
gaaggtgctg aggtacgatg agacccgcac caggtgcaga ccctgcgagt gtggcggtaa   3180
acatattagg aaccagcctg tgatgctgga tgtgaccgag gagctgaggc ccgatcactt   3240
ggtgctggcc tgcacccgcg ctgagtttgg ctctagcgat gaagatacag attgaggtac   3300
tgaaatgtgt gggcgtggct taagggtggg aaagaatata taaggtgggg gtcttatgta   3360
gttttgtatc tgttttgcag cagccgccgc cgccatgagc accaactcgt tgatggaag    3420 cattgtgagc tcatatttga caacgcgcat gccccatgg gccggggtgc gtcagaatgt    3480
gatgggctcc agcattgatg gtcgcccgt cctgccgca aactctacta ccttgaccta     3540
cgagaccgtg tctggaacgc cgttggagac tgcagcctcc gccgccgctt cagccgctgc   3600
```

-continued

```
agccaccgcc cgcgggattg tgactgactt tgctttcctg agcccgcttg caagcagtgc    3660
agcttcccgt tcatccgccc gcgatgacaa gttgacggct cttttggcac aattggattc    3720
tttgacccgg gaacttaatg tcgtttctca gcagctgttg gatctgcgcc agcaggtttc    3780
tgccctgaag gcttcctccc ctcccaatgc ggtttaaaac ataaataaaa aaccagactc    3840
tgtttggatt tggatcaagc aagtgtcttg ctgtctttat ttaggggttt tgcgcgcgcg    3900
gtaggcccgg gaccagcggt ctcggtcgtt gagggtcctg tgtattttt ccaggacgtg     3960 gtaaaggtga ctctggatgt tcagatacat gggcataagc ccgtctctgg ggtggaggta    4020
gcaccactgc agagcttcat gctgcggggt ggtgttgtag atgatccagt cgtagcagga    4080
gcgctgggcg tggtgcctaa aaatgtcttt cagtagcaag ctgattgcca ggggcaggcc    4140
cttggtgtaa gtgtttacaa agcggttaag ctgggatggg tgcatacgtg gggatatgag    4200
atgcatcttg gactgtattt ttaggttggc tatgttccca gccatatccc tccgggatt     4260 catgttgtgc agaaccacca gcacagtgta tccggtgcac ttgggaaatt tgtcatgtag    4320
cttagaagga aatgcgtgga agaacttgga gacgcccttg tgacctccaa gattttccat    4380
gcattcgtcc ataatgatgg caatgggccc acgggcggcg gcctgggcga agatatttct    4440
gggatcacta acgtcatagt tgtgttccag gatgagatcg tcataggcca ttttacaaa     4500 gcgcgggcgg agggtgccag actgcggtat aatggttcca tccggcccag gggcgtagtt    4560
accctcacag atttgcattt cccacgcttt gagttcagat gggggatca tgtctacctg     4620 cggggcgatg aagaaaacgg tttccggggt aggggagatc agctgggaag aaagcaggtt    4680
cctgagcagc tgcgacttac cgcagccggt gggcccgtaa atcacaccta ttaccggctg    4740
caactggtag ttaagagagc tgcagctgcc gtcatccctg agcaggggg ccacttcgtt     4800 aagcatgtcc ctgactcgca tgttttccct gaccaaatcc gccagaaggc gctcgccgcc    4860
cagcgatagc agttcttgca aggaagcaaa gttttcaac ggtttgagac cgtccgccgt     4920
aggcatgctt tgagcgtttg accaagcag ttccaggcgg tcccacagct cggtcacctg     4980
ctctacggca tctcgatcca gcatatctcc tcgtttcgcg ggttggggcg ctttcgctg     5040 tacggcagta gtcggtgctc gtccagacgg gccagggtca tgtctttcca cgggcgcagg    5100
gtcctcgtca gcgtagtctg ggtcacggtg aaggggtgcg ctccgggctg cgcgctggcc    5160
agggtgcgct tgaggctggt cctgctggtg ctgaagcgct gccggtcttc gccctgcgcg    5220
tcggccaggt agcatttgac catggtgtca tagtccagcc cctccgcggc gtggcccttg    5280
gcgcgcagct gcccttgga ggaggcgccg cacgaggggc agtgcagact tttgagggcg     5340
tagagcttgg gcgcgagaaa taccgattcc ggggagtagg catccgcgcc gcaggccccg    5400
cagacggtct cgcattccac gagccaggtg agctctggcc gttcggggtc aaaaaccagg    5460 tttccccat gcttttgat gcgtttctta cctctggttt ccatgagccg tgtccacgc       5520 tcggtgacga aaaggctgtc cgtgtcccg tatacagact tgagaggcct gtcctcgagc     5580
ggtgttccgc ggtcctcctc gtatagaaac tcggaccact ctgagacaaa ggctcgcgtc    5640
caggccagca cgaaggaggc taagtgggag gggtagcggt cgttgtccac tagggggtcc    5700
actcgctcca gggtgtgaag acacatgtcg ccctcttcgg catcaaggaa ggtgattggt    5760
ttgtaggtgt aggccacgtg accgggtgtt cctgaagggg ggctataaaa gggggtgggg    5820
gcgcgttcgt cctcactctc ttccgcatcg ctgtctgcga gggccagctg ttggggtgag    5880
tactccctct gaaaagcggg catgacttct gcgctaagat tgtcagtttc caaaaacgag    5940
gaggatttga tattcacctg gcccgcggtg atgcctttga gggtggccgc atccatctgg    6000
```

```
tcagaaaaga caatctttt gttgtcaagc ttggtggcaa acgacccgta gagggcgttg    6060
gacagcaact tggcgatgga gcgcagggtt tggttttgt cgcgatcggc gcgctccttg    6120
gccgcgatgt ttagctgcac gtattcgcgc gcaacgcacc gccattcggg aaagacggtg    6180
gtgcgctcgt cgggcaccag gtgcacgcgc caaccgcgcg tgtgcagggt gacaaggtca    6240
acgctggtgg ctacctctcc gcgtaggcgc tcgttggtcc agcagaggcg gccgcccttg    6300
cgcgagcaga atggcggtag ggggtctagc tgcgtctcgt ccgggggggtc tgcgtccacg    6360
gtaaagaccc cgggcagcag gcgcgcgtcg aagtagtcta tcttgcatcc ttgcaagtct    6420
agcgcctgct gccatgcgcg ggcggcaagc gcgcgctcgt atgggttgag tgggggaccc    6480
catggcatgg ggtgggtgag cgcggaggcg tacatgccgc aaatgtcgta acgtagagg    6540
ggctctctga gtattccaag atatgtaggg tagcatcttc caccgcggat gctggcgcgc    6600
acgtaatcgt atagttcgtg cgagggagcg aggaggtcgg gaccgaggtt gctacgggcg    6660
ggctgctctg ctcggaagac tatctgcctg aagatggcat gtgagttgga tgatatggtt    6720
ggacgctgga agacgttgaa gctggcgtct gtgagaccta ccgcgtcacg cacgaaggag    6780
gcgtaggagt cgcgcagctt gttgaccagc tcggcggtga cctgcacgtc tagggcgcag    6840
tagtccaggg tttccttgat gatgtcatac ttatcctgtc cctttttttt ccacagctcg    6900
cggttgagga caaactcttc gcggtctttc cagtactctt ggatcggaaa cccgtcggcc    6960
tccgaacggt aagagcctag catgtagaac tggttgacgg cctggtaggc gcagcatccc    7020
ttttctacgg gtagcgcgta tgcctgcgcg gccttccggc atgaccagca tgaagggcac    7080
gagctgcttc ccaaaggccc ccatccaagt ataggtctct acatcgtagg tgacaaagag    7140
acgctcggtg cgaggatgcg agccgatcgg gaagaactgg atctcccgcc accaattgga    7200
ggagtggcta ttgatgtggt gaaagtagaa gtccctgcga cgggccgaac actcgtgctg    7260
gcttttgtaa aaacgtgcgc agtactggca gcggtgcacg ggctgtacat cctgcacgag    7320
gttgacctga cgaccgcgca caaggaagca gagtgggaat ttgagcccct cgcctggcgg    7380
gtttggctgg tggtcttcta cttcggctgc ttgtccttga ccgtctggct gctcgagggg    7440
agttacggtg gatcggacca ccacgccgcg cgagcccaaa gtccagatgt ccgcgcgcgg    7500
cggtcggagc ttgatgacaa catcgcgcag atgggagctg tccatggtct ggagctcccg    7560
cggcgtcagg tcaggcggga gctcctgcag gtttacctcg catagacggg tcagggcgcg    7620
ggctagatcc aggtgatacc taatttccag gggctggttg gtggcggcgt cgatggcttg    7680
caagaggccg catccccgcg gcgcgactac ggtaccgcgc ggcgggcggt gggccgcggg    7740
ggtgtccttg gatgatgcat ctaaaagcgg tgacgcgggc gagccccgg aggtaggggg    7800
ggctccggac ccgccgggag aggggcagg ggcacgtcgg cgccgcgcgc gggcaggagc    7860
tggtgctgcg cgcgtaggtt gctggcgaac gcgacgacgc ggcggttgat ctcctgaatc    7920
tggcgcctct gcgtgaagac gacgggcccg gtgagcttga acctgaaaga gagttcgaca    7980
gaatcaattt cggtgtcgtt gacggcggcc tggcgcaaaa tctcctgcac gtctcctgag    8040
ttgtcttgat aggcgatctc ggccatgaac tgctcgatct cttcctcctg gagatctccg    8100
cgtccggctc gctccacggt ggcggcgagg tcgttggaaa tgcgggccat gagctgcgag    8160
aaggcgttga ggcctccctc gttccagacg cggctgtaga ccacgccccc ttcggcatcg    8220
cgggcgcgca tgaccacctg cgcgagattg agctccacgt gccgggcgaa gacggcgtag    8280
tttcgcaggc gctgaaagag gtagttgagg gtggtggcgg tgtgttctgc cacgaagaag    8340
```

| | |
|---|---|
| tacataaccc agcgtcgcaa cgtggattcg ttgataattg ttgtgtaggt actccgccgc | 8400 |
| cgagggacct gagcgagtcc gcatcgaccg gatcggaaaa cctctcgaga aaggcgtcta | 8460 |
| accagtcaca gtcgcaaggt aggctgagca ccgtggcggg cggcagcggg cggcggtcgg | 8520 |
| ggttgtttct ggcggaggtg ctgctgatga tgtaattaaa gtaggcggtc ttgagacggc | 8580 |
| ggatggtcga cagaagcacc atgtccttgg gtccggcctg ctgaatgcgc aggcggtcgg | 8640 |
| ccatgcccca ggcttcgttt tgacatcggc gcaggtcttt gtagtagtct tgcatgagcc | 8700 |
| tttctaccgg cacttcttct tctccttcct cttgtcctgc atctcttgca tctatcgctg | 8760 |
| cggcggcggc ggagtttggc cgtaggtggc gccctcttcc tcccatgcgt gtgaccccga | 8820 |
| agcccctcat cggctgaagc agggctaggt cggcgacaac gcgctcggct aatatggcct | 8880 |
| gctgcacctg cgtgagggta gactggaagt catccatgtc cacaaagcgg tggtatgcgc | 8940 |
| ccgtgttgat ggtgtaagtg cagttggcca taacggacca gttaacggtc tggtgacccg | 9000 |
| gctgcgagag ctcggtgtac ctgagacgcg agtaagccct cgagtcaaat acgtagtcgt | 9060 |
| tgcaagtccg caccaggtac tggtatccca ccaaaaagtg cggcggcggc tggcggtaga | 9120 |
| ggggccagcg tagggtggcc ggggctccgg gggcgagatc ttccaacata aggcgatgat | 9180 |
| atccgtagat gtacctggac atccaggtga tgccggcggc ggtggtggag gcgcgcggaa | 9240 |
| agtcgcggac gcggttccag atgttgcgca gcggcaaaaa gtgctccatg gtcgggacgc | 9300 |
| tctggccggt caggcgcgcg caatcgttga cgctctagcg tgcaaaagga gagcctgtaa | 9360 |
| gcgggcactc ttccgtggtc tggtggataa attcgcaagg gtatcatggc ggacgaccgg | 9420 |
| ggttcgagcc ccgtatccgg ccgtccgccg tgatccatgc ggttaccgcc cgcgtgtcga | 9480 |
| acccaggtgt gcgacgtcag acaacggggg agtgctcctt ttggcttcct tccaggcgcg | 9540 |
| gcggctgctg cgctagcttt tttggccact ggccgcgcgc agcgtaagcg gttaggctgg | 9600 |
| aaagcgaaag cattaagtgg ctcgctccct gtagccggag ggttattttc caagggttga | 9660 |
| gtcgcgggac ccccggttcg agtctcggac cggccggact gcggcgaacg ggggtttgcc | 9720 |
| tccccgtcat gcaagacccc gcttgcaaat tcctccggaa acagggacga gcccctttt | 9780 |
| tgcttttccc agatgcatcc ggtgctgcgg cagatgcgcc cccctcctca gcagcggcaa | 9840 |
| gagcaagagc agcggcagac atgcagggca ccctccccctc ctcctaccgc gtcaggaggg | 9900 |
| gcgacatccg cggttgacgc ggcagcagat ggtgattacg aacccccgcg gcgccgggcc | 9960 |
| cggcactacc tggacttgga ggagggcgag ggcctggcgc ggctaggagc gccctctcct | 10020 |
| gagcggcacc caagggtgca gctgaagcgt gatacgcgtg aggcgtacgt gccgcggcag | 10080 |
| aacctgtttc gcgaccgcga gggagaggag cccgaggaga tgcgggatcg aaagttccac | 10140 |
| gcagggcgcg agctgcggca tggcctgaat cgcgagcggt tgctgcgcga ggaggacttt | 10200 |
| gagcccgacg cgcgaaccgg gattagtccc gcgcgcgcac acgtggcggc cgccgacctg | 10260 |
| gtaaccgcat acgagcagac ggtgaaccag gagattaact ttcaaaaaag ctttaacaac | 10320 |
| cacgtgcgta cgcttgtggc gcgcgaggag gtggctatag gactgatgca tctgtgggac | 10380 |
| tttgtaagcg cgctggagca aaacccaaat agcaagccgc tcatggcgca gctgttcctt | 10440 |
| atagtgcagc acagcaggga caacgaggca ttcaggatg cgctgctaaa catagtagag | 10500 |
| cccgagggcc gctggctgct cgatttgata aacatcctgc agagcatagt ggtgcaggag | 10560 |
| cgcagcttga gcctggctga caaggtggcc gccatcaact attccatgct tagcctgggc | 10620 |
| aagttttacg cccgcaagat ataccatacc ccttacgttc ccatagacaa ggaggtaaag | 10680 |
| atcgagggt tctacatgcg catggcgctg aaggtgctta ccttgagcga cgacctgggc | 10740 |

```
gtttatcgca acgagcgcat ccacaaggcc gtgagcgtga gccggcggcg cgagctcagc   10800
gaccgcgagc tgatgcacag cctgcaaagg gccctggctg gcacgggcag cggcgataga   10860
gaggccgagt cctactttga cgcgggcgct gacctgcgct gggccccaag ccgacgcgcc   10920
ctggaggcag ctggggccgg acctgggctg gcggtggcac ccgcgcgcgc tggcaacgtc   10980
ggcggcgtgg aggaatatga cgaggacgat gagtacgagc cagaggacgg cgagtactaa   11040
gcggtgatgt ttctgatcag atgatgcaag acgaacgga cccggcggtg cgggcggcgc    11100
tgcagagcca gccgtccggc cttaactcca cggacgactg gcgccaggtc atggaccgca   11160
tcatgtcgct gactgcgcgc aatcctgacg cgttccggca gcagccgcag ccaaccggc    11220 tctccgcaat tctggaagcg gtggtcccgg cgcgcgcaaa ccccacgcac gagaaggtgc   11280
tggcgatcgt aaacgcgctg gccgaaaaca gggccatccg gcccgacgag gccggcctgg   11340
tctacgacgc gctgcttcag cgcgtggctc gttacaacag cggcaacgtg cagaccaacc   11400
tggaccggct ggtgggggat gtgcgcgagg ccgtggcgca gcgtgagcgc gcgcagcagc   11460
agggcaacct gggctccatg gttgcactaa acgccttcct gagtacacag cccgccaacg   11520
tgccgcgggg acaggaggac tacaccaact ttgtgagcgc actgcggcta atggtgactg   11580
agacaccgca aagtgaggtg taccagtctg gccagacta ttttttccag accagtagac    11640
aaggcctgca gaccgtaaac ctgagccagg cttttcaaaaa cttgcagggg ctgtgggggg   11700
tgcgggctcc cacaggcgac cgcgcgaccg tgtctagctt gctgacgccc aactcgcgcc   11760
tgttgctgct gctaatagcg cccttcacgg acagtggcag cgtgtcccgg acacatacc    11820 taggtcactt gctgacactg taccgcgagg ccataggtca ggcgcatgtg gacgagcata   11880 cttt ccagga gattacaagt gtcagccgcg cgctggggca ggaggacacg ggcagcctgg   11940
aggcaaccct aaactacctg ctgaccaacc ggcggcagaa gatcccctcg ttgcacagtt   12000
taaacagcga ggaggagcgc attttgcgct acgtgcagca gagcgtgagc cttaacctga   12060
tgcgcgacgg ggtaacgccc agcgtggcgc tggacatgac cgcgcgcaac atggaaccgg   12120
gcatgtatgc ctcaaaccgg ccgtttatca accgcctaat ggactacttg catcgcgcgg   12180
ccgccgtgaa ccccgagtat ttcaccaatg ccatcttgaa cccgcactgg ctaccgcccc   12240 ctggttttcta caccggggga ttcgaggtgc ccgagggtaa cgatggattc ctctgggacg   12300
acatagacga cagcgtgttt tccccgcaac cgcagaccct gctagagttg caacagcgcg   12360
agcaggcaga ggcggcgctg cgaaaggaaa gcttccgcag gccaagcagc ttgtccgatc   12420
taggcgctgc ggccccgcgg tcagatgcta gtagcccatt tccaagcttg ataggtctc    12480 ttaccagcac tcgcaccacc cgcccgcgcc tgctgggcga ggaggagtac ctaaacaact   12540
cgctgctgca gccgcagcgc gaaaaaaacc tgcctccggc atttcccaac aacgggatag   12600
agagcctagt ggacaagatg agtagatgga agacgtacgc gcaggagcac agggacgtgc   12660
caggcccgcg cccgcccacc cgtcgtcaaa ggcacgaccg tcagcggggt ctggtgtggg   12720
aggacgatga ctcggcagac gacagcagcg tcctggattt ggagggagt ggcaacccgt    12780 ttgcgcacct tcgcccccagg ctggggagaa tgttttaaaa aaaaaaaagc atgatgcaaa   12840
ataaaaaact caccaaggcc atggcaccga gcgttggttt tcttgtattc cccttagtat   12900
gcggcgcgcg gcgatgtatg aggaaggtcc tcctccctcc tacgagagtg tggtgagcgc   12960
ggcgccagtg gcggcggcgc tgggttctcc cttcgatgct ccctggacc cgccgttgt     13020 gcctccgcgg tacctgcggc ctaccggggg gagaaacagc atccgttact ctgagttggc   13080
```

```
accccctattc gacaccaccc gtgtgtacct ggtggacaac aagtcaacgg atgtggcatc    13140
cctgaactac cagaacgacc acagcaactt tctgaccacg gtcattcaaa caatgacta     13200 cagcccgggg gaggcaagca cacagaccat caatcttgac gaccggtcgc actgggcgg     13260 cgacctgaaa accatcctgc ataccaacat gccaaatgtg aacgagttca tgtttaccaa    13320
taagtttaag gcgcgggtga tggtgtcgcg cttgcctact aaggacaatc aggtggagct    13380
gaaatacgag tgggtggagt tcacgctgcc cgagggcaac tactccgaga ccatgaccat    13440
agaccttatg aacaacgcga tcgtggagca ctacttgaaa gtgggcagac agaacggggt    13500
tctggaaagc gacatcgggg taaagtttga cacccgcaac ttcagactgg ggtttgaccc    13560
cgtcactggt cttgtcatgc tgggggtata tacaaacgaa gccttccatc cagacatcat    13620
tttgctgcca ggatgcgggg tggacttcac ccacagccgc ctgagcaact tgttgggcat    13680
ccgcaagcgg caaccccttcc aggagggctt taggatcacc tacgatgatc tggagggtgg    13740
taacattccc gcactgttgg atgtggacgc ctaccaggcg agcttgaaag atgacaccga    13800
acagggcggg ggtggcgcag gcggcagcaa cagcagtggc agcggcgcgg aagagaactc    13860
caacgcggca gccgcggcaa tgcagccggt ggaggacatg aacgatcatg ccattcgcgg    13920
cgacaccttt gccacgcggg ctgaggagaa gcgcgctgag gccgaagcag cggccgaagc    13980
tgccgccccc gctgcgcaac ccgaggtcga gaagcctcag aagaaaccgg tgatcaaacc    14040
cctgacagag gacagcaaga aacgcagtta caacctaata agcaatgaca gcaccttcac    14100
ccagtaccgc agctggtacc ttgcatacaa ctacggcgac cctcagaccg gaatccgctc    14160
atggaccctg ctttgcactc ctgacgtaac ctgcggctcg gagcaggtct actggtcgtt    14220
gccagacatg atgcaagacc ccgtgacctt ccgctccacg cgccagatca gcaactttcc    14280
ggtggtgggc gccgagctgt tgcccgtgca ctccaagagc ttctacaacg accaggccgt    14340
ctactcccaa ctcatccgcc agtttacctc tctgacccac gtgttcaatc gctttcccga    14400
gaaccagatt ttggcgcgcc cgccagcccc caccatcacc accgtcagtg aaaacgttcc    14460
tgctctcaca gatcacggga cgctaccgct gcgcaacagc atcggaggag tccagcgagt    14520
gaccattact gacgccagac gccgcacctg cccctacgtt tacaaggccc tgggcatagt    14580
ctcgccgcgc gtcctatcga gccgcacttt ttgagcaagc atgtccatcc ttatatcgcc    14640
cagcaataac acaggctggg gcctgcgctt cccaagcaag atgtttggcg gggccaagaa    14700
gcgctccgac caacacccag tgcgcgtgcg cgggcactac cgcgcgccct ggggcgcgca    14760
caaacgcggc cgcactgggc gcaccaccgt cgatgacgcc atcgacgcgg tggtggagga    14820
ggcgcgcaac tacacgccca cgccgccacc agtgtccaca gtggacgcgg ccattcagac    14880
cgtggtgcgc ggagcccggc gctatgctaa aatgaagaga cggcggaggc gcgtagcacg    14940
tcgccaccgc cgccgacccg gcactgccgc ccaacgcgcg gcggcggccc tgcttaaccg    15000
cgcacgtcgc accggccgac gggcggccat gcgggccgct cgaaggctgg ccgcgggtat    15060
tgtcactgtg ccccccaggt ccaggcgacg agcggccgcc gcagcagccg cggccattag    15120
tgctatgact cagggtcgca ggggcaacgt gtattgggtg cgcgactcgg ttagcggcct    15180
gcgcgtgccc gtgcgcaccc gccccccgcg caactagatt gcaagaaaaa actacttaga    15240
ctcgtactgt tgtatgtatc cagcggcggc ggcgcgcaac gaagctatgt ccaagcgcaa    15300
aatcaaagaa gagatgctcc aggtcatcgc gccggagatc tatggccccc cgaagaagga    15360
agagcaggat tacaagcccc gaaagctaaa gcgggtcaaa aagaaaaaga agatgatga    15420 tgatgaactt gacgacgagg tggaactgct gcacgctacc gcgcccaggc gacgggtaca    15480
```

```
gtggaaaggt cgacgcgtaa aacgtgtttt gcgacccggc accaccgtag tctttacgcc    15540
cggtgagcgc tccacccgca cctacaagcg cgtgtatgat gaggtgtacg gcgacgagga    15600
cctgcttgag caggccaacg agcgcctcgg ggagtttgcc tacggaaagc ggcataagga    15660
catgctggcg ttgccgctgg acgagggcaa cccaacacct agcctaaagc ccgtaacact    15720
gcagcaggtg ctgcccgcgc ttgcaccgtc cgaagaaaag cgcggcctaa agcgcgagtc    15780
tggtgacttg gcaccaccg tgcagctgat ggtacccaag cgccagcgac tggaagatgt    15840
cttggaaaaa atgaccgtgg aacctgggct ggagcccgag gtccgcgtgc ggccaatcaa    15900
gcaggtggcg ccgggactgg gcgtgcagac cgtggacgtt cagatacccca ctaccagtag    15960 caccagtatt gccaccgcca cagagggcat ggagacacaa acgtccccgg ttgcctcagc    16020
ggtggcggat gccgcggtgc aggcggtcgc tgcggccgcg tccaagacct ctacggaggt    16080
gcaaacggac ccgtggatgt ttcgcgtttc agccccccgg cgcccgcgcc gttcgaggaa    16140
gtacggcgcc gccagcgcgc tactgcccga atatgcccta catccttcca ttgcgcctac    16200
ccccggctat cgtggctaca cctaccgccc cagaagacga gcaactaccc gacgccgaac    16260
caccactgga acccgccgcc gccgtcgccg tcgccagccc gtgctggccc cgatttccgt    16320
gcgcagggtg gctcgcgaag gaggcaggac cctggtgctg ccaacagcgc gctaccaccc    16380
cagcatcgtt taaaagccgg tctttgtggt tcttgcagat atggccctca cctgccgcct    16440
ccgtttcccg gtgccgggat tccgaggaag aatgcaccgt aggaggggca tggccggcca    16500
cggcctgacg ggcggcatgc gtcgtgcgca ccaccggcgg cggcgcgcgt cgcaccgtcg    16560
catgcgcggc ggtatcctgc ccctccttat tccactgatc gccgcggcga ttggcgccgt    16620
gcccggaatt gcatccgtgg ccttgcaggc gcagagacac tgattaaaaa caagttgcat    16680
gtggaaaaat caaaataaaa agtctggact ctcacgctcg cttggtcctg taactatttt    16740
gtagaatgga agacatcaac tttgcgtctc tggccccgcg acacggctcg cgcccgttca    16800
tgggaaactg gcaagatatc ggcaccagca atatgagcgg tggcgccttc agctggggct    16860
cgctgtggag cggcattaaa aatttcggtt ccaccgttaa gaactatggc agcaaggcct    16920
ggaacagcag cacaggccag atgctgaggg ataagttgaa agagcaaaat ttccaacaaa    16980
aggtggtaga tggcctggcc tctggcatta gcggggtggt ggacctggcc aaccaggcag    17040
tgcaaaataa gattaacagt aagcttgatc ccgcccctcc cgtagaggag cctccaccgg    17100
ccgtggagac agtgtctcca gaggggcgtg gcgaaaagcg tccgcgcccc gacagggaag    17160 aaaactctggt gacgcaaata gacgagcctc cctcgtacga ggaggcacta agcaaggcc    17220 tgcccaccac ccgtcccatc gcgcccatgg ctaccggagt gctgggccag cacacacccg    17280
taacgctgga cctgcctccc cccgccgaca cccagcagaa acctgtgctg ccaggcccga    17340
ccgccgttgt tgtaacccgt cctagccgcg cgtccctgcg ccgcgccgcc agcggtccgc    17400
gatcgttgcg gcccgtagcc agtggcaact ggcaaagcac actgaacagc atcgtgggtc    17460
tgggggtgca atccctgaag cgccgacgat gcttctgata gctaacgtgt cgtatgtgtg    17520
tcatgtatgc gtccatgtcg ccgccagagg agctgctgag ccgccgcgcg cccgcttttcc    17580 aagatggcta ccccttcgat gatgccgcag tggtcttaca tgcacatctc gggccaggac    17640
gcctcggagt acctgagccc cgggctggtg cagtttgccc gcgccaccga cgtacttc    17700 agcctgaata acaagtttag aaaccccacg gtggcgccta cgcacgacgt gaccacagac    17760
cggtcccagc gtttgacgct gcggttcatc cctgtggacc gtgaggatac tgcgtactcg    17820
```

```
tacaaggcgc ggttcaccct agctgtgggt gataaccgtg tgctggacat ggcttccacg    17880
tactttgaca tccgcggcgt gctggacagg ggccctactt ttaagcccta ctctggcact    17940
gcctacaacg ccctggctcc caagggtgcc ccaaatcctt gcgaatggga tgaagctgct    18000
actgctcttg aaataaacct agaagaagag gacgatgaca acgaagacga agtagacgag    18060
caagctgagc agcaaaaaac tcacgtattt gggcaggcgc cttattctgg tataaatatt    18120
acaaaggagg gtattcaaat aggtgtcgaa ggtcaaacac ctaaatatgc cgataaaaca    18180
tttcaacctg aacctcaaat aggagaatct cagtggtacg aaacagaaat taatcatgca    18240
gctgggagag tcctaaaaaa gactacccca atgaaaccat gttacggttc atatgcaaaa    18300
cccacaaatg aaaatggagg gcaaggcatt cttgtaaagc aacaaatgg aaagctagaa      18360
agtcaagtgg aaatgcaatt tttctcaact actgaggcag ccgcaggcaa tggtgataac    18420
ttgactccta aagtggtatt gtacagtgaa gatgtagata tagaaacccc agacactcat    18480
atttcttaca tgcccactat taaggaaggt aactcacgag aactaatggg ccaacaatct    18540
atgcccaaca ggcctaatta cattgctttt agggacaatt ttattggtct aatgtattac    18600
aacagcacgg gtaatatggg tgttctggcg ggccaagcat cgcagttgaa tgctgttgta    18660
gatttgcaag acagaaacac agagcttttca taccagcttt tgcttgattc cattggtgat    18720
agaaccaggt acttttctat gtggaatcag gctgttgaca gctatgatcc agatgttaga    18780
attattgaaa atcatggaac tgaagatgaa cttccaaatt actgctttcc actgggaggt    18840
gtgattaata cagagactct taccaaggta aaacctaaaa caggtcagga aaatggatgg    18900
gaaaaagatg ctacagaatt ttcagataaa aatgaaataa gagttggaaa taattttgcc    18960
atggaaatca atctaaatgc caacctgtgg agaaatttcc tgtactccaa catagcgctg    19020
tatttgcccg acaagctaaa gtacagtcct tccaacgtaa aaatttctga taacccaaac    19080
acctacgact acatgaacaa gcgagtggtg gctcccgggc tagtggactg ctacattaac    19140
cttggagcac gctggtccct tgactatatg gacaacgtca acccatttaa ccaccaccgc    19200
aatgctggcc tgcgctaccg ctcaatgttg ctgggcaatg gtcgctatgt gcccttccac    19260
atccaggtgc ctcagaagtt ctttgccatt aaaaaacctcc ttctcctgcc gggctcatac    19320
acctacgagt ggaacttcag gaaggatgtt aacatggttc tgcagagctc cctaggaaat    19380
gacctaaggg ttgacggagc cagcattaag tttgatagca tttgccttta cgccaccttc    19440
ttccccatgg cccacaacac cgcctccacg cttgaggcca tgcttagaaa cgacaccaac    19500
gaccagtcct ttaacgacta tctctccgcc gccaacatgc tctaccctat acccgccaac    19560
gctaccaacg tgcccatatc catcccctcc cgcaactggg cggctttccg cggctgggcc    19620
ttcacgcgcc ttaagactaa ggaaaccccca tcactgggct cgggctacga cccttattac    19680
acctactctg gctctatacc ctacctagat ggaaccttt acctcaacca cacctttaag    19740
aaggtggcca ttacctttga ctcttctgtc agctggcctg gcaatgaccg cctgcttacc    19800
cccaacgagt ttgaaattaa gcgctcagtt gacggggagg gttacaacgt tgcccagtgt    19860
aacatgacca agactggtt cctggtacaa atgctagcta actataacat tggctaccag    19920
ggcttctata tccagagag ctacaaggac cgcatgtact ccttctttag aaacttccag    19980
cccatgagcc gtcaggtggt ggatgatact aaatacaagg actaccaaca ggtgggcatc    20040
ctacaccaac acaacaactc tggatttgtt ggctaccttg ccccccaccat gcgcgaagga    20100
caggcctacc ctgctaactt ccccctatccg cttataggca agaccgcagt tgacagcatt    20160
acccagaaaa agtttctttg cgatcgcacc ctttggcgca tcccattctc cagtaacttt    20220
```

```
atgtccatgg gcgcactcac agacctgggc caaaaccttc tctacgccaa ctccgcccac    20280
gcgctagaca tgacttttga ggtggatccc atggacgagc ccaccttct ttatgttttg     20340
tttgaagtct ttgacgtggt ccgtgtgcac cagccgcacc gcggcgtcat cgaaaccgtg    20400
tacctgcgca cgcccttctc ggccggcaac gccacaacat aaagaagcaa gcaacatcaa    20460
caacagctgc cgccatgggc tccagtgagc aggaactgaa agccattgtc aaagatcttg    20520
gttgtgggcc atatttttg gcacctatg acaagcgctt tccaggcttt gtttctccac      20580
acaagctcgc ctgcgccata gtcaatacgg ccggtcgcga gactgggggc gtacactgga    20640
tggcctttgc ctggaacccg cactcaaaaa catgctacct cttttgagccc tttggctttt   20700
ctgaccagcg actcaagcag gtttaccagt ttgagtacga gtcactcctg cgccgtagcg    20760
ccattgcttc ttcccccgac cgctgtataa cgctggaaaa gtccacccaa agcgtacagg    20820
ggcccaactc ggccgcctgt ggactattct gctgcatgtt tctccacgcc tttgccaact    20880
ggccccaaac tccatggat cacaaccca ccatgaacct tattaccggg gtacccaact      20940
ccatgctcaa cagtccccag gtacagccca ccctgcgtcg caaccaggaa cagctctaca    21000
gcttcctgga gcgccactcg ccctacttcc gcagccacag tgcgcagatt aggagcgcca    21060
cttcttttg tcacttgaaa aacatgtaaa aataatgtac tagagacact ttcaataaag      21120
gcaaatgctt ttatttgtac actctcgggt gattatttac ccccacccct gccgtctgcg    21180
ccgtttaaaa atcaaagggg ttctgccgcg catcgctatg cgccactggc agggacacgt    21240
tgcgatactg gtgtttagtg ctccacttaa actcaggcac aaccatccgc ggcagctcgg    21300
tgaagttttc actccacagg ctgcgcacca tcaccaacgc gtttagcagg tcgggcgccg    21360
atatcttgaa gtcgcagttg gggcctccgc cctgcgcgcg cgagttgcga tacacagggt    21420
tgcagcactg gaacactatc agcgccgggt ggtgcacgct ggccagcacg ctcttgtcgg    21480
agatcagatc cgcgtccagg tcctccgcgt tgctcagggc gaacggagtc aactttggta    21540
gctgccttcc caaaagggc gcgtgcccag gctttgagtt gcactcgcac cgtagtggca    21600
tcaaaaggtg accgtgcccg gtctgggcgt taggatacag cgcctgcata aaagccttga    21660
tctgcttaaa agccacctga gcctttgcgc cttcagagaa gaacatgccg caagacttgc    21720
cggaaaactg attggccgga caggccgcgt cgtgcacgca gcaccttgcg tcggtgttgg    21780
agatctgcac cacatttcgg ccccaccggt tcttcacgat cttggccttg ctagactgct    21840
ccttcagcgc gcgctgcccg ttttcgctcg tcacatccat ttcaatcacg tgctccttat    21900
ttatcataat gcttccgtgt agacacttaa gctcgccttc gatctcagcg cagcggtgca    21960
gccacaacgc gcagcccgtg ggctcgtgat gcttgtaggt cacctctgca aacgactgca    22020
ggtacgcctg caggaatcgc cccatcatcg tcacaaaggt cttgttgctg gtgaaggtca    22080
gctgcaaccc gcggtgctcc tcgttcagcc aggtcttgca tacggccgcc agagcttcca    22140
cttggtcagg cagtagtttg aagttcgcct ttagatcgtt atccacgtgg tacttgtcca    22200
tcagcgcgcg cgcagcctcc atgcccttct cccacgcaga cacgatcggc acactcagcg    22260
ggttcatcac cgtaatttca ctttccgctt cgctgggctc ttcctcttcc tcttgcgtcc    22320
gcataccacg cgccactggg tcgtcttcat tcagccgccg cactgtgcgc ttacctcctt    22380
tgccatgctt gattagcacc ggtgggttgc tgaaacccac catttgtagc gccacatctt    22440
ctctttcttc ctcgctgtcc acgattacct ctggtgatgg cgggcgctcg gcttgggag     22500
aagggcgctt ctttttcttc ttgggcgcaa tggccaaatc cgccgccgag gtcgatggcc    22560
```

-continued

```
gcgggctggg tgtgcgcggc accagcgcgt cttgtgatga gtcttcctcg tcctcggact   22620
cgatacgccg cctcatccgc ttttttgggg gcgcccgggg aggcggcggc gacggggacg   22680
gggacgacac gtcctccatg gttggggggac gtcgcgccgc accgcgtccg cgctcggggg   22740
tggtttcgcg ctgctcctct tcccgactgg ccatttcctt ctcctatagg cagaaaaaga   22800
tcatggagtc agtcgagaag aaggacagcc taaccgcccc ctctgagttc gccaccaccg   22860
cctccaccga tgccgccaac gcgcctacca ccttccccgt cgaggcaccc ccgcttgagg   22920
aggaggaagt gattatcgag caggacccag gttttgtaag cgaagacgac gaggaccgct   22980
cagtaccaac agaggataaa aagcaagacc aggacaacgc agaggcaaac gaggaacaag   23040
tcgggcgggg ggacgaaagg catggcgact acctagatgt gggagacgac gtgctgttga   23100
agcatctgca gcgccagtgc gccattatct gcgacgcgtt gcaagagcgc agcgatgtgc   23160
ccctcgccat agcggatgtc agccttgcct acgaacgcca cctattctca ccgcgcgtac   23220
cccccaaacg ccaagaaaac ggcacatgcg agcccaaccc gcgcctcaac ttctaccccg   23280
tatttgccgt gccagaggtg cttgccacct atcacatctt tttccaaaac tgcaagatac   23340
ccctatcctg ccgtgccaac cgcagccgag cggacaagca gctggccttg cggcagggcg   23400
ctgtcatacc tgatatcgcc tcgctcaacg aagtgccaaa aatctttgag ggtcttggac   23460
gcgacgagaa gcgcgcggca aacgctctgc aacaggaaaa cagcgaaaat gaaagtcact   23520
ctggagtgtt ggtggaactc gagggtgaca acgcgcgcct agccgtacta aaacgcagca   23580
tcgaggtcac ccactttgcc tacccggcac ttaacctacc ccccaaggtc atgagcacag   23640
tcatgagtga gctgatcgtg cgccgtgcgc agccctgga gagggatgca aatttgcaag   23700
aacaaacaga ggagggccta cccgcagttg gcgacgagca gctagcgcgc tggcttcaaa   23760
cgcgcgagcc tgccgacttg gaggagcgac gcaaactaat gatggccgca gtgctcgtta   23820
ccgtggagct tgagtgcatg cagcggttct ttgctgaccc ggagatgcag cgcaagctag   23880
aggaaacatt gcactacacc tttcgacagg gctacgtacg ccaggcctgc aagatctcca   23940
acgtggagct ctgcaacctg gtctcctacc ttggaatttt gcacgaaaac cgccttgggc   24000
aaaacgtgct tcattccacg ctcaagggcg aggcgcgccg cgactacgtc cgcgactgcg   24060
tttacttatt tctatgctac acctggcaga cggccatggg cgtttggcag cagtgcttgg   24120
aggagtgcaa cctcaaggag ctgcagaaac tgctaaagca aaacttgaag gacctatgga   24180
cggccttcaa cgagcgctcc gtggccgcgc acctggcgga catcattttc cccgaacgcc   24240
tgcttaaaac cctgcaacag ggtctgccag acttcaccag tcaaagcatg ttgcagaact   24300
ttaggaactt tatcctagag cgctcaggaa tcttgcccgc cacctgctgt gcacttccta   24360
gcgactttgt gcccattaag taccgcgaat gccctccgcc gctttggggc cactgctacc   24420
ttctgcagct agccaactac cttgcctacc actctgacat aatggaagac gtgagcggtg   24480
acggtctact ggagtgtcac tgtcgctgca acctatgcac cccgcaccgc tccctggttt   24540
gcaattcgca gctgcttaac gaaagtcaaa ttatcggtac ctttgagctg cagggtcccc   24600
cgcctgacga aaagtccgcg gctccggggt tgaaactcac tccggggctg tggacgtcgg   24660
cttaccttcg caaatttgta cctgaggact accacgccca cgagattagg ttctacgaag   24720
accaatcccg cccgcctaat gcggagctta ccgcctgcgt cattacccag gccacattc   24780
ttggccaatt gcaagccatc aacaaagccc gccaagagtt tctgctacga aagggacggg   24840
gggtttactt ggaccccag tccgcgagg agctcaaccc aatcccccg ccgccgcagc   24900
cctatcagca gcagccgcgg gccccttgctt cccaggatgg cacccaaaaa gaagctgcag   24960
```

```
ctgccgccgc cacccacgga cgaggaggaa tactgggaca gtcaggcaga ggaggttttg   25020
gacgaggagg aggaggacat gatggaagac tgggagagcc tagacgagga agcttccgag   25080
gtcgaagagg tgtcagacga aacaccgtca ccctcggtcg cattcccctc gccggcgccc   25140
cagaaatcgg caaccggttc cagcatggct acaacctccg ctcctcaggc gccgccggca   25200
ctgcccgttc gccgacccaa ccgtagatgg gacaccactg gaaccagggc cggtaagtcc   25260
aagcagccgc cgccgttagc ccaagagcaa caacagcgcc aaggctaccg ctcatggcgc   25320
gggcacaaga acgccatagt tgcttgcttg caagactgtg ggggcaacat ctccttcgcc   25380
cgccgctttc ttctctacca tcacggcgtg gccttccccc gtaacatcct gcattactac   25440
cgtcatctct acagcccata ctgcaccggc ggcagcggca gcaacagcag cggccacaca   25500
gaagcaaagg cgaccggata gcaagactct gacaaagccc aagaaatcca cagcggcggc   25560
agcagcagga ggaggagcgc tgcgtctggc gcccaacgaa cccgtatcga cccgcgagct   25620
tagaaacagg attttttccca ctctgtatgc tatatttcaa cagagcaggg gccaagaaca   25680
agagctgaaa ataaaaaaca ggtctctgcg atccctcacc cgcagctgcc tgtatcacaa   25740
aagcgaagat cagcttcggc gcacgctgga agacgcggag gctctcttca gtaaatactg   25800
cgcgctgact cttaaggact agtttcgcgc cctttctcaa atttaagcgc gaaaactacg   25860
tcatctccag cggccacacc cggcgccagc acctgttgtc agcgccatta tgagcaagga   25920
aattcccacg ccctacatgt ggagttacca gccacaaatg ggacttgcgg ctggagctgc   25980
ccaagactac tcaacccgaa taaactacat gagcgcggga ccccacatga tatcccgggt   26040
caacggaata cgcgcccacc gaaaccgaat tctcctggaa caggcggcta ttaccaccac   26100
acctcgtaat aaccttaatc cccgtagttg gccgctgcc ctggtgtacc aggaaagtcc   26160
cgctcccacc actgtggtac ttcccagaga cgcccaggcc gaagttcaga tgactaactc   26220
aggggcgcag cttgcgggcg gctttcgtca cagggtgcgg tcgcccgggc agggtataac   26280
tcacctgaca atcagagggc gaggtattca gctcaacgac gagtcggtga gctcctcgct   26340
tggtctccgt ccggacggga catttcagat cggcggcgcc ggccgctctt cattcacgcc   26400
tcgtcaggca atcctaactc tgcagacctc gtcctctgag ccgcgctctg gaggcattgg   26460
aactctgcaa tttattgagg agtttgtgcc atcggtctac tttaaccct tctcgggacc   26520 tcccggccac tatccggatc aatttattcc taactttgac gcggtaaagg actcggcgga   26580
cggctacgac tgaatgttaa gtggagaggc agagcaactg cgcctgaaac acctggtcca   26640
ctgtcgccgc cacaagtgct tgcccgcga ctccggtgag ttttgctact ttgaattgcc   26700
cgaggatcat atcgagggcc cggcgcacgg cgtccggctt accgcccagg gagagcttgc   26760
ccgtagcctg attcgggagt ttacccgcg ccccctgcta gttgagcggg acaggggacc   26820
ctgtgttctc actgtgattt gcaactgtcc taaccctgga ttacatcaag atcctctagt   26880
taatgtcagg tcgcctaagt cgattaacta gagtacccgg ggatcttatt ccctttaact   26940
aataaaaaaa aataataaag catcacttac ttaaaatcag ttagcaaatt tctgtccagt   27000
ttattcagca gcacctcctt gccctcctcc cagctctggt attgcagctt cctcctggct   27060
gcaaactttc tccacaatct aaatggaatg tcagtttcct cctgttcctg tccatccgca   27120
cccactatct tcatgttgtt gcagatgaag cgcgcaagac cgtctgaaga taccttcaac   27180
cccgtgtatc catatgacac ggaaaccggt cctccaactg tgccttttct tactcctccc   27240
tttgtatccc ccaatgggtt tcaagagagt ccccctgggg tactctcttt gcgcctatcc   27300
```

-continued

```
gaacctctag ttacctccaa tggcatgctt gcgctcaaaa tgggcaacgg cctctctctg    27360
gacgaggccg gcaaccttac ctcccaaaat gtaaccactg tgagcccacc tctcaaaaaa    27420
accaagtcaa acataaacct ggaaatatct gcacccctca cagttacctc agaagcccta    27480
actgtggctg ccgccgcacc tctaatggtc gcgggcaaca cactcaccat gcaatcacag    27540
gccccgctaa ccgtgcacga ctccaaactt agcattgcca cccaaggacc cctcacagtg    27600
tcagaaggaa agctagccct gcaaacatca ggcccctca ccaccaccga tagcagtacc    27660
cttactatca ctgcctcacc ccctctaact actgccactg gtagcttggg cattgacttg    27720
aaagagccca tttatacaca aaatggaaaa ctaggactaa agtacggggc tcctttgcat    27780
gtaacagacg acctaaacac tttgaccgta gcaactggtc caggtgtgac tattaataat    27840
acttccttgc aaactaaagt tactggagcc ttgggttttg attcacaagg caatatgcaa    27900
cttaatgtag caggaggact aaggattgat tctcaaaaca gacgccttat acttgatgtt    27960
agttatccgt ttgatgctca aaaccaacta aatctaagac taggacaggg ccctctttt    28020
ataaactcag cccacaactt ggatattaac tacaacaaag gcctttactt gtttacagct    28080
tcaaacaatt ccaaaagct tgaggttaac ctaagcactg ccagggggtt gatgtttgac    28140
gctacagcca tagccattaa tgcaggagat gggcttgaat ttggttcacc taatgcacca    28200
aacacaaatc ccctcaaaac aaaaattggc catggcctag aatttgattc aaacaaggct    28260
atggttccta aactaggaac tggccttagt tttgacagca caggtgccat tacagtagga    28320
aacaaaaata atgataagct aactttgtgg accacaccag ctccatctcc taactgtaga    28380
ctaaatgcag agaagatgc taaactcact ttggtcttaa caaatgtgg cagtcaaata    28440
cttgctacag tttcagtttt ggctgttaaa ggcagtttgg ctccaatatc tggaacagtt    28500
caaagtgctc atcttattat aagatttgac gaaaatggag tgctactaaa caattccttc    28560
ctggacccag aatattggaa ctttagaaat ggagatctta ctgaaggcac agcctataca    28620
aacgctgttg gatttatgcc taacctatca gcttatccaa aatctcacgg taaaactgcc    28680
aaaagtaaca ttgtcagtca agtttactta aacggagaca aaactaaacc tgtaacacta    28740
accattacac taaacggtac acaggaaaca ggagacacaa ctccaagtgc atactctatg    28800
tcattttcat gggactggtc tggccacaac tacattaatg aaatatttgc cacatcctct    28860
tacactttt catacattgc ccaagaataa agaatcgttt gtgttatgtt tcaacgtgtt    28920
tattttcaa ttgcagaaaa tttcaagtca tttttcattc agtagtatag ccccaccacc    28980
acatagctta tacagatcac cgtaccttaa tcaaactcac agaacccctag tattcaacct    29040
gccacctccc tcccaacaca cagagtacac agtcctttct ccccggctgg ccttaaaaag    29100
catcatatca tgggtaacag acatattctt aggtgttata ttccacacgg tttcctgtcg    29160
agccaaacgc tcatcagtga tattaataaa ctccccgggc agctcactta agttcatgtc    29220
gctgtccagc tgctgagcca caggctgctg tccaacttgc ggttgcttaa cgggcggcga    29280
aggagaagtc cacgcctaca tggggtaga gtcataatcg tgcatcagga tagggcggtg    29340
gtgctgcagc agcgcgcgaa taaactgctg ccgccgccgc tccgtcctgc aggaatacaa    29400
catggcagtg gtctcctcag cgatgattcg caccgcccgc agcataaggc gccttgtcct    29460
ccgggcacag cagcgcaccc tgatctcact taaatcagca cagtaactgc agcacagcac    29520
cacaatattg ttcaaaatcc cacagtgcaa ggcgctgtat ccaaagctca tggcggggac    29580
cacagaaccc acgtggccat cataccacaa gcgcaggtag attaagtggc gacccctcat    29640
aaacacgctg gacataaaca ttacctcttt tggcatgttg taattcacca cctcccggta    29700
```

```
ccatataaac ctctgattaa acatggcgcc atccaccacc atcctaaacc agctggccaa    29760
aacctgcccg ccggctatac actgcaggga accgggactg gaacaatgac agtggagagc    29820
ccaggactcg taaccatgga tcatcatgct cgtcatgata tcaatgttgg cacaacacag    29880
gcacacgtgc atacacttcc tcaggattac aagctcctcc cgcgttagaa ccatatccca    29940
gggaacaacc cattcctgaa tcagcgtaaa tcccacactg cagggaagac ctcgcacgta    30000
actcacgttg tgcattgtca aagtgttaca ttcgggcagc agcggatgat cctccagtat    30060
ggtagcgcgg gtttctgtct caaaaggagg tagacgatcc ctactgtacg gagtgcgccg    30120
agacaaccga gatcgtgttg gtcgtagtgt catgccaaat ggaacgccgg acgtagtcat    30180
atttcctgaa gcaaaaccag gtgcgggcgt gacaaacaga tctgcgtctc cggtctcgcc    30240
gcttagatcg ctctgtgtag tagttgtagt atatccactc tctcaaagca tccaggcgcc    30300
ccctggcttc gggttctatg taaactcctt catgcgccgc tgccctgata acatccacca    30360
ccgcagaata agccacaccc agccaaccta cacattcgtt ctgcgagtca cacacgggag    30420
gagcgggaag agctggaaga accatgtttt tttttttatt ccaaaagatt atccaaaacc    30480
tcaaaatgaa gatctattaa gtgaacgcgc tcccctccgg tggcgtggtc aaactctaca    30540
gccaaagaac agataatggc atttgtaaga tgttgcacaa tggcttccaa aaggcaaacg    30600
gccctcacgt ccaagtggac gtaaaggcta aaccettcag ggtgaatctc tctataaac    30660 attccagcac cttcaaccat gcccaaataa ttctcatctc gccaccttct caatatatct    30720
ctaagcaaat cccgaatatt aagtccggcc attgtaaaaa tctgctccag agcgccctcc    30780
accttcagcc tcaagcagcg aatcatgatt gcaaaaattc aggttcctca cagacctgta    30840
taagattcaa aagcggaaca ttaacaaaaa taccgcgatc ccgtaggtcc cttcgcaggg    30900
ccagctgaac ataatcgtgc aggtctgcac ggaccagcgc ggccacttcc ccgccaggaa    30960
ccatgacaaa agaacccaca ctgattatga cacgcatact cggagctatg ctaaccagcg    31020 tagcccgat gtaagcttgt tgcatgggcg gcgatataaa atgcaaggtg ctgctcaaaa    31080
aatcaggcaa agcctcgcgc aaaaaagaaa gcacatcgta gtcatgctca tgcagataaa    31140
ggcaggtaag ctccggaacc accacagaaa aagacaccat ttttctctca aacatgtctg    31200
cgggtttctg cataaacaca aaataaaata acaaaaaaac atttaaacat tagaagcctg    31260
tcttacaaca ggaaaaacaa cccttataag cataagacgg actacggcca tgccggcgtg    31320
accgtaaaaa aactggtcac cgtgattaaa aagcaccacc gacagctcct cggtcatgtc    31380
cggagtcata atgtaagact cggtaaacac atcaggttga ttcacatcgg tcagtgctaa    31440
aaagcgaccg aaatagcccg ggggaataca tacccgcagg cgtagagaca acattacagc    31500
ccccatagga ggtataacaa aattaatagg agagaaaaac acataaacac ctgaaaaacc    31560
ctcctgccta ggcaaaatag caccctcccg ctccagaaca acatacagcg cttccacagc    31620
ggcagccata acagtcagcc ttaccagtaa aaagaaaac ctattaaaaa aacaccactc    31680
gacacggcac cagctcaatc agtcacagtg taaaaaaggg ccaagtgcag agcgagtata    31740
tataggacta aaaaatgacg taacggttaa agtccacaaa aaacacccag aaaaccgcac    31800
gcgaacctac gcccagaaac gaaagccaaa aaacccacaa cttcctcaaa tcgtcacttc    31860
cgttttccca cgttacgtca cttcccattt taagaaaact acaattccca acacatacaa    31920
gttactccgc cctaaaacct acgtcacccg ccccgttccc acgccccgcg ccacgtcaca    31980
aactccaccc cctcattatc atattggctt caatccaaaa taaggtatat tattgatgat    32040
```

```
<210> SEQ ID NO 90
<211> LENGTH: 31465
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactgtaata gtaatcaatt     360
acggggtcat tagttcatag cccatatatg gagttccgcg ttacataact tacggtaaat     420
ggcccgcctg gctgaccgcc caacgacccc cgcccattga cgtcaataat gacgtatgtt     480
cccatagtaa cgccaatagg gactttccat tgacgtcaat gggtggagta tttacggtaa     540
actgcccact tggcagtaca tcaagtgtat catatgccaa gtacgccccc tattgacgtc     600
aatgacggta aatggcccgc ctggcattat gcccagtaca tgaccttatg gactttcct      660
acttggcagt acatctacgt attagtcatc gctattacca tggtgatgcg gttttggcag     720
tacatcaatg ggcgtggata gcggtttgac tcacggggat ttccaagtct ccaccccatt     780
gacgtcaatg ggagtttgtt ttggcaccaa aatcaacggg actttccaaa atgtcgtaac     840
aactccgccc cattgacgca aatgggcggt aggcgtgtac ggtgggaggt ctatataagc     900
agagctggtt tagtgaaccg tcagatccgc tagagatctg gtaccgtcga cgcggccgct     960
cgagcctaag cttctagatg catgctcgag cggccgccag tgtgatggat atctgcagaa    1020
ttcgcccttg cttctagagc caccatgagc tcccctggca ccgagagcgc gggaaagagc    1080
ctgcagtacc gagtggacca cctgctgagc gccgtggaga atgagctgca ggcgggcagc    1140
gagaagggcg acccccacaga gcgcgaactg cgcgtgggcc tggaggagag cgagctgtgg    1200
ctgcgcttca aggagctcac caatgagatg atcgtgacca gaacggcag gaggatgttt    1260
ccggtgctga aggtgaacgt gtctggcctg gaccccaacg ccatgtactc cttcctgctg    1320
gacttcgtgg cggcggacaa ccaccgctgg aagtacgtga acgggaatg ggtgccgggg    1380
ggcaagccgg agccgcaggc gcccagctgc gtctacatcc accccgactc gcccaacttc    1440
ggggcccact ggatgaaggc tcccgtctcc ttcagcaaag tcaagctcac caacaagctc    1500
aacgaggggg gccagatcat gctgaactcc ttgcataagt atgagcctcg aatccacata    1560
gtgagagttg ggggtccaca gcgcatgatc accagccact gcttccctga cccagttc      1620
atagcggtga ctgctagaag tgatcacaaa gagatgatgg aggaacccgg agacagccag    1680
caacctgggt actcccaatg ggggtggctt cttcctggaa ccagcaccgt gtgtccacct    1740
gcaaatcctc atcctcagtt tggaggtgcc ctctccctcc cctccacgca cagctgtgac    1800
aggtacccaa ccctgaggag ccaccggtcc tcacccctacc ccagccccta tgctcatcgg    1860
aacaattctc caacctattc tgacaactca cctgcatgtt tatccatgct gcaatcccat    1920
gacaattggt ccagccttgg aatgcctgcc catcccagca tgctcccgt gagccacaat     1980
gccagcccac ctaccagctc cagtcagtac cccagcctgt ggtctgtgag caacggcgcc    2040
```

```
gtcaccccgg gctcccaggc agcagccgtg tccaacgggc tgggggccca gttcttccgg    2100
ggctcccccg cgcactacac acccctcacc catccggtct cggcgccctc ttcctcggga    2160
tccccactgt acgaaggggc ggccgcggcc acagacatcg tggacagcca gtacgacgcc    2220
gcagcccaag gccgcctcat agcctcatgg acacctgtgt cgccaccttc catgtgagat    2280
atccgatcca ccggatctag ataactgatc ataatcagcc ataccacatt tgtagaggtt    2340
ttacttgctt taaaaaacct cccacacctc cccctgaacc tgaaacataa aatgaatgca    2400
attgttgttg ttaacttgtt tattgcagct tataatggtt acaaataaag caatagcatc    2460
acaaatttca caaataaagc attttttca ctgcattcta gttgtggttt gtccaaactc    2520
atcaatgtat cttaacgcgg atctggaagg tgctgaggta cgatgagacc cgcaccaggt    2580
gcagaccctg cgagtgtggc ggtaaacata ttaggaacca gcctgtgatg ctggatgtga    2640
ccgaggagct gaggcccgat cacttggtgc tggcctgcac ccgcgctgag tttggctcta    2700
gcgatgaaga tacagattga ggtactgaaa tgtgtgggcg tggcttaagg gtgggaaaga    2760
atatataagg tgggggtctt atgtagtttt gtatctgttt tgcagcagcc gccgccgcca    2820
tgagcaccaa ctcgtttgat ggaagcattg tgagctcata tttgacaacg cgcatgcccc    2880
catgggccgg ggtgcgtcag aatgtgatgg gctccagcat tgatggtcgc cccgtcctgc    2940
ccgcaaactc tactaccttg acctacgaga ccgtgtctgg aacgccgttg gagactgcag    3000
cctccgccgc cgcttcagcc gctgcagcca ccgcccgcgg gattgtgact gactttgctt    3060
tcctgagccc gcttgcaagc agtgcagctt cccgttcatc cgcccgcgat gacaagttga    3120
cggctctttt ggcacaattg gattctttga cccgggaact taatgtcgtt tctcagcagc    3180
tgttggatct gcgccagcag gtttctgccc tgaaggcttc ctcccctccc aatgcggttt    3240
aaaacataaa taaaaaacca gactctgttt ggatttggat caagcaagtg tcttgctgtc    3300
tttatttagg ggttttgcgc gcgcggtagg cccgggacca gcggtctcgg tcgttgaggg    3360
tcctgtgtat tttttccagg acgtggtaaa ggtgactctg gatgttcaga tacatgggca    3420
taagcccgtc tctggggtgg aggtagcacc actgcagagc ttcatgctgc ggggtggtgt    3480
tgtagatgat ccagtcgtag caggagcgct gggcgtggtg cctaaaaatg tctttcagta    3540
gcaagctgat tgccaggggc aggcccttgg tgtaagtgtt tacaaagcgg ttaagctggg    3600
atgggtgcat acgtggggat atgagatgca tcttggactg tattttagg ttggctatgt    3660 tcccagccat atccctccgg ggattcatgt tgtgcagaac caccagcaca gtgtatccgg    3720
tgcacttggg aaatttgtca tgtagcttag aaggaaatgc gtggaagaac ttggagacgc    3780
ccttgtgacc tccaagattt tccatgcatt cgtccataat gatggcaatg ggcccacggg    3840
cggcggcctg ggcgaagata tttctgggat cactaacgtc atagttgtgt tccaggatga    3900
gatcgtcata ggccattttt acaaagcgcg gcggagggt gccagactgc ggtataatgg    3960
ttccatccgg cccagggggcg tagttaccct cacagatttg catttcccac gctttgagtt    4020
cagatggggg gatcatgtct acctgcgggg cgatgaagaa aacggtttcc ggggtagggg    4080
agatcagctg ggaagaaagc aggttcctga gcagctgcga cttaccgcag ccggtgggcc    4140
cgtaaatcac acctattacc ggctgcaact ggtagttaag agagctgcag ctgccgtcat    4200
ccctgagcag gggggccact tcgttaagca tgtccctgac tcgcatgttt tccctgacca    4260
aatccgccaa aaggcgctcg ccgcccagcg atagcagttc ttgcaaggaa gcaaagtttt    4320
tcaacggttt gagaccgtcc gccgtaggca tgcttttgag cgtttgacca agcagttcca    4380
ggcggtccca cagctcggtc acctgctcta cggcatctcg atccagcata tctcctcgtt    4440
```

```
tcgcggggttg gggcggctttt cgctgtacgg cagtagtcgg tgctcgtcca gacgggccag   4500
ggtcatgtct ttccacgggc gcagggtcct cgtcagcgta gtctgggtca cggtgaaggg   4560
gtgcgctccg ggctgcgcgc tggccagggt gcgcttgagg ctggtcctgc tggtgctgaa   4620
gcgctgccgg tcttcgccct gcgcgtcggc caggtagcat ttgaccatgg tgtcatagtc   4680
cagcccctcc gcggcgtggc ccttggcgcg cagcttgccc ttggaggagg cgccgcacga   4740
ggggcagtgc agactttga gggcgtagag cttgggcgcg agaaataccg attccgggga   4800
gtaggcatcc gcgccgcagg ccccgcagac ggtctcgcat tccacgagcc aggtgagctc   4860
tggccgttcg gggtcaaaaa ccaggtttcc cccatgcttt ttgatgcgtt tcttacctct   4920
ggtttccatg agccggtgtc cacgctcggt gacgaaaagg ctgtccgtgt ccccgtatac   4980
agacttgaga ggcctgtcct cgagcggtgt tccgcggtcc tcctcgtata gaaactcgga   5040
ccactctgag acaaaggctc gcgtccaggc cagcacgaag gaggctaagt gggaggggta   5100
gcggtcgttg tccactaggg ggtccactcg ctccagggtg tgaagacaca tgtcgccctc   5160
ttcggcatca aggaaggtga ttggtttgta ggtgtaggcc acgtgaccgg tgttcctga   5220 aggggggcta taaaggggg tggggcgcg ttcgtcctca ctctcttccg catcgctgtc   5280
tgcgagggcc agctgttggg gtgagtactc cctctgaaaa gcgggcatga cttctgcgct   5340
aagattgtca gtttccaaaa acgaggagga tttgatattc acctggcccg cggtgatgcc   5400
tttgagggtg gccgcatcca tctggtcaga aaagacaatc tttttgttgt caagcttggt   5460
ggcaaacgac ccgtagaggg cgttggacag caacttggcg atggagcgca gggtttggtt   5520
tttgtcgcga tcggcgcgct ccttggccgc gatgtttagc tgcacgtatt cgcgcgcaac   5580
gcaccgccat tcgggaaaga cggtggtgcg ctcgtcgggc accaggtgca cgcgccaacc   5640
gcggttgtgc agggtgacaa ggtcaacgct ggtggctacc tctccgcgta ggcgctcgtt   5700
ggtccagcag aggcggccgc ccttgcgcga gcagaatggc ggtaggggt ctagctgcgt   5760 ctcgtccggg gggtctgcgt ccacggtaaa gaccccgggc agcaggcgcg cgtcgaagta   5820
gtctatcttg catccttgca agtctagcgc ctgctgccat gcgcgggcgg caagcgcgcg   5880
ctcgtatggg ttgagtgggg gaccccatgg catgggtgg gtgagcgcgg aggcgtacat   5940
gccgcaaatg tcgtaaacgt agaggggctc tctgagtatt ccaagatatg tagggtagca   6000
tcttccaccg cggatgctgg cgcgcacgta atcgtatagt tcgtgcgagg gagcgaggag   6060
gtcgggaccg aggttgctac gggcgggctg ctctgctcgg aagactatct gcctgaagat   6120
ggcatgtgag ttgatgata tggttggacg ctggaagacg ttgaagctgg cgtctgtgag   6180
acctaccgcg tcacgcacga aggaggcgta ggagtcgcgc agcttgttga ccagctcggc   6240
ggtgacctgc acgtctaggg cgcagtagtc cagggtttcc ttgatgatgt catacttatc   6300
ctgtcccttt tttttccaca gctcgcggtt gaggacaaac tcttcgcggt cttccagta   6360 ctcttggatc ggaaacccgt cggcctccga acgtaagag cctagcatgt agaactggtt   6420
gacggcctgg taggcgcagc atccctttc tacgggtagc gcgtatgcct gcgcggcctt   6480
ccggcatgac cagcatgaag ggcacgagct gcttcccaaa ggcccccatc caagtatagg   6540
tctctacatc gtaggtgaca aagagacgct cggtgcgagg atgcgagccg atcgggaaga   6600
actggatctc ccgccaccaa ttggaggagt ggctattgat gtggtgaaag tagaagtccc   6660
tgcgacgggc cgaacactcg tgctggcttt tgtaaaaacg tgcgcagtac tggcagcggt   6720
gcacgggctg tacatcctgc acgaggttga cctgacgacc gcgcacaagg aagcagagtg   6780
```

```
ggaatttgag cccctcgcct ggcgggtttg gctggtggtc ttctacttcg gctgcttgtc    6840
cttgaccgtc tggctgctcg aggggagtta cggtggatcg gaccaccacg ccgcgcgagc    6900
ccaaagtcca gatgtccgcg cgcggcggtc ggagcttgat gacaacatcg cgcagatggg    6960
agctgtccat ggtctggagc tcccgcggcg tcaggtcagg cgggagctcc tgcaggttta    7020
cctcgcatag acgggtcagg gcgcgggcta gatccaggtg atacctaatt tccaggggct    7080
ggttggtggc ggcgtcgatg gcttgcaaga ggccgcatcc ccgcggcgcg actacggtac    7140
cgcgcggcgg gcggtgggcc gcggggtgt ccttggatga tgcatctaaa agcggtgacg     7200
cgggcgagcc cccggaggta ggggggggctc cggacccgcc gggagagggg gcaggggcac   7260
gtcggcgccg cgcgcgggca ggagctggtg ctgcgcgcgt aggttgctgg cgaacgcgac    7320
gacgcggcgg ttgatctcct gaatctggcg cctctgcgtg aagacgacgg gcccggtgag    7380
cttgaacctg aaagagagtt cgacagaatc aatttcggtg tcgttgacgg cggcctggcg    7440
caaaatctcc tgcacgtctc ctgagttgtc ttgataggcg atctcggcca tgaactgctc    7500
gatctcttcc tcctggagat ctccgcgtcc ggctcgctcc acggtggcgg cgaggtcgtt    7560
ggaaatgcgg gccatgagct gcgagaaggc gttgaggcct ccctcgttcc agacgcggct    7620
gtagaccacg ccccccttcgg catcgcgggc gcgcatgacc acctgcgcga gattgagctc   7680
cacgtgccgg gcgaagacgg cgtagtttcg caggcgctga agaggtagt tgagggtggt    7740
ggcggtgtgt tctgccacga agaagtacat aacccagcgt cgcaacgtgg attcgttgat    7800
aattgttgtg taggtactcc gccgccgagg gacctgagcg agtccgcatc gaccggatcg    7860
gaaaacctct cgagaaaggc gtctaaccag tcacagtcgc aaggtaggct gagcaccgtg    7920
gcggcggca gcgggcggcg gtcgggggttg tttctggcgg aggtgctgct gatgatgtaa    7980
ttaaagtagg cggtcttgag acggcggatg gtcgacagaa gcaccatgtc cttgggtccg    8040
gcctgctgaa tgcgcaggcg gtcggccatg ccccaggctt cgttttgaca tcggcgcagg    8100
tctttgtagt agtcttgcat gagcctttct accggcactt cttcttctcc ttcctcttgt    8160
cctgcatctc ttgcatctat cgctgcggcg gcggcggagt ttggccgtag gtggcgccct    8220
cttcctccca tgcgtgtgac cccgaagccc ctcatcggct gaagcagggc taggtcggcg    8280
acaacgcgct cggctaatat ggcctgctgc acctgcgtga gggtagactg gaagtcatcc    8340
atgtccacaa agcggtggta tgcgcccgtg ttgatggtgt aagtgcagtt ggccataacg    8400
gaccagttaa cggtctggtg acccggctgc gagagctcgg tgtacctgag acgcgagtaa    8460
gccctcgagt caaatacgta gtcgttgcaa gtccgcacca ggtactggta tcccaccaaa    8520
aagtgcggcg gcggctggcg gtagaggggc cagcgtaggg tggccggggc tccggggcg    8580
agatcttcca acataaggcg atgatatccg tagatgtacc tggacatcca ggtgatgccg    8640
gcggcggtgg tggaggcgcg cggaaagtcg cggacgcggt tccagatgtt gcgcagcggc    8700
aaaaagtgct ccatggtcgg gacgctctgg ccggtcaggc gcgcgcaatc gttgacgctc    8760
tagcgtgcaa aaggagagcc tgtaagcggg cactcttccg tggtctggtg gataaattcg    8820
caagggtatc atggcggacg accgggggttc gagccccgta tccggccgtc cgccgtgatc    8880
catgcggtta ccgcccgcgt gtcgaaccca ggtgtgcgac gtcagacaac gggggagtgc    8940
tccttttggc ttccttccag gcgcggcggc tgctgcgcta gcttttttgg ccactggccg    9000
cgcgcagcgt aagcggttag gctggaaagc gaaagcatta agtggctcgc tccctgtagc    9060
cggagggtta ttttcaaagg gttgagtcgc gggaccccccg gttcgagtct cggaccggcc    9120
ggactgcggc gaacgggggt ttgcctcccc gtcatgcaag accccgcttg caaattcctc    9180
```

```
cggaaacagg gacgagcccc ttttttgctt ttcccagatg catccggtgc tgcggcagat   9240 gcgccccct  cctcagcagc ggcaagagca agagcagcgg cagacatgca gggcaccctc   9300
ccctcctcct accgcgtcag gaggggcgac atccgcggtt gacgcggcag cagatggtga   9360
ttacgaaccc ccgcggcgcc gggcccggca ctacctggac ttggaggagg gcgagggcct   9420
ggcgcggcta ggagcgccct ctcctgagcg gcacccaagg gtgcagctga agcgtgatac   9480
gcgtgaggcg tacgtgccgc ggcagaacct gtttcgcgac cgcagggag aggagcccga    9540 ggagatgcgg gatcgaaagt tccacgcagg gcgcgagctg cggcatggcc tgaatcgcga   9600
gcggttgctg cgcgaggagg actttgagcc cgacgcgcga accgggatta gtcccgcgcg   9660
cgcacacgtg gcggccgccg acctggtaac cgcatacgag cagacggtga accaggagat   9720
taactttcaa aaaagcttta acaaccacgt gcgtacgctt gtggcgcgcg aggaggtggc   9780
tataggactg atgcatctgt gggactttgt aagcgcgctg gagcaaaacc caaatagcaa   9840
gccgctcatg gcgcagctgt tccttatagt gcagcacagc agggacaacg aggcattcag   9900
ggatgcgctg ctaaacatag tagagcccga gggccgctgg ctgctcgatt tgataaacat   9960
cctgcagagc atagtggtgc aggagcgcag cttgagcctg gctgacaagg tggccgccat  10020
caactattcc atgcttagcc tgggcaagtt ttacgcccgc aagatatacc ataccccta   10080 cgttcccata gacaaggagg taaagatcga ggggttctac atgcgcatgg cgctgaaggt  10140
gcttaccttg agcgacgacc tgggcgttta tcgcaacgag cgcatccaca aggccgtgag  10200
cgtgagccgg cggcgcgagc tcagcgaccg cgagctgatg cacagcctgc aaagggccct  10260
ggctggcacg ggcagcggcg atagagaggc cgagtcctac tttgacgcgg gcgctgacct  10320
gcgctgggcc ccaagccgac gcgccctgga ggcagctggg gccggacctg gctggcggt   10380 ggcacccgcg cgcgctggca acgtcggcgg cgtggaggaa tatgacgagg acgatgagta  10440
cgagccagag gacggcgagt actaagcggt gatgtttctg atcagatgat gcaagacgca  10500
acggacccgg cggtgcgggc ggcgctgcag agccagccgt ccggccttaa ctccacggac  10560
gactggcgcc aggtcatgga ccgcatcatg tcgctgactg cgcgcaatcc tgacgcgttc  10620
cggcagcagc cgcaggccaa ccggctctcc gcaattctgg aagcggtggt cccggcgcgc  10680
gcaaacccca cgcacgagaa ggtgctggcg atcgtaaacg cgctggccga aaacagggcc  10740
atccggcccg acgaggccgg cctggtctac gacgcgctgc ttcagcgcgt ggctcgttac  10800
aacagcggca acgtgcagac caacctggac cggctggtgg gggatgtgcg cgaggccgtg  10860
gcgcagcgtg agcgcgcgca gcagcagggc aacctgggct ccatggttgc actaaacgcc  10920
ttcctgagta cacagcccgc caacgtgccg cggggacagg aggactacac caactttgtg  10980
agcgcactgc ggctaatggt gactgagaca ccgcaaagtg aggtgtacca gtctgggcca  11040
gactattttt tccagaccag tagacaaggc ctgcagaccg taaacctgag ccaggctttc  11100
aaaaacttgc aggggctgtg gggggtgcgg gctcccacag gcgaccgcgc gaccgtgtct  11160
agcttgctga cgcccaactc gcgcctgttg ctgctgctaa tagcgcccct cacggacagt  11220
ggcagcgtgt cccgggacac ataccctaggt cacttgctga cactgtaccg cgaggccata  11280
ggtcaggcgc atgtgaacga gcatactttc caggagatta caagtgtcag ccgcgcgctg  11340
gggcaggagg acacgggcag cctggaggca accctaaact acctgctgac caaccggcgg  11400
cagaagatcc cctcgttgca cagttttaaac agcgaggagg agcgcatttt gcgctacgtg  11460
cagcagagcg tgagccttaa cctgatgcgc gacggggtaa cgcccagcgt ggcgctggac  11520
```

```
atgaccgcgc gcaacatgga accgggcatg tatgcctcaa accggccgtt tatcaaccgc  11580
ctaatggact acttgcatcg cgcggccgcc gtgaaccccg agtatttcac caatgccatc  11640
ttgaacccgc actggctacc gccccctggt ttctacaccg ggggattcga ggtgcccgag  11700
ggtaacgatg gattcctctg gacgacata  gacgacagcg tgttttcccc gcaaccgcag  11760
accctgctag agttgcaaca gcgcgagcag gcagaggcgg cgctgcgaaa ggaaagcttc  11820
cgcaggccaa gcagcttgtc cgatctaggc gctgcggccc gcggtcaga  tgctagtagc  11880 ccatttccaa gcttgatagg gtctcttacc agcactcgca ccacccgccc gcgcctgctg  11940
ggcgaggagg agtacctaaa caactcgctg ctgcagccgc agcgcgaaaa aaacctgcct  12000
ccggcatttc ccaacaacgg gatagagagc ctagtggaca agatgagtag atggaagacg  12060
tacgcgcagg agcacaggga cgtgccaggc ccgcgcccgc ccacccgtcg tcaaaggcac  12120
gaccgtcagc ggggtctggt gtgggaggac gatgactcgg cagacgacag cagcgtcctg  12180
gatttgggag ggagtggcaa cccgtttgcg caccttcgcc ccaggctggg agaatgttt  12240 taaaaaaaaa aaagcatgat gcaaataaa  aaactcacca aggccatggc accgagcgtt  12300
ggttttcttg tattccccctt agtatgcggc gcgcggcgat gtatgaggaa ggtcctcctc  12360
cctcctacga gagtgtggtg agcgcggcgc cagtggcggc ggcgctgggt tctcccttcg  12420
atgctcccct ggacccgccg tttgtgcctc cgcggtacct gcggcctacc gggggggagaa  12480 acagcatccg ttactctgag ttggcacccc tattcgacac cacccgtgtg tacctggtgg  12540
acaacaagtc aacggatgtg gcatccctga actaccagaa cgaccacagc aactttctga  12600
ccacggtcat tcaaaacaat gactacagcc gggggaggc  aagcacacag accatcaatc  12660
ttgacgaccg gtcgcactgg ggcggcgacc tgaaaaccat cctgcatacc aacatgccaa  12720
atgtgaacga gttcatgttt accaataagt ttaaggcgcg ggtgatggtg tcgcgcttgc  12780
ctactaagga caatcaggtg gagctgaaat acgagtgggt ggagttcacg ctgcccgagg  12840
gcaactactc cgagaccatg accatagacc ttatgaacaa cgcgatcgtg gagcactact  12900
tgaaagtggg cagacagaac ggggttctgg aaagcgacat cggggtaaag tttgacaccc  12960
gcaacttcag actggggttt gaccccgtca ctggtcttgt catgcctggg gtatatacaa  13020
acgaagcctt ccatccagac atcattttgc tgccaggatg cggggtggac ttcacccaca  13080
gccgcctgag caacttgttg ggcatccgca agcggcaacc cttccaggag gctttagga  13140 tcacctacga tgatctggag ggtggtaaca ttcccgcact gttggatgtg gacgcctacc  13200
aggcgagctt gaaagatgac accgaacagg gcggggtgg  cgcaggcggc agcaacagca  13260
gtggcagcgg cgcggaagag aactccaacg cggcagccgc ggcaatgcag ccggtggagg  13320
acatgaacga tcatgccatt cgcggcgaca cctttgccac acgggctgag gagaagcgcg  13380
ctgaggccga agcagcggcc gaagctgccg ccccccgctgc gcaacccgag gtcgagaagc  13440
ctcagaagaa accggtgatc aaaccccctga cagaggacag caagaaacgc agttacaacc  13500
taataagcaa tgacagcacc ttcacccagt accgcagctg gtaccttgca tacaactacg  13560
gcgaccctca gaccggaatc cgctcatgga ccctgctttg cactcctgac gtaacctgcg  13620
gctcggagca ggtctactgg tcgttgccag acatgatgca agaccccgtg accttccgct  13680
ccacgcgcca gatcagcaac tttccggtgg tgggcgccga gctgttgccc gtgcactcca  13740
agagcttcta caacgaccag gccgtctact cccaactcat ccgccagttt acctctctga  13800
cccacgtgtt caatcgcttt cccgagaacc agatttttggc gcgcccgcca gcccccacca  13860
tcaccaccgt cagtgaaaac gttcctgctc tcacagatca cgggacgcta ccgctgcgca  13920
```

```
acagcatcgg aggagtccag cgagtgacca ttactgacgc cagacgccgc acctgcccct   13980
acgtttacaa ggccctgggc atagtctcgc cgcgcgtcct atcgagccgc acttttttgag  14040 caagcatgtc catccttata tcgcccagca ataacacagg ctggggcctg cgcttcccaa   14100
gcaagatgtt tggcggggcc aagaagcgct ccgaccaaca cccagtgcgc gtgcgcgggc   14160
actaccgcgc gccctggggc gcgcacaaac gcggccgcac tgggcgcacc accgtcgatg   14220
acgccatcga cgcggtggtg gaggaggcgc gcaactacac gcccacgccg ccaccagtgt   14280
ccacagtgga cgcggccatt cagaccgtgg tgcgcggagc ccggcgctat gctaaaatga   14340
agagacggcg gaggcgcgta gcacgtcgcc accgccgccg accggcact gccgcccaac    14400 gcgcggcggc ggccctgctt aaccgcgcac gtcgcaccgg ccgacgggcg gccatgcggg   14460
ccgctcgaag gctggccgcg ggtattgtca ctgtgccccc caggtccagg cgacgagcgg   14520
ccgccgcagc agccgcggcc attagtgcta tgactcaggg tcgcaggggc aacgtgtatt   14580
gggtgcgcga ctcggttagc ggcctgcgcg tgcccgtgcg cacccgcccc ccgcgcaact   14640
agattgcaag aaaaaactac ttagactcgt actgttgtat gtatccagcg gcggcggcgc   14700
gcaacgaagc tatgtccaag cgcaaaatca aagaagagat gctccaggtc atcgcgccgg   14760
agatctatgg ccccccgaag aaggaagagc aggattacaa gccccgaaag ctaaagcggg   14820
tcaaaaagaa aaagaaagat gatgatgatg aacttgacga cgaggtggaa ctgctgcacg   14880
ctaccgcgcc caggcgacgg gtacagtgga aggtcgacg cgtaaaacgt gttttgcgac    14940
ccggcaccac cgtagtcttt acgcccggtg agcgctccac ccgcacctac aagcgcgtgt   15000
atgatgaggt gtacggcgac gaggacctgc ttgagcaggc caacgagcgc ctcggggagt   15060
ttgcctacgg aaagcggcat aaggacatgc tggcgttgcc gctggacgag ggcaacccaa   15120
cacctagcct aaagcccgta acactgcagc aggtgctgcc cgcgcttgca ccgtccgaag   15180
aaaagcgcgg cctaaagcgc gagtctggtg acttggcacc caccgtgcag ctgatggtac   15240
ccaagcgcca gcgactggaa gatgtcttgg aaaaaatgac cgtggaacct gggctggagc   15300
ccgaggtccg cgtgcggcca atcaagcagg tggcgccggg actgggcgtg cagaccgtgg   15360
acgttcagat acccactacc agtagcacca gtattgccac cgccacagag ggcatggaga   15420
cacaaacgtc cccggttgcc tcagcggtgg cggatgccgc ggtgcaggcg gtcgctgcgg   15480
ccgcgtccaa gacctctacg gaggtgcaaa cggaccgtg gatgtttcgc gtttcagccc   15540
cccggcgccc gcgccgttcg aggaagtacg gcgccgccag cgcgctactg cccgaatatg   15600
ccctacatcc ttccattgcg cctaccccg gctatcgtgg ctacacctac cgccccagaa   15660
gacgagcaac tacccgacgc cgaaccacca ctggaacccg ccgccgccgt cgccgtcgcc   15720
agcccgtgct ggccccgatt tccgtgcgca gggtggctcg cgaaggaggc aggaccctgg   15780
tgctgccaac agcgcgctac cacccccagca tcgtttaaaa gccggtcttt gtggttcttg   15840
cagatatggc cctcacctgc cgcctccgtt tccggtgcc gggattccga ggaagaatgc    15900
accgtaggag gggcatggcc ggccacggcc tgacgggcgg catgcgtcgt gcgcaccacc   15960
ggcggcggcg cgcgtcgcac cgtcgcatgc gcggcggtat cctgcccctc cttattccac   16020
tgatcgccgc ggcgattggc gccgtgcccg gaattgcatc cgtggccttg caggcgcaga   16080
gacactgatt aaaaacaagt tgcatgtgga aaaatcaaaa taaaaagtct ggactctcac   16140
gctcgcttgg tcctgtaact attttgtaga atggaagaca tcaactttgc gtctctggcc   16200
ccgcgacacg gctcgcgccc gttcatggga aactggcaag atatcggcac cagcaatatg   16260
```

```
agcggtggcg ccttcagctg gggctcgctg tggagcggca ttaaaaattt cggttccacc    16320
gttaagaact atggcagcaa ggcctggaac agcagcacag gccagatgct gagggataag    16380
ttgaaagagc aaaatttcca acaaaaggtg gtagatggcc tggcctctgg cattagcggg    16440
gtggtggacc tggccaacca ggcagtgcaa aataagatta acagtaagct tgatccccgc    16500
cctcccgtag aggagcctcc accggccgtg gagacagtgt ctccagaggg gcgtggcgaa    16560
aagcgtccgc gccccgacag ggaagaaact ctggtgacgc aaatagacga gcctccctcg    16620
tacgaggagg cactaaagca aggcctgccc accacccgtc ccatcgcgcc catggctacc    16680
ggagtgctgg ccagcacac acccgtaacg ctggacctgc ctcccccgc cgacacccag    16740 cagaaacctg tgctgccagg cccgaccgcc gttgttgtaa cccgtcctag ccgcgcgtcc    16800
ctgcgccgcg ccgccagcgg tccgcgatcg ttgcggcccg tagccagtgg caactggcaa    16860
agcacactga acagcatcgt gggtctgggg gtgcaatccc tgaagcgccg acgatgcttc    16920
tgatagctaa cgtgtcgtat gtgtgtcatg tatgcgtcca tgtcgccgcc agaggagctg    16980
ctgagccgcc gcgcgcccgc tttccaagat ggctacccct tcgatgatgc cgcagtggtc    17040
ttacatgcac atctcgggcc aggacgcctc ggagtacctg agccccgggc tggtgcagtt    17100
tgcccgcgcg accgagacgt acttcagcct gaataacaag tttagaaacc ccacggtggc    17160
gcctacgcac gacgtgacca cagaccggtc ccagcgtttg acgctgcggt tcatccctgt    17220
ggaccgtgag gatactgcgt actcgtacaa ggcgcggttc accctagctg tgggtgataa    17280
ccgtgtgctg acatggctt ccacgtactt tgacatccgc ggcgtgctgg acaggggccc    17340 tactttaag ccctactctg gcactgccta caacgccctg gctcccaagg gtgccccaaa    17400
tccttgcgaa tgggatgaag ctgctactgc tcttgaaata aacctagaag aagaggacga    17460
tgacaacgaa gacgaagtag acgagcaagc tgagcagcaa aaaactcacg tatttgggca    17520
ggcgccttat tctggtataa atattacaaa ggagggtatt caaataggtg tcgaaggtca    17580
aacacctaaa tatgccgata aaacatttca acctgaacct caaataggag aatctcagtg    17640
gtacgaaaca gaaattaatc atgcagctgg gagagtccta aaaaagacta ccccaatgaa    17700
accatgttac ggttcatatg caaaacccac aaatgaaaat ggagggcaag gcattcttgt    17760
aaagcaacaa aatggaaagc tagaaagtca agtggaaatg caattttcct caactactga    17820
ggcagccgca ggcaatggtg ataacttgac tcctaaagtg gtattgtaca gtgaagatgt    17880
agatatagaa accccagaca ctcatatttc ttacatgccc actattaagg aaggtaactc    17940
acgagaacta atgggccaac aatctatgcc caacaggcct aattacattg cttttaggga    18000
caattttatt ggtctaatgt attacaacag cacgggtaat atgggtgttc tggcgggcca    18060
agcatcgcag ttgaatgctg ttgtagattt gcaagacaga aacacagagc tttcatacca    18120
gcttttgctt gattccattg gtgatagaac caggtacttt tctatgtgga atcaggctgt    18180
tgacagctat gatccagatg ttagaattat tgaaaatcat ggaactgaag atgaacttcc    18240
aaattactgc tttccactgg gaggtgtgat taatacagag actcttacca aggtaaaacc    18300
taaaacaggt caggaaatg gatgggaaaa agatgctaca gaattttcag ataaaatga    18360 aataagagtt ggaaataatt ttgccatgga aatcaatcta aatgccaacc tgtggagaaa    18420
tttcctgtac tccaacatag cgctgtattt gcccgacaag ctaaagtaca gtccttccaa    18480
cgtaaaaatt tctgataacc caaacaccta cgactacatg aacaagcgag tggtggctcc    18540
cgggctagtg gactgctaca ttaaccttgg agcacgctgg tcccttgact atatggacaa    18600
cgtcaaccca tttaaccacc accgcaatgc tggcctgcgc taccgctcaa tgttgctggg    18660
```

```
caatggtcgc tatgtgccct tccacatcca ggtgcctcag aagttctttg ccattaaaaa  18720
cctccttctc ctgccgggct catacaccta cgagtggaac ttcaggaagg atgttaacat  18780
ggttctgcag agctccctag gaaatgacct aagggttgac ggagccagca ttaagtttga  18840
tagcatttgc ctttacgcca ccttcttccc catggcccac aacaccgcct ccacgcttga  18900
ggccatgctt agaaacgaca ccaacgacca gtcctttaac gactatctct ccgccgccaa  18960
catgctctac cctatacccg ccaacgctac aacgtgccc atatccatcc cctcccgcaa   19020
ctgggcggct ttccgcggct gggccttcac gcgccttaag actaaggaaa ccccatcact  19080
gggctcgggc tacgacccct tattacaccta ctctggctct ataccctacc tagatggaac  19140
cttttacctc aaccacacct ttaagaaggt ggccattacc tttgactctt ctgtcagctg  19200
gcctggcaat gaccgcctgc ttaccccaa cgagtttgaa attaagcgct cagttgacgg  19260
ggagggttac aacgttgccc agtgtaacat gaccaaagac tggttcctgg tacaaatgct  19320
agctaactat aacattggct accagggctt ctatatccca gagagctaca aggaccgcat  19380
gtactccttc tttagaaaact tccagcccat gagccgtcag gtggtggatg atactaaata  19440
caaggactac aacaggtgg gcatcctaca ccaacacaac aactctggat tgttggcta   19500
ccttgccccc accatgcgcg aaggacaggc ctaccctgct aacttcccct atccgcttat  19560
aggcaagacc gcagttgaca gcattaccca gaaaaagttt ctttgcgatc gcaccctttg  19620
gcgcatccca ttctccagta actttatgtc catgggcgca ctcacagacc tgggccaaaa  19680
ccttctctac gccaactccg cccacgcgct agacatgact tttgaggtgg atcccatgga  19740
cgagcccacc cttctttatg ttttgtttga agtctttgac gtggtccgtg tgcaccagcc  19800
gcaccgcggc gtcatcgaaa ccgtgtacct gcgcacgccc ttctcggccg caacgccac   19860
aacataaaga agcaagcaac atcaacaaca gctgccgcca tgggctccag tgagcaggaa  19920
ctgaaagcca ttgtcaaaga tcttggttgt gggccatatt ttttgggcac ctatgacaag  19980
cgctttccag gctttgtttc tccacacaag ctcgcctgcg ccatagtcaa tacggccggt  20040
cgcgagactg ggggcgtaca ctggatggcc tttgcctgga accgcactc aaaaacatgc   20100
tacctctttg agccctttgg cttttctgac cagcgactca gcaggttta ccagtttgag   20160
tacgagtcac tcctgcgccg tagcgccatt gcttcttccc ccgaccgctg tataacgctg  20220
gaaaagtcca cccaaagcgt acaggggccc aactcggccg cctgtggact attctgctgc  20280
atgtttctcc acgcctttgc caactggccc caaactccca tggatcacaa ccccaccatg  20340
aaccttatta ccggggtacc caactccatg ctcaacagtc cccaggtaca gcccaccctg  20400
cgtcgcaacc aggaacagct ctacagcttc ctggagcgcc actcgcccta cttccgcagc  20460
cacagtgcgc agattaggag cgccacttct ttttgtcact tgaaaaacat gtaaaaataa  20520
tgtactagag acactttcaa taaaggcaaa tgcttttatt tgtacactct cgggtgatta  20580
tttaccccca cccttgccgt ctgcgccgtt taaaaatcaa aggggttctg ccgcgcatcg  20640
ctatgcgcca ctggcaggga cacgttgcga tactggtgtt tagtgctcca cttaaactca  20700
ggcacaacca tccgcggcag ctcggtgaag ttttcactcc acaggctgcg caccatcacc  20760
aacgcgttta gcaggtcggg cgccgatatc ttgaagtcgc agttggggcc tccgccctgc  20820
gcgcgcgagt tgcgatacac agggttgcag cactggaaca ctatcagcgc cgggtggtgc  20880
acgctggcca gcacgctctt gtcggagatc agatccgcgt ccaggtcctc cgcgttgctc  20940
agggcgaacg gagtcaactt tggtagctgc cttcccaaaa agggcgcgtg cccaggcttt  21000
```

```
gagttgcact cgcaccgtag tggcatcaaa aggtgaccgt gcccggtctg ggcgttagga    21060
tacagcgcct gcataaaagc cttgatctgc ttaaaagcca cctgagcctt tgcgccttca    21120
gagaagaaca tgccgcaaga cttgccggaa aactgattgg ccggacaggc cgcgtcgtgc    21180
acgcagcacc ttgcgtcggt gttggagatc tgcaccacat ttcggcccca ccggttcttc    21240
acgatcttgg ccttgctaga ctgctccttc agcgcgcgct gcccgttttc gctcgtcaca    21300
tccatttcaa tcacgtgctc cttatttatc ataatgcttc cgtgtagaca cttaagctcg    21360
ccttcgatct cagcgcagcg gtgcagccac aacgcgcagc ccgtgggctc gtgatgcttg    21420
taggtcacct ctgcaaacga ctgcaggtac gcctgcagga atcgcccat catcgtcaca     21480
aaggtcttgt tgctggtgaa ggtcagctgc aacccgcggt gctcctcgtt cagccaggtc    21540
ttgcatacgg ccgccagagc ttccacttgg tcaggcagta gtttgaagtt cgcctttaga    21600
tcgttatcca cgtggtactt gtccatcagc gcgcgcgcag cctccatgcc cttctcccac    21660
gcagacacga tcggcacact cagcgggttc atcaccgtaa tttcactttc cgcttcgctg    21720
ggctcttcct cttcctcttg cgtccgcata ccacgcgcca ctgggtcgtc ttcattcagc    21780
cgccgcactg tgcgcttacc tccttttgcca tgcttgatta gcaccggtgg gttgctgaaa   21840
cccaccattt gtagcgccac atcttctctt tcttcctcgc tgtccacgat tacctctggt    21900
gatggcgggc gctcgggctt gggagaaggg cgcttcttt tcttcttggg cgcaatggcc     21960
aaatccgccg ccgaggtcga tggccgcggg ctgggtgtgc gcggcaccag cgcgtcttgt    22020
gatgagtctt cctcgtcctc ggactcgata cgccgcctca tccgcttttt tgggggcgcc    22080
cggggaggcg gcggcgacgg ggacgggac gacacgtcct ccatggttgg gggacgtcgc     22140
gccgcaccgc gtccgcgctc gggggtggtt tcgcgctgct cctcttcccg actggccatt    22200
tccttctcct ataggcagaa aaagatcatg gagtcagtcg agaagaagga cagcctaacc    22260
gcccctctg agttcgccac caccgcctcc accgatgccg ccaacgcgcc taccaccttc      22320
cccgtcgagg caccccgct tgaggaggag gaagtgatta tcgagcagga cccaggtttt     22380
gtaagcgaag acgacgagga ccgctcagta ccaacagagg ataaaaagca agaccaggac    22440
aacgcagagc caaacgagga acaagtcggg cgggggacg aaaggcatgg cgactaccta     22500
gatgtgggag acgacgtgct gttgaagcat ctgcagcgcc agtgcgccat tatctgcgac    22560
gcgttgcaag agcgcagcga tgtgccctc gccatagcgg atgtcagcct tgcctacgaa      22620
cgccacctat tctcaccgcg cgtaccccc aaacgccaag aaaacggcac atgcgagccc      22680
aacccgcgcc tcaacttcta ccccgtattt gccgtgccag aggtgcttgc cacctatcac    22740
atcttttttcc aaaactgcaa gatacccta tcctgccgtg ccaaccgcag ccgagcggac    22800
aagcagctgg ccttgcggca gggcgctgtc atacctgata tcgcctcgct caacgaagtg    22860
ccaaaaatct ttgagggtct tggacgcgac gagaagcgcg cggcaaacgc tctgcaacag    22920
gaaaacagcg aaaatgaaag tcactctgga gtgttggtgg aactcgaggg tgacaacgcg    22980
cgcctagccg tactaaaacg cagcatcgag gtcacccact ttgcctaccc ggcacttaac    23040
ctacccccca aggtcatgag cacagtcatg agtgagctga tcgtgcgccg tgcgcagccc    23100
ctggagaggg atgcaaattt gcaagaacaa acagaggagg cctaccgc agttggcgac      23160
gagcagctag cgcgctggct tcaaacgcgc gagcctgccg acttggagga gcgacgcaaa    23220
ctaatgatgg ccgcagtgct cgttaccgtg gagcttgagt gcatgcagcg gttctttgct    23280
gacccggaga tgcagcgcaa gctagaggaa acattgcact acacctttcg acagggctac    23340
gtacgccagg cctgcaagat ctccaacgtg gagctctgca acctggtctc ctaccttgga    23400
```

```
attttgcacg aaaaccgcct tgggcaaaac gtgcttcatt ccacgctcaa gggcgaggcg   23460
cgccgcgact acgtccgcga ctgcgtttac ttatttctat gctacacctg gcagacggcc   23520
atgggcgttt ggcagcagtg cttggaggag tgcaacctca aggagctgca gaaactgcta   23580
aagcaaaact tgaaggacct atggacggcc ttcaacgagc gctccgtggc cgcgcacctg   23640
gcggacatca ttttccccga acgcctgctt aaaaccctgc aacagggtct gccagacttc   23700
accagtcaaa gcatgttgca gaactttagg aactttatcc tagagcgctc aggaatcttg   23760
cccgccacct gctgtgcact tcctagcgac tttgtgccca ttaagtaccg gaatgccct   23820 ccgccgcttt ggggccactg ctaccttctg cagctagcca actaccttgc ctaccactct   23880
gacataatgg aagacgtgag cggtgacggt ctactggagt gtcactgtcg ctgcaaccta   23940
tgcaccccgc accgctccct ggtttgcaat tcgcagctgc ttaacgaaag tcaaattatc   24000
ggtacctttg agctgcaggg tccctcgcct gacgaaaagt ccgcggctcc ggggttgaaa   24060
ctcactccgg ggctgtggac gtcggcttac cttcgcaaat ttgtacctga ggactaccac   24120
gcccacgaga ttaggttcta cgaagaccaa tcccgcccgc ctaatgcgga gcttaccgcc   24180
tgcgtcatta cccagggcca cattcttggc caattgcaag ccatcaacaa agcccgccaa   24240
gagtttctgc tacgaaaggg acgggggtt tacttggacc cccagtccgg cgaggagctc   24300
aacccaatcc ccccgccgcc gcagccctat cagcagcagc cgcgggccct tgcttcccag   24360
gatggcaccc aaaaagaagc tgcagctgcc gccgccaccc acggacgagg aggaatactg   24420
ggacagtcag gcagaggagg ttttggacga ggaggaggag gacatgatgg aagactggga   24480
gagcctagac gaggaagctt ccgaggtcga agaggtgtca gacgaaacac cgtcaccctc   24540
ggtcgcattc ccctcgccgg cgccccagaa atcggcaacc ggttccagca tggctacaac   24600
ctccgctcct caggcgccgc cggcactgcc cgttcgccga cccaaccgta gatgggacac   24660
cactggaacc agggccggta agtccaagca gccgccgccg ttagcccaag agcaacaaca   24720
gcgccaaggc taccgctcat ggcgcgggca caagaacgcc atagttgctt gcttgcaaga   24780
ctgtgggggc aacatctcct tcgcccgccg ctttcttctc taccatcacg gcgtggcctt   24840
cccccgtaac atcctgcatt actaccgtca tctctacagc ccatactgca ccggcggcag   24900
cggcagcaac agcagcggcc acacagaagc aaaggcgacc ggatagcaag actctgacaa   24960
agcccaagaa atccacagcg gcggcagcag caggaggagg agcgctgcgt ctggcgccca   25020
acgaacccgt atcgacccgc gagcttagaa acaggatttt tcccactctg tatgctatat   25080
ttcaacagag caggggccaa gaacaagagc tgaaaataaa aaacaggtct ctgcgatccc   25140
tcacccgcag ctgcctgtat cacaaaagcg aagatcagct tcggcgcacg ctggaagacg   25200
cggaggctct cttcagtaaa tactgcgcgc tgactcttaa ggactagttt cgcgcccttt   25260
ctcaaattta agcgcgaaaa ctacgtcatc tccagcggcc acaccggcg ccagcacctg   25320 ttgtcagcgc cattatgagc aaggaaattc ccacgcccta catgtggagt taccagccac   25380
aaatgggact tgcggctgga gctgcccaag actactcaac ccgaataaac tacatgagcg   25440
cgggacccca catgatatcc cgggtcaacg gaatacgcgc ccaccgaaac cgaattctcc   25500
tggaacaggc ggctattacc accacacctc gtaataacct taatcccgt agttggcccg   25560 ctgccctggt gtaccaggaa agtcccgctc ccaccactgt ggtacttccc agagacgccc   25620
aggccgaagt tcagatgact aactcagggg cgcagcttgc gggcggcttt cgtcacaggg   25680
tgcggtcgcc cgggcagggt ataactcacc tgacaatcag agggcgaggt attcagctca   25740
```

```
acgacgagtc ggtgagctcc tcgcttggtc tccgtccgga cgggacattt cagatcggcg   25800
gcgccggccg ctcttcattc acgcctcgtc aggcaatcct aactctgcag acctcgtcct   25860
ctgagccgcg ctctggaggc attggaactc tgcaatttat tgaggagttt gtgccatcgg   25920
tctactttaa ccccttctcg ggacctcccg gccactatcc ggatcaattt attcctaact   25980
ttgacgcggt aaaggactcg gcggacggct acgactgaat gttaagtgga gaggcagagc   26040
aactgcgcct gaaacacctg gtccactgtc gccgccacaa gtgctttgcc cgcgactccg   26100
gtgagttttg ctactttgaa ttgcccgagg atcatatcga gggcccggcg cacggcgtcc   26160
ggcttaccgc ccagggagag cttgcccgta gcctgattcg ggagtttacc cagcgccccc   26220
tgctagttga gcgggacagg ggaccctgtg ttctcactgt gatttgcaac tgtcctaacc   26280
ctggattaca tcaagatcct ctagttaatg tcaggtcgcc taagtcgatt aactagagta   26340
cccgggatc ttattcccctt taactaataa aaaaaaataa taaagcatca cttacttaaa   26400
atcagttagc aaatttctgt ccagtttatt cagcagcacc tccttgccct cctcccagct   26460
ctggtattgc agcttcctcc tggctgcaaa ctttctccac aatctaaatg gaatgtcagt   26520
ttcctcctgt tcctgtccat ccgcacccac tatcttcatg ttgttgcaga tgaagcgcgc   26580
aagaccgtct gaagatacct tcaacccccgt gtatccatat gacacggaaa ccggtcctcc   26640
aactgtgcct tttcttactc ctccctttgt atccccccaat gggtttcaag agagtccccc   26700
tggggtactc tctttgcgcc tatccgaacc tctagttacc tccaatggca tgcttgcgct   26760
caaaatgggc aacggcctct ctctggacga ggccggcaac cttacctccc aaaatgtaac   26820
cactgtgagc ccacctctca aaaaaaccaa gtcaaacata aacctggaaa tatctgcacc   26880
cctcacagtt acctcagaag ccctaactgt ggctgccgcc gcacctctaa tggtcgcggg   26940
caacacactc accatgcaat cacaggcccc gctaaccgtg cacgactcca aacttagcat   27000
tgccacccaa ggacccctca cagtgtcaga aggaaagcta gccctgcaaa catcaggccc   27060
cctcaccacc accgatagca gtaccccttac tatcactgcc tcacccccctc taactactgc   27120
cactggtagc ttgggcattg acttgaaaga gcccatttat acacaaaatg gaaaactagg   27180
actaaagtac ggggctcctt tgcatgtaac agacgaccta aacactttga ccgtagcaac   27240
tggtccaggt gtgactatta ataatacttc cttgcaaact aaagttactg gagccttggg   27300
ttttgattca caaggcaata tgcaacttaa tgtagcagga ggactaagga ttgattctca   27360
aaacagacgc cttatacttg atgttagtta tccgtttgat gctcaaaacc aactaaatct   27420
aagactagga cagggccctc ttttttataaa ctcagcccac aacttggata ttaactacaa   27480
caaaggcctt tacttgttta cagcttcaaa caattccaaa aagcttgagg ttaacctaag   27540
cactgccaag gggttgatgt ttgacgctac agccatagcc attaatgcag agatgggcct   27600
tgaatttggt tcacctaatg caccaaacac aaatcccctc aaaacaaaaa ttggccatgg   27660
cctagaattt gattcaaaca aggctatggt tcctaaacta ggaactggcc ttagttttga   27720
cagcacaggt gccattacag taggaaacaa aaataatgat aagctaactt tgtggaccac   27780
accagctcca tctcctaact gtagactaaa tgcagagaaa gatgctaaac tcactttggt   27840
cttaacaaaa tgtggcagtc aaatacttgc tacagtttca gttttggctg ttaaaggcag   27900
tttggctcca atatctggaa cagttcaaag tgctcatctt attataagat tgacgaaaa   27960
tggagtgcta ctaaacaatt ccttcctgga cccagaatat tggaacttta gaaatggaga   28020
tcttactgaa ggcacagcct atacaaacgc tgttggattt atgcctaacc tatcagctta   28080
tccaaaatct cacggtaaaa ctgccaaaag taacattgtc agtcaagttt acttaaacgg   28140
```

```
agacaaaact aaacctgtaa cactaaccat tacactaaac ggtacacagg aaacaggaga   28200
cacaactcca agtgcatact ctatgtcatt ttcatgggac tggtctggcc acaactacat   28260
taatgaaata tttgccacat cctcttacac tttttcatac attgcccaag aataaagaat   28320
cgtttgtgtt atgtttcaac gtgttttattt ttcaattgca gaaaatttca agtcattttt   28380
cattcagtag tatagcccca ccaccacata gcttatacag atcaccgtac cttaatcaaa   28440
ctcacagaac cctagtattc aacctgccac ctccctccca acacacagag tacacagtcc   28500
tttctccccg gctggcctta aaaagcatca tatcatgggt aacagacata ttcttaggtg   28560
ttatattcca cacggtttcc tgtcgagcca aacgctcatc agtgatatta ataaactccc   28620
cgggcagctc acttaagttc atgtcgctgt ccagctgctg agccacaggc tgctgtccaa   28680
cttgcggttg cttaacgggc ggcgaaggag aagtccacgc ctacatgggg gtagagtcat   28740
aatcgtgcat caggataggg cggtggtgct gcagcagcgc gcgaataaac tgctgccgcc   28800
gccgctccgt cctgcaggaa tacaacatgg cagtggtctc ctcagcgatg attcgcaccg   28860
cccgcagcat aaggcgcctt gtcctccggg cacagcagcg caccctgatc tcacttaaat   28920
cagcacagta actgcagcac agcaccacaa tattgttcaa aatcccacag tgcaaggcgc   28980
tgtatccaaa gctcatggcg gggaccacag aacccacgtg gccatcatac acaagcgca   29040 ggtagattaa gtggcgaccc ctcataaaca cgctggacat aaacattacc tcttttggca   29100
tgttgtaatt caccacctcc cggtaccata taaacctctg attaaacatg gcgccatcca   29160
ccaccatcct aaaccagctg gccaaaacct gcccgccggc tatacactgc agggaaccgg   29220
gactggaaca atgacagtgg agagcccagg actcgtaacc atggatcatc atgctcgtca   29280
tgatatcaat gttggcacaa acaggcaca cgtgcataca cttcctcagg attacaagct   29340
cctcccgcgt tagaaccata tcccagggaa caacccattc ctgaatcagc gtaaatccca   29400
cactgcaggg aagacctcgc acgtaactca cgttgtgcat tgtcaaagtg ttacattcgg   29460
gcagcagcgg atgatcctcc agtatggtag cgcgggtttc tgtctcaaaa ggaggtagac   29520
gatccctact gtacggagtg cgccgagaca accgagatcg tgttggtcgt agtgtcatgc   29580
caaatggaac gccggacgta gtcatatttc ctgaagcaaa accaggtgcg ggcgtgacaa   29640
acagatctgc gtctccggtc tcgccgctta gatcgctctg tgtagtagtt gtagtatatc   29700
cactctctca aagcatccag gcgcccctg gcttcgggtt ctatgtaaac tccttcatgc   29760
gccgctgccc tgataacatc caccaccgca gaataagcca cacccagcca acctacacat   29820
tcgttctgcg agtcacacac gggaggagcg ggaagagctg gaagaaccat gtttttttt   29880 ttattccaaa agattatcca aaacctcaaa atgaagatct attaagtgaa cgcgctcccc   29940
tccggtggcg tggtcaaact ctacagccaa agaacagata atggcatttg taagatgttg   30000
cacaatggct tccaaaaggc aaacggccct cacgtccaag tggacgtaaa ggctaaaccc   30060
ttcagggtga atctcctcta taaacattcc agcaccttca accatgccca aataattctc   30120
atctcgccac cttctcaata tatctctaag caaatcccga atattaagtc cggccattgt   30180
aaaaatctgc tccagagcgc cctccacctt cagcctcaag cagcgaatca tgattgcaaa   30240
aattcaggtt cctcacagac ctgtataaga ttcaaaagcg gaacattaac aaaaataccg   30300
cgatcccgta ggtcccttcg cagggccagc tgaacataat cgtgcaggtc tgcacggacc   30360
agcgcggcca cttccccgcc aggaaccatg acaaaagaac ccacactgat tatgacacgc   30420
atactcggag ctatgctaac cagcgtagcc ccgatgtaag cttgttgcat gggcggcgat   30480
```

-continued

```
ataaaatgca aggtgctgct caaaaaatca ggcaaagcct cgcgcaaaaa agaaagcaca    30540
tcgtagtcat gctcatgcag ataaaggcag gtaagctccg gaaccaccac agaaaaagac    30600 accattttc  tctcaaacat gtctgcgggt ttctgcataa acacaaaata aaataacaaa    30660
aaaacattta aacattagaa gcctgtctta caacaggaaa aacaaccctt ataagcataa    30720
gacggactac ggccatgccg gcgtgaccgt aaaaaaactg gtcaccgtga ttaaaaagca    30780
ccaccgacag ctcctcggtc atgtccggag tcataatgta agactcggta aacacatcag    30840
gttgattcac atcggtcagt gctaaaaagc gaccgaaata gcccggggga atacataccc    30900
gcaggcgtag agacaacatt acagccccca taggaggtat aacaaaatta ataggagaga    30960
aaaacacata aacacctgaa aaaccctcct gcctaggcaa aatagcaccc tcccgctcca    31020
gaacaacata cagcgcttcc acagcggcag ccataacagt cagccttacc agtaaaaaag    31080
aaaacctatt aaaaaaacac cactcgacac ggcaccagct caatcagtca cagtgtaaaa    31140
aagggccaag tgcagagcga gtatatatag gactaaaaaa tgacgtaacg gttaaagtcc    31200
acaaaaaaca cccagaaaac cgcacgcgaa cctacgccca gaaacgaaag ccaaaaaacc    31260
cacaacttcc tcaaatcgtc acttccgttt tcccacgtta cgtcacttcc cattttaaga    31320
aaactacaat tcccaacaca tacaagttac tccgccctaa aacctacgtc acccgccccg    31380
ttcccacgcc ccgcgccacg tcacaaactc cacccccctca ttatcatatt ggcttcaatc    31440
caaaataagg tatattattg atgat                                          31465
```

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Glu Gln Val Trp Gly Met Ala Val Arg
1               5

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Cys Gln Gly Pro Glu Gln Val Trp Gly Met Ala Val Arg Glu Leu
1               5                   10                  15

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Gly Glu Thr Val Thr Met Pro Cys Pro
1               5

<210> SEQ ID NO 94
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asn Val Gly Glu Thr Val Thr Met Pro Cys Pro Lys Val Phe Ser
1               5                   10                  15

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Leu Gly Ala Gln Cys Ser Glu Ala
1               5

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asn Asn Gly Leu Gly Ala Gln Cys Ser Glu Ala Val Thr Leu Asn
1               5                   10                  15

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Lys Leu Thr Thr Glu Leu Thr Ile
1               5

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Gly Pro Glu Arg Arg Lys Leu Thr Thr Glu Leu Thr Ile Ile
1               5                   10                  15

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Pro Glu Arg Arg Lys Leu Thr Thr Glu
```

```
<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Met Asp Trp Val Trp Met Asp Thr Thr
1               5

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Val Met Asp Trp Val Trp Met Asp Thr Thr Leu Ser Leu Ser
1               5                   10                  15

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Val Trp Met Asp Thr Thr Leu Ser Leu
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Lys Thr Leu Asn Pro Ser Gln Thr
1               5

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Trp Phe Arg Glu Gly Lys Thr Leu Asn Pro Ser Gln Thr Ser
1               5                   10                  15

<210> SEQ ID NO 105
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 105

Arg Glu Gly Lys Thr Leu Asn Pro Ser
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Val Arg Asn Ala Thr Ser Tyr Arg Cys
1               5

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Pro Asn Val Thr Val Arg Asn Ala Thr Ser Tyr Arg Cys Gly
1               5                   10                  15

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asn Val Thr Val Arg Asn Ala Thr Ser
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Phe Ala Met Ala Gln Ile Pro Ser Leu
1               5

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Pro Phe Ala Met Ala Gln Ile Pro Ser Leu Ser Leu Arg Ala Val
1               5                   10                  15
```

```
<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Gln Ile Pro Ser Leu Ser Leu Arg
1               5
```

COMPOSITIONS AND METHODS FOR TUMOR VACCINATION AND IMMUNOTHERAPY INVOLVING HER ANTIGENS

CROSS REFERENCE TO RELATED APPLICATIONS

This application is a national stage application under 35 U.S.C. 371 and claims the benefit of PCT Application No. PCT/US2018/035759 having an international filing date of 2 Jun. 2018, which designated the United States, which PCT application claimed the benefit of U.S. Provisional Patent Application No. 62/514,666 filed Jun. 2, 2017, the entire disclosures of which are incorporated herein by reference in their entireties.

REFERENCE TO SEQUENCE LISTING

This application contains a Sequence Listing submitted as an electronic text file named "Sequence_Listing_file.TXT", having a size in bytes of 319000 bytes, and created on Jun. 2, 2018. The information contained in this electronic file is hereby incorporated by reference in its entirety pursuant to 37 CFR § 1.52(e)(5).

STATEMENT OF GOVERNMENT INTEREST

The invention was made with government support under SBIR Grant No. 1R43CA139663-01, SBIR Contract No. HHSN261201100090C, SBIR Contract No. HHSN261201300066C awarded by the National Cancer Institute (NCI), and Award W81XWH-12-1-0574; BC113107 from the Department of Defense. The government has certain rights in the invention.

BACKGROUND

Vaccines help the body fight disease by training the immune system to recognize and destroy harmful substances and diseased cells. Vaccines can be largely grouped into two types, preventive and treatment vaccines. Prevention vaccines are given to healthy people to prevent the development of specific diseases, while treatment vaccines, also referred to as immunotherapies, are given to a person who has been diagnosed with disease to help stop the disease from growing and spreading or as a preventive measure.

Viral vaccines are currently being developed to help fight infectious diseases and cancers. These viral vaccines work by inducing expression of a small fraction of genes associated with a disease within the host's cells, which in turn, enhance the host's immune system to identify and destroy diseased cells. As such, clinical response of a viral vaccine can depend on the ability of the vaccine to obtain a high-level immunogenicity and have sustained long-term expression.

Cancer immunotherapy achieved by delivering viral vaccines encoding tumor-associated antigens (TAA) may have survival benefits; however, limitations to these strategies exist and more immunologically potent vaccines are needed. Therefore, there remains a need to discover novel compositions and methods for enhanced therapeutic response to complex diseases such as cancer.

SUMMARY

In some aspects, a composition comprises a recombinant adenovirus vector comprising a nucleic acid sequence encoding a full length HER3 antigen or a nucleic acid sequence encoding a truncated HER3 antigen; a recombinant adenovirus vector comprising a nucleic acid sequence encoding a MUC1 antigen; and a recombinant adenovirus vector comprising a nucleic acid sequence encoding a Brachyury antigen.

In some aspects, a composition comprises a recombinant adenovirus vector comprising: a deletion in an E2b region of the recombinant adenovirus vector; and a nucleic acid sequence encoding a truncated HER3 antigen comprising at least 80%, at least 85%, at least 90%, at least 95%, at least 97%, or at least 99% sequence identity to SEQ ID NO: 6 or SEQ ID NO: 87.

In some aspects, a composition comprising: a recombinant adenovirus vector comprising a nucleic acid sequence encoding a full length HER3 antigen or a nucleic acid sequence encoding a truncated HER3 antigen; and a recombinant adenovirus vector comprising a nucleic acid sequence encoding a costimulatory molecule.

In some embodiments, the composition further comprises a recombinant adenovirus vector comprising a nucleic acid sequence encoding a full length HER3 antigen; a recombinant adenovirus vector comprising a nucleic acid sequence encoding a MUC1 antigen; a recombinant adenovirus vector comprising a nucleic acid sequence encoding a Brachyury antigen, or any combination thereof. In some embodiments, a composition further comprises a recombinant adenovirus vector comprising a nucleic acid sequence encoding a costimulatory molecule. In some embodiments, two or more of: (i) the nucleic acid sequence encoding the full length HER3 antigen or the nucleic acid sequence encoding the truncated HER3 antigen; (ii) the nucleic acid sequence encoding the MUC1 antigen; and (iii) the nucleic acid sequence encoding the Brachyury antigen are comprised within a same recombinant adenovirus vector. In some embodiments, one or more of: (i) the nucleic acid sequence encoding the full length HER3 antigen or the nucleic acid sequence encoding the truncated HER3 antigen; (ii) the nucleic acid sequence encoding the MUC1 antigen; and (iii) the nucleic acid sequence encoding the Brachyury antigen are comprised within a separate recombinant adenovirus vector. In some embodiments, two or more of: (i) the nucleic acid sequence encoding a full length HER3 antigen or a nucleic acid sequence encoding a truncated HER3 antigen; and (ii) the nucleic acid sequence encoding a costimulatory molecule are comprised within the same recombinant adenovirus vector. In some embodiments, one or more of: (i) the nucleic acid sequence encoding a full length HER3 antigen or a nucleic acid sequence encoding a truncated HER3 antigen; and (ii) the nucleic acid sequence encoding a costimulatory molecule are comprised within a separate recombinant adenovirus vector. In some embodiments, the truncated HER3 antigen comprises at least 80% at least 85%, at least 90%, at least 92%, at least 95%, at least 97%, or at least 99% sequence identity to SEQ ID NO: 87. In some embodiments, the truncated HER3 antigen comprises at least amino acid residue 8 to amino acid residue 162, at least amino acid residue 10 to amino acid residue 100, at least amino acid residue 100 to amino acid residue 300, at least amino acid residue 300 to amino acid residue 500, or at least amino acid residue 500 to amino acid residue 650 of SEQ ID NO: 87. In some embodiments, a full length HER3 antigen comprises at least 80%, at least 85%, at least 90%, at least 92%, at least 95%, at least 97%, or at least 99% sequence identity to SEQ ID NO: 86. In some embodiments, the MUC1 antigen comprises at least 80%, at least 85%, at least 90%, at least 92%, at least 95%, at least 97%, or at least 99% sequence identity to SEQ ID NO: 12 or SEQ ID NO: 11, or the nucleic acid sequence encoding a MUC1 antigen comprises positions 1105-2532 of SEQ ID NO: 89. In some embodiments, the Brachyury antigen comprises at least 80%, at least 85%, at least 90%, at least 92%, at least 95%, at least 97%, or at least 99% sequence identity to SEQ ID NO: 13 or the nucleic acid sequence encoding a Brachyury antigen comprises positions 1045-2277 of SEQ ID NO: 90. In some embodiments, the truncated HER3 antigen comprises at least 80%, at least 85%, at least 90%, at least 92%, at least 95%, at least 97%, or at least 99% sequence identity to SEQ ID NO: 6. In some embodiments, the composition further comprises a nucleic acid sequence encoding an immune checkpoint inhibitor, an immune checkpoint modulator, or combination thereof. In some embodiments, the composition further comprises a nucleic acid sequence encoding an antibody that activates or potentiates an immune response. In some embodiments, the composition further comprises a recombinant adenovirus vector comprising a nucleic acid sequence encoding a HER1 antigen, a HER2/neu antigen, a HER4 antigen, or any combination thereof. In some embodiments, the composition further comprises a recombinant adenovirus vector comprising a nucleic acid sequence encoding HER2/neu. In some embodiments, the composition further comprises a recombinant adenovirus vector comprising a nucleic acid sequence encoding HER1. In some embodiments, the composition further comprises a recombinant adenovirus vector comprising a nucleic acid sequence encoding HER4. In some embodiments, the nucleic acid sequence encoding HER2/neu comprises at least 80%, at least 85%, at least 90%, or at least 95% sequence identity with SEQ ID NO: 1 or positions 1033-3107 of SEQ ID NO: 3. In some embodiments, the recombinant adenovirus vector comprises the nucleic acid sequence encoding HER2/neu has at least 80%, at least 85%, at least 90%, or at least 95% sequence identity with SEQ ID NO: 3. In some embodiments, the nucleic acid sequence encodes HER2/neu lacks an intracellular domain of a native HER2/neu protein. In some embodiments, the HER2/neu antigen comprises at least 80%, at least 85%, at least 90%, or at least 95% sequence identity with SEQ ID NO: 2. In some embodiments, the nucleic acid sequence encoding HER2/neu comprises a transmembrane domain and an extracellular domain of a native HER2/neu protein. In some embodiments, any of the recombinant adenovirus vectors comprise a replication defective adenovirus vector. In some embodiments, any of the recombinant adenovirus vectors comprises an adenovirus subtype 5 (Ad5)-based vector. In some embodiments, any of the recombinant adenovirus vectors comprise a deletion in an E1 region, an E3 region, an E4 region, or any combination thereof. In some embodiments, any of the recombinant adenovirus vectors comprise a deletion in an E1 region and an E3 region. In some embodiments, the composition consists of $1\times10^{10}$ to $5\times10^{12}$ viral particles (VPs). In some embodiments, the composition comprises at least $1\times10^{10}$ virus particles. In some embodiments, the composition comprises at least $1\times10^{11}$ virus particles. In some embodiments, the composition comprises at least $5\times10^{11}$ virus particles. In some embodiments, the composition comprises at least $5\times10^{12}$ virus particles. In some embodiments, the costimulatory molecule comprises B7, ICAM-1, LFA-3, or any combination thereof. In some embodiments, the costimulatory molecule comprises a combination of B7, ICAM-1, and LFA-3. In some embodiments, the composition further comprises a recombinant adenovirus vector comprising a nucleic acid sequence encoding one or more additional target antigens or immunological epitopes thereof. In some embodiments, the nucleic acids sequence encoding one or more additional target antigens or immunological epitopes are within a same recombinant adenovirus vector with another nucleic acid sequence encoding one or more additional target antigens or immunological epitopes. In some embodiments, the nucleic acids sequence encoding one or more additional target antigens or immunological epitopes are within a different recombinant adenovirus vector with another nucleic acid sequence encoding one or more additional target antigens or immunological epitopes. In some embodiments, the one or more additional target antigens is a tumor neo-antigen, tumor neo-epitope, tumor-specific antigen, tumor-associated antigen, bacterial antigen, viral antigen, yeast antigen, fungal antigen, protozoan antigen, parasite antigen, mitogen, or any combination thereof. In some embodiments, the one or more additional target antigens is HER1, HER2/neu, HER4, folate receptor alpha, WT1, p53, MAGE-A1, MAGE-A2, MAGE-A3, MAGE-A4, MAGE-A6, MAGE-A10, MAGE-A12, BAGE, DAM-6, -10, GAGE-1, -2, -8, GAGE-3, -4, -5, -6, -7B, NA88-A, NY-ESO-1, MART-1, MC1R, Gp100, Tyrosinase, TRP-1, TRP-2, ART-4, CAMEL, CEA, Cyp-B, BRCA1, BRACHYURY, BRACHYURY (TIVS7-2, polymorphism), BRACHYURY (IVS7 T/C polymorphism), T BRACHYURY, T, hTERT, hTRT, iCE, MUC1, MUC1 (VNTR polymorphism), MUC1c, MUC1n, MUC2, PRAME, P15, RU1, RU2, SART-1, SART-3, WT1, AFP, β-catenin/m, Caspase-8/m, CEA, CDK-4/m, Her3, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARα, or TEL/AML1, or a modified variant, a splice variant, a functional epitope, an epitope agonist, or any combination thereof. In some embodiments, the one or more additional target antigens comprises CEA, Brachyury, and MUC1. In some embodiments, the one or more additional target antigens comprises CEA. In some embodiments, CEA comprises at least 80%, at least 85%, at least 90%, at least 92%, at least 95%, at least 97%, or at least 99% sequence identity to SEQ ID NO: 7, SEQ ID NO: 9, or positions 1057-3165 of SEQ ID NO: 10. In some embodiments, a recombinant adenovirus vector comprising the nucleic acid sequence encoding the CEA has at least 80%, at least 85%, at least 90%, or at least 95% sequence identity with SEQ ID NO: 3. In some embodiments, any of the recombinant adenovirus vectors further comprise a selectable marker. In some embodiments, the selectable marker is a lacZ gene, thymidine kinase, gpt, GUS, or a vaccinia K1L host range gene, or a combination thereof. In some embodiments, the recombinant adenovirus further comprises a nucleic acid sequence encoding an immunological fusion partner.

In some aspects, a pharmaceutical composition comprises the composition according to any one of the preceeding embodiments and a pharmaceutically acceptable carrier.

In some aspects, a host cell comprising the composition according to any one the preceeding embodiments.

In some aspects, an engineered natural killer cell comprising the composition according to any one the preceeding embodiments.

In some aspects, a method of preparing a tumor vaccine comprises preparing a pharmaceutical composition according any one the preceeding embodiments.

In some aspects, a method of enhancing an immune response in a subject in need thereof comprises administering a therapeutically effective amount of the composition of any one the preceeding embodiments or the pharmaceutical composition of any one the preceeding embodiments to the subject.

In some aspects, a method of treating a cancer in a subject in need thereof comprises administering a therapeutically effective amount of the composition of any one the preceeding embodiments or the pharmaceutical composition of any one the preceeding embodiments to the subject. In some embodiments, the therapeutically effective amount comprises from $1\times10^{10}$ to $5\times10^{12}$ viral particles (VPs) of the recombinant adenovirus vector. In some embodiments, the therapeutically effective amount comprises at least $1\times10^{10}$ virus particles. In some embodiments, the therapeutically effective amount comprises at least $1\times10^{11}$ virus particles. In some embodiments, the therapeutically effective amount comprises at least $5\times10^{11}$ virus particles. In some embodiments, the therapeutically effective amount comprises at least $5\times10^{12}$ virus particles. In some embodiments the method further comprises administering an immune checkpoint modulator. In some embodiments the method further comprises administering a costimulatory molecule. In some embodiments, the costimulatory molecule comprises a combination of B7, ICAM-1, and LFA-3. In some embodiments the method further comprises administering an immune checkpoint inhibitor. In some embodiments, the immune checkpoint inhibitor inhibits PD1, PDL1, PDL2, CD28, CD80, CD86, CTLA4, B7RP1, ICOS, B7RPI, B7-H3, B7-H4, BTLA, HVEM, KIR, TCR, LAG3, CD137, CD137L, OX40, OX40L, CD27, CD70, CD40, CD40L, TIM3, GAL9, ADORA, CD276, VTCN1, IDO1, KIR3DL1, HAVCR2, VISTA, or CD244. In some embodiments, the immune checkpoint inhibitor inhibits PD1, PDL1, or CTLA-4. In some embodiments, the immune checkpoint inhibitor is an anti-PD1 antibody, anti-PDL1 antibody, or an anti-CTLA-4 antibody. In some embodiments, the immune checkpoint inhibitor is an anti-PDL1 antibody. In some embodiments, the administering comprises a delivery route selected from intravenous, subcutaneous, intralymphatic, intratumoral, intradermal, intramuscular, intraperitoneal, intrarectal, intravaginal, intranasal, oral, via bladder instillation, or via scarification. In some embodiments, upon administration of the composition, an immune response is initiated. In some embodiments, the immune response is a cell-mediated or humoral response. In some embodiments, the immune response is an enhancement of B-cell proliferation, CD4+ T cell proliferation, CD8+ T cell proliferation, or a combination thereof.

The method as disclosed herein, wherein the immune response is an enhancement of IL-2 production, IFN-γ production, or combination thereof. In some embodiments, the immune response is an enhancement of antigen presenting cell proliferation, function, or combination thereof. In some embodiments, the subject has been previously administered an adenovirus vector. In some embodiments, the subject has pre-existing immunity to adenovirus vectors. In some embodiments, the subject is determined to have pre-existing immunity to adenovirus vectors. In some embodiments the method further comprises administering to the subject a chemotherapy, radiation, a different immunotherapy, or a combination thereof. In some embodiments, the chemotherapy is administered at a dose comprising 50 mg of cyclophosphamide. In some embodiments, the dose is administered twice a day. In some embodiments, cyclophosphamide is administered orally or subcutaneously on day 1, day 2, day 3, day 4, day 5, day 8, day 9, day 10, day 11, and day 12, every two weeks for a total of 8 weeks. In some embodiments, the radiation comprises sterotatctic body radiotherapy (SBRT) and is administered to the subject at a dose comprising 8 Gy. In some embodiments, four doses of SBRT is administered to the subject. In some embodiments, SBRT is administered every two weeks. In some embodiments, SBRT is administered on day 8, day 22, day 36, and day 50. In some embodiments, the subject is a human or a non-human animal. In some embodiments, the subject has previously been treated for cancer. In some embodiments, the administering the therapeutically effective amount of the composition is repeated for a total of three administrations. In some embodiments, the administering the therapeutically effective amount of the composition is repeated every one, two, or three weeks. In some embodiments, the administering the therapeutically effective amount of the composition is followed by one or more booster immunization comprising the same composition or pharmaceutical composition. In some embodiments, the booster immunization is administered every one, two, or three months. In some embodiments, the booster immunization is repeated three times or more. In some embodiments, the administering the therapeutically effective amount of the composition is a primary immunization repeated every one, two, or three weeks for three times followed by a booster immunization repeated every one, two, or three months for three times or more. In some embodiments, the method further comprises administering to the subject a pharmaceutical composition comprising a population of engineered natural killer (NK) cells. In some embodiments, the engineered NK cells comprise one or more NK cells that have been modified as essentially lacking the expression of KIR (killer inhibitory receptors), one or more NK cells that have been modified to express a high affinity CD16 variant, and one or more NK cells that have been modified to express a CAR (chimeric antigen receptors), or any combinations thereof. In some embodiments, the population of engineered NK cells comprises a dose of at least 2×109 activated engineered NK cells per treatment.

The method as disclosed herein, wherein the dose of at least 2×109 activated engineered NK cells are infused intraveneously on day −2, day 12, day 26, day 40, or any combination thereof. In some embodiments, the engineered NK cells comprise one or more NK cells that have been modified as essentially lacking the expression KIR. In some embodiments, the engineered NK cells comprise one or more NK cells that have been modified to express a high affinity CD16 variant. In some embodiments, the engineered NK cells comprise one or more NK cells that have been modified to express a CAR. In some embodiments, the CAR is a CAR for a tumor neo-antigen, tumor neo-epitope, HER1, HER2/neu, HER3, HER4, WT1, p53, MAGE-A1, MAGE-A2, MAGE-A3, MAGE-A4, MAGE-A6, MAGE-A10, MAGE-A12, BAGE, DAM-6, DAM-10, Folate receptor alpha, GAGE-1, GAGE-2, GAGE-8, GAGE-3, GAGE-4, GAGE-5, GAGE-6, GAGE-7B, NA88-A, NY-ESO-1, MART-1, MC1R, Gp100, Tyrosinase, TRP-1, TRP-2, ART-4, CAMEL, CEA, Cyp-B, HER2/neu, Her3, BRCA1, Brachyury, Brachyury (TIVS7-2, polymorphism), Brachyury (IVS7 T/C polymorphism), T Brachyury, T, hTERT, hTRT, iCE, MUC1, MUC1 (VNTR polymorphism), MUC1c, MUC1n, MUC2, PRAME, P15, RU1, RU2, SART-1, SART-3, AFP, β-catenin/m, Caspase-8/m, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TP1/mbcr-abl, ETV6/AML, LDLR/FUT, Pml/RARα, TEL/AML1, or any combination thereof. In some embodiments, the composition of any one of preceding embodiments is comprised in a cell. In some embodiments, the cell is a dendritic cell (DC). In some embodiments, the method further comprises administering a pharmaceutical composition comprises a therapeutically effective amount of IL-15 or a recombinant adenovirus vector comprising a nucleic acid sequence encoding IL-15. In some embodiments, the recombinant adenovirus vector further comprises a nucleic acid encoding for the IL-15 superagoinst complex. In some embodiments, the administering is of the IL-15 superagoinst complex is administered subcutaneously on week 1, week 2, week 3, week 4, week 5, week 7, week 8. In some embodiments, the method further comprises administering the IL-15 superagoinst complex at a dose of 10 microgram per kilogram. In some embodiments, the subject has HER1-expressing cancer, HER2/neu-expressing cancer, HER3-expressing cancer, HER4-expressing cancer, or any combination thereof. In some embodiments, the subject has HER1-expressing breast cancer, HER2/neu-expressing breast cancer, HER3-expressing breast cancer, HER4-expressing breast cancer, or any combination thereof. In some embodiments, the subject has HER1-expressing bone cancer, HER2/neu-expressing bone cancer, HER3-expressing bone cancer, HER4-expressing bone cancer, or any combination thereof. In some embodiments, the cancer is osteosarcoma. In some embodiments, the cancer is gastric cancer. In some embodiments, the subject has unresectable, locally, advanced or metastatic cancer. In some embodiments, the method further comprises administering an additional cancer therapy to the subject. In some embodiments, the subject has breast cancer, colon cancer, lung cancer, prostate cancer, ovarian cancer, cervical cancer, endometrial cancer, gastric cancer, pancreatic cancer, bladder cancer, head and neck cancer, liver cancer, and esophageal cancer.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the results of analysis of breast tumor gene expression data.

FIG. 1A shows that up-regulated mRNA expression of HRG/NRG1 was correlated with lower relapse free survival in ER+ HER2/Neu− breast cancer patients.

FIG. 1B shows that HRG/NRG1 mRNA was elevated in tumors from patients with early recurrence (less than 5 years) or late recurrence (from 5-10 years) after diagnosis compared to non-recurring tumors.

FIG. 10A illustrates tumor growth in mice vaccinated with Ad-hHER3FL.

FIG. 10B illustrates tumor growth in mice vaccinated with Ad-GFP.

DETAILED DESCRIPTION

Figure 2:
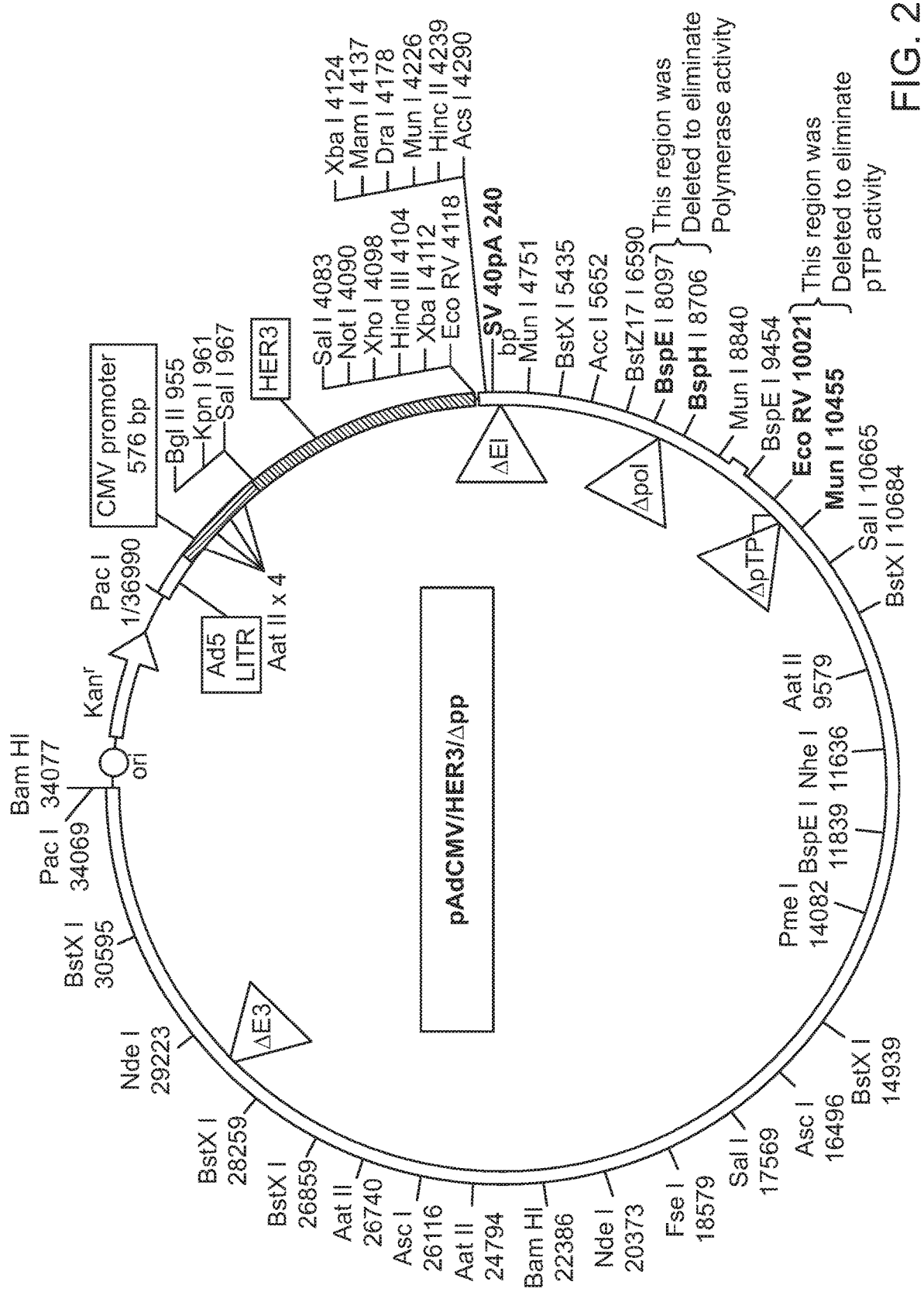
FIG. 2 illustrates an embodiment of a restriction map of the Ad5 [E1−, E2b−]-HER2/neu vector, pAdCMV/HER3/Δpp.
Figure 3:
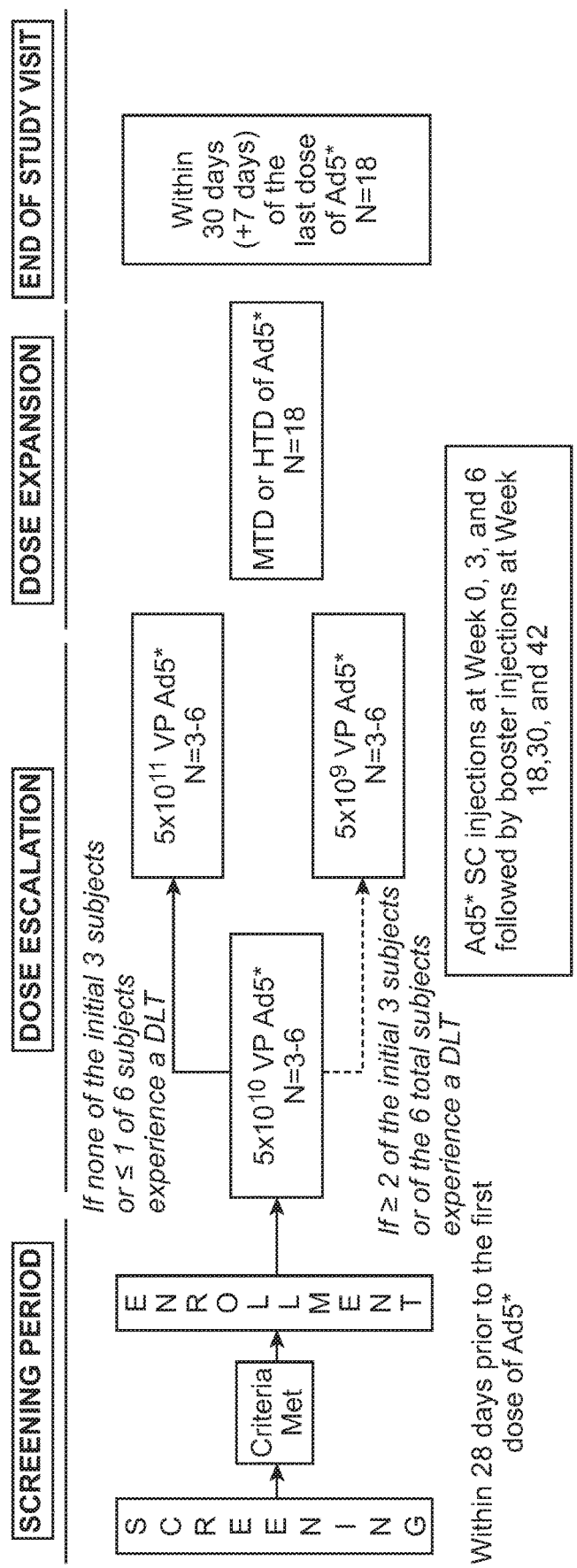
FIG. 3 illustrates an embodiment of study design and treatment schema of clinical study.

While the making and using of various embodiments are discussed in detail below, it should be appreciated that the many applicable inventive concepts provided herein can be embodied in a wide variety of specific contexts. The specific embodiments discussed herein are merely illustrative of specific ways to make and use the invention and do not delimit the scope of the invention.

To facilitate the understanding of certain aspects, a number of terms are defined below. Terms defined herein have meanings as commonly understood by a person of ordinary skill in the areas relevant to the present invention.

Terms such as "a," "an" and "the" are not intended to refer to only a singular entity, but include the general class of which a specific example may be used for illustration. The terminology herein is used to describe specific embodiments of the invention, but their usage does not delimit the invention, except as outlined in the claims.

By "individual," "subject" or "patient" is meant any single subject for which therapy is desired, including but not limited to humans, non-human primates, rodents, dogs, or pigs. Also intended to be included as a subject are any subjects involved in clinical research trials not showing any clinical sign of disease, or subjects involved in epidemiological studies, or subjects used as controls.

As used herein, the term "gene" refers to a functional protein, polypeptide or peptide-encoding unit. As will be understood by those in the art, this functional term includes genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated. The term "allele" or "allelic form" refers to an alternative version of a gene encoding the same functional protein but containing differences in nucleotide sequence relative to another version of the same gene. In certain aspects, the term "gene" means the gene and all currently known variants thereof and any further variants which may be elucidated.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

As used herein, unless otherwise indicated, the article "a" means one or more unless explicitly otherwise provided for.

As used herein, unless otherwise indicated, terms such as "contain," "containing," "include," "including," and the like mean "comprising."

As used herein, unless otherwise indicated, the term "or" can be conjunctive or disjunctive.

As used herein, unless otherwise indicated, any embodiment can be combined with any other embodiment.

As used herein, unless otherwise indicated, some inventive embodiments herein contemplate numerical ranges. A variety of aspects can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

The term "adenovirus" or "Ad" refers to a group of non-enveloped DNA viruses from the family Adenoviridae. In addition to human hosts, these viruses can be found in, but are not limited to, avian, bovine, porcine and canine species. Certain aspects may contemplate the use of any adenovirus from any of the four genera of the family Adenoviridae (e.g., Aviadenovirus, Mastadenovirus, Atadenovirus and Siadenovirus) as the basis of an E2b deleted virus vector, or vector containing other deletions as described herein. In addition, several serotypes are found in each species. Ad also pertains to genetic derivatives of any of these viral serotypes, including but not limited to, genetic mutation, deletion or transposition of homologous or heterologous DNA sequences.

A "helper adenovirus" or "helper virus" refers to an Ad that can supply viral functions that a particular host cell cannot (the host may provide Ad gene products such as E1 proteins). This virus is used to supply, in trans, functions (e.g., proteins) that are lacking in a second virus, or helper dependent virus (e.g., a gutted or gutless virus, or a virus deleted for a particular region such as E2b or other region as described herein); the first replication-incompetent virus is said to "help" the second, helper dependent virus thereby permitting the production of the second viral genome in a cell.

The term "Adenovirus5 null (Ad5 null)," as used herein, refers to a non-replicating Ad that does not contain any heterologous nucleic acid sequences for expression.

The term "First Generation adenovirus," as used herein, refers to an Ad that has the early region 1 (E1) deleted. In additional cases, the nonessential early region 3 (E3) may also be deleted.

The term "gutted" or "gutless," as used herein, refers to an adenovirus vector that has been deleted of all viral coding regions.

The term "transfection" as used herein refers to the introduction of foreign nucleic acid into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign nucleic acid, DNA or RNA, into the genome of the transfected cell. The term "stable transfectant" refers to a cell which has stably integrated foreign DNA into the genomic DNA.

The term "reporter gene" indicates a nucleotide sequence that encodes a reporter molecule (including an enzyme). A "reporter molecule" is detectable in any of a variety of detection systems, including, but not limited to enzyme-based detection assays (e.g., ELISA, as well as enzyme-based histochemical assays), fluorescent, radioactive, and luminescent systems.

A "subject" refers to any animal, including, but not limited to, humans, non-human primates (e.g., rhesus or other types of macaques), mice, pigs, horses, donkeys, cows, sheep, rats and fowls.

An "immunogenic fragment" refers to a fragment of a polypeptide that is specifically recognized (i.e., specifically bound) by a B-cell and/or T-cell surface antigen receptor resulting in a generation of an immune response specifically against a fragment.

A "target antigen" or "target protein" refers to a molecule, such as a protein, against which an immune response is to be directed.

"E2b deleted" refers to a DNA sequence mutated in such a way so as to prevent expression and/or function of at least one E2b gene product. Thus, in certain embodiments, "E2b deleted" is used in relation to a specific DNA sequence that is deleted (removed) from an Ad genome. E2b deleted or "containing a deletion within an E2b region" refers to a deletion of at least one base pair within an E2b region of an Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, a deletion is of more than 150, 160, 170, 180, 190, 200, 250, or 300 base pairs within an E2b region of an Ad genome. An E2b deletion may be a deletion that prevents expression and/or function of at least one E2b gene product and therefore, encompasses deletions within exons of encoding portions of E2b-specific proteins as well as deletions within promoter and leader sequences. In certain embodiments, an E2b deletion is a deletion that prevents expression and/or function of one or both a DNA polymerase and a preterminal protein of an E2b region. In a further embodiment, "E2b deleted" refers to one or more point mutations in a DNA sequence of this region of an Ad genome such that one or more encoded proteins is non-functional. Such mutations include residues that are replaced with a different residue leading to a change in an amino acid sequence that result in a nonfunctional protein.

"E1-deleted" refers to a DNA sequence that is mutated in such a way so as to prevent expression and/or function of at least one E1 gene product. Thus, in certain embodiments, "E1 deleted" is used in relation to a specific DNA sequence that is deleted (removed) from the Ad genome. E1 deleted or "containing a deletion within the E1 region" refers to a deletion of at least one base pair within the E1 region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E1 region of the Ad genome. An E1 deletion may be a deletion that prevents expression and/or function of at least one E1 gene product and therefore, encompasses deletions within exons of encoding portions of E1-specific proteins as well as deletions within promoter and leader sequences. In certain embodiments, an E1 deletion is a deletion that prevents expression and/or function of one or both of a trans-acting transcriptional regulatory factor of the E1 region. In a further embodiment, "E1 deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

"Generating an immune response" or "inducing an immune response" refers to a statistically significant change, e.g., increase or decrease, in the number of one or more immune cells (T-cells, B-cells, antigen-presenting cells, dendritic cells, neutrophils, and the like) or in the activity of one or more of these immune cells (CTL activity, HTL activity, cytokine secretion, change in profile of cytokine secretion, etc.).

In one embodiment, there may be provided the *E. coli* β-galactosidase gene (available from Pharmacia Biotech, Pistacataway, N.J.), green fluorescent protein (GFP) (commercially available from Clontech, Palo Alto, Calif.), the human placental alkaline phosphatase gene, the chloramphenicol acetyltransferase (CAT) gene as reporter genes; other reporter genes are known to the art and may be employed.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The nucleic acid sequence thus codes for the amino acid sequence.

The term "heterologous nucleic acid sequence," as used herein, refers to a nucleotide sequence that is ligated to, or is manipulated to become ligated to, a nucleic acid sequence to which it is not ligated in nature, or to which it is ligated at a different location in nature. Heterologous nucleic acid may include a nucleotide sequence that is naturally found in the cell into which it is introduced or the heterologous nucleic acid may contain some modification relative to the naturally occurring sequence.

The term "transgene" refers to any gene coding region, either natural or heterologous nucleic acid sequences or fused homologous or heterologous nucleic acid sequences, introduced into the cells or genome of a test subject. In certain aspects, transgenes are carried on any viral vector that is used to introduce the transgenes to the cells of the subject.

The term "Second Generation Adenovirus," as used herein, refers to an Ad that has all or parts of the E1, E2, E3, and, in certain embodiments, E4 DNA gene sequences deleted (removed) from the virus.

As used herein, the term "fragment or segment," as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases amino acid positions in common.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

A "vector" is a composition which can transduce, transfect, transform or infect a cell, thereby causing the cell to express nucleic acids and/or proteins other than those native to the cell, or in a manner not native to the cell. A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target genes. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base.

An "antigen" is any substance that reacts specifically with antibodies or T lymphocytes (T cells). An "antigen-binding site" is the part of an immunoglobulin molecule that specifically binds an antigen. Additionally, an antigen-binding site includes any such site on any antigen-binding molecule, including, but not limited to, an MHC molecule or T cell receptor. "Antigen processing" refers to the degradation of an antigen into fragments (e.g., the degradation of a protein into peptides) and the association of one or more of these fragments (e.g., via binding) with MHC molecules for presentation by "antigen-presenting cells" to specific T cells.

"Dendritic cells" (DC) are potent antigen-presenting cells, capable of triggering a robust adaptive immune response in vivo. It has been shown that activated, mature DCs provide the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC" defined above) class I or II protein on the surface of APCs. The second type of signal, called a co-stimulatory signal, is neither antigen-specific nor MHC-restricted, and can lead to a full proliferation response of T cells and induction of T cell effector functions in the presence of the first type of signals. This two-fold signaling can, therefore, result in a vigorous immune response. As noted supra, in most non-avian vertebrates, DCs arise from bone marrow-derived precursors. Immature DCs are found in the peripheral blood and cord blood and in the thymus. Additional immature populations may be present elsewhere. DCs of various stages of maturity are also found in the spleen, lymph nodes, tonsils, and human intestine. Avian DC may also be found in the bursa of Fabricius, a primary immune organ unique to avians. In a particular embodiment, the dendritic cells are mammalian, preferably human, mouse, or rat.

A "co-stimulatory molecule" encompasses any single molecule or combination of molecules which, when acting together with a peptide MHC complex bound by a T cell receptor on the surface of a T cell, provides a co-stimulatory effect which achieves activation of the T cell that binds the peptide.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used herein, the phrase "consisting essentially of" limits the scope of a claim to the specified materials or steps and those that do not materially affect the bask and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. A skilled artisan will understand that typically there is no limit on the number of items or terms in any combination, unless otherwise apparent from the context.

As used herein, words of approximation such as, without limitation, "about," "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety to the same extent as if each individual publication, patent, or patent application was specifically and individually indicated to be incorporated by reference.

Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

I. HER1, HER2, HER3, and HER4 in Malignancy

In certain aspects, there may be provided expression constructs or vectors comprising nucleic acid sequences that encode one or more target proteins of interest or target antigens, such as a HER3 antigen or epitope as described herein. The human epidermal growth factor receptor (HER) family, including HER1 (also known as EGFR), HER2/neu, HER3 and HER4 (also known as ErbB2, ErbB3, and ErbB4 respectively), is an important receptor family for the development of many malignancies.

The HER1, HER3, or HER4 antigen may be a full length protein or may be an immunogenic fragment (e.g., an epitope) thereof. In some cases an immunogenic epitope such as a HER3 epitope can be 8 to 10 amino acids long. In some cases a HER epitope is four to ten amino acids long or over 10 amino acids long. An immunogenic epitope such as a HER1, HER3, or HER4 epitope can comprise a length of or can comprise a length of at least, about, or at most 1, 2, 3, 4, 5, 6, 7, 8, 9, 10, 11, 12, 13, 14, 15, 16, 17, 18, 19, 20 amino acids or any number or ranges derived therefrom. An immunogenic epitope such as a HER1, HER3, or HER4 epitope can be any length of amino acids.

In some embodiments, an immunogenic fragment of any of the antigens described herein (e.g., HER1, HER2, HER3, HER4) can comprise at least 50%, at least 60%, at least 70%, at least 80%, at least 90%, at least 92%, at least 95%, at least 97%, at least 99%, at least 1-99%, at least 1-10%, at least 10-20%, at least 20-30%, at least 30-40%, at least 40-50%, at least 50-60%, at least 60-70%, at least 70-80%, at least 80-90%, at least 90-95%, at least 95-99%, at least 20-40%, at least 40-60%, or at least 60-80% the length of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 50%, at least 60%, at least 70%, at least 80%, at least 90%, at least 92%, at least 95%, at least 97%, at least 99%, at least 1-99%, at least 1-10%, at least 10-20%, at least 20-30%, at least 30-40%, at least 40-50%, at least 50-60%, at least 60-70%, at least 70-80%, at least 80-90%, at least 90-95%, at least 95-99%, at least 20-40%, at least 40-60%, or at least 60-80% the length of a truncated antigen, such as the full length HER3 antigen set forth in SEQ ID NO: 86.

In some embodiments, an immunogenic fragment of any of the antigens described herein (e.g., HER1, HER2, HER3, HER4) can comprise at least 8 amino acid residues to 662 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 10 amino acid residues to 40 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 40 amino acid residues to 70 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 70 amino acid residues to 100 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 100 amino acid residues to 130 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 130 amino acid residues to 160 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 160 amino acid residues to 190 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 190 amino acid residues to 220 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 220 amino acid residues to 250 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 250 amino acid residues to 280 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 280 amino acid residues to 310 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 310 amino acid residues to 340 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 340 amino acid residues to 370 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 370 amino acid residues to 400 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 400 amino acid residues to 430 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 430 amino acid residues to 460 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 460 amino acid residues to 490 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 490 amino acid residues to 520 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 520 amino acid residues to 550 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 550 amino acid residues to 580 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 580 amino acid residues to 610 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 610 amino acid residues to 640 amino acid residues of a truncated antigen, such as the truncated HER3 antigen set forth in SEQ ID NO: 87. In some embodiments, an immunogenic fragment of any of the antigens described herein (e.g., HER1, HER2, HER3, HER4) can comprise at least 640 amino acid residues to 662 amino acid residues of a truncated antigen, such as the truncated HER3 antigen set forth in SEQ ID NO: 87. In some embodiments, a truncation, can be an immunogenic fragment of any of the antigens described herein (e.g., HER1, HER2, HER3, HER4) and can comprise at least 10-100 amino acid residues, 100-300 amino acid residues, 300-500 amino acid residues, or 500-650 amino acid residues of an antigen (e.g., a truncated HER3 antigen as set forth in SEQ ID NO: 87).

A. HER1

In some embodiments, HER1 (EGFR) can also be overexpressed in a variety of different cancers, including breast cancer, colon cancer, non-small cell lung cancer (NSCLC), ovarian cancer, and pancreatic cancer. In certain embodiments, HER1/EGFR can signal through MAPK and Akt pathways, and lead to downstream effects that can stimulate tumor progression. Ligands of HER1 can include EGF or transforming growth factor-α and upon binding its ligand, HER1 can homodimerize with another HER1 receptor or heterodimerize with another member of the HER family. In some embodiments, HER1 targeted vaccines are directed to cells overexpressing HER1. In other embodiments, HER1 expression on cancer cells can be used as a prognostic tool to track progress and response to a HER1 vaccine.

B. HER2

In certain aspects, there may be provided expression constructs or vectors comprising nucleic acid sequences that encode one or more target proteins of interest or target antigens, such as a HER2/neu antigen or epitope as described herein.

HER2/neu (p185) is the protein product of the HER2/neu oncogene. In some aspects, the HER2/neu gene is amplified and the HER2/neu protein is overexpressed in a variety of cancers including breast, ovarian, gastric, colon, lung, prostate, and bone. In some aspects, HER2/neu is related to malignant transformation. In some aspects, it is found in 50%-60% of ductal in situ carcinoma and 20%-40% of all breast cancers, as well as a substantial fraction of adenocarcinomas arising in the ovaries, prostate, colon and lung. In some aspects, the HER2/neu protein is overexpressed in cancers of the bone, including osteosarcoma. In some aspects, HER2/neu is intimately associated not only with the malignant phenotype, but also with the aggressiveness of the malignancy, being found in one-fourth of all invasive breast cancers. In some aspects, HER2/neu overexpression is correlated with a poor prognosis in both breast and ovarian cancer.

In some aspects, HER2/neu is a transmembrane protein with a relative molecular mass of 185 kd that is approximately 1255 amino acids (aa) in length. It has an extracellular binding domain (ECD) of approximately 645 aa, with 40% homology to epidermal growth factor receptor (EGFR), a highly hydrophobic transmembrane domain (TM), and an intracellular domain of approximately 580 aa with 80% homology to EGFR.

In further aspects, there may be provided expression constructs or vectors that may contain nucleic acid encoding at least, at most or about one, two, three, four, five, six, seven, eight, nine, ten, 11, 12, 13, 14, 15, 16, 17, 18, 19, 20, 30, 40, 50, 60, 70, 80, 90, 100, 200, 300, 400 or 500 different target antigens of interest or any number or ranges derived therefrom. The expression constructs or vectors may contain nucleic acid sequences encoding multiple fragments or epitopes from one HER2/neu antigen or may contain one or more fragments or epitopes from numerous different target antigens including a HER2/neu antigen or epitope as described herein.

The HER2/neu antigen may be a full length protein or may be an immunogenic fragment (e.g., an epitope) thereof. Immunogenic fragments may be identified using available techniques, such as those summarized in Paul, Fundamental Immunology, 3rd ed., 243-247 (Raven Press, 1993) and references cited therein. Representative techniques for identifying immunogenic fragments include screening polypeptides for the ability to react with antigen-specific antisera and/or T-cell lines or clones. An immunogenic fragment of a particular target polypeptide may be a fragment that reacts with such antisera and/or T-cells at a level that is not substantially less than the reactivity of the full length target polypeptide (e.g., in an ELISA and/or T-cell reactivity assay). In other words, an immunogenic fragment may react within such assays at a level that is similar to or greater than the reactivity of the full length polypeptide. Such screens may generally be performed using methods available to those of ordinary skill in the art, such as those described in Harlow and Lane, Antibodies: A Laboratory Manual, Cold Spring Harbor Laboratory, 1988.

In some cases an immunogenic epitope such as a HER2/neu epitope can be 8 to 10 amino acids long. In some cases a Her epitope is four to ten amino acids long or over 10 amino acids long. An immunogenic epitope such as a HER2/neu epitope can comprise a length of or can comprise a length of at least, about, or at most 1, 2, 3, 4, 5, 6, 7, 8, 9, 10, 11, 12, 13, 14, 15, 16, 17, 18, 19, 20 amino acids or any number or ranges derived therefrom. An immunogenic epitope such as a HER2/neu epitope can be any length of amino acids.

In some aspects, HER3 can be overexpressed in breast, lung, gastric, head and neck, and ovarian cancer and melanoma. In some embodiments, overexpression of HER3 can be associated with poor prognosis. Because of the negligible tyrosine kinase function of HER3, it can be present in heterodimers with HER1 or HER2/neu, through which downstream signaling involving extracellular-signal-regulated kinase (ERK) 1/2 and AKT (1) occurs. In some embodiments, one of the major roles of HER3 can be to link receptor tyrosine kinase activation with PI3K pathway activation. In other embodiments, HER3 can function as a feedback regulator that can contribute to resistance to PI3K/AKT-directed therapy.

In some embodiments, the present disclosure provides a sequence of a HER2/neu antigen. For example, a HER2/neu antigen of the present disclosure can comprise a truncated HER2/neu protein having a transmembrane domain and an extracellular matrix domain, while lacking the intracellular domain. The truncated HER2/neu protein can have at least 80%, at least 85%, at least 90%, at least 92%, at least 95%, at least 97%, or at least 99% sequence identity to SEQ ID NO: 1 or positions 1033-3107 of SEQ ID NO: 3. In some embodiments, a HER2/neu antigen of the present disclosure has a sequence as set forth in SEQ ID NO: 1 or positions 1033-3107 of SEQ ID NO: 3. In some embodiments, the present disclosure provides a sequence encoding for HER2/neu, wherein the HER2/neu protein sequence has at least 80%, at least 85%, at least 90%, at least 92%, at least 95%, at least 97%, or at least 99% sequence identity to SEQ ID NO: 2. In some embodiments, the present disclosure provides a HER2/neu protein that has a sequence as set forth in SEQ ID NO: 2. In some embodiments, an adenovirus vector (e.g., Ad5 [E1−, E2b−]) encoding for HER2/neu can have a sequence that has at least 80%, at least 85%, at least 90%, at least 92%, at least 95%, at least 97%, or at least 99% sequence identity to SEQ ID NO: 3. In some embodiments, an adenovirus vector (e.g., Ad5 [E1−, E2b−]) encoding for HER2/neu has a sequence as set forth in SEQ ID NO: 3.

C. HER3

In some embodiments, the role of HER3 in breast cancer can be associated with resistance to anti-HER2/neu therapeutics. In other embodiments, HER3 can also be a cause of endocrine resistance in breast cancer. In patients with ER+ breast cancer previously treated with tamoxifen, HER3-overexpression can be associated with a shorter progression-free survival. In some embodiments, HER3 expression can be induced in vitro in ER-positive breast cancer cells (e.g. MCF-7, T47D), which are treated with fulvestrant. In some embodiments, overexpression of heregulin (HRG), the ligand for HER3, can also be associated with resistance to antiestrogens in vitro and in vivo. Thus, HER3 and its ligand can play a key role in therapeutic resistance and targeting HER3 can be an effective strategy to overcome anti-endocrine and anti-HER2/neu therapeutic resistance.

In some embodiments, "HER3" can be referred to as "ErbB3." In certain aspects, downregulation of ErbB3 by siRNA can reverse HER2/neu-driven tamoxifen resistance, and can enhance the ability of tamoxifen to inhibit growth and enhance apoptosis. Thus, in some aspects, it can be possible to overcome tamoxifen resistance via inhibition of ErbB3 driven activation of Akt. ErbB3-mediated resistance to tyrosine-kinase inhibitors targeting ErbB1 and ErbB2/HER2/neu can also stem from the sustained activation of Akt, which can be linked to ErbB3 expression, suggesting that ErbB3 can be a broadly applicable resistance mechanism. In some embodiments, the ErbB3 receptor can interact with the α6β4 integrin, which assists in sustaining the PI3K/Akt survival pathway of breast cancer tumor cells. In further embodiments, continued signaling via Akt can be important for continued cell growth.

In some embodiments, tumor cells can overexpress membrane-bound HER3. In other embodiments, HER3 peptides can be presented at the cell surface by MHC complexes for presentation to T cells. In certain embodiments, treatment for HER2/neu expressing cancers can result in the overexpression of HER3.

In some embodiments, HER3 can be used as protein antigen in an adenovirus of the present disclosure (e.g., Ad5 [E1−, E2−]). The resulting Ad5 [E1−, E2−]-HER3 vaccine can be used to immunize against HER1, HER2/neu, HER3, and/or HER4-expressing cancers in a subject in need thereof. In certain embodiments, vaccinating against HER3 can be a method to combat the development of resistance. For example, in some embodiments, the HER3 receptor can be a target in endocrine therapy-resistance breast cancer. In certain embodiments, a HER3 vaccine plays a similar role in other malignancies to prevent resistance. A HER3 vaccine can be used in combination with other therapies such as endocrine therapy in breast cancer to prevent the onset of therapeutic resistance mediated by HER3 overexpression.

Figure 14:
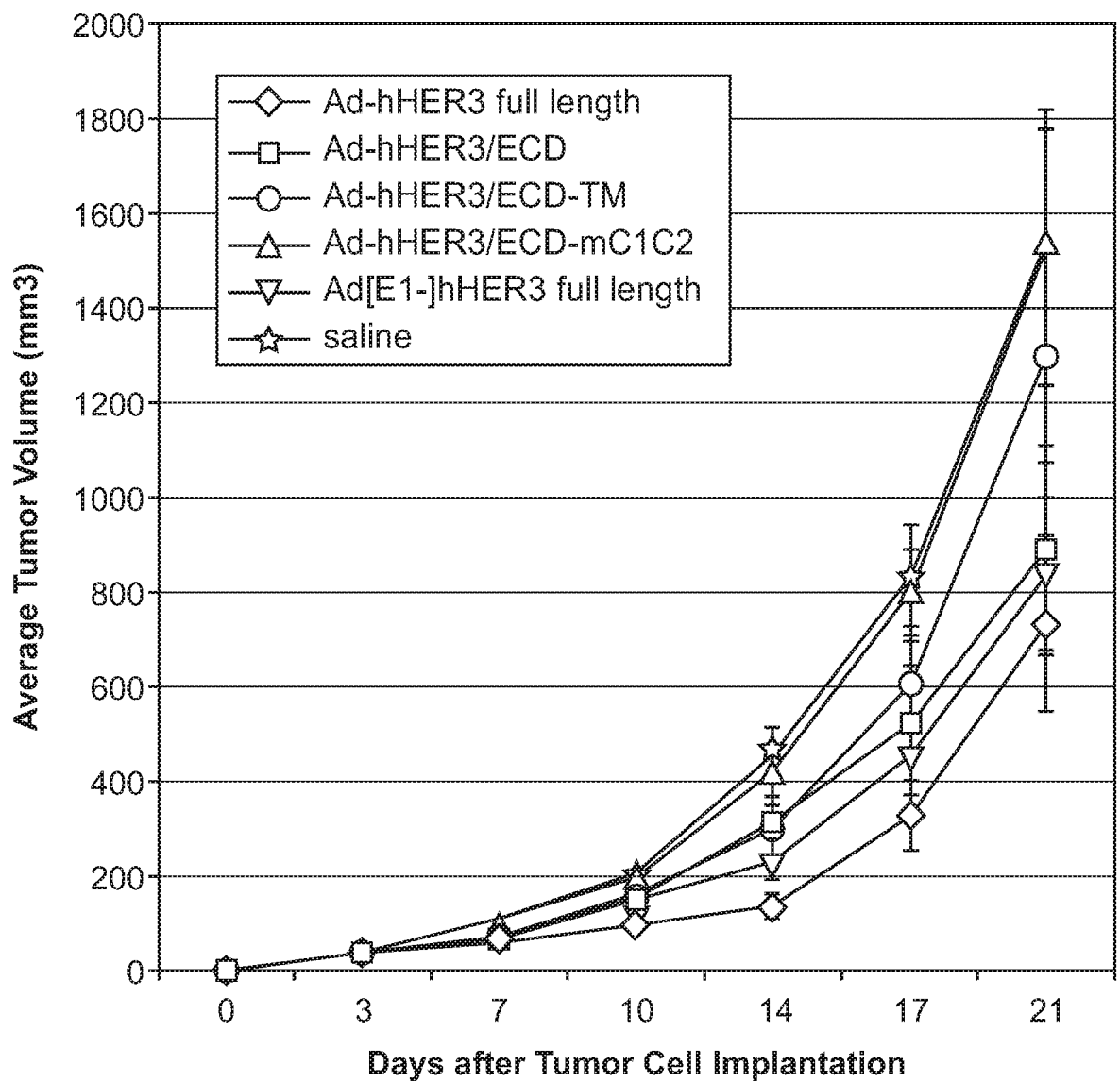
FIG. 14 illustrates JC-HER3 tumor growth in HER3+ F1 Hybrid mice treated with Ad-HER3 vaccines.

In some embodiments, an adenovirus vector of the present disclosure (e.g., Ad5 [E1−, E2b−]) comprises a sequence that encodes for a full length (FL) protein, such as FL HER3. Vaccination with an adenovirus vector (e.g., Ad5 [E1−, E2b−]) encoding for FL HER3 can potentiate or enhance an immune response in tumor bearing mice. In some embodiments, the adenovirus vector (e.g., Ad5 [E1−, E2b−]) comprises a sequence that encodes a truncated protein, such as a truncated HER3 protein. A truncated protein can be a protein wherein one or more nucleotide or amino acids of the corresponding full length protein is absent. In some embodiments, the truncation corresponds to lack of a particular region of the full length protein. For example, the truncation corresponds to partial or complete lack of a structural domain. For example, HER3 can include three structural domains, an intracellular domain, a transmembrane (TM) domain, and an extracellular (ECD) domain. A truncated HER3 protein can lack any one of the intracellular domain, the TM domain, or the ECD domain or can lack any combination of the intracellular domain, the TM domain, and the ECD domain. In particular instances, the truncated HER3 protein lacks the intracellular domain, thus comprising the TM and ECD domains. Vaccination with an adenovirus vector that comprises the truncated sequence of HER3 (Ad5 [E1−, E2b−]-human HER3 ECD-TM) can also induce an immune response in preclinical studies as shown in FIG. 14. In some cases, vaccination with the truncated HER3 protein induces as strong an immune response or stronger immune responses than with a full length HER3 protein. In some cases, vaccination with the truncated HER3 antigen can be less oncogenic than with the full length HER3 protein.

In some embodiments, the ErbB3 (HER3) protein does not have intrinsic signaling capability as it lacks an enzymatically active tyrosine kinase domain. As such, the ErbB3 protein can heterodimerize with another growth factor receptor (GFR) family member that has an activate kinase domain. Upon binding of its cognate ligand, heregulin, the ErbB3 protein can dimerize with a GFR family member, namely ErbB2 to form an ErbB2/ErbB3 heterodimeric complex, leading to ErbB2 transactivation and potent intracellular signaling. In some aspects, tumor cells express the active form of the ErbB2/ErbB3 complex, which enables robust signaling within the cell. Thus, the active ErbB2/ErbB3 complex may lead to the migration, proliferation and transformation of cancer cells.

In some embodiments, ErbB2 can preferentially interact with ErbB3 despite the ability of ErbB3 to heterodimerize with other GFRs such as ErbB1 or ErbB4. The structural feature necessary to sustain intracellular signaling within the ErbB2/ErbB3 complex can be the intracellular (ICD) domain of ErbB3. In some aspects, deletion or mutation of residues within the intracellular (ICD) domain of ErbB3 can result in a complete reduction of the phosphorylation of ErbB2 within the ErbB2/ErbB3 complex. Thus, mutating or deleting any region of the ICD can lead to reduced oncogenicity, and thereby be safer for administration to a subject. In some embodiments, at least 3 amino acid residues of the ICD can be mutated to prevent signaling and result in decreased oncogenicity, and thereby a safer protein antigen. In some embodiments, the entire ICD can be removed, for example leaving just the transmembrane and extracellular domain, to prevent signaling and result in decreased oncogenicity, and thereby a safer protein antigen.

In some embodiments, the present disclosure provides a sequence of a truncated HER3 antigen. For example, a truncated HER3 antigen of the present disclosure can have a transmembrane domain and an extracellular matrix domain, while lacking an intracellular domain. A truncated HER3 antigen of the present disclosure can have at least 80%, at least 85%, at least 90%, at least 92%, at least 95%, at least 97%, or at least 99% sequence identity to SEQ ID NO: 6. In some embodiments, a truncated HER3 antigen of the present disclosure has a sequence as set forth in SEQ ID NO: 6.

In some embodiments, the present disclosure provides a truncated HER3 antigen can have at least 80%, at least 85%, at least 90%, at least 92%, at least 95%, at least 97%, or at least 99% sequence identity to SEQ ID NO: 87. In some embodiments, a full length HER3 antigen can have at least 80%, at least 85%, at least 90%, at least 92%, at least 95%, at least 97%, or at least 99% sequence identity to SEQ ID NO: 86.

D. HER4

In some embodiments, HER4 targeted vaccines are directed to cells overexpressing HER4. In certain aspects, HER2/neu expression can be more pronounced than HER4 expression in breast carcinomas. In some aspects, HER4 can be overexpressed in cells also overexpressing estrogen receptor. HER4 can bind neuregulins and activate, leading to downstream processes such as induction of cellular differentiation. HER4 can also be activated by binding of certain EGF ligands. In other embodiments, HER4 expression on cancer cells can be used as a prognostic tool to track progress and response to a HER4 vaccine.

II. Combination HER Vaccines

In some embodiments, Ad5 vaccines of this disclosure target a HER1 antigen or epitope. In other embodiments, Ad5 vaccines of this disclosure target a HER2/neu antigen or epitope. In still other embodiments, Ad5 vaccines of this disclosure target a HER3 antigen or epitope. In some embodiments, Ad5 vaccines of this disclosure target a HER4 antigen or epitope. In some cases, HER1, HER2/neu, HER3, HER4, or any combination thereof can be targeted by an Ad5 vaccine of the disclosure. In certain embodiments, HER1, HER2/neu, HER3, HER4, or any combination thereof can be used as a prognostic marker to track progress and responsiveness to HER-targeted vaccination.

III. CEA Antigen Targets

Disclosed herein include compositions comprising replication-defective vectors comprising one or more nucleic acid sequences encoding HER3 antigen, and/or one or more nucleic acid sequences encoding mucin family antigen such as CEA, and/or one or more nucleic acid sequences encoding Brachyury, and/or one or more nucleic acid sequences encoding MUC1, and/or one or nucleic acid sequences encoding HER1, HER2/neu, HER4, or any combination, in same or separate replication-defective vectors.

CEA represents an attractive target antigen for immunotherapy since it is over expressed in nearly all colorectal cancers and pancreatic cancers, and is also expressed by some lung and breast cancers, and uncommon tumors such as medullary thyroid cancer, but is not expressed in other cells of the body except for low-level expression in gastrointestinal epithelium. CEA contains epitopes that may be recognized in an MHC restricted fashion by T-cells.

It was discovered that multiple homologous immunizations with Ad5 [E1−, E2b−]-CEA(6D), encoding the tumor antigen CEA, induced CEA-specific cell-mediated immune (CMI) responses with antitumor activity in mice despite the presence of pre-existing or induced Ad5-neutralizing antibody. In the present phase I/II study, cohorts of patients with advanced colorectal cancer were immunized with escalating doses of Ad5 [E1−, E2b−]-CEA(6D). CEA-specific CMI responses were observed despite the presence of pre-existing Ad5 immunity in a majority (61.3%) Of patients. Importantly, there was minimal toxicity, and overall patient survival (48% at 12 months) was similar regardless of pre-existing Ad5 neutralizing antibody titers. The results demonstrate that, in cancer patients, the novel Ad5 [E1−, E2b−] gene delivery platform generates significant CMI responses to the tumor antigen CEA in the setting of both naturally acquired and immunization-induced Ad5 specific immunity.

CEA antigen specific CMI can be, for example, greater than 10, 20, 30, 40, 50, 100, 200, 300, 400, 500, 600, 700, 800, 900, 1000, 5000, 10000, or more IFN-γ spot forming cells (SFC) per $10^6$ peripheral blood mononuclear cells (PBMC). In some embodiments, the immune response is raised in a human subject with a preexisting inverse Ad5 neutralizing antibody titer of greater than 50, 100, 150, 200, 300, 400, 500, 600, 700, 800, 900, 1000, 1500, 2000, 2500, 3000, 3500, 4000, 4500, 5000, 6000, 7000, 8000, 9000, 1000, 12000, 15000, or higher. The immune response may comprise a cell-mediated immunity and/or a humoral immunity as described herein. The immune response may be measured by one or more of intracellular cytokine staining (ICS), ELISpot, proliferation assays, cytotoxic T-cell assays including chromium release or equivalent assays, and gene expression analysis using any number of polymerase chain reaction (PCR) or RT-PCR based assays, as described herein and to the extent they are available to a person skilled in the art, as well as any other suitable assays known in the art for measuring immune response.

In some embodiments, the replication defective adenovirus vector comprises a modified sequence encoding a subunit with at least 75%, 80%, 85%, 90%, 95%, 98%, 99%, 99.5%, or 99.9% identity to a wild-type subunit of the polypeptide.

The immunogenic polypeptide may be a mutant CEA or a fragment thereof. In some embodiments, the immunogenic polypeptide comprises a mutant CEA with an Asn->Asp substitution at position 610. In some embodiments, the replication defective adenovirus vector comprises a sequence encoding a polypeptide with at least 75%, 80%, 85%, 90%, 95%, 98%, 99%, 99.5%, or 99.9% identity to the immunogenic polypeptide. In some embodiments, the sequence encoding the immunogenic polypeptide comprises the sequence of SEQ ID NO: 7 (nucleic acid sequence for CEA-CAP1(6D)) or SEQ ID NO: 9 (amino acid sequence for the mutated CAP1(6D) epitope).

In some aspects, the CEA antigen comprises at least 80%, at least 85%, at least 87%, at least 90%, at least 92%, at least 95%, at least 97%, or at least 99% sequence identity to SEQ ID NO: 9. In some aspects, the nucleic acid sequence encoding for the CEA antigen comprises at least 80%, at least 85%, at least 87%, at least 90%, at least 92%, at least 95%, at least 97%, or at least 99% sequence identity to SEQ ID NO: 7. In some aspects, the nucleic acid sequence encoding for the CEA antigen comprises at least 80%, at least 85%, at least 87%, at least 90%, at least 92%, at least 95%, at least 97%, or at least 99% sequence identity to positions 1057 to 3165 of SEQ ID NO: 10.

In some embodiments, the sequence encoding the immunogenic polypeptide comprises a sequence with at least 70% 75%, 80%, 85%, 90%, 95%, 98%, 99%, 99.5%, or 99.9% identity to SEQ ID NO: 7 or SEQ ID NO: 9 or a sequence generated from SEQ ID NO: 7 or SEQ ID NO: 9 by alternative codon replacements. In some embodiments, the immunogenic polypeptide encoded by the adenovirus vectors comprise up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human CEA sequence.

In some embodiments, the immunogenic polypeptide comprises a sequence from SEQ ID NO: 7 or SEQ ID NO: 9 or a modified version, e.g., comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, of SEQ ID NO: 7 or SEQ ID NO: 9.

Members of the CEA gene family are subdivided into three subgroups based on sequence similarity, developmental expression patterns and their biological functions: the CEA-related Cell Adhesion Molecule (CEACAM) subgroup containing twelve genes (CEACAM1, CEACAM3-CEACAM8, CEACAM16 and CEACAM18-CEACAM21), the Pregnancy Specific Glycoprotein (PSG) subgroup containing eleven closely related genes (PSG1-PSG11) and a subgroup of eleven pseudogenes (CEACAMP1-CEACAMP11). Most members of the CEACAM subgroup have similar structures that consist of an extracellular Ig-like domains composed of a single N-terminal V-set domain, with structural homology to the immunoglobulin variable domains, followed by varying numbers of C2-set domains of A or B subtypes, a transmembrane domain and a cytoplasmic domain. There are two members of CEACAM subgroup (CEACAM16 and CEACAM20) that show a few exceptions in the organization of their structures. CEACAM16 contains two Ig-like V-type domains at its N and C termini and CEACAM20 contains a truncated Ig-like V-type 1 domain. The CEACAM molecules can be anchored to the cell surface via their transmembrane domains (CEACAM5 thought CEACAM8) or directly linked to glycophosphatidylinositol (GPI) lipid moiety (CEACAM5, CEACAM18 thought CEACAM21).

CEA family members are expressed in different cell types and have a wide range of biological functions. CEACAMs are found prominently on most epithelial cells and are present on different leucocytes. In humans, CEACAM1, the ancestor member of CEA family, is expressed on the apical side of epithelial and endothelial cells as well as on lymphoid and myeloid cells. CEACAM1 mediates cell-cell adhesion through hemophilic (CEACAM1 to CEACAM1) as well as heterothallic (e.g., CEACAM1 to CEACAM5) interactions. In addition, CEACAM1 is involved in many other biological processes, such as angiogenesis, cell migration, and immune functions. CEACAM3 and CEACAM4 expression is largely restricted to granulocytes, and they are able to convey uptake and destruction of several bacterial pathogens including *Neisseria, Moraxella*, and *Haemophilus* species.

Thus, in various embodiments, compositions and methods relate to raising an immune response against a CEA, selected from the group consisting of CEACAM1, CEACAM3, CEACAM4, CEACAM5, CEACAM6, CEACAM7, CEACAM8, CEACAM16, CEACAM18, CEACAM19, CEACAM20, CEACAM21, PSG1, PSG2, PSG3, PSG4, PSG5, PSG6, PSG7, PSG8, PSG9, and PSG11. An immune response may be raised against cells, e.g. cancer cells, expressing or overexpressing one or more of the CEAs, using the methods and compositions. In some embodiments, the overexpression of the one or more CEAs in such cancer cells is over 5, 10, 20, 30, 40, 50, 60, 70, 80, 90, 100 fold or more compared to non-cancer cells.

In certain embodiments, the CEA antigen used herein is a wild-type CEA antigen or a modified CEA antigen having a least a mutation in YLSGANLNL (SEQ ID NO: 8), a CAP1 epitope of CEA. The mutation can be conservative or non-conservative, substitution, addition, or deletion. In certain embodiments, the CEA antigen used herein has an amino acid sequence set forth in YLSGADLNL (SEQ ID NO: 9), a mutated CAP1 epitope. In further embodiments, the first replication-defective vector or a replication-defective vector that express CEA has a nucleotide sequence at least 50%, 60%, 65%, 70%, 75%, 80%, 85%, 90%, 95%, 98%, 99%, 99.5%, 99.9%, or 100% identical to any portion of SEQ ID NO: 10 (the predicted sequence of an adenovirus vector expressing a modified CEA antigen), such as positions 1057 to 3165 of SEQ ID NO: 10 or full-length SEQ ID NO: 10.

IV. Mucin Family Antigen Targets

Disclosed herein include compositions comprising replication-defective vectors comprising one or more nucleic acid sequences encoding HER3 antigen, and/or one or more nucleic acid sequences encoding mucin family antigen such as MUC1, and/or one or more nucleic acid sequences encoding Brachyury, and/or one or more nucleic acid sequences encoding CEA, and/or one or nucleic acid sequences encoding HER1, HER2/neu, HER4, or any combination thereof in same or separate replication-defective vectors.

The human mucin family (MUC1 to MUC21) includes secreted and transmembrane mucins that play a role in forming protective mucous barriers on epithelial surfaces in the body. These proteins function in to protecting the epithelia lining the respiratory, gastrointestinal tracts, and lining ducts in important organs such as, for example the mammary gland, liver, stomach, pancreas, and kidneys.

MUC1 (CD227) is a TAA that is over-expressed on a majority of human carcinomas and several hematologic malignancies. MUC1 (GenBank: X80761.1, NCBI: NM 001204285.1) and activates many important cellular pathways known to be involved in human disease. MUC1 is a heterodimeric protein formed by two subunits that is commonly overexpressed in several human cancers. MUC1 undergoes autoproteolysis to generate two subunits MUC1n and MUC1c that, in turn, form a stable noncovalent heterodimer.

The MUC1 C-terminal subunit (MUC1c) can comprise a 58 aa extracellular domain (ED), a 2R aa transmembrane domain (TM) and a 72 aa cytoplasmic domain (CD). The MUC1c also can contain a "CQC" motif that can allow for dimerization of MUC1 and it can also impart oncogenic function to a cell. In some cases, MUC1 can in part oncogenic function through inducing cellular signaling via MUC1c. MUC1c can interact with EGFR, ErbB2 and other receptor tyrosine kinases and contributing to the activation of the PI3K→AKT and MEK→ERK cellular pathways. In the nucleus, MUC1c activates the Wnt/β-catenin, STAT, and NF-κB RelA cellular pathways. In some cases MUC1 can impart oncogenic function through inducing cellular signaling via MUC1n. The MUC1 N-terminal subunit (MUC1n) can comprise variable numbers of 20 amino acid tandem repeats that can be glycosylated. MUC1 is normally expressed at the surface of glandular epithelial cells and is over-expressed and aberrantly glycosylated in carcinomas. MUC1 is a TAA that can be utilized as a target for tumor immunotherapy. Several clinical trials have been and are being performed to evaluate the use of MUC1 in immunotherapeutic vaccines. Importantly, these trials indicate that immunotherapy with MUC1 targeting is safe and may provide survival benefit.

However, clinical trials have also shown that MUC1 is a relatively poor immunogen. To overcome this, the present disclosure identifies a T lymphocyte immune enhancer peptide sequence in the C terminus region of the MUC1 oncoprotein (MUC1-C or MUC1c). Compared with the native peptide sequence, the agonist in their modified MUC1-C (a) bound HLA-A2 at lower peptide concentrations, (b) demonstrated a higher avidity for HLA-A2, (c) when used with antigen-presenting cells, induced the production of more IFN-γ by T-cells than with the use of the native peptide, and (d) was capable of more efficiently generating MUC1-specific human T-cell lines from cancer patients. Importantly, T-cell lines generated using the agonist epitope were more efficient than those generated with the native epitope for the lysis of targets pulsed with the native epitope and in the lysis of HLA-A2 human tumor cells expressing MUC1. Additionally, the present disclosure identifies additional CD8+ cytotoxic T lymphocyte immune enhancer agonist sequence epitopes of MUC1-C.

In certain aspects, there is provided a potent MUC1-C modified for immune enhancer capability (mMUC1-C or MUC1-C or MUC1c). The present disclosure provides a potent MUC1-C modified for immune enhancer capability incorporated it into a recombinant Ad5 [E1−, E2b−] platform to produce a new and more potent immunotherapeutic vaccine. For example, the immunotherapeutic vaccine can be Ad5 [E1−, E2b−]-mMUC1-C for treating MUC1 expressing cancers or infectious diseases.

Post-translational modifications play an important role in controlling protein function in the body and in human disease. For example, in addition to proteolytic cleavage discussed above, MUC1 can have several post-translational modifications such as glycosylation, sialylation, palmitoylation, or a combination thereof at specific amino acid residues. Provided herein are immunotherapies targeting glycosylation, sialylation, phosphorylation, or palmitoylation modifications of MUC1.

MUC1 can be highly glycosylated (N- and O-linked carbohydrates and sialic acid at varying degrees on serine and threonine residues within each tandem repeat, ranging from mono- to penta-glycosylation). Differentially 0-glycosylated in breast carcinomas with 3,4-linked GlcNAc. N-glycosylation consists of high-mannose, acidic complex-type and hybrid glycans in the secreted form MUC1/SEC, and neutral complex-type in the transmembrane form, MUC1/TM.4. The present disclosure provides for immunotherapies targeting differentially O-glycosylated forms of MUC1.

Further, MUC1 can be sialylated. Membrane-shed glycoproteins from kidney and breast cancer cells have preferentially sialylated core 1 structures, while secreted forms from the same tissues display mainly core 2 structures. The O-glycosylated content is overlapping in both these tissues with terminal fucose and galactose, 2- and 3-linked galactose, 3- and 3,6-linked GalNAc-ol and 4-linked GlcNAc predominating. The present disclosure provides for immunotherapies targeting various sialylation forms of MUC1. Dual palmitoylation on cysteine residues in the CQC motif is required for recycling from endosomes back to the plasma membrane. The present disclosure provides for immunotherapies targeting various palmitoylation forms of MUC1.

Phosphorylation can affect MUC1's ability to induce specific cell signaling responses that are important for human health. The present disclosure provides for immunotherapies targeting various phosphorylated forms of MUC1. For example, MUC1 can be phosphorylated on tyrosine and serine residues in the C-terminal domain. Phosphorylation on tyrosines in the C-terminal domain can increase nuclear location of MUC1 and β-catenin. Phosphorylation by PKC delta can induce binding of MUC1 to β-catenin/CTNNB1 and decrease formation of β-catenin/E-cadherin complexes. Src-mediated phosphorylation of MUC1 can inhibit interaction with GSK3B. Src- and EGFR-mediated phosphorylation of MUC1 on Tyr-1229 can increase binding to β-catenin/CTNNB1. GSK3B-mediated phosphorylation of MUC1 on Ser-1227 can decrease this interaction, but restores the formation of the β-cadherin/E-cadherin complex. PDGFR-mediated phosphorylation of MUC1 can increase nuclear colocalization of MUC1CT and CTNNB1. The present disclosure provides for immunotherapies targeting different phosphorylated forms of MUC1, MUC1c, and MUC1n known to regulate its cell signaling abilities.

The disclosure provides for immunotherapies that modulate MUC1c cytoplasmic domain and its functions in the cell. The disclosure provides for immunotherapies that comprise modulating a CQC motif in MUC1c. The disclosure provides for immunotherapies that comprise modulating the extracellular domain (ED), the transmembrane domain (TM), the cytoplasmic domain (CD) of MUC1c, or a combination thereof. The disclosure provides for immunotherapies that comprise modulating MUC1c's ability to induce cellular signaling through EGFR, ErbB2, or other receptor tyrosine kinases. The disclosure provides for immunotherapies that comprise modulating MUC1c's ability to induce PI3K→AKT, MEK→ERK, Wnt/β-catenin, STAT, NF-κB RelA cellular pathways, or combination thereof.

In some embodiments, the MUC1c immunotherapy can further comprise HER2/neu, CEA, or Brachyury immunotherapy in the same replication-defective virus vectors or separate replication-defective virus vectors.

The disclosure also provides for immunotherapies that modulate MUC1n and its cellular functions. The disclosure also provides for immunotherapies comprising tandem repeats of MUC1n, the glycosylation sites on the tandem repeats of MUC1n, or a combination thereof. In some embodiments, the MUC1n immunotherapy further comprises HER2/neu, CEA, or Brachyury immunotherapy in the same replication-defective virus vectors or separate replication-defective virus vectors.

The disclosure also provides vaccines comprising MUC1n, MUC1c, HER2/neu, HER1, HER3, HER4, brachyury, CEA, or a combination thereof. The disclosure provides vaccines comprising MUC1c and HER1, HER3, HER4, HER2/neu, brachyury, CEA, or a combination thereof. The disclosure also provides vaccines targeting MUC1n and HER1, HER3, HER4, HER2/neu, Brachyury, CEA, or a combination thereof. In some embodiments, the antigen combination is contained in one vector as provided herein. In some embodiments, the antigen combination is contained in a separate vector as provided herein.

The present invention relates to a replication defective adenovirus vector of serotype 5 comprising a sequence encoding an immunogenic polypeptide. The immunogenic polypeptide may be an isoform of MUC1 or a subunit or a fragment thereof. In some embodiments, the replication defective adenovirus vector comprises a sequence encoding a polypeptide with at least 75%, 80%, 85%, 90%, 95%, 98%, 99%, 99.5%, or 99.9% identity to the immunogenic polypeptide. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human MUC1 sequence.

In some embodiments, a MUC1-c antigen of this disclosure can be a modified MUC1 and can have a nucleotide sequence that is at least 80%, at least 85%, at least 90%, at least 92%, at least 95%, at least 97%, or at least 99% identical to SEQ ID NO: 11. In certain embodiments, a MUC1-c antigen of this disclosure can have an nucleotide sequence as set forth in SEQ ID NO: 11.

In some embodiments, a MUC1-c antigen of this disclosure can be a modified MUC1 and can have an amino sequence that is at least 80%, at least 85%, at least 90%, at least 92%, at least 95%, at least 97%, or at least 99% identical to SEQ ID NO: 12. In certain embodiments, a MUC1-c antigen of this disclosure can have an amino acid sequence as set forth in SEQ ID NO: 12.

In some aspects, the MUC1 antigen comprises at least 80%, at least 85%, at least 87%, at least 90%, at least 92%, at least 95%, at least 97%, or at least 99% sequence identity to SEQ ID NO: 12. In some aspects, the nucleic acid sequence encoding for the MUC antigen comprises at least 80%, at least 85%, at least 87%, at least 90%, at least 92%, at least 95%, at least 97%, or at least 99% sequence identity to SEQ ID NO: 11. In some aspects, the nucleic acid sequence encoding for the CEA antigen comprises at least 80%, at least 85%, at least 87%, at least 90%, at least 92%, at least 95%, at least 97%, or at least 99% sequence identity to positions 1105-2532 of of SEQ ID NO: 89.

V. Brachyury Antigen Targets

Disclosed herein include compositions comprising replication-defective vectors comprising one or more nucleic acid sequences encoding HER2/neu antigen, and/or one or more nucleic acid sequences encoding mucin family antigen such as MUC1, and/or one or more nucleic acid sequences encoding Brachyury, and/or one or more nucleic acid sequences encoding CEA, and/or one or more nucleic acid sequences encoding HER1, HER3, HER4, or any combination, in same or separate replication-defective vectors.

The disclosure provides for immunotherapies that comprise one or more antigens to Brachyury. Brachyury (also known as the "T" protein in humans) is a member of the T-box family of transcription factors that play key roles during early development, mostly in the formation and differentiation of normal mesoderm and is characterized by a highly conserved DNA-binding domain designated as T-domain. The epithelial to mesenchymal transition (EMT) is a key step during the progression of primary tumors into a metastatic state in which Brachyury plays a crucial role. The expression of Brachyury in human carcinoma cells induces changes characteristic of EMT, including up-regulation of mesenchymal markers, down-regulation of epithelial markers, and an increase in cell migration and invasion. Conversely, inhibition of Brachyury resulted in down-regulation of mesenchymal markers and loss of cell migration and invasion and diminished the ability of human tumor cells to form metastases. Brachyury can function to mediate epithelial-mesenchymal transition and promotes invasion.

The disclosure also provides for immunotherapies that modulate Brachyury effect on epithelial-mesenchymal transition function in cell proliferation diseases, such as cancer. The disclosure also provides immunotherapies that modulate Brachyury's ability to promote invasion in cell proliferation diseases, such as cancer. The disclosure also provides for immunotherapies that modulate the DNA binding function of T-box domain of Brachyury. In some embodiments, the Brachyury immunotherapy can further comprise one or more antigens to HER1, HER3, HER4, HER2/neu, CEA, MUC1, MUC1c, MUC1n, or any combination thereof.

Brachyury expression is nearly undetectable in most normal human tissues and is highly restricted to human tumors and often overexpressed making it an attractive target antigen for immunotherapy. In humans, Brachyury is encoded by the T gene (GenBank: AJ001699.1, NCBI: NM_003181.3). There are at least two different isoforms produced by alternative splicing found in humans. Each isoform has a number of natural variants.

Brachyury is immunogenic and Brachyury-specific CD8+ T-cells expanded in vitro can lyse Brachyury expressing tumor cells. These features of Brachyury make it an attractive tumor associated antigen (TAA) for immunotherapy. The Brachyury protein is a T-box transcription factor. It can bind to a specific DNA element, a near palindromic sequence "TCACACCT" through a region in its N-terminus, called the T-box to activate gene transcription when bound to such a site.

The disclosure also provides vaccines comprising Brachyury, HER1, HER3, HER4, HER2/neu, MUC1, CEA, or a combination thereof. In some embodiments, the antigen combination is contained in one vector as provided herein. In some embodiments, the antigen combination is contained in a separate vector as provided herein.

In particular embodiments, the present invention relates to a replication defective adenovirus vector of serotype 5 comprising a sequence encoding an immunogenic polypeptide. The immunogenic polypeptide may be an isoform of Brachyury or a subunit or a fragment thereof. In some embodiments, the replication defective adenovirus vector comprises a sequence encoding a polypeptide with at least 70%, 75%, 80%, 85%, 90%, 95%, 98%, 99%, 99.5%, or 99.9% identity to the immunogenic polypeptide. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human Brachyury sequence.

In some embodiments, a Brachyury antigen of this disclosure can have an amino sequence that is at least 80%, at least 85%, at least 90%, at least 92%, at least 95%, at least 97%, or at least 99% identical to SEQ ID NO: 13. In certain embodiments, a Brachyury antigen of this disclosure can have an amino acid sequence as set forth in SEQ ID NO: 13. In some embodiments, a Brachyury antigen of the present disclosure has at least 80%, at least 85%, at least 90%, at least 92%, at least 95%, at least 97%, or at least 99% identical to SEQ ID NO: 85. In some embodiments, a Brachury antigen of the present disclosure has a sequence as set forth in SEQ ID NO: 85.

In some aspects, the Brachyury antigen comprises at least 80%, at least 85%, at least 87%, at least 90%, at least 92%, at least 95%, at least 97%, or at least 99% sequence identity to SEQ ID NO: 85. In some aspects, the nucleic acid sequence encoding for the Brachyury antigen comprises at least 80%, at least 85%, at least 87%, at least 90%, at least 92%, at least 95%, at least 97%, or at least 99% sequence identity to SEQ ID NO: 13. In some aspects, the nucleic acid sequence encoding for the CEA antigen comprises at least 80%, at least 85%, at least 87%, at least 90%, at least 92%, at least 95%, at least 97%, or at least 99% sequence identity to positions 1045 to 2277 of SEQ ID NO: 90.

VI. General Target Antigens

Additional non-limiting examples of target antigens include human epidermal growth factor receptor 2 (HER2/neu, also referred to herein as ErbB2), HER3 (also referred to herein as ErbB3), HER4 (also referred to herein as ErbB4), carcinoembryonic antigen (CEA), a tumor neoantigens or tumor neo-epitope, folate receptor alpha, WT1, brachyury (TIVS7-2, polymorphism), brachyury (IVS7 T/C polymorphism), T brachyury, T, hTERT, hTRT, iCE, BAGE, DAM-6, -10, GAGE-1, -2, -8, GAGE-3, -4, -5, -6, -7B, NA88-A, NY-ESO-1, MART-1, MC1R, Gp100, Tyrosinase, TRP-1, TRP-2, ART-4, CAMEL, Cyp-B, HER1 (also referred to herein as EGFR), MUC1, MUC1 (VNTR polymorphism), MUC1-c, MUC1-n, MUC2, PRAME, P15, RU1, RU2, SART-1, SART-3, β-catenin/m, Caspase-8/m, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARα, TEL/AML1, alpha-actinin-4, ARTC1, CAR-ABL fusion protein (b3a2), B-RAF, CASP-5, CASP-8, beta-catenin, Cdc27, CDK4, CDKN2A, COA-1, dek-can fusion protein, EFTUD2, Elongation factor 2, ETV6-AML1 fusion protein, FLT3-ITD, FN1, GPNMB, LDLR-fucosyltransferase fusion protein, HLA-A2d, HLA-A1 1d, hsp70-2, KIAAO205, MART2, ME1, Myosin class I, NFYC, OGT, OS-9, pml-RARalpha fusion protein, PRDX5, PTPRK, K-ras, N-ras, RBAF600, SIRT2, SNRPD1, SYT-SSX1- or -SSX2 fusion protein, TGF-betaRII, triosephosphate isomerase, BAGE-1, GAGE-1, 2, 8, Gage 3, 4, 5, 6, 7, GnTVf, HERV-K-MEL, KK-LC-1, KM-HN-1, LAGE-1, MAGE-A1, MAGE-A2, MAGE-A3, MAGE-A4, MAGE-A6, MAGE-A9, MAGE-A10, MAGE-A12, MAGE-C2, mucin, NA-88, NY-ESO-1/LAGE-2, SAGE, Sp17, SSX-2, SSX-4, TAG-1, TAG-2, TRAG-3, TRP2-INT2g, XAGE-1b, gp100/PmeI17, mammaglobin-A, Melan-A/MART-1, NY-BR-1, OA1, RAB38/NY-MEL-1, TRP-1/gp75, adipophilin, AIM-2, ALDH1A1, BCLX (L), BCMA, BING-4, CPSF, cyclin D1, DKK1, ENAH (hMena), EP-CAM, EphA3, EZH2, FGF5, G250/MN/CAIX, IL13Ralpha2, intestinal carboxyl esterase, alpha fetoprotein, M-CSFT, MCSP, mdm-2, MMP-2, p53, PBF, PRAME, RAGE-1, RGS5, RNF43, RU2AS, secernin 1, SOX10, survivin, Telomerase, VEGF, or any combination thereof.

Illustrative useful tumor proteins include, but are not limited to any one or more of, CEA, human epidermal growth factor receptor 1 (HER1), human epidermal growth factor receptor 2 (HER2/neu); human epidermal growth factor receptor 3 (HER3), human epidermal growth factor receptor 4 (HER4), MUC1, Prostate-specific antigen (PSA), PSMA, WT1, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, PSA, PSM, Tyrosinase, TRP-1, TRP-2, ART-4, CAMEL, CEA, Cyp-B, BRCA1, Brachyury, Brachyury (TIVS7-2, polymorphism), Brachyury (IVS7 T/C polymorphism), T Brachyury, T, hTERT, hTRT, iCE, MUC1, MUC1 (VNTR polymorphism), MUC1c, MUC1n, MUC2, PRAME, P15, RU1, RU2, SART-1, SART-3, AFP, β-catenin/m, Caspase-8/m, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARα, HPV E6, HPV E7, and TEL/AML1.

In some embodiments, the viral vector comprises a target antigen sequence encoding a modified polypeptide selected from CEA, human epidermal growth factor receptor 1 (HER1), human epidermal growth factor receptor 2 (HER2/neu), human epidermal growth factor receptor 3 (HER3), human epidermal growth factor receptor 4 (HER4), MUC1, Prostate-specific antigen (PSA), PSMA (i.e., PSM), WT1, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, Tyrosinase, TRP-1, TRP-2, ART-4, CAMEL, Cyp-B, BRCA1, Brachyury, Brachyury (TIVS7-2, polymorphism), Brachyury (IVS7 T/C polymorphism), T Brachyury, T, hTERT, hTRT, iCE, MUC1 (VNTR polymorphism), MUC1c, MUC1n, MUC2, PRAME, P15, RU1, RU2, SART-1, SART-3, AFP, β-catenin/m, Caspase- 8/m, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, PmI/RARα, HPV E6, HPV E7, and TEL/AML1, wherein the polypeptide or a fragment thereof has at least 60%, 65%, 70%, 75%, 80%, 85%, 90%, 95%, 98%, 99%, 99.5%, or 99.9% identity to the corresponding native sequence.

Additional illustrative useful tumor proteins useful include, but are not limited to any one or more of alpha-actinin-4, ARTC1, CAR-ABL fusion protein (b3a2), B-RAF, CASP-5, CASP-8, beta-catenin, Cdc27, CDK4, CDKN2A, COA-1, dek-can fusion protein, EFTUD2, Elongation factor 2, ETV6-AML1 fusion protein, FLT3-ITD, FN1, GPNMB, LDLR-fucosyltransferase fusion protein, HLA-A2d, HLA-A1 1d, hsp70-2, KIAAO205, MART2, ME1, MUM-1f, MUM-2, MUM-3, neo-PAP, Myosin class I, NFYC, OGT, OS-9, p53, pml-RARalpha fusion protein, PRDX5, PTPRK, K-ras, N-ras, RBAF600, SIRT2, SNRPD1, SYT-SSX1- or -SSX2 fusion protein, TGF-betaRII, triosephosphate isomerase, BAGE-1, GnTVf, HERV-K-MEL, KK-LC-1, KM-HN-1, LAGE-1, MAGE-A9, MAGE-C2, mucink, NA-88, NY-ESO-1/LAGE-2, SAGE, Sp17, SSX-2, SSX-4, TAG-1, TAG-2, TRAG-3, TRP2-INT2g, XAGE-1b, gp100/Pmel17, Kallikrein 4, mammaglobin-A, Melan-A/MART-1, NY-BR-1, OA1, PSA, RAB38/NY-MEL-1, TRP-1/gp75, TRP-2, tyrosinase, adipophilin, AIM-2, ALDH1A1, BCLX(L), BCMA, BING-4, CPSF, cyclin D1, DKK1, ENAH (hMena), EP-CAM, EphA3, EZH2, FGF5, G250/MN/CAIX, IL13Ralpha2, intestinal carboxyl esterase, alpha fetoprotein, M-CSFT, MCSP, mdm-2, MMP-2, PBF, PRAME, RAGE-1, RGS5, RNF43, RU2AS, secernin 1, SOX10, STEAP1, survivin, Telomerase, and/or VEGF.

Tumor-associated antigens may be antigens from infectious agents associated with human malignancies. Examples of infectious agents associated with human malignancies include Epstein-Barr virus, *Helicobacter pylori*, Hepatitis B virus, Hepatitis C virus, Human heresvirus-8, Human immunodeficiency virus, Human papillomavirus, Human T-cell leukemia virus, liver flukes, and *Schistosoma* haematobium.

In some aspects, tumor neo-epitopes as used herein are tumor-specific epitopes, such as EQVWGMAVR (SEQ ID NO:91) or CQGPEQVWGMAVREL (SEQ ID NO:92) (R346W mutation of FLRT2), GETVTMPCP (SEQ ID NO:93) or NVGETVTMPCPKVFS (SEQ ID NO:94) (V73M mutation of VIPR2), GLGAQCSEA (SEQ ID NO:95) or NNGLGAQCSEAVTLN (SEQ ID NO:96) (R286C mutation of FCRL1), RKLTTELTI (SEQ ID NO:97), LGPERRKLTTELTII (SEQ ID NO:98), or PERRKLTTE (SEQ ID NO:99) (S1613L mutation of FAT4), MDWVWMDTT (SEQ ID NO:100), AVMDWVWMDTTLSLS (SEQ ID NO:101), or VWMDTTLSL (SEQ ID NO:102) (T2356M mutation of PIEZO2), GKTLNPSQT (SEQ ID NO:103), SWFREGKTLNPSQTS (SEQ ID NO:104), or REGKTLNPS (SEQ ID NO:105) (A292T mutation of SIGLEC14), VRNATSYRC (SEQ ID NO:106), LPNVTVRNATSYRCG (SEQ ID NO:107), or NVTVRNATS (SEQ ID NO:108) (D1143N mutation of SIGLEC1), FAMAQIPSL (SEQ ID NO:109), PFAMAQIPSLSRAV (SEQ ID NO:110), or AQIPSLSLR (SEQ ID NO: 111) (Q678P mutation of SLC4A11).

Tumor-associated antigens may be antigens not normally expressed by the host; they can be mutated, truncated, misfolded, or otherwise abnormal manifestations of molecules normally expressed by the host; they can be identical to molecules normally expressed but expressed at abnormally high levels; or they can be expressed in a context or environment that is abnormal. Tumor-associated antigens may be, for example, proteins or protein fragments, complex carbohydrates, gangliosides, haptens, nucleic acids, other biological molecules or any combinations thereof.

VII. Infectious Disease-Associated Antigen Targets

Target antigens include, but are not limited to, antigens derived from any of a variety of infectious agents such as parasites, bacteria, virus, prions, and the like. An infectious agent may refer to any living organism capable of infecting a host. Infectious agents include, for example, bacteria, any variety of viruses, such as, single stranded RNA viruses, single stranded DNA viruses, fungi, parasites, and protozoa.

Examples of infectious disease associated target antigens that can be used with the compositions and the methods can be derived from the following: *Actinobacillus* spp., *Actinomyces* spp., Adenovirus (types 1, 2, 3, 4, 5, 6, and 7), Adenovirus (types 40 and 41), *Aerococcus* spp., *Aeromonas hydrophila*, *Ancylostoma duodenale*, *Angiostrongylus cantonensis*, *Ascaris lumbricoides*, *Ascaris* spp., *Aspergillus* spp., *Babesia* spp, *B. microti*, *Bacillus anthracis*, *Bacillus cereus*, *Bacteroides* spp., *Balantidium coli*, *Bartonella baciliformis*, *Blastomyces dermatitidis*, *Bluetongue virus*, *Bordetella bronchiseptica*, *Bordetella pertussis*, *Borrelia afzelii*, *Borrelia burgdorferi*, *Borrelia garinii*, *Branhamella catarrhalis*, *Brucella* spp. (*B. abortus*, *B. canis*, *B. melitensis*, *B. suis*), *Brugia* spp., *Burkholderia*, (*Pseudomonas*) *mallei*, *Burkholderia* (*Pseudomonas*) *pseudomallei*, California serogroup, *Campylobacter fetus* subsp. Fetus, *Campylobacter jejuni*, *C. coli*, *C. fetus* subsp. Jejuni, *Candida albicans*, *Capnocytophaga* spp., Chikungunya virus, *Chlamydia psittaci*, *Chlamydia trachomatis*, *Citrobacter* spp., *Clonorchis sinensis*, *Clostridium botulinum*, *Clostridium difficile*, *Clostridium perfringens*, *Clostridium tetani*, *Clostridium* spp. (with the exception of those species listed above), *Coccidioides immitis*, Colorado tick fever virus, *Corynebacterium diphtheriae*, *Coxiella burnetii*, Coxsackievirus, Creutzfeldt-Jakob agent, Kuru agent, Crimean-Congo hemorrhagic fever virus, *Cryptococcus neoformans*, *Cryptosporidium parvum*, Cytomegalovirus, *Cyclospora cayatanesis*, Dengue virus (1, 2, 3, 4), Diphtheroids, Eastern (Western) equine encephalitis virus, Ebola virus, *Echinococcus granulosus*, *Echinococcus multilocularis*, Echovirus, *Edwardsiella tarda*, *Entamoeba histolytica*, *Enterobacter* spp., Enterovirus 70, *Epidermophyton floccosum*, *Ehrlichia* spp., *Ehrlichia sennetsu*, *Microsporum* spp., *Trichophyton* spp., Epstein-Barr virus, *Escherichia coli*, enterohemorrhagic, *Escherichia coli*, enteroinvasive, *Escherichia coli*, enteropathogenic, *Escherichia coli*, enterotoxigenic, *Fasciola hepatica*, *Francisella tularensis*, *Fusobacterium* spp., *Gemella haemolysans*, *Giardia lamblia*, Guanarito virus, *Haemophilus ducreyi*, *Haemophilus influenzae* (group b), Hantavirus, Hepatitis A virus, Hepatitis B virus, Hepatitis C virus, Hepatitis D virus, Hepatitis E virus, Herpes simplex virus, *Herpesvirus simiae*, *Histoplasma capsulatum*, Human coronavirus, Human immunodeficiency virus, Human papillomavirus, Human rotavirus, Human T-lymphotrophic virus, Influenza virus including H5N1, Junin virus/Machupo virus, *Klebsiella* spp., Kyasanur Forest disease virus, *Lactobacillus* spp., Lassa virus, *Legionella pneumophila*, *Leishmania major*, *Leishmania infantum*, *Leishmania* spp., *Leptospira interrogans*, *Listeria monocytogenes*, Lymphocytic choriomeningitis virus, Machupo virus, Marburg virus, Measles virus, *Micrococcus* spp., *Moraxella* spp., *Mycobacterium* spp. (other than *M. bovis*, *M. tuberculosis*, *M. avium*, *M. leprae*), *Mycobacterium tuberculosis*, *M. bovis*, *Mycoplasma hominis*, M. orale, M. salivarium, *M. fermentans*, *Mycoplasma pneumoniae*, *Naegleria fowleri*, *Necator*

*americanus, Neisseria gonorrhoeae, Neisseria meningitides, Neisseria* spp. (other than *N. gonorrhoeae* and *N. meningitidis*), *Nocardia* spp., Norwalk virus, Omsk hemorrhagic fever virus, *Onchocerca volvulus, Opisthorchis* spp., Parvovirus B19, *Pasteurella* spp., Peptococcus spp., *Peptostreptococcus* spp., *Plasmodium falciparum, Plasmodium vivax, Plasmodium* spp., *Plesiomonas shigelloides*, Powassan encephalitis virus, *Proteus* spp., *Pseudomonas* spp. (other than *P. mallei, P. pseudomallei*), Rabies virus, Respiratory syncytial virus, Rhinovirus, *Rickettsia akari, Rickettsia prowazekii*, R. Canada, *Rickettsia rickettsii*, Rift Valley virus, Ross river virus/O'Nyong-Nyong virus, Rubella virus, *Salmonella choleraesuis, Salmonella paratyphi, Salmonella typhi, Salmonella* spp. (with the exception of those species listed above), *Schistosoma* spp., Scrapie agent, *Serratia* spp., *Shigella* spp., Sindbis virus, *Sporothrix schenckii*, St. Louis encephalitis virus, Murray Valley encephalitis virus, *Staphylococcus aureus, Streptobacillus moniliformis, Streptococcus agalactiae, Streptococcus faecalis, Streptococcus pneumoniae, Streptococcus pyogenes, Streptococcus salivarius, Taenia saginata, Taenia solium, Toxocara canis, T. cati, T. cruzi, Toxoplasma gondii, Treponema pallidum, Trichinella* spp., *Trichomonas vaginalis, Trichuris trichiura, Trypanosoma brucei, Trypanosoma cruzi, Ureaplasma urealyticum,* Vaccinia virus, Varicella-zoster virus, eastern equine encephalitis virus (EEEV), severe acute respiratory virus (SARS), Venezuelan equine encephalitis virus (VEEV), Vesicular stomatitis virus, Vibrio cholerae, serovar 01, Vibrio parahaemolyticus, West Nile virus, Wuchereria bancrofti, Yellow fever virus, Yersinia enterocolitica, Yersinia pseudotuberculosis, and Yersinia pestis. Target antigens may include proteins, or variants or fragments thereof, produced by any of the infectious organisms.

A number of viruses are associated with viral hemorrhagic fever, including filoviruses (e.g., Ebola, Marburg, and Reston), arenaviruses (e.g., Lassa, Junin, and Machupo), and bunyaviruses. In addition, phleboviruses, including, for example, Rift Valley fever virus, have been identified as etiologic agents of viral hemorrhagic fever. Etiological agents of hemorrhagic fever and associated inflammation may also include paramyxoviruses, particularly respiratory syncytial virus. In addition, other viruses causing hemorrhagic fevers in man have been identified as belonging to the following virus groups: togavirus (Chikungunya), flavivirus (dengue, yellow fever, Kyasanur Forest disease, Omsk hemorrhagic fever), nairovirus (Crimian-Congo hemorrhagic fever) and hantavirus (hemorrhagic fever with renal syndrome, nephropathic epidemia). Furthermore, Sin Nombre virus was identified as the etiologic agent of the 1993 outbreak of hantavirus pulmonary syndrome in the American Southwest.

Target antigens may include viral coat proteins, i.e., influenza neuraminidase and hemagglutinin, HIV gp160 or derivatives thereof, HIV Gag, HIV Nef, HIV Pol, SARS coat proteins, herpes virion proteins, WNV proteins, etc. Target antigens may also include bacterial surface proteins including pneumococcal PsaA, PspA, LytA, surface or virulence associated proteins of bacterial pathogens such as Nisseria gonnorhea, outer membrane proteins or surface proteases.

VIII. Personalized Tumor-Associated Antigens

In certain embodiments tumor-associated antigens used with the compositions and methods as described herein may be identified directly from an individual with a proliferative disease or cancer. In certain embodiments, cancers may include benign tumors, metastatic tumors, carcinomas, or sarcomas and the like. In some embodiments, a personalized tumor antigen comprises HER3 characterized from a patient and further utilized as the target antigen as a whole, in part or as a variant.

In this regard, screens can be carried out using a variety of known technologies to identify tumor target antigens from an individual. For example, in one embodiment, a tumor biopsy is taken from a patient, RNA is isolated from the tumor cells and screened using a gene chip (for example, from Affymetrix, Santa Clara, Calif.) and a tumor antigen is identified. Once the tumor target antigen is identified, it may then be cloned, expressed, and purified using techniques known in the art.

This target antigen can then linked to one or more epitopes or incorporated or linked to cassettes or viral vectors described herein and administered to the patient in order to alter the immune response to the target molecule isolated from the tumor. In this manner, "personalized" immunotherapy and vaccines are contemplated in certain embodiments. Where cancer is genetic (i.e., inherited), for example, the patient has been identified to have a BRAC1 or BRAC2 mutation, the vaccine can be used prophylactically. When the cancer is sporadic this immunotherapy can be used to reduce the size of the tumor, enhance overall survival and reduce reoccurrence of the cancer in a subject.

IX. Vectors

A. Viral Vectors for Immunotherapies and Vaccines

Recombinant viral vectors can be used to express any antigen disclosed herein. Examples of viral vectors that can be used herein include lentiviruses, provirus, Vaccinia virus, adenoviruses, adeno-associated viruses, self-complementary adeno-associated virus, Cytomegalovirus, Sendai virus, HPV virus, or adenovirus. In some embodiments, retroviruses can be used such as Moloney murine leukemia virus (MoMLV). In some embodiments, lentivirus can be used such as HIV to encode for an antigen described herein. In some embodiments, a cytomegalovirus (CMV) vector or a Sendai virus vector (SeV) can be used to encode for an antigen described herein.

B. Adenovirus Vectors

In general, adenoviruses are attractive for clinical because they can have a broad tropism, they can infect a variety of dividing and non-dividing cell types and they can be used systemically as well as through more selective mucosal surfaces in a mammalian body. In addition, their relative thermostability further facilitates their clinical use.

Certain aspects include transferring into a cell an expression construct comprising one or more nucleic acid sequences encoding one or more target antigens such as an antigen in epitope of HER1, HER2/neu, HER3, HER4, or any combination thereof. In certain embodiments, transfer of an expression construct into a cell may be accomplished using a viral vector. A viral vector may be used to include those constructs containing viral sequences sufficient to express a recombinant gene construct that has been cloned therein.

In particular embodiments, the viral vector is an adenovirus vector. Adenoviruses are a family of DNA viruses characterized by an icosahedral, non-enveloped capsid containing a linear double-stranded genome. Of the human adenoviruses, none are associated with any neoplastic disease, and only cause relatively mild, self-limiting illness in immunocompetent individuals.

Adenovirus vectors may have low capacity for integration into genomic DNA. Adenovirus vectors may result in highly efficient gene transfer. Additional advantages of adenovirus vectors include that they are efficient at gene delivery to both nondividing and dividing cells and can be produced in large quantities.

In contrast to integrating viruses, the adenoviral infection of host cells may not result in chromosomal integration because adenoviral DNA can replicate in an episomal manner without potential genotoxicity. Also, adenovirus vectors may be structurally stable, and no genome rearrangement has been detected after extensive amplification. Adenovirus is particularly suitable for use as a gene transfer vector because of its mid-sized genome, ease of manipulation, high titer, wide target-cell range and high infectivity.

The first genes expressed by the virus are the E1 genes, which act to initiate high-level gene expression from the other Ad5 gene promoters present in the wild type genome. Viral DNA replication and assembly of progeny virions occur within the nucleus of infected cells, and the entire life cycle takes about 36 hr with an output of approximately 104 virions per cell.

The wild type Ad5 genome is approximately 36 kb, and encodes genes that are divided into early and late viral functions, depending on whether they are expressed before or after DNA replication. The early/late delineation is nearly absolute, since it has been demonstrated that super-infection of cells previously infected with an Ad5 results in lack of late gene expression from the super-infecting virus until after it has replicated its own genome. Without being bound by theory, this is likely due to a replication dependent cis-activation of the Ad5 major late promoter (MLP), preventing late gene expression (primarily the Ad5 capsid proteins) until replicated genomes are present to be encapsulated. The composition and methods may take advantage of these features in the development of advanced generation Ad vectors/vaccines.

The adenovirus vector may be replication defective, or at least conditionally defective. The adenovirus may be of any of the 42 different known serotypes or subgroups A-F and other serotypes or subgroups are envisioned. Adenovirus type 5 of subgroup C may be used in particular embodiments in order to obtain a replication-defective adenovirus vector. This is because Adenovirus type 5 is a human adenovirus about which a great deal of biochemical and genetic information is known, and it has historically been used for most constructions employing adenovirus as a vector.

Adenovirus growth and manipulation is known to those of skill in the art, and exhibits broad host range in vitro and in vivo. Modified viruses, such as adenoviruses with alteration of the CAR domain, may also be used. Methods for enhancing delivery or evading an immune response, such as liposome encapsulation of the virus, are also envisioned The adenovirus vectors can include a deletion in the E2b region of the Ad genome and, optionally, the E1 region. In some cases, such vectors do not have any other regions of the Ad genome deleted. The adenovirus vectors can include a deletion in the E2b region of the Ad genome and deletions in the E1 and E3 regions. In some cases, such vectors have no other regions deleted. The adenovirus vectors can include a deletion in the E2b region of the Ad genome and deletions in the E1, E3 and partial or complete removal of the E4 regions. In some cases, such vectors have no other deletions. The adenovirus vectors can include a deletion in the E2b region of the Ad genome and deletions in the E1 and/or E4 regions. In some cases, such vectors contain no other deletions. The adenovirus vectors can include a deletion in the E2a, E2b and/or E4 regions of the Ad genome. In some cases, such vectors have no other deletions. The adenovirus vectors can have the E1 and/or DNA polymerase functions of the E2b region deleted. In some cases, such vectors have no other deletions. The adenovirus vectors can have the E1 and/or the preterminal protein functions of the E2b region deleted. In some cases, such vectors have no other deletions. The adenovirus vectors can have the E1, DNA polymerase and/or the preterminal protein functions deleted. In some cases, such vectors have no other deletions. The adenovirus vectors can have at least a portion of the E2b region and/or the E1 region. In some cases, such vectors are not gutted adenovirus vectors. In this regard, the vectors may be deleted for both the DNA polymerase and the preterminal protein functions of the E2b region. The adenovirus vectors can have a deletion in the E1, E2b and/or 100K regions of the adenovirus genome. The adenovirus vectors can comprise vectors having the E1, E2b and/or protease functions deleted. In some cases, such vectors have no other deletions. The adenovirus vectors can have the E1 and/or the E2b regions deleted, while the fiber genes have been modified by mutation or other alterations (for example to alter Ad tropism). Removal of genes from the E3 or E4 regions may be added to any of the adenovirus vectors mentioned. In certain embodiments, adenovirus vectors may have a deletion in the E1 region, the E2b region, the E3 region, the E4 region, or any combination thereof. In certain embodiments, the adenovirus vector may be a gutted adenovirus vector.

Other regions of the Ad genome can be deleted. A "deletion" in a particular region of the Ad genome refers to a specific DNA sequence that is mutated or removed in such a way so as to prevent expression and/or function of at least one gene product encoded by that region (e.g., E2b functions of DNA polymerase or preterminal protein function). Deletions can encompass deletions within exons encoding portions of proteins as well as deletions within promoter and leader sequences. A deletion within a particular region refers to a deletion of at least one base pair within that region of the Ad genome. More than one base pair can be deleted. For example, at least 20, 30, 40, 50, 60, 70, 80, 90, 100, 110, 120, 130, 140, or 150 base pairs can be deleted from a particular region. The deletion can be more than 150, 160, 170, 180, 190, 200, 250, or 300 base pairs within a particular region of the Ad genome. These deletions can prevent expression and/or function of the gene product encoded by the region. For example, a particular region of the Ad genome can include one or more point mutations such that one or more encoded proteins is non-functional. Such mutations include residues that are replaced with a different residue leading to a change in the amino acid sequence that result in a nonfunctional protein. Exemplary deletions or mutations in the Ad genome include one or more of E1a, E1b, E2a, E2b, E3, E4, L1, L2, L3, L4, L5, TP, POL, IV, and VA regions. Deleted adenovirus vectors can be made, for example, using recombinant techniques.

The vector may comprise a genetically engineered form of adenovirus, such as an E2 deleted adenoviral vector, or more specifically, an E2b deleted adenoviral vector. The term "E2b deleted," as used herein, refers to a specific DNA sequence that is mutated in such a way so as to prevent expression and/or function of at least one E2b gene product. Thus, in certain embodiments, "E2b deleted" refers to a specific DNA sequence that is deleted (removed) from the Ad genome. E2b deleted or "containing a deletion within the E2b region" refers to a deletion of at least one base pair within the E2b region of the Ad genome. In certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E2b region of the Ad genome. An E2b deletion may be a deletion that prevents expression and/or function of at least one E2b gene product and therefore, encompasses deletions within exons encoding portions of E2b-specific proteins as well as deletions within promoter and leader sequences. In certain embodiments, an E2b deletion is a deletion that prevents expression and/or function of one or both of the DNA polymerase and the preterminal protein of the E2b region. In a further embodiment, "E2b deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

As would be understood by the skilled artisan upon reading the present disclosure, other regions of the Ad genome can be deleted. Thus to be "deleted" in a particular region of the Ad genome, as used herein, refers to a specific DNA sequence that is mutated in such a way so as to prevent expression and/or function of at least one gene product encoded by that region. In certain embodiments, to be "deleted" in a particular region refers to a specific DNA sequence that is deleted (removed) from the Ad genome in such a way so as to prevent the expression and/or the function encoded by that region (e.g., E2b functions of DNA polymerase or preterminal protein function). "Deleted" or "containing a deletion" within a particular region refers to a deletion of at least one base pair within that region of the Ad genome.

Thus, in certain embodiments, more than one base pair is deleted and in further embodiments, at least 20, 30, 40, 50, 60, 70, 80, 90, 100, 110, 120, 130, 140, or 150 base pairs are deleted from a particular region. In another embodiment, the deletion is more than 150, 160, 170, 180, 190, 200, 250, or 300 base pairs within a particular region of the Ad genome. These deletions are such that expression and/or function of the gene product encoded by the region is prevented. Thus deletions encompass deletions within exons encoding portions of proteins as well as deletions within promoter and leader sequences. In a further embodiment, "deleted" in a particular region of the Ad genome refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

In certain embodiments, the adenovirus vectors contemplated for use include E2b deleted adenovirus vectors that have a deletion in the E2b region of the Ad genome and, optionally, the E1 region. In some cases, such vectors do not have any other regions of the Ad genome deleted.

In another embodiment, the adenovirus vectors contemplated for use include E2b deleted adenovirus vectors that have a deletion in the E2b region of the Ad genome and, optionally, deletions in the E1 and E3 regions. In some cases, such vectors have no other regions deleted.

In a further embodiment, the adenovirus vectors contemplated for use include adenovirus vectors that have a deletion in the E2b region of the Ad genome and, optionally, deletions in the E1, E3 and, also optionally, partial or complete removal of the E4 regions. In some cases, such vectors have no other deletions.

In another embodiment, the adenovirus vectors contemplated for use include adenovirus vectors that have a deletion in the E2b region of the Ad genome and, optionally, deletions in the E1 and/or E4 regions. In some cases, such vectors contain no other deletions.

In an additional embodiment, the adenovirus vectors contemplated for use include adenovirus vectors that have a deletion in the E2a, E2b and/or E4 regions of the Ad genome. In some cases, such vectors have no other deletions.

In one embodiment, the adenovirus vectors for use herein comprise vectors having the E1 and/or DNA polymerase functions of the E2b region deleted. In some cases, such vectors have no other deletions.

In a further embodiment, the adenovirus vectors for use herein have the E1 and/or the preterminal protein functions of the E2b region deleted. In some cases, such vectors have no other deletions.

In another embodiment, the adenovirus vectors for use herein have the E1, DNA polymerase and/or the preterminal protein functions deleted. In some cases, such vectors have no other deletions. In one particular embodiment, the adenovirus vectors contemplated for use herein are deleted for at least a portion of the E2b region and/or the E1 region.

In some cases, such vectors are not "gutted" adenovirus vectors. In this regard, the vectors may be deleted for both the DNA polymerase and the preterminal protein functions of the E2b region. In an additional embodiment, the adenovirus vectors for use include adenovirus vectors that have a deletion in the E1, E2b and/or 100K regions of the adenovirus genome. In certain embodiments, the adenovirus vector may be a "gutted" adenovirus vector.

In one embodiment, the adenovirus vectors for use herein comprise vectors having the E1, E2b and/or protease functions deleted. In some cases, such vectors have no other deletions.

In a further embodiment, the adenovirus vectors for use herein have the E1 and/or the E2b regions deleted, while the fiber genes have been modified by mutation or other alterations (e.g., to alter Ad tropism). Removal of genes from the E3 or E4 regions may be added to any of the mentioned adenovirus vectors.

The deleted adenovirus vectors can be generated using recombinant techniques known in the art (see e.g., Amalfitano, et al. J. Virol. 1998; 72:926-33; Hodges, et al. J Gene Med 2000; 2:250-59). As would be recognized by a skilled artisan, the adenovirus vectors for use in certain aspects can be successfully grown to high titers using an appropriate packaging cell line that constitutively expresses E2b gene products and products of any of the necessary genes that may have been deleted. In certain embodiments, HEK-293-derived cells that not only constitutively express the E1 and DNA polymerase proteins, but also the Ad-preterminal protein, can be used. In one embodiment, E.C7 cells are used to successfully grow high titer stocks of the adenovirus vectors (see e.g., Amalfitano, et al. J. Virol. 1998; 72:926-33; Hodges, et al. J Gene Med 2000; 2:250-59).

In order to delete critical genes from self-propagating adenovirus vectors, the proteins encoded by the targeted genes may be coexpressed in HEK-293 cells, or similar, along with the E1 proteins. Therefore, only those proteins which are non-toxic when coexpressed constitutively (or toxic proteins inducibly-expressed) can be utilized. Coexpression in HEK-293 cells of the E1 and E4 genes has been demonstrated (utilizing inducible, not constitutive, promoters) (Yeh, et al. J. Virol. 1996; 70:559; Wang et al. Gene Therapy 1995; 2:775; and Gorziglia, et al. J. Virol. 1996; 70:4173). The E1 and protein IX genes (a virion structural protein) have been coexpressed (Caravokyri, et al. J. Virol. 1995; 69: 6627), and coexpression of the E1, E4, and protein IX genes has also been described (Krougliak, et al. Hum. Gene Ther. 1995; 6:1575). The E1 and 100 k genes have been successfully expressed in transcomplementing cell lines, as have E1 and protease genes (Oualikene, et al. Hum Gene Ther 2000; 11:1341-53; Hodges, et al. J. Virol 2001; 75:5913-20).

Cell lines coexpressing E1 and E2b gene products for use in growing high titers of E2b deleted Ad particles are described in U.S. Pat. No. 6,063,622. The E2b region encodes the viral replication proteins which are absolutely required for Ad genome replication (Doerfler, et al. Chromosoma 1992; 102:S39-S45). Useful cell lines constitutively express the approximately 140 kDa Ad-DNA polymerase and/or the approximately 90 kDa preterminal protein. In particular, cell lines that have high-level, constitutive coexpression of the E1, DNA polymerase, and preterminal proteins, without toxicity (e.g., E.C7), are desirable for use in propagating Ad for use in multiple vaccinations. These cell lines permit the propagation of adenovirus vectors deleted for the E1, DNA polymerase, and preterminal proteins.

Certain embodiments use the new Ad5 [E1−, E2b−] vector system to deliver a long sought-after need for the development of a therapeutic vaccine for various cancers, overcome barriers found with other Ad5 systems and permit the immunization of people who have previously been exposed to Ad5.

The innate immune response to wild type Ad can be complex, and it appears that Ad proteins expressed from adenovirus vectors play an important role. Specifically, the deletions of pre-terminal protein and DNA polymerase in the E2b deleted vectors appear to reduce inflammation during the first 24 to 72 h following injection, whereas First Generation adenovirus vectors stimulate inflammation during this period. In addition, it has been reported that the additional replication block created by E2b deletion also leads to a 10,000-fold reduction in expression of Ad late genes, well beyond that afforded by E1, E3 deletions alone First generation vectors can have reduced efficacy due to Ad-specific neutralizing antibodies. Without being bound by theory, Ad5-based vectors with deletions of the E1 and the E2b regions (Ad5 [E1−, E2b−]), the latter encoding the DNA polymerase and the pre-terminal protein, for example by virtue of diminished late phase viral protein expression, may avoid immunological clearance and induce more potent immune responses against the encoded tumor antigen transgene in Ad-immune hosts.

Some embodiments relate to methods and compositions (e.g., viral vectors) for generating immune responses against target antigens, in particular, those associated or related to infectious disease or proliferative cell disease such as cancer. Some embodiments relate to methods and compositions for generating immune responses in an individual against target antigens, in particular, those related to cell proliferation diseases such as cancer. In some embodiments, compositions and methods described herein relate to generating an immune response in an individual against cells expressing and/or presenting a target antigen or a target antigen signature comprising at least one target antigen.

The compositions and methods can be used to generate an immune response against a target antigen expressed and/or presented by a cell. For example, the compositions and methods can be used to generate immune responses against a HER2 or HER3 protein expressed or presented by a cell. For example, the compositions and methods can be used to generate an immune response against CEA(6D) expressed or presented by a cell. For example, the compositions and methods can be used to generate an immune response against Mucin 1 (MUC1) expressed and/or presented by a cell. For example, the compositions and methods can be used to generate an immune response against MUC1c expressed and/or presented by a cell. For example, the compositions and methods can be used to generate an immune response against Brachyury (T protein (T)) expressed and/or presented by a cell.

The compositions and methods can be used to generate an immune response against multiple target antigens expressed and/or presented by a cell. For example, the compositions and methods can be used to generate an immune response against HER3.

A modified form of HER3 can be used in a vaccine directed to raising an immune response against HER3 or cells expressing and/or presenting HER2 or HER3. In particular, some embodiments provide an improved Ad-based vaccine such that multiple vaccinations against one or more antigenic target entity can be achieved. In some embodiments, the improved Ad-based vaccine comprises a replication defective adenovirus carrying a target antigen, a fragment, a variant or a variant fragment thereof, such as Ad5 [E1−, E2b−]-HER3 or Ad5 [E1−, E2b−]-truncatedHER3. Variants or fragments of target antigens, such as HER3, can be selected based on a variety of factors, including immunogenic potential. Importantly, vaccination can be performed in the presence of preexisting immunity to the Ad or administered to subjects previously immunized multiple times with the Ad vector as described herein or other Ad vectors. The Ad vectors can be administered to subjects multiple times to induce an immune response against an antigen of interest, such as HER, including but not limited to, the production of antibodies and CMI responses against one or more target antigens.

The recombinant Ad can be propagated using techniques known in the art. For example, in certain embodiments, tissue culture plates containing E.C7 cells are infected with the adenovirus vector virus stocks at an appropriate MOI (e.g., 5) and incubated at 37.0° C. for 40-96 h. The infected cells are harvested, resuspended in 10 mM Tris-CI (pH 8.0), and sonicated, and the virus is purified by two rounds of cesium chloride density centrifugation. In certain techniques, the virus containing band is desalted over a Sephadex CL-6B column (Pharmacia Biotech, Piscataway, N.J.), sucrose or glycerol is added, and aliquots are stored at −80° C. In some embodiments, the virus is placed in a solution designed to enhance its stability, such as A195 (Evans, et al. J Pharm Sci 2004; 93:2458-75). The titer of the stock is measured (e.g., by measurement of the optical density at 260 nm of an aliquot of the virus after SDS lysis). In another embodiment, plasmid DNA, either linear or circular, encompassing the entire recombinant E2b deleted adenovirus vector can be transfected into E.C7, or similar cells, and incubated at 37.0° C. until evidence of viral production is present (e.g., the cytopathic effect). The conditioned media from these cells can then be used to infect more E.C7, or similar cells, to expand the amount of virus produced, before purification. Purification can be accomplished by two rounds of cesium chloride density centrifugation or selective filtration. In certain embodiments, the virus may be purified by column chromatography, using commercially available products (e.g., Adenopure from Puresyn, Inc., Malvem, Pa.) or custom made chromatographic columns.

In certain embodiments, the recombinant adenovirus vector may comprise enough of the virus to ensure that the cells to be infected are confronted with a certain number of viruses. Thus, there may be provided a stock of recombinant Ad, particularly an RCA-free stock of recombinant Ad. The preparation and analysis of Ad stocks can use any methods available in the art. Viral stocks vary considerably in titer, depending largely on viral genotype and the protocol and cell lines used to prepare them. The viral stocks can have a titer of at least about $10^6$, $10^7$, or $10^8$ virus particles (VPs)/ml, and many such stocks can have higher titers, such as at least about $10^9$, $10^{10}$, $10^{11}$, or $10^{12}$ VPs/ml.

Certain aspects contemplate the use of E2b deleted adenovirus vectors, such as those described in U.S. Pat. Nos. 6,063,622; 6,451,596; 6,057,158; 6,083,750; and 8,298,549. The vectors with deletions in the E2b regions in many cases cripple viral protein expression and/or decrease the frequency of generating replication competent Ad (RCA).

Propagation of these E2b deleted adenovirus vectors can be done utilizing cell lines that express the deleted E2b gene products. Certain aspects also provide such packaging cell lines; for example E.C7 (formally called C-7), derived from the HEK-293 cell line.

In further aspects, the E2b gene products, DNA polymerase and preterminal protein, can be constitutively expressed in E.C7, or similar cells along with the E1 gene products. Transfer of gene segments from the Ad genome to the production cell line has immediate benefits: (1) increased carrying capacity; and, (2) a decreased potential of RCA generation, typically requiring two or more independent recombination events to generate RCA. The E1, Ad DNA polymerase and/or preterminal protein expressing cell lines used herein can enable the propagation of adenovirus vectors with a carrying capacity approaching 13 kb, without the need for a contaminating helper virus. In addition, when genes critical to the viral life cycle are deleted (e.g., the E2b genes), a further crippling of Ad to replicate or express other viral gene proteins occurs. This can decrease immune recognition of virally infected cells, and allow for extended durations of foreign transgene expression.

E1, DNA polymerase, and preterminal protein deleted vectors are typically unable to express the respective proteins from the E1 and E2b regions. Further, they may show a lack of expression of most of the viral structural proteins. For example, the major late promoter (MLP) of Ad is responsible for transcription of the late structural proteins L1 through L5. Though the MLP is minimally active prior to Ad genome replication, the highly toxic Ad late genes are primarily transcribed and translated from the MLP only after viral genome replication has occurred. This cis-dependent activation of late gene transcription is a feature of DNA viruses in general, such as in the growth of polyoma and SV-40. The DNA polymerase and preterminal proteins are important for Ad replication (unlike the E4 or protein IX proteins). Their deletion can be extremely detrimental to adenovirus vector late gene expression, and the toxic effects of that expression in cells such as APCs.E1-deleted adenovirus vectors Certain aspects contemplate the use of E1-deleted adenovirus vectors. First generation, or E1-deleted adenovirus vectors Ad5 [E1-] are constructed such that a transgene replaces only the E1 region of genes. Typically, about 90% of the wild-type Ad5 genome is retained in the vector. Ad5 [E1-] vectors have a decreased ability to replicate and cannot produce infectious virus after infection of cells not expressing the Ad5 E1 genes. The recombinant Ad5 [E1-] vectors are propagated in human cells (typically 293 cells) allowing for Ad5 [E1-] vector replication and packaging. Ad5 [E1-] vectors have a number of positive attributes; one of the most important is their relative ease for scale up and cGMP production. Currently, well over 220 human clinical trials utilize Ad5 [E1-] vectors, with more than two thousand subjects given the virus sc, im, or iv.

Additionally, Ad5 vectors do not integrate; their genomes remain episomal. Generally, for vectors that do not integrate into the host genome, the risk for insertional mutagenesis and/or germ-line transmission is extremely low if at all. Conventional Ad5 [E1-] vectors have a carrying capacity that approaches 7 kb.

Studies in humans and animals have demonstrated that pre-existing immunity against Ad5 can be an inhibitory factor to commercial use of Ad-based vaccines. The preponderance of humans have antibody against Ad5, the most widely used subtype for human vaccines, with two-thirds of humans studied having lympho-proliferative responses against Ad5. This pre-existing immunity can inhibit immunization or re-immunization using typical Ad5 vaccines and may preclude the immunization of a vaccine against a second antigen, using an Ad5 vector, at a later time. Overcoming the problem of pre-existing anti-vector immunity has been a subject of intense investigation. Investigations using alternative human (non-Ad5 based) Ad5 subtypes or even non-human forms of Ad5 have been examined. Even if these approaches succeed in an initial immunization, subsequent vaccinations may be problematic due to immune responses to the novel Ad5 subtype.

To avoid the Ad5 immunization barrier, and improve upon the limited efficacy of first generation Ad5 [E1-] vectors to induce optimal immune responses, there are provided certain embodiments related to a next generation Ad5 vector based vaccine platform. The next generation Ad5 platform has additional deletions in the E2b region, removing the DNA polymerase and the preterminal protein genes. The Ad5 [E1-, E2b-] platform has an expanded cloning capacity that is sufficient to allow inclusion of many possible genes. Ad5 [E1-, E2b-] vectors have up to about 12 kb gene-carrying capacity as compared to the 7 kb capacity of Ad5 [E1-] vectors, providing space for multiple genes if needed. In some embodiments, an insert of more than 1, 2, 3, 4, 5, 6, 7, 8, 9, 10, or 11 kb is introduced into an Ad5 vector, such as the Ad5 [E1-, E2b-] vector.

Deletion of the E2b region may confer advantageous immune properties on the Ad5 vectors, often eliciting potent immune responses to target transgene antigens, such as antigens or epitopes of HER1, HER2/neu, HER3, HER4, or any combination thereof, while minimizing the immune responses to Ad viral proteins.

In various embodiments, Ad5 [E1-, E2b-] vectors may induce a potent CMI, as well as antibodies against the vector expressed target antigens, such as antigens or epitopes of HER1, HER2/neu, HER3, HER4, or any combination thereof, even in the presence of Ad immunity.

Ad5 [E1-, E2b-] vectors also have reduced adverse reactions as compared to Ad5 [E1-] vectors, in particular the appearance of hepatotoxicity and tissue damage.

Certain aspects of these Ad5 vectors are that expression of Ad late genes is greatly reduced. For example, production of the capsid fiber proteins could be detected in vivo for Ad5 [E1-] vectors, while fiber expression was ablated from Ad5 [E1-, E2b-] vector vaccines. The innate immune response to wild type Ad is complex. Proteins deleted from the Ad5 [E1-, E2b-] vectors generally play an important role. Specifically, Ad5 [E1-, E2b-] vectors with deletions of preterminal protein or DNA polymerase display reduced inflammation during the first 24 to 72 hours following injection compared to Ad5 [E1-] vectors. In various embodiments, the lack of Ad5 gene expression renders infected cells invisible to anti-Ad activity and permits infected cells to express the transgene for extended periods of time, which develops immunity to the target.

Various embodiments contemplate increasing the capability for the Ad5 [E1-, E2b-] vectors to transduce dendritic cells, improving antigen specific immune responses in the vaccine by taking advantage of the reduced inflammatory response against Ad5 [E1-, E2b-] vector viral proteins and the resulting evasion of pre-existing Ad immunity.

In some cases, this immune induction may take months. Ad5 [E1-, E2b-] vectors not only are safer than, but appear to be superior to Ad5 [E1-] vectors in regard to induction of antigen specific immune responses, making them much better suitable as a platform to deliver tumor vaccines that can result in a clinical response. In other cases, immune induction may take months.

In certain embodiments, methods and compositions are provided by taking advantage of an Ad5 [E1-, E2b-] vector system for developing a therapeutic tumor vaccine that overcomes barriers found with other Ad5 systems and permits the immunization of people who have previously been exposed to Ad5.

E2b deleted vectors may have up to a 13 kb gene-carrying capacity as compared to the 5 to 6 kb capacity of First Generation adenovirus vectors, easily providing space for nucleic acid sequences encoding any of a variety of target antigens, such as antigens or epitopes of HER1, HER2/neu, HER3, HER4, or any combination thereof.

The E2b deleted adenovirus vectors also have reduced adverse reactions as compared to First Generation adenovirus vectors. E2b deleted vectors have reduced expression of viral genes, and this characteristic leads to extended transgene expression in vivo.

Compared to first generation adenovirus vectors, certain embodiments of the Second Generation E2b deleted adenovirus vectors contain additional deletions in the DNA polymerase gene (pol) and deletions of the pre-terminal protein (pTP). E2b deleted vectors have up to a 13 kb gene-carrying capacity as compared to the 5 to 6 kb capacity of First Generation adenovirus vectors, easily providing space for nucleic acid sequences encoding any of a variety of target antigens. The E2b deleted adenovirus vectors also have reduced adverse reactions as compared to first generation adenovirus vectors.

It appears that Ad proteins expressed from adenovirus vectors play an important role. Specifically, the deletions of pre-terminal protein and DNA polymerase in the E2b deleted vectors appear to reduce inflammation during the first 24 to 72 hours following injection, whereas First Generation adenovirus vectors stimulate inflammation during this period.

In addition, it has been reported that the additional replication block created by E2b deletion also leads to a 10,000 fold reduction in expression of Ad late genes, well beyond that afforded by E1, E3 deletions alone. The decreased levels of Ad proteins produced by E2b deleted adenovirus vectors effectively reduce the potential for competitive, undesired, immune responses to Ad antigens, responses that prevent repeated use of the platform in Ad immunized or exposed individuals. The reduced induction of inflammatory response by second generation E2b deleted vectors results in increased potential for the vectors to express desired vaccine antigens.

The reduced induction of inflammatory response by second generation E2b deleted vectors results in increased potential for the vectors to express desired vaccine antigens, such as antigens or epitopes of HER1, HER2/neu, HER3, HER4, or any combination thereof, during the infection of antigen presenting cells (i.e., dendritic cells), decreasing the potential for antigenic competition, resulting in greater immunization of the vaccine to the desired antigen relative to identical attempts with First Generation adenovirus vectors.

E2b deleted adenovirus vectors provide an improved Ad-based vaccine candidate that is safer, more effective, and more versatile than previously described vaccine candidates using First Generation adenovirus vectors.

Thus, first generation, E1-deleted Adenovirus subtype 5 (Ad5)-based vectors, although promising platforms for use as vaccines, may be impeded in activity by naturally occurring or induced Ad-specific neutralizing antibodies.

Without being bound by theory, Ad5-based vectors with deletions of the E1 and the E2b regions (Ad5 [E1-, E2b-]), the latter encoding the DNA polymerase and the pre-terminal protein, for example by virtue of diminished late phase viral protein expression, may avoid immunological clearance and induce more potent immune responses against the encoded antigen transgene, such as antigens or epitopes of HER1, HER2/neu, HER3, HER4, or any combination thereof, in Ad-immune hosts.

The Ad vectors can comprise a product that can be detected or selected for, such as a reporter gene whose product can be detected, such as by fluorescence, enzyme activity on a chromogenic or fluorescent substrate, and the like, or selected for by growth conditions. Exemplary reporter genes include green fluorescent protein (GFP), β-galactosidase, chloramphenicol acetyltransferase (CAT), luciferase, neomycin phosphotransferase, secreted alkaline phosphatase (SEAP), and human growth hormone (HGH). Exemplary selectable markers include drug resistances, such as neomycin (G418), hygromycin, and the like.

The Ad vectors can also comprise a promoter or expression control sequence. The choice of the promoter will depend in part upon the targeted cell type and the degree or type of control desired. Promoters that are suitable include, without limitation, constitutive, inducible, tissue specific, cell type specific, temporal specific, or event-specific. Examples of constitutive or nonspecific promoters include the SV40 early promoter, the SV40 late promoter, CMV early gene promoter, bovine papilloma virus promoter, and adenovirus promoter. In addition to viral promoters, cellular promoters are also amenable and useful in some embodiments. In particular, cellular promoters for the so-called housekeeping genes are useful (e.g., β-actin). Viral promoters are generally stronger promoters than cellular promoters. Inducible promoters may also be used. These promoters include MMTV LTR, inducible by dexamethasone, metallothionein, inducible by heavy metals, and promoters with cAMP response elements, inducible by cAMP, heat shock promoter. By using an inducible promoter, the nucleic acid may be delivered to a cell and will remain quiescent until the addition of the inducer. This allows further control on the timing of production of the protein of interest. Event-type specific promoters (e.g., HIV LTR) can be used, which are active or upregulated only upon the occurrence of an event, such as tumorigenicity or viral infection, for example. The HIV LTR promoter is inactive unless the tat gene product is present, which occurs upon viral infection. Some event-type promoters are also tissue-specific. Preferred event-type specific promoters include promoters activated upon viral infection.

Examples of promoters include promoters for α-fetoprotein, α-actin, myo D, carcinoembryonic antigen, VEGF-receptor; FGF receptor; TEK or tie 2; tie; urokinase receptor; E- and P-selectins; VCAM-1; endoglin; endosialin; αV-β3 integrin; endothelin-1; ICAM-3; E9 antigen; von Willebrand factor; CD44; CD40; vascular-endothelial cadherin; notch 4, high molecular weight melanoma-associated antigen; prostate specific antigen-1, probasin, FGF receptor, VEGF receptor, erb B2; erb B3; erb B4; MUC-1; HSP-27; int-1; int-2, CEA, HBEGF receptor; EGF receptor; tyrosinase, MAGE, IL-2 receptor; prostatic acid phosphatase, probasin, prostate specific membrane antigen, α-crystallin, PDGF receptor, integrin receptor, α-actin, SM1 and SM2 myosin heavy chains, calponin-hl, SM22 α-angiotensin receptor, IL-1, IL-2, IL-3, IL-4, IL-5, IL-6, IL-7, IL-8, IL-9, IL-10, IL-11, IL-12, IL-13, IL-14, immunoglobulin heavy chain, immunoglobulin light chain, and CD4.

Repressor sequences, negative regulators, or tissue-specific silencers may be inserted to reduce non-specific expression of the polynucleotide. Multiple repressor elements may be inserted in the promoter region. Repression of transcription is independent of the orientation of repressor elements or distance from the promoter. One type of repressor sequence is an insulator sequence. Such sequences inhibit transcription and can silence background transcription. Negative regulatory elements can be located in the promoter regions of a number of different genes. The repressor element can function as a repressor of transcription in the absence of factors, such as steroids, as does the NSE in the promoter region of the ovalbumin gene. These negative regulatory elements can bind specific protein complexes from oviduct, none of which are sensitive to steroids. Three different elements are located in the promoter of the ovalbumin gene. In some embodiments, oligonucleotides corresponding to portions of these elements can repress viral transcription of the TK reporter. For example, one such silencer element is TCTCTCCNA (SEQ ID NO: 88), which has sequence identity with silencers that are present in other genes.

Elements that increase the expression of the desired target antigen can be incorporated into the nucleic acid sequence of the Ad vectors described herein. Exemplary elements include internal ribosome binding sites (IRESs). IRESs can increase translation efficiency. As well, other sequences may enhance expression. For some genes, sequences especially at the 5' end may inhibit transcription and/or translation. These sequences are usually palindromes that can form hairpin structures. In some cases, such sequences in the nucleic acid to be delivered are deleted. Expression levels of the transcript or translated product can be assayed to confirm or ascertain which sequences affect expression. Transcript levels may be assayed by any known method, including Northern blot hybridization, RNase probe protection and the like. Protein levels may be assayed by any known method, including ELISA.

Ad5 [E1−] vectors encoding a variety of antigens can be used to efficiently transduce 95% of ex vivo exposed DC's to high titers of the vector. In certain embodiments, increasing levels of foreign gene expression in the DC was found to correlate with increasing multiplicities of infection (MOI) with the vector. DCs infected with Ad5 [E1−] vectors can encode a variety of antigens (including the tumor antigens MART-1, MAGE-A4, DF3/MUC1, p53, hugp100 melanoma antigen, polyoma virus middle-T antigen) that have the propensity to induce antigen specific CTL responses, have an enhanced antigen presentation capacity, and/or have an improved ability to initiate T-cell proliferation in mixed lymphocyte reactions. Immunization of animals with dendritic cells (DCs) previously transduced by Ad5 vectors encoding tumor specific antigens can be used to induce significant levels of protection for the animals when challenged with tumor cells expressing the respective antigen. Interestingly, intra-tumoral injection of Ads encoding IL-7 is less effective than injection of DCs transduced with IL-7 encoding Ad5 vectors at inducing antitumor immunity. Ex vivo transduction of DCs by Ad5 vectors is contemplated in certain embodiments. Ex vivo DC transduction strategies can been used to induce recipient host tolerance. For example, Ad5 mediated delivery of the CTLA4Ig into DCs can block interactions of the DCs CD80 with CD28 molecules present on T-cells.

Ad5 vector capsid interactions with DCs may trigger several beneficial responses, which may be enhancing the propensity of DCs to present antigens encoded by Ad5 vectors. For example, immature DCs, though specialized in antigen uptake, are relatively inefficient effectors of T-cell activation. DC maturation coincides with the enhanced ability of DCs to drive T-cell immunity. In some instances, the compositions and methods take advantage of an Ad5 infection resulting in direct induction of DC maturation Ad vector infection of immature bone marrow derived DCs from mice may upregulate cell surface markers normally associated with DC maturation (MHC I and II, CD40, CD80, CD86, and ICAM-1) as well as down-regulation of CD11c, an integrin down regulated upon myeloid DC maturation. In some instances, Ad vector infection triggers IL-12 production by DCs, a marker of DC maturation. Without being bound by theory, these events may possibly be due to Ad5 triggered activation of NF-κB pathways. Mature DCs can be efficiently transduced by Ad vectors, and do not lose their functional potential to stimulate the proliferation of naive T-cells at lower MOI, as demonstrated by mature CD83+ human DC (derived from peripheral blood monocytes). However, mature DCs may also be less infectable than immature ones. Modification of capsid proteins can be used as a strategy to optimize infection of DC by Ad vectors, as well as enhancing functional maturation, for example using the CD40L receptor as a viral vector receptor, rather than using the normal CAR receptor infection mechanisms.

X. Heterologous Nucleic Acids

In some embodiments, vectors, such as adenovirus vectors, may comprise heterologous nucleic acid sequences that encode one or more tumor antigens such as antigens or epitopes of HER1, HER2/neu, HER3, HER4, or any combination thereof, fusions thereof or fragments thereof, which can modulate the immune response. In certain aspects, there may be provided a Second Generation E2b deleted adenovirus vectors that comprise a heterologous nucleic acid sequence encoding one or more tumor antigens such as antigens or epitopes of HER1, HER2/neu, HER3, HER4, or any combination thereof.

As such, there may be provided polynucleotides that encode antigens or epitopes of HER1, HER2/neu, HER3, HER4, or any combination thereof from any source as described further herein, vectors or constructs comprising such polynucleotides and host cells transformed or transfected with such vectors or expression constructs.

The terms "nucleic acid" and "polynucleotide" are used essentially interchangeably herein. Polynucleotides may be single-stranded (coding or antisense) or double-stranded, and may be DNA (e.g., genomic, cDNA, or synthetic) or RNA molecules. As will be also recognized by the skilled artisan, polynucleotides used herein may be single-stranded (coding or antisense) or double-stranded, and may be DNA (genomic, cDNA, or synthetic) or RNA molecules RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide as disclosed herein, and a polynucleotide may, but need not, be linked to other molecules and/or support materials. An isolated polynucleotide, as used herein, means that a polynucleotide is substantially away from other coding sequences. For example, an isolated DNA molecule as used herein does not contain large portions of unrelated coding DNA, such as large chromosomal fragments or other functional genes or polypeptide coding regions. Of course, this refers to the DNA molecule as originally isolated, and does not exclude genes or coding regions later added to the segment through recombination in the laboratory.

As will be understood by those skilled in the art, the polynucleotides can include genomic sequences, extra-genomic and plasmid-encoded sequences and smaller engineered gene segments that express, or may be adapted to express target antigens as described herein, fragments of antigens, peptides and the like. Such segments may be naturally isolated, or modified synthetically by the hand of man.

Polynucleotides may comprise a native sequence (i.e., an endogenous sequence that encodes one or more tumor antigens such as antigens or epitopes of HER1, HER2/neu, HER3, HER4, or any combination thereof or a portion thereof) or may comprise a sequence that encodes a variant or derivative of such a sequence. In certain embodiments, the polynucleotide sequences set forth herein encode one or more mutated tumor antigens such as antigens or epitopes of HER1, HER2/neu, HER3, HER4, or any combination thereof. In some embodiments, polynucleotides represent a novel gene sequence that has been optimized for expression in specific cell types (i.e., human cell lines) that may substantially vary from the native nucleotide sequence or variant but encode a similar protein antigen.

In other related embodiments, there may be provided polynucleotide variants having substantial identity to native sequences encoding one or more tumor antigens such as antigens or epitopes of HER1, HER2/neu, HER3, HER4, or any combination thereof, for example those comprising at least 60, 70, 80, 90, 95, 96, 97, 98, 99, 100% sequence identity (or any derivable range or value thereof), particularly at least 75% up to 99% or higher, sequence identity compared to a HER2/neu sequence set forth in SEQ ID NO: 1 (HER2 extracellular domain (ECD) and transmembrane domains (TM)), a HER1 sequence, a HER3 sequence as set forth in SEQ ID NO: 6 (HER3 extracellular and transmembrane domains), or a HER4 sequence, or any combination thereof. In some embodiments, a polynucleotide sequence encoding one or more tumor antigens such as antigens or epitopes of HER1, HER2/neu, HER3, HER4, or any combination thereof or an amino acid sequence with at least 60, 70, 80, 90, 95, 96, 97, 98, 99, 100% (or any derivable range or value thereof), particularly at least 75% up to 99% or higher sequence identity with SEQ ID NO: 2 or SEQ ID NO: 6 using the methods described herein (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the epitope of the polypeptide encoded by the variant polynucleotide or such that the immunogenicity of the heterologous target protein is not substantially diminished relative to a polypeptide encoded by the native polynucleotide sequence. In some cases, the one or more substitutions, additions, deletions and/or insertions may result in an increased immunogenicity of the epitope of the polypeptide encoded by the variant polynucleotide. As described elsewhere herein, the polynucleotide variants can encode a variant of the target antigen. As described elsewhere herein, the polynucleotide variants preferably encode a variant of one or more tumor antigens such as antigens or epitopes of HER1, HER2/neu, HER3, HER4, or any combination thereof, or a fragment (e.g., an epitope) thereof wherein the propensity of the variant polypeptide or fragment (e.g., epitope) thereof to react with antigen-specific antisera and/or T-cell lines or clones is not substantially diminished relative to the native polypeptide. The polynucleotide variants can encode a variant of the target antigen, or a fragment thereof wherein the propensity of the variant polypeptide or fragment thereof to react with antigen-specific antisera and/or T-cell lines or clones is substantially increased relative to the native polypeptide.

The term "variants" should also be understood to encompass homologous genes of xenogenic origin. In particular embodiments, variants or fragments of target antigens are modified such that they have one or more reduced biological activities. For example, an oncogenic protein target antigen may be modified to reduce or eliminate the oncogenic activity of the protein, or a viral protein may be modified to reduce or eliminate one or more activities or the viral protein. An example of a modified HER3 protein is a truncated HER3 protein having just the transmembrane and extracellular domains, resulting in a variant protein with increased immunogenicity.

In certain aspects, there may be provided polynucleotides that comprise or consist of at least about 5 up to a 1000 or more contiguous nucleotides encoding a polypeptide, including target protein antigens, as described herein, as well as all intermediate lengths there between. It will be readily understood that "intermediate lengths," in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence as described herein may be extended at one or both ends by additional nucleotides not found in the native sequence encoding a polypeptide as described herein, such as an epitope or heterologous target protein. This additional sequence may consist of 1 up 20 nucleotides or more, at either end of the disclosed sequence or at both ends of the disclosed sequence.

The polynucleotides or fragments thereof, regardless of the length of the coding sequence itself, may be combined with other DNA sequences, such as promoters, expression control sequences, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 1000, 2000, 3000, 4000, 5000, 6000, 7000, 8000, 9000, 10,000, about 500, about 200, about 100, about 50 base pairs in length, and the like, (including all intermediate lengths) are contemplated to be useful in certain aspects.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff M O (1978) A model of evolutionary change in proteins—Matrices for detecting distant relationships. In Dayhoff M O (ed.) Atlas of Protein Sequence and Structure, National Biomedical Research Foundation, Washington D.C. Vol. 5, Suppl. 3, pp. 345-358; Hein J Unified Approach to Alignment and Phylogenes, pp. 626-645 (1990); Methods in Enzymology vol. 183, Academic Press, Inc., San Diego, Calif.; Higgins, et al. PM CABIOS 1989; 5:151-53; Myers E W, et al. CABIOS 1988; 4:11-17; Robinson ED Comb. Theor 1971; 11A 05; Saitou N, et al. Mol. Biol. Evol. 1987; 4:406-25; Sneath P H A and Sokal R R Numerical Taxonomy—the Principles and Practice of Numerical Taxonomy, Freeman Press, San Francisco, Calif. (1973); Wilbur W J, et al. Proc. Natl. Acad., Sci. USA 1983 80:726-30).

Alternatively, optimal alignment of sequences for comparison may be conducted by the local identity algorithm of Smith, et al. Add. APL. Math 1981; 2:482, by the identity alignment algorithm of Needleman, et al. Mol. Biol. 1970 48:443, by the search for similarity methods of Pearson and Lipman, Proc. Natl. Acad. Sci. USA 1988; 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, W1), or by inspection.

One example of algorithms that are suitable for determining percent sequence identity and sequence similarity are the BLAST and BLAST 2.0 algorithms, which are described in Altschul et al., Nucl. Acids Res. 1977 25:3389-3402, and Altschul et al. J. Mol. Biol. 1990 215:403-10, respectively. BLAST and BLAST 2.0 can be used, for example with the parameters described herein, to determine percent sequence identity for the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff, et al. Proc. Natl. Acad. Sci. USA 1989; 89:10915) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It is appreciated by those of ordinary skill in the art that, as a result of the degeneracy of the genetic code, there are many nucleotide sequences that encode a particular antigen of interest, or fragment thereof, as described herein. Some of these polynucleotides bear minimal homology to the nucleotide sequence of any native gene. Nonetheless, polynucleotides that vary due to differences in codon usage are specifically contemplated.

Further, alleles of the genes comprising the polynucleotide sequences provided herein may also be contemplated. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment, a mutagenesis approach, such as site-specific mutagenesis, is employed for the preparation of variants and/or derivatives of nucleic acid sequences encoding one or more tumor antigens such as antigens or epitopes of HER1, HER2/neu, HER3, HER4, or any combination thereof, or fragments thereof, as described herein. By this approach, specific modifications in a polypeptide sequence can be made through mutagenesis of the underlying polynucleotides that encode them. These techniques provide a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

Polynucleotide segments or fragments encoding the polypeptides may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology (see for example, Current Protocols in Molecular Biology, John Wiley and Sons, NY, N.Y.).

In order to express a desired tumor antigen such as antigens or epitopes of HER1, HER2/neu, HER3, HER4, or any combination thereof, polypeptide or fragment thereof, or fusion protein comprising any of the above, as described herein, the nucleotide sequences encoding the polypeptide, or functional equivalents, are inserted into an appropriate vector such as a replication-defective adenovirus vector as described herein using recombinant techniques known in the art. The appropriate vector contains the necessary elements for the transcription and translation of the inserted coding sequence and any desired linkers.

Methods that are available to those skilled in the art may be used to construct these vectors containing sequences encoding one or more tumor antigens such as antigens or epitopes of HER1, HER2/neu, HER3, HER4, or any combination thereof and appropriate transcriptional and translational control elements. These methods include in vitro recombinant DNA techniques, synthetic techniques, and in vivo genetic recombination. Such techniques are described, for example, in Amalfitano, et al. J. Virol. 1998; 72:926-33; Hodges, et al. J Gene Med 2000; 2:250-259; Sambrook J, et al. (1989) Molecular Cloning, A Laboratory Manual, Cold Spring Harbor Press, Plainview, N.Y., and Ausubel F M, et al. (1989) Current Protocols in Molecular Biology, John Wiley & Sons, New York. N.Y.

A variety of vector/host systems may be utilized to contain and produce polynucleotide sequences. These include, but are not limited to, microorganisms such as bacteria transformed with recombinant bacteriophage, plasmid, or cosmid DNA vectors; yeast transformed with yeast vectors; insect cell systems infected with virus vectors (e.g., baculovirus); plant cell systems transformed with virus vectors (e.g., cauliflower mosaic virus, CaMV; tobacco mosaic virus, TMV) or with bacterial vectors (e.g., Ti or pBR322 plasmids); or animal cell systems.

The "control elements" or "regulatory sequences" present in a vector, such as an adenovirus vector, are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, sequences encoding one or more tumor antigens such as antigens or epitopes of HER1, HER2/neu, HER3, HER4, or any combination thereof may be ligated into an Ad transcription/translation complex consisting of the late promoter and tripartite leader sequence. Insertion in a non-essential E1 or E3 region of the viral genome may be used to obtain a viable virus that is capable of expressing the polypeptide in infected host cells (Logan J, et al. Proc. Natl. Acad. Sci 1984; 87:3655-59). In addition, transcription enhancers, such as the Rous sarcoma virus (RSV) enhancer, may be used to increase expression in mammalian host cells.

Specific initiation signals may also be used to achieve more efficient translation of sequences encoding one or more tumor antigens such as antigens or epitopes of HER1, HER2/neu, HER3, HER4, or any combination thereof. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers that are appropriate for the particular cell system which is used, such as those described in the literature (Scharf D., et al. Results Probl. Cell Differ. 1994; 20:125-62). Specific termination sequences, either for transcription or translation, may also be incorporated in order to achieve efficient translation of the sequence encoding the polypeptide of choice.

A variety of protocols for detecting and measuring the expression of polynucleotide-encoded products (e.g., one or more tumor antigens such as antigens or epitopes of HER1, HER2/neu, HER3, HER4, or any combination thereof, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton R et al. (1990; Serological Methods, a Laboratory Manual, APS Press, St Paul. Minn.) and Maddox D E, et al. J. Exp. Med. 1983; 758:1211-16).

In certain embodiments, elements that increase the expression of the desired tumor antigens such as antigens or epitopes of HER1, HER2/neu, HER3, HER4, or any combination thereof may be incorporated into the nucleic acid sequence of expression constructs or vectors such as adenovirus vectors described herein. Such elements include internal ribosome binding sites (IRES; Wang, et al. Curr. Top. Microbiol. Immunol 1995; 203:99; Ehrenfeld, et al. Curr. Top. Microbiol. Immunol. 1995; 203:65; Rees, et al. Biotechniques 1996; 20:102; Sugimoto, et al. Biotechnology 1994; 2:694). Internal ribosome entry site (IRES) increases translation efficiency. As well, other sequences may enhance expression. For some genes, sequences especially at the 5' end inhibit transcription and/or translation. These sequences are usually palindromes that can form hairpin structures. Any such sequences in the nucleic acid to be delivered are generally deleted. Expression levels of the transcript or translated product are assayed to confirm or ascertain which sequences affect expression. Transcript levels may be assayed by any known method, including Northern blot hybridization, RNase probe protection and the like. Protein levels may be assayed by any known method, including ELISA.

As would be recognized by a skilled artisan, vectors, such as adenovirus vectors described herein, that comprise heterologous nucleic acid sequences can be generated using recombinant techniques known in the art, such as those described in Maione, et al. Proc Natl Acad Sci USA 2001; 98:5986-91; Maione, et al. Hum Gene Ther 2000 1:859-68; Sandig, et al. Proc Natl Acad Sci USA, 2000; 97:1002-07; Harui, et al. Gene Therapy 2004; 11:1617-26; Parks et al. Proc Natl Acad Sci USA 1996; 93:13565-570; DelloRusso, et al. Proc Natl Acad Sci USA 2002; 99:12979-984; Current Protocols in Molecular Biology, John Wiley and Sons, NY, N.Y.).

XI. Pharmaceutical Compositions

In certain aspects, there may be provided pharmaceutical compositions that comprise nucleic acid sequences encoding one or more one or more tumor antigens such as antigens or epitopes of HER1, HER2/neu, HER3, HER/1, or any combination thereof against which au immune response is to be generated. For example, tumor antigens may include, but are not limited to, antigens or epitopes of HER1, HER2/neu, HER3, HER4, or any combination thereof or in combination with one or more additional tumor antigens as described herein or available in the art.

For example, the adenovirus vector stock described herein may be combined with an appropriate buffer, physiologically acceptable carrier, excipient or the like. In certain embodiments, an appropriate number of adenovirus vector particles are administered in an appropriate buffer, such as, sterile PBS. In certain circumstances it will be desirable to deliver the adenovirus vector compositions disclosed herein parenterally, intravenously, intramuscularly, or even intraperitoneally.

In certain embodiments, solutions of the pharmaceutical compositions as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. In other embodiments, E2b deleted adenovirus vectors may be delivered in pill form, delivered by swallowing or by suppository.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria, molds and fungi.

The carrier can be a solvent or dispersion medium containing, for example, water, lipids, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution may be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biology standards.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

Routes and frequency of administration of the therapeutic compositions described herein, as well as dosage, will vary from individual to individual, and from disease to disease, and may be readily established using standard techniques. In general, the pharmaceutical compositions and vaccines may be administered by injection (e.g., intracutaneous, intramuscular, intravenous or subcutaneous), intranasally (e.g., by aspiration), in pill form (e.g., swallowing, suppository for vaginal or rectal delivery). In certain embodiments, between 1 and 3 doses may be administered over a 6 week period and further booster vaccinations may be given periodically thereafter.

For example, a suitable dose is an amount of an adenovirus vector that, when administered as described above, is capable of promoting a target antigen immune response as described elsewhere herein. In certain embodiments, the immune response is at least 10-50% above the basal (i.e., untreated) level. Such response can be monitored by measuring the antibodies against the target antigen in a patient or by vaccine-dependent generation of cytolytic effector cells capable of killing the target antigen-expressing cells in vitro, or other methods known in the art for monitoring immune responses. The target antigen is antigens or epitopes of HER1, HER2/neu, HER3, HER4, or any combination thereof, as described herein In general, an appropriate dosage and treatment regimen provides the adenovirus vectors in an amount sufficient to provide prophylactic benefit. Protective immune responses may generally be evaluated using standard proliferation, cytotoxicity or cytokine assays, which may be performed using samples obtained from a patient before and after immunization (vaccination).

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

While one advantage of compositions and methods described herein is the capability to administer multiple vaccinations with the same adenovirus vectors, particularly in individuals with preexisting immunity to Ad, the adenoviral vaccines described herein may also be administered as part of a prime and boost regimen. A mixed modality priming and booster inoculation scheme may result in an enhanced immune response. Thus, one aspect is a method of priming a subject with a plasmid vaccine, such as a plasmid vector comprising nucleic acid sequences encoding one or more tumor antigens such as antigens or epitopes of HER1, HER2/neu, HER3, HER4, or any combination thereof, by administering the plasmid vaccine at least one time, allowing a predetermined length of time to pass, and then boosting by administering the adenovirus vector described herein.

Multiple primings, e.g., 1-3, may be employed, although more may be used. The length of time between priming and boost may typically vary from about six months to a year, but other time frames may be used.

In certain embodiments, pharmaceutical compositions may comprise, for example, at least about 0.1% of therapeutic agents, such as the expression constructs or vectors used herein as vaccine, a related lipid nanovesicle, or an exosome or nanovesicle loaded with therapeutic agents. In other embodiments, the therapeutic agent may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 microgram/kg/body weight to about 100 mg/kg/body weight, about 5 microgram/kg/body weight to about 500 milligram/kg/body weight, etc., can be administered.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

In certain aspects, compositions comprising a vaccination regime as described herein can be administered either alone or together with a pharmaceutically acceptable carrier or excipient, by any routes, and such administration can be carried out in both single and multiple dosages. More particularly, the pharmaceutical composition can be combined with various pharmaceutically acceptable inert carriers in the form of tablets, capsules, lozenges, troches, hand candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. The compositions described throughout can be formulated into a pharmaceutical medicament and be used to treat a human or mammal, in need thereof, diagnosed with a disease, e.g., cancer, or to enhances an immune response.

In certain embodiments, the viral vectors or compositions described herein may be administered in conjunction with one or more immunostimulants, such as an adjuvant. An immunostimulant refers to essentially any substance that enhances or potentiates an immune response (antibody and/or cell-mediated) to an antigen. One type of immunostimulant comprises an adjuvant. Many adjuvants contain a substance designed to protect the antigen from rapid catabolism, such as aluminum hydroxide or mineral oil, and a stimulator of immune responses, such as lipid A, Bortadella pertussis or *Mycobacterium tuberculosis* derived proteins. Certain adjuvants are commercially available as, for example, Freund's Incomplete Adjuvant and Complete Adjuvant (Difco Laboratories); Merck Adjuvant 65 (Merck and Company, Inc.) AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, IFN-$\gamma$, TNF$\alpha$, IL-2, IL-8, IL-12, IL-18, IL-7, IL-3, IL-4, IL-5, IL-6, IL-9, IL-10, IL-13, IL-15, IL-16, IL-17, IL-23, and/or IL-32, and others, like growth factors, may also be used as adjuvants.

Within certain embodiments, the adjuvant composition can be one that induces an immune response predominantly of the Th1 type. High levels of Th1-type cytokines (e.g., IFN-$\gamma$, TNF$\alpha$, IL-2, and IL-12) tend to favor the induction of cell mediated immune responses to an administered antigen. In contrast, high levels of Th2-type cytokines (e.g., IL-4, IL-5, IL-6, and IL-10) tend to favor the induction of humoral immune responses. Following application of a vaccine as provided herein, a patient may support an immune response that includes Th1- and/or Th2-type responses. Within certain embodiments, in which a response is predominantly Th1-type, the level of Th1-type cytokines will increase to a greater extent than the level of Th2-type cytokines. The levels of these cytokines may be readily assessed using standard assays. Thus, various embodiments relate to therapies raising an immune response against a target antigen, for example antigens or epitopes of HER1, HER2/neu, HER3, HER4, or any combination thereof, using cytokines, e.g., IFN-$\gamma$, TNF$\alpha$, IL-2, IL-8, IL-12, IL-18, IL-7, IL-3, IL-4, IL-5, IL-6, IL-9, IL-10, IL-13, IL-15, IL-16, IL-17, IL-23, and/or IL-32 supplied concurrently with a replication defective viral vector treatment. In some embodiments, a cytokine or a nucleic acid encoding a cytokine, is administered together with a replication defective viral described herein. In some embodiments, cytokine administration is performed prior or subsequent to viral vector administration. In some embodiments, a replication defective viral vector capable of raising an immune response against a target antigen, for example antigens or epitopes of HER1, HER2/neu, HER3, HER4, or any combination thereof, further comprises a sequence encoding a cytokine.

Certain illustrative adjuvants for eliciting a predominantly Th1-type response include, for example, a combination of monophosphoryl lipid A, such as 3-de-O-acylated monophosphoryl lipid A, together with an aluminum salt. MPL® adjuvants are commercially available (see, e.g., U.S. Pat. Nos. 4,436,727; 4,877,611; 4,866,034 and 4,912,094). CpG-containing oligonucleotides (in which the CpG dinucleotide is unmethylated) also induce a predominantly Th1 response. (see, e.g., WO 96/02555, WO 99/33488 and U.S. Pat. Nos. 6,008,200 and 5,856,462). Immunostimulatory DNA sequences can also be used.

Another adjuvant for use in some embodiments comprises a saponin, such as Quil A, or derivatives thereof, including QS21 and QS7 (Aquila Biopharmaceuticals Inc.), Escin; Digitonin; or Gypsophila or Chenopodium quinoa saponins. Other formulations may include more than one saponin in the adjuvant combinations, e.g., combinations of at least two of the following group comprising QS21, QS7, Quil A, β-escin, or digitonin.

In some embodiments, the compositions may be delivered by intranasal sprays, inhalation, and/or other aerosol delivery vehicles. The delivery of drugs using intranasal microparticle resins and lysophosphatidyl-glycerol compounds can be employed (see, e.g., U.S. Pat. No. 5,725,871). Likewise, illustrative transmucosal drug delivery in the form of a polytetrafluoroetheylene support matrix can be employed (see, e.g., U.S. Pat. No. 5,780,045).

Liposomes, nanocapsules, microparticles, lipid particles, vesicles, and the like, can be used for the introduction of the compositions as described herein into suitable hot cells/organisms. Compositions as described herein may be formulated for delivery either encapsulated in a lipid particle, a liposome, a vesicle, a nanosphere, or a nanoparticle or the like. Alternatively, compositions as described herein can be bound, either covalently or non-covalently, to the surface of such carrier vehicles. Liposomes can be used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery. In some embodiments, liposomes are formed from phospholipids dispersed in an aqueous medium and spontaneously form multilamellar concentric bilayer vesicles (i.e., multilamellar vesicles (MLVs)).

In some embodiments, there are provided pharmaceutically-acceptable nanocapsule formulations of the compositions or vectors as described herein. Nanocapsules can generally entrap pharmaceutical compositions in a stable and reproducible way. To avoid side effects due to intracellular polymeric overloading, such ultrafine particles (sized around 0.1 μm) may be designed using polymers able to be degraded in vivo.

In certain aspects, a pharmaceutical composition comprising IL-15 may be administered to an individual in need thereof, in combination with one or more therapy provided herein, particularly one or more adenoviral vectors comprising nucleic acid sequences encoding one or more target antigens such as antigens or epitopes of HER1, HER2/neu, HER3, HER4, or any combination thereof.

Interleukin 15 (IL-15) is a cytokine with structural similarity to IL-2. Like IL-2, IL-15 binds to and signals through a complex composed of IL-2/IL-15 receptor beta chain (CD122) and the common gamma chain (gamma-C, CD132). IL-15 is secreted by mononuclear phagocytes (and some other cells) following infection by virus(es). This cytokine induces cell proliferation of natural killer cells; cells of the innate immune system whose principal role is to kill virally infected cells.

IL-15 can enhance the anti-tumor immunity of CD8+ T cells in pre-clinical models. A phase I clinical trial to evaluate the safety, dosing, and anti-tumor efficacy of IL-15 in patients with metastatic melanoma and renal cell carcinoma (kidney cancer) has begun to enroll patients at the National Institutes of Health.

IL-15 disclosed herein may also include mutants of IL-15 that are modified to maintain the function of its native form.

IL-15 is 14-15 kDa glycoprotein encoded by the 34 kb region 4q31 of chromosome 4, and by the central region of chromosome 8 in mice. The human IL-15 gene comprises nine exons (1-8 and 4A) and eight introns, four of which (exons 5 through 8) code for the mature protein. Two alternatively spliced transcript variants of this gene encoding the same protein have been reported. The originally identified isoform, with long signal peptide of 48 amino acids (IL-15 LSP) consisted of a 316 bp 5'-untranslated region (UTR), 486 bp coding sequence and the C-terminus 400 bp 3'-UTR region. The other isoform (IL-15 SSP) has a short signal peptide of 21 amino acids encoded by exons 4A and 5. Both isoforms shared 11 amino acids between signal sequences of the N-terminus. Although both isoforms produce the same mature protein, they differ in their cellular trafficking. IL-15 LSP isoform was identified in Golgi apparatus [GC], early endosomes and in the endoplasmic reticulum (ER). It exists in two forms, secreted and membrane-bound particularly on dendritic cells. On the other hand, IL-15 SSP isoform is not secreted and it appears to be restricted to the cytoplasm and nucleus where it plays an important role in the regulation of cell cycle.

It has been demonstrated that two isoforms of IL-15 mRNA are generated by alternatively splicing in mice. The isoform which had an alternative exon 5 containing another 3' splicing site, exhibited a high translational efficiency, and the product lack hydrophobic domains in the signal sequence of the N-terminus. This suggests that the protein derived from this isoform is located intracellularly. The other isoform with normal exon 5, which is generated by integral splicing of the alternative exon 5, may be released extracellularly.

Although IL-15 mRNA can be found in many cells and tissues including mast cells, cancer cells or fibroblasts, this cytokine is produce as a mature protein mainly by dendritic cells, monocytes and macrophages. This discrepancy between the wide appearance of IL-15 mRNA and limited production of protein might be explained by the presence of the twelve in humans and five in mice upstream initiating codons, which can repress translation of IL-15 mRNA. Translational inactive mRNA is stored within the cell and can be induced upon specific signal. Expression of IL-15 can be stimulated by cytokine such as GM-CSF, double-strand mRNA, unmethylated CpG oligonucleotides, lipopolysaccharide (LPS) through Toll-like receptors (TLR), interferon gamma (IFN-γ) or after infection of monocytes herpes virus, *Mycobacterium tuberculosis* and *Candida albicans*.

XII. Natural Killer (NK) Cells

In certain embodiments, native or engineered NK cells may be provided to be administered to a subject in need thereof, in combination with adenoviral vector-based compositions or immunotherapy as described herein.

The immune system is a tapestry of diverse families of immune cells each with its own distinct role in protecting from infections and diseases. Among these immune cells are the natural killer, or NK, cells as the body's first line of defense. NK cells have the innate ability to rapidly seek and destroy abnormal cells, such as cancer or virally-infected cells, without prior exposure or activation by other support molecules. In contrast to adaptive immune cells such as T cells, NK cells have been utilized as a cell-based "off-the-shelf" treatment in phase 1 clinical trials, and have demonstrated tumor killing abilities for cancer.

1. aNK Cells

In addition to native NK cells, there may be provided NK cells for administering to a patient that has do not express Killer Inhibitory Receptors (KIR), which diseased cells often exploit to evade the killing function of NK cells. This unique activated NK, or aNK, cell lack these inhibitory receptors while retaining the broad array of activating receptors which enable the selective targeting and killing of diseased cells. aNK cells also carry a larger pay load of granzyme and perforin containing granules, thereby enabling them to deliver a far greater payload of lethal enzymes to multiple targets.

2. taNK Cells

Chimeric antigen receptor (CAR) technology is among the most novel cancer therapy approaches currently in development. CARs are proteins that allow immune effector cells to target cancer cells displaying specific surface antigen (target-activated Natural Killer) is a platform in which aNK cells are engineered with one or more CARs to target proteins found on cancers and is then integrated with a wide spectrum of CARs. This strategy has multiple advantages over other CAR approaches using patient or donor sourced effector cells such as autologous T-cells, especially in terms of scalability, quality control and consistency.

Much of the cancer cell killing relies upon ADCC (antibody dependent cell-mediated cytotoxicity) whereupon effector immune cells attach to antibodies, which are in turn bound to the target cancer cell, thereby facilitating killing of the cancer by the effector cell. NK cells are the key effector cell in the body for ADCC and utilize a specialized receptor (CD16) to bind antibodies.

3. haNK Cells

Studies have shown that perhaps only 20% of the human population uniformly expresses the "high-affinity" variant of CD16 (haNK cells), which is strongly correlated with more favorable therapeutic outcomes compared to patients with the "low-affinity" CD16. Additionally, many cancer patients have severely weakened immune systems due to chemotherapy, the disease itself or other factors.

In certain aspects, NK cells are modified to express high-affinity CD16 (haNK cells). As such, haNK cells may potentiate the therapeutic efficacy of a broad spectrum of antibodies directed against cancer cells.

XIII. Combination Therapy

The compositions comprising an adenoviral vector-based vaccination comprising a nucleic acid sequence encoding tumor antigens such as antigens or epitopes of HER1, HER2/neu, HER3, HER4, or any combination thereof described throughout can be formulated into a pharmaceutical medicament and be used to treat a human or mammal in need thereof or diagnosed with a disease, e.g., cancer. These medicaments can be co-administered with one or more additional vaccines or other cancer therapy to a human or mammal.

In further embodiments, the present invention provides compositions for further combination therapies which include the Ad5 [E1−, E2b−]-HER3 vaccine, an IL-15 super-agonist, such as ALT-803, and one or more of the following agents: a chemotherapeutic agent, costimulatory molecules, checkpoint inhibitors, antibodies against a specific antigen (e.g., HER3), engineered NK cells, or any combination thereof. For example, the present invention provides a method of treating a HER3-expressing cancer in an individual in need thereof, the method comprising: administering to the individual a first pharmaceutical composition comprising a replication-defective vector comprising a nucleic acid sequence encoding a HER3 antigen or any suitable antigen, administering to the individual an IL-15 superagonist such as ALT-803, and administering to the individual an anti-HER3 antibody and engineered NK cells. In some embodiments, the method can further comprise administering to the individual a VEGF inhibitor, a chemotherapy, or a combination thereof. In other embodiments, the method can further comprise administering to the individual engineered NK cells and a checkpoint inhibitor. Any combination of chemotherapeutic agents, costimulatory molecules, checkpoint inhibitors, antibodies against a specific antigen (e.g., HER3), or engineered NK cells can be included in combination therapy with the Ad5 [E1−, E2b−] vaccine encoding for an antigen, such as HER3, and an IL-15 super-agonist or super-agonist complex, such as ALT-803.

In certain embodiments, the chemotherapy used herein is capecitabine, leucovorin, fluorouracil, oxaliplatin, fluoropyrimidine, irinotecan, mitomycin, regorafenib, cetuximab, panitumumab, acetinophen, or a combination thereof. In particular embodiments, the chemotherapy used herein is FOLFOX (leucovorin, fluorouracil and oxaliplatin) or capecitabine. In certain embodiments, the immune checkpoint inhibitor is an anti-PD-1 or anti-PD-L1 antibody, such as avelumab. In certain embodiments, the VEGF inhibitor is an anti-VEGF antibody, such as bevacizumab. The agents which can be used in combination therapy alongside the replication defective vector and ALT-803 are described in further detail below.

In certain aspects, the medicaments as described herein can be combined with one or more available therapy for breast cancer, for example, conventional cancer therapy such as surgery, radiation therapy or medications such as hormone blocking therapy, chemotherapy or monoclonal antibodies. In some embodiments, any vaccine described herein (e.g., Ad5 [E1−, E2b−]-HER3) can be combined with low dose chemotherapy or low dose radiation. For example, in some embodiment, any vaccine described herein (e.g., Ad5 [E1−, E2b−]-HER3) can be combined with chemotherapy, such that the dose of chemotherapy administered is lower than the clinical standard of care. In some embodiments, the chemotherapy can be cyclophosphamide. The cyclophasmade can administered at a dose that is lower than the clinical standard of care dosing. For example, the chemotherapy can be administered at 50 mg twice a day (BID) on days 1-5 and 8-12 every 2 weeks for a total of 8 weeks. In some embodiments, any vaccine described herein (e.g., Ad5 [E1−, E2b−]-HER3) can be combined with radiation, such that the dose of radiation administered is lower than the clinical standard of care. For example, in some embodiments, concurrent sterotactic body radiotherapy (SBRT) at 8 Gy can be given on day 8, 22, 36, 50 (every 2 weeks for 4 doses). Radiation can be administered to all feasible tumor sites using SBRT.

In certain aspects, medications used for breast cancer treatment include hormone-blocking agents, chemotherapy, and monoclonal antibodies. Some breast cancers require estrogen to continue growing. They can be identified by the presence of estrogen receptors (ER+) and progesterone receptors (PR+) on their surface (sometimes referred to together as hormone receptors). These ER+ cancers can be treated with drugs that either block the receptors, e.g., tamoxifen, or alternatively block the production of estrogen with an aromatase inhibitor, e.g., anastrozole or letrozole.

The use of tamoxifen is recommended for 10 years. Aromatase inhibitors are useful for women after menopause; however, in this group, they appear better than tamoxifen. This is because the active aromatase in postmenopausal women is different from the prevalent form in premenopausal women, and therefore these agents are ineffective in inhibiting the predominant aromatase of premenopausal women.

Chemotherapy is predominantly used for cases of breast cancer in stages 2-4, and is particularly beneficial in estrogen receptor-negative (ER–) disease. The chemotherapy medications are administered in combinations, usually for periods of 3-6 months. One of the most common regimens, known as "AC," combines cyclophosphamide with doxorubicin. Sometimes a taxane drug, such as docetaxel (Taxotere), is added, and the regime is then known as "CAT." Another common treatment is cyclophosphamide, methotrexate, and fluorouracil (or "CMF"). Most chemotherapy medications work by destroying fast-growing and/or fast-replicating cancer cells, either by causing DNA damage upon replication or by other mechanisms. However, the medications also damage fast-growing normal cells, which may cause serious side effects. Damage to the heart muscle is the most dangerous complication of doxorubicin, for example.

HER2/neu is the target of the monoclonal antibody trastuzumab (marketed as Herceptin). Trastuzumab, a monoclonal antibody to HER2/neu (a cell receptor that is especially active in some breast cancer cells), has improved the 5-year disease free survival of stage 1-3 HER2/neu-positive breast cancers to about 87% (overall survival 95%). One year of trastuzumab therapy is recommended for all patients with HER2/neu-positive breast cancer who are also receiving chemotherapy.

When stimulated by certain growth factors, HER2/neu causes cellular growth and division; in the absence of stimulation by the growth factor, the cell normally stops growing. Between 25% and 30% of breast cancers overexpress the HER2/neu gene or its protein product, and overexpression of HER2/neu in breast cancer is associated with increased disease recurrence and worse prognosis. When trastuzumab binds to the HER2/neu in breast cancer cells that overexpress the receptor, trastuzumab prevents growth factors from being able to bind to and stimulate the receptors, effectively blocking the growth of the cancer cells. An important downstream effect of trastuzumab binding to HER2/neu is an increase in p27, a protein that halts cell proliferation. Thus, Trastuzumab is useful for breast cancer patients with HER2/neu amplification/overexpression.

Another monoclonal antibody, Pertuzumab, which inhibits dimerisation of HER2/neu and HER3 receptors, was approved by the FDA for use in combination with trastuzumab in June 2012.

Additionally, NeuVax (Galena Biopharma) is a peptide-based immunotherapy that directs "killer" T cells to target and destroy cancer cells that express HER2/neu. It has entered phase 3 clinical trials.

It has been found that patients with ER+ (Estrogen receptor positive)/HER2/neu+ compared with ER–/HER2/neu+ breast cancers may actually benefit more from drugs that inhibit the PI3K/AKT molecular pathway.

Over-expression of HER2/neu can also be suppressed by the amplification of other genes. Research is currently being conducted to discover which genes may have this desired effect.

The expression of HER2/neu is regulated by signaling through estrogen receptors. Normally, estradiol and tamoxifen acting through the estrogen receptor down-regulate the expression of HER2/neu. However, when the ratio of the coactivator AIB-3 exceeds that of the corepressor PAX2, the expression of HER2/neu is upregulated in the presence of tamoxifen, leading to tamoxifen-resistant breast cancer.

In certain aspects, these medicaments as described herein can be combined together with one or more conventional cancer therapies or alternative cancer therapies or immune pathway checkpoint modulators as described herein. The combination therapy involving the adenovirus vector-based medicaments can be used to treat any cancer, particularly, breast cancer, or unresectable, locally advanced, or metastatic cancer.

Conventional cancer therapies include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

Radiation therapy that causes DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens or 10 to 500 roentgens for prolonged periods of time (3 to 4 wk), to single doses of 2000 to 6000 roentgens or 1000 to 8000 roentegens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment described herein, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that treatment methods described herein may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, 7, 8, 9, 10, 11, 12, 13, or 14 days, or every 1, 2, 3, 4, 5, 6, 7, 8, 9, 10, 11, 12, 13, 14, 15, 16, 17, 18, 19, or 20 weeks or every 1, 2, 3, 4, 5, 6, 7, 8, 9, 10, 11, 12, 13, 14, 15, 16, 18, 20, 22, 23, or 24 months. These treatments may be of varying dosages as well.

Alternative cancer therapies include any cancer therapy other than surgery, chemotherapy and radiation therapy, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into a subject's cells and tissues to treat a disease. Antisense therapy is also a form of gene therapy. A therapeutic polynucleotide may be administered before, after, or at the same time of a first cancer therapy. Delivery of a vector encoding a variety of proteins is provided in some embodiments. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with pharmaceutical compositions described herein to improve the anti-hyperproliferative efficacy of the treatments. Inhibitors of cell adhesion are contemplated to improve the efficacy of pharmaceutical compositions described herein. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with pharmaceutical compositions described herein to improve the treatment efficacy.

Hormonal therapy may also be used in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

A "Chemotherapeutic agent" or "chemotherapeutic compound" and their grammatical equivalents as used herein, can be a chemical compound useful in the treatment of cancer. The chemotherapeutic cancer agents that can be used in combination with the disclosed T cell include, but are not limited to, mitotic inhibitors (vinca alkaloids). These include vincristine, vinblastine, vindesine and Navelbine™ (vinorelbine, 5'-noranhydroblastine). In yet other embodiments, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that can be used in the methods and compositions disclosed herein are podophyllotoxin derivatives, such as etoposide, teniposide and mitopodozide.

In certain aspects, methods or compositions described herein further encompass the use of other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The disclosure encompasses antimetabolites as chemotherapeutic agents. Examples of these types of agents include cytosine arabinoside, fluorouracil, methotrexate, mercaptopurine, azathioprime, and procarbazine.

An additional category of chemotherapeutic cancer agents that may be used in the methods and compositions disclosed herein includes antibiotics. Examples include without limitation doxorubicin, bleomycin, dactinomycin, daunorubicin, mithramycin, mitomycin, mytomycin C, and daunomycin. There are numerous liposomal formulations commercially available for these compounds. In certain aspects, methods or compositions described herein further encompass the use of other chemotherapeutic cancer agents including without limitation anti-tumor antibodies, dacarbazine, azacytidine, amsacrine, melphalan, ifosfamide and mitoxantrone.

The disclosed adenovirus vaccine herein can be administered in combination with other anti-tumor agents, including cytotoxic/antineoplastic agents and anti-angiogenic agents. Cytotoxic/anti-neoplastic agents can be defined as agents who attack and kill cancer cells. Some cytotoxic/anti-neoplastic agents can be alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents can be antimetabolites for tumor cells, e.g., cytosine arabinoside, fluorouracil, methotrexate, mercaptopuirine, azathioprime, and procarbazine. Other cytotoxic/anti-neoplastic agents can be antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/antineoplastic agents can be mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Additional formulations comprising population(s) of CAR T cells, T cell receptor engineered T cells, B cell receptor engineered cells, can be administered to a subject in conjunction, before, or after the administration of the pharmaceutical compositions described herein. A therapeutically-effective population of adoptively transferred cells can be administered to subjects when the methods described herein are practiced. In general, formulations are administered that comprise between about $1 \times 10^4$ and about $1 \times 10^{10}$ CAR T cells, T cell receptor engineered cells, or B cell receptor engineered cells. In some cases, the formulation comprises between about $1 \times 10^5$ and about $1 \times 10^9$ engineered cells, from about $5 \times 10^5$ to about $5 \times 10^8$ engineered cells, or from about $1 \times 10^6$ to about $1 \times 10^7$ engineered cells. However, the number of engineered cells administered to a subject will vary between wide limits, depending upon the location, source, identity, extent and severity of the cancer, the age and condition of the subject to be treated etc. A physician will ultimately determine appropriate dosages to be used.

Anti-angiogenic agents can also be used. Suitable anti-angiogenic agents for use in the disclosed methods and compositions include anti-VEGF antibodies, including humanized and chimeric antibodies, anti-VEGF aptamers and antisense oligonucleotides. Other inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

In some cases, for example, in the compositions, formulations and methods of treating cancer, the unit dosage of the composition or formulation administered can be 5, 10, 15, 20, 25, 30, 35, 40, 45, 50, 55, 60, 65, 70, 75, 80, 85, 90, 95 or 100 mg or any intervening value or range derived therefrom. In some cases, the total amount of the composition or formulation administered can be 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 40, 50, 60, 70, 80, 90, or 100 g or any intervening value or range derived therefrom.

XIV. Immunological Fusion Partner Antigen Targets

The viral vectors or composition described herein may further comprise nucleic acid sequences that encode proteins, or an "immunological fusion partner," that can increase the immunogenicity of the target antigen such as HER3, HER2/neu, HER1, HER4, or any combination thereof, or any other target antigen disclosed herein. In this regard, the protein produced following immunization with the viral vector containing such a protein may be a fusion protein comprising the target antigen of interest fused to a protein that increases the immunogenicity of the target antigen of interest. Furthermore, combination therapy with Ad5[E1–, E2b–] vectors encoding for HER3, HER2/neu, HER1, HER4, or any combination thereof as well as an immunological fusion partner can result in boosting the immune response, such that the combination of both therapeutic moieties acts to synergistically boost the immune response than either the Ad5[E1–, E2b–] vectors encoding for HER3, HER2/neu, HER1, HER4, or any combination thereof alone, or the immunological fusion partner alone. For example, combination therapy with Ad5[E1–, E2b–] vectors encoding for HER3, HER2/neu, HER1, HER4, or any combination thereof, as well as an immunological fusion partner can result in synergistic enhancement of stimulation of antigen-specific effector CD4+ and CD8+ T cells, stimulation of NK cell response directed towards killing infected cells, stimulation of neutrophils or monocyte cell responses directed towards killing infected cells via antibody dependent cell-mediated cytotoxicity (ADCC), antibody dependent cellular phagocytosis (ADCP) mechanisms, or any combination thereof. This synergistic boost can vastly improve survival outcomes after administration to a subject in need thereof. In certain embodiments, combination therapy with Ad5[E1–, E2b–] vectors encoding for HER3, HER2/neu, HER1, HER4, or any combination thereof, as well as an immunological fusion partner can result in generating an immune response comprises an increase in target antigen-specific CTL activity of about 1.5 to 20, or more fold in a subject administered the adenovirus vectors as compared to a control. In another embodiment, generating an immune response comprises an increase in target-specific CTL activity of about 1.5 to 20, or more fold in a subject administered the Ad5[E1–, E2b–] vectors encoding for HER3, HER2/neu, HER1, HER4 antigens, or any combination thereof, as well as an immunological fusion partner as compared to a control. In a further embodiment, generating an immune response that comprises an increase in target antigen-specific cell-mediated immunity activity as measured by ELISpot assays measuring cytokine secretion, such as interferon-gamma (IFN-γ), interleukin-2 (IL-2), tumor necrosis factor-alpha (TNF-α), or other cytokines, of about 1.5 to 20, or more fold as compared to a control. In a further embodiment, generating an immune response comprises an increase in target-specific antibody production of between 1.5 and 5 fold in a subject administered the Ad5[E1–, E2b–] vectors encoding for HER3, HER2/neu, HER1, HER4 antigens, or any combination thereof, as well as an immunological fusion partner as described herein as compared to an appropriate control. In another embodiment, generating an immune response comprises an increase in target-specific antibody production of about 1.5 to 20, or more fold in a subject administered the adenovirus vector as compared to a control.

As an additional example, combination therapy with Ad5[E1–, E2b–] vectors encoding for target epitope antigens and an immunological fusion partner can result in synergistic enhancement of stimulation of antigen-specific effector CD4+ and CD8+ T cells, stimulation of NK cell response directed towards killing infected cells, stimulation of neutrophils or monocyte cell responses directed towards killing infected cells via antibody dependent cell-mediated cytotoxicity (ADCC), antibody dependent cellular phagocytosis (ADCP) mechanisms, or any combination thereof. This synergistic boost can vastly improve survival outcomes after administration to a subject in need thereof. In certain embodiments, combination therapy with Ad5[E1–, E2b–] vectors encoding for target epitope antigens and an immunological fusion partner can result in generating an immune response comprises an increase in target antigen-specific CTL activity of about 1.5 to 20, or more fold in a subject administered the adenovirus vectors as compared to a control. In another embodiment, generating an immune response comprises an increase in target-specific CTL activity of about 1.5 to 20, or more fold in a subject administered the Ad5[E1–, E2b–] vectors encoding for target epitope antigens and an immunological fusion partner as compared to a control. In a further embodiment, generating an immune response that comprises an increase in target antigen-specific cell-mediated immunity activity as measured by ELISpot assays measuring cytokine secretion, such as interferon-gamma (IFN-γ), interleukin-2 (IL-2), tumor necrosis factor-alpha (TNF-α), or other cytokines, of about 1.5 to 20, or more fold as compared to a control. In a further embodiment, generating an immune response comprises an increase in target-specific antibody production of between 1.5 and 5 fold in a subject administered the adenovirus vectors as described herein as compared to an appropriate control. In another embodiment, generating an immune response comprises an increase in target-specific antibody production of about 1.5 to 20, or more fold in a subject administered the adenovirus vector as compared to a control.

In one embodiment, such an immunological fusion partner is derived from a *Mycobacterium* sp., such as a *Mycobacterium tuberculosis*-derived Ra12 fragment. The immunological fusion partner derived from *Mycobacterium* sp. can be any one of the sequences set forth in SEQ ID NO: 14-SEQ ID NO: 22. Ra12 compositions and methods for their use in enhancing the expression and/or immunogenicity of heterologous polynucleotide/polypeptide sequences are described in U.S. Pat. No. 7,009,042, which is herein incorporated by reference in its entirety. Briefly, Ra12 refers to a polynucleotide region that is a subsequence of a *Mycobacterium tuberculosis* MTB32A nucleic acid. MTB32A is a serine protease of 32 kDa encoded by a gene in virulent and avirulent strains of *M. tuberculosis*. The nucleotide sequence and amino acid sequence of MTB32A have been described (see, e.g., U.S. Pat. No. 7,009,042; Skeiky et al., Infection and Immun. 67:3998-4007 (1999), incorporated herein by reference in their entirety). C-terminal fragments of the MTB32A coding sequence can be expressed at high levels and remain as soluble polypeptides throughout the purification process. Moreover, Ra12 may enhance the immunogenicity of heterologous immunogenic polypeptides with which it is fused. A Ra12 fusion polypeptide can comprise a 14 kDa C-terminal fragment corresponding to amino acid residues 192 to 323 of MTB32A. Other Ra12 polynucleotides generally can comprise at least about 15, 30, 60, 100, 200, 300, or more nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants can have at least about 70%, 80%, or 90% identity, or more, to a polynucleotide sequence that encodes a native Ra12 polypeptide or a portion thereof.

In certain aspects, an immunological fusion partner can be derived from protein D, a surface protein of the gram-negative bacterium *Haemophilus influenzae* B. The immunological fusion partner derived from protein D can be the sequence set forth in SEQ ID NO: 23. In some cases, a protein D derivative comprises approximately the first third of the protein (e.g., the first N-terminal 100-110 amino acids). A protein D derivative may be lipidated. Within certain embodiments, the first 109 residues of a Lipoprotein D fusion partner is included on the N-terminus to provide the polypeptide with additional exogenous T-cell epitopes, which may increase the expression level in *E. coli* and may function as an expression enhancer. The lipid tail may ensure optimal presentation of the antigen to antigen presenting cells. Other fusion partners can include the non-structural protein from influenza virus, NS1 (hemagglutinin). Typically, the N-terminal 81 amino acids are used, although different fragments that include T-helper epitopes may be used.

In certain aspects, the immunological fusion partner can be the protein known as LYTA, or a portion thereof (particularly a C-terminal portion). The immunological fusion partner derived from LYTA can the sequence set forth in SEQ ID NO: 24. LYTA is derived from *Streptococcus pneumoniae*, which synthesizes an N-acetyl-L-alanine amidase known as amidase LYTA (encoded by the LytA gene). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus can be employed. Within another embodiment, a repeat portion of LYTA may be incorporated into a fusion polypeptide. A repeat portion can, for example, be found in the C-terminal region starting at residue 178. One particular repeat portion incorporates residues 188-305.

In some embodiments, the target antigen is fused to an immunological fusion partner, also referred to herein as an "immunogenic component," comprising a cytokine selected from the group of IFN-γ, TNFα, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1a, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. The target antigen fusion can produce a protein with substantial identity to one or more of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. The target antigen fusion can encode a nucleic acid encoding a protein with substantial identity to one or more of IFN-γ, TNFα, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. In some embodiments, the target antigen fusion further comprises one or more immunological fusion partner, also referred to herein as an "immunogenic components," comprising a cytokine selected from the group of IFN-γ, TNFα, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. The sequence of IFN-γ can be, but is not limited to, a sequence as set forth in SEQ ID NO: 25. The sequence of TNFα can be, but is not limited to, a sequence as set forth in SEQ ID NO: 26. The sequence of IL-2 can be, but is not limited to, a sequence as set forth in SEQ ID NO: 27. The sequence of IL-8 can be, but is not limited to, a sequence as set forth in SEQ ID NO: 28. The sequence of IL-12 can be, but is not limited to, a sequence as set forth in SEQ ID NO: 29. The sequence of IL-18 can be, but is not limited to, a sequence as set forth in SEQ ID NO: 30. The sequence of IL-7 can be, but is not limited to, a sequence as set forth in SEQ ID NO: 31. The sequence of IL-3 can be, but is not limited to, a sequence as set forth in SEQ ID NO: 32. The sequence of IL-4 can be, but is not limited to, a sequence as set forth in SEQ ID NO: 33. The sequence of IL-5 can be, but is not limited to, a sequence as set forth in SEQ ID NO: 34. The sequence of IL-6 can be, but is not limited to, a sequence as set forth in SEQ ID NO: 35. The sequence of IL-9 can be, but is not limited to, a sequence as set forth in SEQ ID NO: 36. The sequence of IL-10 can be, but is not limited to, a sequence as set forth in SEQ ID NO: 37. The sequence of IL-13 can be, but is not limited to, a sequence as set forth in SEQ ID NO: 38. The sequence of IL-15 can be, but is not limited to, a sequence as set forth in SEQ ID NO: 39. The sequence of IL-16 can be, but is not limited to, a sequence as set forth in SEQ ID NO: 66. The sequence of IL-17 can be, but is not limited to, a sequence as set forth in SEQ ID NO: 67. The sequence of IL-23 can be, but is not limited to, a sequence as set forth in SEQ ID NO: 68. The sequence of IL-32 can be, but is not limited to, a sequences as set forth in SEQ ID NO: 69.

In some embodiments, the target antigen is fused or linked to an immunological fusion partner, also referred to herein as an "immunogenic component," comprising a cytokine selected from the group of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-10, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. In some embodiments, the target antigen is co-expressed in a cell with an immunological fusion partner, also referred to herein as an "immunogenic component," comprising a cytokine selected from the group of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF.

In some embodiments, the target antigen is fused or linked to an immunological fusion partner, comprising CpG ODN (a non-limiting example sequence is shown in SEQ ID NO: 40), cholera toxin (a non-limiting example sequence is shown in SEQ ID NO: 41), a truncated A subunit coding region derived from a bacterial ADP-ribosylating exotoxin (a non-limiting example sequence is shown in (a non-limiting example sequence is shown in SEQ ID NO: 42), a truncated B subunit coding region derived from a bacterial ADP-ribosylating exotoxin (a non-limiting example sequence is shown in SEQ ID NO: 43), Hp91 (a non-limiting example sequence is shown in SEQ ID NO: 44), CCL20 (a non-limiting example sequence is shown in SEQ ID NO: 45), CCL3 (a non-limiting example sequence is shown in SEQ ID NO: 46), GM-CSF (a non-limiting example sequence is shown in SEQ ID NO: 47), G-CSF (a non-limiting example sequence is shown in SEQ ID NO: 48), LPS peptide mimic (non-limiting example sequences are shown in SEQ ID NO: 49-SEQ ID NO: 60), shiga toxin (a non-limiting example sequence is shown in SEQ ID NO: 61), diphtheria toxin (a non-limiting example sequence is shown in SEQ ID NO: 62), or $CRM_{197}$ (a non-limiting example sequence is shown in SEQ ID NO: 65).

In some embodiments, the target antigen is fused or linked to an immunological fusion partner, comprising an IL-15 superagonist. Interleukin 15 (IL-15) is a naturally occurring inflammatory cytokine secreted after viral infections. Secreted IL-15 can carry out its function by signaling via the its cognate receptor on effector immune cells, and thus, can lead to overall enhancement of effector immune cell activity.

Based on IL-15's broad ability to stimulate and maintain cellular immune responses, it is believed to be a promising immunotherapeutic drug that could potentially cure certain cancers. However, major limitations in clinical development of IL-15 can include low production yields in standard mammalian cell expression systems and short serum half-life. Moreover, the IL-15:IL-15Ra complex, comprising proteins co-expressed by the same cell, rather than the free IL-15 cytokine, can be responsible for stimulating immune effector cells bearing IL-15 βγc receptor.

To contend with these shortcomings, a novel IL-15 super-agonist mutant (IL-15N72D) was identified that has increased ability to bind IL-15Rβγc and enhanced biological activity. Addition of either mouse or human IL-15Rα and Fc fusion protein (the Fc region of immunoglobulin) to equal molar concentrations of IL-15N72D can provide a further increase in IL-15 biologic activity, such that IL-15N72D:IL-15Rα/fc super-agonist complex exhibits a median effective concentration (EC50) for supporting IL-15-dependent cell growth that was greater than 10-fold lower than that of free IL-15 cytokine.

In some embodiments, the IL-15 superagonist can be a novel IL-15 superagonist mutant (IL-15N72D). In certain embodiments, addition of either mouse or human IL-15Rα and Fc fusion protein (the Fc region of immunoglobulin) to equal molar concentrations of IL-15N72D can provide a further increase in IL-15 biologic activity, such that IL-15N72D:IL-15Ra/Fc super-agonist complex exhibits a median effective concentration ($EC_{50}$) for supporting IL-15-dependent cell growth that can be greater than 10-fold lower than that of free IL-15 cytokine Thus, in some embodiments, the present disclosure provides a IL-15N72D:IL-15Ra/Fc super-agonist complex with an EC50 for supporting IL-15-dependent cell growth that is greater than 2-fold lower, greater than 3-fold lower, greater than 4-fold lower, greater than 5-fold lower, greater than 6-fold lower, greater than 7-fold lower, greater than 8-fold lower, greater than 9-fold lower, greater than 10-fold lower, greater than 15-fold lower, greater than 20-fold lower, greater than 25-fold lower, greater than 30-fold lower, greater than 35-fold lower, greater than 40-fold lower, greater than 45-fold lower, greater than 50-fold lower, greater than 55-fold lower, greater than 60-fold lower, greater than 65-fold lower, greater than 70-fold lower, greater than 75-fold lower, greater than 80-fold lower, greater than 85-fold lower, greater than 90-fold lower, greater than 95-fold lower, or greater than 100-fold lower than that of free IL-15 cytokine.

In some embodiments, the interaction of IL-15N72D, soluble IL-15Ra, and Fc fusion protein have been exploited to create a biologically active protein complex, ALT-803. It is known that a soluble IL-15Rα fragment, containing the so-called "sushi" domain at the N terminus (Su), bears most of the structural elements responsible for high affinity cytokine binding. A soluble fusion protein can be generated by linking the human IL-15RαSu domain (amino acids 1-65 of the mature human IL-15Rα protein) with the human IgG1 CH2-CH3 region containing the Fc domain (232 amino acids). This IL-15RαSu/IgG1 Fc fusion protein has the advantages of dimer formation through disulfide bonding via IgG1 domains and ease of purification using standard Protein A affinity chromatography methods. A diagram of ALT-803 superagonist is presented in FIG. 1.

ALT-803 is a soluble complex consisting of 2 protein subunits of a human IL-15 variant (two IL-15N72D subunits) associated with high affinity to a dimeric IL-15Rα sushi domain/human IgG1 Fcfusion protein and. The IL-15 variant is a 114-amino acid polypeptide comprising the mature human IL-15 cytokine sequence with an Asn to Asp substitution at position 72 of helix C N72D). The human IL-15R sushi domain/human IgG1 Fc fusion protein comprises the sushi domain of the IL-15R subunit (amino acids 1-65 of the mature human IL-15Rα protein) linked with the human IgG1 CH2-CH3 region containing the Fc domain (232 amino acids). Aside from the N72D substitution, all of the protein sequences are human. Based on the amino acid sequence of the subunits, the calculated molecular weight of the complex comprising two IL-15N72D polypeptides and a disulfide linked homodimeric IL-15RαSu/IgG1 Fc protein is 92.4 kDa. Each IL-15N720 polypeptide has a calculated molecular weight of approximately 12.8 kDa and the IL-15RαSu/IgG 1 Fc fusion protein has a calculated molecular weight of approximately 33.4 kDa. Both the IL-15N72D and IL-15RαSu/IgG 1 Fc proteins are glycosylated resulting in an apparent molecular weight of ALT-803 as approximately 114 kDa by size exclusion chromatography. The isoelectric point (pI) determined for ALT-803 can range from approximately 5.6 to 6.5. Thus, the fusion protein can be negatively charged at pH 7. The calculated molar extinction coefficient at A280 for ALT-803 is 116,540 M or, in other words, one OD280 is equivalent to 0.79 mg/mL solution of ALT-803.

Additionally, it has been demonstrated that intracellular complex formation with IL-15Rα prevents IL-15 degradation in the endoplasm reticulum and facilitates its secretion. Using a co-expression strategy in Chinese hamster ovary (CHO) cells, the IL-15N72D and IL-15RαSu/IgG1 Fc proteins can be produced at high levels and formed a soluble, stable complex. The biological activity of CHO-produced ALT-803 complex can be equivalent to in-vitro assembled IL-15N72D:IL-15RαSu/IgG1 Fc complexes in standard cell-based potency assays using IL-15-dependent cell lines. The methods provided herein, thus represent a better approach for generating active, fully characterized cGMP grade IL-15:IL-15Rα complex than current strategies employing in vitro assembly of individually produced and, in some cases, refolded proteins.

Recent studies show that ALT-803 (1) can promote the development of high effector NK cells and CD8+ T cell responders of the innate phenotype, (2) can enhance the function of NK cells, and (3) can play a vital role in reducing tumor metastasis and ultimately survival, especially in combination with checkpoint inhibitors, which are further described below.

In some embodiments, an IL-15 super-agonist or an IL-15 super-agonist complex, ALT-803, can be administered parenterally, subcutaneously, intramuscularly, by intravenous infusion, by implantation, intraperitoneally, or intravascularly. In some embodiments 0.1-5 µg of the IL-15 superagonist can be administered in a single dose. In some embodiments, 0.1-0.2 µg, 0.2-0.3 µg, 0.3-0.4 µg, 0.4-0.5 µg, 0.5-0.6 µg, 0.6-0.7 µg, 0.7-0.8 µg, 0.8-0.9 µg, 0.9-1 µg, 1-1.5 µg, 1.5-2 µg, 2-2.5 µg, 2.5-3 µg, 3-3.5 µg, 3.5-4 µg, 4-4.5 µg, or 4.5-5 µg of the IL-15 superagonist can be administered in a single dose. In certain embodiments, 1 µg of the ALT-803 can be administered in a single dose. In some embodiments, ALT-803 can be administered at an effective dose of from about 0.1 µg/kg to abut 100 mg/kg body weight, e.g., 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, or 900 µg/kg body weight or 1, 2, 3, 4, 5, 6, 7, 8, 9, 10, 20, 30, 40, 50, 60, 70, 80, 90, 95, 99, or 100 mg/kg body weight. In some embodiments, an IL-15 superagonist can be administered with an Ad5 [E1-, E2b-]-HER3 (e.g., a truncated or full length HER3) vaccine. In some embodiments, an IL-15 superagonist can be administered as a mixture with the Ad5 [E1-, E2b-]-HER3 (e.g., a truncated or full length HER3) vaccine. In other embodiments, an IL-15 superagonist can be administered as a separate dose immediately before or after the Ad5 [E1-, E2b-]-HER3 vaccine. In other embodiments, an ALT-803 is administered within 1 day, within 2 days, within 3 days, within 4 days, within 5 days, or within 6 days of administration of an Ad5 [E1-, E2b-]-HER3 vaccine. In some embodiments, an ALT-803 is administered 3 days after an Ad5 [E1-, E2b-]-HER3 vaccine. In some embodiments, ALT-803 is administered continuously or several times per day, e.g., every 1 hour, every 2 hours, every 3 hours, every 4 hours, every 5 hours, every 6 hours, every 7 hours, every 8 hours, every 9 hours, every 10 hours, every 11 hours, or every 12 hours. Daily effective doses of ALT-803 can include from 0.1 µg/kg and 100 µg/kg body weight, e.g., 0.1, 0.3, 0.5, 1, 5, 10, 15, 20, 25, 30, 35, 40, 45, 50, 55, 60, 65, 70, 75, 80, 85, 90, 95, or 99 µg/kg body weight. In some embodiments, ALT-803 is administered once per week, twice per week, three times per week, four times per week, five times per week, six times per week, or seven times per week. Effective weekly doses of ALT-803 include between 0.0001 mg/kg and 4 mg/kg body weight, e.g., 0.001, 0.003, 0.005, 0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, or 4 mg/kg body weight. ALT-803 can be administered at a dose from about 0.1 µg/kg body weight to about 5000 µg/kg body weight; or from about 1 µg/kg body weight to about 4000 µg/kg body weight or from about 10 µg/kg body weight to about 3000 µg/kg body weight. In other embodiments, ALT-803 can be administered at a dose of about 0.1, 0.3, 0.5, 1, 3, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 µg/kg. In some embodiments, ALT-803 can be administered at a dose from about 0.5 µg compound/kg body weight to about 20 µg compound/kg body weight. In other embodiments, the doses may be about 0.5, 1, 3, 6, 10, or 20 mg/kg body weight. In some embodiments, or example in parenteral administration, ALT-803 can be administered at a dose of about 0.5 µg/kg-about 15 µg/kg (e.g., 0.5, 1, 3, 5, 10, or 15 µg/kg).

In some embodiments, a subject in need thereof receiving combination therapy with the Ad5 [E1−, E2b−]-HER3 vaccine and ALT-803 is administered one or more dose of the Ad5 [E1−, E2b−]-HER3 vaccine and ALT-803 over a 21-day period. For example, as shown in FIG. 2A, a subject in need thereof can be administered the Ad-HER3 vaccine on Day 7, Day 14, and Day 21. Additionally, a subject in need thereof can be administered the IL-15 superagonist (ALT-803) on Day 10 and Day 17. In some embodiments, a subject in need thereof receiving combination therapy with the Ad5 [E1−, E2b−]-HER3 vaccine and ALT-803 is administered one or more dose of the Ad5 [E1−, E2b−]-HER3 vaccine and ALT-803 over an 8-week period. In some embodiments, a subject can be administered the Ad5 [E1−, E2b−]-HER3 vaccine on weeks 3 and 6 and can be administered the IL-15 superagonist (ALT-803) on weeks 1, 2, 4, 5, 7, and 8. Thus, in some embodiments, the subject is administered more than one dose of ALT-803 in a complete dosing regimen. In some embodiments, the subject can be administered at least 1 dose, at least 2 doses, at least 3 doses, at least 4 doses, or at least 5 doses of the IL-15 superagonist. In certain embodiments, the subject can be administered one less dose of ALT-803 than the Ad5 [E1−, E2b−]-HER3 vaccine.

In some embodiments, the IL-15 superagonist, such as ALT-803, can be encoded as an immunological fusion with the HER3 antigen. For example, in some embodiments the Ad5 [E1−, E2b−] vaccine can encode for HER3 and ALT-803 (Ad5 [E1−, E2b−]-HER3/ALT-803). In these embodiments, upon administration to a subject in need thereof, Ad5 [E1−, E2b−] vectors encoding for HER3 and ALT-803 induce expression of HER3 and ALT-803 as an immunological fusion, which is therapeutically active.

Combination therapy with Ad5[E1−, E2b−] vectors encoding for HER3 and ALT-803 can result in boosting the immune response, such that the combination of both therapeutic moieties acts to synergistically boost the immune response than either therapy alone. For example, combination therapy with Ad5[E1−, E2b−] vectors encoding for HER3 and ALT-803 can result in synergistic enhancement of stimulation of antigen-specific effector CD4+ and CD8+ T cells, stimulation of NK cell response directed towards killing infected cells, stimulation of neutrophils or monocyte cell responses directed towards killing infected cells via antibody dependent cell-mediated cytotoxicity (ADCC) or antibody dependent cellular phagocytosis (ADCP) mechanisms. Combination therapy with Ad5[E1−, E2b−] vectors encoding for HER3 and ALT-803 can synergistically boost any one of the above responses, or a combination of the above responses, to vastly improve survival outcomes after administration to a subject in need thereof.

In some embodiments, the IL-15 super agonist is a biologically active protein complex of two IL-15N72D molecules and a dimer of soluble IL-15Ra/Fc fusion protein, also known as ALT-803. The composition of ALT-803 and methods of producing and using ALT-803 are described in U.S. Patent Application Publication 2015/0374790, which is herein incorporated by reference. It is known that a soluble IL-15Rα fragment, containing the so-called "sushi" domain at the N terminus (Su), can bear most of the structural elements responsible for high affinity cytokine binding. A soluble fusion protein can be generated by linking the human IL-15RαSu domain (amino acids 1-65 of the mature human IL-15Rα protein) with the human IgG1 CH2-CH3 region containing the Fc domain (232 amino acids). This IL-15RαSu/IgG1 Fc fusion protein can have the advantages of dimer formation through disulfide bonding via IgG1 domains and ease of purification using standard Protein A affinity chromatography methods.

In some embodiments, ALT-803 can have a soluble complex consisting of 2 protein subunits of a human IL-15 variant associated with high affinity to a dimeric IL-15Rα sushi domain/human IgG1 Fc fusion protein. The IL-15 variant is a 114 amino acid polypeptide comprising the mature human IL-15 cytokine sequence with an Asn to Asp substitution at position 72 of helix C N72D). The human IL-15R sushi domain/human IgG1 Fc fusion protein comprises the sushi domain of the IL-15R subunit (amino acids 1-65 of the mature human IL-15Rα protein) linked with the human IgG1 CH2-CH3 region containing the Fc domain (232 amino acids). Aside from the N72D substitution, all of the protein sequences are human. Based on the amino acid sequence of the subunits, the calculated molecular weight of the complex comprising two IL-15N72D polypeptides (an example IL-15N72D sequence is shown in SEQ ID NO: 63) and a disulfide linked homodimeric IL-15RαSu/IgG1 Fc protein (an example IL-15RαSu/Fc domain is shown in SEQ ID NO: 64) is 92.4 kDa. In some embodiments, a recombinant vector encoding for a target antigen and for ALT-803 can have any sequence described herein to encode for the target antigen and can have SEQ ID NO: 63, SEQ ID NO: 63, SEQ ID NO: 64, and SEQ ID NO: 64 in any order, to encode for ALT-803. In other embodiments, an IL-15 superagonist, such as ALT-803, can be administered as a separate pharmaceutical composition before or after immunization with a recombinant vector encoding for a target antigen. In further embodiments, an IL-15 superagonist, such as ALT-803, can be administered in a separate pharmaceutical composition as a protein complex or as a recombinant vector, which encodes for the protein complex.

Each IL-15N720 polypeptide has a calculated molecular weight of approximately 12.8 kDa and the IL-15RαSu/IgG 1 Fc fusion protein has a calculated molecular weight of approximately 33.4 kDa. Both the IL-15N72D and IL-15RαSu/IgG 1 Fc proteins can be glycosylated resulting in an apparent molecular weight of ALT-803 of approximately 114 kDa by size exclusion chromatography. The isoelectric point (pI) determined for ALT-803 can range from approximately 5.6 to 6.5. Thus, the fusion protein can be negatively charged at pH 7.

Combination therapy with Ad5 [E1−, E2b−] vectors encoding for HER3, HER2/neu, HER1, HER4, or any combination thereof, and ALT-803 can result in boosting the immune response, such that the combination of both therapeutic moieties acts to synergistically boost the immune response than either therapy alone. For example, combination therapy with Ad5 [E1−, E2b−] vectors encoding for HER3, HER2/neu, HER1, or HER4 antigens, or any combination thereof and ALT-803 can result in synergistic enhancement of stimulation of antigen-specific effector CD4+ and CD8+ T cells, stimulation of NK cell response directed towards killing infected cells, stimulation of neutrophils or monocyte cell responses directed towards killing infected cells via antibody dependent cell-mediated cytotoxicity (ADCC), or antibody dependent cellular phagocytosis (ADCP) mechanisms. Combination therapy with Ad5 [E1−, E2b−] vectors encoding for HER3, HER2/neu, HER1, or HER4 antigens, or any combination thereof and ALT-803 can synergistically boost any one of the above responses, or a combination of the above responses, to vastly improve survival outcomes after administration to a subject in need thereof.

Any of the immunogenicity enhancing agents described herein can be fused or linked to a target antigen by expressing the immunogenicity enhancing agents and the target antigen in the same recombinant vector, using any recombinant vector described herein.

Nucleic acid sequences that encode for such immunogenicity enhancing agents can be any one of SEQ ID NO: 14-SEQ ID NO: 69 and are summarized in TABLE 1.

TABLE 1

| Sequence of Immunogenicity Enhancing Agents | |
|---|---|
| SEQ ID NO: 14 | TAASDNFQLSQGGQGFAIPIGQAMAIAGQIRSGGGSPTVHIGPTAFLGLGVVDNNGNGARVQRVVGSAPAASLGISTGDVITAVDGAPINSATAMADALNGHHPGDVISVTWQTKSGGTRTGNVTLAEGPPA |
| SEQ ID NO: 15 | MHHHHHHTAASDNFQLSQGGQGFAIPIGQAMAIAGQIRSGGGSPTVHIGPTAFLGLGVVDNNGNGARVQRVVGSAPAASLGISTGDVITAVDGAPINSATAMADALNGHHPGDVISVTWQTKSGGTRTGNVTLAEGPPAEFDDDDKDPPDPHQPDMTKGYCPGGRWGFGDLAVCDGEKYPDGSFWHQWMQTWFTGPQFYFDCVSGGEPLPGPPPPGGCGGAIPSEQPNAP |
| SEQ ID NO: 16 | MHHHHHHTAASDNFQLSQGGQGFAIPIGQAMAIAGQIRSGGGSPTVHIGPTAFLGLGVVDNNGNGARVQRVVGSAPAASLGISTGDVITAVDGAPINSATAMADALNGHHPGDVISVTWQTKSGGTRTGNVTLAEGPPAEFPLVPRGSPMGSDVRDLNALLPAVPSLGGGGCALPVSGAAQWAPVLDFAPPGASAYGSLGGPAPPPAPPPPPPPHSFIKQEPSWGGAEPHEEQCLSAFTVHFSGQFTGTAGACRYGPFGPPPPSQASSGQARMFPNAPYLPSCLESQPAIRNQGYSTVTFDGTPSYGHTPSHHAAQFPNHSFKHEDPMGQQGSLGEQQYSVPPPVYGCHTPTDSCTGSQALLLRTPYSSDNLYQMTSQLECMTWNQMNLGATLKGHSTGYESDNHTTPILCGAQYRIHTHGVFRGIQDVRRVPGVAPTLVRSASETSEKRPFMCAYSGCNKRYFKLSHLQMHSRKHTGEKPYQCDFKDCERRFFRSDQLKRHQRRHTGVKPFQCKTCQRKFSRSDHLKTHTRTHTGEKPFSCRWPSCQKKFARSDELVRHHNMHQRNMTKLQLAL |
| SEQ ID NO: 17 | MHHHHHHTAASDNFQLSQGGQGFAIPIGQAMAIAGQIRSGGGSPTVHIGPTAFLGLGVVDNNGNGARVQRVVGSAPAASLGISTGDVITAVDGAPINSATAMADALNGHHPGDVISVTWQTKSGGTRTGNVTLAEGPPAEFIEGRGSGCPLLENVISKTINPQVSKTEYKELLQEFIDDNATTNAIDELKECFLNQTDETLSNVEVFMQLIYDSSLCDLF |
| SEQ ID NO: 18 | MHHHHHHTAASDNFQLSQGGQGFAIPIGQAMAIAGQIRSGGGSPTVHIGPTAFLGLGVVDNNGNGARVQRVVGSAPAASLGISTGDVITAVDGAPINSATAMADALNGHHPGDVISVTWQTKSGGTRTGNVTLAEGPPAEFMVDFGALPPEINSARMYAGPGSASLVAAAQMWDSVASDLFSAASAFQSVVWGLTVGSWIGSSAGLMVAAASPYVAWMSVTAGQAELTAAQVRVAAAAYETAYGLTVPPPVIAENRAELMILIATNLLGQNTPAIAVNEAEYGEMWAQDAAAMFGYAAATATATATLLPFEEAPEMTSAGGLLEQAAAVEEASDTAAANQLMNNVPQALQQLAQPTQGTTPSSKLGGLWKTVSPHRSPISNMVSMANNHMSMTNSGVSMTNTLSSMLKGFAPAAAAQAVQTAAQNGVRAMSSLGSSLGSSGLGGGVAANLGRAASVGSLSVPQAWAAANQAVTPAARALPLTSLTSAAERGPGQMLGGLPVGQMGARAGGGLSGVLRVPPRPYVMPHSPAAGDIAPPALSQDRFADFPALPLDPSAMVAQVGPQVVNINTKLGYNNAVGAGTGIVIDPNGVVLTNNHVIAGATDINAFSVGSGQTYGVDVVGYDRTQDVAVLQLRGAGGLPSAAIGGGVAVGEPVVAMGNSGGQGGTPRAVPGRVVALGQTVQASDSLTGAEETLNGLIQFDAAIQPGDSGGPVVNGLGQVVGMNTAAS |
| SEQ ID NO: 19 | TAASDNFQLSQGGQGFAIPIGQAMAIAGQI |
| SEQ ID NO: 20 | TAASDNFQLSQGGQGFAIPIGQAMAIAGQIKLPTVHIGPTAFLGLGVVDNNGNGARVQRVVGSAPAASLGISTGDVITAVDGAPINSATAMADALNGHHPGDVISVTWQTKSGGTRTGNVTLAEGPPA |
| SEQ ID NO: 21 | TAASDNFQLSQGGQGFAIPIGQAMAIAGQIRSGGGSPTVHIGPTAFLGLGVVDNNGNGARVQRVVGSAPAASLGISTGDVITAVDGAPINSATAMADALNGHHPGDVISVTWQTKSGGTRTGNVTLAE |
| SEQ ID NO: 22 | MSNSRRRSLRWSWLLSVLAAVGLGLATAPAQAAPPALSQDRFADFPALPLDPSAMVAQVGPQVVNINTKLGYNNAVGAGTGIVIDPNGVVLTNNHVIAGATDINAFSVGSGQTYGVDVVGYDRTQDVAVLQLRGAGGLPSAAIGGGVAVGEPVVAMGNSGGQGGTPRAVPGRVVALGQTVQASDSLTGAEETLNGLIQFDAAIQPGDSGGPVVNGLGQVVGMNTAASDNFQLSQGGQGFAIPIGQAMAIAGQIRSGGGSPTVHIGPTAFLGLGVVDNNGNGARVQRVVGSAPAASLGISTGDVITAVDGAPINSATAMADALNGHHPGDVISVTWQTKSGGTRTGNVTLAEGPPA |
| SEQ ID NO: 23 | MKLKTLALSLLAAGVLAGCSSHSSNMANTQMKSDKIIIAHRGASGYLPEHTLESKALAFAQQADYLEQDLAMTKDGRLVVIHDHFLDGLTDVAKKFPHRHRKDGRYYVIDFTLKEIQSLEMTENFETKDGKQAQVYPNRFPLWKSHFRIHTFEDEIEFIQGLEKSTGKKVGIYPEIKAPWFHHQNGKDIAAETLKVLKKYGYDKKTDMVYLQTFDFNELKRIKTELLPQMGMDLKLVQLIAYTDWKETQEKDPKGYWVNYNYDWMFKPGAMAEVVKYADGVGPGWYMLVNKEESKPDNIVYTPLVKELAQYNVEVHPYTVRKDALPAFFTDVNQMYDVLLNKSGATGVFTDFPPDTGVEFLKGIK |
| SEQ ID NO: 24 | MEINVSKLRTDLPQVGVQPYRQVHASTGNPHSTVQNEADYHWRKDPELGFFSHIVGNGCIMQVGPVDNGAWDVGGGWNAETYAAVELIESHSTKEEFMTDYRLYIELLRNLADEAGLPKTLDTGSLAGIKTHEYCTNNQPNNHSDHVDPYPYLAKWGISREQFKHDIENGLTIETGWQKNDTGYWYVHSDGSYPKDKFEKINGTWYYFDSSGYMLADRWRKHTDGNWYWFDNSGEMATGWKKIADKWYYFNEEGAMKTGWVKYKDTWYYLDAKEGAMVSNAFIQSADGTGWYYLKPDGTLADRPEFRMSQMA |
| SEQ ID NO: 25 | MKYTSYILAFQLCIVLGSLGCYCQDPYVKEAENLKKYFNAGHSDVADNGTLFLGILKNWKEESDRKIMQSQIVSFYFKLFKNFKDDQSIQKSVETIKEDMNVKFFNSNKKKRDDFEKLTNYSVTDLNVQRKAIHELIQVMAELSPAAKTGKRKRSQMLFRGRRASQ |
| SEQ ID NO: 26 | MSTESMIRDVELAEEEALPKKTGGPQGSRRCLFLSLFSFLIVAGATTLFCLLHFGVIGPQREEFPRDLSLISPLAQAVRSSSRTPSDKPVAHVVANPQAEGQLQWLNRRANALLANGVELRDNQLVVPSEGLYLIYSQVLFKGQGCPSTHVLLTHTISRIAVSYQTKVNLLSAIKSPCQRETPEGAEAKPWYEPIYLGGVFQLEKGDRLSAEINRPDYLDFAESGQVYFGIIAL |
| SEQ ID NO: 27 | MYRMQLLSCIALSLALVTNSAPTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLT |
| SEQ ID NO: 28 | MTSKLAVALLAAFLISAALCEGAVLPRSAKELRCQCIKTYSKPFHPKFIKELRVIESGPHCANTEIIVKLSDGRELCLDPKENWVQRVVEKFLKRAENS |
| SEQ ID NO: 29 | MEPLVTWVVPLLFLFLLSRQGAACRTSECCFQDPPYPDADSGSASGPRDLRCYRISSDRYECSWQYEGPTAGVSHFLRCCLSSGRCCYFAAGSATRLQFSDQAGVSVLYTVTLWVESWARNQTEKSPEVTLQLYNSVKYEPPLGDIKVSKLAGQLRMEWETPDNQVGAEVQFRHRTPSSPWKLGDCGPQDDDTESCLCPLEMNVAQEFQLRRRQLGSQGSSWSKWSSPVCVPPENPPQPQVRFSVEQLGQDGRRRLTLKEQPTQLELPEGCQGLAPGTEVTYRLQLHMLSCPCKAKATRTLHLGICMPYLSGAAYNVAVISSNQFGPGLNQTWHIPADTHTEPVALNISVGTNGTTMYWPARAQSMTYCIEWQPVGQDGGLATCSLTAPQDPDPAGMATYSWSRESGAMGQEKCYYITIFASAIIPEICLTLWSTVLSTYHFGGNASAAGTPHHVSVKNHSLDSVSVDWAPSLLSTCPGVLKEYVVRCRDEDSKQVSEHPVQPTETQVTLSGLRAGVAYTVQVRADTAWLRGVWSQPQRFSIEVQVSDWLIFFASLGSFLSILLVGVLGYLGLNRAARHLCPPLPTPCASSAIEFPGGKETWQWINPVDFQEEASLQEALVVEMSWDKGERTEPLEKTELPEGAPELALDTELSLEDGDRCKAKM |

TABLE 1-continued

Sequence of Immunogenicity Enhancing Agents

| SEQ ID NO: | |
|---|---|
| SEQ ID NO: 30 | MAAEPVEDNCINFVAMKFIDNTLYFIAEDDENLESDYFGKLESKLS VIRNLNDQVLFIDQGNRPLFEDMTDSDCRDNAPRTIFIISMYKDSQ PRGMAVTISVKCEKISTLSCENKIISFKEMNPPDNIKDTKSDIIFF QRSVPGHDNKMQFESSSYEGYFLACEKERDLFKLILKKEDELGDRS IMFTVQNED |
| SEQ ID NO: 31 | MFHVSFRYIFGLPPLILVLLPVASSDCDIEGKDGKQYESVLMVSID QLLDSMKEIGSNCLNNEFNFFKRHICDANKEGMFLFRAARKLRQFL KMNSTGDFDLHLLKVSEGTTILLNCTGQVKGRKPAALGEAQPTKSL EENKSLKEQKKLNDLCFLKRLLQEIKTCWNKILMGTKEH |
| SEQ ID NO: 32 | MSRLPVLLLLQLLVRPGLQAPMTQTTSLKTSWVNCSNMIDEIITHL KQPPLPLLDFNNLNGEDQDILMENNLRRPNLEAFNRAVKSLQNASA IESILKNLLPCLPLATAAPTRIPIHIKDGDWNEFRRKLTFYLKTLE NAQAQQTTLSLAIF |
| SEQ ID NO: 33 | MGLTSQLLPPLFFLLACAGNFVHGHKCDITLQEIIKTLNSLTEQKT LCTELTVTDIFAASKNTTEKETFCRAATVLRQFYSHHEKDTRCLGA TAQQFHRHKQLIRFLKRLDRNLWGLAGLNSCPVKEANQSTLENFLE RLKTIMREKYSKCSS |
| SEQ ID NO: 34 | MRMLLHLSLLALGAAYVYAIPTEIPTSALVKETLALLSTHRTLLIA NETLRIPVPVHKNHQLCTEEIFQGIGTLESQTVQGGTVERLFKNLS LIKKYIDGQKKKCGEERRRVNQFLDYLQEFLGVMNTEWIIES |
| SEQ ID NO: 35 | MNSFSTSAFGPVAFSLGLLLVLPAAFPAPVPPGEDSKDVAAPHRQP LTSSERIDKQIRYILDGISALRKETCNKSNMCESSKEALAENNLNL PKMAEKDGCFQSGFNEETCLVKIITGLLEFEVYLEYLQNRFESSEE QARAVQMSTKVLIQFLQKKAKNLDAITTPDPTTNASLLTKLQAQNQ WLQDMTTHLILRSFKEFLQSSLRALRQM |
| SEQ ID NO: 36 | MVLTSALLLCSVAGQGCPTLAGILDINFLINKMQEDPASKCHCSAN VTSCLCLGIPSDNCTRPCFSERLSQMTNTTMQTRYPLIFSRVKKSV EVLKNNKCPYFSCEQPCNQTTAGNALTFLKSLLEIFQKEKMRGMRG KI |
| SEQ ID NO: 37 | MHSSALLCCLVLLTGVRASPGQGTQSENSCTHFPGNLPNMLRDLRD AFSRVKTFFQMKDQLDNLLLKESLLEDFKGYLGCQALSEMIQFYLE EVMPQAENQDPDIKAHVNSLGENLKTLRLRLRRCHRFLPCENKSKA VEQVKNAFNKLQEKGIYKAMSEFDIFINYIEAYMTMKIRN |
| SEQ ID NO: 38 | MALLLTTVIALTCLGGFASPGPVPPSTALRELIEELVNITQNQKAP LCNGSMVWSINLTAGMYCAALESLINVSGCSAIEKTQRMLSGFCPH KVSAGQFSSLHVRDTKIEVAQFVKDLLLHLKKLFREGQFNRNFESI IICRDRT |
| SEQ ID NO: 39 | MDFQVQIFSFLLISASVIMSRANWVNVISDLKKIEDLIQSMHIDAT LYTESDVHPSCKVTAMKCFLLELQVISLESGDASIHDTVENLIILA NNSLSSNGNVTESGCKECEELEEKNIKEFLQSFVHIVQMFINTS |
| SEQ ID NO: 40 | MEGDGSDPEPPDAGEDSKSENGENAPIYCICRKPDINCFMIGCDNC NEWFHGDCIRITEKMAKAIREWYCRECREKDPKLEIRYRHKKSRER DGNERDSSEPRDEGGGRKRPVPDPNLQRRAGSGTGVGAMLARGSAS PHKSSPQPLVATPSQHHQQQQQQIKRSARMCGECEACRRTEDCGHC DFCRDMKKFGGPNKIRQKCRLRQCQLRARESYKYFPSSLSPVTPSE LSPRPRRPLPTQQQPQPSQKLGRIREDEGAVASSTVKEPPEATATP EPLSDEDLPLDPDLYQDFCAGAFDDNGLPWMSDTEESPFLDPALRK RAVKVKHVKRREKKSEKKKEERYKRHRQKQKHKDKWKPPERADAKD PASLPQCLGPGCVRPAQPSSKYCSDDCGMKLAANRIYEILPQRIQQ WQQSPCIAEEHGKKLLERIRREQQSARTRLQEMERRFHELEAIILR AKQQAVREDEESNEGDSDDTDLQIFCVSCGHPINPRVALRHMERCY AKYESQTSFGSMYPTRIEGATRLFCDVYNPQSKTYCKRLQVLCPEH SRDPKVPADEVCGCPLRDVFELTGDFCRLPKRQCNRHYCWEKLRR AEVDLERVRVWYKLDELFEQERNVRTAMTNRAGLLALMLHQTIQHD PLTTDLRSSADR |
| SEQ ID NO: 41 | MIKLKFGVFFTVLLSSAYAHGTPQNITDLCAEYHNTQIYTLNDKIF SYTESLAGKREMAIITFKNGAIFQVEVPGSQHIDSQKKAIERMKDT LRIAYLTEAKVEKLCVWNNKTPHAIAAISMAN |
| SEQ ID NO: 42 | MVKIIFVFFIFLSSFSYANDDKLYRADSRPPDEIKQSGGLMPRGQN EYFDRGTQMNINLYDHARGTQTGFVRHDDGYVSTSISLRSAHLVGQ TILSGHSTYYIYVIATAPNMFNVNDVLGAYSPHPDEQEVSALGGIP YSQIYGWYRVHFGVLDEQLHRNRGYRDRYYSNLDIAPAADGYGLAG FPPEHRAWREEPWIHHAPPGCGNAPRSSMSNTCDEKTQSLGVKFLD EYQSKVKRQIFSGYQSDIDTHNRIKDEL |
| SEQ ID NO: 43 | MIKLKFGVFFTVLLSSAYAHGTPQNITDLCAEYHNTQIHTLNDKIL SYTESLAGNREMAIITFKNGATFQVEVPGSQHIDSQKKAIERMKDT LRIAYLTEAKVEKLCVWNNKTPHAIAAISMAN |
| SEQ ID NO: 44 | DPNAPKRPPSAFFLFCSE |
| SEQ ID NO: 45 | MCCTKSLLLAALMSVLLLHLCGESEAASNFDCCLGYTDRILHPKFI VGFTRQLANEGCDINAIIFHTKKKLSVCANPKQTWVKYIVRLLSKK VKNM |
| SEQ ID NO: 46 | MQVSTAALAVLLCTMALCNQFSASLAADTPTACCFSYTSRQIPQNF IADYFETSSQCSKPGVIFLTKRSRQVCADPSEEWVQKYVSDLELSA |
| SEQ ID NO: 47 | MWLQSLLLLGTVACSISAPARSPSPSTQPWEHVNAIQEARRLLNLS RDTAAEMNETVEVISEMFDLQEPTCLQTRLELYKQGLRGSLTKLKG PLTMMASHYKQHCPPTPETSCATQIITFESFKENLKDFLLVIPFDC WEPVQE |
| SEQ ID NO: 48 | MAGPATQSPMKLMALQLLLWHSALWTVQEATPLGPASSLPQSFLL KCLEQVRKIQGDGAALQEKLCATYKLCHPEELVLLGHSLGIPWAPL SSCPSQALQLAGCLSQLHSGLFLYQGLLQALEGISPELGPTLDTLQ LDVADFATTIWQQMEELGMAPALQPTQGAMPAFASAFQRRAGGVL VASHLQSFLEVSYRVLRHLAQP |
| SEQ ID NO: 49 | QEINSSY |
| SEQ ID NO: 50 | SHPRLSA |
| SEQ ID NO: 51 | SMPNPMV |
| SEQ ID NO: 52 | GLQQVLL |
| SEQ ID NO: 53 | HELSVLL |
| SEQ ID NO: 54 | YAPQRLP |
| SEQ ID NO: 55 | TPRTLPT |

TABLE 1-continued

Sequence of Immunogenicity Enhancing Agents

| SEQ ID NO: | |
|---|---|
| SEQ ID NO: 56 | APVHSSI |
| SEQ ID NO: 57 | APPHALS |
| SEQ ID NO: 58 | TFSNRFI |
| SEQ ID NO: 59 | VVPTPPY |
| SEQ ID NO: 60 | ELAPDSP |
| SEQ ID NO: 61 | TPDCVTGKVEYTKYNDDDTFTVKVGDKELFTNRWNLQSLLLSAQIT GMTVTIKQNACHNGGGFSEVIFR |
| SEQ ID NO: 62 | MSRKLFASILIGALLGIGAPPSAHAGADDVVDSSKSFVMENFSSYH GTKPGYVDSIQKGIQKPKSGTQGNYDDDWKGFYSTDNKYDAAGYSV DNENPLSGKAGGVVKVTYPGLTKVLALKVDNAETIKKELGLSLTEP LMEQVGTEEFIKRFGDGASRVVLSLPFAEGSSSVEYINNWEQAKAL SVELEINFETRGKRGQDAMYEYMAQACAGNRVRRSVGSSLSCINLD WDVIRDKTKTKIESLKEHGPIKNKMSESPNKTVSEEKAKQYLEEFH QTALEHPELSELKTVTGTNPVFAGANYAAWAVNVAQVIDSETADN LEKTTAALSILPGIGSVMGIADGAVHHNTEEIVAQSIALSSLMVAQ AIPLVGELVDIGFAAYNFVESIINLFQVVHNSYNRPAYSPGHKTQP FLHDGYAVSWNTVEDSIIRTGFQGESGHDIKITAENTPLPIAGVLL PTIPGKLDVNKSKTHISVNGRKIRMRCRAIDGDVTFCRPKSPVYVG NGVHANLHVAFHRSSSEKIHSNEISSDSIGVLGYQKTVDHTKVNSK LSLFFEIKS |
| SEQ ID NO: 63 | NWVNVISDLKKIEDLIQSMHIDATLYTESDVHPSCKVTAMKCFLLE LQVISLESGDASIHDTVENLIILANDSLSSNGNVTESGCKECEELE EKNIKEFLQSFVHIVQMFINTS |
| SEQ ID NO: 64 | ITCPPPMSVEHADIWVKSYSLYSRERYICNSGFKRKAGTSSLTECV LNKATNVAHWTTPSLKCIREPKSCDKTHTCPPCPAPELLGGPSVFL FPPKPKDTLMISRTPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLTCLVKGFYPSDIAVE WESNGQPENNYKTTPPVLDSDGSFFLYSKLTVDKSRWQQGNVFSCS VMHEALHNHYTQKSLSLSPGK |
| SEQ ID NO: 65 | GADDVVDSSKSFVMENFSSYHGTKPGYVDSIQKGIQKPKSGTQGNY DDDWKEFYSTDNKYDAAGYSVDNENPLSGKAGGVVKVTYPGLTK VLALKVDNAETIKKELGLSLTEPLMEQVGTEEFIKRFGDGASRVVL SLPFAEGSSSVEYINNWEQAKALSVELEINFETRGKRGQDAMYEYM AQACAGNRVRRSVGSSLSCINLDWDVIRDKTKTKIESLKEHGPIKN KMSESPNKTVSEEKAKQYLEEFHQTALEHPELSELKTVTGTNPVFA GANYAAWAVNVAQVIDSETADNLEKTTAALSILPGIGSVMGIADGA VHHNTEEIVAQSIALSSLMVAQAIPLVGELVDIGFAAYNFVESIIN LFQVVHNSYNRPAYSPGHKTQPFLHDGYAVSWNTVEDSIIRTGFQG ESGHDIKITAENTPLPIAGVLLPTIPGKLDVNKSKTHISVNGRKIR MRCRAIDGDVTFCRPKSPVYVGNGVHANLHVAFHRSSSEKIHSNEI SSDSIGVLGYQKTVDHTKVNSKLSLFFEIKS |
| SEQ ID NO: | MESHSRAGKSRKSAKFRSISRSLMLCNAKTSDDGSSPDEKYPDPFE ISLAQGKEGIFHSSVQLADTSEAGPSSVPDLALASEAAQLQAAGND RGKTCRRIFFMKESSTASSREKPGKLEAQSSNFLFPKACHQRARSN |
| SEQ ID NO: 66 | STSVNPYCTREIDFPMTKKSAAPTDRQPYSLCSNRKSLSQQLDCPA GKAAGTSRPTRSLSTAQLVQPSGGLQASVISNIVLMKGQAKGLGFS IVGGKDSIYGPIGIYVKTIFAGGAAAADGRLQEGDEILELNGESMA GLTHQDALQKFKQAKKGLLTLTVRTRLTAPPSLCSHLSPPLCRSLS SSTCITKDSSSFALESPSAPISTAKPNYRIMVEVSLQKEAGVGLGI GLCSVPYFQCISGIFVHTLSPGSVAHLDGRLRCGDEIVEISDSPVH CLTLNEVYTILSRCDPGPVPIIVSRHPDPQVSEQQLKEAVAQAVEN TKFGKERHQWSLEGVKRLESSWHGRPTLEKEREKNSAPPHRRAQKV MIRSSSDSSYMSGSPGGSPGSGSAEKPSSDVDISTHSPSLPLAREP VVLSIASSRLPQESPPLPESRDSHPPLRLKKSFEILVRKPMSSKPK PPPRKYFKSDSDPQKSLEERENSSCSSGHTPPTCGQEARELLPLLL PQEDTAGRSPSASAGCPGPGIGPQTKSSTEGEPGWRRASPVTQTSP IKHPLLKRQARMDYSFDTTAEDPWVRISDCIKNLFSPIMSENHGHM PLQPNASLNEEEGTQGHPDGTPPKLDTANGTPKVYKSADSSTVKKG PPVAPKPAWFRQSLKGLRNRASDPRGLPDPALSTQPAPASREHLGS HIRASSSSSSIRQRISSFETFGSSQLPDKGAQRLSLQPSSGEAAKP LGKHEEGRFSGLLGRGAAPTLVPQQPEQVLSSGSPAASEARDPGVS ESPPPGRQPNQKTLPPGPDPLLRLLSTQAEESQGPVLKMPSQRARS FPLTRSQSCETKLLDEKTSLLYSISSQVSSAVMKSLLCLPSSISCA QTPCIPKEGASPTSSSNEDSAANGSAETSALDTGFSLNLSELREYT EGLTEAKEDDDGDHSSLQSGQSVISLLSSEELKKLIEEVKVLDEAT LKQLDGIHVTILHKEEGAGLGFSLAGGADLENKVITVHRVFPNGLA SQEGTIQKGNEVLSINGKSLKGTTHHDALAILRQAREPRQAVIVTR KLTPEAMPDLNSSTDSAASASAASDVSVESTEATVCTVTLELMSAG LGFSLEGGKGSLHGDLPLTINRIFKGAASEQSETVQPGDEILQLGG TAMQGLTRFEAWNIIKALPDGPVTIVIRRKSLQSKETTAAGDS |
| SEQ ID NO: 67 | MTPGKTSLVSLLLLLSLEAIVKAGITIPRNPGCPNSEDKNFPRTVM VNLNIHNRNTNTNPKRSSDYYNRSTSPWNLHRNEDPERYPSVIWEA KCRHLGCINADGNVDYHMNSVPIQQEILVLRREPPHCPNSFRLEKI LVSVGCTCVTPIVHHVA |
| SEQ ID NO: 68 | RAVPGGSSPAWTQCQQLSQKLCTLAWSAHPLVGHMDLREEGDEET TNDVPHIQCGDGCDPQGLRDNSQFCLQRIHQGLIFYEKLLGSDIFT GEPSLLPDSPVGQLHASLLGLSQLLQPEGHHWETQQIPSLSPSQPW QRLLLRFKILRSLQAFVAVAARVFAHGAATLSPIWELKKDVYVVEL DWYPDAPGEMVVLTCDTPEEDGITWTLDQSSEVLGSGKTLTIQVKE FGDAGQYTCHKGGEVLSHSLLLLHKKEDGIWSTDILKDQKEPKNKT FLRCEAKNYSGRFTCWWLTTISTDLTFSVKSSRGSSDPQGVTCGAA TLSAERVRGDNKEYEYSVECQEDSACPAAEESLPIEVMVDAVHKLK YENYTSSFFIRDIIKPDPPKNLQLKPLKNSRQVEVSWEYPDTWSTP HSYFSLTFCVQVQGKSKREKKDRVFTDKTSATVICRKNASISVRAQ DRYYSSSWSEWASVPCS |
| SEQ ID NO: 69 | MCFPKVLSDDMKKLKARMVMLLPTSAQGLGAWVSACDTEDTVGH LGPWRDKDPALWCQLCLSSQHQAIERFYDKMQNAESGRGQVMSSL AELEDDFKEGYLETVAAYYEEQHPELTPLLEKERDGLRCRGNRSPV PDVEDPATEEPGESFCDKVMRWFQAMLQRLQTWWHGVLAWVKE KVVALVHAVQALWKQFQSFCCSLSELFMSSFQSYGAPRGDKEELTP QKCSEPQSSK |

In some embodiments, the nucleic acid sequences for the target antigen and the immunological fusion partner are not separated by any nucleic acids. In other embodiments, a nucleic acid sequence that encodes for a linker can be inserted between the nucleic acid sequence encoding for any target antigen described herein and the nucleic acid sequence encoding for any immunological fusion partner described herein. Thus, in certain embodiments, the protein produced following immunization with the viral vector containing a target antigen, a linker, and an immunological fusion partner can be a fusion protein comprising the target antigen of interest followed by the linker and ending with the immunological fusion partner, thus linking the target antigen to an immunological fusion partner that increases the immunogenicity of the target antigen of interest via a linker. In some embodiments, the sequence of linker nucleic acids can be from about 1 to about 150 nucleic acids long, from about 5 to about 100 nucleic acids along, or from about 10 to about 50 nucleic acids in length. In some embodiments, the nucleic acid sequences may encode one or more amino acid residues. In some embodiments, the amino acid sequence of the linker can be from about 1 to about 50, or about 5 to about 25 amino acid residues in length. In some embodiments, the sequence of the linker comprises less than 10 amino acids. In some embodiments, the linker can be a polyalanine linker, a polyglycine linker, or a linker with both alanines and glycines.

Nucleic acid sequences that encode for such linkers can be any one of SEQ ID NO: 60-SEQ ID NO: 84 and are summarized in TABLE 2.

TABLE 2

Sequences of Linkers

| SEQ ID NO | Sequence |
|---|---|
| SEQ ID NO: 70 | MAVPMQLSCSR |
| SEQ ID NO: 71 | RSTG |
| SEQ ID NO: 72 | TR |
| SEQ ID NO: 73 | RSQ |
| SEQ ID NO: 74 | RSAGE |
| SEQ ID NO: 75 | RS |
| SEQ ID NO: 76 | GG |
| SEQ ID NO: 77 | GSGGSGGSG |
| SEQ ID NO: 78 | GGSGGSGGSGG |
| SEQ ID NO: 79 | GGSGGSGGSGGSGG |
| SEQ ID NO: 80 | GGSGGSGGSGGSGGSGG |
| SEQ ID NO: 81 | GGSGGSGGSGGSGGSGGSGG |
| SEQ ID NO: 82 | GGSGGSGGSGGSGGSGGSGGSGG |
| SEQ ID NO: 83 | GGSGGSGGSGGSGGSG |
| SEQ ID NO: 84 | GSGGSGGSGGSGGSGG |

XV. Costimulatory Molecules

In addition to the use of a recombinant adenovirus-based vector vaccine containing target antigens such as antigens or epitopes of HER1, HER2/neu, HER3, HER4, or any combination thereof, co-stimulatory molecules can be incorporated into said vaccine to increase immunogenicity. Initiation of an immune response requires at least two signals for the activation of naive T cells by APCs (Damle, et al. J Immunol 148:1985-92 (1992); Guinan, et al. Blood 84:3261-82 (1994); Hellstrom, et al. Cancer Chemother Pharmacol 38:S40-44 (1996); Hodge, et al. Cancer Res 39:5800-07 (1999)). An antigen specific first signal is delivered through the T cell receptor (TCR) via the peptide/major histocompatibility complex (MHC) and causes the T cell to enter the cell cycle. A second, or costimulatory, signal may be delivered for cytokine production and proliferation.

At least three distinct molecules normally found on the surface of professional antigen presenting cells (APCs) have been reported as capable of providing the second signal critical for T cell activation: B7-1 (CD80), ICAM-1 (CD54), and LFA-3 (human CD58) (Damle, et al. J Immunol 148: 1985-92 (1992); Guinan, et al. Blood 84: 3261-82 (1994); Wingren, et al. Crit Rev Immunol 15: 235-53 (1995); Parra, et al. Scand. J Immunol 38: 508-14 (1993); Hellstrom, et al. Ann NY Acad Sci 690: 225-30 (1993); Parra, et al. J Immunol 158: 637-42 (1997); Sperling, et al. J Immunol 157: 3909-17 (1996); Dubey, et al. J Immunol 155: 45-57 (1995); Cavallo, et al. Eur J Immunol 25: 1154-62 (1995)).

These costimulatory molecules have distinct T cell ligands. B7-1 interacts with the CD28 and CTLA-4 molecules, ICAM-1 interacts with the CD11a/CD18 (LFA-1β2 integrin) complex, and LFA-3 interacts with the CD2 (LFA-2) molecules. Therefore, in a preferred embodiment, it would be desirable to have a recombinant adenovirus vector that contains B7-1, ICAM-1, and LFA-3, respectively, that, when combined with a recombinant adenovirus-based vector vaccine containing one or more nucleic acids encoding target antigens such as antigens or epitopes of HER1, HER2/neu, HER3, HER4, or any combination thereof, will further increase/enhance anti-tumor immune responses directed to specific target antigens.

FOLFOX (5-Fluorouracil, Leucovorin, Oxaliplatin)

A randomized trial comparing irinotecan and bolus fluorouracil plus leucovorin (IFL, control combination), oxaliplatin and infused fluorouracil plus leucovorin (FOLFOX), or irinotecan and oxaliplatin (IROX) established the FOLFOX combination, given for a total of 6 months, as the standard of care for first line treatment in patients with metastatic colorectal cancer (mCRC). Though multiple infusion schedules of FOLFOX have been validated, typically denominated as 'modified FOLFOX, there are no essential changes in the constituent cytotoxic agents of the regimen. Of these, mFOLFOX6 is one of the most widely used.

Oxaliplatin, however, is very difficult for patients to receive for greater than 6 months (12 cycles) due to progressive neurotoxicity. Though 6 months of combination therapy remains the standard of care in mCRC, clinical judgment may influence the decision to limit the number of oxaliplatin-containing cycles towards the end of treatment Other trials, including the CAIRO3 study, have demonstrated the feasibility and benefit of discontinuation of oxaliplatin after a 3 month "induction" period with continuation of 5-FU and leucovorin as "maintenance" therapy.

Bevacizumab (Avastin®)

Addition of bevacizumab to first-line 5-FU and Oxaliplatin containing regimens was demonstrated to increase time to progression in mCRC patients with a manageable side effect profile and non-overlapping toxicities. Later trials indicated that continuing bevacizumab beyond first progression (in combination with subsequent chemotherapy) improved overall survival in an unselected group of patients by KRAS mutational status, which has led to its approved use in the maintenance setting.

Capecitabine

This agent is a prodrug that is enzymatically converted to 5-fluorouracil by 3 enzymatic steps following oral ingestion. As an orally active fluoropyrimidine, capecitabine has been approved for use in the adjuvant setting. In the advanced colon cancer setting, it has been shown to be equally efficacious as 5-fluorouracil, though with more reported rates of hand-foot syndrome. This agent offers the convenience of the oral route with its benefits of reducing infusion commitments for patients in the maintenance setting, while achieving high concentrations intratumorally, given the higher concentrations of thymidine phosphorylase in tumor as compared to normal tissues.

XVI. Immune Pathway Checkpoint Modulators

In certain embodiments, immune pathway checkpoint inhibitors are combined with compositions comprising adenoviral vectors disclosed herein. In certain embodiments, a patient received an immune pathway checkpoint inhibitor in conjunction with a vaccine or pharmaceutical compositions described herein. In further embodiments, compositions are administered with one or more immune pathway checkpoint modulators. A balance between activation and inhibitory signals regulates the interaction between T lymphocytes and disease cells, wherein T-cell responses are initiated through antigen recognition by the T-cell receptor (TCR). The inhibitory pathways and signals are referred to as immune pathway checkpoints. In normal circumstances, immune pathway checkpoints play a critical role in control and prevention of autoimmunity and also protect from tissue damage in response to pathogenic infection.

Certain embodiments provide combination immunotherapies comprising viral vector-based vaccines and compositions for modulating immune pathway checkpoint inhibitory pathways for the prevention and/or treatment of cancer and infectious diseases. In some embodiments, modulating is increasing expression or activity of a gene or protein. In some embodiments, modulating is decreasing expression or activity of a gene or protein. In some embodiments, modulating affects a family of genes or proteins.

In general, the immune inhibitory pathways are initiated by ligand-receptor interactions. It is now clear that in diseases, the disease can co-opt immune-checkpoint pathways as mechanism for inducing immune resistance in a subject.

The induction of immune resistance or immune inhibitory pathways in a subject by a given disease can be blocked by molecular compositions such as siRNAs, antisense, small molecules, mimic, a recombinant form of ligand, receptor or protein, or antibodies (which can be an Ig fusion protein) that are known to modulate one or more of the Immune Inhibitory Pathways. For example, preliminary clinical findings with blockers of immune-checkpoint proteins, such as Cytotoxic T-lymphocyte-associated antigen 4 (CTLA4) and programmed cell death protein 1 (PD1) have shown promise for enhancing anti-tumor immunity.

Because diseased cells can express multiple inhibitory ligands, and disease-infiltrating lymphocytes express multiple inhibitory receptors, dual or triple blockade of immune pathway checkpoints proteins may enhance anti-disease immunity. Combination immunotherapies as provide herein can comprise one or more compositions comprising an immune pathway checkpoint modulator that targets one or more of the following immune-checkpoint proteins: PD1, PDL1, PDL2, CD28, CD80, CD86, CTLA4, B7RP1, ICOS, B7RPI, B7-H3 (also known as CD276), B7-H4 (also known as B7-S1, B7x and VCTN1), BTLA (also known as CD272), HVEM, KIR, TCR, LAG3 (also known as CD223), CD137, CD137L, OX40, OX40L, CD27, CD70, CD40, CD40L, TIM3 (also known as HAVcr2), GAL9, A2aR and Adenosine.

In some aspects, the immune pathway checkpoint modulator comprises siRNAs, antisense, small molecules, mimic, a recombinant form of a ligand, a recombinant form of a receptor, antibodies, or a combination thereof. In some aspects, the immune pathway checkpoint inhibitor is an anti-PD-1 antibody or an anti-PD-L1 antibody. In further aspects, the immune pathway checkpoint inhibitor is Avelumab. In some aspects, the immune response is increased at least 2-, at least 3-, at least 4-, at least 5-, at least 6-, at least 7-, at least 8-, at least 9-, at least 10-, at least 15-, at least 20-, or at least 25-fold.

In some aspects, the immune pathway checkpoint modulator targets a PD1 protein. In some aspects, the immune pathway checkpoint modulator comprises siRNAs, antisense, small molecules, mimic, a recombinant form of a ligand, a recombinant form of a receptor, antibodies, or a combination thereof. In some aspects, the immune pathway checkpoint inhibitor is an anti-PD-1 antibody or an anti-PD-L1 antibody. In some aspects, the immune pathway checkpoint inhibitor is Avelumab. In further aspects, the Avelumab is administered to the subject at least once, at least twice, or at least three times a week. In some aspects, Avelumab is administered on day 1 of week 1, day 1 of week 2, day 1 of week 4, day 1 of week 8, day 1 of week 12, and day 1 of week 16. In further aspects, Avelumab is administered after administration of recombinant adenovirus vector comprising a nucleic acid sequence encoding an antigen. In further aspects, Avelumab is administered to the subject at a dose comprising 1 mg/kg to 20 mg/kg. In still further aspects, the dose comprises 10 mg/kg.

In some embodiments, the molecular composition comprises siRNAs. In some embodiments, the molecular composition comprises a small molecule. In some embodiments, the molecular composition comprises a recombinant form of a ligand. In some embodiments, the molecular composition comprises a recombinant form of a receptor. In some embodiments, the molecular composition comprises an antibody. In some embodiments, the combination therapy comprises more than one molecular composition and/or more than one type of molecular composition. As it will be appreciated by those in the art, future discovered proteins of the immune checkpoint inhibitory pathways are also envisioned to be encompassed by the present disclosure.

In some embodiments, combination immunotherapies comprise molecular compositions for the modulation of CTLA4. In some embodiments, combination immunotherapies comprise molecular compositions for the modulation of PD1. In some embodiments, combination immunotherapies comprise molecular compositions for the modulation of PDL1. In some embodiments, combination immunotherapies comprise molecular compositions for the modulation of LAG3. In some embodiments, combination immunotherapies comprise molecular compositions for the modulation of B7-H3. In some embodiments, combination immunotherapies comprise molecular compositions for the modulation of B7-H4. In some embodiments, combination immunotherapies comprise molecular compositions for the modulation of TIM3. In some embodiments, modulation is an increase or enhancement of expression. In other embodiments, modulation is the decrease of absence of expression.

Two non-limiting exemplary immune pathway checkpoint inhibitors include the cytotoxic T lymphocyte associated antigen-4 (CTLA-4) and the programmed cell death protein-1 (PD1). CTLA-4 can be expressed exclusively on T-cells where it regulates early stages of T-cell activation. CTLA-4 interacts with the co-stimulatory T-cell receptor CD28 which can result in signaling that inhibits T-cell activity. Once TCR antigen recognition occurs, CD28 signaling may enhances TCR signaling, in some cases leading to activated T-cells and CTLA-4 inhibits the signaling activity of CD28. The present disclosure provides immunotherapies as provided herein in combination with anti-CTLA-4 monoclonal antibody for the prevention and/or treatment of cancer and infectious diseases. The present disclosure provides vaccine or immunotherapies as provided herein in combination with CTLA-4 molecular compositions for the prevention and/or treatment of cancer and infectious diseases.

Programmed death cell protein ligand-1 (PDL1) is a member of the B7 family and is distributed in various tissues and cell types. PDL1 can interact with PD1 inhibiting T-cell activation and CTL mediated lysis. Significant expression of PDL1 has been demonstrated on various human tumors and PDL1 expression is one of the key mechanisms in which tumors evade host anti-tumor immune responses. Programmed death-ligand 1 (PDL1) and programmed cell death protein-1 (PD1) interact as immune pathway checkpoints. This interaction can be a major tolerance mechanism which results in the blunting of anti-tumor immune responses and subsequent tumor progression. PD1 is present on activated T cells and PDL1, the primary ligand of PD1, is often expressed on tumor cells and antigen-presenting cells (APC) as well as other cells, including B cells. PDL1 interacts with PD1 on T cells inhibiting T cell activation and cytotoxic T lymphocyte (CTL) mediated lysis. The present disclosure provides immunotherapies as provided herein in combination with anti-PD1 or anti-PDL1 monoclonal antibody for the prevention and/or treatment of cancer and infectious diseases.

Certain embodiments may provide immunotherapies as provided herein in combination with PD1 or anti-PDL1 molecular compositions for the prevention and/or treatment of cancer and infectious diseases. Certain embodiments may provide immunotherapies as provided herein in combination with anti-CTLA-4 and anti-PD1 monoclonal antibodies for the prevention and/or treatment of cancer and infectious diseases. Certain embodiments may provide immunotherapies as provided herein in combination with anti-CTLA-4 and PDL1 monoclonal antibodies. Certain embodiments may provide vaccine or immunotherapies as provided herein in combination with anti-CTLA-4, anti-PD1, anti-PDL1 monoclonal antibodies, or a combination thereof, for the treatment of cancer and infectious diseases.

Immune pathway checkpoint molecules can be expressed by T cells. Immune pathway checkpoint molecules can effectively serve as "brakes" to down-modulate or inhibit an immune response. Immune pathway checkpoint molecules include, but are not limited to Programmed Death 1 (PD1 or PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as hepatitis A virus cellular receptor 2 (HAVCR2), GenBank accession number: JX049979.1), B and T lymphocyte associated (BTLA) (also known as CD272, accession number: NM_181780.3), BY55 (also known as CD160, GenBank accession number: CR541888.1), TIGIT (also known as IVSTM3, accession number: NM_173799), LAIR1 (also known as CD305, GenBank accession number: CR542051.1), SIGLECIO (GenBank accession number: AY358337.1), natural killer cell receptor 2B4 (also known as CD244, accession number: NM_001166664.1), PPP2CA, PPP2CB, PTPN6, PTPN22, CD96, CRTAM, SIGLEC7, SIGLEC9, TNFRSF10B, TNFRSF10A, CASP8, CASP10, CASP3, CASP6, CASP7, FADD, FAS, TGFBRII, TGFR-BRI, SMAD2, SMAD3, SMAD4, SMAD10, SKI, SKIL, TGIF1, ILIORA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3 which directly inhibit immune cells. For example, PD1 can be combined with an adenoviral vector-based composition to treat a patient in need thereof.

Additional immune pathway checkpoints that can be targeted can be adenosine A2a receptor (ADORA), CD276, V-set domain containing T cell activation inhibitor 1 (VTCN1), indoleamine 2,3-dioxygenase 1 (IDO1), killer cell immunoglobulin-like receptor, three domains, long cytoplasmic tail, 1 (KIR3DL1), V-domain immunoglobulin suppressor of T-cell activation (VISTA), cytokine inducible SH2-containing protein (CISH), hypoxanthine phosphoribosyltransferase 1 (HPRT), adeno-associated virus integration site 1 (AAVS1), or chemokine (C—C motif) receptor 5 (gene/pseudogene) (CCR5), or any combination thereof.

TABLE 3, without being exhaustive, shows exemplary immune pathway checkpoint genes that can be inactivated to improve the efficiency of the adenoviral vector-based composition as described herein. Immune pathway checkpoints gene can be selected from such genes listed in TABLE 3 and others involved in co-inhibitory receptor function, cell death, cytokine signaling, arginine tryptophan starvation, TCR signaling, Induced T-reg repression, transcription factors controlling exhaustion or energy, and hypoxia mediated tolerance.

TABLE 3

Examples of Immune Pathway Checkpoint Genes

| Gene Symbol | NCBI # (GRCh38.p2) | Start | Stop | Genome location |
|---|---|---|---|---|
| ADORA2A | 135 | 24423597 | 24442360 | 22q11.23 |
| CD276 | 80381 | 73684281 | 73714518 | 15q23-q24 |
| VTCN1 | 79679 | 117143587 | 117270368 | 1p13.1 |
| BTLA | 151888 | 112463966 | 112499702 | 3q13.2 |
| CTLA4 | 1493 | 203867788 | 203873960 | 2q33 |
| IDO1 | 3620 | 39913809 | 39928790 | 8p12-p11 |
| KIR3DL1 | 3811 | 54816438 | 54830778 | 19q13.4 |
| LAG3 | 3902 | 6772483 | 6778455 | 12p13.32 |
| PDCD1 | 5133 | 241849881 | 241858908 | 2q37.3 |
| HAVCR2 | 84868 | 157085832 | 157109237 | 5q33.3 |
| VISTA | 64115 | 71747556 | 71773580 | 10q22.1 |
| CD244 | 51744 | 160830158 | 160862902 | 1q23.3 |
| CISH | 1154 | 50606454 | 50611831 | 3p21.3 |

The combination of an adenoviral-based composition and an immune pathway checkpoint modulator may result in reduction in infection, progression, or symptoms of a disease in treated patients, as compared to either agent alone. In another embodiment, the combination of an adenoviral-based composition and an immune pathway checkpoint modulator may result in improved overall survival of treated patients, as compared to either agent alone. In some cases, the combination of an adenoviral-based composition and an immune pathway checkpoint modulator may increase the frequency or intensity of disease-specific T cell responses in treated patients as compared to either agent alone.

Certain embodiments may also provide the use of immune pathway checkpoint inhibition to improve performance of an adenoviral vector-based composition. Certain immune pathway checkpoint inhibitors may be administered at the time of an adenoviral vector-based composition. Certain immune pathway checkpoint inhibitors may also be administered after the administration of an adenoviral vector-based composition. Immune pathway checkpoint inhibition may occur simultaneously to an adenoviral vaccine administration. Immune pathway checkpoint inhibition may occur 1, 2, 3, 4, 5, 6, 7, 8, 9, 10, 15, 20, 30, 40, 50, or 60 minutes after vaccination. Immune pathway checkpoint inhibition may also occur 1, 2, 3, 4, 5, 6, 7, 8, 9, 10, 11, 12, 13, 14, 15, 16, 17, 18, 19, 20, 21, 22, 23, or 24 hours after the administration of an adenoviral vector-based composition. In some cases, immune inhibition may occur 1, 2, 3, 4, 5, 6, or 7 days after vaccination. Immune pathway checkpoint inhibition may occur at any time before or after the administration of an adenoviral vector-based composition.

In another aspect, there is provided methods involving a vaccine comprising one or more nucleic acids encoding an antigen and an immune pathway checkpoint modulator. For example, there is provided a method for treating a subject having a condition that would benefit from downregulation of an immune pathway checkpoint protein, PD1 or PDL1 for example, and its natural binding partner(s) on cells of the subject.

An immune pathway checkpoint modulator may be combined with an adenoviral vector-based composition comprising one or more nucleic acids encoding any antigen. For example, an antigen can be a tumor antigen, such as antigens or epitopes of HER1, HER2/neu, HER3, HER4, or any combination thereof, or any antigen described herein.

An immune pathway checkpoint modulator may produce a synergistic effect when combined with an adenoviral vector-based composition, such as a vaccine. An immune pathway checkpoint modulator may also produce a beneficial effect when combined with an adenoviral vector-based composition.

XVII. Cancer

In some embodiments, the methods and compositions of the present disclosure are used to treat cancer in a subject in need thereof. In particular aspects, these cancers overexpress the HER2/neu target antigen. HER2/neu is overexpressed in a range of different cancers, including breast, ovarian, prostate, gastric, colon, lung, and bone. HER2/neu overexpression can be useful as a prognostic marker in cancer treatment. In some embodiments, any one of HER1, HER2/neu, HER3, HER4, or a combination thereof can be useful as a prognostic marker in cancer treatment.

It is specifically contemplated that compositions comprising adenoviral vectors described herein can be used to evaluate or treat stages of disease, such as hyperplasia, dysplasia, neoplasia, pre-cancer, cancer, a primary tumor, or a metastasized tumor. In particular embodiments, the subject has, is at risk of having, or is diagnosed as having a breast cancer, more particularly, a metastatic breast cancer or breast cancer that is unresponsive to other cancer therapy, such as standard breast cancer treatment, unresectable, or locally advanced.

As used herein, the terms "neoplastic cells" and "neoplasia" may be used interchangeably and refer to cells which exhibit relatively autonomous growth, so that they exhibit an aberrant growth phenotype characterized by a significant loss of control of cell proliferation. Neoplastic cells can be malignant or benign. In particular aspects, a neoplasia includes both dysplasia and cancer. Neoplasms may be benign, pre-malignant (carcinoma in situ or dysplasia) or malignant (cancer). Neoplastic cells may form a lump (i.e., a tumor) or not.

The term "dysplasia" may be used when the cellular abnormality is restricted to the originating tissue, as in the case of an early, in-situ neoplasm. Dysplasia may be indicative of an early neoplastic process. The term "cancer" may refer to a malignant neoplasm, including a broad group of various diseases involving unregulated cell growth.

Metastasis, or metastatic disease, may refer to the spread of a cancer from one organ or part to another non-adjacent organ or part. The new occurrences of disease thus generated may be referred to as metastases.

Cancers that may be evaluated or treated by the disclosed methods and compositions include cancer cells particularly from the breast, but may also include cells and cancer cells from the bladder, blood, bone, bone marrow, brain, breast, gastric, colon, esophagus, gastrointestine, gum, head, kidney, liver, lung, nasopharynx, neck, ovary, prostate, skin, stomach, tongue, or uterus.

In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondrobla stoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non- Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Breast Cancer

In certain aspects, methods and compositions comprising replication defective vectors comprising antigens or epitopes of HER1, HER2/neu, HER3, HER4, or any combination thereof are used to treat a subject that has, is at risk of having, or is diagnosed as having a breast cancer, particularly unresectable, locally advanced, or metastatic breast cancer.

In certain aspects, breast cancer is diagnosed by microscopic analysis of a sample—or biopsy—of the affected area of the breast. Also, there are types of breast cancer that require specialized lab exams.

The two most commonly used screening methods, physical examination of the breasts by a healthcare provider and mammography, can offer an approximate likelihood that a lump is cancer, and may also detect some other lesions, such as a simple cyst. When these examinations are inconclusive, a healthcare provider can remove a sample of the fluid in the lump for microscopic analysis (a procedure known as fine needle aspiration, or fine needle aspiration and cytology—FNAC) to help establish the diagnosis. A finding of clear fluid makes the lump highly unlikely to be cancerous, but bloody fluid may be sent off for inspection under a microscope for cancerous cells. Together, physical examination of the breasts, mammography, and FNAC can be used to diagnose breast cancer with a good degree of accuracy.

Other options for biopsy include a core biopsy or vacuum-assisted breast biopsy, which are procedures in which a section of the breast lump is removed; or an excisional biopsy, in which the entire lump is removed. Very often the results of physical examination by a healthcare provider, mammography, and additional tests that may be performed in special circumstances (such as imaging by ultrasound or MRI) are sufficient to warrant excisional biopsy as the definitive diagnostic and primary treatment method.

Breast cancers can be classified by different schemata. Each of these aspects influences treatment response and prognosis. Description of a breast cancer would optimally include all of these classification aspects, as well as other findings, such as signs found on physical exam. A full classification includes histopathological type, grade, stage (TNM), receptor status, and the presence or absence of genes as determined by DNA testing:

Histopathology. The considerable majority of breast cancers are derived from the epithelium lining the ducts or lobules, and are classified as mammary ductal carcinoma. Carcinoma in situ is proliferation of cancer cells within the epithelial tissue without invasion of the surrounding tissue. In contrast, invasive carcinoma invades the surrounding tissue. Perineural and/or lymphovascular space invasion is usually considered as part of the histological description of a breast cancer, and when present may be associated with more aggressive disease.

Grade. Grading focuses on the appearance of the breast cancer cells compared to the appearance of normal breast tissue. Normal cells in an organ like the breast become differentiated, meaning that they take on specific shapes and forms that reflect their function as part of that organ. Cancerous cells lose that differentiation. In cancer, the cells that would normally line up in an orderly way to make up the milk ducts become disorganized. Cell division becomes uncontrolled. Cell nuclei become less uniform. Pathologists describe cells as well differentiated (low-grade), moderately differentiated (intermediate-grade), and poorly differentiated (high-grade) as the cells progressively lose the features seen in normal breast cells. Poorly differentiated cancers have a worse prognosis.

Stage. The TNM classification for staging breast cancer is based on the size of the cancer where it originally started in the body and the locations to which it has travelled. These cancer characteristics are described as the size of the tumor (T), whether or not the tumor has spread to the lymph nodes (N) in the armpits, neck, and inside the chest, and whether the tumor has metastasized (M) (i.e., spread to a more distant part of the body). Larger size, nodal spread, and metastasis have a larger stage number and a worse prognosis.

The main stages are Stage 0, Stage, 1, Stage 2, Stage 3, and Stage 4.

Stage 0 which is in situ disease or Paget's disease of the nipple. Stage 0 is a pre-cancerous or marker condition, either ductal carcinoma in situ (DCIS) orlobular carcinoma in situ (LCIS).

Stages 1-3 are within the breast or regional lymph nodes.

Stage 4 is a metastatic cancer. Metastatic breast cancer has a less favorable prognosis.

Receptor status. Cells have receptors on their surface and in their cytoplasm and nucleus. Chemical messengers such as hormones bind to receptors, and this causes changes in the cell. Breast cancer cells may or may not have many different types of receptors, the three most important in the present classification being: estrogen receptor (ER), progesterone receptor (PR), and HER2/neu. Cells with or without these receptors are called ER positive (ER+), ER negative (ER−), PR positive (PR+), PR negative (PR−), HER2/neu positive (HER2/neu+), and HER2/neu negative (HER2/neu−). Cells with none of these receptors are called basal-like or triple negative.

Osteosarcoma

In some embodiments, methods and compositions comprising replication-defective vectors that comprise antigens or epitopes of HER1, HER2/neu, HER3, HER4, or any combination thereof are used to treat a subject that has, is at risk of having, or is diagnosed as having a bone cancer, particularly osteosarcoma. In certain embodiments, the osteosarcoma can be a high-grade osteosarcoma, an intermediate grade osteosarcoma, or a low-grade osteosarcoma. Osteosarcoma is a cancer of the bone that most commonly is found in subjects in their youth. These cancers most commonly originate in areas of new bone growth. In some embodiments, the methods and compositions of the present disclosure can be administered to treat a subject with any grade or type of osteosarcoma.

Gastric Cancer

In some embodiments, methods and compositions comprising replication-defective vectors that comprise antigens or epitopes of HER1, HER2/neu, HER3, HER4, or any combination thereof are used to treat a subject that has, is at risk of having, or is diagnosed as having gastric cancer. Gastric cancer is a cancer that originates in the stomach, of which nearly 90-95% are adenocarcinomas. In certain embodiments, the gastric cancer can be an adenocarcinoma, lymphoma, gastrointestinal stromal tumor, or a carcinoid tumor. Gastric cancer can also originate from infection by *Helicobacter pylori*. In some embodiments, the methods and compositions of the present disclosure can be administered to treat a subject with any grade or type of osteosarcoma.

XVIII. Methods of Treatment

The replication-defective adenovirus vectors comprising a target antigen such as antigens or epitopes of HER1, HER2/neu, HER3, HER4, or any combination thereof described herein can be used in a number of vaccine settings for generating an immune response against one or more target antigens as described herein. In some embodiments, there are provided methods of generating an immune response against any target antigen such as antigens or epitopes of HER1, HER2/neu, HER3, HER4, or any combination thereof.

The adenovirus vectors are of particular importance because of the unexpected finding that they can be used to generate immune responses in subjects who have preexisting immunity to Ad and can be used in vaccination regimens that include multiple rounds of immunization using the adenovirus vectors, regimens not possible using previous generation adenovirus vectors.

Generally, generating an immune response comprises an induction of a humoral response and/or a cell-mediated response. It may be desirable to increase an immune response against a target antigen of interest.

Generating an immune response may involve a decrease in the activity and/or number of certain cells of the immune system or a decrease in the level and/or activity of certain cytokines or other effector molecules. A variety of methods for detecting alterations in an immune response (e.g., cell numbers, cytokine expression, cell activity) are available and are useful in some aspects. Illustrative methods useful in this context include intracellular cytokine staining (ICS), ELISpot, proliferation assays, cytotoxic T-cell assays including chromium release or equivalent assays, and gene expression analysis using any number of polymerase chain reaction (PCR) or RT-PCR based assays.

Generating an immune response can comprise an increase in target antigen-specific CTL activity of between 1.5 and 5 fold in a subject administered the adenovirus vectors as described herein as compared to a control. In another embodiment, generating an immune response comprises an increase in target-specific CTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vectors as compared to a control.

Generating an immune response can comprise an increase in target antigen-specific HTL activity, such as proliferation of helper T-cells, of between 1.5 and 5 fold in a subject administered the adenovirus vectors as described herein that comprise nucleic acid encoding the target antigen as compared to an appropriate control. In another embodiment, generating an immune response comprises an increase in target-specific HTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold as compared to a control. In this context, HTL activity may comprise an increase as described above, or decrease, in production of a particular cytokine, such as interferon-γ (IFN-γ), interleukin-1 (IL-1), IL-2, IL-3, IL-6, IL-7, IL-12, IL-15, tumor necrosis factor-α (TNF-α), granulocyte macrophage colony-stimulating factor (GM-CSF), granulocyte-colony stimulating factor (G-CSF), or other cytokine. In this regard, generating an immune response may comprise a shift from a Th2 type response to a Th1 type response or in certain embodiments a shift from a Th1 type response to a Th2 type response. In other embodiments, generating an immune response may comprise the stimulation of a predominantly Th1 or a Th2 type response.

Generating an immune response can comprise an increase in target-specific antibody production of between 1.5 and 5 fold in a subject administered the adenovirus vectors as described herein as compared to an appropriate control. In another embodiment, generating an immune response comprises an increase in target-specific antibody production of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vector as compared to a control.

Thus, in certain embodiments, there are provided methods for generating an immune response against a target antigen of interest such as antigens or epitopes of HER1, HER2/neu, HER3, HER4, or any combination thereof, comprising administering to the individual an adenovirus vector comprising: a) a replication defective adenovirus vector, wherein the adenovirus vector has a deletion in the E2b region, and b) a nucleic acid encoding the target antigen such as antigens or epitopes of HER1, HER2/neu, HER3, HER4, or any combination thereof; and readministering the adenovirus vector at least once to the individual; thereby generating an immune response against the target antigen. In certain embodiments, there are provided methods wherein the vector administered is not a gutted vector. In particular embodiments, the target antigen may be a wild-type protein, a fragment, a variant, or a variant fragment thereof. In some embodiments, the target antigen comprises a tumor antigen such as antigens or epitopes of HER1, HER2/neu, HER3, HER4, or any combination thereof, a fragment, a variant, or a variant fragment thereof.

In a further embodiment, there are provided methods for generating an immune response against a target antigen in an individual, wherein the individual has preexisting immunity to Ad, by administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In particular embodiments, the target antigen may be a wild-type protein, a fragment, a variant, or a variant fragment thereof. In some embodiments, the target antigen comprises such as antigens or epitopes of HER1, HER2/neu, HER3, HER4, or any combination thereof, a fragment, a variant, or a variant fragment thereof.

With regard to preexisting immunity to Ad, this can be determined using methods known in the art, such as antibody-based assays to test for the presence of Ad antibodies. Further, in certain embodiments, the methods as described herein include first determining that an individual has preexisting immunity to Ad then administering the E2b deleted adenovirus vectors as described herein.

One embodiment provides a method of generating an immune response against one or more target antigens in an individual comprising administering to the individual a first adenovirus vector comprising a replication defective adenovirus vector, wherein the adenovirus vector has a deletion in the E2b region, and a nucleic acid encoding at least one target antigen; administering to the individual a second adenovirus vector comprising a replication defective adenovirus vector, wherein the adenovirus vector has a deletion in the E2b region, and a nucleic acid encoding at least one target antigen, wherein the at least one target antigen of the second adenovirus vector is the same or different from the at least one target antigen of the first adenovirus vector. In particular embodiments, the target antigen may be a wild-type protein, a fragment, a variant, or a variant fragment thereof. In some embodiments, the target antigen comprises a tumor antigen such as antigens or epitopes of HER1, HER2/neu, HER3, HER4, or any combination thereof, a fragment, a variant, or a variant fragment thereof.

Thus, certain embodiments contemplate multiple immunizations with the same E2b deleted adenovirus vector or multiple immunizations with different E2b deleted adenovirus vectors. In each case, the adenovirus vectors may comprise nucleic acid sequences that encode one or more target antigens as described elsewhere herein. In certain embodiments, the methods comprise multiple immunizations with an E2b deleted adenovirus encoding one target antigen, and re-administration of the same adenovirus vector multiple times, thereby inducing an immune response against the target antigen. In some embodiments, the target antigen comprises a tumor antigen such as antigens or epitopes of HER1, HER2/neu, HER3, HER4, or any combination thereof, a fragment, a variant, or a variant fragment thereof.

In a further embodiment, the methods comprise immunization with a first adenovirus vector that encodes one or more target antigens, and then administration with a second adenovirus vector that encodes one or more target antigens that may be the same or different from those antigens encoded by the first adenovirus vector. In this regard, one of the encoded target antigens may be different or all of the encoded antigens may be different, or some may be the same and some may be different. Further, in certain embodiments, the methods include administering the first adenovirus vector multiple times and administering the second adenovirus multiple times. In this regard, the methods comprise administering the first adenovirus vector 1, 2, 3, 4, 5, 6, 7, 8, 9, 10, 11, 12, 13, 14, 15, or more times and administering the second adenovirus vector 1, 2, 3, 4, 5, 6, 7, 8, 9, 10, 11, 12, 13, 14, 15, or more times. The order of administration may comprise administering the first adenovirus one or multiple times in a row followed by administering the second adenovirus vector one or multiple times in a row. In certain embodiments, the methods include alternating administration of the first and the second adenovirus vectors as one administration each, two administrations each, three administrations each, and so on. In certain embodiments, the first and the second adenovirus vectors are administered simultaneously. In other embodiments, the first and the second adenovirus vectors are administered sequentially. In some embodiments, the target antigen comprises a tumor antigen such as antigens or epitopes of HER1, HER2/neu, HER3, HER4, or any combination thereof, a fragment, a variant, or a variant fragment thereof.

As would be readily understood by the skilled artisan, more than two adenovirus vectors may be used in the methods as described herein. Three, 4, 5, 6, 7, 8, 9, 10 or more different adenovirus vectors may be used in the methods as described herein. In certain embodiments, the methods comprise administering more than one E2b deleted adenovirus vector at a time. In this regard, immune responses against multiple target antigens of interest can be generated by administering multiple different adenovirus vectors simultaneously, each comprising nucleic acid sequences encoding one or more target antigens.

The adenovirus vectors can be used to generate an immune response against a cancer, such as carcinomas or sarcomas (e.g., solid tumors, lymphomas and leukemia). The adenovirus vectors can be used to generate an immune response against a cancer, such as neurologic cancers, melanoma, non-Hodgkin's lymphoma, Hodgkin's disease, leukemia, plasmocytomas, adenomas, gliomas, thymomas, breast cancer, prostate cancer, colorectal cancer, kidney cancer, renal cell carcinoma, uterine cancer, pancreatic cancer, esophageal cancer, lung cancer, ovarian cancer, cervical cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers.

Methods are also provided for treating or ameliorating the symptoms of any of the infectious diseases or cancers as described herein. The methods of treatment comprise administering the adenovirus vectors one or more times to individuals suffering from or at risk from suffering from an infectious disease or cancer as described herein. As such, certain embodiments provide methods for vaccinating against infectious diseases or cancers in individuals who are at risk of developing such a disease. Individuals at risk may be individuals who may be exposed to an infectious agent at some time or have been previously exposed but do not yet have symptoms of infection or individuals having a genetic predisposition to developing a cancer or being particularly susceptible to an infectious agent. Individuals suffering from an infectious disease or cancer described herein may be determined to express and/or present a target antigen, which may be use to guide the therapies herein. For example, an example can be found to express and/or present a target antigen and an adenovirus vector encoding the target antigen, a variant, a fragment or a variant fragment thereof may be administered subsequently.

Certain embodiments contemplate the use of adenovirus vectors for the in vivo delivery of nucleic acids encoding a target antigen, or a fragment, a variant, or a variant fragment thereof. Once injected into a subject, the nucleic acid sequence is expressed resulting in an immune response against the antigen encoded by the sequence. The adenovirus vector vaccine can be administered in an "effective amount," that is, an amount of adenovirus vector that is effective in a selected route or routes of administration to elicit an immune response as described elsewhere herein. An effective amount can induce an immune response effective to facilitate protection or treatment of the host against the target infectious agent or cancer. The amount of vector in each vaccine dose is selected as an amount which induces an immune, immunoprotective or other immunotherapeutic response without significant adverse effects generally associated with typical vaccines. Once vaccinated, subjects may be monitored to determine the efficacy of the vaccine treatment. Monitoring the efficacy of vaccination may be performed by any method known to a person of ordinary skill in the art. In some embodiments, blood or fluid samples may be assayed to detect levels of antibodies. In other embodiments, ELISpot assays may be performed to detect a cell-mediated immune response from circulating blood cells or from lymphoid tissue cells.

In certain embodiments, between 1 and 10 doses may be administered over a 52 week period. In certain embodiments, 6 doses are administered, at intervals of 1, 2, 3, 4, 5, 6, 7, 8, 9, 10, 11, 12, 13, 14, 15, 16, 17, 18, 19, or 20 weeks, 1, 2, 3, 4, 5, 6, 7, 8, 9, 11, 12, 13, 14, 15, 16, 18, 20, 22, 23, or 24 months or any range or value derivable therefrom, and further booster vaccinations may be given periodically thereafter, at intervals of 1, 2, 3, 4, 5, 6, 7, 8, 9, 10, 11, 12, 13, 14, 15, 16, 17, 18, 19, or 20 weeks, 1, 2, 3, 4, 5, 6, 7, 8, 9, 11, 12, 13, 14, 15, 16, 18, 20, 22, 23, or 24 months or any range or value derivable therefrom. Alternate protocols may be appropriate for individual patients. As such, 1, 2, 3, 4, 5, 6, 7, 8, 9, 10, 11, 12, 13, 14, 15, 16, 17, 18, 19, 20, or more doses may be administered over a 1 year period or over shorter or longer periods, such as over 35, 40, 45, 50, 55, 60, 65, 70, 75, 80, 85, 90, 95 or 100 week periods. Doses may be administered at 1, 2, 3, 4, 5, or 6 week intervals or longer intervals. In some aspects, primary immunization can be followed by one or more booster immunizations comprising the same composition or pharmaceutical composition. In some embodiments, the booster immunization is administered every one, two, three, four, five, six, seven, eight, nine, ten, eleven, or twelve months or more. In some embodiments, the booster immunization is repeated three four, five, six, seven, eight, nine, ten, eleven, or twelve or more times. In some embodiments, the administering the therapeutically effective amount is a primary immunization repeated every one, two, or three weeks for three four, five, six, seven, eight, nine, ten, eleven, or twelve or more times followed by a booster immunization repeated every one, two, three, four, five, six, seven, eight, nine, ten, eleven, or twelve or more months for three or more times.

A vaccine can be infused over a period of less than about 4 hours, and more preferably, over a period of less than about 3 hours. For example, the first 25-50 mg could be infused within 30 minutes, preferably even 15 min, and the remainder infused over the next 2-3 hrs. More generally, the dosage of an administered vaccine construct may be administered as one dosage every 2 or 3 weeks, repeated for a total of at least 3 dosages. Or, the construct may be administered twice per week for 4-6 weeks. The dosing schedule can optionally be repeated at other intervals and dosage may be given through various parenteral routes, with appropriate adjustment of the dose and schedule. Compositions as described herein can be administered to a patient in conjunction with (e.g., before, simultaneously, or following) any number of relevant treatment modalities.

A suitable dose is an amount of an adenovirus vector that, when administered as described above, is capable of promoting a target antigen immune response as described elsewhere herein. In certain embodiments, the immune response is at least 10-50% above the basal (i.e., untreated) level. In certain embodiments, the immune response is at least 2, 3, 4, 5, 6, 7, 8, 9, 10, 12, 15, 20, 25, 30, 35, 40, 45, 50, 55, 60, 65, 70, 75, 80, 85, 90, 100, 110, 125, 150, 200, 250, 300, 400, 500 or more over the basal level. Such response can be monitored by measuring the target antigen(s) antibodies in a patient or by vaccine-dependent generation of cytolytic effector cells capable of killing patient tumor or infected cells in vitro, or other methods known in the art for monitoring immune responses. Such vaccines should also be capable of causing an immune response that leads to an improved clinical outcome of the disease in question in vaccinated patients as compared to non-vaccinated patients. In some embodiments, the improved clinical outcome comprises treating disease, reducing the symptoms of a disease, changing the progression of a disease, or extending life.

Any of the compositions provided herein may be administered to an individual. "Individual" may be used interchangeably with "subject" or "patient." An individual may be a mammal, for example a human or animal such as a non-human primate, a rodent, a rabbit, a rat, a mouse, a horse, a donkey, a goat, a cat, a dog, a cow, a pig, or a sheep. In embodiments, the individual is a human. In embodiments, the individual is a fetus, an embryo, or a child. In some cases, the compositions provided herein are administered to a cell ex vivo. In some cases, the compositions provided herein are administered to an individual as a method of treating a disease or disorder. In some embodiments, the individual has a genetic disease. In some cases, the individual is at risk of having the disease, such as any of the diseases described herein. In some embodiments, the individual is at increased risk of having a disease or disorder caused by insufficient amount of a protein or insufficient activity of a protein. If an individual is "at an increased risk" of having a disease or disorder, the method involves preventative or prophylactic treatment. For example, an individual can be at an increased risk of having such a disease or disorder because of family history of the disease. Typically, individuals at an increased risk of having such a disease or disorder benefit from prophylactic treatment (e.g., by preventing or delaying the onset or progression of the disease or disorder).

In some cases, a subject does not have a disease. In some cases, the treatment as described herein is administered before onset of a disease. A subject may have undetected disease. A subject may have a low disease burden. A subject may also have a high disease burden. In certain cases, a subject may be administered a treatment as described herein according to a grading scale. A grading scale can be a Gleason classification. A Gleason classification reflects how different tumor tissue is from normal prostate tissue. It uses a scale from 1 to 5. A physician gives a cancer a number based on the patterns and growth of the cancer cells. The lower the number, the less normal the cancer cells look and the higher the grade. In certain cases, a treatment may be administered to a patient with a low Gleason score. Preferable, a patient with a Gleason score of 3 or below may be administered a treatment as described herein.

Various embodiments relate to compositions and methods for raising an immune response against one or more particular target antigens such as antigens or epitopes of HER1, HER2/neu, HER3, HER4, or any combination thereof, in selected patient populations. Accordingly, methods and compositions as described herein may target patients with a cancer including but not limited to carcinomas or sarcomas such as neurologic cancers, melanoma, non-Hodgkin's lymphoma, Hodgkin's disease, leukemia, plasmocytomas, adenomas, gliomas, thymomas, breast cancer, prostate cancer, colorectal cancer, kidney cancer, renal cell carcinoma, uterine cancer, pancreatic cancer, esophageal cancer, lung cancer, ovarian cancer, cervical cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers can be targeted for therapy. In some cases, the targeted patient population may be limited to individuals having colorectal adenocarcinoma, metastatic colorectal cancer, advanced MUC1, MUC1c, MUC1n, T, or CEA expressing colorectal cancer, head and neck cancer, liver cancer, breast cancer, lung cancer, bladder cancer, or pancreas cancer. A histologically confirmed diagnosis of a selected cancer, for example colorectal adenocarcinoma, may be used. A particular disease stage or progression may be selected, for example, patients with one or more of a metastatic, recurrent, stage III, or stage IV cancer may be selected for therapy with the methods and compositions as described herein. In some embodiments, patients may be required to have received and, optionally, progressed through other therapies including but not limited to fluoropyrimidine, irinotecan, oxaliplatin, bevacizumab, cetuximab, or panitumumab containing therapies. In some cases, individual's refusal to accept such therapies may allow the patient to be included in a therapy eligible pool with methods and compositions as described herein. In some embodiments, individuals to receive therapy using the methods and compositions as described herein may be required to have an estimated life expectancy of at least, 1, 2, 3, 4, 5, 6, 7, 8, 9, 10, 11, 12, 14, 15, 18, 21, or 24 months. The patient pool to receive a therapy using the methods and compositions as described herein may be limited by age. For example, individuals who are older than 2, 3, 4, 5, 6, 7, 8, 9, 10, 11, 12, 13, 14, 15, 16, 17, 18, 19, 20, 21, 25, 30, 35, 40, 50, 60, or more years old can be eligible for therapy with methods and compositions as described herein. For another example, individuals who are younger than 75, 70, 65, 60, 55, 50, 40, 35, 30, 25, 20, or fewer years old can be eligible for therapy with methods and compositions as described herein.

In some embodiments, patients receiving therapy using the methods and compositions as described herein are limited to individuals with adequate hematologic function, for example with one or more of a WBC count of at least 1000, 1500, 2000, 2500, 3000, 3500, 4000, 4500, 5000 or more per microliter, a hemoglobin level of at least 5, 6, 7, 8, 9, 10, 11, 12, 13, 14 or higher g/dL, a platelet count of at least 50,000; 60,000; 70,000; 75,000; 90,000; 100,000; 110,000; 120,000; 130,000; 140,000; 150,000 or more per microliter; with a PT-INR value of less than or equal to 0.8, 1.0, 1.2, 1.3, 1.4, 1.5, 1.6, 1.8, 2.0, 2.5, 3.0, or higher, a PTT value of less than or equal to 1.2, 1.4, 1.5, 1.6, 1.8, 2.0×ULN or more. In various embodiments, hematologic function indicator limits are chosen differently for individuals in different gender and age groups, for example 0-5, 5-10, 10-15, 15-18, 18-21, 21-30, 30-40, 40-50, 50-60, 60-70, 70-80 or older than 80.

In some embodiments, patients receiving therapy using the methods and compositions as described herein are limited to individuals with adequate renal and/or hepatic function, for example with one or more of a serum creatinine level of less than or equal to 0.8, 0.9, 1.0, 1.1, 1.2, 1.3, 1.4, 1.5, 1.6, 1.7, 1.8, 1.9, 2.0, 2.1, 2.2 mg/dL, or more, a bilirubin level of 0.8, 0.9, 1.0, 1.1, 1.2, 1.3, 1.4, 1.5, 1.6, 1.7, 1.8, 1.9, 2.0, 2.1, 2.2 mg/dL, or more, while allowing a higher limit for Gilbert's syndrome, for example, less than or equal to 1.5, 1.6, 1.8, 1.9, 2.0, 2.1, 2.2, 2.3, or 2.4 mg/dL, an ALT and AST value of less than or equal to less than or equal to 1.5, 2.0, 2.5, 3.0× upper limit of normal (ULN) or more. In various embodiments, renal or hepatic function indicator limits are chosen differently for individuals in different gender and age groups, for example 0-5, 5-10, 10-15, 15-18, 18-21, 21-30, 30-40, 40-50, 50-60, 60-70, 70-80 or older than 80.

In some embodiments, the K-ras mutation status of individuals who are candidates for a therapy using the methods and compositions as described herein can be determined. Individuals with a preselected K-ras mutational status can be included in an eligible patient pool for therapies using the methods and compositions as described herein.

In various embodiments, patients receiving therapy using the methods and compositions as described herein are limited to individuals without concurrent cytotoxic chemotherapy or radiation therapy, a history of, or current, brain metastases, a history of autoimmune disease, such as but not restricted to, inflammatory bowel disease, systemic lupus erythematosus, ankylosing spondylitis, scleroderma, multiple sclerosis, thyroid disease and vitiligo, serious intercurrent chronic or acute illness, such as cardiac disease (NYHA class III or IV), or hepatic disease, a medical or psychological impediment to probable compliance with the protocol, concurrent (or within the last 5 years) second malignancy other than non-melanoma skin cancer, cervical carcinoma in situ, controlled superficial bladder cancer, or other carcinoma in situ that has been treated, an active acute or chronic infection including: a urinary tract infection, HIV (e.g., as determined by ELISA and confirmed by Western Blot), and chronic hepatitis, or concurrent steroid therapy (or other immunosuppressives, such as azathioprine or cyclosporin A). In some cases, patients with at least 3, 4, 5, 6, 7, 8, 9, or 10 weeks of discontinuation of any steroid therapy (except that used as premedication for chemotherapy or contrast-enhanced studies) may be included in a pool of eligible individuals for therapy using the methods and compositions as described herein. In some embodiments, patients receiving therapy using the methods and compositions as described herein include individuals with thyroid disease and vitiligo.

In various embodiments, samples, for example serum or urine samples, from the individuals or candidate individuals for a therapy using the methods and compositions as described herein may be collected. Samples may be collected before, during, and/or after the therapy for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 weeks, 3 weeks, 4 weeks, 6 weeks, 8 weeks, 9 weeks, or 12 weeks intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years or longer. The samples may be tested for any of the hematologic, renal, or hepatic function indicators described herein as well as suitable others known in the art, for example a ß-HCG for women with childbearing potential. In that regard, hematologic and biochemical tests, including cell blood counts with differential, PT, INR and PTT, tests measuring Na, K, Cl, CO2, BUN, creatinine, Ca, total protein, albumin, total bilirubin, alkaline phosphatase, AST, ALT and glucose are contemplated in certain aspects. In some embodiments, the presence or the amount of HIV antibody, Hepatitis BsAg, or Hepatitis C antibody are determined in a sample from individuals or candidate individuals for a therapy using the methods and compositions described herein.

Biological markers, such as antibodies to target antigens or the neutralizing antibodies to Ad5 vector can be tested in a sample, such as serum, from individuals or candidate individuals for a therapy using the methods and compositions described herein. In some cases, one or more samples, such as a blood sample can be collected and archived from an individuals or candidate individuals for a therapy using the methods and compositions described herein. Collected samples can be assayed for immunologic evaluation. Individuals or candidate individuals for a therapy using the methods and compositions described herein can be evaluated in imaging studies, for example using CT scans or MRI of the chest, abdomen, or pelvis. Imaging studies can be performed before, during, or after therapy using the methods and compositions described herein, during, and/or after the therapy, for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 week, 3 week, 4 week, 6 week, 8 week, 9 week, or 12 week intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years, or longer.

Compositions and methods described herein contemplate various dosage and administration regimens during therapy. Patients may receive one or more replication defective adenovirus or adenovirus vector, for example Ad5 [E1-, E2B-]-vectors comprising a target antigen that is capable of raising an immune response in an individual against a target antigen described herein.

In various embodiments, the replication defective adenovirus is administered at a dose that suitable for effecting such immune response. In some embodiments, the replication defective adenovirus is administered at a dose from about $1 \times 10^8$ virus particles to about $5 \times 10^{13}$ virus particles per immunization. In some embodiments, the replication defective adenovirus is administered at a dose from about $1 \times 10^9$ virus particles to about $5 \times 10^{12}$ virus particles per immunization. In some embodiments, the replication defective adenovirus is administered at a dose from about $1 \times 10^8$ virus particles to about $5 \times 10^8$ virus particles per immunization. In some embodiments, the replication defective adenovirus is administered at a dose from about $5 \times 10^8$ virus particles to about $1 \times 10^9$ virus particles per immunization. In some embodiments, the replication defective adenovirus is administered at a dose from about $1 \times 10^9$ virus particles to about $5 \times 10^9$ virus particles per immunization. In some embodiments, the replication defective adenovirus is administered at a dose from about $5 \times 10^9$ virus particles to about $1 \times 10^{10}$ virus particles per immunization. In some embodiments, the replication defective adenovirus is administered at a dose from about $1 \times 10^{10}$ virus particles to about $5 \times 10^{10}$ virus particles per immunization. In some embodiments, the replication defective adenovirus is administered at a dose from about $5 \times 10^{10}$ virus particles to about $1 \times 10^{11}$ virus particles per immunization. In some embodiments, the replication defective adenovirus is administered at a dose from about $1 \times 10^{11}$ virus particles to about $5 \times 10^{11}$ virus particles per immunization. In some embodiments, the replication defective adenovirus is administered at a dose from about $5 \times 10^{11}$ virus particles to about $1 \times 10^{12}$ virus particles per immunization. In some embodiments, the replication defective adenovirus is administered at a dose from about $1 \times 10^{12}$ virus particles to about $5 \times 10^{12}$ virus particles per immunization. In some embodiments, the replication defective adenovirus is administered at a dose from about $5 \times 10^{12}$ virus particles to about $1 \times 10^{13}$ virus particles per immunization. In some embodiments, the replication defective adenovirus is administered at a dose from about $1 \times 10^{13}$ virus particles to about $5 \times 10^{13}$ virus particles per immunization. In some embodiments, the replication defective adenovirus is administered at a dose from about $1 \times 10^8$ virus particles to about $5 \times 10^{10}$ virus particles per immunization. In some embodiments, the replication defective adenovirus is administered at a dose from about $1 \times 10^{10}$ virus particles to about $5 \times 10^{12}$ virus particles per immunization. In some embodiments, the replication defective adenovirus is administered at a dose from about $1 \times 10^{11}$ virus particles to about $5 \times 10^{13}$ virus particles per immunization. In some embodiments, the replication defective adenovirus is administered at a dose from about $1 \times 10^8$ virus particles to about $1 \times 10^{10}$ virus particles per immunization. In some embodiments, the replication defective adenovirus is administered at a dose from about $1 \times 10^{10}$ virus particles to about $1 \times 10^{12}$ virus particles per immunization. In some embodiments, the replication defective adenovirus is administered at a dose from about $1 \times 10^{11}$ virus particles to about $5 \times 10^{13}$ virus particles per immunization. In some cases, the replication defective adenovirus is administered at a dose that is greater than or equal to $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $1.5 \times 10^{12}$, $2 \times 10^{12}$, $3 \times 10^{12}$, or more virus particles (VP) per immunization. In some cases, the replication defective adenovirus is administered at a dose that is less than or equal to $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $1 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $1.5 \times 10^{12}$, $2 \times 10^{12}$, $3 \times 10^{12}$, or more virus particles per immunization. In some embodiments, the replication defective adenovirus is administered at a dose of $1 \times 10^9$-$5 \times 10^{12}$ virus particles per immunization. In some embodiments, the composition comprises at least $1.0 \times 10^{11}$, $2.0 \times 10^{11}$, $3.0 \times 10^{11}$, $3.5 \times 10^{11}$, $4.0 \times 10^{11}$, $4.5 \times 10^{11}$, $4.8 \times 10^{11}$, $4.9 \times 10^{11}$, $4.95 \times 10^{11}$, or $4.99 \times 10^{11}$ virus particles comprising the recombinant nucleic acid vector. In some embodiments, the composition comprises at most $7.0 \times 10^{11}$, $6.5 \times 10^{11}$, $6.0 \times 10^{11}$, $5.5 \times 10^{11}$, $5.2 \times 10^{11}$, $5.1 \times 10^{11}$, $5.05 \times 10^{11}$, or $5.01 \times 10^{11}$ virus particles. In some embodiments, the composition comprises $1.0 \times 10^{11}$-$7.0 \times 10^{11}$ or $1.0$-$5.5 \times 10^{11}$ virus particles. In some embodiments, the composition comprises $4.5 \times 10^{11}$-$5.5 \times 10^{11}$ virus particles. In some embodiments, the composition comprises $4.8 \times 10^{11}$-$5.2 \times 10^{11}$ virus particles. In some embodiments, the composition comprises $4.9 \times 10^{11}$-$5.1 \times 10^{11}$ virus particles. In some embodiments, the composition comprises $4.95 \times 10^{11}$-$5.05 \times 10^{11}$ virus particles. In some embodiments, the composition comprises $4.99 \times 10^{11}$-$5.01 \times 10^{11}$ virus particles.

In various embodiments, a desired dose described herein is administered in a suitable volume of formulation buffer, for example a volume of about 0.1-10 mL, 0.2-8 mL, 0.3-7 mL, 0.4-6 mL, 0.5-5 mL, 0.6-4 mL, 0.7-3 mL, 0.8-2 mL, 0.9-1.5 mL, 0.95-1.2 mL, or 1.0-1.1 mL. Those of skill in the art appreciate that the volume may fall within any range bounded by any of these values (e.g., about 0.5 mL to about 1.1 mL). Administration of virus particles can be through a variety of suitable paths for delivery, for example it can be by injection (e.g., intracutaneously, intramuscularly, intravenously or subcutaneously), intranasally (e.g., by aspiration), in pill form (e.g., swallowing, suppository for vaginal or rectal delivery. In some embodiments, a subcutaneous delivery may be preferred and can offer greater access to dendritic cells.

Administration of virus particles to an individual may be repeated. Repeated deliveries of virus particles may follow a schedule or alternatively, may be performed on an as needed basis. For example, an individual's immunity against a target antigen, for example a tumor antigen such as antigens or epitopes of HER1, HER2/neu, HER3, HER4, or any combination thereof, a fragment, a variant, or a variant fragment thereof, may be tested and replenished as necessary with additional deliveries. In some embodiments, schedules for delivery include administrations of virus particles at regular intervals. Joint delivery regimens may be designed comprising one or more of a period with a schedule and/or a period of need based administration assessed prior to administration. For example, a therapy regimen may include an administration, such as subcutaneous administration once every three weeks then another immunotherapy treatment every three months until removed from therapy for any reason including death. Another example regimen comprises three administrations every three weeks then another set of three immunotherapy treatments every three months.

Another example regimen comprises a first period with a first number of administrations at a first frequency, a second period with a second number of administrations at a second frequency, a third period with a third number of administrations at a third frequency, etc., and optionally one or more periods with undetermined number of administrations on an as needed basis. The number of administrations in each period can be independently selected and can for example be 1, 2, 3, 4, 5, 6, 7, 8, 9, 10, 11, 12, 13, 14, 15, 16, 17, 18, 19, 20 or more. The frequency of the administration in each period can also be independently selected, can for example be about every day, every other day, every third day, twice a week, once a week, once every other week, every three weeks, every month, every six weeks, every other month, every third month, every fourth month, every fifth month, every sixth month, once a year etc. The therapy can take a total period of up to 1, 2, 3, 4, 5, 6, 7, 8, 9, 10, 11, 12, 13, 14, 15, 16, 17, 18, 19, 20, 21, 22, 23, 24, 30, 36 months or more.

The scheduled interval between immunizations may be modified so that the interval between immunizations is revised by up to a fifth, a fourth, a third, or half of the interval. For example, for a 3-week interval schedule, an immunization may be repeated between 20 and 28 days (3 weeks−1 day to 3 weeks+7 days). For the first 3 immunizations, if the second and/or third immunization is delayed, the subsequent immunizations may be shifted allowing a minimum amount of buffer between immunizations. For example, for a three week interval schedule, if an immunization is delayed, the subsequent immunization may be scheduled to occur no earlier than 17, 18, 19, or 20 days after the previous immunization.

Compositions described herein can be provided in various states, for example, at room temperature, on ice, or frozen. Compositions may be provided in a container of a suitable size, for example a vial of 2 mL vial. In one embodiment, one 2 ml vial with 1.0 mL of extractable vaccine contains $5 \times 10^{11}$ total virus particles/mL. Storage conditions including temperature and humidity may vary. For example, compositions for use in therapy may be stored at room temperature, 4° C., −20° C., or lower.

In various embodiments, general evaluations are performed on the individuals receiving treatment according to the methods and compositions as described herein. One or more of any tests may be performed as needed or in a scheduled basis, such as on weeks 0, 3, 6 etc. A different set of tests may be performed concurrent with immunization vs. at time points without immunization.

General evaluations may include one or more of medical history, ECOG Performance Score, Karnofsky performance status, and complete physical examination with weight by the attending physician. Any other treatments, medications, biologics, or blood products that the patient is receiving or has received since the last visit may be recorded. Patients may be followed at the clinic for a suitable period, for example approximately 30 minutes, following receipt of vaccine to monitor for any adverse reactions.

In certain embodiments, local and systemic reactogenicity after each dose of vaccine may be assessed daily for a selected time, for example for 3 days (on the day of immunization and 2 days thereafter). Diary cards may be used to report symptoms and a ruler may be used to measure local reactogenicity. Immunization injection sites may be assessed. CT scans or MRI of the chest, abdomen, and pelvis may be performed.

In various embodiments, hematological and biochemical evaluations are performed on the individuals receiving treatment according to the methods and compositions as described herein. One or more of any tests may be performed as needed or in a scheduled basis, such as on weeks 0, 3, 6, etc. A different set of tests may be performed concurrent with immunization vs. at time points without immunization. Hematological and biochemical evaluations may include one or more of blood test for chemistry and hematology, CBC with differential, Na, K, Cl, CO2, BUN, creatinine, Ca, total protein, albumin, total bilirubin, alkaline phosphatase, AST, ALT, glucose, and ANA.

In various embodiments, biological markers are evaluated on individuals receiving treatment according to the methods and compositions as described herein. One or more of any tests may be performed as needed or in a scheduled basis, such as on weeks 0, 3, 6, etc. A different set of tests may be performed concurrent with immunization vs. at time points without immunization.

Biological marker evaluations may include one or more of measuring antibodies to target antigens or viral vectors described herein, from a serum sample of adequate volume, for example about 5 ml Biomarkers may be reviewed if determined and available.

In various embodiments, an immunological assessment is performed on individuals receiving treatment according to the methods and compositions as described herein. One or more of any tests may be performed as needed or in a scheduled basis, such as on weeks 0, 3, 6, etc. A different set of tests may be performed concurrent with immunization vs. at time points without immunization.

Peripheral blood, for example about 90 mL may be drawn prior to each immunization and at a time after at least some of the immunizations, to determine whether there is an effect on the immune response at specific time points during the study and/or after a specific number of immunizations. Immunological assessment may include one or more of assaying peripheral blood mononuclear cells (PBMC) for T-cell responses to target antigens such as antigens or epitopes of HER1, HER2/neu, HER3, HER4, or any combination thereof, using ELISpot, proliferation assays, multiparameter flow cytometric analysis, and cytoxicity assays. Serum from each blood draw may be archived and sent and determined.

In various embodiments, a tumor assessment is performed on individuals receiving treatment according to the methods and compositions as described herein. One or more of any tests may be performed as needed or in a scheduled basis, such as prior to treatment, on weeks 0, 3, 6, etc. A different set of tests may be performed concurrent with immunization vs. at time points without immunization. Tumor assessment may include one or more of CT or MM scans of chest, abdomen, or pelvis performed prior to treatment, at a time after at least some of the immunizations and at approximately every three months following the completion of a selected number, for example 2, 3, or 4, of first treatments and for example until removal from treatment.

Immune responses against a target antigen such as antigens or epitopes of HER1, HER2/neu, HER3, HER4, or any combination thereof, may be evaluated from a sample, such as a peripheral blood sample of an individual using one or more suitable tests for immune response, such as ELISpot, cytokine flow cytometry, or antibody response. A positive immune response can be determined by measuring a T-cell response. A T-cell response can be considered positive if the mean number of spots adjusted for background in six wells with antigen exceeds the number of spots in six control wells by 10 and the difference between single values of the six wells containing antigen and the six control wells is statistically significant at a level of $p \leq 0.05$ using the Student's t-test. Immunogenicity assays may occur prior to each immunization and at scheduled time points during the period of the treatment. For example, a time point for an immunogenicity assay at around week 1, 2, 3, 4, 5, 6, 7, 8, 9, 10, 11, 12, 13, 14, 15, 18, 20, 24, 30, 36, or 48 of a treatment may be scheduled even without a scheduled immunization at this time. In some cases, an individual may be considered evaluable for immune response if they receive at least a minimum number of immunizations, for example 1, 2, 3, 4, 5, 6, 7, 8, 9, or more immunizations.

In some embodiments, disease progression or clinical response determination is made according to the RECIST 1.1 criteria among patients with measurable/evaluable disease. In some embodiments, therapies using the methods and compositions as described herein affect a Complete Response (CR; disappearance of all target lesions for target lesions or disappearance of all non-target lesions and normalization of tumor marker level for non-target lesions) in an individual receiving the therapy. In some embodiments, therapies using the methods and compositions as described herein affect a Partial Response (PR; at least a 30% decrease in the sum of the LD of target lesions, taking as reference the baseline sum LD for target lesions) in an individual receiving the therapy.

In some embodiments, therapies using the methods and compositions as described herein affect a Stable Disease (SD; neither sufficient shrinkage to qualify for PR nor sufficient increase to qualify for PD, taking as reference the smallest sum LD since the treatment started for target lesions) in an individual receiving the therapy. In some embodiments, therapies using the methods and compositions described herein affect an Incomplete Response/Stable Disease (SD; persistence of one or more non-target lesion(s) or/and maintenance of tumor marker level above the normal limits for non-target lesions) in an individual receiving the therapy. In some embodiments, therapies using the methods and compositions as described herein affect a Progressive Disease (PD; at least a 20% increase in the sum of the LD of target lesions, taking as reference the smallest sum LD recorded since the treatment started or the appearance of one or more new lesions for target lesions or persistence of one or more non-target lesion(s) or/and maintenance of tumor marker level above the normal limits for non-target lesions) in an individual receiving the therapy.

XIX. Kits

The compositions, immunotherapy or vaccines described herein may be supplied in the form of a kit. The kits of the present disclosure may further comprise instructions regarding the dosage and or administration including treatment regimen information.

In some embodiments, kits comprise the compositions and methods for providing immunotherapy or vaccines described. In some embodiment's kits may further comprise components useful in administering the kit components and instructions on how to prepare the components. In some embodiments, the kit can further comprise software for conducting monitoring patient before and after treatment with appropriate laboratory tests, or communicating results and patient data with medical staff.

The components comprising the kit may be in dry or liquid form. If they are in dry form, the kit may include a solution to solubilize the dried material. The kit may also include transfer factor in liquid or dry form. If the transfer factor is in dry form, the kit will include a solution to solubilize the transfer factor. The kit may also include containers for mixing and preparing the components. The kit may also include instrument for assisting with the administration such for example needles, tubing, applicator, inhalant, syringe, pipette, forceps, measured spoon, eye dropper or any such medically approved delivery vehicle. The kits or drug delivery systems as described herein also will typically include a means for containing compositions of the present disclosure in close confinement for commercial sale and distribution.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Gene Expression Analysis of Heregulin/Neuregulin

This example describes gene expression analysis of heregulin/neuregulin HRG/NRG1. A collection of breast tumor gene expression data (n=4010) derived from 23 data sets posted on the NCBI Gene Expression Omnibus (GEO) was compiled. mRNA expression from these data sets demonstrated up-regulated mRNA expression of HRG/NRG1 was correlated with lower relapse free survival in ER+ HER2/neu—breast cancer patients. Additionally, HRG/NRG1 mRNA was elevated in tumors from patients with early recurrence (less than 5 years) or late recurrence (5-10 years).

FIG. 1 shows the results of analysis of breast tumor gene expression data. FIG. 1A shows that up-regulated mRNA expression of HRG/NRG1 was correlated with lower relapse free survival in ER+ HER2/neu—breast cancer patients. FIG. 1B shows that HRG/NRG1 mRNA was elevated in tumors from patients with early recurrence (less than 5 years) or late recurrence (from 5-10 years) after diagnosis compared to non-recurring tumors.

Example 2

Construction of Ad5 [E1–, E2b–] Vector

This example describes the construction of the Ad5 [E1–, E2b–] vector. The construction of the Ad5 [E1–, E2b–] vector backbone has previously been described. The approximately 20 kb Xba-BamHI subfragment of pBHG11 was subcloned into pBluescriptKSII+ (Stratagene, La Jolla, Calif.), yielding pAXB. Plasmid pAXB was digested with BspEI, T4 DNA polymerase end filled, and BamHI digested, and the approximately 9.0 kb fragment was isolated. Plasmid pAXB was also digested with BspHI, T4 DNA polymerase end filled, and BamHI digested, and the approximately 13.7 kb fragment was ligated to the previously isolated 9.0 kb fragment, generating pAXB-Δpol.

This subcloning strategy deleted 608 bp (Δpol; Ad5 nucleotides 7274 to 7881) within the amino terminus of the polymerase gene. This deletion also effectively removed open reading frame 9.4 present on the rightward reading strand in this region of the Ad genome. The Xba-BamHI subfragment of pAXB-Δpol was reintroduced into Xba-BamHI-digested pBHG11, to generate pBHG11-Δpol.

Example 3

Construction of the Ad5 [E1−, E2b−]-HER3 Vaccine

This example describes construction of the Ad5 [E1−, E2b−]-HER3/neu vaccine. A truncated HER3 transgene flanked by a minimal cytomegalovirus promoter/enhancer element and the SV40 derived poly adenylation signal was subcloned into the shuttle pShuttleCMV, generating the shuttle plasmid pShuttle CMV/HER3. The shuttle plasmid was linearized with PmeI and homologously recombined (in *E. coli* bacteria) with the plasmid pAdΔpp to generate pAdCMV/HER3/Δpp (FIG. 2).

Ten micrograms of pAdCMV/HER3/Δpp linearized with PacI was CaPO4 cotransfected into Ad E1, polymerase (E2b) and pTP-expressing (E.C7 cells). Sixteen hours after transfection, the cells were harvested and the cell mixture was distributed into nine 24-well tissue culture cluster plates and incubated at 37° C. for 5 to 9 days. Individual wells demonstrating viral cytopathic effects were harvested, and the isolated virus was amplified by repeated infection of greater numbers of E.C7 cells. Isolation of the Ad5 [E1−, E2b−]-HER3 recombinant vector was subsequently confirmed by (1) DNA restriction mapping of the vector genome, (2) confirmation of expression of HER3 and (3) multiple functional studies.

Example 4

Assessment of Preclinical Immunogenicity of Ad5 [E1−, E2b−]-HER3 in BALB/c Mice This example describes assessment of preclinical immunogenicity testing of Ad5 [E1−, E2b−]-HER3 in BALB/c mice. In preliminary studies, the immunogenicity of Ad5 [E1−, E2b−]-HER3fl (full length gene insert) was determined in BALB/c mice. Female mice (10 mice/group) were vaccinated twice at 2-weeks interval, and the human HER3-expressing murine breast cancer cell line (JC-HER3, 1 M cells/mouse) was injected into the flank of mice 4 days later. From each group, 3 mice were sacrificed before tumor cell implantation to collect blood and spleen for immune monitoring. Tumor volume was monitored for the rest of the mice until human endpoint was reached.

Figure 4:
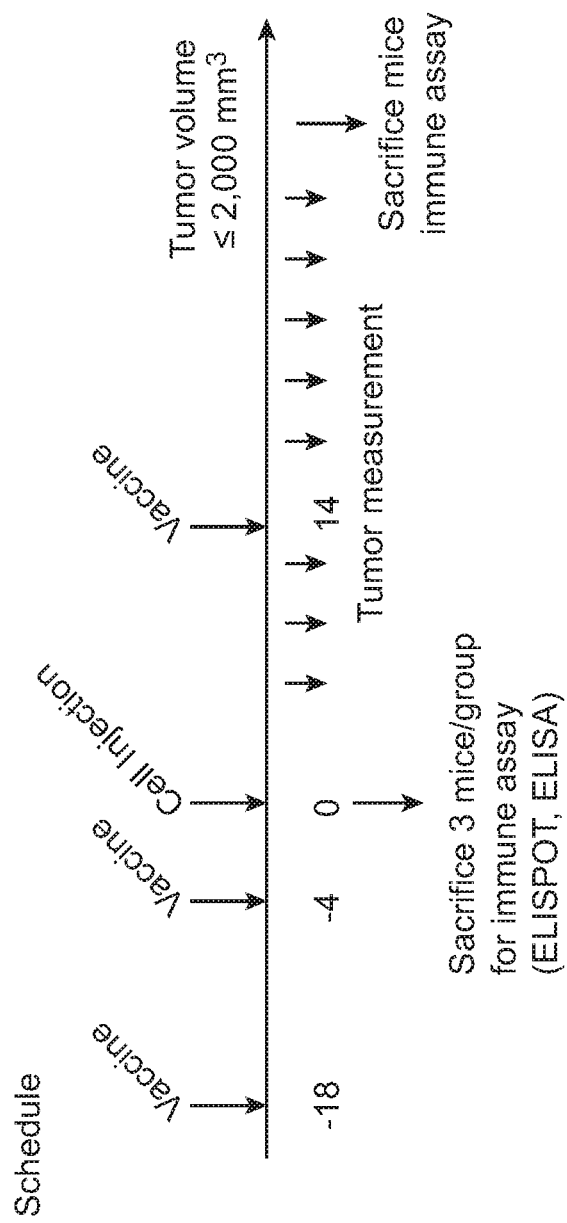
FIG. 4 illustrates a scheme of immunogenicity testing and antitumor efficacy testing.

FIG. 4 shows a scheme of immunogenicity testing and antitumor efficacy testing. On days −18 and −4, mice were vaccinated with Ad-vectors ($2.6 \times 10^{10}$ vp/mouse), and three mice from each group were sacrificed for immune assays on day 0. Splenocytes were harvested for an ELISPOT assay. Blood was collected to test for antibody production. For the other seven mice in each group, JC-HER3 cells were subcutaneously injected into the flank of BALB/c mice and tumor size was measured.

Humoral Immune Response

Humoral immune responses against HER3 were analyzed in mice by a flow-based assay. 4T1 (HER3 negative) or 4T1-HER3 (HER3 transfectant) cells were incubated with mouse sera, which were diluted with saline (1:100 dilution), then with PE-conjugated secondary antibody (anti-mouse IgG). Sera from Ad5 [E1−, E2b−]-GFP (green fluorescent protein) vaccinated mice were used as negative control, commercially available anti-HER3 mAb as positive control, and mouse serum from Ad5 [E1−]-huHER3 vaccinated mice were used for comparison purpose.

Figure 5:
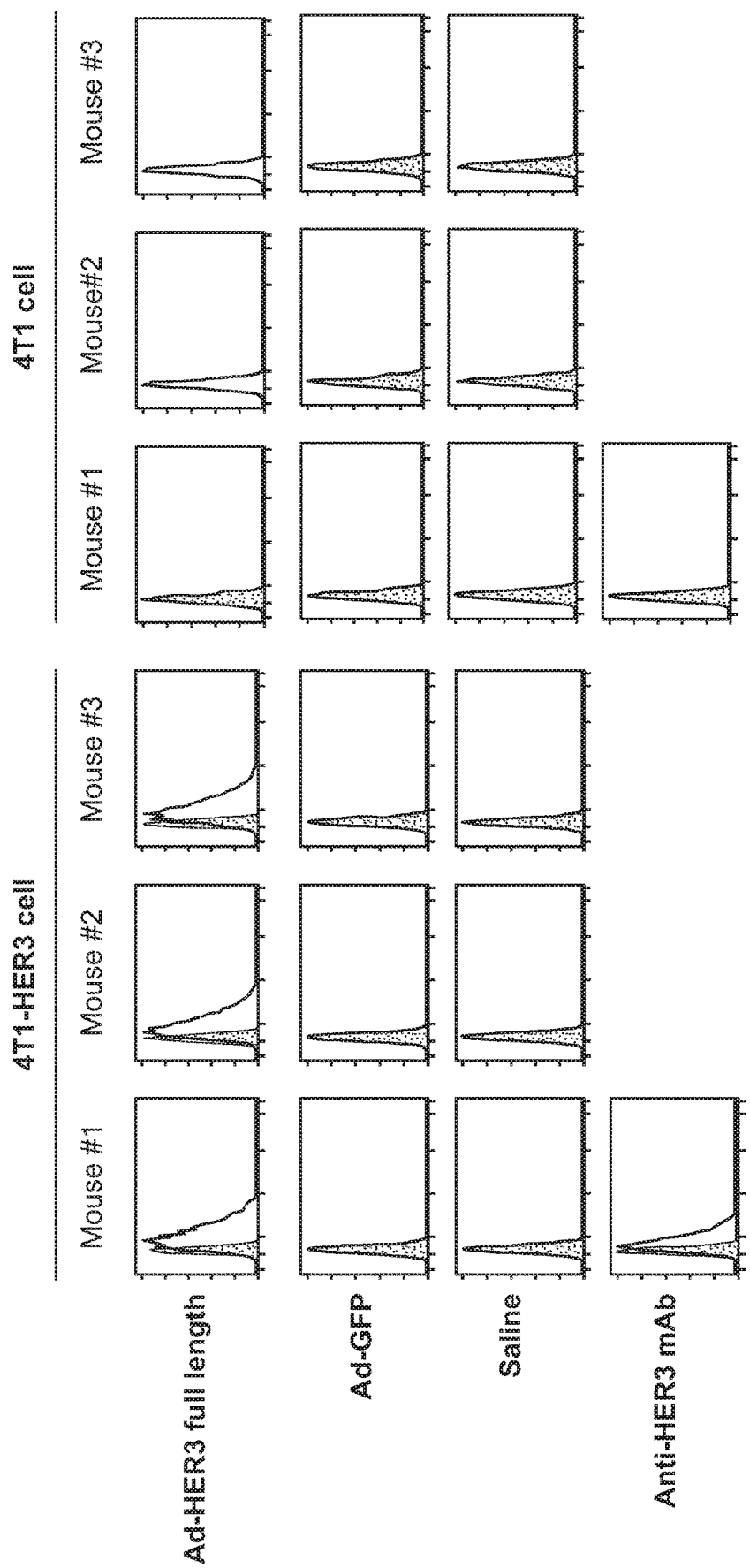
FIG. 5 illustrates anti-HER3 antibody levels in the serum of Ad-HER3 vaccinated mice.

FIG. 5 shows anti-HER3 antibody levels in the serum of Ad-HER3 vaccinated mice. Three mice from each group were sacrificed, and serum was collected. 4T1 (HER3-negative) and 4T1-HER3 (transfectant) were labeled with serum (1:100 dilution) and then with PE-conjugated anti-mouse IgG Ab. Open histograms (black line) show staining with mouse serum, and grey histograms show staining without serum (2° Ab only). Non-transfected cells (4T1 cells) do not express HER3 and do not bind anti-HER3 antibodies in the serum of Ad-HER3 vaccinated mice. Thus, the open histograms and grey histograms fully overlap. A shift in the open histogram to the right was indicative that the serum contained anti-HER3 antibodies, which bound HER3 expressed by 4T1 cells. 4T1 cells transfected with Ad-HER3 (full length HER3) displayed binding of anti-HER3 antibodies in serum of Ad-HER vaccinated mice. The bottom left histogram shows binding of a HER3 monoclonal antibody (anti-HER3 mAb) to HER3 expressing 4T1 cells. The observed shift in the open histogram to the right of the gray histogram indicated non-specific background binding.

Figure 6:
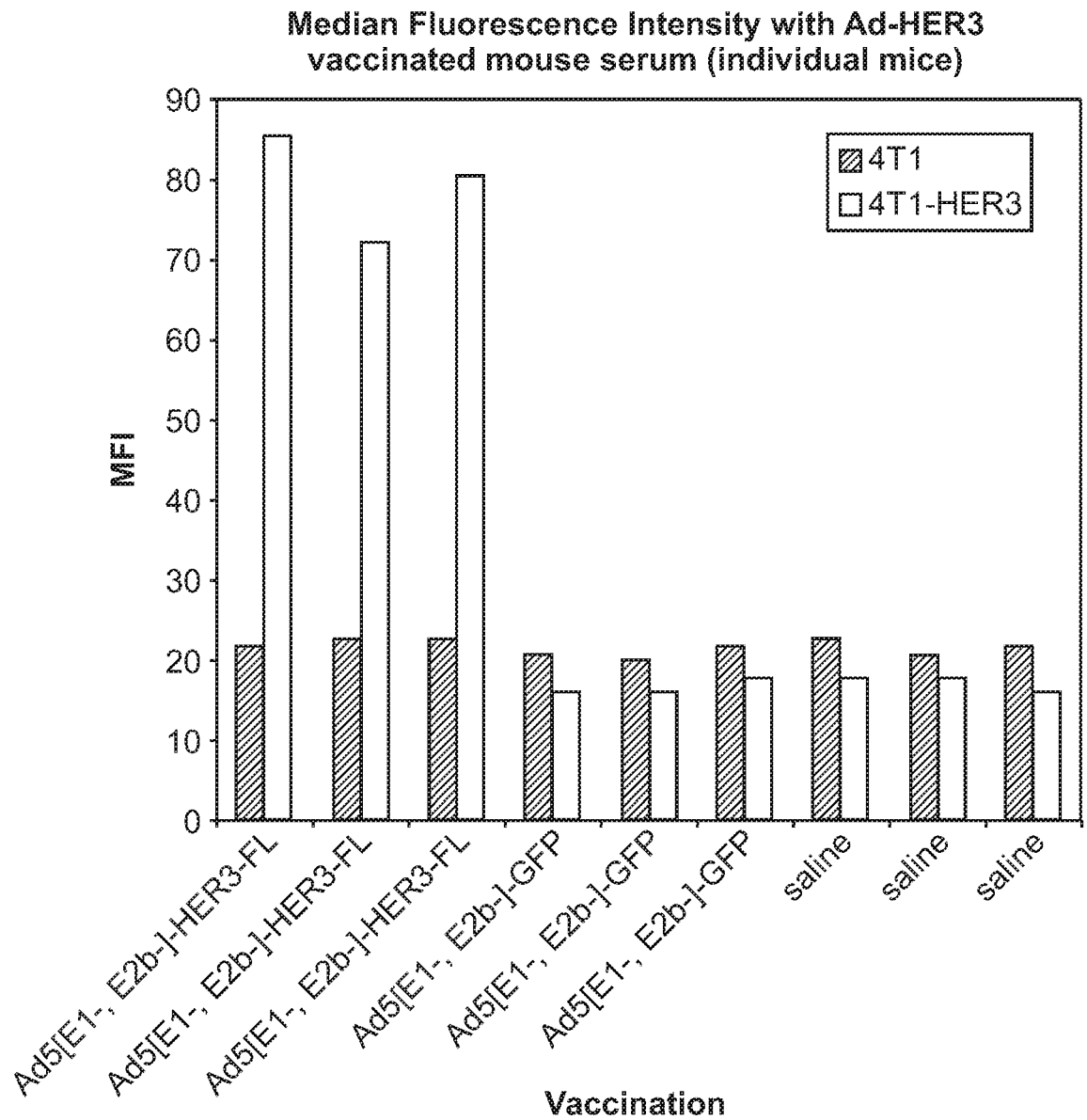
FIG. 6 illustrates median fluorescence intensities for the staining of 4T1 and 4T1-HER3 cells in individual mouse serum after vaccination.

FIG. 6 shows median fluorescence intensities for the staining of 4T1 and 4T1-HER3 cells in individual mouse serum. Mice were immunized with Ad5 vectors encoding for full length HER3 (HER3-FL). Ad5 vectors encoding for GFP and saline were used as a negative control. Ad5 [E2b−]-HER3 induced strong anti-HER3 antibody production, as evidenced by the high mean fluorescent intensity (MFI) quantified in 4T1-HER3 expressing cells incubated with serum from these mice.

Figure 7:
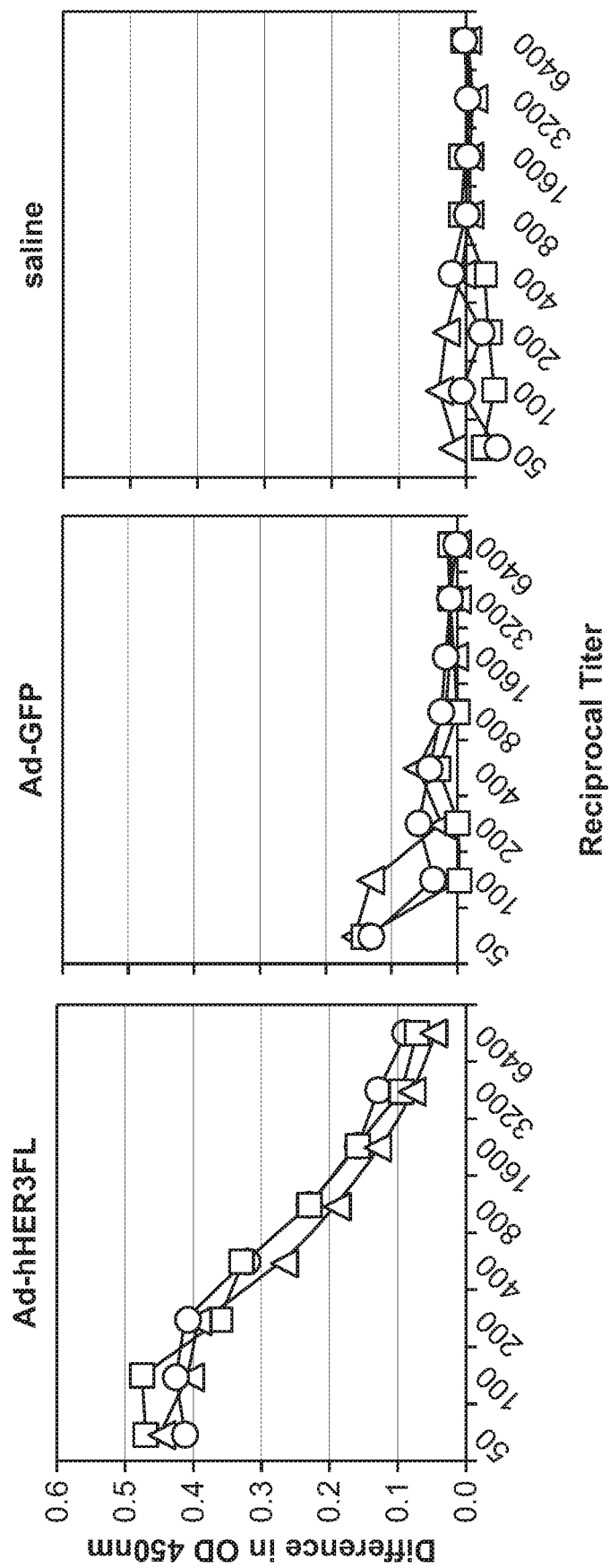
FIG. 7 illustrates the results of a cell-based ELISA with mouse serum.

Anti-HER3 antibody levels in each serum were analyzed by cell-based ELISA. 4T1 murine breast cancer cell line (HER3 negative) and human HER3 transfectant (4T1-HER3) were used in this assay. Sera from individual mice were titrated from 1:50 to 1:6400. FIG. 7 shows the results of a cell-based ELISA with mouse serum. 4T1 and 4T1-HER3 cells were seeded into 96-well plates. After overnight incubation, cells were washed with buffer, and mouse serum with serial dilutions was added (1:50 to 1:6400) and incubated for 1 hour on ice. Cells were fixed with 4% formaldehyde and HRP-labeled Goat anti-mouse IgG (1:1000) was added. After incubation for 1 hour, cells were washed with PBS 3 times, and TMB was added for 5 min. Color development was stopped by adding $H_2SO_4$. Differences of OD450 values (=[value for 4T1-HER3]−[value for 4T1]) are shown. Thus the y-axis shows the absorbance at 450 nm in the HER3 expressing 4T1 cells over the negative control non-HER3 expressing 4T1 cells. Cell-based ELISA results indicating HER3 antibody production in Ad5 [E1−, E2b−]-HER3fl vaccinated mice were confirmed in all mice, and ELISA results showed that absorbance, corresponding to binding, was dose dependent on the reciprocal titer tested. Furthermore, mouse sera from mice vaccinated with negative controls (Ad-GFP or saline) did not show absorbance over negative control cells, indicating that no anti-HER3 antibody was present in the sera.

Antigen-Specific Cellular Immune Response

The antigen-specific cellular immune response was analyzed by IFN-γ ELISPOT assay with mouse splenocytes. Splenocytes from each mouse were incubated with HER3 peptide pool Extracellular Domain (ECD), or Intracellular Domain (ICD), HIV peptide mix as a negative control, and PMA+Ionomycin as a positive control. As expected, T cells responded to the intracellular domain of HER3. T cell responses against the peptide mix of HER3 extracellular domain were variable.

Figure 8:
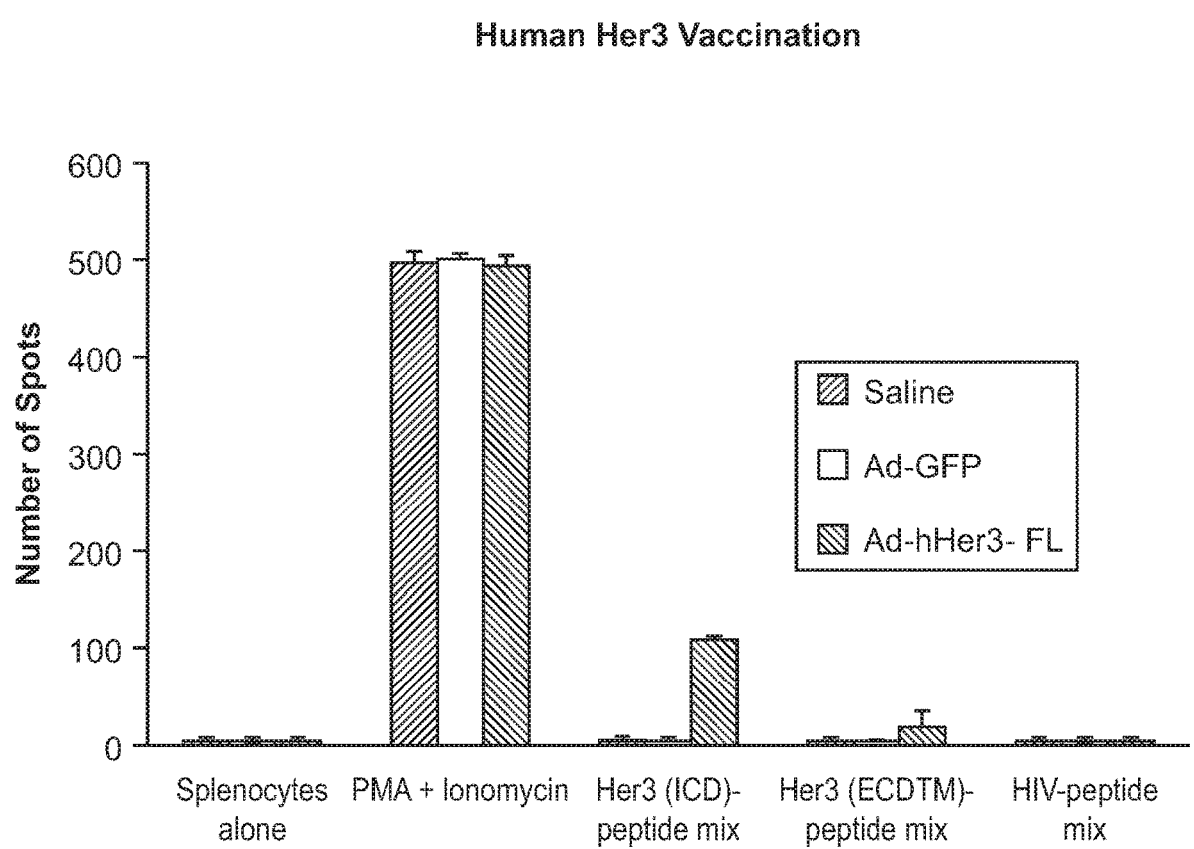
FIG. 8 illustrates the anti-HER3 cellular responses induced by Ad-HER3 vaccination.

FIG. 8 shows anti-HER3 cellular responses induced by Ad-HER3 vaccination. Mice were vaccinated with Ad5 [E1−, E2b−]-HER3, control Ad-GFP ($2.6 \times 10^{10}$ vp/vaccination), or saline alone. Two weeks later, vaccination was repeated with the same Ad vectors and 4 days later, the spleen was collected to assess anti-HER3 cellular response. ELISPOT plates were coated with anti-IFNγ mAb overnight. 500K splenocytes were put into each well with HER3-ECD peptide pool, HER3-ICD peptide pool, HIV peptide pool (negative control), and PMA+Ionomycin (positive control). Cells were incubated overnight, and spots were developed. An average of 3 mice from each group is shown. ELISPOT results showed that cellular responses were induced by Ad-HER3 immunization, as evidenced by the higher number of spots in splenocytes exposed to HER3 (intracellular, "ICD") peptide mix or the HER3 (extracellular domain and transmembrane domain, "ECDTM") peptide mix.

Antitumor Response

Tumor growth was measured twice a week until 34 days after tumor cell implantation. Once the tumor volume reached 2,000 mm³ or tumors had ulceration, mice were euthanized. Until day 20, all mice survived and the average tumor volume was calculated for each group. Preliminary results for the statistical analysis are shown in FIG. 9.

Figure 9:
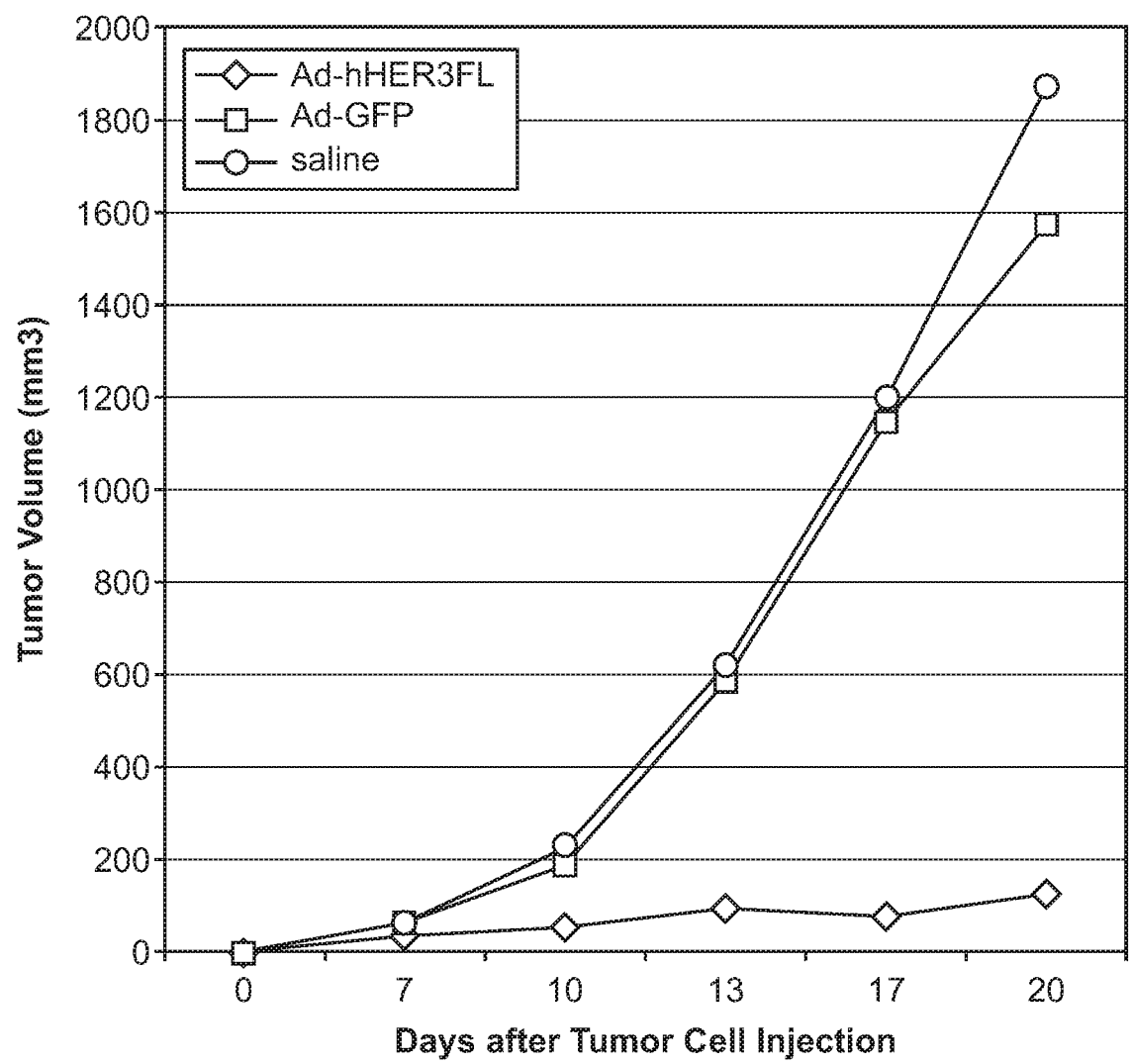
FIG. 9 illustrates the effect of the Ad5-[E1−, E2b−]-HER3fl vaccine on JC-HER3 tumor growth in BALB/c mice.

FIG. 9 shows the effect of the Ad5-[E1−, E2b−]-HER3fl vaccine on JC-HER3 tumor growth in BALB/c mice. BALB/c mice were vaccinated twice before (day−18, day−4) and once after (day 14) tumor cell implantation with Ad5 [E1−, E2b−]-HER3fl, Ad-GFP ($2.6 \times 10^{10}$ particles/mouse) or saline via footpad injection. On day 0, each mouse was implanted with JC-HER3 mouse mammary tumor cells expressing human HER3 ($1 \times 10^6$ cells/mouse). Tumor volume was measured every three days. Error bars show standard error.

Ad5 [E1−, E2b−]-HER3 vaccination demonstrated a robust inhibitory effect for tumor growth in BALB/c mice compared to control groups (saline injection). A mixed model was used to analyze the data. Square root transformation was used for tumor volume to make the relation volume versus time linear and normalize the data. The model results clearly show that the tumor volume increases with time (Days) for the Saline group. The growth rate of tumor volume for the vaccine Ad5 [E1−, E2b−]-HER3 group was significantly slower than that in saline group, while the difference in the tumor growth in saline and Ad-GFP is not significant.

Figure 10:
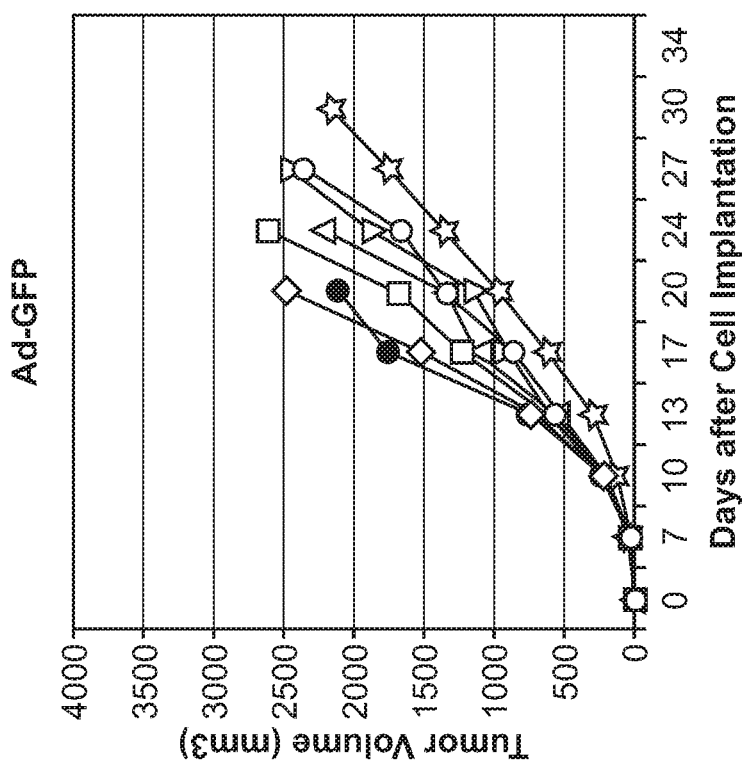
FIG. 10 illustrates the effect of Ad5-[E1−, E2b−]-HER3 vaccination on JC-HER3 tumor growth in BALB/c mice.
Figure 10:
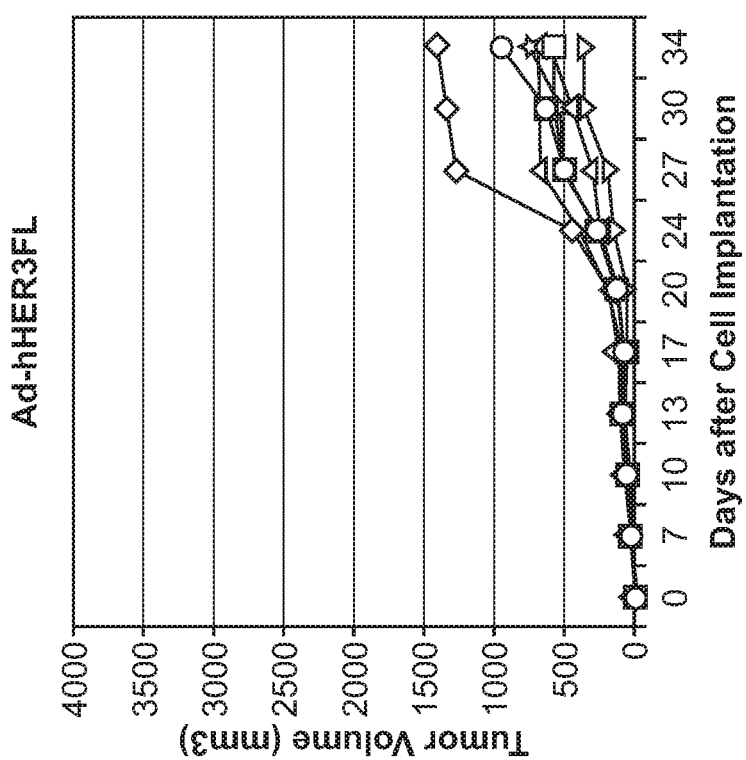

FIG. 10 shows the effect of Ad5 [E1−, E2b−]-HER3 vaccination on JC-HER3 tumor growth in BALB/c mice. FIG. 10A shows tumor growth in mice vaccinated with Ad-hHER3FL. FIG. 10B shows tumor growth in mice vaccinated with Ad-GFP. Mice were euthanized when tumor volume reached 2000 mm³ or had ulceration on the tumor. No mice died in Ad5 [E1−, E2b−]-HER3 vaccine group.

Example 5

Assessment of Preclinical Immunogenicity of Ad5 [E1−, E2b−]-HER3 in a HER3 Transgenic Mouse Model This example describes assessment of preclinical immunogenicity testing of Ad5 [E1−, E2b−]-HER3 in a HER3 transgenic mouse model. A HER3 transgenic mouse model was developed on a BALB/c background (F1 Hybrid mice; BALB/c×MMTV-neu/MMTV-hHER3) to test Ad-HER3 vectors for HER3 specific immunogenicity and anti-tumor effects in a human HER3 expressing mouse.

The following human HER3 (E1−, E2b−, E3−) Adenovirus vectors were compared in immunogenicity, prevention, and treatment assays using a HER3 transgenic mouse model: (1) Ad5 [E1−, E2b−]-HER3-FL; express human HER3 full length, (2) Ad5 [E1−, E2b−]-HER3-ECDTM (truncated); express human HER3 extracellular domain (ECD) and transmembrane domain (TM), (3) Ad5 [E1−, E2b−]-HER3-ECD; express human HER3 ECD, and (4) Ad5 [E1−, E2b−]-HER3-ECDC1C2; express human HER3 ECD and C1C2 domain.

Immunogenicity testing was performed with Ad-HER3 vectors. Vaccinations were repeated in 2 weeks interval and mice were sacrificed for immune assays a week after the boost vaccination.

Figure 11:
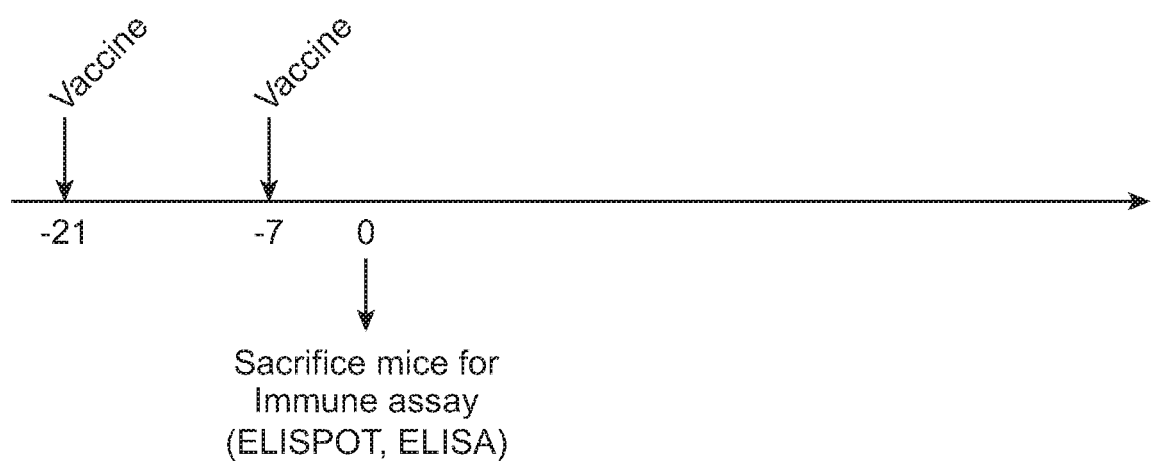
FIG. 11 illustrates a schematic of immunogenicity testing in HER3 transgenic mice.

FIG. 11 shows an immunology schedule of immunogenicity testing in HER3 transgenic mice. On days −18 and −4, mice were vaccinated with Ad-vectors ($2.6 \times 10^{10}$ virus particles/mouse), and four mice from each group were sacrificed for immune assays on day 0. Spleens were harvested for an ELISPOT assay and blood was collected to test for antibody production.

Figure 12:
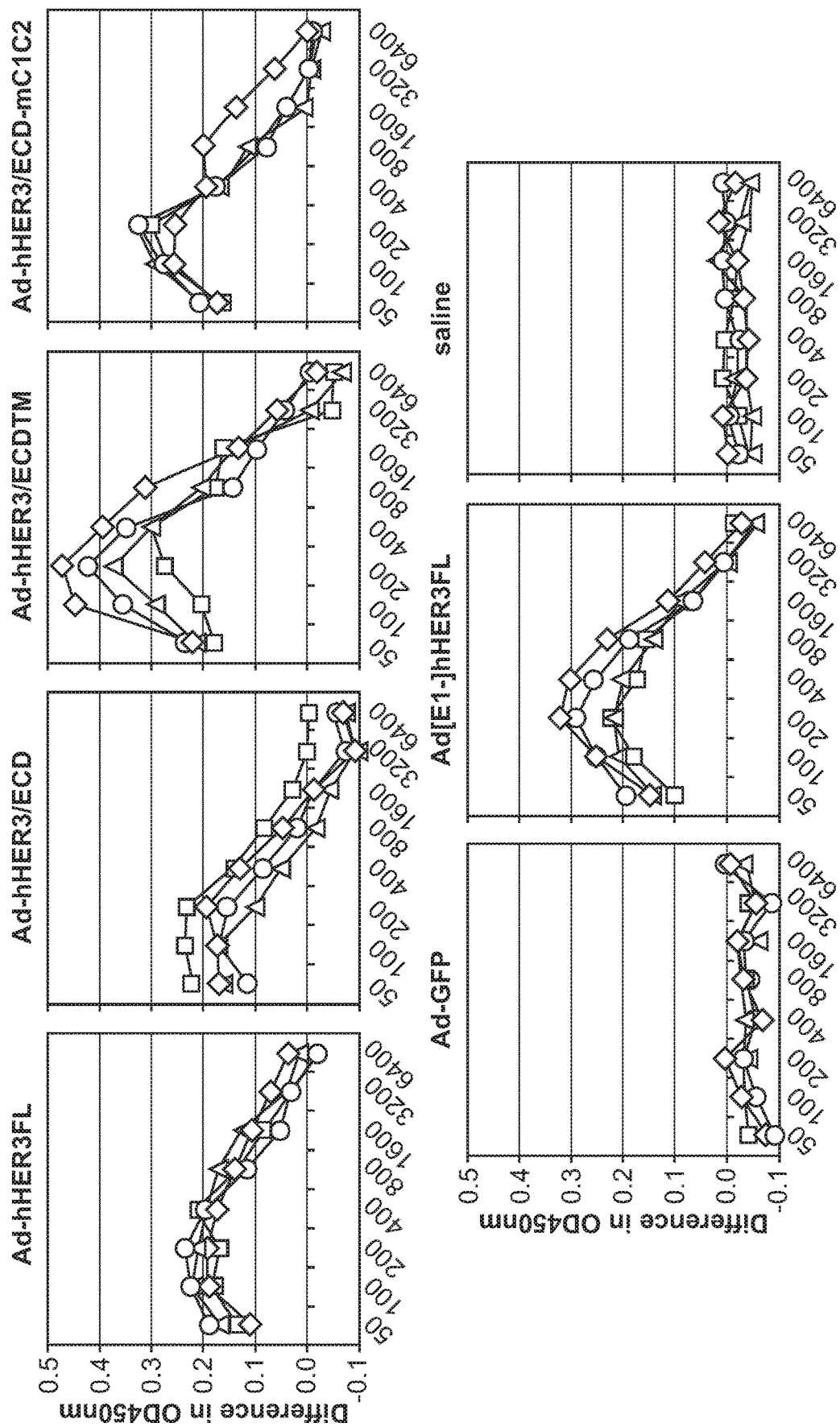
FIG. 12 illustrates the results of cell-based ELISA analysis of serum from HER3 transgenic mice after immunization.

Anti-HER3 serum antibody levels were analyzed using a cell-based ELISA. 4T1 murine breast cancer cell line (HER3 negative) and human HER3 transfectant (4T1-HER3) were used in this assay. Sera from each mouse were titrated from 1:50 to 1:6400. FIG. 12 shows the results of cell-based ELISA analysis of serum from HER3 transgenic mice. HER3 transgenic mice were vaccinated twice with Ad5 [E1−, E2b−]-huHER3 vectors, Ad-GFP control, or saline. Seven days after the last vaccine, mice were euthanized and serum was collected. 4T1 and 4T1-HER3 cells were seeded into 96-well plates. After overnight incubation, cells were washed with buffer and mouse serum with serial dilutions was added (1:50 to 1:6400) and incubated for 1 hour on ice. Cells were fixed and HRP-labeled Goat anti-mouse IgG (1:2000) was added. After 1 hour incubation, cells were washed with PBS three times, and TMB was added for five min. Color development was stopped by adding $H_2SO_4$. Differences of OD450 values (value for 4T1-HER3)−(value for 4T1) are shown for individual mice. Cell-based ELISA assay results, confirmed anti-HER3 antibody production in all Ad5-HER3 vaccinated mice. Each of the 5 adenoviral vectors showed comparable efficacy in induction of humeral immunity in this model, but Ad5 [E1−, E2b−]-huHER3-FL and Ad5 [E1−, E2b−]-huHER3-ECDTM induced slightly higher levels of anti-HER3 antibody. Negative controls Ad-GFP and saline did not induce humoral immunity.

Antigen-Specific Cellular Response

Antigen-specific cellular immune response in HER3 Transgenic mice were analyzed by an IFN-γ ELISPOT assay. Only adenoviral vectors encoding full length HER3 induced T cell responses for the intracellular domain of HER3 antigen. T cell responses against the peptide mix of HER3 extracellular domain were variable. Ad5 [E1−, E2b−]-huHER3-FL, Ad5 [E1−, E2b−]-huHER3-ECDTM, and Ad5 [E1−, E2b−]-huHER3-ECD-TM induced similar levels of strong cellular response against extracellular domain of HER3. Ad5 [E1−]-huHER3 virus encoding full length HER3, however, induced only weak cellular response against extracellular domain, probably because of neutralization by anti-Ad antibody induced by the priming vaccine.

Figure 13:
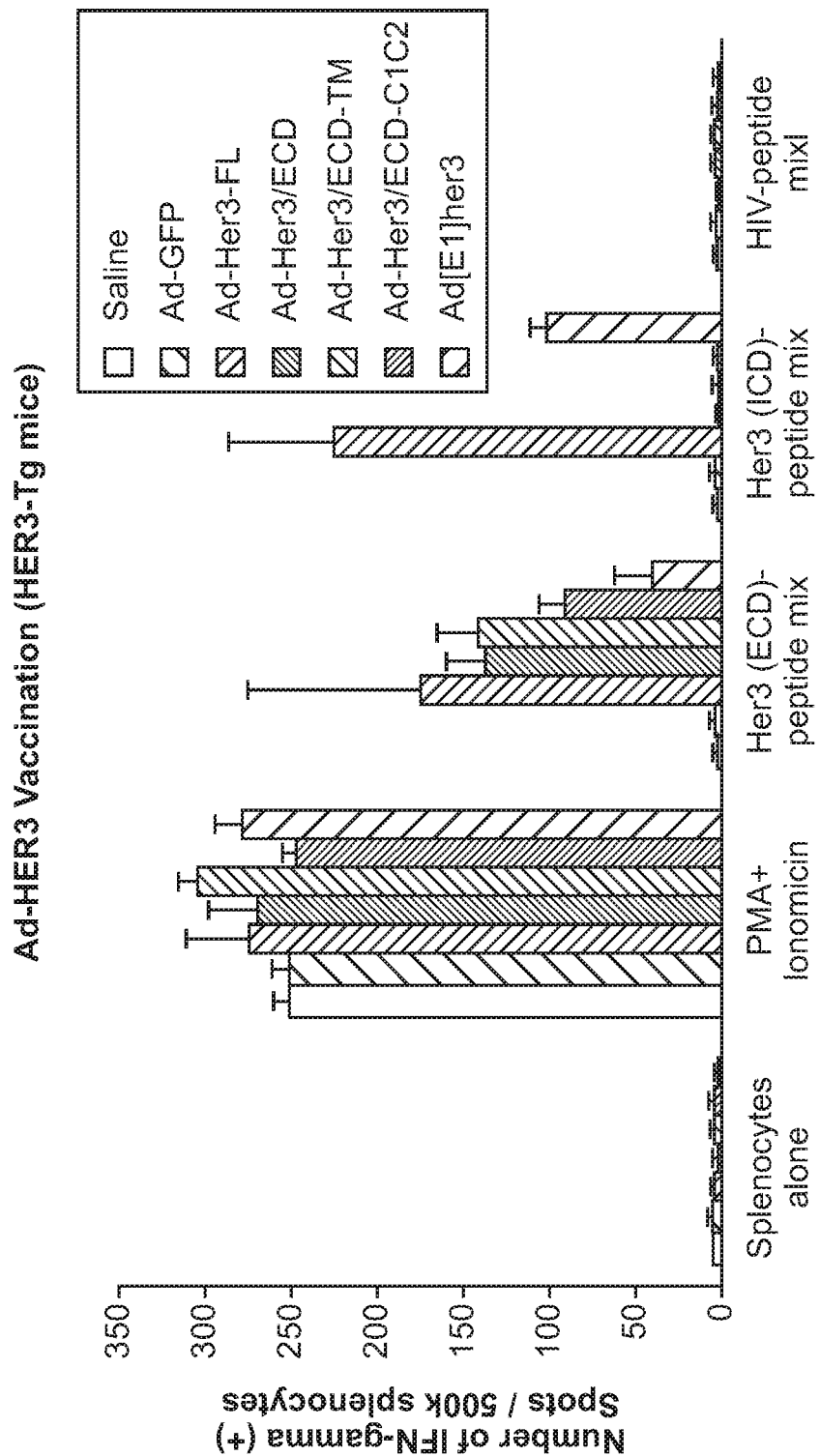
FIG. 13 illustrates anti-HER3 cellular responses induced by vaccination.

FIG. 13 shows anti-HER3 cellular responses induced by vaccination. Mice were vaccinated with Ad5 [E1−, E2b−]-huHER3-full length (FL), Ad5 [E1−, E2b−]-huHER3-ECD, Ad5 [E1−, E2b−]-huHER3-ECD-TM, Ad5 [E1−, E2b−]-huHER3-ECD-mC1C2, or control Ad-GFP, Ad5 [E1−]-HER3 ($2.6 \times 10^{10}$ virus particles/vaccination). Two weeks later, vaccination was repeated with the same Ad vectors, and four days later, spleens were collected to assess anti-HER3 cellular response. ELISPOT plates were coated with anti-IFNγ mAb overnight. 500K splenocytes were put into each well with HER3-ECD peptide pool, HER3-ICD peptide pool, HIV peptide pool (negative control) and PMA+Ionomycin (positive control). Cells were incubated overnight, and spots were developed. An average of 3 mice from each group is shown.

To test Ad-HER3 vaccine efficacy in a HER3 transgenic mouse, a tumor treatment experiment was conducted. Mice were vaccinated with Ad5 [E1–E2b-]-HER3 vectors (Ad5 [E1–, E2b]-HER3-FL, Ad5 [E1–, E2b-]-HER3-ECD, Ad5 [E1–, E2b-]-HER3-ECDTM, and Ad5 [E1, E2b] HER3 ECD-C1C2). Details are shown in TABLE 4.

TABLE 4

Treatment and Assay Schedule

| Group | Mouse # | Day 0 Tumor Injection | Day 3, 10, 17 Vaccine 1, 2, 3 | Day 40 or humane endpoint assessment |
|---|---|---|---|---|
| A | 10 | JC-hHER3 cell injection (5 × 10$^5$ cells/mouse) | Ad5 [E1-E2b-]-HER3-FL | Tumor volume measured until Day 40 or until volume reaches 2000 mm$^3$ |
| B | 10 | | Ad5 [E1-E2b-]-HER3-ECD | |
| C | 10 | | Ad5 [E1-E2b-]-HER3-ECD-TM | |
| D | 10 | | Ad5 [E1-E2b-]-HER3-ECD-C1C2 | |
| E | 10 | | Ad5 [E1-]-HER3 | |
| F | 10 | | Saline | |

FIG. 14 shows JC-HER3 tumor growth in HER3+ F1 Hybrid mice treated with Ad-HER3 vaccines. F1 Hybrid Mice (BALB/c×MMTV-neu/MMTV-HER3) received JC-HER3 tumor cell injections (5×10$^5$ cells/mouse, in 50% Matrigel) on day 0, and were treated with Ad5 [E1–, E2b–]-HER3 (full length, ECD, ECDTM, ECD-C1C2), Ad5 [E1–]-HER3 (2.6×10$^{10}$ vp/injection), or saline on days 3 and 10. Tumor size was measured twice a week. Individual tumor growth is shown and error bars indicate standard error.

Figure 15:
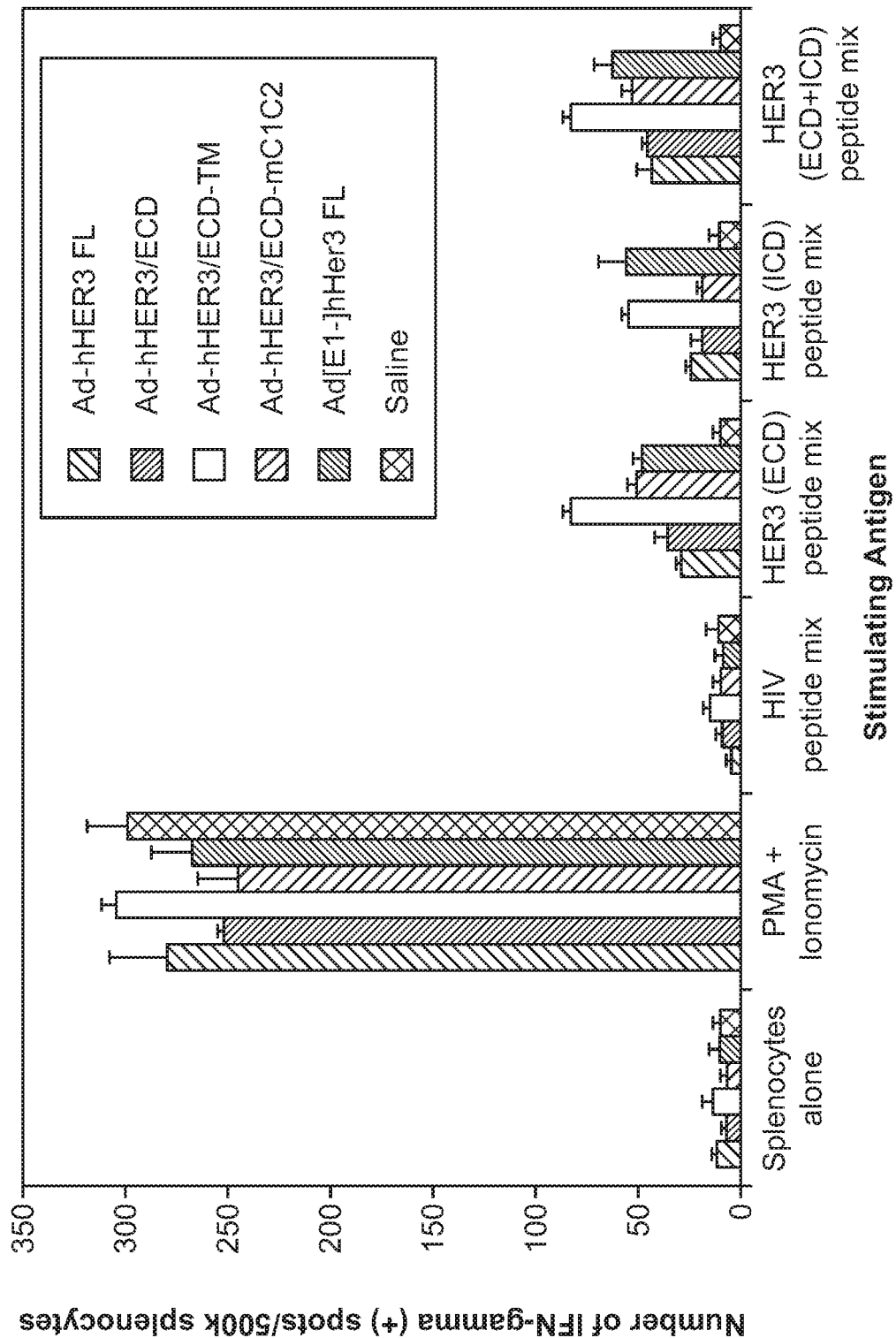
FIG. 15 illustrates anti-HER3 cellular response induced by Ad-HER3 vaccination as measured by IFN-γ production.

FIG. 15 shows anti-HER3 cellular response induced by Ad-HER3 vaccination. F1 Hybrid Mice (BALB/c×MMTV-neu/MMTV-HER3) received JC-HER3 tumor cell injections (5×105 cells/mouse, in 50% Matrigel) on day 0, and treated with Ad [E1–E2b–]-huHER3 (full length, ECD, ECDTM, ECD-C1C2), Ad5 [E1–]-huHER3 (2.6×10E10 vp/injection) or saline on days 3 and 10. When tumor volume reached humane endpoint, mice were sacrificed. ELISPOT plates were coated with anti-IFNγ mAb overnight. 500K splenocytes were put into each well with HER3-ECD peptide pool, HER3-ICD peptide pool, HIV peptide pool (negative control), and PMA+Ionomycin (positive control). Cells were incubated overnight, and spots were developed. An average of 4 mice from each group are shown.

Figure 16:
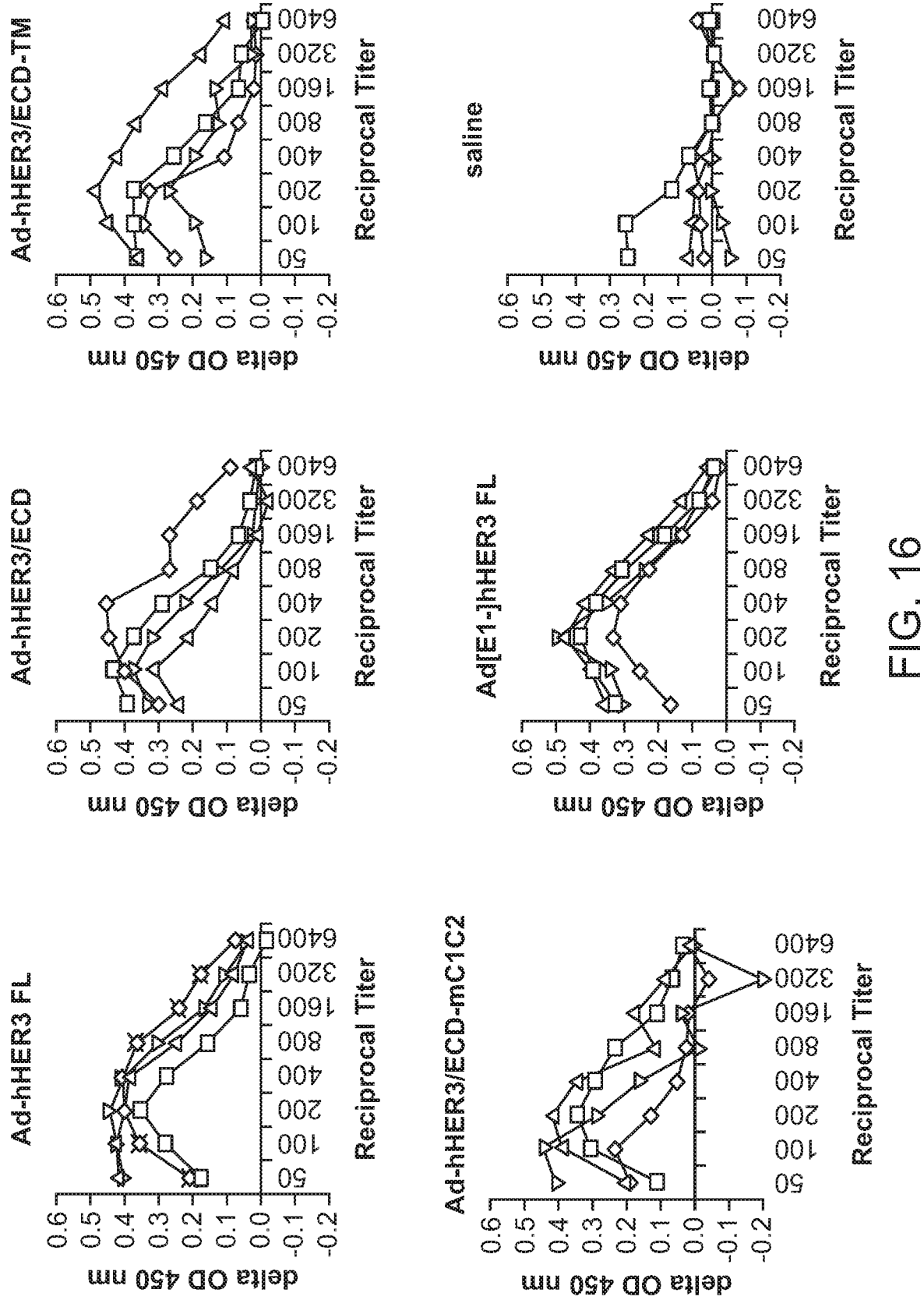
FIG. 16 illustrates anti-HER3 antibody levels in Ad-HER3 vaccinated F1 Hybrid mice (BALB/c×MMTV-neu/MMTV-hHER3) implanted with JC-hHER3 tumor cells in a cell-based ELISA assay.

FIG. 16 shows anti-HER3 antibody levels in Ad-HER3 vaccinated F1 Hybrid mice in a cell-based ELISA assay. Female F1 Hybrid mice (BALB/c×MMTV-neu/MMTV-hHER3) were implanted with JC-hHER3 cells (5×10$^5$ cells/mouse) on day 0, and then vaccinated twice on days 3 and 10 with Ad5 [E1–, E2b–]-huHER3 (full length, ECD, ECD-TM, ECD-C1C2) or Ad [E1–]-HER3 full length (2.6×10$^{10}$ vp/mouse). Once the tumor volume reached a humane endpoint, mice were sacrificed, and blood was collected from each mouse. Serum was used for cell-based ELISA (4T1-HER3 and 4T1 cells as plating cells). HRP-conjugated goat anti-mouse IgG was used as secondary Ab, and color was developed with TMB substrate and reaction was stopped by H$_2$SO$_4$. Individual OD 450 nm values (OD value with 4T1-HER3 cells minus OD value with 4T1 cells) are shown.

HER3 expression in tumors in mice following Ad-huHER3 vaccination was also evaluated. In mice vaccinated with Ad-huHER3, HER3 expression was decreased in tumors compared to saline control showing the anti-HER3 response induced by the Ad-huHER3 vectors not only reduced tumor growth but also reduced expression of HER3 on the tumors.

Figure 17:
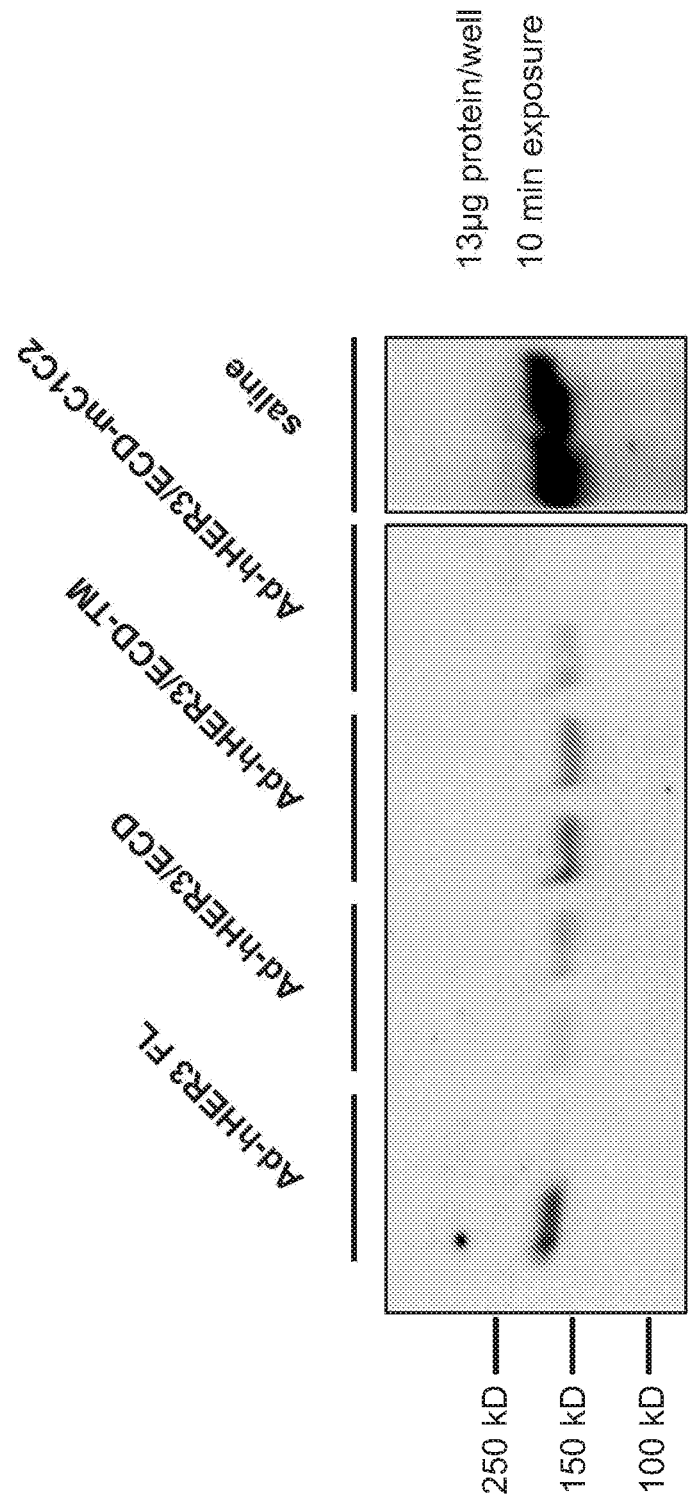
FIG. 17 illustrates HER3 expression in JC-HER3 tumors in Ad-HER3 vaccinated F1 Hybrid Mice (BALB/c×MMTV-neu/MMTV-HER3) implanted with JC-HER3 tumor cells.

FIG. 17 shows HER3 expression in JC-HER3 tumors from mice administered Ad-HER3 vaccines. F1 Hybrid Mice (BALB/c×MMTV-neu/MMTV-HER3) received JC-HER3 tumor cell injections (5×10$^5$ cells/mouse, in 50% Matrigel) on day 0, and were treated with Ad5 [E1–, E2b–]-huHER3 (full length, ECD, ECD-TM, ECD-mC1C2), Ad5 [E1–]-huHER3 (2.6×10$^{10}$ virus particles/injection), or saline on days 3 and 10. When tumor volume reached a humane endpoint, mice were sacrificed. Western blot was performed with anti-hHER3 antibody, followed by biotin-conjugated anti-mouse IgG and streptavidin-HRP.

Figure 18:
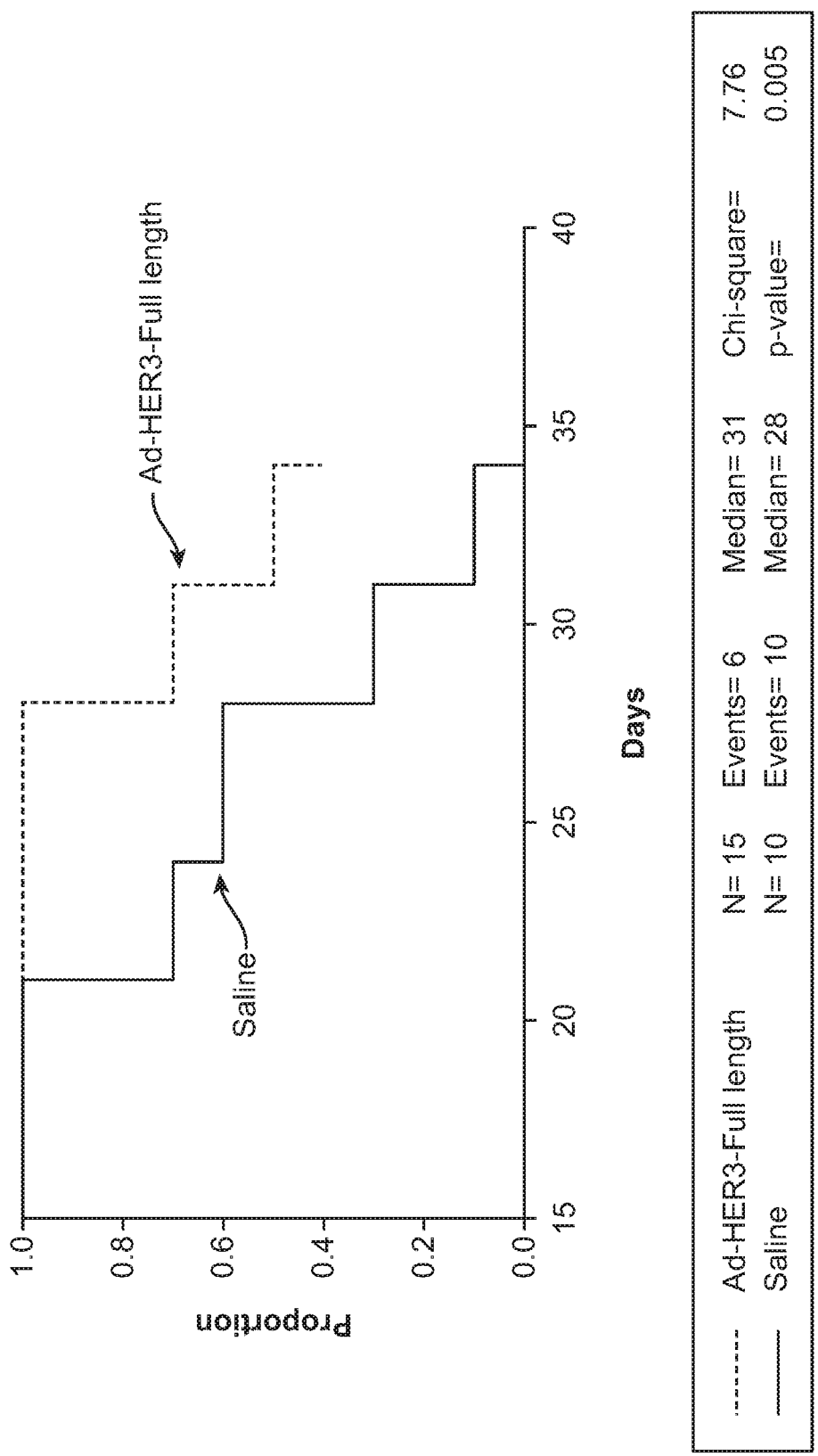
FIG. 18 illustrates survival curves from JC-HER3 treatment in F1 Hybrid female mice (BALB/c×MMTV-neu/MMTV-hHER3) administered Ad5 [E1−, E2b−]-huHER3 full length vaccine or a saline control.

FIG. 18 shows survival curves from JC-HER3 treatment ecomparing Ad5 [E1–, E2b–]-huHER3 full length and saline control. Results demonstrate a significant increase in survival time with the Ad5 [E1–, E2b–]-HER3 full length vaccines. HER3 Transgenic F1 Hybrid female mice (BALB/c×MMTV-neu/MMTV-hHER3) were injected with JC-hHER3 cells (5×105 cells/mouse) on day 0, and treated with Ad5 [E1–E2b–]-huHER3 (full length, 2.6×10E10 vp/injection), or saline on days 3 and 10. Tumor size was measured twice a week. Mice were considered dead at the time the tumor volume reached a humane endpoint. Survival curve for each group was made from survival data of two independent experiments with identical treatment schedule. The Kaplan-Meier method was used to estimate overall survival and groups were compared using a two-sided log-rank test.

Example 6

Phase I Study of Active Immunotherapy with Ad5 [E1–, E2b–]-HER3 Truncated Vaccine in Patients with Advanced or Metastatic Malignancies This example describes a Phase I study of active immunotherapy with Ad5 [E1–, E2b–]-HER3 vaccine in patients with advanced or metastatic malignancies. The primary objective of this study includes (1) to assess the safety and tolerability of Ad5 [E1–, E2b–]-HER3 truncated. The secondary objectives of this study include (1) to evaluate HER3-specific antibody and T cell responses to the vaccination and (2) in patients with ER+ and/or PR+/HER2/neu—breast cancer, refractory to anti-estrogen therapy, to evaluate for markers of HER3 signaling activation in tumor tissue. The exploratory objectives of this study include (1) to evaluate immune cell infiltration into tumor tissue before and after vaccination, (2) to expand tumor tissue for further analysis of pathways and mutations associated with treatment resistance, and (3) report preliminary evidence of clinical activity.

Second generation Ad5 [E1–, E2b–]-vectors induce more potent immune responses despite neutralizing antibodies than first generation Ad5 [E1–] vectors. Ad5 [E1–, E2b–]-HER3 immunizations resulted in longer survival and greater tumor growth control than controls. Based on preclinical data demonstrating that antitumor HER3 directed immune response activity in a HER3 transgenic mouse model was achieved with the Ad5 [E1-E2b-] huHER3-ECDTM vaccine, Ad5 [E1-E2b-]-huHER3 expressing the truncated version of the HER3 (subsequently referred to as Ad5 [E1-, E2b-]-HER3 truncated) is selected for the vaccine to use in this Phase I clinical trial. Additionally, there may be an added safety factor in that the Ad5 [E1-, E2b-]-HER3-ECDTM does not contain a kinase region that may potentially contribute to oncogenic activity.

Rationale for Patient Population. Patients are enrolled with advanced malignancies that are expected to express HER3 who have progressed after standard therapy known to lengthen survival. For these patients, clinical trials are considered an appropriate recommendation for management of their disease. HER3 is overexpressed in breast, colon, lung, prostate, ovarian, cervical, endometrial, gastric, pancreatic, bladder, head and neck, liver, and esophageal cancer.

Rationale for Endpoints Chosen. In the phase I portion of the study, the objective is to identify a safe dose of the vaccine within a feasible range of dose levels. Because the expected mechanism of action for the vaccine is to induce T cell and antibody responses, HER3-specific T cell and antibody responses from the peripheral blood are also examined. Standard assays for measuring this immune response include the ELISPOT to enumerate the proportion of HER3-responsive T cells and cytokine flow cytometry which identifies the CD4+ and CD8+ T cell contributions to the immune response. HER3 specific antibody levels are determined by ELISA.

Patient Selection—Inclusion Criteria

Subject eligibility for the Phase I clinical trial is defined by inclusion criteria and exclusion criteria. Inclusion criteria include the following: histologically confirmed, advanced solid tumors which have progressed after standard therapy known to lengthen survival, histologically confirmed metastatic or inoperable breast cancer and tumor tissue safely accessible for core or punch biopsy. In addition, subjects must have received at least one line of treatment with standard therapy. For the following common cancers, the prior therapy required is defined as follows.

For colorectal cancer—subjects must have received and progressed through at least one line of therapy consisting of one of the following regimens: (1) 5-fluorouracil (or capecitabine) and oxaliplatin, (2) 5-fluorouracil (or capecitabine) and irinotecan, (3) chemotherapy regimen that includes bevacizumab or ziv-aflibercept or ramucirumab, (4) or chemotherapy regimen that includes cetuximab or panitumumab.

For breast cancer—subjects must have received and progressed through at least one line of therapy consisting of one of the following regimens: (1) cytotoxic chemotherapy (anthracycline, capecitabine, or taxane-based), (2) patients with tumors that over-express HER2/neu (IHC 3+ or FISH amplified) must have received and progressed through at least one line of therapy with trastuzumab, pertuzumab, or lapatinib with or without chemotherapy. In the Dose Expansion Cohort, breast cancer patients currently receiving anti-HER2/neu targeted therapy (trastuzumab, pertuzumab, lapatinib) are eligible and may continue these therapies concomitant with study treatment (if they have been on these therapies for at least 3 months), or (3) endocrine therapy if tumor is ER+ and or PR+ (including aromatase inhibitors, tamoxifen, Fulvestrant, GnRH agonists). Breast cancer patients currently receiving endocrine therapy may continue these therapies concomitant with study treatment (if they have been on these therapies for at least 3 months).

For lung cancer—anti-PD1 antibody therapy is not required prior to study participation, however subjects must have received and progressed through at least one line of therapy consisting of one of the following regimens: (1) platinum-based (cisplatin or carboplatin) chemotherapy, (2) taxane-based (docetaxel or paclitaxel) or vinorelbine chemotherapy, or (3) single-agent erlotinib, gefitinib, or crizotinib.

For pancreatic cancer—subjects must have received and progressed through at least one line of therapy consisting of one of the following regimens: (1) gemcitabine alone or with other drugs, (2) fluorouracil with oxaliplatin and/or irinotecan.

For other malignancies, if a first line therapy exists, it should have been administered to subjects and there should have been progressive disease.

Further inclusion criteria are that at least 3 weeks must have passed since prior cytotoxic chemotherapy or radiotherapy to the start of study treatment, an ECOG 0 or 1, an estimated life expectancy >3 months, an age ≥18 years, adequate hematologic function, with ANC >1500/4, hemoglobin ≥9 g/dL, and platelets ≥75,000/μL, adequate renal and hepatic function, with serum creatinine <1.5 mg/dL, bilirubin <1.5 mg/dL (except for Gilbert's syndrome which will allow bilirubin ≤2.0 mg/dL), ALT and AST ≤2.5×ULN or if liver metastases are present ≤5×ULN. ECOG scoring is summarized below in TABLE 5.

TABLE 5

ECOG Performance Status Scale

| Grade | Descriptions |
|---|---|
| 0 | Normal activity. Fully active, able to carry on all pre-disease performance without restriction. |
| 1 | Symptoms, but ambulatory. Restricted in physically strenuous activity, but ambulatory and able to carry out work of a light or sedentary nature (e.g., light housework, office work). |
| 2 | In bed <50% of the time. Ambulatory and capable of all self-care, but unable to carry out any work activities. Up and about more than 50% of waking hours. |
| 3 | In bed >50% of the time. Capable of only limited self-care, confined to bed or chair more than 50% of waking hours. |
| 4 | 100% bedridden. Completely disabled. Cannot carry on any self-care. Totally confined to bed or chair. |
| 5 | Dead. |

Prior immunotherapy must have been discontinued at least 3 months prior to the start of study treatment. Female patients must be of non-child-bearing potential or use effective contraception, e.g., use of oral contraceptives with an additional barrier method (since the study drug may impair the effectiveness of oral contraceptives), double barrier methods (diaphragm with spermicidal gel or condoms with contraceptive foam), Depo-Provera, partner vasectomy, total abstinence, and willing to continue the effective contraception method for 30 days after the last dose of study treatment.

Labs performed as standard of care prior to signing consent can be used to fulfill eligibility requirements if they were performed within 4 weeks of the start of study treatment. Subjects must have the ability to understand and provide signed informed consent, ability to return to the study site for adequate follow-up, as required by this protocol. Negative serum pregnancy test within 7 days prior to the start of study treatment is required for women of childbearing potential only.

Patient Selection—Exclusion Criteria

Subject eligibility for the Phase I clinical trial is defined by inclusion criteria and exclusion criteria. Exclusion criteria include the following: less than 3 weeks have passed between any prior cytotoxic chemotherapy and/or radiotherapy and start of study treatment and patients must have recovered to Grade 1 toxicities from prior treatment (except Grade 2 alopecia or fatigue), known CNS/brain metastases (treated metastases permitted, provided the patient is asymptomatic and off all steroids at least 4 weeks prior to the start of study treatment)—no brain imaging will be required as part of this study, history of auto-immune disease such as, but not restricted to, inflammatory bowel disease, systemic lupus erythematosus, ankylosing spondylitis, scleroderma, or multiple sclerosis (prior history of autoimmune thyroiditis or vitiligo is not exclusion).

Further exclusion criteria are serious chronic or acute illness, which constitute an unwarranted high risk for investigational treatment, medical or psychological impediment to probable compliance with the protocol, concurrent or prior second malignancy (within the past 5 years) other than non-melanoma skin cancer, carcinoma in situ of the bladder and cervix, the presence of active infection or systemic use of antimicrobials within 48 hours prior to the start of study treatment. Patients on continuous steroid therapy for at least 72 hours (or other continuous immunosuppressives such as azathioprine or cyclosporine A) are excluded on the basis of potential immune suppression. Patients must have had 4 weeks of discontinuation of any continuous steroid therapy (taken for at least 72 hours duration) prior to start of study treatment (except steroids used for allergic reactions or as anti-emetics for systemic chemotherapy which are permitted). Exclusion criteria also include the presence of a known active acute or chronic infection including HIV or viral hepatitis (Hepatitis B and C) and pregnant or nursing women.

Subjects receive study treatment every 3 weeks for a total of 3 vaccinations and return 3 weeks after the third vaccination and then every 3 months for up to one year for long term follow-up. Day 0/Week 0 is the day of the first vaccination. The second vaccination is at Day 21/Week 3 and the third vaccination is Day 42/Week 6. Three weeks after the completion of the third vaccination is Day 63/Week 9. Long term follow-up visits are Follow-Up 1/Month 3, Follow-Up 2/Month 6, Follow-Up 3/Month 9, and Follow-Up 4/Month 12.

Treatment Plan

Dosing. Subjects receive Ad5 [E1–, E2b–]-HER3 truncated at a dose of $1\times10^{10}$ virus particles (VPs) (for de-escalation), $1\times10^{11}$ VPs, or $5\times10^{11}$ VPs in 1 mL subcutaneously (SQ) in the same thigh every 3 weeks for 3 vaccinations. The dose for the first patient in the trial is $1\times10^{11}$ VPs based on prior experience of no dose limiting toxicity with our Ad5 [E1–, E2b–]-HER3 vector. DLT will be assessed as defined below.

Dose Limiting Toxicity Definition. Based on NCI CTCAE 4.03, dose limiting toxicity (DLT) is defined as any of the following study treatment-related adverse events occurring within 3 weeks of the first dose of study treatment: Grade 2, 3 or 4 immediate hypersensitivity reactions, Grade 3 or 4 fever that may possibly be associated with the vaccination, Grade ≥2 autoimmune events except for vitiligo or fever for less than 2 days and less than <101.5° F., Grade ≥2 allergic reactions, or Grade ≥3 non-hematologic toxicity.

Study Treatment. Vaccine administration occurs during study visits on Weeks 0, 3, and 6. No premedication is given. Each dose (Ad-HER3) is injected subcutaneously into the thigh. The same thigh is used for each vaccination. Patients remain in the clinic for 1 hour after each vaccination with vital signs checked post-vaccination at 15 minutes, 30 minutes, and 1 hour.

Cohort 1. Three patients receive Ad5 [E1–, E2b–]-HER3-ECDTM at a dose of $1\times10^{11}$ VPs in 0.2 mL subcutaneously (SQ) in the same thigh every 3 weeks for 3 immunizations. Immunizations are separated by 5 cm. Assessment of DLT for dose escalation are made after all patients in this cohort have had a study visit at least 3 weeks after receiving their first dose of vaccine. If there are no DLT (as defined below), then patients may begin enrolling into cohort 2. If there is ≤1 DLT then an additional 3 patients will be enrolled at this dosage level. Assessment of DLT for dose escalation is made after the 3 additional patients have had a study visit at least 3 weeks after receiving their first dose of vaccine. If none of these latter 3 patients have DLT, then patients may begin enrolling into cohort 2. If 2 patients have DLT at this lowest dosage level, dosing is de-escalated to $5\times10^{11}$ VPs and a new cohort instituted. Cohort 2. Three patients receive Ad5 [E1–, E2b–]-HER3-ECDTM at a dose of $5\times10^{11}$ VPs in 1.0 mL SQ in the same thigh every 3 weeks for 3 immunizations. Immunizations site are separated by 5 cm. Assessment of DLT for dose level 2 are made after all patients in this cohort have had a study visit at least 3 weeks after receiving their first dose of vaccine. If there are no DLT, then an additional 3 patients are enrolled. If there is ≤1 of 6 DLT, this dose will be the MTD. Assessment of DLT for dose escalation will be made after the 3 additional patients have had a study visit at least 3 weeks after receiving their first dose of vaccine. If 2 patients have DLT at this dosage level, the dosage level in cohort 1 is considered the MTD. An assessment of immune responses between the 2 dose levels is made before proceeding to Phase II.

Figure 19:
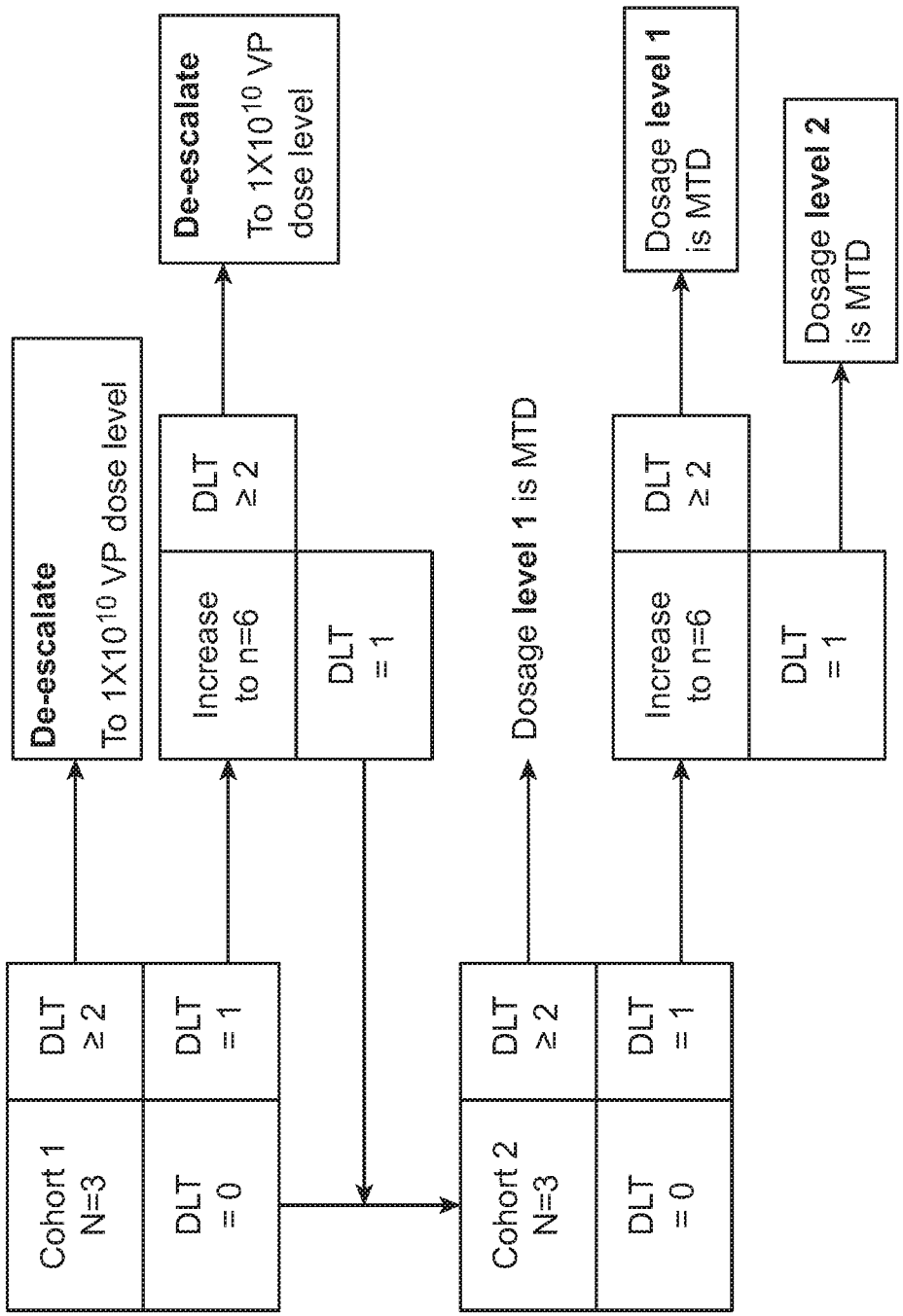
FIG. 19 illustrates a schematic of the dosing in each cohort.

$1\times10^{10}$ Virus Particles Dose De-escalation. $1\times10^{10}$ VP dose for de-escalation are prepared. 1 mL of the diluted Ad5 [E1–, E2b–]-HER3_ECD_TM (extracellular domain and transmembrane domain) is withdrawn, the injection site is prepared with alcohol, and the vaccine is administered to the subject by SC injection in the thigh. Three patients receive Ad5 [E1–, E2b–]-HER3-ECDTM at a dose of $1\times10^{10}$ virus particles in 1.0 mL SQ in the same thigh every 3 weeks for 3 immunizations. Immunizations site are separated by 5 cm. Assessment of DLT for dose de-escalation are made after all patients in this cohort have had a study visit at least 3 weeks after receiving their first dose of vaccine. FIG. 19 shows a schematic of the dosing in each cohort.

Dosage and Administration

Patients receive Ad5 [E1–, E2b–]-HER3 truncated at a dose of $1\times10^{10}$, $1\times10^{11}$, or $5\times10^{11}$ virus particles (VPs) subcutaneously (SQ) in 1 mL of a buffered saline solution every 3 weeks for a total of 3 vaccinations.

Ad5 [E1–, E2b–]-HER3 truncated will be provided in a frozen state in a 2 ml vial with a fill volume of 1 ml of extractable vaccine which contains $5\times10^{11}$ VPs total. The lower doses are produced by dilution in 0.9% saline using the directions as described below. The product is stored at ≤–65° C. until used.

Dose Preparation Instructions

De-esclation. De-esclataion dosing of $1\times10^{10}$ VPs by subcutaneous injection is prepared as following. A tuberculin syringe (syringe #1) is used to aseptically withdraw 0.2 ml from a 10 ml vial of sterile saline for injection. A second 1.0 mL tuberculin syringe (syringe #2) is used to aseptically withdraw 0.2 mL of fluid from an Ad5 [E1–, E2b–]-huHER3-truncated vaccine vial (at $5\times10^{11}$ VP/mL). The virus particles withdrawn into syringe #2 are injected into the saline vial and thoroughly mixed. The new solution is at a concentration of $1\times10^{10}$ VPs/mL. Another syringe is used to withdraw 1 mL of the diluted virus particles contained in the 10 mL saline solution. A new 1-mL sterile syringe is labeled Ad5 [E1−, E2b−]-HER3 truncated, $1\times10^{10}$ VPs. The prepared vaccine (Ad5 [E1−, E2b−]-HER3 truncated, $1\times10^{10}$ vp) can be kept at 4° C. for four hours prior to administration.

$1\times10^{11}$ VPs by SQ injection. A tuberculin syringe (syringe #1) is used to aseptically withdraw 0.2 ml from a vial of Ad5 [E1−, E2b−]-HER3-truncated vaccine. This prepared vaccine (Ad5 [E1−, E2b−]-HER3 truncated, $1\times10^{11}$ vp) can be kept at 4° C. for four hours prior to administration.

$5\times10^{11}$ VPs by SQ injection. A 1-mL sterile syringe is labeled Ad5 [E1−, E2b−]-HER3 truncated, $5\times10^{11}$ VPs. 1 mL of Ad5 [E1−, E2b−]-HER3 truncated vaccine is withdrawn from its vial into the labeled syringe. This prepared vaccine (Ad5 [E1−, E2b−]-HER3 truncated, $5\times10^{11}$ vp) can be kept at 4° C. for four hours prior to administration.

Study Evaluations

A full study schema is summarized in TABLE 6.

Pre-Treatment Evaluations. Patients will have the following pre-treatment evaluations completed within 4 weeks prior to the start of study treatment. General evaluations include medical history, ECOG performance status, and complete physical examination with vital signs, weight and height. Any other treatments, medications, biologics, or blood products that the patient is receiving or has received in the last month is documented. Blood chemistry and hematology, including CBC with differential, sodium, potassium, chloride, bicarbonate, blood urea nitrogen (BUN), creatinine, calcium, total protein, albumin, total bilirubin, alkaline phosphatase, AST, ALT and glucose are completed. For women of child bearing potential, a serum pregnancy test is completed within 7 days prior to the first vaccination. Peripheral blood (approximately 90 ml) is collected at a pre-treatment or screening visit for serum, plasma and peripheral blood mononuclear cells (PBMCs) to assess antibody, and T cell responses, and other markers of immunity. In the dose escalating portion of the study, a core or punch biopsy of tumor tissue is requested (but not required) prior to the first vaccination. In the expanded cohort, a core or punch biopsy of tumor tissue is required prior to the first vaccination. Tumor tissue is analyzed for HER3 signaling, T cell infiltration, and other markers of immune response including PD-L1 expression.

Evaluations during Treatment. Subjects have evaluations on days of vaccinations (i.e., Week 0, Week 3, and Week 6). On days of vaccination, blood is drawn before vaccine administration. Evaluations also occur when study treatment is discontinued prior to the completion of the assigned vaccine schedule (i.e., Off Treatment). General evaluations include medical history, ECOG performance status, and complete physical examination with vital signs and weight. Any other treatments, medications, biologics, or blood products that the patient is receiving or has received since the last visit are documented. Patients remain in the clinic for approximately 1 hour following receipt of vaccine to monitor for any adverse reactions and vital signs are checked post-vaccination at 15 minutes, 30 minutes, and 1 hour. Blood chemistry and hematology, including CBC with differential, sodium, potassium, chloride, bicarbonate, blood urea nitrogen (BUN), creatinine, calcium, total protein, albumin, total bilirubin, alkaline phosphatase, AST, ALT and glucose are completed on Week 0, 3, 6, at discontinuation of study treatment (if assigned vaccine schedule is not completed), and as clinically indicated. Peripheral blood (approximately 90 mL) is collected prior to each vaccination

TABLE 6

Study Schema

| Procedures/Tests | Pre-Treatment[1] (−28 days) | Week 0 | Week 3 | Week 6 | Off Treatment[11] | Week 9 (+/− 14 days) | Months 3, 6, 9, etc.[12] (+/− 28 days) |
|---|---|---|---|---|---|---|---|
| Medical History | X | | | | | | |
| Physical Exam | X | X | X | X | X | X | X |
| ECOG PS [2] | X | X | X | X | X | X | X |
| Vital Signs | X | X[3] | X[3] | X[3] | X | X | |
| Pregnancy Test | X[4] | | | | | | |
| CBC with diff [5] | X | X | X | X | X | X | |
| Chemistries with LFTs [6] | X | X | X | X | X | X | |
| Ad5-HER3 truncated Vaccine [7] | | X | X | X | | | |
| AE Assessment [8] | | X | X | X | X | X | |
| Tumor Biopsy [9] | X | | | | | X | |
| Immunological Assessments [10] | X | X | X | X | X | X | X |
| Survival | | | | | | | X |

Note:
Imaging studies (including brain imaging) are not required but reports may be reviewed at the discretion of the Principal Investigator.

[1]Pre-treatment procedures/tests except for pregnancy test must be performed within 28 days prior to first vaccine (Week 0).
[2] Eastern Cooperative Oncology Group (ECOG) performance status assessment.
[3]Vital signs checked post-vaccination at 15 minutes, 30 minutes, and 1 hour.
[4]For women of childbearing potential, serum β-HCG (human chorionic gonadotrophin) pregnancy test must be completed within 7 days prior to the first vaccine (Week 0).
[5] Complete blood count with differential.
[6] Na, K, Cl, $CO_2$, BUN, creatinine, Ca, total protein, albumin, total bilirubin, alkaline phosphatase, AST, ALT and glucose.
[7] After the first vaccine, vaccinations may be performed −1 to +7 days after the specified week. Subsequent vaccinations should be 3 weeks afterwards and keep to the every 3 week interval. Patients will remain in the clinic for 1 hour after each vaccination.
[8] Adverse event assessment using NCI CTCAE 4.03.
[9] In the dose escalation cohorts, a core or punch biopsy of tumor tissue will be requested (i.e., optional) before the first vaccine in Pre-Treatment and after the third vaccine in Week 9. In the expanded cohort, a core or punch biopsy of tumor tissue will be obtained (i.e., required) before the first vaccine in Pre-Treatment and after the third vaccine in Week 9.
[10] Peripheral blood collected for serum, plasma and PBMCs. Blood must be drawn prior to the administration of the vaccine on study days where subject is receiving vaccine. If the screening blood draw is within 3 weeks of Week 0 blood draw, we will not obtain the blood draw before the 2nd immunization (week 3). For kit and arrangements for sample pick-up, contact Dr. Amy Hobeika at 919-684-6112 (office), 919-684-6777 (lab) or amy.hobeika@duke.edu.
[11]Off treatment procedures/tests must be performed when discontinued from study treatment prior to completion of the third vaccine (Week 6).
[12]For patients that complete Week 9 and have not met disease progression (as determined by treating physician), long term follow-up procedures/tests will be performed every 3 months after the Week 9 (+/− 28 days) for up to a year. All patients that have received study treatment will be followed for survival for up to 3 years after their first vaccine.

(Weeks 0, 3, and 6) for PBMCs, plasma, and serum to assess antibody and T cell responses and other markers of immunity. If the screening blood draw was drawn within 3 weeks of the Week 0 blood draw, the blood draw will not be obtained before the 2$^{nd}$ immunization (at the Week 3 visit).

Evaluations after Treatment. Patient evaluations are completed three weeks (+/−14 days) after the third vaccination (i.e., Week 9). General evaluations include medical history, ECOG performance status, and complete physical examination with vital signs and weight. Any other treatments, medications, biologics, or blood products that the patient is receiving or has received since the last visit are documented. Blood chemistry and hematology, including CBC with differential, sodium, potassium, chloride, bicarbonate, blood urea nitrogen (BUN), creatinine, calcium, total protein, albumin, total bilirubin, alkaline phosphatase, AST, ALT and glucose are completed. Peripheral blood (approximately 90 mL) is collected for serum, plasma and PBMCs to assess antibody and T cell responses and other markers of immunity. In the dose escalating portion of the study, a core or punch biopsy of tumor tissue is requested (but not required) after the third vaccination. In the expanded cohort, a core or punch biopsy of tumor tissue is required after the third vaccination. Tumor tissue is analyzed for HER3 signaling, T cell infiltration, and other markers of immune response such as PD-L1 expression.

Long Term Follow-Up. Patients that complete Week 9 and have not met disease progression (as determined by treating physician) will return every 3 months (+/−28 days) after the Week 9 visit for up to 1 year for long term follow-up. At each long term follow-up visit, general evaluation and immunological assessments are completed. For immunological assessments, peripheral blood (approximately 40-90 mL) is collected depending on evidence of an immune response as determined by the Principal Investigator or designee. Long term follow-up visits are not applicable to patients who met disease progression prior to completion of Week 9 or did not complete the assigned vaccine schedule. However, all patients that received study treatment are followed for survival for up to 3 years after their first study vaccine. Survival status is assessed by personal interviews or review of medical or public records.

Statistical Considerations

Safety. The safety aim of this dose finding trial is to determine the maximum tolerated dose (MTD) of Ad5 [E1−, E2b−]-HER3 truncated. Safety is evaluated routinely in each patient. An overall assessment of whether to escalate to the next dose level is made at least 3 weeks after the patient in the previous dose level has received their first injection. Safety is evaluated in every patient at each dosage level in dose escalation. A patient is considered evaluable for safety if treated with at least one immunization. DLTs are observed through 9 weeks to accommodate safety evaluation of all 3 product doses.

Rate of Immune Response. Immune response is assessed among all the patients treated at the maximum tolerated dose (MTD) who receive at least 3 immunizations. Immune responses against HER3 and other antigens are evaluated from the peripheral blood of patients from among the following assays: ELISPOT, cytokine flow cytometry, and antibody responses. Immunogenicity assays occur prior to each immunization and at week 12. The therapy is considered of further interest if at least 6 (50%) of 12 patients treated at the MTD exhibit an immune response as defined above. An observed rate of 0.50 will have an exact 80% confidence interval of 0.28-0.71. If the true immune response rate is 0.30, the probability of observing a response rate of at least 0.50 is 0.12. If the true rate is 0.60, the probability of observing a response rate of at least 0.50 is 0.84.

Evaluation of HER3 Signaling. Tumor tissue obtained before and after the immunizations is assessed for the heregulin mRNA by RT-PCR and/or HER3 by qIHC. High heregulin mRNA expression is defined as a score >−5. Low HER3 by qIHC is defined as Log 10 HER3<5.1 (76). Clinical responses are analyzed by whether patients have the HER3 biomarker. Available imaging studies from before and after immunization will be reviewed. RECIST 1.1 and irRR criteria will be used to report clinical activity.

Example 7

Treatment of an Advanced or Metastatic Malignancy with Ad5 [E1−, E2b−]-HER3 Vaccine This example describes treatment of an advanced or metastatic malignancy with Ad5 [E1−, E2b−]-HER3 vaccine. The Ad5 [E1−, E2b−]-HER3 vaccine is administered to a subject in need thereof. Administration of the vaccine is performed via subcutaneous injection in the thigh. Vaccine doses range from $1\times10^{19}$-$5\times10^{12}$ virus particles per dose. Doses are administered up to a total of three times and are injected at one to three week intervals. Booster immunizations are given at one, two, or three month intervals.

The subject has a malignancy, which is characterized by a condition in which HER3 is overexpressed. The condition is breast cancer, lung cancer, gastric cancer, head and neck cancer, ovariance cancer, or melanoma. HER3 expression is used as a prognostic tool to track response and disease progression in a subject that has received the immunization.

Example 8

Treatment of an Advanced or Metastatic Malignancy with a Combination Ad5 [E1−, E2b−]-HER Vaccine This example describes treatment of an advanced or metastatic malignancy with Ad5 [E1−, E2b−]-HER vaccine. The Ad5 [E1−, E2b−]-HER vaccine includes Ad5 [E1−, E2b−]-HER1, Ad5 [E1−, E2b−]-HER2/neu, Ad5 [E1−, E2b−]-HER3, Ad5 [E1−, E2b−]-HER4, or any combination thereof. The combination vaccine is administered to a subject in need thereof. Administration of the vaccine is performed via subcutaneous injection in the thigh. Vaccine doses range from $1\times10^9$-$5\times10^{12}$ virus particles per dose. Doses are administered up to a total of three times and are injected at one to three week intervals. Booster immunizations are give at one, two, or three month intervals.

The subject has a malignancy, which is characterized by a condition in which HER1, HER2/neu, HER3, HER4, or any combination thereof is overexpressed. The condition is breast cancer, lung cancer, gastric cancer, head and neck cancer, ovarian cancer, or melanoma. HER1, HER2/neu, HER3, or HER4 expression, or any combination thereof, is used as a prognostic tool to track response and disease progression in a subject that has received the immunization.

Example 9

Phase I Study of Active Immunotherapy with Combination Ad5 [E1−, E2b−]-HER Vaccine in Patients with Advanced or Metastatic Malignancies This example describes a Phase I study of active immunotherapy with a combination Ad5 [E1−, E2b−]-HER vaccine in patients with advanced or metastatic malignancies. A Phase I study is conducted as described in Example 6. The vaccines that are tested include Ad5 [E1−, E2b−]-HER1, Ad5 [E1−, E2b−]-HER2/neu, Ad5 [E1−, E2b−]-HER3, Ad5 [E1−, E2b−]-HER4, or any combination thereof.

Example 10

Treatment of Cancer with Combination Ad5 [E1−, E2b−]-HER Vaccine

This example describes treatment of cancer in a subject in need thereof with a combination Ad5 [E1−, E2b−]-HER vaccine. The subjects in need thereof are patients with advanced or metastatic malignancies. A pharmaceutical composition of Ad5 [E1−, E2b−]-HER1, Ad5 [E1−, E2b−]-HER2/neu, Ad5 [E1−, E2b−]-HER3, Ad5 [E1−, E2b−]-HER4, or any combination thereof is administered subcutaneously in the thigh. The total vaccine dose delivered is $1\times10^9$-$5\times10^{11}$ virus particles. Immunizations are administered to the patients every three weeks for a total of three vaccinations. Booster immunizations are given at one, two, or three month intervals.

Example 11

Combination Treatment of HER-Expressing Cancer with Ad5 [E1−, E2b−]-HER3 and Co-Stimulatory Molecules This example describes treatment of HER-expressing cancer cells, in a subject in need thereof. Ad5 [E1−, E2b−] vectors encoding for HER3, or any combination of HER3 with HER1, HER2/neu, and/or HER4, are administered to a subject in need thereof at a dose of $1\times10^9$-$5\times10^{11}$ virus particles (VPs) subcutaneously in combination with a costimulatory molecule. Vaccines are administered a total of 3 times and each vaccination is separated by a 3 week interval. Thereafter, bi-monthly booster injections are administered. The co-stimulatory molecule is B7-1, ICAM-1, or LFA-3. The subject is any animal, for example a mammal, such as a mouse, human, or non-human primate. Upon administration of the vaccine and co-stimulatory molecule, the cellular and humoral responses are initiated against the HER-expressing cancer and the cancer is eliminated.

Example 12

Combination Treatment of HER-Expressing Cancer with Ad5 [E1−, E2b−]-HER3 and Checkpoint Inhibitors This example describes treatment of HER-expressing cancer cells, in a subject in need thereof. Ad5 [E1−, E2b−] vectors encoding for HER3, or any combination of HER3 with HER1, HER2/neu, and/or HER4, are administered to a subject in need thereof at a dose of $1\times10^9$-$5\times10^{11}$ virus particles (VPs) subcutaneously in combination with a checkpoint inhibitor. Vaccines are administered a total of 3 times and each vaccination is separated by a 3-week interval. Thereafter, bi-monthly booster injections are administered. The checkpoint inhibitor is an anti-PDL1 antibody, such as Avelumab. Avelumab is dosed and administered as per package insert labeling at 10 mg/kg. The subject is any animal, for example a mammal, such as a mouse, human, or non-human primate. Upon administration of the vaccine and the checkpoint inhibitor, the cellular and humoral responses are initiated against the HER-expressing cancer and the cancer is eliminated.

Example 13

Combination Treatment of HER-Expressing Cancer with Ad5 [E1−, E2b−]-HER3 and Engineered NK Cells This example describes treatment of HER-expressing cancer cells, in a subject in need thereof. Ad5 [E1−, E2b−] vectors encoding for HER3, or any combination of HER3 with HER1, HER2/neu, and/or HER4, are administered to a subject in need thereof at a dose of $1\times10^9$-$5\times10^{11}$ virus particles (VPs) subcutaneously in combination with a costimulatory molecule. Vaccines are administered a total of 3 times and each vaccination is separated by a 3-week interval. Thereafter, bi-monthly booster injections are administered. Subjects are additionally administered engineered NK cells, specifically activated NK cells (aNK cells). aNK cells are infused on days −2, 12, 26, and 40 at a dose of $2\times10^9$ cells per treatment. Subjects in need thereof have HER-expressing cancer cells and the cancer is eliminated. Subjects are any mammal, such as a human or a non-human primate.

Example 14

Combination Treatment of HER-Expressing Cancer with Ad5 [E1−, E2b−]-HER3 and ALT-803

This example describes treatment of HER-expressing cancer cells, in a subject in need thereof. Ad5 [E1−, E2b−] vectors encoding for HER3, or any combination of HER3 with HER1, HER2/neu, and/or HER4, are administered to a subject in need thereof at a dose of $1\times10^9$-$5\times10^{11}$ virus particles (VPs) subcutaneously in combination with a costimulatory molecule. Vaccines are administered a total of 3 times and each vaccination is separated by a 3-week interval. Thereafter, bi-monthly booster injections are administered. Subjects are also administered a super-agonist/super-agonist complex, such as ALT-803, at a dose of 10 µg/kg SC on weeks 1, 2, 4, 5, 7, and 8, respectively. Subjects in need thereof have HER-expressing cancer, and the cancer is eliminated. Subjects are any mammal, such as a human or a non-human animal.

Example 15

Combination Treatment of HER-Expressing Cancer with Ad5 [E1−, E2b−]-HER3 and Low Dose Chemotherapy This example describes treatment of HER-expressing cancer cells, in a subject in need thereof. Ad5 [E1−, E2b−] vectors encoding for HER3, or any combination of HER3 with HER1, HER2/neu, and/or HER4, are administered to a subject in need thereof at a dose of $1\times10^9$-$5\times10^{11}$ virus particles (VPs) subcutaneously in combination with a costimulatory molecule. Vaccines are administered a total of 3 times and each vaccination is separated by a 3-week interval. Thereafter, bi-monthly booster injections are administered.

Subjects are also administered low dose chemotherapy. The chemotherapy is cyclophosphamide. The chemotherapy is administered at a dose that is lower than the clinical standard of care dosing. For example, the chemotherapy is administered at 50 mg twice a day (BID) on days 1-5 and 8-12 every 2 weeks for a total of 8 weeks. The cyclophosphamide is administered orally or intravenously. Subjects in need thereof have HER-expressing cancer, and the cancer is eliminated. Subjects are any mammal, such as a human or a non-human animal.

Example 16

Combination Treatment of HER-Expressing Cancer with Ad5 [E1−, E2b−]-HER3 and Low Dose Radiation This example describes treatment of HER-expressing cancer cells, in a subject in need thereof. Ad5 [E1−, E2b−] vectors encoding for HER3, or any combination of HER3 with HER1, HER2/neu, and/or HER4, are administered to a subject in need thereof at a dose of $1\times10^9$-$5\times10^{11}$ virus particles (VPs) subcutaneously in combination with a costimulatory molecule. Vaccines are administered a total of 3 times and each vaccination is separated by a 3-week interval. Thereafter, bi-monthly booster injections are administered.

Subjects are also administered low dose radiation. The low dose radiation is administered at a dose that is lower than the clinical standard of care dosing. Concurrent sterotactic body radiotherapy (SBRT) at 8 Gy is given on day 8, 22, 36, 50 (every 2 weeks for 4 doses). Radiation is administered to all feasible tumor sites using SBRT. Subjects in need thereof have HER-expressing cancer, and the cancer is eliminated. Subjects are any mammal, such as a human or a non-human animal.

Example 17

Treatment of HER-Expressing Cancer with Combination Ad5 [E1−, E2b−]-HER3, Ad5 [E1−, E2b−]-HER2, Ad5 [E1−, E2b−]-Brachyury, Ad5 [E1−, E2b−]-MUC1 Vaccine and Checkpoint Inhibitors This example describes treatment of HER-expressing cancer cells, in a subject in need thereof with a combination Ad5 [E1−, E2b−]-HER vaccine. A pharmaceutical composition of Ad5 [E1−, E2b−]-HER3 (full length HER3 or truncated HER3), Ad5 [E1−, E2b−]-HER2/neu (full length HER2 or truncated HER2), Ad5 [E1−, E2b−]-Brachyury, Ad5 [E1−, E2b−]-MUC1, or any combination thereof is administered to a subject in need thereof at a dose of $1\times10^9$-$5\times10^{11}$ virus particles (VPs) subcutaneously in combination with a checkpoint inhibitor. Thereafter, bi-monthly booster injections are administered. The checkpoint inhibitor is an anti-PDL1 antibody, such as Avelumab. Avelumab is dosed and administered as per package insert labeling at 10 mg/kg. Subjects receive intravenous infusion of avelumab over 1 hour (−10 minutes/+20 minutes, i.e., 50 to 80 minutes) as applicable at a dose of 10 mg/kg. Vaccines are administered a total of 3 times and each vaccination is separated by a 3-week interval. Treatment with avelumab starts on the second vaccine treatment 3 weeks after the first vaccine injection. Alternatively, treatment with avelumab starts concurrently with the first vaccine treatment and is dosed every 2 weeks. The subject is any animal, for example a mammal, such as a mouse, human, or non-human primate. Upon administration of the vaccine and the checkpoint inhibitor, the cellular and humoral responses are initiated against the HER-expressing cancer and the cancer is eliminated.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

SEQUENCES

| SEQ ID NO | Sequence |
|---|---|
| SEQ ID NO: 1 | CTAGAATGGAGCTGGCGGCCTTGTGCCGCTGGGGGCTCCTCCTCGCCCTCTTG CCCCCCGGAGCCGCGAGCACCCAAGTGTGCACCGGCACAGACATGAAGCTGC GGCTCCCTGCCAGTCCCGAGACCCACCTGGACATGCTCCGCCACCTCTACCAG GGCTGCCAGGTGGTGCAGGGAAACCTGGAACTCACCTACCTGCCCACCAATG CCAGCCTGTCCTTCCTGCAGGATATCCAGGAGGTGCAGGGCTACGTGCTCATC GCTCACAACCAAGTGAGGCAGGTCCCACTGCAGAGGCTGCGGATTGTGCGAG GCACCCAGCTCTTTGAGGACAACTATGCCCTGGCCGTGCTAGACAATGGAGA CCCGCTGAACAATACCACCCCTGTCACAGGGGCCTCCCCAGGAGGCCTGCGG GAGCTGCAGCTTCGAAGCCTCACAGAGATCTTGAAAGGAGGGGTCTTGATCC AGCGGAACCCCCAGCTCTGCTACCAGGACACGATTTTGTGGAAGGACATCTT CCACAAGAACAACCAGCTGGCTCTCACACTGATAGACACCAACCGCTCTCGG GCCTGCCACCCCTGTTCTCCGATGTGTAAGGGCTCCCGCTGCTGGGGAGAGA GTTCTGAGGATTGTCAGAGCCTGACGCGCACTGTCTGTGCCGGTGGCTGTGCC CGCTGCAAGGGGCCACTGCCCACTGACTGCTGCCATGAGCAGTGTGCTGCCG GCTGCACGGGCCCCAAGCACTCTGACTGCCTGGCCTGCCTCCACTTCAACCAC AGTGGCATCTGTGAGCTGCACTGCCCAGCCCTGGTCACCTACAACACAGACA CGTTTGAGTCCATGCCCAATCCCGAGGGCCGGTATACATTCGGCGCCAGCTGT GTGACTGCCTGTCCCTACAACTACCTTTCTACGGACGTGGGATCCTGCACCCT CGTCTGCCCCCTGCACAACCAAGAGGTGACAGCAGAGGATGGAACACAGCG GTGTGAGAAGTGCAGCAAGCCCTGTGCCCGAGTGTGCTATGGTCTGGGCATG GAGCACTTGCGAGAGGTGAGGGCAGTTACCAGTGCCAATATCCAGGAGTTTG CTGGCTGCAAGAAGATCTTTGGGAGCCTGGCATTTCTGCCGGAGAGCTTTGAT |

SEQUENCES

| SEQ ID NO | Sequence |
|---|---|
| | GGGGACCCAGCCTCCAACACTGCCCCGCTCCAGCCAGAGCAGCTCCAAGTGT<br>TTGAGACTCTGGAAGAGATCACAGGTTACCTATACATCTCAGCATGGCCGGA<br>CAGCCTGCCTGACCTCAGCGTCTTCCAGAACCTGCAAGTAATCCGGGGACGA<br>ATTCTGCACAATGGCGCCTACTCGCTGACCCTGCAAGGGCTGGGCATCAGCT<br>GGCTGGGGCTGCGCTCACTGAGGGAACTGGGCAGTGGACTGGCCCTCATCCA<br>CCATAACACCCACCTCTGCTTCGTGCACACGGTGCCCTGGGACCAGCTCTTTC<br>GGAACCCGCACCAAGCTCTGCTCCACACTGCCAACCGGCCAGAGGACGAGTG<br>TGTGGGCGAGGGCCTGGCCTGCCACCAGCTGTGCGCCCGAGGGCACTGCTGG<br>GGTCCAGGGCCCACCCAGTGTGTCAACTGCAGCCAGTTCCTTCGGGGCCAGG<br>AGTGCGTGGAGGAATGCCGAGTACTGCAGGGGCTCCCCAGGGAGTATGTGAA<br>TGCCAGGCACTGTTTGCCGTGCCACCCTGAGTGTCAGCCCCAGAATGGCTCA<br>GTGACCTGTTTTGGACCGGAGGCTGACCAGTGTGTGGCCTGTGCCCACTATAA<br>GGACCCTCCCTTCTGCGTGGCCCGCTGCCCCAGCGGTGTGAAACCTGACCTCT<br>CCTACATGCCCATCTGGAAGTTTCCAGATGAGGAGGGCGCATGCCAGCCTTG<br>CCCCATCAACTGCACCCACTCCTGTGTGGACCTGGATGACAAGGGCTGCCCC<br>GCCGAGCAGAGAGCCAGCCCTCTGACGTCCATCGTCTCTGCGGTGGTTGGCA<br>TTCTGCTGGTCGTGGTCTTGGGGGTGGTCTTTGGGATCCTCATCAAGCGACGG<br>CAGCAGAAGATCCGGAAGTACACGTAATCTAGATAA |
| SEQ ID NO: 2 | MRMELAALCRWGLLLALLPPGAASTQVCTGTDMKLRLPASPETHLDMLRHLYQ<br>GCQVVQGNLELTYLPTNASLSFLQDIQEVQGYVLIAHNQVRQVPLQRLRIVRGTQ<br>LFEDNYALAVLDNGDPLNNTTPVTGASPGGLRELQLRSLTEILKGGVLIQRNPQL<br>CYQDTILWKDIFHKNNQLALTLIDTNRSRACHPCSPMCKGSRCWGESSEDCQSLT<br>RTVCAGGCARCKGPLPTDCCHEQCAAGCTGPKHSDCLACLHFNHSGICELHCPA<br>LVTYNTDTFESMPNPEGRYTFGASCVTACPYNYLSTDVGSCTLVCPLHNQEVTA<br>EDGTQRCEKCSKPCARVCYGLGMEHLREVRAVTSANIQEFAGCKKIFGSLAFLPE<br>SFDGDPASNTAPLQPEQLQVFETLEEITGYLYISAWPDSLPDLSVFQNLQVIRGRIL<br>HNGAYSLTLQGLGISWLGLRSLRELGSGLALIHHNTHLCFVHTVPWDQLFRNPH<br>QALLHTANRPEDECVGEGLACHQLCARGHCWGPGPTQCVNCSQFLRGQECVEE<br>CRVLQGLPREYVNARHCLPCHPECQPQNGSVTCFGPEADQCVACAHYKDPPFCV<br>ARCPSGVKPDLSYMPIWKFPDEEGACQPCPINCTHSCVDLDDKGCPAEQRASPLT<br>SIVSAVVGILLVVVLGVVFGILIKRRQQKIRKYT-SR- |
| SEQ ID NO: 3 | CATCATCAATAATATACCTTATTTTGGATTGAAGCCAATATGATAATGAGGGG<br>GTGGAGTTTGTGACGTGGCGCGGGGCGTGGGAACGGGGCGGGTGACGTAGT<br>AGTGTGGCGGAAGTGTGATGTTGCAAGTGTGGCGGAACACATGTAAGCACG<br>GATGTGGCAAAAGTGACGTTTTTGGTGTGCGCCGGTGTACACAGGAAGTGAC<br>AATTTTCGCGCGGTTTTAGGCGGATGTTGTAGTAAATTTGGGCGTAACCGAGT<br>AAGATTTGGCCATTTTCGCGGGAAAACTGAATAAGAGGAAGTGAAATCTGAA<br>TAATTTTGTGTTACTCATAGCGCGTAATACTGTAATAGTAATCAATTACGGGG<br>TCATTAGTTCATAGCCCATATATGGAGTTCCGCGTTACATAACTTACGGTAAA<br>TGGCCCGCCTGGCTGACCGCCCAACGACCCCGCCCATTGACGTCAATAATG<br>ACGTATGTTCCCATAGTAACGCCAATAGGGACTTTCCATTGACGTCAATGGGT<br>GGAGTATTTACGGTAAACTGCCCACTTGGCAGTACATCAAGTGTATCATATGC<br>CAAGTACGCCCCCTATTGACGTCAATGACGGTAAATGGCCCGCCTGGCATTA<br>TGCCCAGTACATGACCTTATGGGACTTTCCTACTTGGCAGTACATCTACGTAT<br>TAGTCATCGCTATTACCATGGTGATGCGGTTTTGGCAGTACATCAATGGGCGT<br>GGATAGCGGTTTGACTCACGGGGATTTCCAAGTCTCCACCCCATTGACGTCAA<br>TGGGAGTTTGTTTTGGCACCAAAATCAACGGGACTTTCCAAAATGTCGTAAC<br>AACTCCGCCCCATTGACGCAAATGGGCGGTAGGCGTGTACGGTGGGAGGTCT<br>ATATAAGCAGAGCTGGTTTAGTGAACCGTCAGATCCGCTAGAGATCTGGTAC<br>CGTCGACGCGGCCGCTCGAGCCTAAGCTTCTAGATGCATGCTCGAGCGGCCG<br>CCAGTGTGATGGATATCTGCAGAATTCGCCCTTGCTCTAGAATGGAGCTGGC<br>GGCCTTGTGCCGCTGGGGGCTCCTCCTCGCCCTCTTGCCCCCCGGAGCCGCGA<br>GCACCCAAGTGTGCACCGGCACAGACATGAAGCTGCGGCTCCCTGCCAGTCC<br>CGAGACCCACCTGGACATGCTCCGCCACCTCTACCAGGGCTGCCAGGTGGTG<br>CAGGGAAACCTGGAACTCACCTACCTGCCCACCAATGCCAGCCTGTCCTTCCT<br>GCAGGATATCCAGGAGGTGCAGGGCTACGTGCTCATCGCTCACAACCAAGTG<br>AGGCAGGTCCCACTGCAGAGGCTGCGGATTGTGCGAGGCACCCAGCTCTTTG<br>AGGACAACTATGCCCTGGCCGTGCTAGACAATGGAGACCCGCTGAACAATAC<br>CACCCCTGTCACAGGGGCCTCCCCAGGAGGCCTGCGGGAGCTGCAGCTTCGA<br>AGCCTCACAGAGATCTTGAAAGGAGGGGTCTTGATCCAGCGGAACCCCCAGC<br>TCTGCTACCAGGACACGATTTTGTGGAAGGACATCTTCCACAAGAACAACCA<br>GCTGGCTCTCACACTGATAGACACCAACCGCTCTCGGGCCTGCCACCCCTGTT<br>CTCCGATGTGTAAGGGCTCCCGCTGCTGGGGAGAGAGTTCTGAGGATTGTCA<br>GAGCCTGACGCGCACTGTCTGTGCCGGTGGCTGTGCCCGCTGCAAGGGGCCA<br>CTGCCCACTGACTGCTGCCATGAGCAGTGTGCTGCCGGCTGCAAGGGCCCCA<br>AGCACTCTGACTGCCTGGCCTGCCTCCACTTCAACCACAGTGGCATCTGTGAG<br>CTGCACTGCCCAGCCCTGGTCACCTACAACACAGACACGTTTGAGTCCATGCC<br>CAATCCCGAGGGCCGGTATACATTCGGCGCCAGCTGTGTGACTGCCTGTCCCT<br>ACAACTACCTTTCTACGGACGTGGGATCCTGCACCCTCGTCTGCCCCCTGCAC<br>AACCAAGAGGTGACAGCAGAGGATGGAACACAGCGGTGTGAGAAGTGCAGC<br>AAGCCCTGTGCCCGAGTGTGCTATGGTCTGGGCATGGAGCACTTGCGAGAGG |

| SEQ ID NO | Sequence |
|---|---|
| | TGAGGGCAGTTACCAGTGCCAATATCCAGGAGTTTGCTGGCTGCAAGAAGAT<br>CTTTGGGAGCCTGGCATTTCTGCCGGAGAGCTTTGATGGGGACCCAGCCTCCA<br>ACACTGCCCCGCTCCAGCCAGAGCAGCTCCAAGTGTTTGAGACTCTGGAAGA<br>GATCACAGGTTACCTATACATCTCAGCATGGCCGGACAGCCTGCCTGACCTC<br>AGCGTCTTCCAGAACCTGCAAGTAATCCGGGGACGAATTCTGCACAATGGCG<br>CCTACTCGCTGACCCTGCAAGGGCTGGGCATCAGCTGGCTGGGGCTGCGCTC<br>ACTGAGGGAACTGGGCAGTGGACTGGCCCTCATCCACCATAACACCcACCTC<br>TGCTTCGTGCACACGGTGCCCTGGGACCAGCTCTTTCGGAACCCGCACCAAG<br>CTCTGCTCCACACTGCCAACCGGCCAGAGGACGAGTGTGTGGGCGAGGGCCT<br>GGCCTGCCACCAGCTGTGCGCCCGAGGGCACTGCTGGGGTCCAGGGCCCACC<br>CAGTGTGTCAACTGCAGCCAGTTCCTTCGGGGCCAGGAGTGCGTGGAGGAAT<br>GCCGAGTACTGCAGGGGCTCCCCAGGGAGTATGTGAATGCCAGGCACTGTTT<br>GCCGTGCCACCCTGAGTGTCAGCCCCAGAATGGCTCAGTGACCTGTTTTGGAC<br>CGGAGGCTGACCAGTGTGTGGCCTGTGCCCACTATAAGGACCCTCCCTTCTGC<br>GTGGCCCGCTGCCCCAGCGGTGTGAAACCTGACCTCTCCTACATGCCCATCTG<br>GAAGTTTCCAGATGAGGAGGGCGCATGCCAGCCTTGCCCCATCAACTGCACC<br>CACTCCTGTGTGGACCTGGATGACAAGGGCTGCCCCGCCGAGCAGAGAGCCA<br>GCCCTCTGACGTCCATCGTCTCTGCGGTGGTTGGCATTCTGCTGGTCGTGGTC<br>TTGGGGGTGGTCTTTGGGATCCTCATCAAGCGACGGCAGCAGAAGATCCGGA<br>AGTACACGTAATCTAGATAAGATATCCGATCCACCGGATCTAGATAACTGAT<br>CATAATCAGCCATACCACATTTGTAGAGGTTTTACTTGCTTTAAAAAACCTCC<br>CACACCTCCCCCTGAACCTGAAACATAAAATGAATGCAATTGTTGTTGTTAAC<br>TTGTTTATTGCAGCTTATAATGGTTACAAATAAAGCAATAGCATCACAAATTT<br>CACAAATAAAGCATTTTTTTCACTGCATTCTAGTTGTGGTTTGTCCAAACTCA<br>TCAATGTATCTTAACGCGGATCTGGAAGGTGCTGAGGTACGATGAGACCCGC<br>ACCAGGTGCAGACCCTGCGAGTGTGGCGGTAAACATATTAGGAACCAGCCTG<br>TGATGCTGGATGTGACCGAGGAGCTGAGGCCCGATCACTTGGTGCTGGCCTG<br>CACCCGCGCTGAGTTTGGCTCTAGCGATGAAGATACAGATTGAGGTACTGAA<br>ATGTGTGGGCGTGGCTTAAGGGTGGGAAAGAATATATAAGGTGGGGGTCTTA<br>TGTAGTTTTGTATCTGTTTTGCAGCAGCCGCCGCCGCCATGAGCACCAACTCG<br>TTTGATGGAAGCATTGTGAGCTCATATTTGACAACGCGCATGCCCCCATGGGC<br>CGGGGTGCGTCAGAATGTGATGGGCTCCAGCATTGATGGTCGCCCCGTCCTG<br>CCCGCAAACTCTACTACCTTGACCTACGAGACCGTGTCTGGAACGCCGTTGG<br>AGACTGCAGCCTCCGCCGCCGCTTCAGCCGCTGCAGCCACCGCCCGCGGGAT<br>TGTGACTGACTTTGCTTTCCTGAGCCCGCTTGCAAGCAGTGCAGCTTCCCGTT<br>CATCCGCCCGCGATGACAAGTTGACGGCTCTTTTGGCACAATTGGATTCTTTG<br>ACCCGGGAACTTAATGTCGTTTCTCAGCAGCTGTTGGATCTGCGCCAGCAGGT<br>TTCTGCCCTGAAGGCTTCCTCCCCTCCCAATGCGGTTTAAAACATAAATAAAA<br>AACCAGACTCTGTTTGGATTTGGATCAAGCAAGTGTCTTGCTGTCTTTATTTA<br>GGGGTTTTGCGCGCGCGGTAGGCCCGGGACCAGCGGTCTCGGTCGTTGAGGG<br>TCCTGTGTATTTTTTCCAGGACGTGGTAAAGGTGACTCTGGATGTTCAGATAC<br>ATGGGCATAAGCCCGTCTCTGGGGTGGAGGTAGCACCACTGCAGAGCTTCAT<br>GCTGCGGGTGGTGTTGTAGATGATCCAGTCGTAGCAGGAGCGCTGGGCGTG<br>GTGCCTAAAAATGTCTTTCAGTAGCAAGCTGATTGCCAGGGGCAGGCCCTTG<br>GTGTAAGTGTTTACAAAGCGGTTAAGCTGGGATGGGTGCATACGTGGGGATA<br>TGAGATGCATCTTGGACTGTATTTTTAGGTTGGCTATGTTCCCAGCCATATCC<br>CTCCGGGGATTCATGTTGTGCAGAACCACCAGCACAGTGTATCCGGTGCACTT<br>GGGAAATTTGTCATGTAGCTTAGAAGGAAATGCGTGGAAGAACTTGGAGACG<br>CCCTTGTGACCTCCAAGATTTTCCATGCATTCGTCCATAATGATGGCAATGGG<br>CCCACGGGCGGCGGCCTGGGCGAAGATATTTCTGGGATCACTAACGTCATAG<br>TTGTGTTCCAGGATGAGATCGTCATAGGCCATTTTTACAAAGCGCGGGCGGA<br>GGGTGCCAGACTGCGGTATAATGGTTCCATCCGGCCCAGGGGCGTAGTTACC<br>CTCACAGATTTGCATTTCCCACGCTTTGAGTTCAGATGGGGGGATCATGTCTA<br>CCTGCGGGGCGATGAAGAAAACGGTTTCCGGGGTAGGGGAGATCAGCTGGG<br>AAGAAAGCAGGTTCCTGAGCAGCTGCGACTTACCGCAGCCGGTGGGCCCGTA<br>AATCACACCTATTACCGGCTGCAACTGGTAGTTAAGAGAGCTGCAGCTGCCG<br>TCATCCCTGAGCAGGGGGGCCACTTCGTTAAGCATGTCCCTGACTCGCATGTT<br>TTCCCTGACCAAATCCGCCAGAAGGCGCTCGCCGCCCAGCGATAGCAGTTCT<br>TGCAAGGAAGCAAAGTTTTTCAACGGTTTGAGACCGTCCGCCGTAGGCATGC<br>TTTTGAGCGTTTGACCAAGCAGTTCCAGGCGGTCCCACAGCTCGGTCACCTGC<br>TCTACGGCATCTCGATCCAGCATATCTCCTCGTTTCGCGGGTTGGGCGGCTT<br>TCGCTGTACGGCAGTAGTCGGTGCTCGTCCAGACGGGCCAGGGTCATGTCTTT<br>CCACGGGCGCAGGGTCCTCGTCAGCGTAGTCTGGGTCACGGTGAAGGGGTGC<br>GCTCCGGGCTGCGCGCTGGCCAGGGTGCGCTTGAGGCTGGTCCTGCTGGTGC<br>TGAAGCGCTGCCGTCTTCGCCCTGCGCGTCGGCCAGGTAGCATTTGACCATG<br>GTGTCATAGTCCAGCCCCTCCGCGGCGTGGCCCTTGGCGCGCAGCTTGCCCTT<br>GGAGGAGGCGCCGCACGAGGGGCAGTGCAGACTTTTGAGGGCGTAGAGCTT<br>GGGCGCGAGAAATACCGATTCCGGGGAGTAGGCATCCGCGCCGCAGGCCCC<br>GCAGACGGTCTCGCATTCCACGAGCCAGGTGAGCTCTGGCCGTTCGGGGTCA<br>AAAACCAGGTTTCCCCCATGCTTTTTGATGCGTTTCTTACCTCTGGTTTCCATG<br>AGCCGGTGTCCACGCTCGGTGACGAAAGGCTGTCCGTGTCCCCGTATACAG<br>ACTTGAGAGGCCTGTCCTCGAGCGGTGTTCCGCGGTCCTCCTCGTATAGAAAC<br>TCGGACCACTCTGAGACAAAGGCTCGCGTCCAGGCCAGCACGAAGGAGGCTA |

SEQUENCES

| SEQ ID NO | Sequence |
|---|---|
| | AGTGGGAGGGGTAGCGGTCGTTGTCCACTAGGGGGTCCACTCGCTCCAGGGT<br>GTGAAGACACATGTCGCCCTCTTCGGCATCAAGGAAGGTGATTGGTTTGTAG<br>GTGTAGGCCACGTGACCGGGTGTTCCTGAAGGGGGCTATAAAAGGGGGTGG<br>GGGCGCGTTCGTCCTCACTCTCTTCCGCATCGCTGTCTGCGAGGGCCAGCTGT<br>TGGGGTGAGTACTCCCTCTGAAAAGCGGGCATGACTTCTGCGCTAAGATTGT<br>CAGTTTCCAAAAACGAGGAGGATTTGATATTCACCTGGCCCGCGGTGATGCC<br>TTTGAGGGTGGCCGCATCCATCTGGTCAGAAAAGACAATCTTTTTGTTGTCAA<br>GCTTGGTGGCAAACGACCCGTAGAGGGCGTTGGACAGCAACTTGGCGATGGA<br>GCGCAGGGTTTGGTTTTTGTCGCGATCGGCGCGCTCCTTGGCCGCGATGTTTA<br>GCTGCACGTATTCGCGCGCAACGCACCGCCATTCGGGAAAGACGGTGGTGCG<br>CTCGTCGGGCACCAGGTGCACGCGCCAACCGCGGTTGTGCAGGGTGACAAGG<br>TCAACGCTGGTGGCTACCTCTCCGCGTAGGCGCTCGTTGGTCCAGCAGAGGC<br>GGCCGCCCTTGCGCGAGCAGAATGGCGGTAGGGGGTCTAGCTGCGTCTCGTC<br>CGGGGGGTCTGCGTCCACGGTAAAGACCCCGGGCAGCAGGCGCGCGTCGAA<br>GTAGTCTATCTTGCATCCTTGCAAGTCTAGCGCCTGCTGCCATGCGCGGGCGG<br>CAAGCGCGCGCTCGTATGGGTTGAGTGGGGACCCCATGGCATGGGTGGGT<br>GAGCGCGGAGGCGTACATGCCGCAAATGTCGTAAACGTAGAGGGGCTCTCTG<br>AGTATTCCAAGATATGTAGGGTAGCATCTTCCACCGCGGATGCTGGCGCGCA<br>CGTAATCGTATAGTTCGTGCGAGGGAGCGAGGAGGTCGGGACCGAGGTTGCT<br>ACGGGCGGGCTGCTCTGCTCGGAAGACTATCTGCCTGAAGATGGCATGTGAG<br>TTGGATGATATGGTTGGACGCTGGAAGACGTTGAAGCTGGCGTCTGTGAGAC<br>CTACCGCGTCACGCACGAAGGAGGCGTAGGAGTCGCGCAGCTTGTTGACCAG<br>CTCGGCGGTGACCTGCACGTCTAGGGCGCAGTAGTCCAGGGTTTCCTTGATG<br>ATGTCATACTTATCCTGTCCCTTTTTTTTCCACAGCTCGCGGTTGAGGACAAA<br>CTCTTCGCGGTCTTTCCAGTACTCTTGGATCGGAAACCCGTCGGCCTCCGAAC<br>GGTAAGAGCCTAGCATGTAGAACTGGTTGACGCCTGGTAGGCGCAGCATCC<br>CTTTTCTACGGGTAGCGCGTATGCCTGCGCGGCCTTCCGGCATGACCAGCATG<br>AAGGGCACGAGCTGCTTCCCAAAGGCCCCCATCCAAGTATAGGTCTCTACAT<br>CGTAGGTGACAAAGAGACGCTCGGTGCGAGGATGCGAGCCGATCGGGAAGA<br>ACTGGATCTCCCGCCACCAATTGGAGGAGTGGCTATTGATGTGGTGAAAGTA<br>GAAGTCCCTGCGACGGGCCGAACACTCGTGCTGGCTTTTGTAAAAACGTGCG<br>CAGTACTGGCAGCGGTGCACGGGCTGTACATCCTGCACGAGGTTGACCTGAC<br>GACCGCGCACAAGGAAGCAGAGTGGGAATTTGAGCCCCTCGCCTGGCGGGTT<br>TGGCTGGTGGTCTTCTACTTCGGCTGCTTGTCCTTGACCGTCTGGCTGCTCGA<br>GGGGAGTTACGGTGGATCGGACCACCACGCCGCGCGAGCCCAAAGTCCAGAT<br>GTCCGCGCGGCGGTCGGAGCTTGATGACAACATCGCGCAGATGGGAGCTG<br>TCCATGGTCTGGAGCTCCCGCGGCGTCAGGTCAGGCGGGAGCTCCTGCAGGT<br>TTACCTCGCATAGACGGGTCAGGGCGCGGGCTAGATCCAGGTGATACCTAAT<br>TTCCAGGGGCTGGTTGGTGGCGCGTCGATGGCTTGCAAGAGGCCGCATCCC<br>CGCGGCGCGACTACGGTACCGCGCGGCGGGCGGTGGGCCGCGGGGTGTCCT<br>TGGATGATGCATCTAAAAGCGGTGACGCGGGCGAGCCCCCGGAGGTAGGGG<br>GGGCTCCGGACCCGCCGGGAGAGGGGGCAGGGGCACGTCGGCGCCGCGCGC<br>GGGCAGGAGCTGGTGCTGCGCGCGTAGGTTGCTGGCGAACGCGACGACGCG<br>GCGGTTGATCTCCTGAATCTGGCGCCTCTGCGTGAAGACGACGGGCCCGGTG<br>AGCTTGAACCTGAAAGAGAGTTCGACAGAATCAATTTCGGTGTCGTTGACGG<br>CGGCCTGGCGCAAAATCTCCTGCACGTCTCCTGAGTTGTCTTGATAGGCGATC<br>TCGGCCATGAACTGCTCGATCTCTTCCTCCTGGAGATCTCCGCGTCCGGCTCG<br>CTCCACGGTGGCGGCGAGGTCGTTGGAAATGCGGGCCATGAGCTGCGAGAAG<br>GCGTTGAGGCCTCCCTCGTTCCAGACGCGGCTGTAGACCACGCCCCCTTCGGC<br>ATCGCGGGCGCGCATGACCACCTGCGCGAGATTGAGCTCCACGTGCCGGGCG<br>AAGACGGCGTAGTTTCGCAGGCGCTGAAAGAGGTAGTTGAGGGTGGTGGCG<br>GTGTGTTCTGCCACGAAGAAGTACATAACCCAGCGTCGCAACGTGGATTCGT<br>TGATAATTGTTGTGTAGGTACTCCGCCGCCGAGGGACCTGAGCGAGTCCGCA<br>TCGACCGGATCGGAAAACCTCTCGAGAAAGGCGTCTAACCAGTCACAGTCGC<br>AAGGTAGGCTGAGCACCGTGGCGGGCGGCAGCGGGCGGCGGTCGGGGTTGT<br>TTCTGGCGGAGGTGCTGCTGATGATGTAATTAAAGTAGGCGGTCTTGAGACG<br>GCGGATGGTCGACAGAAGCACCATGTCCTTGGGTCCGGCCTGCTGAATGCGC<br>AGGCGGTCGGCCATGCCCCAGGCTTCGTTTTGACATCGGCGCAGGTCTTTGTA<br>GTAGTCTTGCATGAGCCTTTCTACCGGCACTTCTTCTTCCTTCCTCTTGTCC<br>TGCATCTCTTGCATCTATCGCTGCGGCGGCGGCGGAGTTTGGCCGTAGGTGGC<br>GCCCTCTTCCTCCCATGCGTGTGACCCCGAAGCCCCTCATCGGCTGAAGCAGG<br>GCTAGGTCGGCGACAACGCGCTCGGCTAATATGGCCTGCTGCACCTGCGTGA<br>GGGTAGACTGGAAGTCATCCATGTCCACAAAGCGGTGGTATGCGCCCGTGTT<br>GATGGTGTAAGTGCAGTTGGCCATAACGGACCAGTTAACGGTCTGGTGACCC<br>GGCTGCGAGAGCTCGGTGTACCTGAGACGCGAGTAAGCCCTCGAGTCAAATA<br>CGTAGTCGTTGCAAGTCCGCACCAGGTACTGGTATCCCACCAAAAAGTGCGG<br>CGGCGGCTGGCGGTAGAGGGGCCAGCGTAGGGTGGCCGGGGCTCCGGGGGC<br>GAGATCTTCCAACATAAGGCGATGATATCCGTAGATGTACCTGGACATCCAG<br>GTGATGCCGGCGGCGGTGGTGGAGGCGCGCGGAAAGTCGCGGACGCGGTTC<br>CAGATGTTGCGCAGCGGCAAAAAGTGCTCCATGGTCGGGACGCTCTGGCCGG<br>TCAGGCGCGCGCAATCGTTGACGCTCTAGCGTGCAAAAGGAGAGCCTGTAAG<br>CGGGCACTCTTCCGTGGTCTGGTGGATAAATTCGCAAGGGTATCATGGCGGA<br>CGACCGGGGTTCGAGCCCCGTATCCGGCCGTCCGCCGTGATCCATGCGGTTA |

| SEQ ID NO | Sequence |
|---|---|
| | CCGCCCGCGTGTCGAACCCAGGTGTGCGACGTCAGACAACGGGGGAGTGCTC<br>CTTTTGGCTTCCTTCCAGGCGCGGCGGCTGCTGCGCTAGCTTTTTTGGCCACT<br>GGCCGCGCGCAGCGTAAGCGGTTAGGCTGGAAAGCGAAAGCATTAAGTGGC<br>TCGCTCCCTGTAGCCGGAGGGTTATTTTCCAAGGGTTGAGTCGCGGGACCCC<br>GGTTCGAGTCTCGGACCGGCCGGACTGCGGCAACGGGGGTTTGCCTCCCCG<br>TCATGCAAGACCCCGCTTGCAAATTCCTCCGGAAACAGGGACGAGCCCCTTT<br>TTTGCTTTTCCCAGATGCATCCGGTGCTGCGGCAGATGCGCCCCCCTCCTCAG<br>CAGCGGCAAGAGCAAGAGCAGCGGCAGACATGCAGGGCACCCTCCCCTCCTC<br>CTACCGCGTCAGGAGGGGCGACATCCGCGGTTGACGCGGCAGCAGATGGTGA<br>TTACGAACCCCCGCGGCGCCGGGCCCGGCACTACCTGGACTTGGAGGAGGGC<br>GAGGGCCTGGCGCGGCTAGGAGCGCCCTCTCCTGAGCGGCACCCAAGGGTGC<br>AGCTGAAGCGTGATACGCGTGAGGCGTACGTGCCGCGGCAGAACCTGTTTCG<br>CGACCGCGAGGGAGAGGAGCCCGAGGAGATGCGGGATCGAAAGTTCCACGC<br>AGGGCGCGAGCTGCGGCATGGCCTGAATCGCGAGCGGTTGCTGCGCGAGGA<br>GGACTTTGAGCCCGACGCGCGAACCGGGATTAGTCCCGCGCGCGCACACGTG<br>GCGGCCGCCGACCTGGTAACCGCATACGAGCAGACGGTGAACCAGGAGATT<br>AACTTTCAAAAAAGCTTTAACAACCACGTGCGTACGCTTGTGGCGCGCGAGG<br>AGGTGGCTATAGGACTGATGCATCTGTGGGACTTTGTAAGCGCGCTGGAGCA<br>AAACCCAAATAGCAAGCCGCTCATGGCGCAGCTGTTCCTTATAGTGCAGCAC<br>AGCAGGGACAACGAGGCATTCAGGGATGCGCTGCTAAACATAGTAGAGCCC<br>GAGGGCCGCTGGCTGCTCGATTTGATAAACATCCTGCAGAGCATAGTGGTGC<br>AGGAGCGCAGCTTGAGCCTGGCTGACAAGGTGGCCGCCATCAACTATTCCAT<br>GCTTAGCCTGGGCAAGTTTTACGCCCGCAAGATATACCATACCCCTTACGTTC<br>CCATAGACAAGGAGGTAAAGATCGAGGGGTTCTACATGCGGCTGAA<br>GGTGCTTACCTTGAGCGACGACCTGGGCGTTTATCGCAACGAGCGCATCCAC<br>AAGGCCGTGAGCGTGAGCCGGCGGCGCGAGCTCAGCGACCGCGAGCTGATG<br>CACAGCCTGCAAAGGGCCCTGGCTGGCACGGGCAGCGGCGATAGAGAGGCC<br>GAGTCCTACTTTGACGCGGGCGCTGACCTGCGCTGGGCCCCAAGCCGACGCG<br>CCCTGGAGGCAGCTGGGGCCGGACCTGGGCTGGCGGTGGCACCCGCGCGCGC<br>TGGCAACGTCGGCGGCGTGGAGGAATATGACGAGGACGATGAGTACGAGCC<br>AGAGGACGGCGAGTACTAAGCGGTGATGTTTCTGATCAGATGATGCAAGACG<br>CAACGGACCCGGCGGTGCGGGCGGCGCTGCAGAGCCAGCCGTCCGGCCTTAA<br>CTCCACGGACGACTGGCGCCAGGTCATGGACCGCATCATGTCGCTGACTGCG<br>CGCAATCCTGACGCGTTCCGGCAGCAGCCGCAGGCCAACCGGCTCTCCGCAA<br>TTCTGGAAGCGGTGGTCCCGGCGCGCGCAAACCCCACGCACGAGAAGGTGCT<br>GGCGATCGTAAACGCGCTGGCCGAAAACAGGGCCATCCGGCCCGACGAGGC<br>CGGCCTGGTCTACGACGCGCTGCTTCAGCGCGTGGCTCGTTACAACAGCGGC<br>AACGTGCAGACCAACCTGGACCGGCTGGTGGGGGATGTGCGCGAGGCCGTG<br>GCGCAGCGTGAGCGCGCGCAGCAGCAGGGCAACCTGGGCTCCATGGTTGCAC<br>TAAACGCCTTCCTGAGTACACAGCCCGCCAACGTGCCGCGGGGACAGGAGGA<br>CTACACCAACTTTGTGAGCGCACTGCGGCTAATGGTGACTGAGACACCGCAA<br>AGTGAGGTGTACCAGTCTGGGCCAGACTATTTTTTCCAGACCAGTAGACAAG<br>GCCTGCAGACCGTAAACCTGAGCCAGGCTTTCAAAAACTTGCAGGGGCTGTG<br>GGGGGTGCGGGCTCCCACAGGCGACCGCGCGACCGTGTCTAGCTTGCTGACG<br>CCCAACTCGCGCCTGTTGCTGCTGCTAATAGCGCCCTTCACGGACAGTGGCAG<br>CGTGTCCCGGGACACATACCTAGGTCACTTGCTGACACTGTACCGCGAGGCC<br>ATAGGTCAGGCGCATGTGGACGAGCATACTTTCCAGGAGATTACAAGTGTCA<br>GCCGCGCGCTGGGGCAGGAGGACACGGGCAGCCTGGAGGCAACCCTAAACT<br>ACCTGCTGACCAACCGGCGGCAGAAGATCCCCTCGTTGCACAGTTTAAACAG<br>CGAGGAGGAGCGCATTTTGCGCTACGTGCAGCAGAGCGTGAGCCTTAACCTG<br>ATGCGCGACGGGGTAACGCCCAGCGTGGCGCTGGACATGACCGCGCGCAAC<br>ATGGAACCGGGCATGTATGCCTCAAACCGGCCGTTTATCAACCGCCTAATGG<br>ACTACTTGCATCGCGCGGCCGCCGTGAACCCCGAGTATTTCACCAATGCCATC<br>TTGAACCCGCACTGGCTACCGCCCCTGGTTTCTACACCGGGGATTCGAGGT<br>GCCCGAGGGTAACGATGGATTCCTCTGGGACGACATAGACGACAGCGTGTTT<br>TCCCCGCAACCGCAGACCCTGCTAGAGTTGCAACAGCGCGAGCAGGCAGAGG<br>CGGCGCTGCGAAAGGAAAGCTTCCGCAGGCCAAGCAGCTTGTCCGATCTAGG<br>CGCTGCGGCCCCGCGGTCAGATGCTAGTAGCCCATTTCCAAGCTTGATAGGG<br>TCTCTTACCAGCACTCGCACCACCCGCCCGCGCCTGCTGGGCGAGGAGGAGT<br>ACCTAAACAACTCGCTGCTGCAGCCGCAGCGCGAAAAAAAACCTGCCTCCGGC<br>ATTTCCCAACAACGGGATAGAGAGCCTAGTGGACAAGATGAGTAGATGGAA<br>GACGTACGCGCAGGAGCACAGGGACGTGCCAGGCCCGCGCCCGCCCACCCGT<br>CGTCAAAGGCACGACCGTCAGCGGGGTCTGGTGTGGGAGGACGATGACTCGG<br>CAGACGACAGCAGCGTCCTGGATTTGGGAGGGAGTGGCAACCCGTTTGCGCA<br>CCTTCGCCCCAGGCTGGGGAGAATGTTTTAAAAAAAAAAAAGCATGATGCAA<br>AATAAAAAACTCACCAAGGCCATGGCACCGAGCGTTGGTTTTCTTGTATTCCC<br>CTTAGTATGCGGCGCGCGGCGATGTATGAGGAAGGTCCTCCTCCCTCCTACG<br>AGAGTGTGGTGAGCGCGGCGCCAGTGGCGGCGGCGCTGGGTTCTCCCCTTCGA<br>TGCTCCCCTGGACCCGCCGTTTGTGCCTCCGCGGTACCTGCGGCCTACCGGGG<br>GGAGAAACAGCATCCGTTACTCTGAGTTGGCACCCCTATTCGACACCACCCG<br>TGTGTACCTGGTGGACAACAAGTCAACGGATGTGGCATCCCTGAACTACCAG<br>AACGACCACAGCAACTTTCTGACCACGGTCATTCAAAACAATGACTACAGCC<br>CGGGGGAGGCAAGCACACAGACCATCAATCTTGACGACCGGTCGCACTGGG |

| SEQ ID NO | Sequence |
|---|---|
| | GCGGCGACCTGAAAACCATCCTGCATACCAACATGCCAAATGTGAACGAGTT
CATGTTTACCAATAAGTTTAAGGCGCGGGTGATGGTGTCGCGCTTGCCTACTA
AGGACAATCAGGTGGAGCTGAAATACGAGTGGGTGGAGTTCACGCTGCCCGA
GGGCAACTACTCCGAGACCATGACCATAGACCTTATGAACAACGCGATCGTG
GAGCACTACTTGAAAGTGGGCAGACAGAACGGGGTTCTGGAAAGCGACATC
GGGGTAAAGTTTGACACCCGCAACTTCAGACTGGGGGTTTGACCCCGTCACTG
GTCTTGTCATGCCTGGGGTATATACAAACGAAGCCTTCCATCCAGACATCATT
TTGCTGCCAGGATGCGGGGTGGACTTCACCCACAGCCGCCTGAGCAACTTGT
TGGGCATCCGCAAGCGGCAACCCTTCCAGGAGGGCTTTAGGATCACCTACGA
TGATCTGGAGGGTGGTAACATTCCCGCACTGTTGGATGTGGACGCCTACCAG
GCGAGCTTGAAAGATGACACCGAACAGGGCGGGGGTGGCGCAGGCGGCAGC
AACAGCAGTGGCAGCGGCGCGGAAGAGAACTCCAACGCGGCAGCCGCGGCA
ATGCAGCCGGTGGAGGACATGAACGATCATGCCATTCGCGGCGACACCTTTG
CCACACGGGCTGAGGAGAAGCGCGCTGAGGCCGAAGCAGCGGCCGAAGCTG
CCGCCCCCGCTGCGCAACCCGAGGTCGAGAAGCCTCAGAAGAAACCGGTGAT
CAAACCCCTGACAGAGGACAGCAAGAAACGCAGTTACAACCTAATAAGCAA
TGACAGCACCTTCACCCAGTACCGCAGCTGGTACCTTGCATACAACTACGGC
GACCCTCAGACCGGAATCCGCTCATGGACCCTGCTTTGCACTCCTGACGTAAC
CTGCGGCTCGGAGCAGGTCTACTGGTCGTTGCCAGACATGATGCAAGACCCC
GTGACCTTCCGCTCCACGCGCCAGATCAGCAACTTTCCGGTGGTGGGCGCCG
AGCTGTTGCCCGTGCACTCCAAGAGCTTCTACAACGACCAGGCCGTCTACTCC
CAACTCATCCGCCAGTTTACCTCTCTGACCCACGTGTTCAATCGCTTTCCCGA
GAACCAGATTTTGGCGCGCCCGCCAGCCCCCACCATCACCACCGTCAGTGAA
AACGTTCCTGCTCTCACAGATCACGGGACGCTACCGCTGCGCAACAGCATCG
GAGGAGTCCAGCGAGTGACCATTACTGACGCCAGACGCCGCACCTGCCCCTA
CGTTTACAAGGCCCTGGGCATAGTCTCGCGCGCGTCCTATCGAGCCGCACTT
TTTGAGCAAGCATGTCCATCCTTATATCGCCCAGCAATAACACAGGCTGGGG
CCTGCGCTTCCCAAGCAAGATGTTTGGCGGGGCCAAGAAGCGCTCCGACCAA
CACCCAGTGCGCGTGCGCGGGCACTACCGCGCGCCCTGGGGCGCGCACAAAC
GCGGCCGCACTGGGCGCACCACCGTCGATGACGCCATCGACGCGGTGGTGGA
GGAGGCGCGCAACTACACGCCCACGCCGCCACCAGTGTCCACAGTGGACGCG
GCCATTCAGACCGTGGTGCGCGGAGCCCGGCGCTATGCTAAAATGAAGAGAC
GGCGGAGGCGCGTAGCACGTCGCCACCGCCGCCGACCCGGCACTGCCGCCCA
ACGCGCGGCGGCGGCCCTGCTTAACCGCGCACGTCGCACCGGCCGACGGGCG
GCCATGCGGGCCGCTCGAAGGCTGGCCGCGGGTATTGTCACTGTGCCCCCCA
GGTCCAGGCGACGAGCGGCCGCCGCAGCAGCCGCGGCCATTAGTGCTATGAC
TCAGGGTCGCAGGGGCAACGTGTATTGGGTGCGCGACTCGGTTAGCGGCCTG
CGCGTGCCCGTGCGCACCCGCCCCCCGCGCAACTAGATTGCAAGAAAAAACT
ACTTAGACTCGTACTGTTGTATGTATCCAGCGGCGGCGGCGCGCAACGAAGC
TATGTCCAAGCGCAAAATCAAAGAAGAGATGCTCCAGGTCATCGCGCCGGAG
ATCTATGGCCCCCGAAGAAGGAAGAGCAGGATTACAAGCCCCGAAAGCTA
AAGCGGGTCAAAAAGAAAAAGAAAGATGATGATGATGAACTTGACGACGAG
GTGGAACTGCTGCACGCTACCGCGCCCAGGCGACGGGTACAGTGGAAAGGTC
GACGCGTAAAACGTGTTTTGCGACCCGGCACCACCGTAGTCTTTACGCCCGGT
GAGCGCTCCACCCGCACCTACAAGCGCGTGTATGATGAGGTGTACGGCGACG
AGGACCTGCTTGAGCAGGCCAACGAGCGCCTCGGGGAGTTTGCCTACGGAAA
GCGGCATAAGGACATGCTGGCGTTGCCGCTGGACGAGGGCAACCCAACACCT
AGCCTAAACTCCCGTAACACTGCAGCAGGTGCTGCCCGCGCTTGCACCGTCCG
AAGAAAAGCGCGGCCTAAAGCGCGAGTCTGGTGACTTGGCACCCACCGTGCA
GCTGATGGTACCCAAGCGCCAGCGACTGGAAGATGTCTTGGAAAAAATGACC
GTGGAACCTGGGCTGGAGCCCGAGGTCCGCGTGCGGCCAATCAAGCAGGTGG
CGCCGGGACTGGGCGTGCAGACCGTGGACGTTCAGATACCCACTACCAGTAG
CACCAGTATTGCCACCGCCACAGAGGGCATGGAGACACAAACGTCCCCGGTT
GCCTCAGCGGTGGCGGATGCCGCGGTGCAGGCGGTCGCTGCGGCCGCGTCCA
AGACCTCTACGGAGGTGCAAACGGACCCGTGGATGTTTCGCGTTTCAGCCCC
CCGGCGCCCGCGCCGTTCGAGGAAGTACGGCGCCGCCAGCGCGCTACTGCCC
GAATATGCCCTACATCCTTCCATTGCGCCTACCCCCGGCTATCGTGGCTACAC
CTACCGCCCCAGAAGACGAGCAACTACCCGACGCCGAACCACCACTGGAACC
CGCCGCCGCCGTCGCCGTCGCCAGCCCGTGCTGGCCCCGATTTCCGTGCGCAG
GGTGGCTCGCGAAGGAGGCAGGACCCTGGTGCTGCAACAGCGCGCTACCAC
CCCAGCATCGTTTAAAAGCCGGTCTTTGTGGTTCTTGCAGATATGGCCCTCAC
CTGCCGCCTCCGTTTCCCGGTGCCGGGATTCCGAGGAAGAATGCACCGTAGG
AGGGGCATGGCCGGCCACGGCCTGACGGGCGGCATGCGTCGTGCGCACCACC
GGCGGCGGCGCGTCGCACCGTCGCATGCGCGGCGGTATCCTGCCCCTCCT
TATTCCACTGATCGCCGCGGCGATTGGCGCCGTGCCCGGAATTGCATCCGTGG
CCTTGCAGGCGCAGAGACACTGATTAAAAACAAGTTGCATGTGGAAAAATCA
AAATAAAAAGTCTGGACTCTCACGCTCGCTTGGTCCTGTAACTATTTTGTAGA
ATGGAAGACATCAACTTTGCGTCTCTGGCCCCGCGACACGGCTCGCGCCCGTT
CATGGGAAACTGGCAAGATATCGGCACCAGCAATATGAGCGGTGGCGCCTTC
AGCTGGGGCTCGCTGTGGAGCGGCATTAAAAATTTCGGTTCCACCGTTAAGA
ACTATGGCAGCAAGGCCTGGAACAGCAGCACAGGCCAGATGCTGAGGGATA
AGTTGAAAGAGCAAAATTTCCAACAAAAGGTGGTAGATGGCCTGGCCTCTGG
CATTAGCGGGGTGGTGGACCTGGCCAACCAGGCAGTGCAAAATAAGATTAAC |

| SEQ ID NO | Sequence |
|---|---|
| | AGTAAGCTTGATCCCCGCCCTCCCGTAGAGGAGCCTCCACCGGCCGTGGAGA<br>CAGTGTCTCCAGAGGGGCGTGGCGAAAAGCGTCCGCGCCCCGACAGGGAAG<br>AAACTCTGGTGACGCAAATAGACGAGCCTCCCTCGTACGAGGAGGCACTAAA<br>GCAAGGCCTGCCCACCACCCGTCCCATCGCGCCCATGGCTACCGGAGTGCTG<br>GGCCAGCACACACCCGTAACGCTGGACCTGCCTCCCCCCGCCGACACCCAGC<br>AGAAACCTGTGCTGCCAGGCCCGACCGCCGTTGTTGTAACCCGTCCTAGCCG<br>CGCGTCCCTGCGCCGCGCCGCCAGCGGTCCGCGATCGTTGCGGCCCGTAGCC<br>AGTGGCAACTGGCAAAGCACACTGAACAGCATCGTGGGTCTGGGGGTGCAAT<br>CCCTGAAGCGCCGACGATGCTTCTGATAGCTAACGTGTCGTATGTGTGTCATG<br>TATGCGTCCATGTCGCCGCCAGAGGAGCTGCTGAGCCGCCGCGCGCCCGCTT<br>TCCAAGATGGCTACCCCTTCGATGATGCCGCAGTGGTCTTACATGCACATCTC<br>GGGCCAGGACGCCTCGGAGTACCTGAGCCCCGGCTGGTGCAGTTTGCCCGC<br>GCCACCGAGACGTACTTCAGCCTGAATAACAAGTTTAGAAACCCCACGGTGG<br>CGCCTACGCACGACGTGACCACAGACCGGTCCCAGCGTTTGACGCTGCGGTT<br>CATCCCTGTGGACCGTGAGGATACTGCGTACTCGTACAAGGCGCGGTTCACC<br>CTAGCTGTGGGTGATAACCGTGTGCTGGACATGGCTTCCACGTACTTTGACAT<br>CCGCGGCGTGCTGGACAGGGGCCCTACTTTTAAGCCCTACTCTGGCACTGCCT<br>ACAACGCCCTGGCTCCCAAGGGTGCCCCAAATCCTTGCGAATGGGATGAAGC<br>TGCTACTGCTCTTGAAATAAACCTAGAAGAAGAGGACGATGACAACGAAGAC<br>GAAGTAGACGAGCAAGCTGAGCAGCAAAAAACTCACGTATTTGGGCAGGCG<br>CCTTATTCTGGTATAAATATTACAAAGGAGGGTATTCAAATAGGTGTCGAAG<br>GTCAAACACCTAAATATGCCGATAAAACATTTCAACCTGAACCTCAAATAGG<br>AGAATCTCAGTGGTACGAAACAGAAATTAATCATGCAGCTGGGAGAGTCCTA<br>AAAAAGACTACCCCAATGAAACCATGTTACGGTTCATATGCAAAACCCACAA<br>ATGAAAATGGAGGGCAAGGCATTCTTGTAAAGCAACAAAATGGAAAGCTAG<br>AAAGTCAAGTGGAAATGCAATTTTTCTCAACTACTGAGGCAGCCGCAGGCAA<br>TGGTGATAACTTGACTCCTAAAGTGGTATTGTACAGTGAAGATGTAGATATA<br>GAAACCCCAGACACTCATATTTCTTACATGCCCACTATTAAGGAAGGTAACTC<br>ACGAGAACTAATGGGCCAACAATCTATGCCCAACAGGCCTAATTACATTGCT<br>TTTAGGGACAATTTTATTGGTCTAATGTATTACAACAGCACGGGTAATATGGG<br>TGTTCTGGCGGGCCAAGCATCGCAGTTGAATGCTGTTGTAGATTTGCAAGAC<br>AGAAACACAGAGCTTTCATACCAGCTTTTGCTTGATTCCATTGGTGATAGAAC<br>CAGGTACTTTTCTATGTGGAATCAGGCTGTTGACAGCTATGATCCAGATGTTA<br>GAATTATTGAAAATCATGGAACTGAAGATGAACTTCCAAATTACTGCTTTCCA<br>CTGGGAGGTGTGATTAATACAGAGACTCTTACCAAGGTAAAACCTAAAACAG<br>GTCAGGAAAATGGATGGGAAAAAGATGCTACAGAATTTTCAGATAAAAATG<br>AAATAAGAGTTGGAAATAATTTTGCCATGGAAATCAATCTAAATGCCAACCT<br>GTGGAGAAATTTCCTGTACTCCAACATAGCGCTGTATTTGCCCGACAAGCTAA<br>AGTACAGTCCTTCCAACGTAAAAATTTCTGATAACCCAAACACCTACGACTA<br>CATGAACAAGCGAGTGGTGGCTCCCGGGCTAGTGGACTGCTACATTAACCTT<br>GGAGCACGCTGGTCCCTTGACTATATGGACAACGTCAACCCATTTAACCACC<br>ACCGCAATGCTGGCCTGCGCTACCGCTCAATGTTGCTGGGCAATGGTCGCTAT<br>GTGCCCTTCCACATCCAGGTGCCTCAGAAGTTCTTTGCCATTAAAAACCTCCT<br>TCTCCTGCCGGGCTCATACACCTACGAGTGGAACTTCAGGAAGGATGTTAAC<br>ATGGTTCTGCAGAGCTCCCTAGGAAATGACCTAAGGGTTGACGGAGCCAGCA<br>TTAAGTTTGATAGCATTTGCCTTTACGCCACCTTCTTCCCCATGGCCCACAAC<br>ACCGCCTCCACGCTTGAGGCCATGCTTAGAAACGACACCAACGACCAGTCCT<br>TTAACGACTATCTCTCCGCCGCCAACATGCTCTACCCTATACCCGCCAACGCT<br>ACCAACGTGCCCATATCCATCCCCTCCCGCAACTGGGCGGCTTTCCGCGGCTG<br>GGCCTTCACGCGCCTTAAGACTAAGGAAACCCCATCACTGGGCTCGGGCTAC<br>GACCCTTATTACACCTACTCTGGCTCTATACCCTACCTAGATGGAACCTTTTA<br>CCTCAACCACACCTTTAAGAAGGTGGCCATTACCTTTGACTCTTCTGTCAGCT<br>GGCCTGGCAATGACCGCCTGCTTACCCCCAACGAGTTTGAAATTAAGCGCTC<br>AGTTGACGGGGAGGGTTACAACGTTGCCCAGTGTAACATGACCAAAGACTGG<br>TTCCTGGTACAAATGCTAGCTAACTATAACATTGGCTACCAGGGCTTCTATAT<br>CCCAGAGAGCTACAAGGACCGCATGTACTCCTTCTTTAGAAACTTCCAGCCC<br>ATGAGCCGTCAGGTGGTGGATGATACTAAATACAAGGACTACCAACAGGTGG<br>GCATCCTACACCAACACAACAACTCTGGATTTGTTGGCTACCTTGCCCCCACC<br>ATGCGCGAAGGACAGGCCTACCCTGCTAACTTCCCCTATCCGCTTATAGGCA<br>AGACCGCAGTTGACAGCATTACCCAGAAAAAGTTTCTTTGCGATCGCACCCTT<br>TGGCGCATCCCATTCTCCAGTAACTTTATGTCCATGGGCGCACTCACAGACCT<br>GGGCCAAAACCTTCTCTACGCCAACTCCGCCCACGCGCTAGACATGACTTTTG<br>AGGTGGATCCCATGGACGAGCCCACCCTTCTTTATGTTTTGTTTGAAGTCTTT<br>GACGTGGTCCGTGTGCACCAGCCGCACCGCGGCGTCATCGAAACCGTGTACC<br>TGCGCACGCCCTTCTCGGCCGGCAACGCCACAACATAAAGAAGCAAGCAACA<br>TCAACAACAGCTGCCGCCATGGGCTCCAGTGAGCAGGAACTGAAAGCCATTG<br>TCAAAGATCTTGGTTGTGGGCCATATTTTTTGGGCACCTATGACAAGCGCTTT<br>CCAGGCTTTGTTTCTCCACACAAGCTCGCCTGCGCCATAGTCAATACGGCCGG<br>TCGCGAGACTGGGGCGTACACTGGATGGCCTTTGCCTGGAACCCGCACTCA<br>AAAACATGCTACCTCTTTGAGCCCTTTGGCTTTTCTGACCAGCGACTCAAGCA<br>GGTTTACCAGTTTGAGTACGAGTCACTCCTGCGCCGTAGCGCCATTGCTTCTT<br>CCCCCGACCGCTGTATAAACGCTGGAAAAGTCCACCCAAAGCGTACAGGGGCC<br>CAACTCGGCCGCCTGTGGACTATTCTGCTGCATGTTTCTCCACGCCTTTGCCA |

| SEQ ID NO | Sequence |
|---|---|
| | ACTGGCCCCAAACTCCCATGGATCACAACCCCACCATGAACCTTATTACCGG<br>GGTACCCAACTCCATGCTCAACAGTCCCCAGGTACAGCCCACCCTGCGTCGC<br>AACCAGGAACAGCTCTACAGCTTCCTGGAGCGCCACTCGCCCTACTTCCGCA<br>GCCACAGTGCGCAGATTAGGAGCGCCACTTCTTTTTGTCACTTGAAAAACATG<br>TAAAAATAATGTACTAGAGACACTTTCAATAAAGGCAAATGCTTTTATTTGTA<br>CACTCTCGGGTGATTATTTACCCCCACCCTTGCCGTCTGCGCCGTTTAAAAAT<br>CAAAGGGGTTCTGCCGCGCATCGCTATGCGCCACTGGCAGGGACACGTTGCG<br>ATACTGGTGTTTAGTGCTCCACTTAAACTCAGGCACAACCATCCGCGGCAGCT<br>CGGTGAAGTTTTCACTCCACAGGCTGCGCACCATCACCAACGCGTTTAGCAG<br>GTCGGGCGCCGATATCTTGAAGTCGCAGTTGGGGCCTCCGCCCTGCGCGCGC<br>GAGTTGCGATACACAGGGTTGCAGCACTGGAACACTATCAGCGCCGGGTGGT<br>GCACGCTGGCCAGCACGCTCTTGTCGGAGATCAGATCCGCGTCCAGGTCCTC<br>CGCGTTGCTCAGGGCGAACGGAGTCAACTTTGGTAGCTGCCTTCCCAAAAAG<br>GGCGCGTGCCCAGGCTTTGAGTTGCACTCGCACCGTAGTGGCATCAAAAGGT<br>GACCGTGCCCGGTCTGGGCGTTAGGATACAGCGCCTGCATAAAAGCCTTGAT<br>CTGCTTAAAAGCCACCTGAGCCTTTGCGCCTTCAGAGAAGAACATGCCGCAA<br>GACTTGCCGGAAAACTGATTGGCCGGACAGGCCGCGTCGTGCACGCAGCACC<br>TTGCGTCGGTGTTGGAGATCTGCACCACATTTCGGCCCCACCGGTTCTTCACG<br>ATCTTGGCCTTGCTAGACTGCTCCTTCAGCGCGCGCTGCCCGTTTTCGCTCGTC<br>ACATCCATTTCAATCACGTGCTCCTTATTTATCATAATGCTTCCGTGTAGACA<br>CTTAAGCTCGCCTTCGATCTCAGCGCAGCGGTGCAGCCACAACGCGCAGCCC<br>GTGGGCTCGTGATGCTTGTAGGTCACCTCTGCAAACGACTGCAGGTACGCCT<br>GCAGGAATCGCCCCATCATCGTCACAAAGGTCTTGTTGCTGGTGAAGGTCAG<br>CTGCAACCCGCGGTGCTCCTCGTTCAGCCAGGTCTTGCATACGGCCGCCAGA<br>GCTTCCACTTGGTCAGGCAGTAGTTTGAAGTTCGCCTTTAGATCGTTATCCAC<br>GTGGTACTTGTCCATCAGCGCGCGCGCAGCCTCCATGCCCTTCTCCCACGCAG<br>ACACGATCGGCACACTCAGCGGGTTCATCACCGTAATTTCACTTTCCGCTTCG<br>CTGGGCTCTTCCTCTTCCTCTTGCGTCCGCATACCACGCGCCACTGGGTCGTCT<br>TCATTCAGCCGCCGCACTGTGCGCTTACCTCCTTTGCCATGCTTGATTAGCAC<br>CGGTGGGTTGCTGAAACCCACCATTTGTAGCGCCACATCTTCTCTTTCTTCCTC<br>GCTGTCCACGATTACCTCTGGTGATGGCGGCGCTCGGGCTTGGGAGAAGGG<br>CGCTTCTTTTTCTTCTTGGGCGCAATGGCCAAATCCGCCGCCGAGGTCGATGG<br>CCGCGGGCTGGGTGTGCGCGGCACCAGCGCGTCTTGTGATGAGTCTTCCTCGT<br>CCTCGGACTCGATACGCCGCCTCATCCGCTTTTTTGGGGGCGCCCGGGGAGGC<br>GGCGGCGACGGGACGGGACGACACGTCCTCCATGGTTGGGGGACGTCGC<br>GCCGCACCGCGTCCGCGCTCGGGGGTGGTTTCGCGCTGCTCCTCTTCCCGACT<br>GGCCATTTCCTTCTCCTATAGGCAGAAAAAGATCATGGAGTCAGTCGAGAAG<br>AAGGACAGCCTAACCGCCCCCTCTGAGTTCGCCACCACCGCCTCCACCGATG<br>CCGCCAACGCGCCTACCACCTTCCCCGTCGAGGCACCCCCGCTTGAGGAGGA<br>GGAAGTGATTATCGAGCAGGACCCAGGTTTTGTAAGCGAAGACGACGAGGA<br>CCGCTCAGTACCAACAGAGGATAAAAAGCAAGACCAGGACAACGCAGAGGC<br>AAACGAGGAACAAGTCGGGCGGGGGGACGAAAGGCATGGCGACTACCTAGA<br>TGTGGGAGACGACGTGCTGTTGAAGCATCTGCAGCGCCAGTGCGCCATTATC<br>TGCGACGCGTTGCAAGAGCGCAGCGATGTGCCCCTCGCCATAGCGGATGTCA<br>GCCTTGCCTACGAACGCCACCTATTCTCACCGCGCGTACCCCCCAAACGCCAA<br>GAAAACGGCACATGCGAGCCCAACCCGCGCCTCAACTTCTACCCCGTATTTG<br>CCGTGCCAGAGGTGCTTGCCACCTATCACATCTTTTTTCCAAAACTGCAAGATA<br>CCCCTATCCTGCCGTGCCAACCGCAGCCGAGCGGACAAGCAGCTGGCCTTGC<br>GGCAGGGCGCTGTCATACCTGATATCGCCTCGCTCAACGAAGTGCCAAAAAT<br>CTTTGAGGGTCTTGGACGCGACGAGAAGCGCGCGGCAAACGCTCTGCAACAG<br>GAAAACAGCGAAAATGAAAGTCACTCTGGAGTGTTGGTGGAACTCGAGGGT<br>GACAACGCGCGCCTAGCCGTACTAAAACGCAGCATCGAGGTCACCCACTTTG<br>CCTACCCGGCACTTAACCTACCCCCCAAGGTCATGAGCACAGTCATGAGTGA<br>GCTGATCGTGCGCCGTGCGCAGCCCCTGGAGAGGGATGCAAATTTGCAAGAA<br>CAAACAGAGGAGGGCCTACCCGCAGTTGGCGACGAGCAGCTAGCGCGCTGG<br>CTTCAAACGCGCGAGCCTGCCGACTTGGAGGAGCGACGCAAACTAATGATGG<br>CCGCAGTGCTCGTTACCGTGGAGCTTGAGTGCATGCAGCGGTTCTTTGCTGAC<br>CCGGAGATGCAGCGCAAGCTAGAGGAAACATTGCACTACACCTTTCGACAGG<br>GCTACGTACGCCAGGCCTGCAAGATCTCCAACGTGGAGCTCTGCAACCTGGT<br>CTCCTACCTTGGAATTTTGCACGAAACCGCCTTGGGCAAACGTGCTTCATT<br>CCACGCTCAAGGGCGAGGCGCGCCGCGACTACGTCCGCGACTGCGTTTACTT<br>ATTTCTATGCTACACCTGGCAGACGGCCATGGGCGTTTGGCAGCAGTGCTTGG<br>AGGAGTGCAACCTCAAGGAGCTGCAGAAACTGCTAAAGCAAAACTTGAAGG<br>ACCTATGGACGGCCTTCAACGAGCGCTCCGTGGCCGCGCACCTGGCGGACAT<br>CATTTTCCCCGAACGCCTGCTTAAAACCCTGCAACAGGGTCTGCCAGACTTCA<br>CCAGTCAAAGCATGTTGCAGAACTTTAGGAACTTTATCCTAGAGCGCTCAGG<br>AATCTTGCCCGCCACCTGCTGTGCACTTCCTAGCGACTTTGTGCCCATTAAGT<br>ACCGCGAATGCCCTCCGCCGCTTTGGGGCCACTGCTACCTTCTGCAGCTAGCC<br>AACTACCTTGCCTACCACTCTGACATAATGGAAGACGTGAGCGGTGACGGTC<br>TACTGGAGTGTCACTGTCGCTGCAACCTATGCACCCCGCACCGCTCCCTGGTT<br>TGCAATTCGCAGCTGCTTAACGAAAGTCAAATTATCGGTACCTTTGAGCTGCA<br>GGGTCCCTCGCCTGACGAAAAGTCCGCGGCTCCGGGGTTGAAACTCACTCCG<br>GGGCTGTGGACGTCGGCTTACCTTCGCAAATTTGTACCTGAGGACTACCACGC |

| SEQ ID NO | Sequence |
|---|---|
| | CCACGAGATTAGGTTCTACGAAGACCAATCCCGCCCGCCTAATGCGGAGCTT<br>ACCGCCTGCGTCATTACCCAGGGCCACATTCTTGGCCAATTGCAAGCCATCAA<br>CAAAGCCCGCCAAGAGTTTCTGCTACGAAAGGGACGGGGGGTTTACTTGGAC<br>CCCCAGTCCGGCGAGGAGCTCAACCCAATCCCCCCGCCGCCGCAGCCCTATC<br>AGCAGCAGCCGCGGGCCCTTGCTTCCCAGGATGGCACCCAAAAAGAAGCTGC<br>AGCTGCCGCCGCCACCCACGGACGAGGAGGAATACTGGGACAGTCAGGCAG<br>AGGAGGTTTTGGACGAGGAGGAGGAGGACATGATGGAAGACTGGGAGAGCC<br>TAGACGAGGAAGCTTCCGAGGTCGAAGAGGTGTCAGACGAAACACCGTCAC<br>CCTCGGTCGCATTCCCCTCGCCGGCGCCCCAGAAATCGGCAACCGGTTCCAG<br>CATGGCTACAACCTCCGCTCCTCAGGCGCCGCCGGCACTGCCCGTTCGCCGAC<br>CCAACCGTAGATGGGACACCACTGGAACCAGGGCCGGTAAGTCCAAGCAGC<br>CGCCGCCGTTAGCCCAAGAGCAACAACAGCGCCAAGGCTACCGCTCATGGCG<br>CGGGCACAAGAACGCCATAGTTGCTTGCTTGCAAGACTGTGGGGGCAACATC<br>TCCTTCGCCCGCCGCTTTCTTCTCTACCATCACGGCGTGGCCTTCCCCCGTAAC<br>ATCCTGCATTACTACCGTCATCTCTACAGCCCATACTGCACCGGCGGCAGCGG<br>CAGCAACAGCAGCGGCCACACAGAAGCAAAGGCGACCGGATAGCAAGACTC<br>TGACAAAGCCCAAGAAATCCACAGCGGCGGCAGCAGCAGGAGGAGGAGCGC<br>TGCGTCTGGCGCCCAACGAACCCGTATCGACCCGCGAGCTTAGAAACAGGAT<br>TTTTCCCACTCTGTATGCTATATTTCAACAGAGCAGGGGCCAAGAACAAGAG<br>CTGAAAATAAAAAACAGGTCTCTGCGATCCCTCACCCGCGACGCTGCCTGTATC<br>ACAAAAGCGAAGATCAGCTTCGGCGCACGCTGGAAGACGCGGAGGCTCTCTT<br>CAGTAAATACTGCGCGCTGACTCTTAAGGACTAGTTTCGCGCCCTTTCTCAAA<br>TTTAAGCGCGAAAACTACGTCATCTCCAGCGGCCACACCCGGCGCCAGCACC<br>TGTTGTCAGCGCCATTATGAGCAAGGAAATTCCCACGCCCTACATGTGGAGTT<br>ACCAGCCACAAATGGGACTTGCGGCTGGAGCTGCCCAAGACTACTCAACCCG<br>AATAAACTACATGAGCGCGGGACCCCACATGATATCCCGGGTCAACGGAATA<br>CGCGCCCACCGAAACCGAATTCTCCTGGAACAGGCGGCTATTACCACCACAC<br>CTCGTAATAACCTTAATCCCCGTAGTTGGCCCGCTGCCCTGGTGTACCAGGAA<br>AGTCCCGCTCCCACCACTGTGGTACTTCCCAGAGACGCCCAGGCCGAAGTTC<br>AGATGACTAACTCAGGGGCGCAGCTTGCGGGCGGCTTTCGTCACAGGGTGCG<br>GTCGCCCGGGCAGGGTATAACTCACCTGACAATCAGAGGGCGAGGTATTCAG<br>CTCAACGACGAGTCGGTGAGCTCCTCGCTTGGTCTCCGTCCGGACGGGACATT<br>TCAGATCGGCGGCGCCGGCCGCTCTTCATTCACGCCTCGTCAGGCAATCCTAA<br>CTCTGCAGACCTCGTCCTCTGAGCCGCGCTCTGGAGGCATTGGAACTCTGCAA<br>TTTATTGAGGAGTTTGTGCCATCGGTCTACTTTAACCCCTTCTCGGGACCTCCC<br>GGCCACTATCCGGATCAATTTATTCCTAACTTTGACGCGGTAAAGGACTCGGC<br>GGACGGCTACGACTGAATGTTAAGTGGAGAGGCAGAGCAACTGCGCCTGAA<br>ACACCTGGTCCACTGTCGCCGCCACAAGTGCTTTGCCCGCGACTCCGGTGAGT<br>TTTGCTACTTTGAATTGCCCGAGGATCATATCGAGGGCCCGGCGCACGGCGTC<br>CGGCTTACCGCCCAGGGAGAGCTTGCCCGTAGCCTGATTCGGGAGTTTACCC<br>AGCGCCCCTGCTAGTTGAGCGGGACAGGGGACCCTGTGTTCTCACTGTGATT<br>TGCAACTGTCCTAACCCTGGATTACATCAAGATCCTCTAGTTAATGTCAGGTC<br>GCCTAAGTCGATTAACTAGAGTACCGGGGATCTTATTCCCTTTAACTAATAA<br>AAAAAAATAATAAAGCATCACTTACTTAAAATCAGTTAGCAAATTTCTGTCC<br>AGTTTATTCAGCAGCACCTCCTTGCCCTCCTCCCAGCTCTGGTATTGCAGCTTC<br>CTCCTGGCTGCAAACTTTCTCCACAATCTAAATGGAATGTCAGTTTCCTCCTG<br>TTCCTGTCCATCCGCACCCACTATCTTCATGTTGTTGCAGATGAAGCGCGCAA<br>GACCGTCTGAAGATACCTTCAACCCCGTGTATCCATATGACACGGAAACCGG<br>TCCTCCAACTGTGCCTTTTCTTACTCCTCCCTTTGTATCCCCCAATGGGTTTCA<br>AGAGAGTCCCCCTGGGGTACTCTCTTTGCGCCTATCCGAACCTCTAGTTACCT<br>CCAATGGCATGCTTGCGCTCAAAATGGGCAACGGCCTCTCTCTGGACGAGGC<br>CGGCAACCTTACCTCCCAAAATGTAACCACTGTGAGCCCACCTCTCAAAAAA<br>ACCAAGTCAAACATAAACCTGGAAATATCTGCACCCCTCACAGTTACCTCAG<br>AAGCCCTAACTGTGGCTGCCGCCGCACCTCTAATGGTCGCGGGCAACACACT<br>CACCATGCAATCACAGGCCCCGCTAACCGTGCACGACTCCAAACTTAGCATT<br>GCCACCCAAGGACCCCTCACAGTGTCAGAAGGAAAGCTAGCCCTGCAAACAT<br>CAGGCCCCCTCACCACCACCGATAGCAGTACCCTTACTATCACTGCCTCACCC<br>CCTCTAACTACTGCCACTGGTAGCTTGGGCATTGACTTGAAAGAGCCCATTTA<br>TACACAAAATGGAAAACTAGGACTAAAGTACGGGGCTCCTTTGCATGTAACA<br>GACGACCTAAACACTTTGACCGTAGCAACTGGTCCAGGTGTGACTATTAATA<br>ATACTTCCTTGCAAACTAAAGTTACTGGAGCTTGGGTTTTGATTCACAAGGC<br>AATATGCAACTTAATGTAGCAGGAGGACTAAGGATTGATTCTCAAAACAGAC<br>GCCTTATACTTGATGTTAGTTATCCGTTTGATGCTCAAAACCAACTAAATCTA<br>AGACTAGGACAGGGCCCTCTTTTTATAAACTCAGCCCACAACTTGGATATTAA<br>CTACAACAAAGGCCTTTACTTGTTTACAGCTTCAAACAATTCCAAAAAGCTTG<br>AGGTTAACCTAAGCACTGCCAAGGGGTTGATGTTTGACGCTACAGCCATAGC<br>CATTAATGCAGGAGATGGGCTTGAATTTGGTTCACCTAATGCACCAAACACA<br>AATCCCCTCAAAACAAAAATTGGCCATGGCCTAGAATTTGATTCAAACAAGG<br>CTATGGTTCCTAAACTAGGAACTGGCCTTAGTTTTGACAGCACAGGTGCCATT<br>ACAGTAGGAAACAAAATAATGATAAGCTAACTTTGTGGACCACACCAGCTC<br>CATCTCCTAACTGTAGACTAAATGCAGAGAAAGATGCTAAACTCACTTTGGT<br>CTTAACAAAATGTGGCAGTCAAATACTTGCTACAGTTTCAGTTTTGGCTGTTA<br>AAGGCAGTTTGGCTCCAATATCTGGAACAGTTCAAAGTGCTCATCTTATTATA |

SEQUENCES

| SEQ ID NO | Sequence |
|---|---|
| | AGATTTGACGAAAATGGAGTGCTACTAAACAATTCCTTCCTGGACCCAGAAT<br>ATTGGAACTTTAGAAATGGAGATCTTACTGAAGGCACAGCCTATACAAACG<br>TGTTGGATTTATGCCTAACCTATCAGCTTATCCAAAATCTCACGGTAAAACTG<br>CCAAAAGTAACATTGTCAGTCAAGTTTACTTAAACGGAGACAAAACTAAACC<br>TGTAACACTAACCATTACACTAAACGGTACACAGGAAACAGGAGACACAACT<br>CCAAGTGCATACTCTATGTCATTTTCATGGGACTGGTCTGGCCACAACTACAT<br>TAATGAAATATTTGCCACATCCTCTTACACTTTTTCATACATTGCCCAAGAAT<br>AAAGAATCGTTTGTGTTATGTTTCAACGTGTTTATTTTTCAATTGCAGAAAAT<br>TTCAAGTCATTTTTCATTCAGTAGTATAGCCCCACCACCACATAGCTTATACA<br>GATCACCGTACCTTAATCAAACTCACAGAACCCTAGTATTCAACCTGCCACCT<br>CCCTCCCAACACACAGAGTACACAGTCCTTTCTCCCCGGCTGGCCTTAAAAAG<br>CATCATATCATGGGTAACAGACATATTCTTAGGTGTTATATTCCACACGGTTT<br>CCTGTCGAGCCAAACGCTCATCAGTGATATTAATAAACTCCCCGGGCAGCTC<br>ACTTAAGTTCATGTCGCTGTCCAGCTGCTGAGCCACAGGCTGCTGTCCAACTT<br>GCGGTTGCTTAACGGGCGGCGAAGGAGAAGTCCACGCCTACATGGGGGTAG<br>AGTCATAATCGTGCATCAGGATAGGGCGGTGGTGCTGCAGCAGCGCGCGAAT<br>AAACTGCTGCCGCCGCCGCTCCGTCCTGCAGGAATACAACATGGCAGTGGTC<br>TCCTCAGCGATGATTCGCACCGCCCGCAGCATAAGGCGCCTTGTCCTCCGGGC<br>ACAGCAGCGCACCCTGATCTCACTTAAATCAGCACAGTAACTGCAGCACAGC<br>ACCACAATATTGTTCAAAATCCCACAGTGCAAGGCGCTGTATCCAAAGCTCA<br>TGGCGGGGACCACAGAACCCACGTGGCCATCATACCACAAGCGCAGGTAGAT<br>TAAGTGGCGACCCCTCATAAACACGCTGGACATAAACATTACCTCTTTTGGCA<br>TGTTGTAATTCACCACCTCCCGGTACCATATAAACCTCTGATTAAACATGGCG<br>CCATCCACCACCATCCTAAACCAGCTGGCCAAAACCTGCCCGCCGGCTATAC<br>ACTGCAGGGAACCGGGACTGGAACAATGACAGTGGAGAGCCCAGGACTCGT<br>AACCATGGATCATCATGCTCGTCATGATATCAATGTTGGCACAACACAGGCA<br>CACGTGCATACACTTCCTCAGGATTACAAGCTCCTCCCGCGTTAGAACCTAT<br>CCCAGGGAACAACCCATTCCTGAATCAGCGTAAATCCCACACTGCAGGGAAG<br>ACCTCGCACGTAACTCACGTTGTGCATTGTCAAAGTGTTACATTCGGGCAGCA<br>GCGGATGATCCTCCAGTATGGTAGCGCGGGTTTCTGTCTCAAAAGGAGGTAG<br>ACGATCCCTACTGTACGGAGTGCGCCGAGACAACCGAGATCGTGTTGGTCGT<br>AGTGTCATGCCAAATGGAACGCCGGACGTAGTCATATTTCCTGAAGCAAAAC<br>CAGGTGCGGGCGTGACAAACAGATCTGCGTCTCCGGTCTCGCCGCTTAGATC<br>GCTCTGTGTAGTAGTTGTAGTATATCCACTCTCTCAAAGCATCCAGGCGCCCC<br>CTGGCTTCGGGTTCTATGTAAACTCCTTCATGCGCCGCTGCCCTGATAACATC<br>CACCACCGCAGAATAAGCCACACCCAGCCAACCTACACATTCGTTCTGCGAG<br>TCACACACGGGAGGAGCGGGAAGAGCTGGAAGAACCATGTTTTTTTTTTTAT<br>TCCAAAAGATTATCCAAAACCTCAAATGAAGATCTATTAAGTGAACGCGCT<br>CCCCTCCGGTGGCGTGGTCAAACTCTACAGCCAAAGAACAGATAATGGCATT<br>TGTAAGATGTTGCACAATGGCTTCCAAAAGGCAAACGGCCCTCACGTCCAAG<br>TGGACGTAAAGGCTAAACCCTTCAGGGTGAATCTCCTCTATAAACATTCCAG<br>CACCTTCAACCATGCCCAAATAATTCTCATCTCGCCACCTTCTCAATATATCT<br>CTAAGCAAATCCCGAATATTAAGTCCGGCCATTGTAAAAATCTGCTCCAGAG<br>CGCCCTCCACCTTCAGCCTCAAGCAGCGAATCATGATTGCAAAAATTCAGGTT<br>CCTCACAGACCTGTATAAGATTCAAAAGCGGAACATTAACAAAAATACCGCG<br>ATCCCGTAGGTCCCTTCGCAGGGCCAGCTGAACATAATCGTGCAGGTCTGCA<br>CGGACCAGCGCGGCCACTTCCCCGCCAGGAACCATGACAAAAGAACCCACAC<br>TGATTATGACACGCATACTCGGAGCTATGCTAACCAGCGTAGCCCGATGTA<br>AGCTTGTTGCATGGGCGGCGATATAAAATGCAAGGTGCTGCTCAAAAAATCA<br>GGCAAAGCCTCGCGCAAAAAAGAAAGCACATCGTAGTCATGCTCATGCAGAT<br>AAAGGCAGGTAAGCTCCGGAACCACCACAGAAAAAGACACCATTTTTCTCTC<br>AAACATGTCTGCGGGTTTCTGCATAAACACAAAATAAAATAACAAAAAAACA<br>TTTAAACATTAGAAGCCTGTCTTACAACAGGAAAAACAACCCTTATAAGCAT<br>AAGACGGACTACGGCCATGCCGGCGTGACCGTAAAAAAACTGGTCACCGTGA<br>TTAAAAAGCACCACCGACAGCTCCTCGGTCATGTCCGGAGTCATAATGTAAG<br>ACTCGGTAAACACATCAGGTTGATTCACATCGGTCAGTGCTAAAAAGCGACC<br>GAAATAGCCCGGGGGAATACATACCCGCAGGCGTAGAGACAACATTACAGC<br>CCCCATAGGAGGTATAACAAAATTAATAGGAGAGAAAAACACATAAACACC<br>TGAAAAACCCTCCTGCCTAGGCAAAATAGCACCCTCCCGCTCCAGAACAACA<br>TACAGCGCTTCCACAGCGGCAGCCATAACAGTCAGCCTTACCAGTAAAAAAG<br>AAAACCTATTAAAAAACACCACTCGACACGGCACCAGCTCAATCAGTCACA<br>GTGTAAAAAGGGCCAAGTGCAGAGCGAGTATATATAGGACTAAAAAATGA<br>CGTAACGGTTAAAGTCCACAAAAAACACCCAGAAAACCGCACGCGAACCTA<br>CGCCCAGAAACGAAAGCCAAAAAAACCCACAACTTCCTCAAATCGTCACTTCC<br>GTTTTCCCACGTTACGTCACTTCCCATTTTAAGAAAACTACAATTCCCAACAC<br>ATACAAGTTACTCCGCCCTAAAACCTACGTCACCCGCCCCGTTCCCACGCCCC<br>GCGCCACGTCACAAACTCCACCCCCTCATTATCATATTGGCTTCAATCCAAAA<br>TAAGGTATATTATTGATGAT |
| SEQ ID NO: 4 | TAGTAATCAATTACGGGTCATTAGTTCATAGCCCATATATGGAGTTCCGCGT<br>TACATAACTTACGGTAAATGGCCCGCCTGGCTGACCGCCCAACGACCCCCGC<br>CCATTGACGTCAATAATGACGTATGTTCCCATAGTAACGCCAATAGGGACTTT<br>CCATTGACGTCAATGGGTGGAGTATTTACGGTAAACTGCCCACTTGGCAGTA |

| SEQ ID NO | Sequence |
|---|---|
| | CATCAAGTGTATCATATGCCAAGTACGCCCCCTATTGACGTCAATGACGGTA<br>AATGGCCCGCCTGGCATTATGCCCAGTACATGACCTTATGGGACTTTCCTACT<br>TGGCAGTACATCTACGTATTAGTCATCGCTATTACCATGGTGATGCGGTTTTG<br>GCAGTACATCAATGGGCGTGGATAGCGGTTTGACTCACGGGGATTTCCAAGT<br>CTCCACCCCATTGACGTCAATGGGAGTTTGTTTTGGCACCAAAATCAACGGG<br>ACTTTCCAAAATGTCGTAACAACTCCGCCCCATTGACGCAAATGGGCGGTAG<br>GCGTGTACGGTGGGAGGTCTATATAAGCAGAGCTGGTTTAGTGAACCGTCAG |
| SEQ ID NO: 5 | ATCTAGATAACTGATCATAATCAGCCATACCACATTTGTAGAGGTTTTACTTG<br>CTTTAAAAAACCTCCCACACCTCCCCCTGAACCTGAAACATAAAATGAATGC<br>AATTGTTGTTGTTAACTTGTTTATTGCAGCTTATAATGGTTACAAATAAAGCA<br>ATAGCATCACAAATTTCACAAATAAAGCATTTTTTTCACTGCATTCTAGTTGT<br>GGTTTGTCCAAACTCATCAATGTATCTTA |
| SEQ ID NO: 6 | atgagggcgaacgacgctctgcaggtgctgggcttgcttttcagcctggcccgggggctccgaggt<br>gggcaactctcaggcagtgtgtcctgggactctgaatggcctgagtgtgtgaccggcgatgctgaga<br>accaataccagacactgtacaagctctacgagaggtgtgaggtggtgatgggaaccttgagatt<br>gtgctcacgggacacaatgccgacctctccttcctgcagtggattcgagaagtgacaggctatgt<br>cctcgtggccatgaatgaattctctactctaccattgcccaacctccgcgtggtgcgagggaccc<br>aggtctacgatgggaagtttgccatcttcgtcatgttgaactataacaccaactccagccacgct<br>ctgcgccagctccgcttgactcagctcaccgagattctgtcagggggtgtttatattgagaagaa<br>cgataagctttgtcacatggacacaattgactggagggacatcgtgagggaccgagatgctgaga<br>tagtggtgaaggacaatggcagaagctgtcccccctgtcatgagggtttgcaaggggcgatgctgg<br>ggtcctggatcagaagactgccagacattgaccaagaccatctgtgctcctcagtgtaatggtca<br>ctgctttgggcccaaccccaaccagtgctgccatgatgagtgtgccgggggctgctcaggccctc<br>aggacacagactgctttgcctgccggcacttcaatgacagtggagcctgtgtacctcgctgtcca<br>cagcctcttgtctacaacaagctaacttttccagctggaacccaatccccacaccaagtatcagta<br>tggaggagtttgtgtagccagctgtccccataactttgtggtggatcaaacatcctgtgtcaggg<br>cctgtCctcctgacaagatggaagtagataaaaatgggctcaagatgtgtgagccttgtggggga<br>ctatgtcccaaagcctgtgagggaacaggctctggagaccgcttccagactgtggactcgagcaa<br>cattgatggatttgtgaactgcaccaagatcctgggcaacctggactttctgatcaccggcctca<br>atggagacccctggcacaagatccctgccctggaccccagagaagctcaatgtcttccggacagta<br>cgggagatcacaggttacctgaacatccagtcctggccgccccacatgcacaacttcagtgtttt<br>ttccaatttgacaaccattggaggcagaagcctctacaaccggggcttctcattgttgatcatga<br>agaacttgaatgtcacatctctgggcttccgatccctgaaggaaattagtgctgggcgtatctat<br>ataagtgccaataggcagctctgctaccaccactctttgaactggaccaaggtgcttcggggggcc<br>tacggaagagcgactagacatcaagcataatcggccgcgcaagactgcgtggcagagggcaaag<br>tgtgtgacccactgtgctcctctggggggatgctggggcccaggccctggtcagtgcttgtcctgt<br>cgaaattatagccgaggaggtgtctgtgtgacccactgcaactttctgaatggggagcctcgaga<br>atttgcccatgaggccgaatgatctcctgccacccggaatgccaacccatggagggcactgccac<br>atgcaatggctcgggctctgatacttgtgctcaatgtgccattttcgagatgggcccactgtg<br>tgagcagctgccccatggagtcctaggtgccaagggcccaatctacaagtacccagatgttcag<br>aatgaatgtcggccctgccatgagaactgcacccagggggtgtaaaggaccagagcttcaagactg<br>tttaggacaaacactggtgctgatcggcaaaacccatctgacaatggctttgacagtgatagcag<br>gattggtagtgattttcatgatgctgggcggcacttttta |
| SEQ ID NO: 7 | ATGGAGTCTCCCTCGGCCCCTCCCCACAGATGGTGCATCCCCTGGCAGAGGCT<br>CCTGCTCACAGCCTCACTTCTAACCTTCTGGAACCCGCCCACCACTGCCAAGC<br>TCACTATTGAATCCACGCGTTCAATGTCGCAGAGGGGAAGGAGGTGCTTCT<br>ACTTGTCCACAATCTGCCCCAGCATCTTTTTGGCTACAGCTGGTACAAAGGTG<br>AAAGAGTGGATGGCAACCGTCAAATTATAGGATATGTAATAGGAACTCAACA<br>AGCTACCCCAGGGCCCGCATACAGTGGTCGAGAGATAATATACCCCAATGCA<br>TCCCTGCTGATCCAGAACATCATCCAGAATGCACAGGATTCTACACCCTAC<br>ACGTCATAAAGTCAGATCTTGTGAATGAAGAAGCAACTGGCCAGTTCCGGGT<br>ATACCCGGAGCTGCCCAAGCCCTCCATCTCCAGCAACAACTCCAAACCCGTG<br>GAGGACAAGGATGCTGTGGCCTTCACCTGTGAACCTGAGACTCAGGACGCAA<br>CCTACCTGTGGTGGGTAAACAATCAGAGCCTCCCGGTCAGTCCCAGGCTGCA<br>GCTGTCCAATGGCAACAGGACCCTCACTCTATTCAATGTCACAAGAAATGAC<br>ACAGCAAGCTACAAATGTGAAACCCAGAACCCAGTGAGTGCCAGGCGCAGT<br>GATTCAGTCATCCTGAATGTCCTCTATGGCCCGGATGCCCCACCATTTCCCC<br>TCTAAACACATCTTACAGATCAGGGGAAAATCTGAACCTCTCCTGCCACGCA<br>GCCTCTAACCCACCTGCACAGTACTCTTGGTTTGTCAATGGGACTTTCCAGCA<br>ATCCACCCAAGAGCTCTTTATCCCCAACATCACTGTGAATAATAGTGGATCCT<br>ATACGTGCCAAGCCCATAACTCAGACACTGGCCTCAATAGGACCACAGTCAC<br>GACGATCACAGTCTATGCAGAGCCACCCAAACCCTTCATCACCAGCAACAAC<br>TCCAACCCCGTGGAGGATGAGGATGCTGTAGCCTTAACCTGTGAACCTGAGA<br>TTCAGAACACAACCTACCTGTGGTGGGTAAATAATCAGAGCCTCCCGGTCAG<br>TCCCAGGCTGCAGCTGTCCAATGACAACAGGACCCTCACTCTACTCAGTGTCA<br>CAAGGAATGATGTAGGACCCTATGAGTGTGGAATCCAGAACGAATTAAGTGT<br>TGACCACAGCGACCCAGTCATCCTGAATGTCCTCTATGGCCCAGACGACCCC<br>ACCATTTCCCCCTCATACACCTATTACCGTCCAGGGGTGAACCTCAGCCTCTC<br>CTGCCATGAGCCTCTAACCCACCTGCACAGTATTCTTGGCTGATTGATGGGA<br>ACATCCAGCAACACACACAAGAGCTCTTTATCTCCAACATCACTGAGAAGAA |

| SEQ ID NO | Sequence |
|---|---|
| | CAGCGGACTCTATACCTGCCAGGCCAATAACTCAGCCAGTGGCCACAGCAGG<br>ACTACAGTCAAGACAATCACAGTCTCTGCGGAGCTGCCCAAGCCCTCCATCT<br>CCAGCAACAACTCCAAACCCGTGGAGGACAAGGATGCTGTGGCCTTCACCTG<br>TGAACCTGAGGCTCAGAACACAACCTACCTGTGGTGGGTAAATGGTCAGAGC<br>CTCCCAGTCAGTCCCAGGCTGCAGCTGTCCAATGGCAACAGGACCCTCACTCT<br>ATTCAATGTCACAAGAAATGACGCAAGAGCCTATGTATGTGGAATCCAGAAC<br>TCAGTGAGTGCAAACCGCAGTGACCCAGTCACCCTGGATGTCCTCTATGGGC<br>CGGACACCCCCATCATTTCCCCCCAGACTCGTCTTACCTTTCGGGAGCGGAC<br>CTCAACCTCTCCTGCCACTCGGCCTCTAACCCATCCCCGCAGTATTCTTGGCG<br>TATCAATGGGATACCGCAGCAACACACACAAGTTCTCTTTATCGCCAAAATC<br>ACGCCAAATAATAACGGGACCTATGCCTGTTTTGTCTCTAACTTGGCTACTGG<br>CCGCAATAATTCCATAGTCAAGAGCATCACAGTCTCTGCATCTGGAACTTCTC<br>CTGGTCTCTCAGCTGGGGCCACTGTCGGCATCATGATTGGAGTGCTGGTTGGG<br>GTTGCTCTGATATAG |
| SEQ ID NO: 8 | YLSGANLNL |
| SEQ ID NO: 9 | YLSGADLNL |
| SEQ ID NO: 10 | CATCATCAATAATATACCTTATTTTGGATTGAAGCCAATATGATAATGAGGGG<br>GTGGAGTTTGTGACGTGGCGCGGGGCGTGGGAACGGGGCGGGTGACGTAGT<br>AGTGTGGCGGAAGTGTGATGTTGCAAGTGTGGCGGAACACATGTAAGCGACG<br>GATGTGGCAAAAGTGACGTTTTTGGTGTGCGCCGGTGTACACAGGAAGTGAC<br>AATTTTCGCGCGGTTTTAGGCGGATGTTGTAGTAAATTTGGGCGTAACCGAGT<br>AAGATTTGGCCATTTTCGCGGGAAAACTGAATAAGAGGAAGTGAAATCTGAA<br>TAATTTTGTGTTACTCATAGCGCGTAATACTGTAATAGTAATCAATTACGGGG<br>TCATTAGTTCATAGCCCATATATGGAGTTCCGCGTTACATAACTTACGGTAAA<br>TGGCCCGCCTGGCTGACCGCCCAACGACCCCCGCCCATTGACGTCAATAATG<br>ACGTATGTTCCCATAGTAACGCCAATAGGGACTTTCCATTGACGTCAATGGGT<br>GGAGTATTTACGGTAAACTGCCCACTTGGCAGTACATCAAGTGTATTCATATGC<br>CAAGTACGCCCCCTATTGACGTCAATGACGGTAAATGGCCCGCCTGGCATTA<br>TGCCCAGTACATGACCTTATGGGACTTTCCTACTTGGCAGTACATCTACGTAT<br>TAGTCATCGCTATTACCATGGTGATGCGGTTTTGGCAGTACATCAATGGGCGT<br>GGATAGCGGTTTGACTCACGGGGATTTCCAAGTCTCCACCCCATTGACGTCAA<br>TGGGAGTTTGTTTTGGCACCAAAATCAACGGGACTTTCCAAAATGTCGTAAC<br>AACTCCGCCCCATTGACGCAAATGGGCGGTAGGCGTGTACGGTGGGAGGTCT<br>ATATAAGCAGAGCTGGTTTAGTGAACCGTCAGATCCGCTAGAGATCTGGTAC<br>CGTCGACGCGGCCGCTCGAGCCTAAGCTTGGTACCGAGCTCGGATCCACTAG<br>TAACGGCCGCCAGTGTGCTGGAATTCGGCTTAAAGGTACCCAGAGCAGACAG<br>CCGCCACCATGGAGTCTCCCTCGGCCCCTCCCCACAGATGGTGCATCCCCTGG<br>CAGAGGCTCCTGCTCACAGCCTCACTTCTAACCTTCTGGAACCCGCCCACCAC<br>TGCCAAGCTCACTATTGAATCCACGCCGTTCAATGTCGCAGAGGGGAAGGAG<br>GTGCTTCTACTTGTCCACAATCTGCCCCAGCATCTTTTTGGCTACAGCTGGTA<br>CAAAGGTGAAAGAGTGGATGGCAACCGTCAAATTATAGGATATGTAATAGG<br>AACTCAACAAGCTACCCCAGGGCCCGCATACAGTGGTCGAGAGATAATATAC<br>CCCAATGCATCCCTGCTGATCCAGAACATCATCCAGAATGACACAGGATTCT<br>ACACCCTACACGTCATAAAGTCAGATCTTGTGAATGAAGAAGCAACTGGCCA<br>GTTCGGGTATACCCGGAGCTGCCCAAGCCCTCCATCTCCAGCAACAACTCC<br>AAACCCGTGGAGGACAAGGATGCTGTGGCCTTCACCTGTGAACCTGAGACTC<br>AGGACGCAACCTACCTGTGGTGGGTAAACAATCAGAGCCTCCCGGTCAGTCC<br>CAGGCTGCAGCTGTCCAATGGCAACAGGACCCTCACTCTATTCAATGTCACA<br>AGAAATGACACAGCAAGCTACAAATGTGAAACCCAGAACCCAGTGAGTGCC<br>AGGCGCAGTGATTCAGTCATCCTGAATGTCCTCTATGCCCGGATGCCCCCAC<br>CATTTCCCCTCTAAACACATCTTACAGATCAGGGGAAAATCTGAACCTCTCCT<br>GCCACGCAGCCTCTAACCCACCTGCACAGTACTCTTGGTTTGTCAATGGGACT<br>TTCCAGCAATCCACCCAAGAGCTCTTTATCCCCAACATCACTGTGAATAATAG<br>TGGATCCTATACGTGCCAAGCCCATAACTCAGACACTGGCCTCAATAGGACC<br>ACAGTCACGACGATCACAGTCTATGCAGAGCCACCCAAACCCTTCATCACCA<br>GCAACAACTCCAACCCCGTGGAGGATGAGGATGCTGTAGCCTTAACCTGTGA<br>ACCTGAGATTCAGAACACAACCTACCTGTGGTGGGTAAATAATCAGAGCCTC<br>CCGGTCAGTCCCAGGCTGCAGCTGTCCAATGACAACAGGACCCTCACTCTAC<br>TCAGTGTCACAAGGAATGATGTAGGACCCTATGAGTGTGGAATCCAGAACGA<br>ATTAAGTGTTGACCACAGCGACCCAGTCATCCTGAATGTCCTCTATGCCCAG<br>ACGACCCCACCATTTCCCCCTCATACACCTATTACCGTCCAGGGGTGAACCTC<br>AGCCTCTCCTGCCATGCAGCCTCTAACCCACCTGCACAGTATTCTTGGCTGAT<br>TGATGGGAACATCCAGCAACACACACAAGAGCTCTTTATCTCCAACATCACT<br>GAGAAGAACAGCGGACTCTATACCTGCCAGGCCAATAACTCAGCCAGTGGCC<br>ACAGCAGGACTACAGTCAAGACAATCACAGTCTCTGCGGAGCTGCCCAAGCC<br>CTCCATCTCCAGCAACAACTCCAAACCCGTGGAGGACAAGGATGCTGTGGCC<br>TTCACCTGTGAACCTGAGGCTCAGAACACAACCTACCTGTGGTGGGTAAATG<br>GTCAGAGCCTCCCAGTCAGTCCCAGGCTGCAGCTGTCCAATGGCAACAGGAC |

| SEQ ID NO | Sequence |
|---|---|
| | CCTCACTCTATTCAATGTCACAAGAAATGACGCAAGAGCCTATGTATGTGGA<br>ATCCAGAACTCAGTGAGTGCAAACCGCAGTGACCCAGTCACCCTGGATGTCC<br>TCTATGGGCCGGACACCCCCATCATTTCCCCCCCAGACTCGTCTTACCTTTCG<br>GGAGCGGACCTCAACCTCTCCTGCCACTCGGCCTCTAACCCATCCCCGCAGTA<br>TTCTTGGCGTATCAATGGGATACCGCAGCAACACACACAAGTTCTCTTTATCG<br>CCAAAATCACGCCAAATAATAACGGGACCTATGCCTGTTTTGTCTCTAACTTG<br>GCTACTGGCCGCAATAATTCCATAGTCAAGAGCATCACAGTCTCTGCATCTGG<br>AACTTCTCCTGGTCTCTCAGCTGGGGCCACTGTCGGCATCATGATTGGAGTGC<br>TGGTTGGGGTTGCTCTGATATAGCAGCCCTGGTGTAGTTTCTTCATTTCAGGA<br>AGACTGACAGTTGTTTTGCTTCTTCCTTAAAGCATTTGCAACAGCTACAGTCT<br>AAAATTGCTTCTTTACCAAGGATATTTACAGAAAAGACTCTGACCAGAGATC<br>GAGACCATCCTCTAGATAAGATATCCGATCCACCGGATCTAGATAACTGATC<br>ATAATCAGCCATACCACATTTGTAGAGGTTTTACTTGCTTTAAAAAACCTCCC<br>ACACCTCCCCCTGAACCTGAAACATAAAATGAATGCAATTGTTGTTGTTAACT<br>TGTTTATTGCAGCTTATAATGGTTACAAATAAAGCAATAGCATCACAAATTTC<br>ACAAATAAAGCATTTTTTTCACTGCATTCTAGTTGTGGTTTGTCCAAACTCAT<br>CAATGTATCTTAACGCGGATCTGGGCGTGGTTAAGGGTGGGAAAGAATATAT<br>AAGGTGGGGTCTTATGTAGTTTTGTATCTGTTTTGCAGCAGCCGCCGCCGCC<br>ATGAGCACCAACTCGTTTGATGGAAGCATTGTGAGCTCATATTTGACAACGC<br>GCATGCCCCATGGGCCGGGTGCGTCAGAATGTGATGGGCTCCAGCATTGA<br>TGGTCGCCCCGTCCTGCCCGCAAACTCTACTACCTTGACCTACGAGACCGTGT<br>CTGGAACGCCGTTGGAGACTGCAGCCTCCGCCGCCGCTTCAGCCGCTGCAGC<br>CACCGCCCGCGGGATTGTGACTGACTTTGCTTTCCTGAGCCCGCTTGCAAGCA<br>GTGCAGCTTCCCGTTCATCCGCCCGCGATGACAAGTTGACGGCTCTTTTGGCA<br>CAATTGGATTCTTTGACCCGGGAACTTAATGTCGTTTCTCAGCAGCTGTTGGA<br>TCTGCGCCAGCAGGTTTCTGCCCTGAAGGCTTCCTCCCCTCCCAATGCGGTTT<br>AAAACATAAATAAAAAACCAGACTCTGTTTGGATTTGGATCAAGCAAGTGTC<br>TTGCTGTCTTTATTTAGGGGTTTTGCGCGCGCGGTAGGCCCGGGACCAGCGGT<br>CTCGGTCGTTGAGGGTCCTGTGTATTTTTTCCAGGACGTGGTAAAGGTGACTC<br>TGGATGTTCAGATACATGGGCATAAGCCCGTCTCTGGGGTGGAGGTAGCACC<br>ACTGCAGAGCTTCATGCTGCGGGTGGTGTTGTAGATGATCCAGTCGTAGCA<br>GGAGCGCTGGGCGTGGTGCCTAAAAATGTCTTTCAGTAGCAAGCTGATTGCC<br>AGGGGCAGGCCCTTGGTGTAAGTGTTTACAAAGCGGTTAAGCTGGGATGGGT<br>GCATACGTGGGGATATGAGATGCATCTTGGACTGTATTTTTAGGTTGGCTATG<br>TTCCCAGCCATATCCCTCCGGGGATTCATGTTGTGCAGAACCACCAGCACAGT<br>GTATCCGGTGCACTTGGGAAATTTGTCATGTAGCTTAGAAGGAAATGCGTGG<br>AAGAACTTGGAGACGCCCTTGTGACCTCCAAGATTTTCCATGCATTCGTCCAT<br>AATGATGGCAATGGGCCCACGGGCGGCGGCCTGGGCGAAGATATTTCTGGGA<br>TCACTAACGTCATAGTTGTGTTCCAGGATGAGATCGTCATAGGCCATTTTTAC<br>AAAGCGCGGGCGGAGGGTGCCAGACTGCGGTATAATGGTTCCATCCGGCCCA<br>GGGGCGTAGTTACCCTCACAGATTTGCATTTCCCACGCTTTGAGTTCAGATGG<br>GGGGATCATGTCTACCTGCGGGGCGATGAAGAAAACGGTTTCCGGGGTAGGG<br>GAGATCAGCTGGGAAGAAAGCAGGTTCCTGAGCAGCTGCGACTTACCGCAGC<br>CGGTGGGCCCGTAAATCACACCTATTACCGGCTGCAACTGGTAGTTAAGAGA<br>GCTGCAGCTGCCGTCATCCCTGAGCAGGGGGGCCACTTCGTTAAGCATGTCC<br>CTGACTCGCATGTTTTCCCTGACCAAATCCGCCAGAAGGCGCTCGCCGCCCAG<br>CGATAGCAGTTCTTGCAAGGAAGCAAAGTTTTTCAACGGTTTGAGACCGTCC<br>GCCGTAGGCATGCTTTTGAGCGTTTGACCAAGCAGTTCCAGGCGGTCCCACA<br>GCTCGGTCACCTGCTCTACGGCATCTCGATCCAGCATATCTCCTCGTTTCGCG<br>GGTTGGGGCGGCTTTCGCTGTACGGCAGTAGTCGGTGCTCGTCCAGACGGGC<br>CAGGGTCATGTCTTTCCACGGGCGCAGGGTCCTCGTCAGCGTAGTCTGGGTCA<br>CGGTGAAGGGGTGCGCTCCGGGCTGCGCGCTGGCCAGGGTGCGCTTGAGGCT<br>GGTCCTGCTGGTGCTGAAGCGCTGCCGGTCTTCGCCCTGCGCGTCGGCCAGGT<br>AGCATTTGACCATGGTGTCATAGTCCAGCCCCTCCGCGGCGTGGCCCTTGGCG<br>CGCAGCTTGCCCTTGGAGGAGGCGCCGCACGAGGGGCAGTGCAGACTTTTGA<br>GGGCGTAGAGCTTGGGCGCGAGAAATACCGATTCCGGGGAGTAGGCATCCGC<br>GCCGCAGGCCCCGCAGACGGTCTCGCATTCCACGAGCCAGGTGAGCTCTGGC<br>CGTTCGGGGTCAAAAACCAGGTTTCCCCCATGCTTTTTGATGCGTTTCTTACC<br>TCTGGTTTCCATGAGCCGGTGTCCACGCTCGGTGACGAAAAGGCTGTCCGTGT<br>CCCCGTATACAGACTTGAGAGGCCTGTCCTCGAGCGGTGTTCCGCGGTCCTCC<br>TCGTATAGAAACTCGGACCACTCTGAGACAAAGGCTCGCGTCCAGGCCAGCA<br>CGAAGGAGGCTAAGTGGGAGGGGTAGCGGTCGTTGTCCACTAGGGGGTCCAC<br>TCGCTCCAGGGTGTGAAGACACATGTCGCCCTCTTCGGCATCAAGGAAGGTG<br>ATTGGTTTGTAGGTGTAGGCCACGTGACCGGGTGTTCCTGAAGGGGGGCTAT<br>AAAAGGGGTGGGGCGCGTTCGTCCTCACTCTCTTCCGCATCGCTGTCTGCG<br>AGGGCCAGCTGTTGGGTGAGTACTCCCTCTGAAAAGCGGGCATGACTTCTG<br>CGCTAAGATTGTCAGTTTCCAAAAACGAGGAGGATTTGATATTCACCTGCC<br>CGCGGTGATGCCTTTGAGGGTGGCCGCATCCATCTGGTCAGAAAAGACAATC<br>TTTTTGTTGTCAAGCTTGGTGGCAAACGACCCGTAGAGGGCGTTGGACAGCA<br>ACTTGGCGATGGAGCGCAGGGTTTGGTTTTTGTCGCGATCGGCGCGCTCCTTG<br>GCCGCGATGTTTAGCTGCACGTATTCGCGCGCAACGCACCGCCATTCGGGAA<br>AGACGGTGGTGCGCTCGTCGGGCACCAGGTGCACGCGCCAACCGCGGTTGTG<br>CAGGGTGACAAGGTCAACGCTGGTGGCTACCTCTCCGCGTAGGCGCTCGTTG |

| SEQ ID NO | Sequence |
|---|---|
| | GTCCAGCAGAGGCGGCCGCCCTTGCGCGAGCAGAATGGCGGTAGGGGTCTA
GCTGCGTCTCGTCCGGGGGGTCTGCGTCCACGGTAAAGACCCCGGGCAGCAG
GCGCGCGTCGAAGTAGTCTATCTTGCATCCTTGCAAGTCTAGCGCCTGCTGCC
ATGCGCGGGCGGCAAGCGCGCGCTCGTATGGGTTGAGTGGGGGACCCCATGG
CATGGGGTGGGTGAGCGCGGAGGCGTACATGCCGCAAATGTCGTAAACGTAG
AGGGGCTCTCTGAGTATTCCAAGATATGTAGGGTAGCATCTTCCACCGCGGA
TGCTGGCGCGCACGTAATCGTATAGTTCGTGCGAGGGAGCGAGGAGGTCGGG
ACCGAGGTTGCTACGGGCGGGCTGCTCTGCTCGGAAGACTATCTGCCTGAAG
ATGGCATGTGAGTTGGATGATATGGTTGGACGCTGGAAGACGTTGAAGCTGG
CGTCTGTGAGACCTACCGCGTCACGCACGAAGGAGGCGTAGGAGTCGCGCAG
CTTGTTGACCAGCTCGGCGGTGACCTGCACGTCTAGGGCGCAGTAGTCCAGG
GTTTCCTTGATGATGTCATACTTATCCTGTCCCTTTTTTTTCCACAGCTCGCGG
TTGAGGACAAACTCTTCGCGGTCTTTCCAGTACTCTTGGATCGGAAACCCGTC
GGCCTCCGAACGGTAAGAGCCTAGCATGTAGAACTGGTTGACGGCCTGGTAG
GCGCAGCATCCCTTTTCTACGGGTAGCGCGTATGCCTGCGCGGCCTTCCGGCA
TGACCAGCATGAAGGGCACGAGCTGCTTCCCAAAGGCCCCCATCCAAGTATA
GGTCTCTACATCGTAGGTGACAAAGAGACGCTCGGTGCGAGGATGCGAGCCG
ATCGGGAAGAACTGGATCTCCCGCCACCAATTGGAGGAGTGGCTATTGATGT
GGTGAAAGTAGAAGTCCCTGCGACGGGCCGAACACTCGTGCTGGCTTTTGTA
AAAACGTGCGCAGTACTGGCAGCGGTGCACGGGCTGTACATCCTGCACGAGG
TTGACCTGACGACCGCGCACAAGGAAGCAGAGTGGGAATTTGAGCCCCTCGC
CTGGCGGGTTTGGCTGGTGGTCTTCTACTTCGGCTGCTTGTCCTTGACCGTCTG
GCTGCTCGAGGGGAGTTACGGTGGATCGGACCACCACGCCGCGCGAGCCCAA
AGTCCAGATGTCCGCGCGCGGCGGTCGGAGCTTGATGACAACATCGCGCAGA
TGGGAGCTGTCCATGGTCTGGAGCTCCCGCGGCGTCAGGTCAGGCGGGAGCT
CCTGCAGGTTTACCTCGCATAGACGGGTCAGGGCGCGGGCTAGATCCAGGTG
ATACCTAATTTCCAGGGGCTGGTTGGTGGCGGCGTCGATGGCTTGCAAGAGG
CCGCATCCCCGCGGCGCGACTACGGTACCGCGCGGCGGGCGGTGGGCCGCGG
GGGTGTCCTTGGATGATGCATCTAAAAGCGGTGACGCGGGCGAGCCCCCGGA
GGTAGGGGGGCTCCGGACCCGCCGGGAGAGGGGGCAGGGGCACGTCGGCG
CCGCGCGCGGGCAGGAGCTGGTGCTGCGCGCGTAGGTTGCTGGCAACGCGA
CGACGCGGCGGTTGATCTCCTGAATCTGGCGCCTCTGCGTGAAGACGACGGG
CCCGGTGAGCTTGAACCTGAAAGAGAGTTCGACAGAATCAATTTCGGTGTCG
TTGACGGCGGCCTGGCGCAAAATCTCCTGCACGTCTCCTGAGTTGTCTTGATA
GGCGATCTCGGCCATGAACTGCTCGATCTCTTCCTCCTGGAGATCTCCGCGTC
CGGCTCGCTCCACGGTGGCGGCGAGGTCGTTGGAAATGCGGGCCATGAGCTG
CGAGAAGGCGTTGAGGCCTCCCTCGTTCCAGACGCGGCTGTAGACCACGCCC
CCTTCGGCATCGCGGGCGCGCATGACCACCTGCGCGAGATTGAGCTCCACGT
GCCGGGCGAAGACGGCGTAGTTTCGCAGGCGCTGAAAGAGGTAGTTGAGGG
TGGTGGCGGTGTGTTCTGCCACGAAGAAGTACATAACCCAGCGTCGCAACGT
GGATTCGTTGATAATTGTTGTGTAGGTACTCCGCCGCCGAGGGACCTGAGCG
AGTCCGCATCGACCGGATCGGAAAACCTCTCGAGAAAGGCGTCTAACCAGTC
ACAGTCGCAAGGTAGGCTGAGCACCGTGGCGGGCGGCAGCGGGCGGCGGTC
GGGGTTGTTTCTGGCGGAGGTGCTGCTGATGATGTAATTAAAGTAGGCGGTC
TTGAGACGGCGGATGGTCGACAGAAGCACCATGTCCTTGGGTCCGGCCTGCT
GAATGCGCAGGCGGTCGGCCATGCCCCAGGCTTCGTTTTGACATCGGCGCAG
GTCTTTGTAGTAGTCTTGCATGAGCCTTTCTACCGGCACTTCTTCTTCTCCTTC
CTCTTGTCCTGCATCTCTTGCATCTATCGCTGCGGCGGCGGCGGAGTTTGGCC
GTAGGTGGCGCCCTCTTCCTCCCATGCGTGTGACCCCGAAGCCCCTCATCGGC
TGAAGCAGGGCTAGGTCGGCGACAACGCGCTCGGCTAATATGGCCTGCTGCA
CCTGCGTGAGGGTAGACTGGAAGTCATCCATGTCCACAAAGCGGTGGTATGC
GCCCGTGTTGATGGTGTAAGTGCAGTTGGCCATAACGGACCAGTTAACGGTC
TGGTGACCCGGCTGCGAGAGCTCGGTGTACCTGAGACGCGAGTAAGCCCTCG
AGTCAAATACGTAGTCGTTGCAAGTCCGCACCAGGTACTGGTATCCCACCAA
AAAGTGCGGCGGCGGCTGGCGGTAGAGGGGCAGCGTAGGGTGGCCGGGGC
TCCGGGGGCGAGATCTTCCAACATAAGGCGATGATATCCGTAGATGTACCTG
GACATCCAGGTGATGCCGGCGGCGGTGGTGGAGGCGCGCGGAAAGTCGCGG
ACGCGGTTCCAGATGTTGCGCAGCGGCAAAAAGTGCTCCATGGTCGGGACGC
TCTGGCCGGTCAGGCGCGCAATCGTTGACGCTCTAGCGTGCAAAAGGAGA
GCCTGTAAGCGGGCACTCTTCCGTGGTCTGGTGGATAAATTCGCAAGGGTAT
CATGGCGGACGACCGGGGTTCGAGCCCCGTATCCGGCCGTCCGCCGTGATCC
ATGCGGTTACCGCCCGCGTGTCGAACCCAGGTGTGCGACGTCAGACAACGGG
GGAGTGCTCCTTTTGGCTTCCTTCCAGGCGCGGCGGCTGCTGCGCTAGCTTTT
TTGGCCACTGGCCGCGCGCAGCGTAAGCGGTTAGGCTGGAAAGCGAAAGCAT
TAAGTGGCTCGCTCCCTGTAGCCGGAGGGTTATTTTCCAAGGGTTGAGTCGCG
GGACCCCCGGTTCGAGTCTCGGACCGGCCGGACTGCGGCGAACGGGGGTTTG
CCTCCCCGTCATGCAAGACCCCGCTTGCAAATTCCTCGGAAACAGGGACGA
GCCCCTTTTTTGCTTTTCCCAGATGCATCCGGTGCTGCGGCAGATGCGCCCCC
CTCCTCAGCAGCGGCAAGAGCAAGAGCAGCGGCAGACATGCAGGGCACCCT
CCCCTCCTCCTACCGCGTCAGGAGGGCGACATCCGCGGTTGACGCGGCAGC
AGATGGTGATTACGAACCCCCGCGGCGCCGGGCCCGGCACTACCTGGACTTG
GAGGAGGGCGAGGGCCTGGCGCGGCTAGGAGCGCCCTCTCCTGAGCGGCAC
CCAAGGGTGCAGCTGAAGCGTGATACGCGTGAGGCGTACGTGCCGCGGCAG |

| SEQ ID NO | Sequence |
|---|---|
| | AACCTGTTTCGCGACCGCGAGGGAGAGGAGCCCGAGGAGATGCGGGATCGA<br>AAGTTCCACGCAGGGCGCGAGCTGCGGCATGGCCTGAATCGCGAGCGGTTGC<br>TGCGCGAGGAGGACTTTGAGCCCGACGCGCGAACCGGGATTAGTCCCGCGCG<br>CGCACACGTGGCGGCCGCCGACCTGGTAACCGCATACGAGCAGACGGTGAAC<br>CAGGAGATTAACTTTCAAAAAAGCTTTAACAACCACGTGCGTACGCTTGTGG<br>CGCGCGAGGAGGTGGCTATAGGACTGATGCATCTGTGGGACTTTGTAAGCGC<br>GCTGGAGCAAAACCCAAATAGCAAGCCGCTCATGGCGCAGCTGTTCCTTATA<br>GTGCAGCACAGCAGGGACAACGAGGCATTCAGGGATGCGCTGCTAAACATA<br>GTAGAGCCCGAGGGCCGCTGGCTGCTCGATTTGATAAACATCCTGCAGAGCA<br>TAGTGGTGCAGGAGCGCAGCTTGAGCCTGGCTGACAAGGTGGCCGCCATCAA<br>CTATTCCATGCTTAGCCTGGGCAAGTTTTACGCCCGCAAGATATACCATACCC<br>CTTACGTTCCCATAGACAAGGAGGTAAAGATCGAGGGGTTCTACATGCGCAT<br>GGCGCTGAAGGTGCTTACCTTGAGCGACGACCTGGGCGTTTATCGCAACGAG<br>CGCATCCACAAGGCCGTGAGCGTGAGCCGGCGGCGCGAGCTCAGCGACCGC<br>GAGCTGATGCACAGCCTGCAAAGGGCCCTGGCTGGCACGGGCAGCGGCGAT<br>AGAGAGGCCGAGTCCTACTTTGACGCGGGCGCTGACCTGCGCTGGGCCCCAA<br>GCCGACGCGCCCTGGAGGCAGCTGGGGCCGGACCTGGGCTGGCGGTGGCACC<br>CGCGCGCGCTGGCAACGTCGGCGGCGTGGAGGAATATGACGAGGACGATGA<br>GTACGAGCCAGAGGACGGCGAGTACTAAGCGGTGATGTTTCTGATCAGATGA<br>TGCAAGACGCAACGGACCCGGCGGTGCGGGCGGCGCTGCAGAGCCAGCCGT<br>CCGGCCTTAACTCCACGGACGACTGGCGCCAGGTCATGGACCGCATCATGTC<br>GCTGACTGCGCGCAATCCTGACGCGTTCCGGCAGCAGCCGCAGGCCAACCGG<br>CTCTCCGCAATTCTGGAAGCGGTGGTCCCGGCGCGCGCAAACCCCACGCACG<br>AGAAGGTGCTGGCGATCGTAAACGCGCTGGCCGAAAACAGGGCCATCCGGC<br>CCGACGAGGCCGGCCTGGTCTACGACGCGCTGCTTCAGCGCGTGGCTCGTTA<br>CAACAGCGGCAACGTGCAGACCAACCTGGACCGGCTGGTGGGGATGTGCG<br>CGAGGCCGTGGCGCAGCGTGAGCGCGCGCAGCAGCAGGGCAACCTGGGCTC<br>CATGGTTGCACTAAACGCCTTCCTGAGTACACAGCCCGCCAACGTGCCGCGG<br>GGACAGGAGGACTACACCAACTTTGTGAGCGCACTGCGGCTAATGGTGACTG<br>AGACACCGCAAAGTGAGGTGTACCAGTCTGGGCCAGACTATTTTTTCCAGAC<br>CAGTAGACAAGGCCTGCAGACCGTAAACCTGAGCCAGGCTTTCAAAAACTTG<br>CAGGGGCTGTGGGGGGTGCGGGCTCCCACAGGCGACCGCGGCGACCGTGTCTA<br>GCTTGCTGACGCCCAACTCGCGCCTGTTGCTGCTGCTAATAGCGCCCTTCACG<br>GACAGTGGCAGCGTGTCCCGGGACACATACCTAGGTCACTTGCTGACACTGT<br>ACCGCGAGGCCATAGGTCAGGCGCATGTGGACGAGCATACTTTCCAGGAGAT<br>TACAAGTGTCAGCCGCGCGCTGGGGCAGGAGGACACGGGCAGCCTGGAGGC<br>AACCCTAAACTACCTGCTGACCAACCGGCGGCAGAAGATCCCCTCGTTGCAC<br>AGTTTAAACAGCGAGGAGGAGCGCATTTTGCGCTACGTGCAGCAGAGCGTGA<br>GCCTTAACCTGATGCGCGACGGGGTAACGCCCAGCGTGGCGCTGGACATGAC<br>CGCGCGCAACATGGAACCGGGCATGTATGCCTCAAACCGGCCGTTTATCAAC<br>CGCCTAATGGACTACTTGCATCGCGCGGCCGCCGTGAACCCCGAGTATTTCAC<br>CAATGCCATCTTGAACCCGCACTGGCTACCGCCCCCTGGTTTCTACACCGGGG<br>GATTCGAGGTGCCCGAGGGTAACGATGGATTCCTCTGGGACGACATAGACGA<br>CAGCGTGTTTTCCCCGCAACCGCAGACCCTGCTAGAGTTGCAACAGCGCGAG<br>CAGGCAGAGGCGGCGCTGCGAAAGGAAAGCTTCCGCAGGCCAAGCAGCTTG<br>TCCGATCTAGGCGCTGCGGCCCCGCGGTCAGATGCTAGTAGCCCATTTCCAA<br>GCTTGATAGGGTCTCTTACCAGCACTCGCACCACCCGCCCGCGCCTGCTGGGC<br>GAGGAGGAGTACCTAAACAACTCGCTGCTGCAGCCGCAGCGCGAAAAAAAC<br>CTGCCTCCGGCATTTCCCAACAACGGGATAGAGAGCCTAGTGGACAAGATGA<br>GTAGATGGAAGACGTACGCGCAGGAGCACAGGGACGTGCCAGGCCCGCGCC<br>CGCCCACCCGTCGTCAAAGGCACGACCGTCAGCGGGGTCTGGTGTGGGAGGA<br>CGATGACTCGGCAGACGACAGCAGCGTCCTGGATTTGGGAGGGAGTGGCAAC<br>CCGTTTGCGCACCTTCGCCCCAGGCTGGGGAGAATGTTTTAAAAAAAAAAAA<br>GCATGATGCAAAATAAAAAACTCACCAAGGCCATGGCACCGAGCGTTGGTTT<br>TCTTGTATTCCCCTTAGTATGCGGCGCGCGGCGATGTATGAGGAAGGTCCTCC<br>TCCCTCCTACGAGAGTGTGGTGAGCGCGGCGCCAGTGGCGGCGGCGCTGGGT<br>TCTCCCTTCGATGCTCCCCTGGACCCGCCGTTTGTGCCTCCGCGGTACCTGCG<br>GCCTACCGGGGGGAGAAACAGCATCCGTTACTCTGAGTTGGCACCCCTATTC<br>GACACCACCCGTGTGTACCTGGTGGACAACAAGTCAACGGATGTGGCATCCC<br>TGAACTACCAGAACGACCACAGCAACTTTCTGACCACGGTCATTCAAACAA<br>TGACTACAGCCCGGGGAGGCAAGCACACAGACCATCAATCTTGACGACCGG<br>TCGCACTGGGGCGGCGACCTGAAAACCATCCTGCATACCAACATGCCAAATG<br>TGAACGAGTTCATGTTTACCAATAAGTTTAAGGCGCGGGTGATGGTGTCGCG<br>CTTGCCTACTAAGGACAATCAGGTGGAGCTGAAATACGAGTGGGTGGAGTTC<br>ACGCTGCCCGAGGGCAACTACTCCGAGACCATGACCATAGACCTTATGAACA<br>ACGCGATCGTGGAGCACTACTTGAAAGTGGGCAGACAGAACGGGGTTCTGGA<br>AAGCGACATCGGGGTAAAGTTTGACACCCGCAACTTCAGACTGGGGTTTGAC<br>CCCGTCACTGGTCTTGTCATGCCTGGGGTATATACAAACGAAGCCTTCCATCC<br>AGACATCATTTTGCTGCCAGGATGCGGGGTGGACTTCACCCACAGCCGCCTG<br>AGCAACTTGTTGGGCATCCGCAAGCGGCAACCCTTCCAGGAGGGCTTTAGGA<br>TCACCTACGATGATCTGGAGGGTGGTAACATTCCCGCACTGTTGGATGTGGA<br>CGCCTACCAGGCGAGCTTGAAAGATGACACCGAACAGGGCGGGGTGGCGC<br>AGGCGGCAGCAACAGCAGTGGCAGCGGCGCGGAAGAGAACTCCAACGCGGC |

| SEQ ID NO | Sequence |
|---|---|
| | AGCCGCGGCAATGCAGCCGGTGGAGGACATGAACGATCATGCCATTCGCGGC<br>GACACCTTTGCCACACGGGCTGAGGAGAAGCGCGCTGAGGCCGAAGCAGCG<br>GCCGAAGCTGCCGCCCCCGCTGCGCAACCCGAGGTCGAGAAGCCTCAGAAGA<br>AACCGGTGATCAAACCCCTGACAGAGGACAGCAAGAAACGCAGTTACAACC<br>TAATAAGCAATGACAGCACCTTCACCCAGTACCGCAGCTGGTACCTTGCATA<br>CAACTACGGCGACCCTCAGACCGGAATCCGCTCATGGACCCTGCTTTGCACTC<br>CTGACGTAACCTGCGGCTCGGAGCAGGTCTACTGGTCGTTGCCAGACATGAT<br>GCAAGACCCCGTGACCTTCCGCTCCACGCGCCAGATCAGCAACTTTCCGGTG<br>GTGGGCGCCGAGCTGTTGCCCGTGCACTCCAAGAGCTTCTACAACGACCAGG<br>CCGTCTACTCCCAACTCATCCGCCAGTTTACCTCTCTGACCCACGTGTTCAAT<br>CGCTTTCCCGAGAACCAGATTTTGGCGCGCCCGCCAGCCCCCACCATCACCAC<br>CGTCAGTGAAAACGTTCCTGCTCTCACAGATCACGGGACGCTACCGCTGCGC<br>AACAGCATCGGAGGAGTCCAGCGAGTGACCATTACTGACGCCAGACGCCGCA<br>CCTGCCCCTACGTTTACAAGGCCCTGGGCATAGTCTCGCCGCGCGTCCTATCG<br>AGCCGCACTTTTTGAGCAAGCATGTCCATCCTTATATCGCCCAGCAATAACAC<br>AGGCTGGGGCCTGCGCTTCCCAAGCAAGATGTTTGGCGGGGCCAAGAAGCGC<br>TCCGACCAACACCCAGTGCGCGTGCGCGGGCACTACCGCGCGCCCTGGGGCG<br>CGCACAAACGCGGCCGCACTGGGCGCACCACCGTCGATGACGCCATCGACGC<br>GGTGGTGGAGGAGGCGCGCAACTACACGCCCACGCCGCCACCAGTGTCCACA<br>GTGGACGCGGCCATTCAGACCGTGGTGCGCGGAGCCCGGCGCTATGCTAAAA<br>TGAAGAGACGGCGGAGGCGCGTAGCACGTCGCCACCGCCGCCGACCCGGCA<br>CTGCCGCCCAACGCGCGGCGGCGGCCCTGCTTAACCGCGCACGTCGCACCGG<br>CCGACGGGCGGCCATGCGGGCCGCTCGAAGGCTGGCCGCGGGTATTGTCACT<br>GTGCCCCCAGGTCCAGGCGACGAGCGGCCGCCGCAGCAGCGCGGCCATTA<br>GTGCTATGACTCAGGGTCGCAGGGGCAACGTGTATTGGGTGCGCGACTCGGT<br>TAGCGGCCTGCGCGTGCCCGTGCGCACCCGCCCCCCGCGCAACTAGATTGCA<br>AGAAAAAACTACTTAGACTCGTACTGTTGTATGTATCCAGCGGCGGCGGCGC<br>GCAACGAAGCTATGTCCAAGCGCAAAATCAAAGAAGAGATGCTCCAGGTCAT<br>CGCGCCGGAGATCTATGGCCCCCCGAAGAAGGAAGAGCAGGATTACAAGCC<br>CCGAAAGCTAAAGCGGGTCAAAAAGAAAAAGAAAGATGATGATGATGAACT<br>TGACGACGAGGTGGAACTGCTGCACGCTACCGCGCCCAGGCGACGGGTACAG<br>TGGAAAGGTCGACGCGTAAAACGTGTTTTGCGACCCGGCCACCACCGTAGTCT<br>TTACGCCCGGTGAGCGCTCCACCCGCACCTACAAGCGCGTGTATGATGAGGT<br>GTACGGCGACGAGGACCTGCTTGAGCAGGCCAACGAGCGCCTCGGGGAGTTT<br>GCCTACGGAAAGCGGCATAAGGACATGCTGGCGTTGCCGCTGGACGAGGGC<br>AACCCAACACCTAGCCTAAAGCCCGTAACACTGCAGCAGGTGCTGCCCGCGC<br>TTGCACCGTCCGAAGAAAAAGCGCGGCCTAAAGCGCGAGTCTGGTGACTTGGC<br>ACCCACCGTGCAGCTGATGGTACCCAAGCGCCAGCGACTGGAAGATGTCTTG<br>GAAAAAATGACCGTGGAACCTGGGCTGGAGCCCGAGGTCCGCGTGCGGCCA<br>ATCAAGCAGGTGGCGCCGGGACTGGGCGTGCAGACCGTGGACGTTCAGATAC<br>CCACTACCAGTGCACCAGTATTGCCACCGCCACAGAGGGCATGGAGACACA<br>AACGTCCCCGGTTGCCTCAGCGGTGGCGGATGCCGCGGTGCAGGCGGTCGCT<br>GCGGCCGCGTCCAAGACCTCTACGGAGGTGCAAACGGACCCGTGGATGTTTC<br>GCGTTTCAGCCCCCCGGCGCCCGCGCCGTTCGAGGAAGTACGGCGCCGCCAG<br>CGCGCTACTGCCCGAATATGCCCTACATCCTTCCATTGCGCCTACCCCCGGCT<br>ATCGTGGCTACACCTACCGCCCCAGAAGACGAGCAACTACCCGACGCCGAAC<br>CACCACTGGAACCCGCCGCCGCCGTCGCCGTCGCCAGCCCGTGCTGGCCCCG<br>ATTTCCGTGCGCAGGGTGGCTCGCGAAGGAGGCAGGACCCTGGTGCTGCCAA<br>CAGCGCGCTACCACCCCAGCATCGTTTAAAAGCCGGTCTTTGTGGTTCTTGCA<br>GATATGGCCCTCACCTGCCGCCTCCGTTTCCCGGTGCCGGGATTCCGAGGAAG<br>AATGCACCGTAGGAGGGCATGGCCGGCCACGGCCTGACGGGCGGCATGCG<br>TCGTGCGCACCACCGGCGGCGGCGCGCGTCGCACCGTCGCATGCGCGGCGGT<br>ATCCTGCCCCTCCTTATTCCACTGATCGCCGCGGCGATTGGCGCCGTGCCCGG<br>AATTGCATCCGTGGCCTTGCAGGCGCAGAGACACTGATTAAAAACAAGTTGC<br>ATGTGGAAAAATCAAATAAAAAGTCTGGACTCTCACGCTCGCTTGGTCCTG<br>TAACTATTTTGTAGAATGGAAGACATCAACTTTGCGTCTCTGGCCCCGCGACA<br>CGGCTCGCGCCCGTTCATGGGAAACTGGCAAGATATCGGCACCAGCAATATG<br>AGCGGTGGCGCCTTCAGCTGGGGCTCGCTGTGGAGCGGCATTAAAAATTTCG<br>GTTCCACCGTTAAGAACTATGGCAGCAAGGCCTGGAACAGCAGCACAGGCCA<br>GATGCTGAGGGATAAGTTGAAAGAGCAAAATTTCCAACAAAAGGTGGTAGA<br>TGGCCTGGCCTCTGGCATTAGCGGGTGGTGGACCTGGCCAACCAGGCAGTG<br>CAAAATAAGATTAACAGTAAGCTTGATCCCCGCCTCCCGTAGAGGAGCCTC<br>CACCGGCCGTGGAGACAGTGTCTCCAGAGGGGCGTGGCGAAAAGCGTCCGC<br>GCCCCGACAGGGAAGAAACTCTGGTGACGCAAATAGACGAGCCTCCCTCGTA<br>CGAGGAGGCACTAAAGCAAGGCCTGCCCACCACCCGTCCCATCGCGCCCATG<br>GCTACCGGAGTGCTGGGCCAGCACACACCCGTAACGCTGGACCTGCCTCCCC<br>CCGCCGACACCCAGCAGAAACCTGTGCTGCCAGGCCCGACCGCCGTTGTTGT<br>AACCCGTCCTAGCCGCGCGTCCCTGCGCCGCGCCGCCAGCGGTCCGCGATCG<br>TTGCGGCCCGTAGCCAGTGGCAACTGGCAAAGCACACTGAACAGCATCGTGG<br>GTCTGGGGGTGCAATCCCTGAAGCGCCGACGATGCTTCTGATAGCTAACGTG<br>TCGTATGTGTGTCATGTATGCGTCCATGTCGCCGCCAGAGGAGCTGCTGAGCC<br>GCCGCGCGCCCGCTTTCCAAGATGGCTACCCCTTCGATGATGCCGCAGTGGTC<br>TTACATGCACATCTCGGGCCAGGACGCCTCGGAGTACCTGAGCCCCGGGCTG |

| SEQUENCES | |
|---|---|
| SEQ ID NO | Sequence |
| | GTGCAGTTTGCCCGCGCCACCGAGACGTACTTCAGCCTGAATAACAAGTTTA GAAACCCCACGGTGGCGCCTACGCACGACGTGACCACAGACCGGTCCCAGCG TTTGACGCTGCGGTTCATCCCTGTGGACCGTGAGGATACTGCGTACTCGTACA AGGCGCGGTTCACCCTAGCTGTGGGTGATAACCGTGTGCTGGACATGGCTTC CACGTACTTTGACATCCGCGGCGTGCTGGACAGGGGCCCTACTTTTAAGCCCT ACTCTGGCACTGCCTACAACGCCCTGGCTCCCAAGGGTGCCCCAAATCCTTGC GAATGGGATGAAGCTGCTACTGCTCTTGAAATAAACCTAGAAGAAGAGGACG ATGACAACGAAGACGAAGTAGACGAGCAAGCTGAGCAGCAAAAAACTCACG TATTTGGGCAGGCGCCTTATTCTGGTATAAATATTACAAAGGAGGGTATTCAA ATAGGTGTCGAAGGTCAAACACCTAAATATGCCGATAAACATTTCAACCTG AACCTCAAATAGGAGAATCTCAGTGGTACGAAACAGAAATTAATCATGCAGC TGGGAGAGTCCTAAAAAAGACTACCCCAATGAAACCATGTTACGGTTCATAT GCAAAACCCACAAATGAAATGGAGGGCAAGGCATTCTTGTAAAGCAACAA AATGGAAAGCTAGAAAGTCAAGTGGAAATGCAATTTTTCTCAACTACTGAGG CAGCCGCAGGCAATGGTGATAACTTGACTCCTAAAGTGGTATTGTACAGTGA AGATGTAGATATAGAAACCCCAGACACTCATATTTCTTACATGCCCACTATTA AGGAAGGTAACTCACGAGAACTAATGGGCCAACAATCTATGCCCAACAGGCC TAATTACATTGCTTTTAGGGACAATTTTATTGGTCTAATGTATTACAACAGCA CGGGTAATATGGGTGTTCTGGCGGGCCAAGCATCGCAGTTGAATGCTGTTGT AGATTTGCAAGACAGAAACACAGAGCTTTCATACCAGCTTTTGCTTGATTCCA TTGGTGATAGAACCAGGTACTTTTCTATGTGGAATCAGGCTGTTGACAGCTAT GATCCAGATGTTAGAATTATTGAAAATCATGGAACTGAAGATGAACTTCCAA ATTACTGCTTTCCACTGGGAGGTGTGATTAATACAGAGACTCTTACCAAGGTA AAACCTAAAACAGGTCAGGAAAATGGATGGGAAAAAGATGCTACAGAATTT TCAGATAAAAATGAAATAAGAGTTGGAAATAATTTTGCCATGGAAATCAATC TAAATGCCAACCTGTGGAGAAATTTCCTGTACTCCAACATAGCGCTGTATTTG CCCGACAAGCTAAAGTACAGTCCTTCCAACGTAAAAATTTCTGATAACCCAA ACACCTACGACTACATGAACAAGCGAGTGGTGGCTCCCGGGCTAGTGGACTG CTACATTAACCTTGGAGCACGCTGGTCCCTTGACTATATGGACAACGTCAACC CATTTAACCACCACCGCAATGCTGGCCTGCGCTACCGCTCAATGTTGCTGGGC AATGGTCGCTATGTGCCCTTCCACATCCAGGTGCCTCAGAAGTTCTTTGCCAT TAAAAAACCTCCTTCTCCTGCCGGGCTCATACACCTACGAGTGGAACTTCAGGA AGGATGTTAACATGGTTCTGCAGAGCTCCCTAGGAAATGACCTAAGGGTTGA CGGAGCCAGCATTAAGTTTGATAGCATTTGCCTTTACGCCACCTTCTTCCCCA TGGCCCACAACACCGCCTCCACGCTTGAGGCCATGCTTAGAAACGACACCAA CGACCAGTCCTTTAACGACTATCTCTCCGCCGCCAACATGCGCTACCCCTATAC CCGCCAACGCTACCAACGTGCCCATATCCATCCCCTCCCGCAACTGGGCGGCT TTCCGCGGCTGGGCCTTCACGCGCCTTAAGACTAAGGAAACCCCATCACTGG GCTCGGGCTACGACCCTTATTACACCTACTCTGGCTCTATACCCTACCTAGAT GGAACCTTTTACCTCAACCACACCTTTAAGAAGGTGGCCATTACCTTTGACTC TTCTGTCAGCTGGCCTGGCAATGACCGCCTGCTTACCCCCAACGAGTTTGAAA TTAAGCGCTCAGTTGACGGGGAGGGTTACAACGTTGCCCAGTGTAACATGAC CAAAGACTGGTTCCTGGTACAAATGCTAGCTAACTATAACATTGGCTACCAG GGCTTCTATATCCCAGAGAGCTACAAGGACCGCATGTACTCCTTCTTTAGAAA CTTCCAGCCCATGAGCCGTCAGGTGGTGGATGATACTAAATACAAGGACTAC CAACAGGTGGGCATCCTACACCAACACAACAACTCTGGATTTGTTGGCTACC TTGCCCCCACCATGCGCGAAGGACAGGCCTACCCTGCTAACTTCCCCTATCCG CTTATAGGCAAGACCGCAGTTGACAGCATTACCCAGAAAAAGTTTCTTTGCG ATCGCACCCTTTGGCGCATCCCATTCTCCAGTAACTTTATGTCCATGGGCGCA CTCACAGACCTGGGCCAAAACCTTCTCTACGCCAACTCCGCCCACGCGCTAG ACATGACTTTTGAGGTGGATCCCATGGACGAGCCCACCCTTCTTTATGTTTTG TTTGAAGTCTTTGACGTGGTCCGTGTGCACCAGCCGCACCGCGGCGTCATCGA AACCGTGTACCTGCGCACGCCCTTCTCGGCCGGCAACGCCACAACATAAAGA AGCAAGCAACATCAACAACAGCTGCCGCCATGGGCTCCAGTGAGCAGGAACT GAAAGCCATTGTCAAAGATCTTGGTTGTGGGCCATATTTTTTGGGCACCTATG ACAAGCGCTTTCCAGGCTTTGTTTCTCCACACAAGCTCGCCTGCGCCATAGTC AATACGGCCGGTCGCGAGACTGGGGGCGTACACTGGATGGCCTTTGCCTGGA ACCCGCACTCAAAAACATGCTACCTCTTTGAGCCCTTTGGCTTTTCTGACCAG CGACTCAAGCAGGTTTACCAGTTTGAGTACGAGTCACTCCTGCGCCGTAGCG CCATTGCTTCTTCCCCCGACCGCTGTATAACGCTGGAAAAGTCCACCCAAAGC GTACAGGGGCCCAACTCGGCCGCCTGTGGACTATTCTGCTGCATGTTTCTCCA CGCCTTTGCCAACTGGCCCCAAACTCCCATGGATCACAACCCACCATGAAC CTTATTACCGGGGTACCCAACTCCATGCTCAACAGTCCCCAGGTACAGCCCAC CCTGCGTCGCAACCAGGAACAGCTCTACAGCTTCCTGGAGCGCCACTCGCCC TACTTCCGCAGCCACAGTGCGCAGATTAGGAGCGCCACTTCTTTTTGTCACTT GAAAAACATGTAAAAATAATGTACTAGAGACACTTTCAATAAAGGCAAATGC TTTTATTTGTACACTCTCGGGTGATTATTTACCCCCACCCTTGCCGTCTGCGCC GTTTAAAAATCAAAGGGGTTCTGCCGCGCATCGCTATGCGCCACTGGCAGGG ACACGTTGCGATACTGGTGTTTAGTGCTCCACTTAAACTCAGGCACAACCATC CGCGGCAGCTCGGTGAAGTTTTCACTCCACAGGCTGCGCACCATCACCAACG CGTTTAGCAGGTCGGGCGCCGATATCTTGAAGTCGCAGTTGGGGCCTCCGCC CTGCGCGCGCGAGTTGCGATACACAGGGTTGCAGCACTGGAACACTATCAGC GCCGGGTGGTGCACGCTGGCCAGCACGCTCTTGTCGGAGATCAGATCCGCGT |

-continued

| SEQUENCES | |
|---|---|
| SEQ ID NO | Sequence |
| | CCAGGTCCTCCGCGTTGCTCAGGGCGAACGGAGTCAACTTTGGTAGCTGCCTT
CCCAAAAAGGGCGCGTGCCCAGGCTTTGAGTTGCACTCGCACCGTAGTGGCA
TCAAAAGGTGACCGTGCCCGGTCTGGGCGTTAGGATACAGCGCCTGCATAAA
AGCCTTGATCTGCTTAAAAGCCACCTGAGCCTTTGCGCCTTCAGAGAAGAAC
ATGCCGCAAGACTTGCCGGAAAACTGATTGGCCGGACAGGCCGCGTCGTGCA
CGCAGCACCTTGCGTCGGTGTTGGAGATCTGCACCACATTTCGGCCCCACCGG
TTCTTCACGATCTTGGCCTTGCTAGACTGCTCCTTCAGCGCGCGCTGCCCGTTT
TCGCTCGTCACATCCATTTCAATCACGTGCTCCTTATTTATCATAATGCTTCCG
TGTAGACACTTAAGCTCGCCTTCGATCTCAGCGCAGCGGTGCAGCCACAACG
CGCAGCCCGTGGGCTCGTGATGCTTGTAGGTCACCTCTGCAAACGACTGCAG
GTACGCCTGCAGGAATCGCCCCATCATCGTCACAAAGGTCTTGTTGCTGGTGA
AGGTCAGCTGCAACCCGCGGTGCTCCTCGTTCAGCCAGGTCTTGCATACGGCC
GCCAGAGCTTCCACTTGGTCAGGCAGTAGTTTGAAGTTCGCCTTTAGATCGTT
ATCCACGTGGTACTTGTCCATCAGCGCGCGCAGCCTCCATGCCCTTCTCCC
ACGCAGACACGATCGGCACACTCAGCGGGTTCATCACCGTAATTTCACTTTCC
GCTTCGCTGGGCTCTTCCTCTTCCTCTTGCGTCCGCATACCACGCGCCACTGG
GTCGTCTTCATTCAGCCGCCGCACTGTGCGCTTACCTCCTTTGCCATGCTTGAT
TAGCACCGGTGGGTTGCTGAAACCCACCATTTGTAGCGCCACATCTTCTCTTT
CTTCCTCGCTGTCCACGATTACCTCTGGTGATGGCGGGCGCTCGGGCTTGGGA
GAAGGGCGCTTCTTTTTCTTGGGCGCAATGGCCAAATCCGCCGCCGAGGT
CGATGGCCGCGGGCTGGGTGTGCGCGGCACCAGCGCGTCTTGTGATGAGTCT
TCCTCGTCCTCGGACTCGATACCTCCGCCTCATCCGCTTTTTTGGGGGCGCCCG
GGGAGGCGGCGGCGACGGGGACGGGGACGACACGTCCTCCATGGTTGGGGG
ACGTCGCGCCGCACCGCGTCCGCGCTCGGGGGTGGTTTCGCGCTGCTCCTCTT
CCCGACTGGCCATTTCCTTCTCCTATAGGCAGAAAAGATCATGGAGTCAGTC
GAGAAGAAGGACAGCCTAACCGCCCCCTCTGAGTTCGCCACCACCGCCTCCA
CCGATGCCGCCAACGCGCCTACCACCTTCCCCGTCGAGGCACCCCCGCTTGA
GGAGGAGGAAGTGATTATCGAGCAGGACCCAGGTTTTGTAAGCGAAGACGA
CGAGGACCGCTCAGTACCAACAGAGGATAAAAAGCAAGACCAGGACAACGC
AGAGGCAAACGAGGAACAAGTCGGGCGGGGGACGAAAGGCATGGCGACTA
CCTAGATGTGGGAGACGACGTGCTGTTGAAGCATCTGCAGCGCCAGTGCGCC
ATTATCTGCGACGCGTTGCAAGAGCGCAGCGATGTGCCCCTCGCCATAGCGG
ATGTCAGCCTTGCCTACGAACGCCACCTATTCTCACCGCGCGTACCCCCCAAA
CGCCAAGAAAACGGCACATGCGAGCCCAACCCGCGCCTCAACTTCTACCCCG
TATTTGCCGTGCCAGAGGTGCTTGCCACCTATCACATCTTTTTCCAAAACTGC
AAGATACCCCTATCCTGCCGTGCCAACCGCAGCCGAGCGGACAAGCAGCTGG
CCTTGCGGCAGGGCGCTGTCATACCTGATATCGCCTCGCTCAACGAAGTGCC
AAAAATCTTTGAGGGTCTTGGACGCGACGAGAAGCGCGCGGCAAACGCTCTG
CAACAGGAAAACAGCGAAAATGAAAGTCACTCTGGAGTGTTGGTGGAACTC
GAGGGTGACAACGCGCGCCTAGCCGTACTAAAACGCAGCATCGAGGTCACCC
ACTTTGCCTACCCGGCACTTAACCTACCCCCAAGGTCATGAGCACAGTCATG
AGTGAGCTGATCGTGCGCCGTGCGCAGCCCCTGGAGAGGGATGCAAATTTGC
AAGAACAAACAGAGGAGGGCCTACCCGCAGTTGGCGACGAGCAGCTAGCGC
GCTGGCTTCAAACGCGCGAGCCTGCCGACTTGGAGGAGCGACGCAAACTAAT
GATGGCCGCAGTGCTCGTTACCGTGGAGCTTGAGTGCATGCAGCGGTTCTTTG
CTGACCCGGAGATGCAGCGCAAGCTAGAGGAAACATTGCACTACACCTTTCG
ACAGGGCTACGTACGCCAGGCCTGCAAGATCTCCAACGTGGAGCTCTGCAAC
CTGGTCTCCTACCTTGGAATTTTGCACGAAAACGCCTTGGGCAAACGTGCT
TCATTCCACGCTCAAGGGCGAGGCGCGCGCGACTACGTCCGCGACTGCGTT
TACTTATTTCTATGCTACACCTGGCAGACGGCCATGGGCGTTTGGCAGCAGTG
CTTGGAGGAGTGCAACCTCAAGGAGCTGCAGAAACTGCTAAAGCAAAACTTG
AAGGACCTATGGACGGCCTTCAACGAGCGCTCCGTGGCCGCGCACCTGGCGG
ACATCATTTTCCCCGAACGCCTGCTTAAAACCCTGCAACAGGGTCTGCCAGAC
TTCACCAGTCAAAGCATGTTGCAGAACTTTAGGAACTTTATCCTAGAGCGCTC
AGGAATCTTGCCCGCCACCTGCTGTGCACTTCCTAGCGACTTTGTGCCCATTA
AGTACCGCGAATGCCCTCCGCCGCTTTGGGGCCACTGCTACCTTCTGCAGCTA
GCCAACTACCTTGCCTACCACTCTGACATAATGGAAGACGTGAGCGGTGACG
GTCTACTGGAGTGTCACTGTGCGCTGCAACCTATGCACCCCGCACCGCTCCCTG
GTTTGCAATTCGCAGCTGCTTAACGAAAGTCAAATTATCGGTACCTTTGAGCT
GCAGGGTCCCTCGCCTGACGAAAAGTCCGCGGCTCCGGGGTTGAAACTCACT
CCGGGGCTGTGGACGTCGGCTTACCTTCGCAAATTTGTACCTGAGGACTACCA
CGCCCACGAGATTAGGTTCTACGAAGACCAATCCCGCCGCCTAATGCGGAG
CTTACCGCCTGCGTCATTACCCAGGGCCACATTCTTGGCCAATTGCAAGCCAT
CAACAAAGCCCGCCAAGAGTTTCTGCTACGAAAGGGACGGGGGGTTTACTTG
GACCCCCAGTCCGGCGAGGAGCTCAACCCAATCCCCCGCCGCCGCAGCCCT
ATCAGCAGCAGCCGCGGGCCCTTGCTTCCCAGGATGGCACCCAAAAAGAAGC
TGCAGCTGCCGCCGCCACCCACGGACGAGGAGGAATACTGGACAGTCAGG
CAGAGGAGGTTTTGGACGAGGAGGAGGAGGACATGATGGAAGACTGGGAGA
GCCTAGACGAGGAAGCTTCCGAGGTCGAAGAGGTGTCAGACGAAACACCGT
CACCCTCGGTCGCATTCCCCTCGCCGGCGCCCCAGAAATCGGCAACCGGTTCC
AGCATGGCTACAACCTCCGCTCCTCAGGCGCCGCCGGCACTGCCCGTTCGCC
GACCCAACCGTAGATGGGACACCACTGGAACCAGGGCCGGTAAGTCCAAGC
AGCCGCCGCCGTTAGCCCAAGAGCAACAACAGCGCCAAGGCTACCGCTCATG |

| SEQ ID NO | Sequence |
|---|---|
| | GCGCGGGCACAAGAACGCCATAGTTGCTTGCTTGCAAGACTGTGGGGCAAC<br>ATCTCCTTCGCCCGCCGCTTTCTTCTCTACCATCACGGCGTGGCCTTCCCCCGT<br>AACATCCTGCATTACTACCGTCATCTCTACAGCCCATACTGCACCGGCGGCAG<br>CGGCAGCAACAGCAGCGGCCACACAGAAGCAAAGGCGACCGGATAGCAAGA<br>CTCTGACAAAGCCCAAGAAATCCACAGCGGCGGCAGCAGCAGGAGGAGGAG<br>CGCTGCGTCTGGCGCCCAACGAACCCGTATCGACCCGCGAGCTTAGAAACAG<br>GATTTTTCCCACTCTGTATGCTATATTTCAACAGAGCAGGGGCCAAGAACAA<br>GAGCTGAAAATAAAAAACACTGTCTCTGCGATCCCTCACCCGCAGCTGCCTGT<br>ATCACAAAAGCGAAGATCAGCTTCGGCGCACGCTGGAAGACGCGGAGGCTCT<br>CTTCAGTAAATACTGCGCGCTGACTCTTAAGGACTAGTTTCGCGCCCTTTCTC<br>AAATTTAAGCGCGAAAACTACGTCATCTCCAGCGGCCACACCCGGCGCCAGC<br>ACCTGTTGTCAGCGCCATTATGAGCAAGGAAATTCCCACGCCCTACATGTGG<br>AGTTACCAGCCACAAATGGGACTTGCGGCTGGAGCTGCCCAAGACTACTCAA<br>CCCGAATAAACTACATGAGCGCGGGACCCCACATGATATCCCGGGTCAACGG<br>AATACGCGCCCACCGAAACCGAATTCTCCTGGAACAGGCGGCTATTACCACC<br>ACACCTCGTAATAACCTTAATCCCCGTAGTTGGCCCGCTGCCCTGGTGTACCA<br>GGAAAGTCCCGCTCCCACCACTGTGGTACTTCCCAGAGACGCCCAGGCCGAA<br>GTTCAGATGACTAACTCAGGGGCGCAGCTTGCGGGCGGCTTTCGTCACAGGG<br>TGCGGTCGCCCGGGCAGGGTATAACTCACCTGACAATCAGAGGGCGAGGTAT<br>TCAGCTCAACGACGAGTCGGTGAGCTCCTCGCTTGGTCTCCGTCCGGACGGG<br>ACATTTCAGATCGGCGGCGCCGGCCGCTCTTCATTCACGCCTCGTCAGGCAAT<br>CCTAACTCTGCAGACCTCGTCCTCTGAGCCGCGCTCTGGAGGCATTGGAACTC<br>TGCAATTTATTGAGGAGTTTGTGCCATCGGTCTACTTTAACCCCTTCTCGGGA<br>CCTCCCGGCCACTATCCGGATCAATTTATTCCTAACTTTGACGCGGTAAAGGA<br>CTCGGCGGACGGCTACGACTGAATGTTAAGTGGAGAGGCAGAGCAACTGCGC<br>CTGAAACACCTGGTCCACTGTCGCCGCCACAAGTGCTTTGCCCGCGACTCCGG<br>TGAGTTTTGCTACTTTGAATTGCCCGAGGATCATATCGAGGGCCCGGCGCACG<br>GCGTCCGGCTTACCGCCCAGGGAGAGCTTGCCCGTAGCCTGATTCGGGAGTT<br>TACCCAGCGCCCCCTGCTAGTTGAGCGGGACAGGGGACCCTGTGTTCTCACT<br>GTGATTTGCAACTGTCCTAACCCTGGATTACATCAAGATCCTCTAGTTAATGT<br>CAGGTCGCCTAAGTCGATTAACTAGAGTACCCGGGGATCTTATTCCCTTTAAC<br>TAATAAAAAAAAATAATAAAGCATCACTTACTTAAAATCAGTTAGCAAATTT<br>CTGTCCAGTTTATTCAGCAGCACCTCCTTGCCCTCCTCCCAGCTCTGGTATTGC<br>AGCTTCCTCCTGGCTGCAAACTTTCTCCACAATCTAAATGGAATGTCAGTTTC<br>CTCCTGTTCCTGTCCATCCGCACCCACTATCTTCATGTTGTTGCAGATGAAGC<br>GCGCAAGACCGTCTGAAGATACCTTCAACCCCGTGTATCCATATGACACGGA<br>AACCGGTCCTCCAACTGTGCCTTTTCTTACTCCTCCCTTTGTATCCCCCAATGG<br>GTTTCAAGAGAGTCCCCCTGGGGTACTCTCTTTGCGCCTATCCGAACCTCTAG<br>TTACCTCCAATGGCATGCTTGCGCTCAAAATGGGCAACGGCCTCTCTCTGGAC<br>GAGGCCGGCAACCTTACCTCCCAAAATGTAACCACTGTGAGCCCACCTCTCA<br>AAAAAACCAAGTCAAACATAAACCTGGAAATATCTGCACCCCTCACAGTTAC<br>CTCAGAAGCCCTAACTGTGGCTGCCGCCGCACCTCTAATGGTCGCGGGCAAC<br>ACACTCACCATGCAATCACAGGCCCCGCTAACCGTGCACGACTCCAAACTTA<br>GCATTGCCACCCAAGGACCCCTCACAGTGTCAGAAGGAAAGCTAGCCCTGCA<br>AACATCAGGCCCCCTCACCACCACCGATAGCAGTACCCTTACTATCACTGCCT<br>CACCCCCTCTAACTACTGCCACTGGTAGCTTGGGCATTGACTTGAAAGAGCCC<br>ATTTATACACAAAATGGAAAACTAGGACTAAAGTACGGGGCTCCTTTGCATG<br>TAACAGACGACCTAAACACTTTGACCGTAGCAACTGGTCCAGGTGTGACTAT<br>TAATAATACTTCCTTGCAAACTAAAGTTACTGGAGCCTTGGGTTTTGATTCAC<br>AAGGCAATATGCAACTTAATGTAGCAGGAGGACTAAGGATTGATTCTCAAAA<br>CAGACGCCTTATACTTGATGTTAGTTATCCGTTTGATGCTCAAAACCAACTAA<br>ATCTAAGACTAGGACAGGGCCCTCTTTTTATAAACTCAGCCCACAACTTGGAT<br>ATTAACTACAACAAAGGCCTTTACTTGTTTACAGCTTCAAACAATTCCAAAAA<br>GCTTGAGGTTAACCTAAGCACTGCCAAGGGGTTGATGTTTGACGCTACAGCC<br>ATAGCCATTAATGCAGGAGATGGGCTTGAATTTGGTTCACCTAATGCACCAA<br>ACACAAATCCCCTCAAAACAAAAATTGGCCATGGCCTAGAATTTGATTCAAA<br>CAAGGCTATGGTTCCTAAACTAGGAACTGGCCTTAGTTTTGACAGCACAGGT<br>GCCATTACAGTAGGAAACAAAAATAATGATAAGCTAACTTTGTGGACCACAC<br>CAGCTCCATCTCCTAACTGTAGACTAAATGCAGAGAAAGATGCTAAACTCAC<br>TTTGGTCTTAACAAAATGTGGCAGTCAAATACTTGCTACAGTTTCAGTTTTGG<br>CTGTTAAAGGCAGTTTGGCTCCAATATCTGGAACAGTTCAAAGTGCTCATCTT<br>ATTATAAGATTTGACGAAAATGGAGTGCTACTAAACAATTCCTTCCTGGACCC<br>AGAATATTGGAACTTTAGAAATGGAGATCTTACTGAAGGCACAGCCTATACA<br>AACGCTGTTGGATTTATGCCTAACCTATCAGCTTATCCAAAATCTCACGGTAA<br>AACTGCCAAAAGTAACATTGTCAGTCAAGTTTACTTAAACGGAGACAAAACT<br>AAACCTGTAACACTAACCATTACACTAAACGGTACACAGGAAACAGGAGAC<br>ACAACTCCAAGTGCATACTCTATGTCATTTTCATGGGACTGGTCTGGCCACAA<br>CTACATTAATGAAATATTTGCCACATCCTCTTACACTTTTTCATACATTGCCCA<br>AGAATAAAGAATCGTTTGTGTTATGTTTCAACGTGTTTATTTTTCAATTGCAG<br>AAAATTTCAAGTCATTTTTCATTCAGTAGTATAGCCCCACCACCACATAGCTT<br>ATACAGATCACCGTACCTTAATCAAACTCACAGAACCCTAGTATTCAACCTGC<br>CACCTCCCTCCCAACACACAGAGTACACAGTCCTTTCTCCCCGGCTGGCCTTA<br>AAAAGCATCATATCATGGGTAACAGACATATTCTTAGGTGTTATATTCCACAC |

| SEQ ID NO | Sequence |
|---|---|
| | GGTTTCCTGTCGAGCCAAACGCTCATCAGTGATATTAATAAACTCCCCGGGCA<br>GCTCACTTAAGTTCATGTCGCTGTCCAGCTGCTGAGCCACAGGCTGCTGTCCA<br>ACTTGCGGTTGCTTAACGGGCGGCGAAGGAGAAGTCCACGCCTACATGGGGG<br>TAGAGTCATAATCGTGCATCAGGATAGGGCGGTGGTGCTGCAGCAGCGCGCG<br>AATAAACTGCTGCCGCCGCCGCTCCGTCCTGCAGGAATACAACATGGCAGTG<br>GTCTCCTCAGCGATGATTCGCACCGCCCGCAGCATAAGGCGCCTTGTCCTCCG<br>GGCACAGCAGCGCACCCTGATCTCACTTAAATCAGCACAGTAACTGCAGCAC<br>AGCACCACAATATTGTTCAAAATCCCACAGTGCAAGGCGCTGTATCCAAAGC<br>TCATGGCGGGGACCACAGAACCCACGTGGCCATCATACCACAAGCGCAGGTA<br>GATTAAGTGGCGACCCCTCATAAACACGCTGGACATAAACATTACCTCTTTTG<br>GCATGTTGTAATTCACCACCTCCCGGTACCATATAAACCTCTGATTAAACATG<br>GCGCCATCCACCACCATCCTAAACCAGCTGGCCAAAACCTGCCCGCCGGCTA<br>TACACTGCAGGGAACCGGGACTGGAACAATGACAGTGGAGAGCCCAGGACT<br>CGTAACCATGGATCATCATGCTCGTCATGATATCAATGTTGGCACAACACAG<br>GCACACGTGCATACACTTCCTCAGGATTACAAGCTCCTCCCGCGTTAGAACCA<br>TATCCCAGGGAACAACCCATTCCTGAATCAGCGTAAATCCCACACTGCAGGG<br>AAGACCTCGCACGTAACTCACGTTGTGCATTGTCAAAGTGTTACATTCGGGCA<br>GCAGCGGATGATCCTCCAGTATGGTAGCGCGGGTTTCTGTCTCAAAAGGAGG<br>TAGACGATCCCTACTGTACGGAGTGCGCCGAGACAACCGAGATCGTGTTGGT<br>CGTAGTGTCATGCCAAATGGAACGCCGGACGTAGTCATATTTCCTGAAGCAA<br>AACCAGGTGCGGGCGTGACAAACAGATCTGCGTCTCCGGTCTCGCCGCTTAG<br>ATCGCTCTGTGTAGTAGTTGTAGTATATCCACTCTCTCAAAGCATCCAGGCGC<br>CCCCTGGCTTCGGGTTCTATGTAAACTCCTTCATGCGCCGCTGCCCTGATAAC<br>ATCCACCACCGCAGAATAAGCCACACCCAGCCAACCTACACATTCGTTCTGC<br>GAGTCACACACGGGAGGAGCGGGAAGAGCTGGAAGAACCATGTTTTTTTTTT<br>TATTCCAAAAGATTATCCAAAACCTCAAAATGAAGATCTATTAAGTGAACGC<br>GCTCCCCTCCGGTGGCGTGGTCAAACTCTACAGCCAAAGAACAGATAATGGC<br>ATTTGTAAGATGTTGCACAATGGCTTCCAAAAGGCAAACGGCCCTCACGTCC<br>AAGTGGACGTAAAGGCTAAACCCTTCAGGGTGAATCTCCTCTATAAACATTC<br>CAGCACCTTCAACCATGCCCAAATAATTCTCATCTCGCCACCTTCTCAATATA<br>TCTCTAAGCAAATCCCGAATATTAAGTCCGGCCATTGTAAAAATCTGCTCCAG<br>AGCGCCCTCCACCTTCAGCCTCAAGCAGCGAATCATGATTGCAAAAATTCAG<br>GTTCCTCACAGACCTGTATAAGATTCAAAAGCGGAACATTAACAAAAATACC<br>GCGATCCGTAGGTCCCTTCGCAGGGCCAGCTGAACATAATCGTGCAGGTCT<br>GCACGGACCAGCGCGGCCACTTCCCCGCCAGGAACCATGACAAAAGAACCC<br>ACACTGATTATGACACGCATACTCGGAGCTATGCTAACCAGCGTAGCCCCGA<br>TGTAAGCTTGTTGCATGGGCGGCGATATAAAATGCAAGGTGCTGCTCAAAAA<br>ATCAGGCAAAGCCTCGCGCAAAAAGAAAGCACATCGTAGTCATGCTCATGC<br>AGATAAAGGCAGGTAAGCTCCGGAACCACCACAGAAAAAGACACCATTTTTC<br>TCTCAAACATGTCTGCGGGTTTCTGCATAAACACAAATAAAATAACAAAAA<br>AACATTTAAACATTAGAAGCCTGTCTTACAACAGGAAAAACAACCCTTATAA<br>GCATAAGACGGACTACGGCCATGCCGGCGTGACCGTAAAAAAACTGGTCACC<br>GTGATTAAAAAGCACCACCGACAGCTCCTCGGTCATGTCCGGAGTCATAATG<br>TAAGACTCGGTAAACACATCAGGTTGATTCACATCGGTCAGTGCTAAAAGC<br>GACCGAAATAGCCCGGGGGAATACATACCCGCAGGCGTAGAGACAACATTA<br>CAGCCCCCATAGGAGGTATAACAAAATTAATAGGAGAGAAAACACATAAA<br>CACCTGAAAAACCCTCCTGCCTAGGCAAAATAGCACCCTCCCGCTCCAGAAC<br>AACATACAGCGCTTCCACAGCGGCAGCCATAACAGTCAGCCTTACCAGTAAA<br>AAAGAAAACCTATTAAAAAAACACCACTCGACACGGCACCAGCTCAATCAGT<br>CACAGTGTAAAAAGGGCCAAGTGCAGAGCGAGTATATATAGGACTAAAAA<br>ATGACGTAACGGTTAAAGTCCACAAAAAACACCCAGAAAACCGCACGCGAA<br>CCTACGCCCAGAAACGAAAGCCAAAAAACCCACAACTTCCTCAAATCGTCAC<br>TTCCGTTTTCCCACGTTACGTCACTTCCCATTTTAAGAAAACTACAATTCCCA<br>ACACATACAAGTTACTCCGCCCTAAAACCTACGTCACCCGCCCCGTTCCCACG<br>CCCCGCGCCACGTCACAAACTCCACCCCCTCATTATCATATTGGCTTCAATCC<br>AAAATAAGGTATATTATTGATGAT |
| SEQ ID NO: 11 | ATGACACCGGGCACCCAGTCTCCTTTCTTCCTGCTGCTGCTCCTCACAGTGCT<br>TACAGTTGTTACGGGTTCTGGTCATGCAAGCTCTACCCCAGGTGGAGAAAAG<br>GAGACTTCGGCTACCCAGAGAAGTTCAGTGCCCAGCTCTACTGAAGAATG<br>CTGTGAGTATGACCAGCAGCGTACTCTCCAGCCACAGCCCCGGTTCAGGCTC<br>CTCCACCACTCAGGGACAGGATGTCACTCTGGCCCCGGCCACGGAACCAGCT<br>TCAGGTTCAGCTGCCCTTTGGGGACAGGATGTCACCTCGGTCCCAGTCACCAG<br>GCCAGCCCTGGGCTCCACCACCCCGCCAGCCCACGATGTCACCTCAGCCCCG<br>GACAACAAGCCAGCCCCGGGCTCCACCGCCCCCCAGCCCACGGTGTCACCT<br>CGTATCTTGACACCAGGCCGGCCCCGGTTTATCTTGCCCCCCCAGCCCATGGT<br>GTCACCTCGGCCCCGGACAACAGGCCCGCCTTGGGCTCCACCGCCCCTCCAG<br>TCCACAATGTCACCTCGGCCTCAGGCTCTGCATCAGGCTCAGCTTCTACTCTG<br>GTGCACAACGGCACCTCTGCCAGGGCTACCACAACCCCAGCCAGCAAGAGCA<br>CTCCATTCTCAATTCCCAGCCACCACTCTGATACTCCTACCACCCTTGCCAGC<br>CATAGCACCAAGACTGATGCCAGTAGCACTCACCATAGACACGGTACCTCCTC<br>TCACCTCCTCCAATCACAGCACTTCTCCCCAGTTGTCTACTGGGGTCTCTTTCT<br>TTTTCCTGTCTTTTCACATTTCAAACCTCCAGTTTAATTCCTCTCTGGAAGATC |

| SEQ ID NO | Sequence |
|---|---|
| | CCAGCACCGACTACTACCAAGAGCTGCAGAGAGACATTTCTGAAATGTTTTT<br>GCAGATTTATAAACAAGGGGTTTTCTGGGCCTCTCCAATATTAAGTTCAGGC<br>CAGGATCTGTGGTGGTACAATTGACTCTGGCCTTCCGAGAAGGTACCATCAA<br>TGTCCACGACGTGGAGACACAGTTCAATCAGTATAAAACGGAAGCAGCCTCT<br>CGATATAACCTGACGATCTCAGACGTCAGCGTGAGTGATGTGCCATTTCCTTT<br>CTCTGCCCAGTCTGGGGCTGGGGTGCCAGGCTGGGGCATCGCGCTGCTGGTG<br>CTGGTCTGTGTTCTGGTTTATCTGGCCATTGTCTATCTCATTGCCTTGGCTGTC<br>GCTCAGGTTCGCCGAAAGAACTACGGGCAGCTGGACATCTTTCCAGCCCGGG<br>ATAAATACCATCCTATGAGCGAGTACGCTCTTTACCACACCCATGGGCGCTAT<br>GTGCCCCCTAGCAGTCTTTTCCGTAGCCCCTATGAGAAGGTTTCTGCAGGTAA<br>TGGTGGCAGCTATCTCTCTTACACAAACCCAGCAGTGGCAGCCGCTTCTGCCA<br>ACTTGTAG |
| SEQ ID NO: 12 | MTPGTQSPFFLLLLLTVLTVVTGSGHASSTPGGEKETSATQRSSVPSSTEKNAVS<br>MTSSVLSSHSPGSGSSTTQGQDVTLAPATEPASGSAALWGQDVTSVPVTRPALGS<br>TTPPAHDVISAPDNKPAPGSTAPPAHGVTSYLDTRPAPVYLAPPAHGVTSAPDNR<br>PALGSTAPPVHNVTSASGSASGSASTLVHNGTSARATTTPASKSTPFSIPSHHSDTP<br>TTLASHSTKTDASSTHHSTVPPLTSSNHSTSPQLSTGVSFFFLSFHISNLQFNSSLED<br>PSTDYYQELQRDISEMFLQIYKQGGFLGLSNIKFRPGSVVVQLTLAFREGTINVHD<br>VETQFNQYKTEAASRYNLTISDVSVSDVPFPFSAQSGAGVPGWGIALLVLVCVLV<br>YLAIVYLIALAVAQVRRKNYGQLDIFPARDKYRPMSEYALYHTHGRYVPPSSLF<br>RSPYEKVSAGNGGSYLSYTNPAVAAASANL |
| SEQ ID NO: 13 | ATGAGCTCCCCTGGCACCGAGAGCGCGGGAAAGAGCCTGCAGTACCGAGTG<br>GACCACCTGCTGAGCGCCGTGGAGAATGAGCTGCAGGCGGGCAGCGAGAAG<br>GGCGACCCCACAGAGCGCGAACTGCGCGTGGGCCTGGAGGAGAGCGAGCTG<br>TGGCTGCGCTTCAAGGAGCTCACCAATGAGATGATCGTGACCAAGAACGGCA<br>GGAGGATGTTTCCGGTGCTGAAGGTGAACGTGTCTGGCCTGGACCCCAACGC<br>CATGTACTCCTTCCTGCTGGACTTCGTGGCGGCGGACAACCACCGCTGGAAGT<br>ACGTGAACGGGGAATGGGTGCCGGGGGGCAAGCCGGAGCCGCAGGCGCCCA<br>GCTGCGTCTACATCCACCCCGACTCGCCCAACTTCGGGGCCCACTGGATGAA<br>GGCTCCCGTCTCCTTCAGCAAAGTCAAGCTCACCAACAAGCTCAACGGAGGG<br>GGCCAGATCATGCTGAACTCCTTGCATAAGTATGAGCCTCGAATCCACATAG<br>TGAGAGTTGGGGGTCCACAGCGCATGATCACCAGCCACTGCTTCCCTGAGAC<br>CCAGTTCATAGCGGTGACTGCTAGAAGTGATCACAAAGAGATGATGGAGGAA<br>CCCGGAGACAGCCAGCAACCTGGGTACTCCCAATGGGGGTGGCTTCTTCCTG<br>GAACCAGCACCGTGTGTCCACCTGCCAAATCCTCATCCTCAGTTTGGAGGTGCC<br>CTCTCCCTCCCCTCCACGCACAGCTGTGACAGGTACCCAACCCTGAGGAGCC<br>ACCGGTCCTCACCCTACCCCAGCCCCTATGCTCATCGGAACAATTCTCCAACC<br>TATTCTGACAACTCACCTGCATGTTTATCCATGCTGCAATCCCATGACAATTG<br>GTCCAGCCTTGGAATGCCTGCCCATCCCAGCATGCTCCCCGTGAGCCCACAATG<br>CCAGCCCACCTACCAGCTCCAGTCAGTACCCCAGCCTGTGGTCTGTGAGCAA<br>CGGCGCCGTCACCCCGGGCTCCCAGGCAGCAGCCGTGTCCAACGGGCTGGGG<br>GCCCAGTTCTTCCGGGGCTCCCCCGCGCACTACACACCCCTCACCCATCCGGT<br>CTCGGCGCCCTCTTCCTCGGGATCCCCACTGTACGAAGGGGCGGCCGCGGCC<br>ACAGACATCGTGGACAGCCAGTACGACGCCGCAGCCCAAGGCCGCCTCATAG<br>CCTCATGGACACCTGTGTCGCCACCTTCCATGTGA |
| SEQ ID NO: 85 | MSSPGTESAGKSLQYRVDHLLSAVENELQAGSEKGDPTERELRVGLEESELWLR<br>FKELTNEMIVTKNGRRMFPVLKVNVSGLDPNAMYSFLLDFVAADNHRWKYVN<br>GEWVPGGKPEPQAPSCVYIHPDSPNEGAHWMKAPVSFSKVKLTNKLNGGGQIM<br>LNSLHKYEPRIHIVRVGGPQRMITSHCFPETQFIAVTARSDHKEMMEEPGDSQQP<br>GYSQWGWLLPGTSTVCPPANPRPQFGGALSLPSTHSCDRYPTLRSHRSSPYPSPY<br>AHRNNSPPTYSDNSPACLSMLQSHDNWSSLGMPAHPSMLPVSHNASPPTSSSQYPS<br>LWSVSNGAVTPGSQAAAVSNGLGAQFFRGSPAHYTPLTHPVSAPSSSGSPLYEGA<br>AAATDIVDSQYDAAAQGRLIASWTPVSPPSM |
| SEQ ID NO: 86 | MRANDALQVLGLLFSLARGSEVGNSQAVCPGTLNGLSVTGDAENQYQTLYKLY<br>ERCEVVMGNLEIVLTGHNADLSFLQWIREVTGYVLVAMNEFSTLPLPNLRVVRG<br>TQVYDGKFAIFVMLNYNTNSSHALRQLRLTQLTEILSGGVYIEKNDKLCHMDTID<br>WRDIVRDRDAEIVVKDNGRSCPPCHEVCKGRCWGPGSEDCQTLTKTICAPQCNG<br>HCFGPNPNQCCHDECAGGCSGPQDTDCFACRHFNDSGACVPRCPQPLVYNKLTF<br>QLEPNPHTKYQYGGVCVASCPHNFVVDQTSCVRACPPDKMEVDKNGLKMCEPC<br>GGLCPKACEGTGSGSRFQTVDSSNIDGFVNCTKILGNLDFLITGLNGDPWHKIPAL<br>DPEKLNVFRTVREITGYLNIQSWPPHMHNFSVFSNLTTIGGRSLYNRGFSLLIMKN<br>LNVTSLGFRSLKEISAGRIYISANRQLCYHHSLNWTKVLRGPTEERLDIKHNRPRR<br>DCVAEGKVCDPLCSSGGCWGPGPGQCLSCRNYSRGGVCVTHCNFLNGEPREFA<br>HEAECFSCHPECQPMEGTATCNGSGSDTCAQCARFRDGPHCVSSCPHGVLGAKG<br>PIYKYPDVQNECRPCHENCTQGCKGPELQDCLGQTLVLIGKTHLTMALTVIAGL<br>VVIFMMLGGTFLYWRGRRIQNKRAMRRYLERGESIEPLDPSEKANKVLARIFKET<br>ELRKLKVLGSGVFGTVHKGVWIPEGESIKIPVCIKVIEDKSGRQSFQAVTDHMLAI<br>GSLDIIAHIVRLLGLCPGSSLQLVTQYLPLGSLLDHVRQHRGALGPQLLLNWGVQ<br>IAKGMYYLEEHGMVHRNLAARNVLLKSPSQVQVADEGVADLLPPDDKQLLYSE |

SEQUENCES

| SEQ ID NO | Sequence |
|---|---|
| | AKTPIKWMALESIHFGKYTHQSDVWSYGVTVWELMTFGAEPYAGLRLAEVPDL<br>LEKGERLAQPQICTIDVYMVMVKCWMIDENIRPTFKELANEFTRMARDPPRYLVI<br>KRESGPGIAPGPEPHGLTNKKLEEVELEPELDLDLDLEAEEDNLATTTLGSALSLP<br>VGTLNRPRGSQSLLSPSSGYMPMNQGNLGESCQESAVSGSSERCPRPVSLHPMPR<br>GCLASESSEGHVTGSEAELQEKVSMCRSRSRSRSPRPRGDSAYHSQRHSLLTPVT<br>PLSPPGLEEEDVNGYVMPDTHLKGTPSSREGTLSSVGLSSVLGTEEEDEDEEYEY<br>MNRRRRHSPPHPPRPSSLEELGYEYMDVGSDLSASLGSTQSCPLHPVPIMPTAGT<br>TPDEDYEYMNRQRDGGGPGGDYAAMGACPASEQGYEEMRAFQGPGHQAPHVH<br>YARLKTLRSLEATDSAFDNPDYWHSRLFPKANAQRT |
| SEQ ID NO: 87 | MRANDALQVLGLLFSLARGSEVGNSQAVCPGTLNGLSVTGDAENQYQTLYKLY<br>ERCEVVMGNLEIVLTGHNADLSFLQWIREVTGYVLVAMNEFSTLPLPNLRVVRG<br>TQVYDGKFAIFVMLNYNTNSSHALRQLRLTQLTEILSGGVYIEKNDKLCHMDTID<br>WRDIVRDRDAEIVVKDNGRSCPPCHEVCKGRCWGPGSEDCQTLTKTICAPQCNG<br>HCFGPNPNQCCHDECAGGCSGPQDTDCFACRHFNDSGACVPRCPQPLVYNKLTF<br>QLEPNPHTKYQYGGVCVASCPHNFVVDQTSCVRACPPDKMEVDKNGLKMCEPC<br>GGLCPKACEGTGSGSRFQTVDSSNIDGFVNCTKILGNLDFLITGLNGDPWHKIPAL<br>DPEKLNVFRTVREITGYLNIQSWPPHMHNFSVFSNLTTIGGRSLYNRGFSLLIMKN<br>LNVTSLGFRSLKEISAGRIYISANRQLCYHHSLNWTKVLRGPTEERLDIKHNRPRR<br>DCVAEGKVCDPLCSSGGCWGPGPGQCLSCRNYSRGGVCVTHCNFLNGEPREFA<br>HEAECFSCHPECQPMEGTATCNGSGSDTCAQCAHFRDGPHCVSSCPHGVLGAKG<br>PIYKYPDVQNECRPCHENCTQGCKGPELQDCLGQTLVLIGKTHLTMALTVIAGL<br>VVIFMMLGGTF |
| SEQ ID NO: 89 | CATCATCAATAATATACCTTATTTTGGATTGAAGCCAATATGATAATGAGGGG<br>GTGGAGTTTGTGACGTGGCGCGGGGCGTGGGAACGGGGCGGGTGACGTAGT<br>AGTGTGGCGGAAGTGTGATGTTGCAAGTGTGGCGGAACACATGTAAGCGACG<br>GATGTGGCAAAAGTGACGTTTTTGGTGTGCGCCGGTGTACACAGGAAGTGAC<br>AATTTTCGCGCGGTTTTAGGCGGATGTTGTAGTAAATTTGGGCGTAACCGAGT<br>AAGATTTGGCCATTTTCGCGGGAAAACTGAATAAGAGGAAGTGAAATCTGAA<br>TAATTTTGTGTTACTCATAGCGCGTAATACTGTAATAGTAATCAATTACGGGG<br>TCATTAGTTCATAGCCCATATATGGAGTTCCGCGTTACATAACTTACGGTAAA<br>TGGCCCGCCTGGCTGACCGCCAACGACCCCCGCCCATTGACGTCAATAATG<br>ACGTATGTTCCCATAGTAACGCCAATAGGGACTTTCCATTGACGTCAATGGGT<br>GGAGTATTTACGGTAAACTGCCCACTTGGCAGTACATCAAGTGTATCATATGC<br>CAAGTACGCCCCCTATTGACGTCAATGACGGTAAATGGCCCGCCTGGCATTA<br>TGCCCAGTACATGACCTTATGGGACTTTCCTACTTGGCAGTACATCTACGTAT<br>TAGTCATCGCTATTACCATGGTGATGCGGTTTTGGCAGTACATCAATGGGCGT<br>GGATAGCGGTTTGACTCACGGGGATTTCCAAGTCTCCACCCCATTGACGTCAA<br>TGGGAGTTTGTTTTGGCACCAAAATCAACGGGACTTTCCAAAATGTCGTAAC<br>AACTCCGCCCCATTGACGCAAATGGGCGGTAGGCGTGTACGGTGGGAGGTCT<br>ATATAAGCAGAGCTGGTTTAGTGAACCGTCAGATCCGCTAGAGATCTGGTAC<br>CGTCGACGCGGCCGCTCGAGCCTAAGCTTCTAGATGCATGCTCGAGCGGCCG<br>CCAGTGTGATGGATATCTGCAGAATTCGCCCTTGCTCGCTCCACCTCTCAAGC<br>AGCCAGCGCCTGCCTGAATCTGTTCTGCCCCTCCCCACCCATTTCACCACCA<br>CCATGACACCGGGCACCCAGTCTCCTTTCTTCCTGCTGCTGCTCCTCACAGTG<br>CTTACAGTTGTTACGGGTTCTGGTCATGCAAGCTCTACCCCAGGTGGAGAAA<br>AGGAGACTTCGGCTACCCAGAGAAGTTCAGTGCCCAGCTCTACTGAAGAAGAA<br>TGCTGTGAGTATGACCAGCAGCGTACTCTCCAGCCACAGCCCCGGTTCAGGC<br>TCCTCCACCACTCAGGGACAGGATGTCACTCTGGCCCCGGCCACGGAACCAG<br>CTTCAGGTTCAGCTGCCCTTTGGGGACAGGATGTCACCTCGGTCCCAGTCACC<br>AGGCCAGCCCTGGGCTCCACCACCCCGCCAGCCCACGATGTCACCTCAGCCC<br>CGGACAACAAGCCAGCCCCGGGCTCCACCGCCCCCCAGCCCACGGTGTCAC<br>CTCGTATCTTGACACCAGGCCGGCCCCGGTTTATCTTGCCCCCCCAGCCCATG<br>GTGTCACCTCGGCCCCGGACAACAGGCCCGCCTTGGGCTCCACCGCCCCTCC<br>AGTCCACAATGTCACCTCGGCCTCAGGCTCTGCATCAGGCTCAGCTTCTACTC<br>TGGTGCACAACGGCACCTCTGCCAGGGCTACCACAACCCCAGCCAGCAAGAG<br>CACTCCATTCTCAATTCCCAGCCACCACTCTGATACTCCTACCACCCTTGCCA<br>GCCATAGCACCAAGACTGATGCCAGTAGCACTCACCATAGCACGGTACCTCC<br>TCTCACCTCCTCCAATCACAGCACTTCTCCCCAGTTGTCTACTGGGGTCTCTTT<br>CTTTTTCCTGTCTTTTCACATTTCAAACCTCCAGTTTAATTCCTCTCTGGAAGA<br>TCCCAGCACCGACTACTACCAAGAGCTGCAGAGAGACATTTCTGAAATGTTT<br>TTGCAGATTTATAAACAAGGGGGTTTTCTGGGCCTCTCCAATATTAAGTTCAG<br>GCCAGGATCTGTGGTGGTACAATTGACTCTGGCCTTCGAGAAGGTACCATC<br>AATGTCCACGACGTGGAGACACAGTTCAATCAGTATAAAACGGAAGCAGCCT<br>CTCGATATAACCTGACGATCTCAGACGTCAGCGTGAGTGATGTGCCATTTCCT<br>TTCTCTGCCCAGTCTGGGGCTGGGGTGCCAGGCTGGGGCATCGCGCTGCTGGT<br>GCTGGTCTGTGTTCTGGTTTATCTGGCCATTGTCTATCTCATTGCCTTGGCTGT<br>CGCTCAGGTTCGCCGAAAGAACTACGGGCAGCTGGACATCTTTCCAGCCCGG<br>GATAAATACCATCCTATGAGCGAGTACGCTCTTTACCACACCCATGGGCGCT<br>ATGTGCCCCCTAGCAGTCTTTTCCGTAGCCCCTATGAGAAGGTTTCTGCAGGT<br>AATGGTGGCAGCTATCTCTCTTACACAAACCCAGCAGTGGCAGCCGCTTCTGC<br>CAACTTGTAGGGGCACGTCGCCCGCTGAGCTGAGTGGCCAGCCAGTGCCATT |

| SEQ ID NO | Sequence |
|---|---|
| | CCACTCCACTCAGGTTCTTCAGGGCCAGAGCCCCTGCACCCTGTTTGGGCTGG
TGAGCTGGGAGTTCAGGTGGGCTGCTCACAGCCTCCTTCAGAGGCCCCACCA
ATTTCTCGGACACTTCTCAGTGTGTGGAAGCTCATGTGGGCCCCTGAGGGCTC
ATGCCTGGGAAGTGTTGTGGTGGGGGCTCCCAGGAGGACTGGCCCAGAGAGC
CCTGAGATAGCGGGGATCCTGAACTGGACTGAATAAAACGTGGTCTCCCACT
GCGCCAAAAAAAAAAAAAAAAAACGATCCACCGGATCTAGATAACTGATCAT
AATCAGCCATACCACATTTGTAGAGGTTTTACTTGCTTTAAAAAACCTCCCAC
ACCTCCCCCTGAACCTGAAACATAAAATGAATGCAATTGTTGTTGTTAACTTG
TTTATTGCAGCTTATAATGGTTACAAATAAAGCAATAGCATCACAAATTTCAC
AAATAAAGCATTTTTTTCACTGCATTCTAGTTGTGGTTTGTCCAAACTCATCA
ATGTATCTTAACGCGGATCTGGAAGGTGCTGAGGTACGATGAGACCCGCACC
AGGTGCAGACCCTGCGAGTGTGGCGGTAAACATATTAGGAACCAGCCTGTGA
TGCTGGATGTGACCGAGGAGCTGAGGCCCGATCACTTGGTGCTGGCCTGCAC
CCGCGCTGAGTTTGGCTCTAGCGATGAAGATACAGATTGAGGTACTGAAATG
TGTGGGCGTGGCTTAAGGGTGGGAAAGAATATATAAGGTGGGGGTCTTATGT
AGTTTTGTATCTGTTTTGCAGCAGCCGCCGCCGCCATGAGCACCAACTCGTTT
GATGGAAGCATTGTGAGCTCATATTTGACAACGCGCATGCCCCCATGGGCCG
GGGTGCGTCAGAATGTGATGGGCTCCAGCATTGATGGTCGCCCCGTCCTGCC
CGCAAACTCTACTACCTTGACCTACGAGACCGTGTCTGGAACGCCGTTGGAG
ACTGCAGCCTCCGCCGCCGCTTCAGCCGCTGCAGCCACCGCCGCGGGATTG
TGACTGACTTTGCTTTCCTGAGCCCGCTTGCAAGCAGTGCAGCTTCCCGTTCA
TCCGCCCGCGATGACAAGTTGACGGCTCTTTTGGCACAATTGGATTCTTTGAC
CCGGGAACTTAATGTCGTTTCTCAGCAGCTGTTGGATCTGCGCCAGCAGGTTT
CTGCCCTGAAGGCTTCCTCCCCTCCCAATGCGGTTTAAAACATAAATAAAAA
ACCAGACTCTGTTTGGATTTGGATCAAGCAAGTGTCTTGCTGTCTTTATTTAG
GGGTTTTGCGCGCGCGGTAGGCCCGGGACCAGCGGTCTCGGTCGTTGAGGGT
CCTGTGTATTTTTTCCAGGACGTGGTAAAGGTGACTCTGGATGTTCAGATACA
TGGGCATAAGCCCGTCTCTGGGGTGGAGGTAGCACCACTGCAGAGCTTCATG
CTGCGGGGTGGTGTTGTAGATGATCCAGTCGTAGCAGGAGCGCTGGGCGTGG
TGCCTAAAAATGTCTTTCAGTAGCAAGCTGATTGCCAGGGGCAGGCCCTTGG
TGTAAGTGTTTACAAAGCGGTTAAGCTGGGATGGGTGCATACGTGGGGATAT
GAGATGCATCTTGGACTGTATTTTTAGGTTGGCTATGTTCCCAGCCATATCCC
TCCGGGATTCATGTTGTGCAGAACCACCAGCACAGTGTATCCGGTGCACTT
GGGAAATTTGTCATGTAGCTTAGAAGGAAATGCGTGGAAGAACTTGGAGACG
CCCTTGTGACCTCCAAGATTTTCCATGCATTCGTCCATAATGATGGCAATGGG
CCCACGGGCGGCGGCCTGGGCGAAGATATTTCTGGGATCACTAACGTCATAG
TTGTGTTCCAGGATGAGATCGTCATAGGCCATTTTTACAAAGCGCGGGCGGA
GGGTGCCAGACTGCGGTATAATCTGTTCCATCCGGCCCAGGGGCGTAGTTACC
CTCACAGATTTGCATTTCCCACGCTTTGAGTTCAGATGGGGGGATCATGTCTA
CCTGCGGGGCGATGAAGAAAACGGTTTCCGGGGTAGGGGAGATCAGCTGGG
AAGAAAGCAGGTTCCTGAGCAGCTGCGACTTACCGCAGCCGGTGGGCCCGTA
AATCACACCTATTACCGGCTGCAACTGGTAGTTAAGAGAGCTGCAGCTGCCG
TCATCCCTGAGCAGGGGGGCCACTTCGTTAAGCATGTCCCTGACTCGCATGTT
TTCCCTGACCAAATCCGCCAGAAGGCGCTCGCCGCCCAGCGATAGCAGTTCT
TGCAAGGAAGCAAAGTTTTTCAACGGTTTGAGACCGTCCGCCGTAGGCATGC
TTTTGAGCGTTTGACCAAGCAGTTCCAGGCGGTCCCACAGCTCGGTCACCTGC
TCTACGGCATCTCGATCCAGCATATCTCCTCGTTTCGCGGGTTGGGGCGGCTT
TCGCTGTACGGCAGTAGTCGGTGCTCGTCCAGACGGGCCAGGGTCATGTCTTT
CCACGGGCGCAGGGTCCTCGTCAGCGTAGTCTGGGTCACGGTGAAGGGGTGC
GCTCCGGGCTGCGCGCTGGCCAGGGTGCGCTTGAGGCTGGTCCTGCTGGTGC
TGAAGCGCTGCCGGTCTTCGCCCTGCGCGTCGGCCAGGTAGCATTTGACCATG
GTGTCATAGTCCAGCCCCTCCGCGGCGTGGCCCTTGGCGCGCAGCTTGCCCTT
GGAGGAGGCGCCGCACGAGGGGCAGTGCAGACTTTTGAGGGCGTAGAGCTT
GGGCGCGAGAAATACCGATTCCGGGGAGTAGGCATCCGCGCCGCAGGCCCC
GCAGACGGTCTCGCATTCCACGAGCCAGGTGAGCTCTGGCCGTTCGGGGTCA
AAAACCAGGTTTCCCCCATGCTTTTTGATGCGTTTCTTACCTCTGGTTTCCATG
AGCCGGTGTCCACGCTCGGTGACGAAAAGGCTGTCCGTGTCCCCGTATACAG
ACTTGAGAGGCCTGTCCTCGAGCGGTGTTCCGCGGTCCTCCTCGTATAGAAAC
TCGGACCACTCTGAGACAAAGGCTCGCGTCCAGGCCAGCACGAAGGAGGCTA
AGTGGGAGGGTAGCGGTCGTTGTCCACTAGGGGTCCACTCGCTCCAGGGT
GTGAAGACACATGTCGCCCTCTTCGGCATCAAGGAAGGTGATTGGTTTGTAG
GTGTAGGCCACGTGACCGGGTGTTCCTGAAGGGGGGCTATAAAAGGGGTGG
GGGCGCGTTCGTCCTCACTCTCTTCCGCATCGCTGTCTGCGAGGGCCAGCTGT
TGGGGTGAGTACTCCCTCTGAAAAGCGGGCATGACTTCTGCGCTAAGATTGT
CAGTTTCCAAAAACGAGGAGGATTTGATATTCACCTGGCCCGCGGTGATGCC
TTTGAGGGTGGCCGCATCCATCTGGTCAGAAAAGACAATCTTTTTGTTGTCAA
GCTTGGTGGCAAACGACCCGTAGAGGGCGTTGGACAGCAACTTGGCGATGGA
GCGCAGGGTTTGGTTTTTGTCGCGATCGGCGCGCTCCTTGGCCGCGATGTTTA
GCTGCACGTATTCGCGCGCAACGCACCGCCATTCGGGAAAGACGGTGGTGCG
CTCGTCGGGCACCAGGTGCACGCGCCAACCGCGGTTGTGCAGGGTGACAAGG
TCAACGCTGGTGGCTACCTCTCCGCGTAGGCGCTCGTTGGTCCAGCAGAGGC
GGCCGCCCTTGCGCGAGCAGAATGGCGGTAGGGGGTCTAGCTGCGTCTCGTC
CGGGGGGTCTGCGTCCACGGTAAAGACCCCGGGCAGCAGGCGCGCGTCGAA |

| SEQ ID NO | Sequence |
|---|---|
| | GTAGTCTATCTTGCATCCTTGCAAGTCTAGCGCCTGCTGCCATGCGCGGGCGG
CAAGCGCGCGCTCGTATGGGTTGAGTGGGGGACCCCATGGCATGGGGTGGGT
GAGCGCGGAGGCGTACATGCCGCAAATGTCGTAAACGTAGAGGGGCTCTCTG
AGTATTCCAAGATATGTAGGGTAGCATCTTCCACCGCGGATGCTGGCGCGCA
CGTAATCGTATAGTTCGTGCGAGGGAGCGAGGAGGTCGGGACCGAGGTTGCT
ACCTGGCGGGCTGCTCTGCTCGGAAGACTATCTGCCTGAAGATGGCATGTGAG
TTGGATGATATGGTTGGACGCTGGAAGACGTTGAAGCTGGCGTCTGTGAGAC
CTACCGCGTCACGCACGAAGGAGGCGTAGGAGTCGCGCAGCTTGTTGACCAG
CTCGGCGGTGACCTGCACGTCTAGGGCGCAGTAGTCCAGGGTTTCCTTGATG
ATGTCATACTTATCCTGTCCCTTTTTTTCCACAGCTCGCGGTTGAGGACAAA
CTCTTCGCGGTCTTTCCAGTACTCTTGGATCGGAAACCCGTCGGCCTCCGAAC
GGTAAGAGCCTAGCATGTAGAACTGGTTGACGGCCTGGTAGGCGCAGCATCC
CTTTTCTACGGGTAGCGCGTATGCCTGCGCGGCCTTCCGGCATGACCAGCATG
AAGGGCACGAGCTGCTTCCCAAAGGCCCCCATCCAAGTATAGGTCTCTACAT
CGTAGGTGACAAAGAGACGCTCGGTGCGAGGATGCGAGCCGATCGGGAAGA
ACTGGATCTCCCGCCACCAATTGGAGGAGTGGCTATTGATGTGGTGAAAGTA
GAAGTCCCTGCGACGGGCCGAACACTCGTGCTGGCTTTTGTAAAAACGTGCG
CAGTACTGGCAGCGGTGCACGGGCTGTACATCCTGCACGAGGTTGACCTGAC
GACCGCGCACAAGGAAGCAGAGTGGGAATTTGAGCCCCTCGCCTGGCGGGTT
TGGCTGGTGGTCTTCTACTTCGGCTGCTTGTCCTTGACCGTCTGGCTGCTCGA
GGGGAGTTACGGTGGATCGGACCACCACGCCGCGCGAGCCCAAAGTCCAGAT
GTCCGCGCGCGGCGGTCGGAGCTTGATGACAACATCGCGCAGATGGGAGCTG
TCCATGGTCTGGAGCTCCCGCGCGTCAGGTCAGGCGGGAGCTCCTGCAGGT
TTACCTCGCATAGACGGGTCAGGGCGCGGGCTAGATCCAGGTGATACCTAAT
TTCCAGGGGCTGGTTGGTGGCGGCGTCGATGGCTTGCAAGAGGCCGCATCCC
CGCGGCGCGACTACGGTACCGCGCGGCGGGCGGTGGGCCGCGGGGTGTCCT
TGGATGATGCATCTAAAAGCGGTGACGCGGGCGAGCCCCCGGAGGTAGGGG
GGGCTCCGGACCCGCCGGGAGAGGGGCAGGGGCACGTCGGCGCCGCGCGC
GGGCAGGAGCTGGTGCTGCGCGCGTAGGTTGCTGGCGAACGCGACGACGCG
GCGGTTGATCTCCTGAATCTGGCGCCTCTGCGTGAAGACGACGGGCCCGGTG
AGCTTGAACCTGAAAGAGAGTTCGACAGAATCAATTTCGGTGTCGTTGACGG
CGGCCTGGCGCAAAATCTCCTGCACGTCTCCTGAGTTGTCTTGATAGGCGATC
TCGGCCATGAACTGCTCGATCTCTTCCTCCTGGAGATCTCCGCGTCCGGCTCG
CTCCACGGTGGCGGCGAGGTCGTTGGAAATGCGGGCCATGAGCTGCGAGAAG
GCGTTGAGGCCTCCCTCGTTCCAGACGCGGCTGTAGACCACGCCCCTTCGGC
ATCGCGGGCGCGCATGACCACCTGCGCGAGATTGAGCTCCACGTGCCGGGCG
AAGACGGCGTAGTTTCGCAGGCGCTGAAAGAGGTAGTTGAGGGTGGTGGCG
GTGTGTTCTGCCACGAAGAAGTACATAACCCAGCGTCGCAACGTGGATTCGT
TGATAATTGTTGTGTAGGTACTCCGCCGCCGAGGGACCTGAGCGAGTCCGCA
TCGACCGGATCGGAAAACCTCTCGAGAAAGGCGTCTAACCAGTCACAGTCGC
AAGGTAGGCTGAGCACCGTGGCGGGCGGCAGCGGGCGGCGGTCGGGGTTGT
TTCTGGCGGAGGTGCTGCTGATGATGTAATTAAAGTAGGCGGTCTTGAGACG
GCGGATGGTCGACAGAAGCACCATGTCCTTGGGTCCGGCCTGCTGAATGCGC
AGGCGGTCGGCCATGCCCCAGGCTTCGTTTTGACATCGGCGCAGGTCTTTGTA
GTAGTCTTGCATGAGCCTTTCTACCGGCACTTCTTCTTCTCCTTCCTCTTGTCC
TGCATCTCTTGCATCTATCGCTGCGGCGGCGGCGGAGTTTGGCCGTAGGTGGC
GCCCTCTTCCTCCCATGCGTGTGACCCCGAAGCCCCTCATCGGCTGAAGCAGG
GCTAGGTCGGCGACAACGCGCTCGGCTAATATGGCCTGCTGCACCTGCGTGA
GGGTAGACTGGAAGTCATCCATGTCCACAAAGCGGTGGTATGCGCCCGTGTT
GATGGTGTAAGTGCAGTTGGCCATAACGGACCAGTTAACGGTCTGGTGACCC
GGCTGCGAGAGCTCGGTGTACCTGAGCGCGAGTAAGCCCTCGAGTCAAATA
CGTAGTCGTTGCAAGTCCGCACCAGGTACTGGTATCCCACCAAAAAGTGCGG
CGGCGGCTGGCGGTAGAGGGGCCAGCGTAGGGTGGCCGGGGCTCCGGGGGC
GAGATCTTCCAACATAAGGCGATGATATCCGTAGATGTACCTGGACATCCAG
GTGATGCCGGCGGCGGTGGTGGAGGCGCGCGGAAAGTCGCGGACGCGGTTC
CAGATGTTGCGCAGCGGCAAAAAGTGCTCCATGGTCGGGACGCTCTGGCCGG
TCAGGCGCGCGCAATCGTTGACGCTCTAGCGTGCAAAAGGAGAGCCTGTAAG
CGGGCACTCTTCCGTGGTCTGGTGGATAAATTCGCAAGGGTATCATGGCGGA
CGACCGGGTTCGAGCCCCGTATCCGGCCGTCCGCCGTGATCCATGCGGTTA
CCGCCCGCGTGTCGAACCCAGGTGTGCGACGTCAGACAACGGGGAGTGCTC
CTTTTTGGCTTCCTTCCAGGCGCGGCGGCTGCTGCGCTAGCTTTTTTGGCCACT
GGCCGCGCGCAGCGTAAGCGGTTAGGCTGGAAAGCGAAAGCATTAAGTGGC
TCGCTCCCTGTAGCCGGAGGGTTATTTTCCAAGGGTTGAGTCGCGGGACCCCC
GGTTCGAGTCTCGGACCGGCCGGACTGCGGCGAACGGGGGTTTGCCTCCCCG
TCATGCAAGACCCCGCTTGCAAATTCCTCCGGAAACAGGGACGAGCCCCTTT
TTTGCTTTTCCCAGATGCATCCGGTGCTGCGGCAGATGCGCCCCCCTCCTCAG
CAGCGGCAAGAGCAAGAGCAGCGGCAGACATGCAGGGCACCCTCCCCTCCTC
CTACCGCGTCAGGAGGGGCGACATCCGCGGTTGACGCGGCAGCAGATGGTGA
TTACGAACCCCCGCGGCGCCGGGCCCGGCACTACCTGGACTTGGAGGAGGGC
GAGGGCCTGGCGCGGCTAGGAGCGCCCTCTCCTGAGCGGCACCCAAGGGTGC
AGCTGAAGCGTGATACGCGTGAGGCGTACGTGCCGCGGCAGAACCTGTTTCG
CGACCGCGAGGGAGAGGAGCCCGAGGAGATGCGGGATCGAAAGTTCCACGC
AGGGCGCGAGCTGCGGCATGGCCTGAATCGCGAGCGGTTGCTGCGCGAGGA |

| SEQUENCES | |
|---|---|
| SEQ ID NO | Sequence |
| | GGACTTTGAGCCCGACGCGCGAACCGGGATTAGTCCCGCGCGCGCACACGTG<br>GCGGCCGCCGACCTGGTAACCGCATACGAGCAGACGGTGAACCAGGAGATT<br>AACTTTCAAAAAAGCTTTAACAACCACGTGCGTACGCTTGTGGCGCGCGAGG<br>AGGTGGCTATAGGACTGATGCATCTGTGGGACTTTGTAAGCGCGCTGGAGCA<br>AAACCCAAATAGCAAGCCGCTCATGGCGCAGCTGTTCCTTATAGTGCAGCAC<br>AGCAGGGACAACGAGGCATTCAGGGATGCGCTGCTAAACATAGTAGAGCCC<br>GAGGGCCGCTGGCTGCTCGATTTGATAAACATCCTGCAGAGCATAGTGGTGC<br>AGGAGCGCAGCTTGAGCCTGGCTGACAAGGTGGCCGCCATCAACTATTCCAT<br>GCTTAGCCTGGGCAAGTTTTACGCCCGCAAGATATACCATACCCCTTACGTTC<br>CCATAGACAAGGAGGTAAAGATCGAGGGGTTCTACATGCGCATGGCGCTGAA<br>GGTGCTTACCTTGAGCGACGACCTGGGCGTTTATCGCAACGAGCGCATCCAC<br>AAGGCCGTGAGCGTGAGCCGGCGGCGCGAGCTCAGCGACCGCGAGCTGATG<br>CACAGCCTGCAAAGGGCCCTGGCTGGCACGGGCAGCGGCGATAGAGAGGCC<br>GAGTCCTACTTTGACGCGGGCGCTGACCTGCGCTGGGCCCCAAGCCGACGCG<br>CCCTGGAGGCAGCTGGGGCCGGACCTGGGCTGGCGGTGGCACCCGCGCGCGC<br>TGGCAACGTCGGCGGCGTGGAGGAATATGACGAGGACGATGAGTACGAGCC<br>AGAGGACGGCGAGTACTAAGCGGTGATGTTTCTGATCAGATGATGCAAGACG<br>CAACGGACCCGGCGGTGCGGGCGGCGCTGCAGAGCCAGCCGTCCGGCCTTAA<br>CTCCACGGACGACTGGCGCCAGGTCATGGACCGCATCATGTCGCTGACTGCG<br>CGCAATCCTGACGCGTTCCGGCAGCAGCCGCAGGCCAACCGGCTCTCCGCAA<br>TTCTGGAAGCGGTGGTCCCGGCGCGCGCAAACCCCACGCACGAGAAGGTGCT<br>GGCGATCGTAAACGCGCTGGCCGAAAACAGGGCCATCCGGCCCGACGAGGC<br>CGGCCTGGTCTACGACGCGCTGCTTCAGCGCGTGGCTCGTTACAACAGCGGC<br>AACGTGCAGACCAACCTGGACCGGCTGGTGGGGATGTGCGCGAGGCCGTG<br>GCGCAGCGTGAGCGCGCGCAGCAGCAGGGCAACCTGGGCTCCATGGTTGCAC<br>TAAACGCCTTCCTGAGTACACAGCCCGCCAACGTGCCGCGGGGACAGGAGGA<br>CTACACCAACTTTGTGAGCGCACTGCGGCTAATGGTGACTGAGACACCGCAA<br>AGTGAGGTGTACCAGTCTGGGCCAGACTATTTTTTCCAGACCAGTAGACAAG<br>GCCTGCAGACCGTAAACCTGAGCCAGGCTTTTCAAAAACTTGCAGGGGCTGTG<br>GGGGGTGCGGGCTCCCACAGGCGACCGCGCGACCGTGTCTAGCTTGCTGACG<br>CCCAACTCGCGCCTGTTGCTGCTGCTAATAGCGCCCTTCACGGACAGTGGCAG<br>CGTGTCCCGGGACACATACCTAGGTCACTTGCTGACACTGTACCGCGAGGCC<br>ATAGGTCAGGCGCATGTGGACGAGCATACTTTCCAGGAGATTACAAGTGTCA<br>GCCGCGCGCTGGGGCAGGAGGACACGGGCAGCCTGGAGGCAACCCTAAACT<br>ACCTGCTGACCAACCGGCGGCAGAAGATCCCCTCGTTGCACAGTTTAAACAG<br>CGAGGAGGAGCGCATTTTGCGCTACGTGCAGCAGAGCGTGAGCCTTAACCTG<br>ATGCGCGACGGGGTAACGCCCAGCGTGGCGCTGGACATGACCGCGCAAC<br>ATGGAACCGGGCATGTATGCCTCAAACCGGCCGTTTATCAACCGCCTAATGG<br>ACTACTTGCATCGCGCGGCCGCCGTGAACCCCGAGTATTTCACCAATGCCATC<br>TTGAACCCGCACTGGCTACCGCCCCTGGTTTCTACACCGGGGGATTCGAGGT<br>GCCCGAGGGTAACGATGGATTCCTCTGGGACGACATAGACGACAGCGTGTTT<br>TCCCCGCAACCGCAGACCCTGCTAGAGTTGCAACAGCGCGAGCAGGCAGAGG<br>CGGCGCTGCGAAAGGAAAGCTTCCGCAGGCCAAGCAGCTTGTCCGATCTAGG<br>CGCTGCGGCCCCGCGGTCAGATGCTAGTAGCCCATTTCCAAGCTTGATAGGG<br>TCTCTTACCAGCACTCGCACCACCCGCCCGCGCCTGCTGGGCGAGGAGGAGT<br>ACCTAAACAACTCGCTGCTGCAGCCGCAGCGCGAAAAAAACCTGCCTCCGGC<br>ATTTCCCAACAACGGGATAGAGAGCCTAGTGGACAAGATGAGTAGATGGAA<br>GACGTACGCGCAGGAGCACAGGGACGTGCCAGGCCCGCGCCCGCCCACCCGT<br>CGTCAAAGGCACGACCGTCAGCGGGGTCTGGTGTGGGAGGACGATGACTCGG<br>CAGACGCAGCAGCGTCCTGGATTTGGGAGGGAGTGGCAACCCGTTTGCGCA<br>CCTTCGCCCCAGGCTGGGGAGAATGTTTTAAAAAAAAAAAAGCATGATGCAA<br>AATAAAAAACTCACCAAGGCCATGGCACCGAGCGTTGGTTTTCTTGTATTCCC<br>CTTAGTATGCGGCGCGCGGCGATGTATGAGGAAGGTCCTCCTCCCTCCTACG<br>AGAGTGTGGTGAGCGCGGCGCCAGTGGCGGCGGCGCTGGGTTCTCCCTTCGA<br>TGCTCCCCTGGACCCGCCGTTTGTGCCTCCGCGGTACCTGCGGCCTACCGGGG<br>GGAGAAACAGCATCCGTTACTCTGAGTTGGCACCCCTATTCGACACCACCCG<br>TGTGTACCTGGTGGACAACAAGTCAACGGATGTGGCATCCCTGAACTACCAG<br>AACGACCACAGCAACTTTCTGACCACGGTCATTCAAAACAATGACTACAGCC<br>CGGGGGAGGCAAGCACACAGACCATCAATCTTGACGACCGGTCGCACTGGG<br>GCGGCGACCTGAAAACCATCCTGCATACCAACATGCCAAATGTGAACGAGTT<br>CATGTTTACCAATAAGTTTAAGGCGCGGGTGATGGTGTCGCGCTTGCCTACTA<br>AGGACAATCAGGTGGAGCTGAAATACGAGTGGGTGGAGTTCACGCTGCCCGA<br>GGGCAACTACTCCGAGACCATGACCATAGACCTTATGAACAACGCGATCGTG<br>GAGCACTACTTGAAAGTGGGCAGACAGAACGGGGTTCTGGAAAGCGACATC<br>GGGGTAAAGTTTGACACCCGCAACTTCAGACTGGGGTTTGACCCCGTCACTG<br>GTCTTGTCATGCCTGGGGTATATACAAACGAAGCCTTCCATCCAGACATCATT<br>TTGCTGCCAGGATGCGGGGTGGACTTCACCCACAGCCGCCTGAGCAACTTGT<br>TGGGCATCCGCAAGCGGCAACCCTTCCAGGAGGGCTTTAGGATCACCTACGA<br>TGATCTGGAGGGTGGTAACATTCCCGCACTGTTGGATGTGGACGCCTACCAG<br>GCGAGCTTGAAAGATGACACCGAACAGGGCGGGGTGGCGCAGGCGGCAGC<br>AACAGCAGTGGCAGCGGCGCGGAAGAGAACTCCAACGCGGCAGCCGCGGCA<br>ATGCAGCCGGTGGAGGACATGAACGATCATGCCATTCGCGGCGACACCTTTG<br>CCACACGGGCTGAGGAGAAGCGCGCTGAGGCCGAAGCAGCGGCCGAAGCTG |

| SEQ ID NO | Sequence |
|---|---|
| | CCGCCCCCGCTGCGCAACCCGAGGTCGAGAAGCCTCAGAAGAAACCGGTGAT
CAAACCCCTGACAGAGGACAGCAAGAAACGCAGTTACAACCTAATAAGCAA
TGACAGCACCTTCACCCAGTACCGCAGCTGGTACCTTGCATACAACTACGGC
GACCCTCAGACCGGAATCCGCTCATGGACCCTGCTTTGCACTCCTGACGTAAC
CTGCGGCTCGGAGCAGGTCTACTGGTCGTTGCCAGACATGATGCAAGACCCC
GTGACCTTCCGCTCCACGCGCCAGATCAGCAACTTTCCGGTGGTGGGCGCCG
AGCTGTTGCCCGTGCACTCCAAGAGCTTCTACAACGACCAGGCCGTCTACTCC
CAACTCATCCGCCAGTTTACCTCTCTGACCCACGTGTTCAATCGCTTTCCCGA
GAACCAGATTTTGGCGCGCCCGCCAGCCCCACCATCACCACCGTCAGTGAA
AACGTTCCTGCTCTCACAGATCACGGGACGCTACCGCTGCGCAACAGCATCG
GAGGAGTCCAGCGAGTGACCATTACTGACGCCAGACGCCGCACCTGCCCCTA
CGTTTACAAGGCCCTGGGCATAGTCTCGCCGCGCGTCCTATCGAGCCGCACTT
TTTGAGCAAGCATGTCCATCCTTATATCGCCCAGCAATAACACAGGCTGGGG
CCTGCGCTTCCCAAGCAAGATGTTTGGCGGGGCCAAGAAGCGCTCCGACCAA
CACCCAGTGCGCGTQCGCGGGCACTACCGCGCGCCCTGGGGCGCGCACAAAC
GCGGCCGCACTGGGCGCACCACCGTCGATGACGCCATCGACGCGGTGGTGGA
GGAGGCGCGCAACTACACGCCCACGCCGCCACCAGTGTCCACAGTGGACGCG
GCCATTCAGACCGTGGTGCGCGGAGCCCGGCGCTATGCTAAAATGAAGAGAC
GGCGGAGGCGCGTAGCACGTCGCCACCGCCGCCGACCCGGCACTGCCGCCCA
ACGCGCGGCGGCGGCCCTGCTTAACCGCGCACGTCGCACCGGCCGACGGGCG
GCCATGCGGGCCGCTCGAAGGCTGGCCGCGGGTATTGTCACTGTGCCCCCCA
GGTCCAGGCGACGAGCGGCCGCCGCAGCAGCCGCGGCCATTAGTGCTATGAC
TCAGGGTCGCAGGGGCAACGTGTATTGGGTGCGCGACTCGGTTAGCGGCCTG
CGCGTGCCCGTGCGCACCCGCCCCCCGCGCAACTAGATTGCAAGAAAAAACT
ACTTAGACTCGTACTGTTGTATGTATCCAGCGGCGGCGGCGCGCAACGAAGC
TATGTCCAAGCGCAAATCAAAGAAGAGATGCTCCAGGTCATCGCGCCGGAG
ATCTATGCCCCCCGAAGAAGGAAGAGCAGGATTACAAGCCCCGAAAGCTA
AAGCGGGTCAAAAAGAAAAAGAAAGATGATGATGATGAACTTGACGACGAG
GTGGAACTGCTGCACGCTACCGCGCCCAGGCGACGGGTACAGTGGAAAGGTC
GACGCGTAAAACGTGTTTTGCGACCCGGCACCACCGTAGTCTTTACGCCCGGT
GAGCGCTCCACCCGCACCTACAAGCCTCGTGTATGATGAGGTGTACGGCGACG
AGGACCTGCTTGAGCAGGCCAACGAGCGCCTCGGGGAGTTTGCCTACGGAAA
GCGGCATAAGGACATGCTGGCGTTGCCGCTGGACGAGGGCAACCCAACACCT
AGCCTAAAGCCCGTAACACTGCAGCAGGTGCTGCCCGCGCTTGCACCGTCCG
AAGAAAAGCGCGGCCTAAAGCGCGAGTCTGGTGACTTGGCACCCACCGTGCA
GCTGATGGTACCCAAGCGCCAGCGACTGGAAGATGTCTTGGAAAAAATGACC
GTGGAACCTGGGCTGGAGCCCGAGGTCCGCGTGCGGCCAATCAAGCAGGTGG
CGCCGGGACTGGGCGTGCAGACCGTGGACGTTCAGATACCCACTACCAGTAG
CACCAGTATTGCCACCGCCACAGAGGGCATGGAGACACAAACGTCCCCGGTT
GCCTCAGCGGTGGCGGATGCCGCGGTGCAGGCGGTCGCTGCGGCCGCGTCCA
AGACCTCTACGGAGGTGCAAACGGACCCGTGGATGTTTCGCGTTTTCAGCCCC
CCGGCGCCCGCGCCGTTCGAGGAAGTACGGCGCCGCCAGCGCGCTACTGCCC
GAATATGCCCTACATCCTTCCATTGCGCCTACCCCCGGCTATCGTGGCTACAC
CTACCGCCCCAGAAGACGAGCAACTACCCGACGCCGAACCACCACTGGAACC
CGCCGCCGCCGTCGCCGTCGCCAGCCCGTGCTGGCCCCGATTTCCGTGCGCAG
GGTGGCTCGCGAAGGAGGCAGGACCCTGGTGCTGCCAACAGCGCGCTACCAC
CCCAGCATCGTTTAAAAGCCGGTCTTTGTGGTTCTTGCAGATATGGCCCTCAC
CTGCCGCCTCCGTTTCCCGGTGCCGGGATTCCGAGGAAGAATGCACCGTAGG
AGGGGCATGGCCGGCCACGGCCTGACGGGCGGCATGCGTCGTGCGCACCACC
GGCGGCGGCGCGCGTCGCACCGTCGCATGCGCGGCGGTATCCTGCCCCTCCT
TATTCCACTGATCGCCGGCGATTGGCGCCGTGCCCGGAATTGCATCCGTGG
CCTTGCAGGCGCAGAGACACTGATTAAAAACAAGTTGCATGTGGAAAAATCA
AAATAAAAAGTCTGGACTCTCACGCTCGCTTGGTCCTGTAACTATTTTGTAGA
ATGGAAGACATCAACTTTGCGTCTCTGGCCCCGCGACACGGCTCGCGCCCGTT
CATGGGAAACTGGCAAGATATCGGCACCAGCAATATGAGCGGTGGCGCCTTC
AGCTGGGGCTCGCTGTGGAGCGGCATTAAAAATTTCGGTTCCACCGTTAAGA
ACTATGGCAGCAAGGCCTGGAACAGCAGCACAGGCCAGATGCTGAGGGATA
AGTTGAAAGAGCAAAATTTCCAACAAAGGTGGTAGATGGCCTGGCCTCTGG
CATTAGCGGGTGGTGGACCTGGCCAACCAGGCAGTGCAAAATAAGATTAAC
AGTAAGCTTGATCCCCGCCCTCCCGTAGAGGAGCCTCCACCGGCCGTGGAGA
CAGTGTCTCCAGAGGGGCGTGGCGAAAGCGTCCGCGCCCCGACAGGGAAG
AAACTCTGGTGACGCAAATAGACGAGCCTCCCTCGTACGAGGAGGCACTAAA
GCAAGGCCTGCCCCACCACCCGTCCCATCGCGCCCATGGCTACCGGAGTGCTG
GGCCAGCACACACCCGTAACGCTGGACCTGCCTCCCCCGCCGACACCCAGC
AGAAACCTGTGCTGCCAGGCCCGACCGCCGTTGTTGTAACCCGTCCTAGCCG
CGCGTCCCTGCGCCGCGCCGCCAGCGGTCCGCGATCGTTGCGCCCGTAGCC
AGTGGCAACTGGCAAAGCACACTGAACAGCATCGTGGGTCTGGGGGTGCAAT
CCCTGAAGCGCCGACGATGCTTCTGATAGCTAACGTGTCGTATGTGTGTCATG
TATGCGTCCATGTCGCCGCCAGAGGAGCTGCTGAGCCGCCGCGCGCCCGCTT
TCCAAGATGGCTACCCCTTCGATGATGCCGCAGTGGTCTTACATGCACATCTC
GGGCCAGGACGCCTCGGAGTACCTGAGCCCCGGCTGGTGCAGTTTGCCCGC
GCCACCGAGACGTACTTCAGCCTGAATAACAAGTTTAGAAACCCCACGGTGG
CGCCTACGCACGACGTGACCACAGACCGGTCCCAGCGTTTGACGCTGCGGTT |

| SEQUENCES | |
|---|---|
| SEQ ID NO | Sequence |
| | CATCCCTGTGGACCGTGAGGATACTGCGTACTCGTACAAGGCGCGGTTCACC CTAGCTGTGGGTGATAACCGTGTGCTGGACATGGCTTCCACGTACTTTGACAT CCGCGGCGTGCTGGACAGGGGCCCTACTTTTAAGCCCTACTCTGGCACTGCCT ACAACGCCCTGGCTCCCAAGGGTGCCCCAAATCCTTGCGAATGGGATGAAGC TGCTACTGCTCTTGAAATAAACCTAGAAGAAGAGGACGATGACAACGAAGAC GAAGTAGACGAGCAAGCTGAGCAGCAAAAAACTCACGTATTTGGGCAGGCG CCTTATTCTGGTATAAATATTACAAAGGAGGGTATTCAAATAGGTGTCGAAG GTCAAACACCTAAATATGCCGATAAAACATTTCAACCTGAACCTCAAATAGG AGAATCTCAGTGGTACGAAACAGAATTAATCATGCAGCTGGGAGAGTCCTA AAAAAGACTACCCCAATGAAACCATGTTACGGTTCATATGCAAAACCCACAA ATGAAAATGGAGGGCAAGGCATTCTTGTAAAGCAACAAATGGAAAGCTAG AAAGTCAAGTGGAAATGCAATGTTCTCAACTACTGAGGCAGCCGCAGGCAA TGGTGATAACTTGACTCCTAAAGTGGTATTGTACAGTGAAGATGTAGATATA GAAACCCCAGACACTCATATTTCTTACATGCCCACTATTAAGGAAGGTAACTC ACGAGAACTAATGGGCCAACAATCTATGCCCAACAGGCCTAATTACATTGCT TTTAGGGACAATTTTATTGGTCTAATGTATTACAACAGCACGGGTAATATGGG TGTTCTGGCGGGCCAAGCATCGCAGTTGAATGCTGTTGTAGATTTGCAAGAC AGAAACACAGAGCTTTCATACCAGCTTTTGCTTGATTCCATTGGTGATAGAAC CAGGTACTTTTCTATGTGGAATCAGGCTGTTGACAGCTATGATCCAGATGTTA GAATTATTGAAAATCATGGAACTGAAGATGAACTTCCAAATTACTGCTTTCCA CTGGGAGGTGTGATTAATACAGAGACTCTTACCAAGGTAAAACCTAAAACAG GTCAGGAAAATGGATGGGAAAAAGATGCTACAGAATTTTCAGATAAAAATG AAATAAGAGTTGGAAATAATTTTGCCATGGAAATCAATCTAAATGCCAACCT GTGGGAGAAATTTCCTGTACTCCAACATAGCGCTGTATTTGCCCGACAAGCTAA AGTACAGTCCTTCCAACGTAAAAATTTCTGATAACCCAAACACCTACGACTA CATGAACAAGCGAGTGGTGGCTCCCGGGCTAGTGGACTGCTACATTAACCTT GGAGCACGCTGGTCCCTTGACTATATGGACAACGTCAACCCATTTAACCACC ACCGCAATGCTGGCCTGCGCTACCGCTCAATGTTGCTGGGCAATGGTCGCTAT GTGCCCTTCCACATCCAGGTGCCTCAGAAGTTCTTTGCCATTAAAAACCTCCT TCTCCTGCCGGGCTCATACACCTACGAGTGGAACTTCAGGAAGGATGTTAAC ATGGTTCTGCAGAGCTCCCTAGGAAATGACCTAAGGGTTGACGGAGCCAGCA TTAAGTTTGATAGCATTTGCCTTTACGCCACCTTCTTCCCCATGGCCCACAAC ACCGCCTCCACGCTTGAGGCCATGCTTAGAAACGACACCAACGACCAGTCCT TTAACGACTATCTCTCCGCCGCCAACATGCTCTACCCTATACCCGCCAACGCT ACCAACGTGCCCATATCCATCCCCTCCCGCAACTGGGCGGCTTTCCGCGGCTG GGCCTTCACGCGCCTTAAGACTAAGGAAACCCCATCACTGGGCTCGGGCTAC GACCCTTATTACACTACTCTGGCTCTATACCCTACCTAGATGGAACCTTTTA CCTCAACCACACCTTTAAGAAGGTGGCCATTACCTTTGACTCTTCTGTCAGCT GGCCTGGCAATGACCGCCTGCTTACCCCCAACGAGTTTGAAATTAAGCGCTC AGTTGACGGGGAGGGTTACAACGTTGCCCAGTGTAACATGACCAAAGACTGG TTCCTGGTACAAATGCTAGCTAACTATAACATTGGCTACCAGGGCTTCTATAT CCCAGAGAGCTACAAGGACCGCATGTACTCCTTCTTTAGAAACTTCCAGCCC ATGAGCCGTCAGGTGGTGGATGATACTAAATACAAGGACTACCAACAGGTGG GCATCCTACACCAACACAACAACTCTGGATTTGTTGGCTACCTTGCCCCCACC ATGCGCGAAGGACAGGCCTACCCTGCTAACTTCCCCTATCCGCTTATAGGCA AGACCGCAGTTGACAGCATTACCCAGAAAAAGTTTCTTTGCGATCGCACCCTT TGGCGCATCCCATTCTCCAGTAACTTTATGTCCATGGGCGCACTCACAGACCT GGGCCAAAACCTTCTCTACGCCAACTCCGCCCACGCGCTAGACATGACTTTTG AGGTGGATCCCATGGACGAGCCCACCCTTCTTTATGTTTTGTTTGAAGTCTTT GACGTGGTCCGTGTGCACCAGCCGCACCGCGGCGTCATCGAAACCGTGTACC TGCGCACGCCCTTCTCGGCCGGCAACGCCACAACATAAAGAAGCAAGCAACA TCAACAACAGCTGCCGCCATGGGCTCCAGTGAGCAGGAACTGAAAGCCATTG TCAAAGATCTTGGTTGTGGGCCATATTTTTTGGGCACCTATGACAAGCGCTTT CCAGGCTTTGTTTCTCCACACAAGCTCGCCTGCGCCATAGTCAATACGGCCGG TCGCGAGACTGGGGCGTACACTGGATGGCCTTTGCCTGGAACCCGCACTCA AAAACATGCTACCTCTTTGAGCCCTTTGGCTTTTCTGACCAGCGACTCAAGCA GGTTTACCAGTTTGAGTACGAGTCACTCCTGCGCCGTAGCGCCATTGCTTCTT CCCCCGACCGCTGTATAACGCTGGAAAAGTCCACCCAAAGCGTACAGGGGCC CAACTCGCCGCCTGTGGACTATTCTGCTGCATGTTTCTCCACGCCTTTGCCA ACTGGCCCCAAACTCCCATGGATCACAACCCCACCATGAACCTTATTACCGG GGTACCCAACTCCATGCTCAACAGTCCCCAGGTACAGCCCACCCTGCGTCGC AACCAGGAACAGCTCTACAGCTTCCTGGAGCGCCACTCGACCTCGCCCACTTCCGCA GCCACAGTGCGCAGATTAGGAGCGCCACTTCTTTTTGTCACTTGAAAAACATG TAAAAATAATGTACTAGAGACACTTTCAATAAAGGCAAATGCTTTTATTTGTA CACTCTCGGGTGATTATTTACCCCCACCCTTGCCGTCTGCGCCGTTTAAAAAT CAAAGGGGTTCTGCCGCGCATCGCTATGCGCCACTGGCAGGGACACGTTGCG ATACTGGTGTTTAGTGCTCCACTTAAACTCAGGCACAACCATCCGCGGCAGCT CGGTGAAGTTTTCACTCCACAGGCTGCGCACCATCACCAACGCGTTTAGCAG GTCGGGCGCCGATATCTTGAAGTCGCAGTTGGGGCCTCCGCCCTGCGCGCGC GAGTTGCGATACACAGGGTTGCAGCACTGGAACACTATCAGCGCCGGGTGGT GCACGCTGGCCAGCACGCTCTTGTCGGAGATCAGATCCGCGTCCAGGTCCTC CGCGTTGCTCAGGGCGAACGGAGTCAACTTTGGTAGCTGCCTTCCCAAAAAG GGCGCGTGCCCAGGCTTTGAGTTGCACTCGCACCGTAGTGGCATCAAAAGGT |

| SEQ ID NO | Sequence |
|---|---|
| | GACCGTGCCCGGTCTGGGCGTTAGGATACAGCGCCTGCATAAAAGCCTTGAT<br>CTGCTTAAAAGCCACCTGAGCCTTTGCGCCTTCAGAGAAGAACATGCCGCAA<br>GACTTGCCGGAAAACTGATTGGCCGGACAGGCCGCGTCGTGCACGCAGCACC<br>TTGCGTCGGTGTTGGAGATCTGCACCACATTTCGGCCCCACCGGTTCTTCACG<br>ATCTTGGCCTTGCTAGACTGCTCCTTCAGCGCGCGCTGCCCGTTTTCGCTCGTC<br>ACATCCATTTCAATCACGTGCTCCTTATTTATCATAATGCTTCCGTGTAGACA<br>CTTAAGCTCGCCTTCGATCTCAGCGCAGCGGTGCAGCCACAACGCGCAGCCC<br>GTGGGCTCGTGATGCTTGTAGGTCACCTCTGCAAACGACTGCAGGTACGCCT<br>GCAGGAATCGCCCCATCATCGTCACAAAGGTCTTGTTGCTGGTGAAGGTCAG<br>CTGCAACCCGCGGTGCTCCTCGTTCAGCCAGGTCTTGCATACGGCCGCCAGA<br>GCTTCCACTTGGTCAGGCAGTAGTTTGAAGTTCGCCTTTAGATCGTTATCCAC<br>GTGGTACTTGTCCATCAGCGCGCGCAGCCTCCATGCCCTTCTCCCACGCAG<br>ACACGATCGGCACACTCAGCGGGTTCATCACCGTAATTTCACTTTCCGCTTCG<br>CTGGGCTCTTCCTCTTCCTCTTGCGTCCGCATACCACGCGCCACTGGGTCGTCT<br>TCATTCAGCCGCCGCACTGTGCGCTTACCTCCTTTGCCATGCTTGATTAGCAC<br>CGGTGGGTTGCTGAAACCCACCATTTGTAGCGCCACATCTTCTCTTTCTTCCTC<br>GCTGTCCACGATTACCTCTGGTGATGGCGGGCGCTCGGGCTTGGGAGAAGGG<br>CGCTTCTTTTCTTCTTGGGCGCAATGGCCAAATCCGCCGCCGAGGTCGATGG<br>CCGCGGGCTGGGTGTGCGCGGCACCAGCGCGTCTTGTGATGAGTCTTCCTCGT<br>CCTCGGACTCGATACGCCGCCTCATCCGCTTTTTTGGGGGCGCCCGGGGAGGC<br>GGCGGCGACGGGGACGGGGACGACACGTCCTCCATGGTTGGGGGACGTCGC<br>GCCGCACCGCGTCCGCGCTCGGGGTGTTTCGCGCTGCTCCTCTTCCCGACT<br>GGCCATTTCCTTCTCCTATAGGCAGAAAAAGATCATGGAGTCAGTCGAGAAG<br>AAGGACAGCCTAACCGCCCCCTCTGAGTTCGCCACCACCGCCTCCACCGATG<br>CCGCCAACGCGCCTACCACCTTCCCCGTCGAGGCACCCCCGCTTGAGGAGGA<br>GGAAGTGATTATCGAGCAGGACCCAGGTTTTGTAAGCGAAGACGACGAGGA<br>CCGCTCAGTACCAACAGAGGATAAAAAGCAAGACCAGGACAACGCAGAGGC<br>AAACGAGGAACAAGTCGGGCGGGGGACGAAAGGCATGGCGACTACCTAGA<br>TGTGGGAGACGACGTGCTGTTGAAGCATCTGCAGCGCCAGTGCGCCATTATC<br>TGCGACGCGTTGCAAGAGCGCAGCGATGTGCCCCTCGCCATAGCGGATGTCA<br>GCCTTGCCTACGAACGCCACCTATTCTCACCGCGCGTACCCCCAAACGCCAA<br>GAAAACGGCACATGCGAGCCCAACCCGCGCCTCAACTTCTACCCCGTATTTG<br>CCGTGCCAGAGGTGCTTGCCACCCTATCACATCTTTTTCCAAAACTGCAAGATA<br>CCCCTATCCTGCCGTGCCAACCGCAGCCGAGCGGACAAGCAGCTGGCCTTGC<br>GGCAGGGCGCTGTCATACCTGATATCGCCTCGCTCAACGAAGTGCCAAAAAT<br>CTTTGAGGGTCTTGGACGCGACGAGAAGCGCGCGGCAAACGCTCTGCAACAG<br>GAAAACAGCGAAAATGAAAGTCACTCTGGAGTGTTGGTGGAACTCGAGGGT<br>GACAACGCGCGCCTAGCCGTACTAAAACGCAGCATCGAGGTCACCCACTTTG<br>CCTACCCGGCACTTAACCTACCCCCCAAGGTCATGAGCACAGTCATGAGTGA<br>GCTGATCGTGCGCCGTGCGCAGCCCCTGGAGAGGGATGCAAATTTGCAAGAA<br>CAAACAGAGGAGGGCCTACCCGCAGTTGGCGACGAGCAGCTAGCGCGCTGG<br>CTTCAAACGCGCGAGCCTGCCGACTTGGAGGAGCGACGCAAACTAATGATGG<br>CCGCAGTGCTCGTTACCGTGGAGCTTGAGTGCATGCAGCGGTTCTTTGCTGAC<br>CCGGAGATGCAGCGCAAGCTAGAGGAAACATTGCACTACACCTTTCGACAGG<br>GCTACGTACGCCAGGCCTGCAAGATCTCCAACGTGGAGCTCTGCAACCTGGT<br>CTCCTACCTTGGAATTTTGCACGAAAACCGCCTTGGGCAAAACGTGCTTCATT<br>CCACGCTCAAGGGCGAGGCGCGCCGCGACTACGTCCGCGACTGCGTTTACTT<br>ATTTCTATGCTACACCTGGCAGACGGCCATGGGCGTTTGGCAGCAGTGCTTGG<br>AGGAGTGCAACCTCAAGGAGCTGCAGAAACTGCTAAAGCAAAACTTGAAGG<br>ACCTATGGACGGCCTTCAACGAGCGCTCCGTGGCCGCGCACCTGGCGGACAT<br>CATTTTCCCCGAACGCCTGCTTAAAACCCTGCAACAGGGTCTGCCAGACTTCA<br>CCAGTCAAAGCATGTTGCAGAACTTTAGGAACTTTATCCTAGAGCGCTCAGG<br>AATCTTGCCCGCCACCTGCTGTGCACTTCCTAGCGACTTTGTGCCCATTAAGT<br>ACCGCGAATGCCCTCCGCCGCTTTGGGGCCACTGCTACCTTCTGCAGCTAGCC<br>AACTACCTTGCCTACCACTCTGACATAATGGAAGACGTGAGCGGTGACGGTC<br>TACTGGAGTGTCACTGTCGCTGCAACCTATGCACCCCGCACCGCTCCCTGGTT<br>TGCAATTCGCAGCTGCTTAACGAAAGTCAAATTATCGGTACCTTTGAGCTGCA<br>GGGTCCCTCGCCTGACGAAAAGTCCGCGGCTCCGGGGTTGAAACTCACTCCG<br>GGGCTGTGGACGTCGGCTTACCTTCGCAAATTTGTACCTGAGGACTACCACGC<br>CCACGAGATTAGGTTCTACGAAGACCAATCCCGCCCGCCTAATGCGGAGCTT<br>ACCGCCTGCGTCATTACCCAGGGCCACATTCTTGGCCAATTGCAAGCCATCAA<br>CAAAGCCCGCCAAGAGTTTCTGCTACGAAAGGGACGGGGGTTTACTTGGAC<br>CCCCAGTCCGGCGAGGAGCTCAACCCAATCCCCCCGCCGCCGCAGCCCTATC<br>AGCAGCAGCCGCGGGCCCTTGCTTCCCAGGATGGCACCCAAAAAGAAGCTGC<br>AGCTGCCGCCGCCACCCACGGACGAGGAGGAATACTGGGACAGTCAGGCAG<br>AGGAGGTTTTGGACGAGGAGGAGGAGGACATGATGGAAGACTGGGAGAGCC<br>TAGACGAGGAAGCTTCCGAGGTCGAAGAGGTGTCAGACGAAACACCGTCAC<br>CCTCGGTCGCATTCCCCTCGCCGGCGCCCCAGAAATCGGCAACCGGTTCCAG<br>CATGGCTACAACCTCCGCTCCTCAGGCGCCGCCGGCACTGCCCGTTCGCCGAC<br>CCAACCGTAGATGGGACACCACTGGAACAGGGCCGGTAAGTCCAAGCAGC<br>CGCCGCCGTTAGCCCAAGAGCAACAACAGCGCCAAGGCTACCGCTCATGGCG<br>CGGGCACAAGAACGCCATAGTTGCTTGCTTGCAAGACTGTGGGGCAACATC<br>TCCTTCGCCCGCCGCTTTCTTCTCTACCATCACGGCGTGGCCTTCCCCCGTAAC |

| SEQ ID NO | Sequence |
|---|---|
| | ATCCTGCATTACTACCGTCATCTCTACAGCCCATACTGCACCGGCGGCAGCGG<br>CAGCAACAGCAGCGGCCACACAGAAGCAAAGGCGACCGGATAGCAAGACTC<br>TGACAAAGCCCAAGAAATCCACAGCGGCGGCAGCAGCAGGAGGAGGAGCGC<br>TGCGTCTGGCGCCCAACGAACCCGTATCGACCCGCGAGCTTAGAAACAGGAT<br>TTTTCCCACTCTGTATGCTATATTTCAACAGAGCAGGGGCCAAGAACAAGAG<br>CTGAAAATAAAAAACAGGTCTCTGCGATCCCTCACCCGCAGCTGCCTGTATC<br>ACAAAAGCGAAGATCAGCTTCGGCGCACGCTGGAAGACGCGGAGGCTCTCTT<br>CAGTAAATACTGCGCGCTGACTCTTAAGGACTAGTTTCGCGCCCTTTCTCAAA<br>TTTAAGCGCGAAAACTACGTCATCTCCAGCGGCCACACCCGGCGCCAGCACC<br>TGTTGTCAGCGCCATTATGAGCAAGGAAATTCCCACGCCCTACATGTGGAGTT<br>ACCAGCCACAAATGGGACTTGCGGCTGGAGCTGCCCAAGACTACTCAACCCG<br>AATAAACTACATGAGCGCGGGACCCCACATGATATCCCGGGTCAACGGAATA<br>CGCGCCCACCGAAACCGAATTCTCCTGGAACAGGCGGCTATTACCACCACAC<br>CTCGTAATAACCTTAATCCCCGTAGTTGGCCCGCTGCCCTGGTGTACCAGGAA<br>AGTCCCGCTCCCACCACTGTGGTACTTCCCAGAGACGCCCAGGCCGAAGTTC<br>AGATGACTAACTCAGGGGCGCAGCTTGCGGGCGGCTTTCGTCACAGGGTGCG<br>GTCGCCCGGGCAGGGTATAACTCACCTGACAATCAGAGGGCGAGGTATTCAG<br>CTCAACGACGAGTCGGTGAGCTCCTCGCTTGGTCTCCGTCCGGACCTGGACATT<br>TCAGATCGGCGGCGCCGGCCGCTCTTCATTCACGCCTCGTCAGGCAATCCTAA<br>CTCTGCAGACCTCGTCTCTGAGCCGCGCTCTGGAGGCATTGGAACTCTGCAA<br>TTTATTGAGGAGTTTGTGCCATCGGTCTACTTTAACCCCTTCTCGGGACCTCCC<br>GGCCACTATCCGGATCAATTTATTCCTAACTTTGACGCGGTAAAGGACTCGGC<br>GGACGGCTACGACTGAATGTTAAGTGGAGAGGCAGAGCAACTGCGCCTGAA<br>ACACCTGGTCCACTGTCGCCGCCACAAGTGCTTTGCCCGCGACTCCGGTGAGT<br>TTTGCTACTTTGAATTGCCCGAGGATCATATCGAGGGCCCGGCGCACGGCGTC<br>CGGCTTACCGCCCAGGGAGAGCTTGCCCGTAGCCTGATTCGGGAGTTTACCC<br>AGCGCCCCTGCTAGTTGAGCGGGACAGGGGACCCTGTGTTCTCACTGTGATT<br>TGCAACTGTCCTAACCCTGGATTACATCAAGATCCTCTAGTTAATGTCAGGTC<br>GCCTAAGTCGATTAACTAGAGTACCCGGGGATCTTATTCCCTTTAACTAATAA<br>AAAAAAATAATAAAGCATCACTTACTTAAAATCAGTTAGCAAATTTCTGTCC<br>AGTTTATTCAGCAGCACCTCCTTGCCCTCCTCCCAGCTCTGGTATTGCAGCTTC<br>CTCCTGGCTGCAAACTTTCTCCACAATCTAAATGGAATGTCAGTTTCCTCCTG<br>TTCCTGTCCATCCGCACCCACTATCTTCATGTTGTTGCAGATGAAGCGCGCAA<br>GACCGTCTGAAGATACCTTCAACCCCGTGTATCCATATGACACGGAAACCGG<br>TCCTCCAACTGTGCCTTTTCTTACTCCTCCCTTTGTATCCCCCAATGGGTTTCA<br>AGAGAGTCCCCCTGGGGTACTCTCTTTGCGCCTATCCGAACCTCTAGTTACCT<br>CCAATGGCATGCTTGCGCTCAAAATGGGCAACGGCCTCTCTCTGGACGAGGC<br>CGGCAACCTTACCTCCCAAAATGTAACCACTGTGAGCCCACCTCTCAAAAAA<br>ACCAAGTCAAACATAAACCTGGAAATATCTGCACCCCTCACAGTTACCTCAG<br>AAGCCCCTAACTGTGGCTGCCGCCGCACCTCTAATGGTCGCGGGCAACACACT<br>CACCATGCAATCACAGGCCCCGCTAACCGTGCACGACTCCAAACTTAGCATT<br>GCCACCCAAGGACCCCTCACAGTGTCAGAAGGAAAGCTAGCCCTGCAAACAT<br>CAGGCCCCCTCACCACCACCGATAGCAGTACCCTTACTATCACTGCCTCACCC<br>CCTCTAACTACTGCCACTGGTAGCTTGGGCATTGACTTGAAAGAGCCCATTTA<br>TACACAAAATGGAAAACTAGGACTAAAGTACGGGGCTCCTTTGCATGTAACA<br>GACGACCTAAACACTTTGACCGTAGCAACTGGTCCAGGTGTGACTATTAATA<br>ATACTTCCTTGCAAACTAAAGTTACTGGAGCCTTGGGTTTTGATTCACAAGGC<br>AATATGCAACTTAATGTAGCAGGAGGACTAAGGATTGATTCTCAAAACAGAC<br>GCCTTATACTTGATGTTAGTTATCCGTTTGATGCTCAAAACCAACTAAATCTA<br>AGACTAGGACAGGGCCCTCTTTTTATAAACTCAGCCCACAACTTGGATATTAA<br>CTACAACAAAGGCCTTTACTTGTTTACAGCTTCAAACAATTCCAAAAAGCTTG<br>AGGTTAACCTAAGCACTGCCAAGGGGTTGATGTTTGACGCTACAGCCATAGC<br>CATTAATGCAGGAGATGGGCTTGAATTTGGTTCACCTAATGCACCAAACACA<br>AATCCCCTCAAAACAAAAATTGGCCATGGCCTAGAATTTGATTCAAACAAGG<br>CTATGGTTCCTAAACTAGGAACTGGCCTTAGTTTTGACAGCACAGGTGCCATT<br>ACAGTAGGAAACAAAATAATGATAAGCTAACTTTGTGGACCACACCAGCTC<br>CATCTCCTAACTGTAGACTAAATGCAGAGAAAGATGCTAAACTCACTTTGGT<br>CTTAACAAAATGTGGCAGTCAAATACTTGCTACAGTTTCAGTTTTGGCTCTTTA<br>AAGGCAGTTTGGCTCCAATATCTGGAACAGTTCAAAGTGCTCATCTTATTATA<br>AGATTTGACGAAAATGGAGTGCTACTAAACAATTCCTTCCTGGACCCAGAAT<br>ATTGGAACTTTAGAAATGGAGATCTTACTGAAGGCACAGCCTATACAAACGC<br>TGTTGGATTTATGCCTAACCTATCAGCTTATCAAAATCTCACGGTAAAACTG<br>CCAAAAGTAACATTGTCAGTCAAGTTTACTTAAACGGAGACAAAACTAAACC<br>TGTAACACTAACCATTACACTAAACGGTACACAGGAAACAGGAGACACAACT<br>CCAAGTGCATACTCTATGTCATTTTCATGGGACTGGTCTGGCCACAACTACAT<br>TAATGAAATATTTGCCACATCCTCTTACACTTTTTCATACATTGCCCAAGAAT<br>AAAGAATCGTTTGTGTTATGTTTCAACGTGTTTATTTTTCAATTGCAGAAAAT<br>TTCAAGTCATTTTTCATTCAGTAGTATAGCCCCACCACCACATAGCTTATACA<br>GATCACCGTACCTTAATCAAACTCACAGAACCCTAGTATTCAACCTGCCACCT<br>CCCTCCCAACACACAGAGTACACAGTCCTTTCTCCCCGGCTGGCCTTAAAAG<br>CATCATATCATGGGTAACAGACATATTCTTAGGTGTTATATTCCACACGGTTT<br>CCTGTCGAGCCAAACGCTCATCAGTGATATTAATAAACTCCCCGGGCAGCTC<br>ACTTAAGTTCATGTCGCTGTCCAGCTGCTGAGCCACAGGCTGCTGTCCAACTT |

| SEQ ID NO | Sequence |
|---|---|
| | GCGGTTGCTTAACGGGCGGCGAAGGAGAAGTCCACGCCTACATGGGGGTAG<br>AGTCATAATCGTGCATCAGGATAGGGCGGTGGTGCTGCAGCAGCGCGCGAAT<br>AAACTGCTGCCGCCGCCGCTCCGTCCTGCAGGAATACAACATGGCAGTGGTC<br>TCCTCAGCGATGATTCCTCACCGCCCGCAGCATAAGGCGCCTTGTCCTCCGGGC<br>ACAGCAGCGCACCCTGATCTCACTTAAATCAGCACAGTAACTGCAGCACAGC<br>ACCACAATATTGTTCAAAATCCCACAGTGCAAGGCGCTGTATCCAAAGCTCA<br>TGGCGGGGACCACAGAACCCACGTGGCCATCATACCACAAGCGCAGGTAGAT<br>TAAGTGGCGACCCCTCATAAACACGCTGGACATAAACATTACCTCTTTTGGCA<br>TGTTGTAATTCACCACCTCCCGGTACCATATAAACCTCTGATTAAACATGGCG<br>CCATCCACCACCATCCTAAACCAGCTGGCCAAAACCTGCCCGCCGGCTATAC<br>ACTGCAGGGAACCCGGGACTGGAACAATGACAGTGGAGAGCCCAGGACTCGT<br>AACCATGGATCATCATGCTCGTCATGATATCAATGTTGGCACAACACAGGCA<br>CACGTGCATACACTTCCTCAGGATTACAAGCTCCTCCCGCGTTAGAACCATAT<br>CCCAGGGAACAACCCATTCCTGAATCAGCGTAAATCCCACACTGCAGGGAAG<br>ACCTCGCACGTAACTCACGTTGTGCATTGTCAAAGTGTTACATTCGGGCAGCA<br>GCGGATGATCCTCCAGTATGGTAGCGCGGGTTTCTGTCTCAAAAGGAGGTAG<br>ACGATCCCTACTGTACGGAGTGCGCCGAGACAACCGAGATCGTGTTGGTCGT<br>AGTGTCATGCCAAATGGAACGCCGGACGTAGTCATATTTCCTGAAGCAAAAC<br>CAGGTGCGGGCGTGACAAACAGATCTGCGTCTCCGGTCTCGCCGCTTAGATC<br>GCTCTGTGTAGTAGTTGTAGTATATCCACTCTCTCAAAGCATCCAGGCGCCCC<br>CTGGCTTCGGGTTCTATGTAAACTCCTTCATGCGCCGCTGCCCTGATAACATC<br>CACCACCGCAGAATAAGCCACACCCAGCCAACCTACACATTCGTTCTGCGAG<br>TCACACACGGGAGGAGCGGGAAGAGCTGGAAGAACCATGTTTTTTTTTTTAT<br>TCCAAAAGATTATCAAAACCTCAAAATGAAGATCTATTAAGTGAACGCGCT<br>CCCCTCCGGTGGCGTGGTCAAACTCTACAGCCAAAGAACAGATAATGGCATT<br>TGTAAGATGTTGCACAATGGCTTCCAAAAGGCAAACGGCCCTCACGTCCAAG<br>TGGACGTAAAGGCTAAACCCTTCAGGGTGAATCTCCTCTATAAACATTCCAG<br>CACCTTCAACCATGCCCAAATAATTCTCATCTCGCCACCTTCTCAATATATCT<br>CTAAGCAAATCCCGAATATTAAGTCCGGCCATTGTAAAAATCTGCTCCAGAG<br>CGCCCTCCACCTTCAGCCTCAAGCAGCGAATCATGATTGCAAAAATTCAGGTT<br>CCTCACAGACCTGTATAAGATTCAAAAGCGGAACATTAACAAAAATACCGCG<br>ATCCCGTAGGTCCCTTCGCAGGGCCAGCTGAACATAATCGTGCAGGTCTGCA<br>CGGACCAGCGCGGCCACTTCCCCGCCAGGAACCATGACAAAAGAACCCACAC<br>TGATTATGACACGCATACTCGGAGCTATGCTAACCAGCGTAGCCCCGATGTA<br>AGCTTGTTGCATGGGCGGCGATATAAAATGCAAGGTGCTGCTCAAAAAATCA<br>GGCAAAGCCTCGCGCAAAAAAGAAAGCACATCGTAGTCATGCTCATGCAGAT<br>AAAGGCAGGTAAGCTCCGGAACCACCACAGAAAAAGACACCATTTTTCTCTC<br>AAACATGTCTGCGGGTTTCTGCATAAACACAAAATAAAATAACAAAAAAACA<br>TTTAAACATTAGAAGCCTGTCTTACAACAGGAAAAACAACCCTTATAAGCAT<br>AAGACGGACTACGGCCATGCCGGCGTGACCGTAAAAAAACTGGTCACCGTGA<br>TTAAAAAGCACCACCGACAGCTCCTCGGTCATGTCCGGAGTCATAATGTAAG<br>ACTCGGTAAACACATCAGGTTGATTCACATCGGTCAGTGCTAAAAAGCGACC<br>GAAATAGCCCGGGGAATACATACCCGCAGGCGTAGAGACAACATTACAGC<br>CCCCATAGGAGGTATAACAAAATTAATAGGAGAGAAAAACACATAAACACC<br>TGAAAAACCCTCCTGCCTAGGCAAAATAGCACCCTCCCGCTCCAGAACAACA<br>TACAGCGCTTCCACAGCGGCAGCCATAACAGTCAGCCTTACCAGTAAAAAAG<br>AAAACCTATTAAAAAAACACCACTCGACACGGCACCAGCTCAATCAGTCACA<br>GTGTAAAAAAGGGCCAAGTGCAGAGCGAGTATATATAGGACTAAAAAATGA<br>CGTAACGGTTAAAGTCCACAAAAAACACCCAGAAAACCGCACGCGAACCTA<br>CGCCCAGAAACGAAAGCCAAAAAACCCACAACTTCCTCAAATCGTCACTTCC<br>GTTTTCCCACGTTACGTCACTTCCCATTTTAAGAAAACTACAATTCCCAACAC<br>ATACAAGTTACTCCGCCCTAAAACCTACGTCACCCGCCCCGTTCCCACGCCCC<br>GCGCCACGTCACAAACTCCACCCCCTCATTATCATATTGGCTTCAATCCAAAA<br>TAAGGTATATTATTGATGAT |
| SEQ ID NO: 90 | CATCATCAATAATATACCTTATTTTGGATTGAAGCCAATATGATAATGAGGGG<br>GTGGAGTTTGTGACGTGGCGCGGGCGTGGGAACGGGGCGGGTGACGTAGT<br>AGTGTGGCCTCTAAGTGTGATGTTGCAAGTGTGGCGGAACACATGTAAGCGACG<br>GATGTGGCAAAAGTGACGTTTTTGGTGTGCGCCGGTGTACACAGGAAGTGAC<br>AATTTTCGCGCGGTTTTAGGCGGATGTTGTAGTAAATTTGGGCGTAACCGAGT<br>AAGATTTGGCCATTTTCGCGGGAAAACTGAATAAGAGGAAGTGAAATCTGAA<br>TAATTTTGTGTTACTCATAGCGCGTAATACTGTAATAGTAATCAATTACGGGG<br>TCATTAGTTCATAGCCCATATATGGAGTTCCGCGTTACATAACTTACGGTAAA<br>TGGCCCGCCTGGCTGACCGCCCAACGACCCCCGCCCATTGACGTCAATAATG<br>ACGTATGTTCCCATAGTAACGCCAATAGGGACTTTCCATTGACGTCAATGGGT<br>GGAGTATTTACGGTAAACTGCCCACTTGGCAGTACATCAAGTGTATCATATGC<br>CAAGTACGCCCCCTATTGACGTCAATGACGGTAAATGGCCCGCCTGGCATTA<br>TGCCCAGTACATGACCTTATGGGACTTTCCTACTTGGCAGTACATCTACGTAT<br>TAGTCATCGCTATTACCATGGTGATGCGGTTTTGGCAGTACATCAATGGGCGT<br>GGATAGCGGTTTGACTCACGGGGATTTCCAAGTCTCCACCCCATTGACGTCAA<br>TGGGAGTTTGTTTTGGCACCAAAATCAACGGGACTTTCCAAAATGTCGTAAC<br>AACTCCGCCCCATTGACGCAAATGGGCGGTAGGCGTGTACGGTGGGAGGTCT<br>ATATAAGCAGAGCTGGTTTAGTGAACCGTCAGATCCGCTAGAGATCTGGTAC |

SEQUENCES

| SEQ ID NO | Sequence |
|---|---|
| | CGTCGACGCGGCCGCTCGAGCCTAAGCTTCTAGATGCATGCTCGAGCGGCCG<br>CCAGTGTGATGGATATCTGCAGAATTCGCCCTTGCTTCTAGAGCCACCATGAG<br>CTCCCCTGGCACCGAGAGCGCGGGAAAGAGCCTGCAGTACCGAGTGGACCAC<br>CTGCTGAGCGCCGTGGAGAATGAGCTGCAGGCGGGCAGCGAGAAGGGCGAC<br>CCCACAGAGCGCGAACTGCGCGTGGGCCTGGAGGAGAGCGAGCTGTGGCTG<br>CGCTTCAAGGAGCTCACCAATGAGATGATCGTGACCAAGAACGGCAGGAGG<br>ATGTTTCCGGTGCTGAAGGTGAACGTGTCTGGCCTGGACCCCAACGCCATGT<br>ACTCCTTCCTGCTGGACTTCGTGGCGGCGACAACCACCGCTGGAAGTACGT<br>GAACGGGGAATGGGTGCCGGGGGGCAAGCCGGAGCCGCAGGCGCCCAGCTG<br>CGTCTACATCCACCCCGACTCGCCCAACTTCGGGGCCCACTGGATGAAGGCT<br>CCCGTCTCCTTCAGCAAAGTCAAGCTCACCAACAAGCTCAACGGAGGGGCC<br>AGATCATGCTGAACTCCTTGCATAAGTATGAGCCTCGAATCCACATAGTGAG<br>AGTTGGGGGTCCACAGCGCATGATCACCAGCCACTGCTTCCCTGAGACCCAG<br>TTCATAGCGGTGACTGCTAGAAGTGATCACAAAGAGATGATGAGGAACCCG<br>GAGACAGCCAGCAACCTGGGTACTCCCAATGGGGGTGGCTTCTTCCTGGAAC<br>CAGCACCGTGTGTCCACCTGCAAATCCTCATCCTCAGTTTGGAGGTGCCCTCT<br>CCCTCCCCTCCACGCACAGCTGTGACAGGTACCCAACCCTGAGGAGCCACCG<br>GTCCTCACCCTACCCCAGCCCCTATGCTCATCGGAACAATTCTCCAACCTATT<br>CTGACAACTCACCTGCATGTTTATCCATGCTGCAATCCCATGACAATTGGTCC<br>AGCCTTGGAATGCCTGCCCATCCCAGCATGCTCCCCGTGAGCCACAATGCCA<br>GCCCACCTACCAGCTCCAGTCAGTACCCCAGCCTGTGGTCTGTGAGCAACGG<br>CGCCGTCACCCCGGGCTCCCAGGCAGCAGCCGTGTCCAACGGGCTGGGGGCC<br>CAGTTCTTCCGGGGCTCCCCCGCGCACTACACACCCCTCACCCATCCGGTCTC<br>GGCCGCCCTCTTCCTCGGGATCCCCACTGTACGAAGGGGCGGCCGCGGCCACA<br>GACATCGTGGACAGCCAGTACGACGCCGCAGCCCAAGGCCGCCTCATAGCCT<br>CATGGACACCTGTGTCGCCACCTTCCATGTGAGATATCCGATCCACCGGATCT<br>AGATAACTGATCATAATCAGCCATACCACATTTGTAGAGGTTTTACTTGCTTT<br>AAAAAACCTCCCACACCTCCCCCTGAACCTGAAACATAAAATGAATGCAATT<br>GTTGTTGTTAACTTGTTTTATTGCAGCTTATAATGGTTACAAATAAAGCAATAG<br>CATCACAAATTTCACAAATAAAGCATTTTTTTCACTGCATTCTAGTTGTGGTTT<br>GTCCAAACTCATCAATGTATCTTAACGCGGATCTGGAAGGTGCTGAGGTACG<br>ATGAGACCCGCACCAGGTGCAGACCCTGCGAGTGTGGCGGTAAACATATTAG<br>GAACCAGCCTGTGATGCTGGATGTGACCGAGGAGCTGAGGCCCGATCACTTG<br>GTGCTGGCCTGCACCCGCGCTGAGTTTGGCTCTAGCGATGAAGATACAGATT<br>GAGGTACTGAAATGTGTGGGCGTGGCTTAAGGGTGGGAAAGAATATATAAG<br>GTGGGGGTCTTATGTAGTTTTGTATCTGTTTTGCAGCAGCCGCCGCCGCCATG<br>AGCACCAACTCGTTTGATGGAAGCATTGTGAGCTCATATTTGACAACGCGCA<br>TGCCCCCATGGGCCGGGGTGCGTCAGAATGTGATGGGCTCCAGCATTGATGG<br>TCGCCCCGTCCTGCCCGCAAACTCTACTACCTTGACCTACGAGACCGTGTCTG<br>GAACGCCGTTGGAGACTGCAGCCTCCGCCGCCGCTTCAGCCGCTGCAGCCAC<br>CGCCCGCGGGATTGTGACTGACTTTGCTTTCCTGAGCCCGCTTGCAAGCAGTG<br>CAGCTTCCCGTTCATCCGCCCGCGATGACAAGTTGACGGCTCTTTTGGCACAA<br>TTGGATTCTTTGACCCGGGAACTTAATGTCGTTTCTCAGCAGCTGTTGGATCT<br>GCGCCAGCAGGTTTCTGCCCTGAAGGCTTCCTCCCCTCCCAATGCGGTTTAAA<br>ACATAAATAAAAAACCAGACTCTGTTTGGATTTGGATCAAGCAAGTGTCTTG<br>CTGTCTTTATTTAGGGGTTTTGCGCGCGCGGTAGGCCCGGGACCAGCGGTCTC<br>GGTCGTTGAGGGTCCTGTGTATTTTTTCCAGGACGTGGTAAAGGTGACTCTGG<br>ATGTTCAGATACATGGGCATAAGCCCGTCTCTGGGGTGGAGGTAGCACCACT<br>GCAGAGCTTCATGCTGCGGGTGGTGTTGTAGATGATCCAGTCGTAGCAGGA<br>GCGCTGGGCGTGGTGCCTAAAAATGTCTTTCAGTAGCAAGCTGATTGCCAGG<br>GGCAGGCCCTTGGTGTAAGTGTTTACAAAGCGGTTAAGCTGGGATGGGTGCA<br>TACGTGGGGATATGAGATGCATCTTGGACTGTATTTTAGGTTGGCTATGTTC<br>CCAGCCATATCCCTCCGGGGATTCATGTTGTGCAGAACCACCAGCACAGTGT<br>ATCCGGTGCACTTGGGAAATTTGTCATGTAGCTTAGAAGGAAATGCGTGGAA<br>GAACTTGGAGACGCCCTTGTGACCTCCAAGATTTTCCATGCATTCGTCCATAA<br>TGATGGCAATGGGCCCACGGCGGCGGCCTGGGCGAAGATATTTCTGGGATC<br>ACTAACGTCATAGTTGTGTTCCAGGATGAGATCGTCATAGGCCATTTTTACAA<br>AGCGCGGGCGGAGGGTGCCAGACTGCGGTATAATGGTTCCATCCGGCCCAGG<br>GGCGTAGTTACCCTCACAGATTTGCATTTCCCACGCTTTGAGTTCAGATGGGG<br>GGATCATGTCTACCTGCGGGGCGATGAAGAAAACGGTTTCCGGGGTAGGGA<br>GATCAGCTGGGAAGAAAGCAGGTTCCTGAGCAGCTGCGACTTACCGCAGCCG<br>GTGGGCCCGTAAATCACACCTATTACCGGCTGCAACTGGTAGTTAAGAGAGC<br>TGCAGCTGCCGTCATCCCTGAGCAGGGGGCCACTTCGTTAAGCATGTCCCTG<br>ACTCGCATGTTTTCCCTGACCAAATCCGCCAGAAGGCGCTCGCCGCCCAGCG<br>ATAGCAGTTCTTGCAAGGAAGCAAAGTTTTTCAACGGTTTGAGACCGTCCGC<br>CGTAGGCATGCTTTTGAGCGTTTGACCAAGCAGTTCCAGGCGGTCCCACAGCT<br>CGGTCACCTGCTCTACGGCATCTCGATCCAGCATATCTCCTCGTTTCGCGGGT<br>TGGGGCGGCTTTCGCTGTACGGCAGTAGTCGGTGCTCGTCCAGACGGCCCAG<br>GGTCATGTCTTTCCACGGGCGCAGGGTCCTCGTCAGCGTAGTCTGGGTCACGG<br>TGAAGGGGTGCGCTCCGGGCTGCGCGCTGGCCAGGGTGCGCTTGAGGCTGGT<br>CCTGCTGGTGCTGAAGCGCTGCCGGTCTTCGCCCTGCGCGTCGGCCAGGTAGC<br>ATTTGACCATGGTGTCATAGTCCAGCCCCTCCGCGGCGTGGCCCTTGGCGCGC<br>AGCTTGCCCTTGGAGGAGGCGCCGCACGAGGGGCAGTGCAGACTTTTGAGGG |

| SEQ ID NO | Sequence |
|---|---|
| | CGTAGAGCTTGGGCGCGAGAAATACCGATTCCGGGGAGTAGGCATCCGCGCC<br>GCAGGCCCCGCAGACGGTCTCGCATTCCACGAGCCAGGTGAGCTCTGGCCGT<br>TCGGGGTCAAAAACCAGGTTTCCCCCATGCTTTTTGATGCGTTTCTTACCTCT<br>GGTTTCCATGAGCCGGTGTCCACGCTCGGTGACGAAAAGGCTGTCCGTGTCC<br>CCGTATACAGACTTGAGAGGCCTGTCCTCGAGCGGTGTTCCGCGGTCCTCCTC<br>GTATAGAAACTCGGACCACTCTGAGACAAAGGCTCGCGTCCAGGCCAGCACG<br>AAGGAGGCTAAGTGGGAGGGGTAGCGGTCGTTGTCCACTAGGGGGTCCACTC<br>GCTCCAGGGTGTGAAGACACATGTCGCCCTCTTCGGCATCAAGGAAGGTGAT<br>TGGTTTGTAGGTGTAGGCCACGTGACCGGGTGTTCCTGAAGGGGGCTATAA<br>AAGGGGGTGGGGCGCGTTCGTCCTCACTCTCTTCCGCATCGCTGTCTGCGAG<br>GGCCAGCTGTTGGGGTGAGTACTCCCTCTGAAAAGCGGGCATGACTTCTGCG<br>CTAAGATTGTCAGTTTCCAAAAACGAGGAGGATTTGATATTCACCTGGCCCG<br>CGGTGATGCCTTTGAGGGTGGCCGCATCCATCTGGTCAGAAAAGACAATCTT<br>TTTGTTGTCAAGCTTGGTGGCAAACGACCCGTAGAGGGCGTTGGACAGCAAC<br>TTGGCGATGGAGCGCAGGGTTTGGTTTTTGTCGCGATCGGCGCGCTCCTTGGC<br>CGCGATGTTTAGCTGCACGTATTCGCGCGCAACGCACCGCCATTCGGGAAAG<br>ACGGTGGTGCGCTCGTCGGGCACCAGGTGCACGCGCCAACCGCGGTTGTGCA<br>GGGTGACAAGGTCAACGCTGGTGGCTACCTCTCCGCGTAGGCGCTCGTTGGT<br>CCAGCAGAGGCGGCCGCCCTTGCGCGAGCAGAATGGCGGTAGGGGGTCTAG<br>CTGCGTCTCGTCCGGGGGGTCTGCGTCCACGGTAAAGACCCCGGGCAGCAGG<br>CGCGCGTCGAAGTAGTCTATCTTGCATCCTTGCAAGTCTAGCGCCTGCTGCCA<br>TGCGCGGGCGGCAAGCGCGCGCTCGTATGGGTTGAGTGGGGGACCCCATGGC<br>ATGGGGTGGGTGAGCGCGGAGGCGTACATGCCGCAAATGTCGTAAACGTAG<br>AGGGGCTCTCTGAGTATTCCAAGATATGTAGGGTAGCATCTTCCACCGCGGA<br>TGCTGGCGCGCACGTAATCGTATAGTTCGTGCGAGGGAGCGAGGAGGTCGGG<br>ACCGAGGTTGCTACGGGCGGGCTGCTCTGCTCGGAAGACTATCTGCCTGAAG<br>ATGGCATGTGAGTTGGATGATATGGTTGGACGCTGGAAGACGTTGAAGCTGG<br>CGTCTGTGAGACCTACCGCGTCACGCACGAAGGAGGCGTAGGAGTCGCGCAG<br>CTTGTTGACCAGCTCGGCGGTGACCTGCACGTCTAGGGCGCAGTAGTCCAGG<br>GTTTCCTTGATGATGTCATACTTATCCTGTCCCTTTTTTTTCCACAGCTCGCGG<br>TTGAGGACAAACTCTTCGCGGTCTTTCCAGTACTCTTGGATCGGAAACCCGTC<br>GGCCTCCGAACGGTAAGAGCCTAGCATGTAGAACTGGTTGACGGCCTGGTAG<br>GCGCAGCATCCCTTTTCTACGGGTAGCGCGTATGCCTGCGCGGCCTTCCGGCA<br>TGACCAGCATGAAGGGCACGAGCTGCTTCCCAAAGGCCCCCATCCAAGTATA<br>GGTCTCTACATCGTAGGTGACAAAGAGACGCTCGGTGCGAGGATGCGAGCCG<br>ATCGGGAAGAACTGGATCTCCCGCCACCAATTGGAGGAGTGGCTATTGATGT<br>GGTGAAAGTAGAAGTCCCTGCGACGGGCCGAACACTCGTGCTGGCTTTTGTA<br>AAAACGTGCGCAGTACTGGCAGCGGTGCACGGGCTGTACATCCTGCACGAGG<br>TTGACCTGACGACCGCGCACAAGGAAGCAGAGTGGGAATTTGAGCCCCTCGC<br>CTGGCGGGTTTGGCTGGTGGTCTTCTACTTCGGCTGCTTGTCCTTGACCGTCTG<br>GCTGCTCGAGGGGAGTTACGGTGGATCGGACCACCACGCCGCGCGAGCCCAA<br>AGTCCAGATGTCCGCGCGCGGCGGTCGGAGCTTGATGACAACATCGCGCAGA<br>TGGGAGCTGTCCATGGTCTGGAGCTCCCGCGGCGTCAGGTCAGGCGGGAGCT<br>CCTGCAGGTTTACCTCGCATAGACGGGTCAGGGCGCGGGCTAGATCCAGGTG<br>ATACCTAATTTCCAGGGGCTGGTTGGTGGCGGCGTCGATGGCTTGCAAGAGG<br>CCGCATCCCCGCGGCGCGACTACGGTACCGCGCGGCGGGCGGTGGGCCGCGG<br>GGGTGTCCTTGGATGATGCATCTAAAAGCGGTGACGCGGGCGAGCCCCCGGA<br>GGTAGGGGGGCTCCGGACCCGCCGGGAGAGGGGGCAGGGGCACGTCGGCG<br>CCGCGCGCGGGCAGGAGCTGGTGCTGCGCGCGTAGGTTGCTGGCGAACGCGA<br>CGACGCGGCGGTTGATCTCCTGAATCTGGCGCCTCTGCGTGAAGACGACGGG<br>CCCGGTGAGCTTGAACCTGAAAGAGAGTTCGACAGAATCAATTTCGGTGTCG<br>TTGACGGCGGCCTGGCGCAAAATCTCCTGCACGTCTCCTGAGTTGTCTTGATA<br>GGCGATCTCGGCCATGAACTGCTCGATCTCTTCCTCCTGGAGATCTCCGCGTC<br>CGGCTCGCTCCACGGTGGCGGCGAGGTCGTTGGAAATGCGGGCCATGAGCTG<br>CGAGAAGGCGTTGAGGCCTCCCTCGTTCCAGACGCGGCTGTAGACCACGCCC<br>CCTTCGGCATCGCGGGCGCGCATGACCACCTGCGCGAGATTGAGCTCCACGT<br>GCCGGGCGAAGACGGCGTAGTTTCGCAGGCGCTGAAAGAGGTAGTTGAGGG<br>TGGTGGCGGTGTGTTCTGCCACGAAGAAGTACATAACCCAGCGTCGCAACGT<br>GGATTCGTTGATAATTGTTGTGTAGGTACTCCGCCGCCGAGGGACCTGAGCG<br>AGTCCGCATCGACCGGATCGGAAAACCTCTCGAGAAAGGCGTCTAACCAGTC<br>ACAGTCGCAAGGTAGGCTGAGCACCGTGGCGGGCGGCAGCGGGCGGCGGTC<br>GGGGTTGTTTCTGGCGGAGGTGCTGCTGATGATGTAATTAAAGTAGGCGGTC<br>TTGAGACGGCGGATGGTCGACAGAAGCACCATGTCCTTGGGTCCGGCCTGCT<br>GAATGCGCAGGCGGTCGGCCATGCCCCAGGCTTCGTTTTGACATCGGCGCAG<br>GTCTTTGTAGTAGTCTTGCATGAGCCTTTCTACCGGCACTTCTTCTTCTCCTTC<br>CTCCTTGTCCTGCATCTCTTGCATCTATCGCTGCGGCGGCGGCGGAGTTTGGCC<br>GTAGGTGGCGCCCTCTTCCTCCCATGCGTGTGACCCCGAAGCCCTCATCGGC<br>TGAAGCAGGGCTAGGTCGGCGACAACGCGCTCGGCTAATATGGCCTGCTGCA<br>CCTGCGTGAGGGTAGACTGGAAGTCATCCATGTCCACAAAGCGGTGGTATGC<br>GCCCGTGTTGATGGTGTAAGTGCAGTTGGCCATAACGACCAGTTAACGCTTC<br>TGGTGACCCGGCTGCGAGAGCTCGGTGTACCTGAGACGCGAGTAAGCCCTCG<br>AGTCAAATACGTAGTCGTTGCAAGTCCGCACCAGGTACTGGTATCCCACCAA<br>AAAGTGCGGCGGCGGCTGGCGGTAGAGGGGCCAGCGTAGGGTGGCCGGGGC |

| SEQ ID NO | Sequence |
|---|---|
| | TCCGGGGGCGAGATCTTCCAACATAAGGCGATGATATCCGTAGATGTACCTG<br>GACATCCAGGTGATGCCGGCGGCGGTGGTGGAGGCGCGCGGAAAGTCGCGG<br>ACGCGGTTCCAGATGTTGCGCAGCGGCAAAAAGTGCTCCATGGTCGGGACGC<br>TCTGGCCGGTCAGGCGCGCGCAATCGTTGACGCTCTAGCGTGCAAAAGGAGA<br>GCCTGTAAGCGGGCACTCTTCCGTGGTCTGGTGGATAAATTCGCAAGGGTAT<br>CATGGCGGACGACCGGGGTTCGAGCCCCGTATCCGGCCGTCCGCCGTGATCC<br>ATGCGGTTACCGCCCGCGTGTCGAACCCAGGTGTGCGACGTCAGACAACGGG<br>GGAGTGCTCCTTTTGGCTTCCTTCCAGGCGCGGCGGCTGCTGCGCTAGCTTTT<br>TTGGCCACTGGCCGCGCGCAGCGTAAGCGGTTAGGCTGGAAAGCGAAAGCAT<br>TAAGTGGCTCGCTCCCTGTAGCCGGAGGGTTATTTTCCAAGGGTTGAGTCGCG<br>GGACCCCCGGTTCGAGTCTCGGACCGGCCGGACTGCGGCGAACGGGGGTTTG<br>CCTCCCCGTCATGCAAGACCCCGCTTGCAAATTCCTCCGGAAACAGGGACGA<br>GCCCCTTTTTGCTTTTCCCAGATGCATCCGGTGCTGCGGCAGATGCGCCCCC<br>CTCCTCAGCAGCGGCAAGAGCAAGAGCAGCGGCAGACATGCAGGGCACCCT<br>CCCCTCCTCCTACCGCGTCAGGAGGGGCGACATCCGCGGTTGACGCGGCAGC<br>AGATGGTGATTACGAACCCCCGCGGCGCCGGGCCCGGCACTACCTGGACTTG<br>GAGGAGGGCGAGGGCCTGGCGCGGCTAGGAGCGCCCTCTCCTGAGCGGCAC<br>CCAAGGGTGCAGCTGAAGCGTGATACGCGTGAGGCGTACGTGCCGCGGCAG<br>AACCTGTTTCGCGACCGCGAGGGAGAGGAGCCCGAGGAGATGCGGGATCGA<br>AAGTTCCACGCAGGGCGCGAGCTGCGGCATGGCCTGAATCGCGAGCGGTTGC<br>TGCGCGAGGAGGACTTTGAGCCCGACGCGCGAACCGGGATTAGTCCCGCGCG<br>CGCACACGTGGCGGCCGCCGACCTGGTAACCGCATACGAGCAGACGGTGAAC<br>CAGGAGATTAACTTTCAAAAAAGCTTTAACAACCACGTGCGTACGCTTGTGG<br>CGCGCGAGGAGGTGGCTATAGGACTGATGCATCTGTGGGACTTTGTAAGCGC<br>GCTGGAGCAAAACCCAAATAGCAAGCCGCTCATGGCGCAGCTGTTCCTTATA<br>GTGCAGCACAGCAGGGACAACGAGGCATTCAGGGATGCGCTGCTAAACATA<br>GTAGAGCCCGAGGGCCGCTGGCTGCTCGATTTGATAAACATCCTGCAGAGCA<br>TAGTGGTGCAGGAGCGCAGCTTGAGCCTGGCTGACAAGGTGGCCGCCATCAA<br>CTATTCCATGCTTAGCCTGGGCAAGTTTTACGCCCGCAAGATATACCATACCC<br>CTTACGTTCCCATAGACAAGGAGGTAAAGATCGAGGGGTTCTACATGCGCAT<br>GGCGCTGAAGGTGCTTACCTTGAGCGACGACCTGGGCGTTTATCGCAACGAG<br>CGCATCCACAAGGCCGTGAGCGTGAGCCGGCGGCGCGAGCTCAGCGACCGC<br>GAGCTGATGCACAGCCTGCAAAGGGCCCTGGCTGGCACGGGCAGCGGCGAT<br>AGAGAGGCCGAGTCCTACTTTGACGCGGGCGCTGACCTGCGCTGGGCCCCAA<br>GCCGACGCGCCCTGGAGGCAGCTGGGGCCGGACCTGGGCTGGCGGTGGCACC<br>CGCGCGCGCTGGCAACGTCGGCGGCGTGGAGGAATATGACGAGGACGATGA<br>GTACGAGCCAGAGGACGGCGAGTACTAAGCGGTGATGTTTCTGATCAGATGA<br>TGCAAGACGCAACGGACCCGGCGGTGCGGGCGGCGCTGCAGAGCCAGCCGT<br>CCGGCCTTAACTCCACGGACGACTGGCCTCCAGGTCATGGACCGCATCATGTC<br>GCTGACTGCGCGCAATCCTGACGCGTTCCGGCAGCAGCCGCAGGCCAACCGG<br>CTCTCCGCAATTCTGGAAGCGGTGGTCCCGGCGCGCGCAAACCCCACGCACG<br>AGAAGGTGCTGGCGATCGTAAACGCGCTGGCCGAAAACAGGGCCATCCGGC<br>CCGACGAGGCCGGCCTGGTCTACGACGCGCTGCTTCAGCGCGTGGCTCGTTA<br>CAACAGCGGCAACGTGCAGACCAACCTGGACCGGCTGGTGGGGGATGTGCG<br>CGAGGCCGTGGCGCAGCGTGAGCGCGCGCAGCAGCAGGGCAACCTGGGCTC<br>CATGGTTGCACTAAACGCCTTCCTGAGTACACAGCCCGCCAACGTGCCGCGG<br>GGACAGGAGGACTACACCAACTTTGTGAGCGCACTGCGGCTAATGGTGACTG<br>AGACACCGCAAAGTGAGGTGTACCAGTCTGGGCCAGACTATTTTTTCCAGAC<br>CAGTAGACAAGGCCTGCAGACCGTAAACCTGAGCCAGGCTTTCAAAAACTTG<br>CAGGGGCTGTGGGGGTGCGGGCTCCCACAGGCGACCGCGCGACCGTGTCTA<br>GCTTGCTGACGCCCAACTCGCGCCTGTTGCTGCTGCTAATAGCGCCCTTCACG<br>GACAGTGGCAGCGTGTCCCGGGACACATACCTAGGTCACTTGCTGACACTGT<br>ACCGCGAGGCCATAGGTCAGGCGCATGTGGACGAGCATACTTTCCAGGAGAT<br>TACAAGTGTCAGCCGCGCGCTGGGGCAGGAGGACACGGGCAGCCTGGAGGC<br>AACCCTAAACTACCTGCTGACCAACCGGCGGCAGAAGATCCCTCGTTGCAC<br>AGTTTAAACAGCGAGGAGGAGCGCATTTTGCGCTACGTGCAGCAGAGCGTGA<br>GCCTTAACCTGATGCGCGACGGGGTAACGCCCAGCGTGGCGCTGGACATGAC<br>CGCGCGCAACATGGAACCGGGCATGTATGCCTCAAACCGGCCGTTTATCAAC<br>CGCCTAATGGACTACTTGCATCGCGCGGCCGCCGTGAACCCCGAGTATTTCAC<br>CAATGCCATCTTGAACCCGCACTGGTACCGCCCCCTGGTTTCTACACCGGGG<br>GATTCGAGGTGCCCGAGGGTAACGATGGATTCCTCTGGGACGACATAGACGA<br>CAGCGTGTTTTCCCCGCAACCGCAGACCCTGCTAGAGTTGCAACAGCGCGAG<br>CAGGCAGAGGCGGCGCTGCGAAAGGAAAGCTTCCGCAGGCCAAGCAGCTTG<br>TCCGATCTAGGCGCTGCGGCCCCGCGGTCAGATGCTAGTAGCCCATTTCCAA<br>GCTTGATAGGGTCTCTTACCAGCACTCGCACCACCCGCCCGCGCCTGCTGGGC<br>GAGGAGGAGTACCTAAACAACTCGCTGCTGCAGCCGCAGCGCGAAAAAAAC<br>CTGCCTCGGCATTTCCCAACAACGGGATAGAGCCTAGTGGACAAGATGA<br>GTAGATGGAAGACGTACGCGCAGGAGCACAGGGACGTGCCAGGCCCGCGCC<br>CGCCCACCCGTCGTCAAAGGCACGACCGTCAGCGGGGTCTGGTGTGGGAGGA<br>CGATGACTCGGCAGACGACAGCAGCGTCCTGGATTTGGGAGGGAGTGGCAAC<br>CCGTTTGCGCACCTTCGCCCCAGGCTGGGGAGAATGTTTTAAAAAAAAAAAA<br>GCATGATGCAAAATAAAAAACTCACCAAGGCCATGGCACCGAGCGTTGGTTT<br>TCTTGTATTCCCCTTAGTATGCGGCGCGCGGCGATGTATGAGGAAGGTCCTCC |

| SEQ ID NO | Sequence |
|---|---|
| | TCCCTCCTACGAGAGTGTGGTGAGCGCGGCGCCAGTGGCGGCGGCGCTGGGT<br>TCTCCCTTCGATGCTCCCCTGGACCCGCCGTTTGTGCCTCCGCGGTACCTGCG<br>GCCTACCGGGGGAGAAACAGCATCCGTTACTCTGAGTTGGCACCCCTATTC<br>GACACCCACCCGTGTGTACCTGGTGGACAACAAGTCAACGGATGTGGCATCCC<br>TGAACTACCAGAACGACCACAGCAACTTTCTGACCACGGTCATTCAAAACAA<br>TGACTACAGCCCGGGGAGGCAAGCACACAGACCATCAATCTTGACGACCGG<br>TCGCACTGGGGCGGCGACCTGAAAACCATCCTGCATACCAACATGCCAAATG<br>TGAACGAGTTCATGTTTACCAATAAGTTTAAGGCGCGGGTGATGGTGTCGCG<br>CTTGCCTACTAAGGACAATCAGGTGGAGCTGAAATACGAGTGGGTGGAGTTC<br>ACGCTGCCCGAGGGCAACTACTCCGAGACCATGACCATAGACCTTATGAACA<br>ACGCGATCGTGGAGCACTACTTGAAAGTGGGCAGACAGAACGGGGTTCTGGA<br>AAGCGACATCGGGGTAAAGTTTGACACCCGCAACTTCAGACTGGGGTTTGAC<br>CCCGTCACTGGTCTTGTCATGCCTGGGGTATATACAAACGAAGCCTTCCATCC<br>AGACATCATTTTGCTGCCAGGATGCGGGGTGGACTTCACCCACAGCCGCCTG<br>AGCAACTTGTTGGGCATCCGCAAGCGGCAACCCTTCCAGGAGGGCTTTAGGA<br>TCACCTACGATGATCTGGAGGGTGGTAACATTCCCGCACTGTTGGATGTGGA<br>CGCCTACCAGGCGAGCTTGAAAGATGACACCGAACAGGGCGGGGGTGGCGC<br>AGGCGGCAGCAACAGCAGTGGCAGCGGCGCGGAAGAGAACTCCAACGCGGC<br>AGCCGCGGCAATGCAGCCGGTGGAGGACATGAACGATCATGCCATTCGCGGC<br>GACACCTTTGCCACACGGGCTGAGGAGAAGCGCGCTGAGGCCGAAGCAGCG<br>GCCGAAGCTGCCGCCCCCGCTGCGCAACCCGAGGTCGAGAAGCCTCAGAAGA<br>AACCGGTGATCAAACCCTGACAGAGGACAGCAAGAAACGCAGTTACAACC<br>TAATAAGCAATGACAGCACCTTCACCCAGTACCGCAGCTGGTACCTTGCATA<br>CAACTACGGCGACCCTCAGACCGGAATCCGCTCATGGACCCTGCTTTGCACTC<br>CTGACGTAACCTGCGGCTCGGAGCAGGTCTACTGGTCGTTGCCAGACATGAT<br>GCAAGACCCCGTGACCTTCCGCTCCACGCGCCAGATCAGCAACTTTCCGGTG<br>GTGGGCGCCGAGCTGTTGCCCGTGCACTCCAAGAGCTTCTACAACGACCAGG<br>CCGTCTACTCCCAACTCATCCGCCAGTTTACCTCTCTGACCCACGTGTTCAAT<br>CGCTTTCCCGAGAACCAGATTTTGGCGCGCCCGCCAGCCCCCACCATCACCAC<br>CGTCAGTGAAAACGTTCCTGCTCTCACAGATCACGGGACGCTACCGCTGCGC<br>AACAGCATCGGAGGAGTCCAGCGAGTGACCATTACTGACGCCAGACGCCGCA<br>CCTGCCCCTACGTTTACAAGGCCCTGGGCATAGTCTCGCCGCGCGTCCTATCG<br>AGCCGCACTTTTTGAGCAAGCATGTCCATCCTTATATCGCCCAGCAATAACAC<br>AGGCTGGGGCCTGCGCTTCCCAAGCAAGATGTTTGGCGGGGCCAAGAAGCGC<br>TCCGACCAACACCCAGTGCGCGTGCGCGGGCACTACCGCGCGCCCTGGGGCG<br>CGCACAAACGCGGCCGCACTGGGCGCACCACCGTCGATGACGCCATCGACGC<br>GGTGGTGGAGGAGGCGCGCAACTACACGCCCACGCCGCCACCAGTGTCCACA<br>GTGGACGCGGCCATTCAGACCGGTGGTGCGCGGAGCCCGGCGCTATGCTAAAA<br>TGAAGAGACGGCGGAGGCGCGTAGCACGTCGCCACCGCCGCCGACCCGGCA<br>CTGCCGCCCAACGCGCGGCGGCGGCCCTGCTTAACCGCGCACGTCGCACCGG<br>CCGACGGGCGGCCATGCGGGCCGCTCGAAGGCTGGCCGCGGGTATTGTCACT<br>GTGCCCCCCAGGTCCAGGCGACGAGCGGCCGCCGCAGCAGCCGCGGCCATTA<br>GTGCTATGACTCAGGGTCGCAGGGGCAACGTGTATTGGGTGCGCGACTCGGT<br>TAGCGGCCTGCGCGTGCCCGTGCGCACCCGCCCCCCGCGCAACTAGATTGCA<br>AGAAAAAAACTACTTAGACTCGTACTGTTGTATGTATCCAGCGGCGGCGGCG<br>GCAACGAAGCTATGTCCAAGCGCAAAATCAAAGAAGAGATGCTCCAGGTCAT<br>CGCGCCGGAGATCTATGGCCCCCCGAAGAAGGAAGAGCAGGATTACAAGCC<br>CCGAAAGCTAAAGCGGGTCAAAAAGAAAAAGAAAGATGATGATGATGAACT<br>TGACGACGAGGTGGAACTGCTGCACGCTACCGCGCCCAGGCGACGGGTACAG<br>TGGAAAGGTCGACGCGTAAAACGTGTTTTGCGACCCGGCACCACCGTAGTCT<br>TTACGCCCGGTGAGCGCTCCACCCGCACCTACAAGCGCGTGTATGATGAGGT<br>GTACGGCGACGAGGACCTGCTTGAGCAGGCCAACGAGCGCCTCGGGGAGTTT<br>GCCTACGGAAAGCGGCATAAGGACATGCTGGCGTTGCCGCTGGACGAGGGC<br>AACCCAACACCTAGCCTAAAGCCCGTAACACTGCAGCAGGTGCTGCCCGCGC<br>TTGCACCGTCCGAAGAAAAGCGCGGCCTAAAGCGCGAGTCTGGTGACTTGGC<br>ACCCACCGTGCAGCTGATGGTACCCAAGCGCCAGCGACTGGAAGATGTCTTG<br>GAAAAAATGACCGTGGAACCTGGGCTGGAGCCCGAGGTCCGCGTGCGGCCA<br>ATCAAGCAGGTGGCGCCGGGACTGGGCGTGCAGACCGTGGACGTTCAGATAC<br>CCACTACCAGTAGCACCAGTATTGCCACCGCCACAGAGGGCATGGAGACACA<br>AACGTCCCCGGTTGCCTCAGCGGTGGCGGATGCCGCGGTGCAGGCGGTCGCT<br>GCGGCCGCGTCCAAGACCTCTACGGAGGTGCAAACGGACCCGTGGATGTTTC<br>GCGTTTCAGCCCCCCGGCGCCCGCGCCGTTCGAGGAAGTACGGCGCCGCCAG<br>CGCGCTACTGCCCGAATATGCCCTACATCCTTCCATTGCGCCTACCCCCGGCT<br>ATCGTGGCTACACCTACCGCCCCAGAAGACGAGCAACTACCCGACGCCGAAC<br>CACCACTGGAACCCGCCGCCGCCGTCGCCGTCGCCAGCCCGTGCTGGCCCCG<br>ATTTCCGTGCGCAGGGTGGCTCGCGAAGGAGGCAGGACCCTGGTGCTGCCAA<br>CAGCGCGCTACCACCCCAGCATCGTTTAAAAGCCGGTCTTTGTGGTTCTTGCA<br>GATATGGCCCTCACCTGCCGCCTCCGTTTCCCGGTGCCGGGATTCCGAGGAAG<br>AATGCACCGTAGGAGGGGCATGGCCGGCCACGGCCTGACGGGCGGCATGCG<br>TCGTGCGCACCACCGGCGGCGGCGCGCGTCGCACCGTCGCATGCGCGGCGGT<br>ATCCTGCCCCTCCTTATTCCACTGATCGCCGCGGCGATTGGCGCCGTGCCCGG<br>AATTGCATCCGTGGCCTTGCAGGCGCAGAGACACTGATTAAAAACAAGTTGC<br>ATGTGGAAAAATCAAAATAAAAAGTCTGGACTCTCACGCTCGCTTGGTCCTG |

| SEQ ID NO | Sequence |
|---|---|
| | TAACTATTTTGTAGAATGGAAGACATCAACTTTGCGTCTCTGGCCCCGCGACA<br>CGGCTCGCGCCCGTTCATGGGAAACTGGCAAGATATCGGCACCAGCAATATG<br>AGCGGTGGCGCCTTCAGCTGGGGCTCGCTGTGGAGCGGCATTAAAAATTTCG<br>GTTCACCGTTAAGAACTATGGCAGCAAGGCCTGGAACAGCAGCACAGGCCA<br>GATGCTGAGGGATAAGTTGAAAGAGCAAAATTTCCAACAAAAGGTGGTAGA<br>TGGCCTGGCCTCTGGCATTAGCGGGGTGGTGGACCTGGCCAACCAGGCAGTG<br>CAAAATAAGATTAACAGTAAGCTTGATCCCCGCCCTCCCGTAGAGGGAGCCTC<br>CACCGGCCGTGGAGACAGTGTCTCCAGAGGGGCGTGGCGAAAAGCGTCCGC<br>GCCCCGACAGGGAAGAAACTCTGGTGACGCAAATAGACGAGCCTCCCTCGTA<br>CGAGGAGGCACTAAAGCAAGGCCTGCCCACCACCCGTCCCATCGCGCCCATG<br>GCTACCGGAGTGCTGGGCCAGCACACACCCGTAACGCTGGACCTGCCTCCCC<br>CCGCCGACACCCAGCAGAAACCTGTGCTGCCAGGCCCGACCGCCGTTGTTGT<br>AACCCGTCCTAGCCGCGCGTCCCTGCGCCGCGCCGCCAGCGGTCCGCGATCG<br>TTGCGGCCCGTAGCCAGTGGCAACTGGCAAAGCACACTGAACAGCATCGTGG<br>GTCTGGGGGTGCAATCCCTGAAGCGCCGACGATGCTTCTGATAGCTAACGTG<br>TCGTATGTGTGTCATGTATGCGTCCATGTCGCCGCCAGAGGAGCTGCTGAGCC<br>GCCGCGCGCCCGCTTTCCAAGATGGCTACCCCTTCGATGATGCCGCAGTGGTC<br>TTACATGCACATCTCGGGCCAGGACGCCTCGGAGTACCTGAGCCCCGGGCTG<br>GTGCAGTTTGCCCGCGCCACCGAGACGTACTTCAGCCTGAATAACAAGTTTA<br>GAAACCCCACGGTGGCGCCTACGCACGACGTGACCACAGACCGGTCCCAGCG<br>TTTGACGCTGCGGTTCATCCCTGTGGACCGTGAGGATACTGCGTACTCGTACA<br>AGGCGCGGTTCACCCTAGCTGTGGGTGATAACCGTGTGCTGGACATGGCTTC<br>CACGTACTTTGACATCCGCGGCGTGCTGGACAGGGGCCCTACTTTTAAGCCCT<br>ACTCTGGCACTGCCTACAACGCCCTGGCTCCCAAGGGTGCCCCAAATCCTTGC<br>GAATGGGATGAAGCTGCTACTGCTCTTGAAATAAACCTAGAAGAAGAGGACG<br>ATGACAACGAAGACGAAGTAGACGAGCAAGCTGAGCAGCAAAAAACTCACG<br>TATTTGGGCAGGCGCCTTATTCTGGTATAAATATTACAAAGGAGGGTATTCAA<br>ATAGGTGTCGAAGGTCAAACACCTAAATATGCCGATAAAACATTTCAACCTG<br>AACCTCAAATAGGAGAATCTCAGTGGTACGAAACAGAAATTAATCATGCAGC<br>TGGGAGAGTCCTAAAAAAGACTACCCCAATGAAACCATGTTACGGTTCATAT<br>GCAAAACCCACAAATGAAATGGAGGGCAAGGCATTCTTGTAAAGCAACAA<br>AATGGAAAGCTAGAAAGTCAAGTGGAAATGCAATTTTTCTCAACTACTGAGG<br>CAGCCGCAGGCAATGGTGATAACTTGACTCCTAAAGTGGTATTGTACAGTGA<br>AGATGTAGATATAGAAACCCCAGACACTCATATTTCTTACATGCCCACTATTA<br>AGGAAGGTAACTCACGAGAACTAATGGGCCAACAATCTATGCCCAACAGGCC<br>TAATTACATTGCTTTTAGGGACAATTTTATTGGTCTAATGTATTACAACAGCA<br>CGGGTAATATGGGTGTTCTGGCGGGCCAAGCATCGCAGTTGAATGCTGTTGT<br>AGATTTGCAAGACAGAAACACAGAGCTTTTCATACCAGCTTTTGCTTGATTCCA<br>TTGGTGATAGAACCAGGTACTTTTCTATGTGGAATCAGGCTGTTGACAGCTAT<br>GATCCAGATGTTAGAATTATTGAAAATCATGGAACTGAAGATGAACTTCCAA<br>ATTACTGCTTTCCACTGGGAGGTGTGATTAATACAGAGACTCTTACCAAGGTA<br>AAACCTAAAACAGGTCAGGAAAATGGATGGGAAAAAGATGCTACAGAATTT<br>TCAGATAAAAATGAAATAAGAGTTGGAAATAATTTTGCCATGGAAATCAATC<br>TAAATGCCAACCTGTGGAGAAATTTCCTGTACTCCAACATAGCGCTGTATTTG<br>CCCGACAAGCTAAAGTACAGTCCTTCCAACGTAAAAATTTCTGATAACCCAA<br>ACACCTACGACTACATGAACAAGCGAGTGGTGGCTCCCGGGCTAGTGGACTG<br>CTACATTAACCTTGGAGCACGCTGGTCCCTTGACTATATGGACAACGTCAACC<br>CATTTAACCACCACCGCAATGCTGGCCTGCGCTACCGCTCAATGTTGCTGGGC<br>AATGGTCGCTATGTGCCCTTCCACATCCAGGTGCCTCAGAAGTTCTTTGCCAT<br>TAAAAACCTCCTTCTCCTGCCGGGCTCATACACCTACGAGTGGAACTTCAGGA<br>AGGATGTTAACATGGTTCTGCAGAGCTCCCTAGGAAATGACCTAAGGGTTGA<br>CGGAGCCAGCATTAAGTTTGATACTCATTTGCCTTTACGCCACCTTCTTCCCCA<br>TGGCCCACAACACCGCCTCCACGCTTGAGGCCATGCTTAGAAACGACACCAA<br>CGACCAGTCCTTTAACGACTATCTCTCCGCCGCCAACATGCTCTACCCTATAC<br>CCGCCAACGCTACCAACGTGCCCATATCCATCCCCTCCCGCAACTGGGCGGCT<br>TTCCGCGGCTGGGCCTTCACGCGCCTTAAGACTAAGGAAACCCCATCACTGG<br>GCTCGGGCTACGACCCTTATTACACCTACTCTGGCTCTATACCCTACCTAGAT<br>GGAACCTTTTACCTCAACCACACCTTTAAGAAGGTGGCCATTACCTTTGACTC<br>TTCTGTCAGCTGGCCTGGCAATGACCGCCTGCTTACCCCCAACGAGTTTGAAA<br>TTAAGCGCTCAGTTGACGGGGAGGGTTACAACGTTGCCCAGTGTAACATGAC<br>CAAAGACTGGTTCCTGGTACAAATGCTAGCTAACTATAACATTGGCTACCAG<br>GGCTTCTATATCCCAGAGAGCTACAAGGACCGCATGTACTCCTTCTTTAGAAA<br>CTTCCAGCCCATGAGCCGTCAGGTGGTGGATGATACTAAATACAAGGACTAC<br>CAACAGGTGGGCATCCTACACCAACACAACAACTCTGGATTTGTTGGCTACC<br>TTGCCCCCACCATGCGCGAAGGACAGGCCTACCCTGCTAACTTCCCCTATCCG<br>CTTATAGGCAAGACCGCAGTTGACAGCATTACCCAGAAAAAGTTTCTTTGCG<br>ATCGCACCCTTTGGCGCATCCCATTCTCCAGTAACTTTATGTCCATGGGCGCA<br>CTCACAGACCTGGGCCAAAACCTTCTCTACGCCAACTCCGCCCACGCGCTAG<br>ACATGACTTTTGAGGTGGATCCCATGGACGAGCCCACCCTTCTTTATGTTTTG<br>TTTGAAGTCTTTGACGTGGTCCGTGTGCACCAGCCGCACCGCGGCGTCATCGA<br>AACCGTGTACCTGCGCACGCCCTTCTCGGCCGGCAACGCCACAACATAAAGA<br>AGCAAGCAACATCAACAACAGCTGCCGCCATGGGCTCCAGTGAGCAGGAACT<br>GAAAGCCATTGTCAAAGATCTTGGTTGTGGGCCATATTTTTTGGGCACCTATG |

-continued

| SEQUENCES | |
|---|---|
| SEQ ID NO | Sequence |
| | ACAAGCGCTTTCCAGGCTTTGTTTCTCCACACAAGCTCGCCTGCGCCATAGTC AATACGGCCGGTCGCGAGACTGGGGGCGTACACTGGATGGCCTTTGCCTGGA ACCCGCACTCAAAAACATGCTACCTCTTTGAGCCCTTTGGCTTTTCTGACCAG CGACTCAAGCAGGTTTACCAGTTTGAGTACGAGTCACTCCTGCGCCGTAGCG CCATTGCTTCTTCCCCCGACCGCTGTATAACGCTGGAAAAGTCCACCCAAAGC GTACAGGGGCCCAACTCGGCCGCCTGTGGACTATTCTGCTGCATGTTTCTCCA CGCCTTTGCCAACTGGCCCCAAACTCCCATGGATCACAACCCCACCATGAAC CTTATTACCGGGGTACCCAACTCCATGCTCAACAGTCCCCAGGTACAGCCCAC CCTGCGTCGCAACCAGGAACAGCTCTACAGCTTCCTGGAGCGCCACTCGCCC TACTTCCGCAGCCACAGTGCGCAGATTAGGAGCGCCACTTCTTTTTGTCACTT GAAAAACATGTAAAAATAATGTACTAGAGACACTTTCAATAAAGGCAAATGC TTTTATTTGTACACTCTCGGGTGATTATTTACCCCCACCCTTGCCGTCTGCGCC GTTTAAAAATCAAAGGGGTTCTGCCGCGCATCGCTATGCGCCACTGGCAGGG ACACGTTGCGATACTGGTGTTTAGTGCTCCACTTAAACTCAGGCACAACCATC CGCGGCAGCTCGGTGAAGTTTTCACTCCACAGGCTGCGCACCATCACCAACG CGTTTAGCAGGTCGGGCGCCGATATCTTGAAGTCGCAGTTGGGGCCTCCGCC CTGCGCGCGCGAGTTGCGATACACAGGGTTGCAGCACTGGAACACTATCAGC GCCGGGTGGTGCACGCTGGCCAGCACGCTCTTGTCGGAGATCAGATCCGCGT CCAGGTCCTCCGCGTTGCTCAGGGCGAACGGAGTCAACTTTGGTAGCTGCCTT CCCAAAAAGGGCGCGTGCCCAGGCTTTGAGTTGCACTCGCACCGTAGTGGCA TCAAAAGGTGACCGTGCCCGGTCTGGGCGTTAGGATACAGCGCCTGCATAAA AGCCTTGATCTGCTTAAAAGCCACCTGAGCCTTTGCGCCTTCAGAGAAGAAC ATGCCGCAAGACTTGCCGGAAAACTGATTGGCCGGACAGGCCGCGTCGTGCA CGCAGCACCTTGCGTCGGTGTTGGAGATCTGCACCACATTTCGGCCCCACCGG TTCTTCACGATCTTGGCCTTGCTAGACTGCTCCTTCAGCGCGCGCTGCCCGTTT TCGCTCGTCACATCCATTTCAATCACGTGCTCCTTATTTATCATAATGCTTCCG TGTAGACACTTAAGCTCGCCTTCGATCTCAGCGCAGCGGTGCAGCCACAACG CGCAGCCCGTGGGCTCGTGATGCTTGTAGGTCACCTCTGCAAACGACTGCAG GTACGCCTGCAGGAATCGCCCCATCATCGTCACAAAGGTCTTGTTGCTGGTGA AGGTCAGCTGCAACCCGCGGTGCTCCTCGTTCAGCCAGGTCTTGCATACGGCC GCCAGAGCTTCCACTTGGTCAGGCAGTAGTTTGAAGTTCGCCTTTAGATCGTT ATCCACGTGGTACTTGTCCATCAGCGCGCGCGCAGCCTCCATGCCCTTCTCCC ACGCAGACACGATCGGCACACTCAGCGGGTTCATCACCGTAATTTCACTTTCC GCTTCGCTGGGCTCTTCCTCTTCCTCTTGCGTCCGCATACCACGCGCCACTGG GTCGTCTTCATTCAGCCGCCGCACTGTGCGCTTACCTCCTTTGCCATGCTTGAT TAGCACCGGTGGGTTGCTGAAACCCACCATTTGTAGCGCCACATCTTCTCTTT CTTCCTCGCTGTCCACGATTACCTCTGGTGATGGCGGGCGCTCGGGCTTGGGA GAAGGGCGCTTCTTTTTCTTCTTGGGCGCAATGGCCAAATCCGCCGCCGAGGT CGATGGCCGCGGGCTGGGTGTGCGCGGCACCAGCGCGTCTTGTGATGAGTCT TCCTCGTCCTCGGACTCGATACGCCGCCTCATCCGCTTTTTTGGGGCGCCCG GGGAGGCGGCGGCGACGGGACGGGACGACACGTCCTCCATGGTTGGGGG ACGTCGCGCCGCACCGCGTCCGCGCTCGGGGGTGGTTTCGCGCTGCTCCTCTT CCCGACTGGCCATTTCCTTCTCCTATAGGCAGAAAAAGATCATGGAGTCAGTC GAGAAGAAGGACAGCCTAACCGCCCCCTCTGAGTTCGCCACCACCGCCTCCA CCGATGCCGCCAACGCGCCTACCACCTTCCCCGTCGAGGCACCCCCGCTTGA GGAGGAGGAAGTGATTATCGAGCAGGACCCAGGTTTTGTAAGCGAAGACGA CGAGGACCGCTCAGTACCAACAGAGGATAAAAAGCAAGACCAGGACAACGC AGAGGCAAACGAGGAACAAGTCGGGCGGGGGGACGAAAGGCATGGCGACTA CCTAGATGTGGGAGACGACGTGCTGTTGAAGCATCTGCAGCGCCAGTGCGCC ATTATCTGCGACGCGTTGCAAGAGCGCAGCGATGCCCCTCGCCATAGCGG ATGTCAGCCTTGCCTACGAACGCCACCTATTCTCACCGCGCGTACCCCCCAAA CGCCAAGAAAACGGCACATGCGAGCCCAACCCGCGCCTCAACTTCTACCCCG TATTTGCCGTGCCAGAGGTGCTTGCCACCTATCACATCTTTTTCCAAAACTGC AAGATACCCCTATCCTGCCGTGCCAACCGCAGCCGAGCGGACAAGCAGCTGG CCTTGCGGCAGGGCGCTGTCATACCTGATATCGCCTCGCTCAACGAAGTGCC AAAAATCTTTGAGGGTCTTGGACGCGACGAGAAGCGCGCGGCAAACGCTCTG CAACAGGAAAACAGCGAAAATGAAAGTCACTCTGGAGTGTTGGTGGAACTC GAGGGTGACAACGCGCGCCTAGCCGTACTAAAACGCAGCATCGAGGTCACCC ACTTTGCCTACCCGGCACTTAACCTACCCCCAAGGTCATGAGCACAGTCATG AGTGAGCTGATCGTGCGCCGTGCGCAGCCCTGGAGAGGGATGCAAATTTGC AAGAACAAACAGAGGAGGGCCTACCCGCAGTTGGCGACGAGCAGCTAGCGC GCTGGCTTCAAACGCGCGAGCCTGCCGACTTGGAGGAGCGACGCAAACTAAT GATGGCCGCAGTGCTCGTTACCGTGGAGCTTGAGTGCATGCAGCGGTTCTTTG CTGACCCGGAGATGCAGCGCAAGCTAGAGGAAACATTGCACTACACCTTTCG ACAGGGCTACGTACGCCAGGCCTGCAAGATCTCCAACGTGGAGCTCTGCAAC CTGGTCTCCTACCTTGGAATTTTGCACGAAAACGCCTTGGGCAAACGTGCT TCATTCCACGCTCAAGGGCGAGGCGCGCGCGACTACGTCCGCGACTGCGTT TACTTATTTCTATGCTACACCTGGCAGACGGCCATGGGCGTTTGGCAGCAGTG CTTGGAGGAGTGCAACCTCAAGGAGCTGCAGAAACTGCTAAAGCAAAACTTG AAGGACCTATGGACGGCCTTCAACGAGCGCTCCGTGGCCGCGCACCTGGCGG ACATCATTTTCCCCGAACGCCTGCTTAAAACCCTGCAACAGGGTCTGCCAGAC TTCACCAGTCAAAGCATGTTGCAGAACTTTAGGAACTTTATCCTAGAGCGCTC AGGAATCTTGCCCGCCACCTGCTGTGCACTTCCTAGCGACTTTGTGCCCATTA |

-continued

| SEQ ID NO | Sequence |
|---|---|
| | AGTACCGCGAATGCCCTCCGCCGCTTTGGGGCCACTGCTACCTTCTGCAGCTA
GCCAACTACCTTGCCTACCACTCTGACATAATGGAAGACGTGAGCGGTGACG
GTCTACTGGAGTGTCACTGTCGCTGCAACCTATGCACCCCGCACCGCTCCCTG
GTTTGCAATTCGCAGCTGCTTAACGAAAGTCAAATTATCGGTACCTTTGAGCT
GCAGGGTCCCTCGCCTGACGAAAAGTCCGCGGCTCCGGGGTTGAAACTCACT
CCGGGGCTGTGGACGTCGGCTTACCTTCGCAAATTTGTACCTGAGGACTACCA
CGCCCACGAGATTAGGTTCTACGAAGACCAATCCCGCCCGCCTAATGCGGAG
CTTACCGCCTGCGTCATTACCCAGGGCCACATTCTTGGCCAATTGCAAGCCAT
CAACAAAGCCCGCCAAGAGTTTCTGCTACGAAAGGGACGGGGGGTTTACTTG
GACCCCCAGTCCGGCGAGGAGCTCAACCCAATCCCCCCGCCGCCGCAGCCCT
ATCAGCAGCAGCCGCGGGCCCTTGCTTCCCAGGATGGCACCCAAAAAGAAGC
TGCAGCTGCCGCCGCCACCCACGGACGAGGAGGAATACTGGGACAGTCAGG
CAGAGGAGGTTTTGGACGAGGAGGAGGAGGACATGATGGAAGACTGGGAGA
GCCTAGACGAGGAAGCTTCCGAGGTCGAAGAGGTGTCAGACGAAACACCGT
CACCCTCGGTCGCATTCCCTCGCCGGCGCCCCAGAAATCGGCAACCGGTTCC
AGCATGGCTACAACCTCCGCTCCTCAGGCGCCGCCGGCACTGCCCGTTCGCC
GACCCAACCGTAGATGGGACACCACTGGAACCAGGGCCGGTAAGTCCAAGC
AGCCGCCGCCGTTAGCCCAAGAGCAACAACAGCGCCAAGGCTACGTCTCATG
GCGCGGGCACAAGAACGCCATAGTTGCTTGCTTGCAAGACTGTGGGGCAAC
ATCTCCTTCGCCCGCCGCTTTCTTCTCTACCATCACGGCGTGGCCTTCCCCCGT
AACATCCTGCATTACTACCGTCATCTCTACAGCCCATACTGCACCGGCGGCAG
CGGCAGCAACAGCAGCGGCCACACAGAAGCAAAGGCGACCGGATAGCAAGA
CTCTGACAAAGCCCAAGAAATCCACAGCGGCGGCAGCAGCAGGAGGAGGAG
CGCTGCGTCTGGCGCCCAACGAACCCGTATCGACCCGCGAGCTTAGAAACAG
GATTTTTCCCACTCTGTATGCTATATTTCAACAGAGCAGGGGCCAAGAACAA
GAGCTGAAAATAAAAAACAGGTCTCTGCGATCCCTCACCCGCAGCTGCCTGT
ATCACAAAAGCGAAGATCAGCTTCGGCGCACGCTGGAAGACGCGGAGGCTCT
CTTCAGTAAATACTGCGCGCTGACTCTTAAGGACTAGTTTCGCGCCCTTTCTC
AAATTTAAGCGCGAAAACTACGTCATCTCCAGCGGCCACACCCGGCGCCAGC
ACCTGTTGTCAGCGCCATTATGAGCAAGGAAATTCCCACGCCCTACATGTGG
AGTTACCAGCCACAAATGGGACTTGCGGCTGGAGCTGCCCAAGACTACTCAA
CCCGAATAAACTACATGAGCGCGGGACCCCACATGATATCCCGGGTCAACGG
AATACGCGCCCACCGAAACCGAATTCTCCTGGAACAGGCGGCTATTACCACC
ACACCTCGTAATAACCTTAATCCCCGTAGTTGGCCCGCTGCCCTGGTGTACCA
GGAAAGTCCCGCTCCCACCACTGTGGTACTTCCCAGAGACGCCCAGGCCGAA
GTTCAGATGACTAACTCAGGGGCGCAGCTTGCGGGCGGCTTTCGTCACAGGG
TGCGGTCGCCCGGGCAGGGTATAACTCACCTGACAATCAGAGGGCGAGGTAT
TCAGCTCAACGACGAGTCGGTGAGCTCCTCGCTTGGTCTCCGTCCGGACGGG
ACATTTCAGATCGGCGGCGCCGGCCGCTCTTCATTCACGCCTCGTCAGGCAAT
CCTAACTCTGCAGACCTCGTCCTCTGAGCCGCGCTCTGGAGGCATTGGAACTC
TGCAATTTATTGAGGAGTTTGTGCCATCGGTCTACTTTAACCCCTTCTCGGGA
CCTCCCGGCCACTATCCGGATCAATTTATTCCTAACTTTGACGCGGTAAAGGA
CTCGGCGGACGGCTACGACTGAATGTTAAGTGGAGAGGCAGAGCAACTGCGC
CTGAAACACCTGGTCCACTGTCGCCGCCACAAGTGCTTTGCCCGCGACTCCGG
TGAGTTTTGCTACTTTGAATTGCCCGAGGATCATATCGAGGGCCCGGCGCACG
GCGTCCGGCTTACCGCCCAGGGAGAGCTTGCCCGTAGCCTGATTCGGGAGTT
TACCCAGCGCCCCTGCTAGTTGAGCGGGACAGGGACCCTGTGTTCTCACT
GTGATTTGCAACTGTCCTAACCCTGGATTACATCAAGATCCTCTAGTTAATGT
CAGGTCGCCTAAGTCGATTAACTAGAGTACCCGGGGATCTTATTCCCTTTAAC
TAATAAAAAAAATAATAAAGCATCACTTACTTAAAATCAGTTAGCAAATTT
CTGTCCAGTTTATTCAGCAGCACCTCCTTGCCCTCCTCCCAGCTCTGGTATTGC
AGCTTCCTCCTGGCTGCAAACTTTCTCCACAATCTAAATGGAATGTCAGTTTC
CTCCTGTTCCTGTCCATCCGACACCCACTATCTTCATGTTGTTGCAGATGAAGC
GCGCAAGACCGTCTGAAGATACCTTCAACCCCGTGTATCCATATGACACGGA
AACCGGTCCTCCAACTGTGCCTTTTCTTACTCCTCCCTTTGTATCCCCCAATGG
GTTTCAAGAGAGTCCCCCTGGGGTACTCTCTTTGCGCCTATCCGAACCTCTAG
TTACCTCCAATGGCATGCTTGCGCTCAAAATGGGCAACGGCCTCTCTCTGGAC
GAGGCCGGCAACCTTACCTCCCAAAATGTAACCACTGTGAGCCCACCTCTCA
AAAAACCAAGTCAAACATAAACCTGGAAATATCTGCACCCCTCACAGTTAC
CTCAGAAGCCCTAACTGTGGCTGCCGCCGCACCTCTAATGGTCGCGGGCAAC
ACACTCACCATGCAATCACAGGCCCCGCTAACCGTGCACGACTCCAAACTTA
GCATTGCCACCCAAGGACCCCTCACAGTGTCAGAAGGAAAGCTAGCCCTGCA
AACATCAGGCCCCCTCACCACCACCGATAGCAGTACCCTTACTATCACTGCCT
CACCCCCTCTAACTACTGCCACTGGTAGCTTGGGCATTGACTTGAAAGAGCCC
ATTTATACACAAAATGGAAAACTAGGACTAAAGTACGGGGCTCCTTTGCATG
TAACAGACGACCTAAACACTTTGACCGTAGCAACTGGTCCAGGTGTGACTAT
TAATAATACTTCCTTGCAAACTAAAGTTACTGAGCCTTGGGTTTTGATTCAC
AAGGCAATATGCAACTTAATGTAGCAGGAGGACTAAGGATTGATTCTCAAAA
CAGACGCCTTATACTTGATGTTAGTTATCCGTTTGATGCTCAAAACCAACTAA
ATCTAAGACTAGGACAGGGCCCTCTTTTTATAAACTCAGCCCACAACTTGGAT
ATTAACTACAACAAAGGCCTTTACTTGTTTACAGCTTCAAACAATTCCAAAAA
GCTTGAGGTTAACCTAAGCACTGCCAAGGGGTTGATGTTTGACGCTACAGCC
ATAGCCATTAATGCAGGAGATGGGCTTGAATTTGGTTCACCTAATGCACCAA |

| SEQUENCES | |
|---|---|
| SEQ ID NO | Sequence |
| | ACACAAATCCCCTCAAAACAAAAATTGGCCATGGCCTAGAATTTGATTCAAA
CAAGGCTATGGTTCCTAAACTAGGAACTGGCCTTAGTTTTGACAGCACAGGT
GCCATTACAGTAGGAAACAAAAATAATGATAAGCTAACTTTGTGGACCACAC
CAGCTCCATCTCCTAACTGTAGACTAAATGCAGAGAAAGATGCTAAACTCAC
TTTGGTCTTAACAAAATGTGGCAGTCAAATACTTGCTACAGTTTCAGTTTTGG
CTGTTAAAGGCAGTTTGGCTCCAATATCTGGAACAGTTCAAAGTGCTCATCTT
ATTATAAGATTTGACGAAAATGGAGTGCTACTAAACAATTCCTTCCTGGACCC
AGAATATTGGAACTTTAGAAATGGAGATCTTACTGAAGGCACAGCCTATACA
AACGCTGTTGGATTTATGCCTAACCTATCAGCTTATCCAAAATCTCACGGTAA
AACTGCCAAAAGTAACATTGTCAGTCAAGTTTACTTAAACGGAGACAAAACT
AAACCTGTAACACTAACCATTACACTAAACGGTACACAGGAAACAGGAGAC
ACAACTCCAAGTGCATACTCTATGTCATTTTCATGGGACTGGTCTGGCCACAA
CTACATTAATGAAATATTTGCCACATCCTCTTACACTTTTTCATACATTGCCCA
AGAATAAAGAATCGTTTGTGTTATGTTTCAACGTGTTTATTTTTCAATTGCAG
AAAATTTCAAGTCATTTTTCATTCAGTAGTATAGCCCCACCACCACATAGCTT
ATACAGATCACCGTACCTTAATCAAACTCACAGAACCCTAGTATTCAACCTGC
CACCTCCCTCCCAACACACAGAGTACACAGTCCTTTCTCCCGGCTGGCCTTA
AAAAGCATCATATCATGGGTAACAGACATATTCTTAGGTGTTATATTCCACAC
GGTTTCCTGTCGAGCCAAACGCTCATCAGTGATATTAATAAACTCCCCGGGCA
GCTCACTTAAGTTCATGTCGCTGTCCAGCTGCTGAGCCACAGGCTGCTGTCCA
ACTTGCGGTTGCTTAACGGGCGGCGAAGGAGAAGTCCACGCCTACATGGGGG
TAGAGTCATAATCGTGCATCAGGATAGGGCGGTGGTGCTGCAGCAGCGCGCG
AATAAACTGCTGCCGCCGCCGCTCCGTCCTGCAGGAATACAACATGGCAGTG
GTCTCCTCAGCGATGATTCGCACCGCCCGCAGCATAAGGCGCCTTGTCCTCCG
GGCACAGCAGCGCACCCTGATCTCACTTAAATCAGCACAGTAACTGCAGCAC
AGCACCACAATATTGTTCAAAATCCCACAGTGCAAGGCGCTGTATCCAAAGC
TCATGGCGGGACCACAGAACCCACGTGGCCATCATACCACAAGCGCAGGTA
GATTAAGTGGCGACCCCTCATAAACACGCTGGACATAAACATTACCTCTTTTG
GCATGTTGTAATTCACCACCTCCCGGTACCATATAAACCTCTGATTAAACATG
GCGCCATCCACCACCATCCTAAACCAGCTGGCCAAAACCTGCCCGCCGGCTA
TACACTGCAGGGAACCGGGACTGGAACAATGACAGTGGAGAGCCCAGGACT
CGTAACCATGGATCATCATGCTCGTCATGATATCAATGTTGGCACAACACAG
GCACACGTGCATACACTTCCTCAGGATTACAAGCTCCTCCCGCGTTAGAACCA
TATCCCAGGGAACAACCCATTCCTGAATCAGCGTAAATCCCACACTGCAGGG
AAGACCTCGCACGTAACTCACGTTGTGCATTGTCAAAGTGTTACATTCGGGCA
GCAGCGGATGATCCTCCAGTATGGTAGCGCGGGTTTCTGTCTCAAAAGGAGG
TAGACGATCCCTACTGTACGGAGTGCGCCGAGACAACCGAGATCGTGTTGGT
CGTAGTGTCATGCCAAATGGAACGCCGGACGTAGTCATATTTCCTGAAGCAA
AACCAGGTGCGGGCGTGACAAACAGATCTGCGTCTCCGGTCTCGCCGCTTAG
ATCGCTCTGTGTAGTAGTTGTAGTATATCCACTCTCTCAAAGCATCCAGGCGC
CCCCTGGCTTCGGGTTCTATGTAAACTCCTTCATGCGCCGCTGCCCTGATAAC
ATCCACCACCGCAGAATAAGCCACACCCAGCCAACCTACACATTCGTTCTGC
GAGTCACACACGGGAGGAGCGGGAAGAGCTGGAAGAACCATGTTTTTTTTTT
TATTCCAAAAGATTATCCAAAACCTCAAAATGAAGATCTATTAAGTGAACGC
GCTCCCCTCCGGTGGCGTGGTCAAACTCTACAGCCAAAGAACAGATAATGGC
ATTTGTAAGATGTTGCACAATGGCTTCCAAAAGGCAAACGGCCCTCACGTCC
AAGTGGACGTAAAGGCTAAACCCTTCAGGGTGAATCTCCTCTATAAACATTC
CAGCACCTTCAACCATGCCCAAATAATTCTCATCTCGCCACCTTCTCAATATA
TCTCTAAGCAAATCCCGAATATTAAGTCCGGCCATTGTAAAAATCTGCTCCAG
AGCGCCCTCCACCTTCAGCCTCAAGCAGCGAATCATGATTGCAAAAATTCAG
GTTCCTCACAGACCTGTATAAGATTCAAAAGCGGAACATTAACAAAAATACC
GCGATCCCGTAGGTCCCTTCGCAGGGCCAGCTGAACATAATCGTGCAGGTCT
GCACGGACCAGCGCGGCCACTTCCCCGCCAGGAACCATGACAAAAGAACCC
ACACTGATTATGACACGCATACTCGGAGCTATGCTAACCAGCGTAGCCCCGA
TGTAAGCTTGTTGCATGGGCGGCGATATAAAATGCAAGGTGCTGCTCAAAAA
ATCAGGCAAAGCCTCGCGCAAAAAAGAAAGCACATCGTAGTCATGCTCATGC
AGATAAAGGCAGGTAAGCTCCGGAACCACCACAGAAAAAGACACCATTTTTC
TCTCAAACATGTCTGCGGGTTTCTGCATAAACACAAATAAAATAACAAAAA
AACATTTAAACATTAGAAGCCTGTCTTACAACAGGAAAAACACCCTTTATAA
GCATAAGACGGACTACGGCCATGCCGGCGTGACCGTAAAAAAACTGGTCACC
GTGATTAAAAAGCACCACCGACAGCTCCTCGGTCATGTCCGGAGTCATAATG
TAAGACTCGGTAAACACATCAGGTTGATTCACATCGGTCAGTGCTAAAAGC
GACCGAAATAGCCCGGGGGAATACATACCCGCAGGCGTAGAGACAACATTA
CAGCCCCCATAGGAGGTATAACAAAATTAATAGGAGAGAAAAACACATAAA
CACCTGAAAAACCCTCCTGCCTAGGCAAAATAGCACCCTCCCGCTCCAGAAC
AACATACAGCGCTTCCACAGCGGCAGCCATAACAGTCAGCCTTACCAGTAAA
AAAGAAAACCTATTAAAAAAACACCACTCGACACGGCACCAGCTCAATCAGT
CACAGTGTAAAAAGGGCCAAGTGCAGAGCGAGTATATATAGGACTAAAAA
ATGACGTAACGGTTAAAGTCCACAAAAAACACCCAGAAAACCGCACGCGAA
CCTACGCCCAGAAACGAAAGCCAAAAAACCCACAACTTCCTCAAATCGTCAC |

| SEQ ID NO | Sequence |
|---|---|
| | TTCCGTTTTCCCACGTTACGTCACTTCCCATTTTAAGAAAACTACAATTCCCA ACACATACAAGTTACTCCGCCCTAAAACCTACGTCACCCGCCCCGTTCCCACG CCCCGCGCCACGTCACAAACTCCACCCCCTCATTATCATATTGGCTTCAATCC AAAATAAGGTATATTATTGATGAT |

---

What is claimed is:

1. A composition comprising:
   a recombinant adenovirus vector comprising a nucleic acid sequence encoding a truncated HER3 antigen, wherein the truncated HER3 antigen lacks a HER3 intracellular domain;
   a recombinant adenovirus vector comprising a nucleic acid sequence encoding a MUC1 antigen; and
   a recombinant adenovirus vector comprising a nucleic acid sequence encoding a Brachyury antigen.

2. A composition comprising a recombinant adenovirus vector comprising:
   a deletion in an E1 gene region and a deletion in an E2b region of the recombinant adenovirus vector; and
   a nucleic acid sequence encoding a truncated HER3 antigen lacking a HER3 intracellular domain and comprising at least 85% sequence identity to SEQ ID NO: 87.

3. The composition of claim 1, further comprising a nucleic acid sequence encoding an immune checkpoint inhibitor, an immune checkpoint modulator, combination thereof, or an antibody that activates or potentiates an immune response.

4. The composition of claim 1, further comprising a recombinant adenovirus vector comprising a nucleic acid sequence encoding a HER1 antigen, a HER2/neu antigen, a HER4 antigen, or any combination thereof.

5. The composition of claim 1, wherein any of the recombinant adenovirus vectors comprise a replication defective adenovirus vector.

6. The composition of claim 5, wherein any of the recombinant adenovirus vectors comprises an adenovirus subtype 5 (Ad5)-based vector.

7. A host cell or a natural killer cell comprising the composition according to claim 1.

8. A method of enhancing an immune response or treating a cancer in a subject in need thereof, the method comprising administering a therapeutically effective amount of the composition of claim 1.

9. The composition of claim 2, further comprising a nucleic acid sequence encoding an immune checkpoint inhibitor, an immune checkpoint modulator, combination thereof, or an antibody that activates or potentiates an immune response.

10. The composition of claim 2, further comprising a recombinant adenovirus vector comprising a nucleic acid sequence encoding a HER1 antigen, a HER2/neu antigen, a HER4 antigen, or any combination thereof.

11. The composition of claim 2, wherein any of the recombinant adenovirus vectors comprise a replication defective adenovirus vector.

12. The composition of claim 11, wherein any of the recombinant adenovirus vectors comprises an adenovirus subtype 5 (Ad5)-based vector.

13. A method of enhancing an immune response or treating a cancer in a subject in need thereof, the method comprising administering a therapeutically effective amount of the composition of claim 2.

14. A host cell or a natural killer cell comprising the composition according to claim 2.

* * * * *